US005994391A

United States Patent [19]
Lee et al.

[11] Patent Number: 5,994,391
[45] Date of Patent: Nov. 30, 1999

[54] BENZOTHIEPINES HAVING ACTIVITY AS INHIBITORS OF ILEAL BILE ACID TRANSPORT AND TAUROCHOLATE UPTAKE

[75] Inventors: Len F. Lee, St. Charles; Shyamal C. Banerjee, Chesterfield; Horng-Chih Huang, Chesterfield; Jinglin J. Li, Chesterfield, all of Mo.; Raymond E. Miller, Fairview Heights, Ill.; David B. Reitz, Chesterfield; Samuel J. Tremont, St. Louis, both of Mo.

[73] Assignee: G.D. Searle and Company, Skokie, Ill.

[21] Appl. No.: 09/109,551

[22] Filed: Jul. 2, 1998

Related U.S. Application Data

[63] Continuation of application No. 08/517,051, Aug. 21, 1995, abandoned, which is a continuation-in-part of application No. 08/305,526, Sep. 12, 1994, abandoned
[60] Provisional application No. 60/068,170, Dec. 19, 1997, and provisional application No. 60/013,119, Mar. 11, 1996.

[51] Int. Cl.⁶ .......................... A61K 31/38; A61K 31/44; C07D 337/00; C07D 211/72
[52] U.S. Cl. .......................... 514/431; 514/336; 514/382; 514/397; 549/9; 546/279.7; 548/252; 548/315.1
[58] Field of Search ................................ 549/9; 514/431, 514/336, 382, 397; 546/279.7; 548/252, 315.1

[56] References Cited

U.S. PATENT DOCUMENTS

| | | |
|---|---|---|
| 3,287,370 | 11/1966 | Mohrbacher et al. . |
| 3,389,144 | 6/1968 | Mohrbacher et al. . |
| 3,444,176 | 5/1969 | Mohrbacher et al. . |
| 3,520,891 | 7/1970 | Mohrbacher . |
| 3,694,446 | 9/1972 | Houlihan et al. . |
| 4,207,239 | 6/1980 | McCall . |
| 5,430,116 | 7/1995 | Kramer et al. . |
| 5,491,152 | 2/1996 | Wilde et al. . |
| 5,512,558 | 4/1996 | Enhsen et al. . |
| 5,610,151 | 3/1997 | Glombik et al. . |
| 5,705,524 | 1/1998 | McGee et al. ........................ 514/431 |

FOREIGN PATENT DOCUMENTS

| | | |
|---|---|---|
| A-30209/92 | 6/1993 | Australia . |
| A-61946/94 | 11/1994 | Australia . |
| A-61948/94 | 11/1994 | Australia . |
| A-61949/94 | 11/1994 | Australia . |
| 2025294 | 3/1991 | Canada . |
| 2078588 | 3/1993 | Canada . |
| 2085782 | 6/1993 | Canada . |
| 2085830 | 6/1993 | Canada . |
| 0 350 846 | 10/1989 | European Pat. Off. . |
| 0 379 161 | 7/1990 | European Pat. Off. . |
| 0 508 425 A1 | 10/1992 | European Pat. Off. . |
| 0 549 967 A1 | 7/1993 | European Pat. Off. . |
| 0 559 064 A2 | 9/1993 | European Pat. Off. . |
| 0 563 731 A1 | 10/1993 | European Pat. Off. . |
| 0 568 898 A1 | 11/1993 | European Pat. Off. . |
| 2 661 676 | 11/1991 | France . |
| 2 698 873 | 6/1994 | France . |
| 3-14576 | 3/1991 | Japan . |
| 1211258 | 4/1970 | United Kingdom . |
| 1428110 | 3/1976 | United Kingdom . |
| WO 89/1477 | 2/1989 | WIPO . |
| WO 92/18462 | 10/1992 | WIPO . |
| WO 93/16055 | 8/1993 | WIPO . |
| WO 94/18183 | 8/1994 | WIPO . |
| WO 94/18184 | 8/1994 | WIPO . |
| WO 96/05188 | 2/1996 | WIPO . |
| WO 96/08484 | 3/1996 | WIPO . |
| WO 96/16051 | 5/1996 | WIPO . |

OTHER PUBLICATIONS

Stedronsky, "Interaction of bile acids and cholesterol with nonsystemic agents having hypocholesterolemic properties", Biochimica et Biophysica Acta, 1210 (1994) 255–287.

Heubi, J.E., et al., "Primary Bile Acid Malabsorption: Defective In Vitro Ileal Active Bile Acid Transport", Gastroenterology, 1982:83:804–11.

Reihnér, E., et al., "Regulation of hepatic cholesterol metabolism in humans: stimulatory effects of cholestyramine on HMG–CoA reductase activity and low density lipoprotein receptor expression in gallstone patients", Journal of Lipid Research, vol. 31, 1990, 2219–2226.

Suckling, et al., "Cholesterol lowering and bile acid excretion in the hamster with cholestyramine treatment", Atherosclerosis, 89 (1991) 183–190.

Kramer, et al., "Intestinal Bile Acid Absorption", The Journal of Biological Chemistry, vol. 268, No. 24, Aug. 25, 1993, 18035–18046.

PCT/US95/10863 "International Search Report"; Jan. 10, 1996.

PCT/US97/04076 "International Preliminary Examination Report" Jun. 16, 1998.

D. Huckle et al. "4–Amino–2,3,4,5,–tetrahydro–1–benzoxepin–5–ols, 4–Amino–2,3,4,5–tetrahydro–1–benzothiepin–5–ols, and Related Compounds"; Journal Chemical Society (C), 1971; pp. 2252–2260.

R. Patra et al., "Conformational And Steric Requirements Of the Side Chain For Sulfur Participation In Benzothiepin Derivatives", Tetrahedron Letters, vol. 30, No. 32, pp. 4279–4282, 1989.

Y. Ishino et al., "Novel Synthesis Of 4, 5–Bis(arylthio)–2, 3,4,5–tetrahydro–1–benzothiepins: Noteworthy Cyclization By the Reaction Of 2–Butynediol With Arenethiols In the Presence Of Zinc Iodide", Synthesis, (9), pp. 827–829, 1987.

(List continued on next page.)

*Primary Examiner*—Deborah C. Lambkin
*Attorney, Agent, or Firm*—Senniger, Powers, Leavitt & Roedel

[57] ABSTRACT

Provided are novel benzothiepines, derivatives, and analogs thereof; pharmaceutical compositions containing them; and methods of using these compounds and compositions in medicine, particularly in the prophylaxis and treatment of hyperlipidemic conditions such as those associated with atherosclerosis or hypercholesterolemia, in mammals.

358 Claims, No Drawings

OTHER PUBLICATIONS

F. Kvis et al., "Benzocycloheptenes And Heterocyclic Analogs As Potential Drugs. VII.", Collect. Czech. Chem. Commun., vol. 37, pp. 3808–3816, 1972.

K. Sindelar et al. "Benzocycloheptenes And Heterocyclic Analogues As Potential Drugs. III. Further Synthetic Experiments In The Series Of 1–Benzothiepine Derivatives", Collect. Czech. Chem. Comun., vol. 37, pp. 1195–1206, 1972.

D. Huckle et al. "4–Amino–2,3,4,5–tetrahydro–1–benzoxepin–5–ols, 4–Amino–2,3,4,5–tetrahydro–1–benzothiepin–5–ols, And Related Compounds", J. Chem. Soc. (C), pp. 2252–2260, 1971.

K. Sindelar et al. "Neurotropic And Psychotropic Compounds XXIX. Derivatives Of 2,3,4,5–tetra- hydro–-1–benzothiepin", Collect. Czech. Chem. Commun., vol. 33, pp. 4315–4327, 1968.

BENZOTHIEPINES HAVING ACTIVITY AS INHIBITORS OF ILEAL BILE ACID TRANSPORT AND TAUROCHOLATE UPTAKE

This application is a continuation of U.S. application Ser. No. 08/517,051, filed Aug. 21, 1995, abandoned, which is a continuation-in-part application of U.S. application Ser. No. 08/305,526, filed Sep. 12, 1994, abandoned. This application also claims priority from U.S. Provisional application Ser. No. 60/068,170 filed Dec. 19, 1997 and provisional application Ser. No. 60/013,119 filed Mar. 11, 1996.

BACKGROUND OF THE INVENTION

1. Field of the Invention

The present invention relates to novel benzothiepines, derivatives and analogs thereof, pharmaceutical compositions containing them, and their use in medicine, particularly in the prophylaxis and treatment of hyperlipidemic conditions such as is associated with atherosclerosis or hypercholesterolemia, in mammals.

2. Description of Related Art

It is well-settled that hyperlipidemic conditions associated with elevated concentrations of total cholesterol and low-density lipoprotein cholesterol are major risk factors for coronary heart disease and particularly atherosclerosis. Interfering with the circulation of bile acids within the lumen of the intestinal tract is found to reduce the levels of serum cholesterol in a causal relationship. Epidemiological data has accumulated which indicates such reduction leads to an improvement in the disease state of atherosclerosis. Stedronsky, in "Interaction of bile acids and cholesterol with nonsystemic agents having hypocholesterolemic properties," *Biochimica et Biophysica Acta,* 1210 (1994) 255–287 discusses the biochemistry, physiology and known active agents surrounding bile acids and cholesterol.

Pathophysiologic alterations are shown to be consistent with interruption of the enterohepatic circulation of bile acids in humans by Heubi, J. E., et al. See "Primary Bile Acid Malabsorption: Defective in Vitro Ileal Active Bile Acid Transport", *Gastroenterology,* 1982:83:804–11.

In fact, cholestyramine binds the bile acids in the intestinal tract, thereby interfering with their normal enterohepatic circulation (Reihnér, E. et al, in "Regulation of hepatic cholesterol metabolism in humans: stimulatory effects of cholestyramine on HMG-CoA reductase activity and low density lipoprotein receptor expression in gallstone patients", *Journal of Lipid Research,* Volume 31, 1990, 2219–2226 and Suckling el al, "Cholesterol Lowering and bile acid excretion in the hamster with cholestyramine treatment", *Atherosclerosis,* 89(1991) 183–190). This results in an increase in liver bile acid synthesis by the liver using cholesterol as well as an upregulation of the liver LDL receptors which enhances clearance of cholesterol and decreases serum LDL cholesterol levels.

In another approach to the reduction of recirculation of bile acids, the ileal bile acid transport system is a putative pharmaceutical target for the treatment of hypercholesterolemia based on an interruption of the enterohepatic circulation with specific transport inhibitors (Kramer, et al, "Intestinal Bile Acid Absorption" *The Journal of Biological Chemistry,* Vol. 268, No. 24, Issue of August 25, pp. 18035–18046, 1993).

In a series of patent applications, eg Canadian Patent Application Nos. 2,025,294; 2,078,588; 2,085,782; and 2,085,830; and EP Application Nos. 0 379 161; 0 549 967; 0 559 064; and 0 563 731, Hoechst Aktiengesellschaft discloses polymers of various naturally occurring constituents of the enterohepatic circulation system and their derivatives, including bile acid, which inhibit the physiological bile acid transport with the goal of reducing the LDL cholesterol level sufficiently to be effective as pharmaceuticals and, in particular for use as hypocholesterolemic agents.

In vitro bile acid transportinhibition is disclosed to show hypolipidemic activity in The Wellcome Foundation Limited disclosure of the world patent application number WO 93/16055 for "Hypolipidemic Benzothiazepine Compounds".

Selected benzothiepines are disclosed in world patent application number WO93/321146 for numerous uses including fatty acid metabolism and coronary vascular diseases.

Other selected benzothiepines are known for use as hypolipaemic and hypocholesterolaemic agents, especially for the treatment or prevention of atherosclerosis as disclosed by application Nos. EP 508425, FR 2661676, and WO 92/18462, each of which is limited by an amide bonded to the carbon adjacent the phenyl ring of the fused bicyclo benzothiepine ring.

The above references show continuing efforts to find safe, effective agents for the prophylaxis and treatment of hyperlipidemic diseases and their usefulness as hypocholesterolemic agents.

Additionally selected benzothiepines are disclosed for use in various disease states not within the present invention utility. These are EP 568 898A as abstracted by Derwent Abstract No. 93-351589; WO 89/1477/A as abstracted in Derwent Abstract No. 89-370688; U.S. Pat. No. 3,520,891 abstracted in Derwent 50701R-B; U.S. Pat. No. 3,287,370, U.S. Pat. No. 3,389,144; U.S. Pat. No. 3,694,446 abstracted in Derwent Abstr. No. 65860T-B and WO 92/18462.

The present invention furthers such efforts by providing novel benzothiepines, pharmaceutical compositions, and methods of use therefor.

SUMMARY OF THE INVENTION

Accordingly, among its various apects, the present invention provides compounds of formula (I):

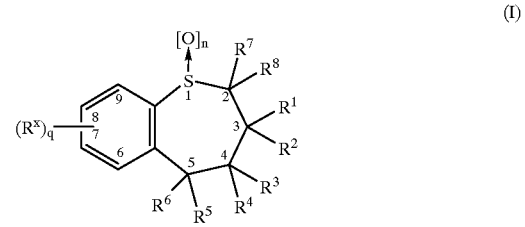

(I)

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, quaternary heterocycle, $OR^9$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A-$, $PR^9$, $P^+R^9R^{10}A-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen, OH, or SH and when $R^5$ is OH, $R^1$, $R^2$, $R^3$, $R^4$, $R^7$ and $R^8$ cannot be all hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl;

provided that when n is 1, $R^1$, $R^3$, $R^7$, and $R^8$ are hydrogen, $R^2$ is hydrogen, alkyl or aryl, $R^4$ is unsubstituted amino or amino substituted with one or more alkyl or aryl radicals, and $R^5$ is hydrogen, alkyl or aryl, then $R^6$ is other than hydroxy; or a pharmaceutically acceptable salt, solvate, or prodrug thereof.

Preferably, $R^5$ and $R^6$ can independently be selected from the group consisting of H, aryl, heterocycle, quaternary heterocycle, and quaternary heteroaryl, wherein said aryl, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R15A-$, $P(OR^{13})OR^{14}$, $S+R^{13}R^{14}A-$, and $N^+R^9R^{11}R^{12}A^-$, wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene, wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and P(O) $(OR^7)OR^8$.

More preferably, $R^5$ or $R^6$ has the formula:

—Ar—(R$^y$)t wherein:
t is an integer from 0 to 5;
Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and one or more $R^y$ are independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo $CONR^7R^8$, $N^+R^7R^8R^9A-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene.

Most preferably, $R^5$ or $R^6$ has the formula (II):

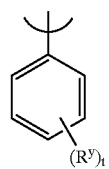

(II)

(R$^y$)$_t$

Another embodiment of the invention is further directed to compounds of Formula I wherein at least one or more of the following conditions exist:

(1) $R^1$ and $R^2$ are independently selected from the group consisting of hydrogen and alkyl. Preferably, $R^1$ and $R^2$ are independently selected from the group consisting of $C_{1-6}$ alkyl. More preferably, $R^1$ and $R^2$ are the same $C_{1-6}$ alkyl. Still more preferably, $R^1$ and $R^2$ are n-butyl; and/or (2) $R^3$ and $R^4$ are independently selected from the group consisting of hydrogen and $OR^9$ wherein $R^9$ is defined as set forth above. Preferably, $R^3$ is hydrogen and $R^4$ is $OR^9$. Still more preferably, $R^3$ is hydrogen and $R^4$ is hydroxy; and/or (3) $R^5$ is substituted aryl. Preferably, $R^5$ is substituted phenyl. More preferably, $R^5$ is phenyl substituted with a radical selected from the group consisting of $OR^{13}$, $NR^{13}C(O)R^{14}$, $NR^{13}C(O)NR^{13}R^{15}$, $NR^{14}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, and $NR^{13}SO_2NR^{14}R^{15}$ wherein $R^{13}$, $R^{14}$ and $R^{15}$ are as set forth above. Still more preferably, $R^5$ is phenyl substituted with $OR^{13}$. Still more preferably, $R^5$ is phenyl substituted at the para or meta position with $OR^{13}$ wherein $R^{13}$ comprises a quaternary heterocycle, quaternary heteroaryl or substituted amino; and/or (4) $R^6$ is hydrogen; and/or (5) $R^7$ and $R^8$ are independently selected from the group consisting of hydrogen and alkyl. Preferably, $R^1$ and $R^2$ are independently selected from the group $C_{1-6}$ alkyl. Still more preferably, $R^1$ and $R^2$ are hydrogen; and/or (6) $R^x$ is selected from the group consisting of $OR^{13}$ and $NR^{13}R^{14}$. Preferably, $R^x$ is selected from the group consisting of alkoxy, amino, alkylamino and dialkylamino. Still more preferably, $R^x$ is selected from the group consisting of methoxy and dimethylamino.

Another embodiment of the invention is further directed to compounds of formula 1:

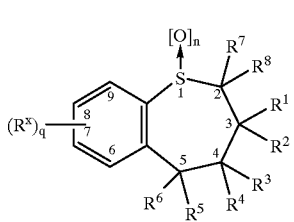

(I)

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or
$R^1$ and $R^2$ taken together with the carbon to which they are attached form $C_3$–$C_{10}$ cycloalkyl;
$R^3$ and $R^4$ are independently selected from the group consisting of H, alkyl, alkenyl, alkynyl, acyloxy, aryl, heterocycle, $OR^9$, $SR^9$, $S(O)R^9$, $SO_2R^9$, and $SO_3R^9$, wherein $R^9$ and $R^{10}$ are as defined above; or
$R^3$ and $R^4$ together form $=$O, $=$NOR$^{11}$, $=$S, $=$NNR$^{11}$R$^{12}$, $=$NR$^9$, or $=$CR$^{11}$R$^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ is selected from the group consisting of H, alkyl, alkenyl, alkynyl, aryl, cycloalkyl, heterocycle, quaternary heterocycle, $OR^9$, $SR^9$, $S(O)R^9$, $SO_2R^9$, and $SO_3R^9$,
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,
wherein:
$A^-$ is a pharmaceutically acceptable anion and M is a pharmaceutically acceptable cation,
said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^9R^8A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)$ $(OR^7)$ $OR^8$, and
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7A^8R-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl,
wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and
$R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM,
wherein $R^{16}$ and $R^{17}$ are independently selected from the substituents constituting $R^9$ and M; or
$R^{13}$ and $R^{14}$, together with the nitrogen atom to which they are attached form a mono- or polycyclic heterocycle that is optionally substituted with one or more radicals selected from the group consisting of oxo, carboxy and quaternary salts; or
$R^{14}$ and $R^{15}$, together with the nitrogen atom to which they are attached, form a cyclic ring; and
$R^6$ is hydroxy; and
$R^7$ and $R^8$ are independently selected from the group consisting of hydrogen and alkyl; and
one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, $CN$, $OM$, $SO_2OM$, $SO_2NR^{13}R^{14}$, $NR^{14}C(O)R^{13}$, $C(O)NR^{13}R^{14}$, $NR^{14}C(O)R^{13}$, $C(O)OM$, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9$, $R^{10}$, $N^+R^9R^{11}R^{12}A^-$, $SR^9$, $S(O)R^9$, $SO_2R^9$, $SO_3R^9$, oxo, $CO_2R^9$, $CN$, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or $C(O)OM$, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, $CN$, halogen, $CONR^9R^{10}$, $SO_3R^9$, $SO_2OM$, $SO_2NR^9R^{10}$, $PO(OR^{16})OR^{17}$, and $C(O)OM$, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, $CN$, $OM$, $SO_2OM$, $SO_2NR^{13}R^{14}$, $C(O)NR^{13}R^{14}$, $C(O)OM$, $COR^{13}$, $P(O)R^{13}R^{14}$, $P^+R^{13}R^{14}R15A-$, $P(OR^{13})OR^{14}$, $S^+R^{13}R^{14}A^-$, and $N^+R^9R^{11}R^{12}A^-$, provided that both $R^5$ and $R^6$ cannot be hydrogen, OH, or SH;

provided that when $R^5$ is phenyl, only one of $R^1$ or $R^2$ is H; or a pharmaceutically acceptable salt, solvate, or prodrug thereof.

The invention is further directed to a compound selected from among:

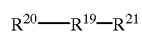

(Formula DI)

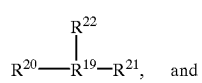, and (Formula DII)

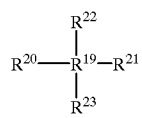

(Formula DIII)

wherein $R^{19}$ is selected from the group consisting of alkane diyl, alkene diyl, alkyne diyl, polyalkane diyl, alkoxy diyl, polyether diyl, polyalkoxy diyl, carbohydrate, amino acid, peptide, and polypeptide, wherein alkane diyl, alkene diyl, alkyne diyl, polyalkane diyl, alkoxy diyl, polyether diyl, polyalkoxy diyl, carbohydrate, amino acid, peptide, and polypeptide can optionally have one or more carbon atoms replaced by O, $NR^7$, $N^+R^7R^8$, S, SO, $SO_2$, $S^+R^7R^8$, $PR^7$, $P^+R^7R^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, $CN$, $OM$, $SO_2OM$, $SO_2NR^{13}R^{14}$, $C(O)NR^{13}R^{14}$, $C(O)OM$, $COR^{13}$, $P(O)R^{13}R^{14}$, $P^+R^{13}R^{14}R15A-$, $P(OR^{13})OR^{14}$, $S^+R^{13}R^{14}A^-$, and $N^+R^9R^{11}R^{12}A^-$;

wherein $R^{19}$ further comprises functional linkages by which $R^{19}$ is bonded to $R^{20}$, $R^{21}$, or $R^{22}$ in the compounds of Formulae DII and DIII, and $R^{23}$ in the compounds of Formula DIII. Each of $R^{20}$, $R^{21}$, or $R^{22}$ and $R^{23}$ comprises a benzothiepine moiety as described above that is therapeutically effective in inhibiting ileal bile acid transport.

The invention is also directed to a compound selected from among Formula DI, Formula DII and Formula DIII in which each of $R^{20}$, $R^{21}$, $R^{22}$ and $R^{23}$ comprises a benzothiepine moiety corresponding to the Formula:

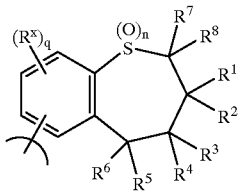

(Formula DIV)

or:

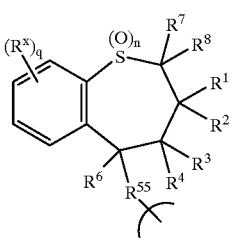

(Formula DIVA)

wherein $R^1$, $R^2$, $R^3$, $R^4$, $R^5$, $R^6$, $R^7$, $R^8$, $R^x$, q, and n are as defined in Formula I as described above, and $R^{55}$ is either a covalent bond or arylene.

In compounds of Formula DIV, it is particularly preferred that each of $R^{20}$, $R^{21}$, and $R^{22}$ in Formulae DII and DIII, and $R^{23}$ in Formula DIII, be bonded at its 7- or 8-position to $R^{19}$. In compounds of Formula DIVA, it is particularly preferred that $R^{55}$ comprise a phenylene moiety bonded at a m- or p-carbon thereof to $R^{19}$.

Examples of Formula DI include:

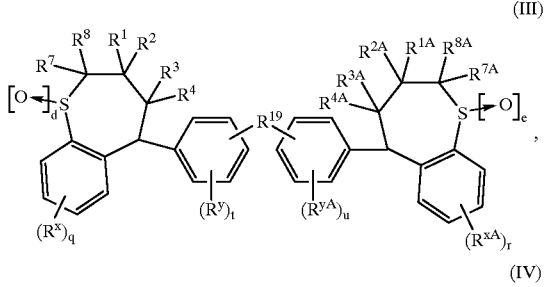
(III)

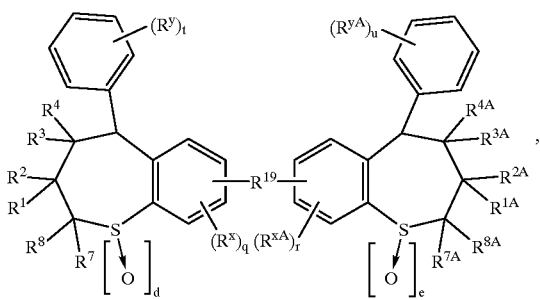
(IV)

and

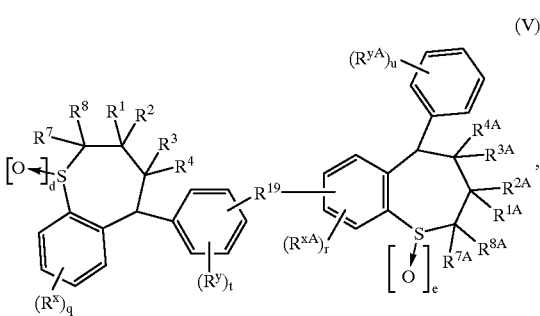
(V)

In any of the dimeric or multimeric structures discussed immediately above, benzothiepine compounds of the present invention can be used alone or in various combinations.

In any of the compounds of the present invention, $R^1$ and $R^2$ can be ethyl/butyl or butyl/butyl.

In another aspect, the present invention provides a pharmaceutical composition for the prophylaxis or treatment of a disease or condition for which a bile acid transport inhibitor is indicated, such as a hyperlipidemic condition, for example, atherosclerosis. Such compositions comprise any of the compounds disclosed above, alone or in combination, in an amount effective to reduce bile acid levels in the blood, or to reduce transport thereof across digestive system membranes, and a pharmaceutically acceptable carrier, excipient, or diluent.

In a further aspect, the present invention also provides a method of treating a disease or condition in mammals, including humans, for which a bile acid transport inhibitor is indicated, comprising administering to a patient in need thereof a compound of the present invention in an effective amount in unit dosage form or in divided doses.

In yet a further aspect, the present invention also provides processes for the preparation of compounds of the present invention.

Further scope of the applicability of the present invention will become apparent from the detailed description provided below. However, it should be understood that the following detailed dscription and examples, while indicating preferred embodiments of the invention, are given by way of illustration only since various changes and modifications within the spirit and scope of the invention will beomce apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the emobodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

In order to aid the reader in understanding the following detailed description, the following definitions are provided:

"Alkyl", "alkenyl," and "alkynyl" unless otherwise noted are each straight chain or branched chain hydrocarbons of from one to twenty carbons for alkyl or two to twenty carbons for alkenyl and alkynyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocyle, including, but not limited to, substituted or unsubstituted phenyl, naphthyl, or anthracenyl.

"Heterocycle" means a saturated or unsaturated mono- or multi-ring carbocycle wherein one or more carbon atoms can be replaced by N, S, P, or O. This includes, for example, the following structures:

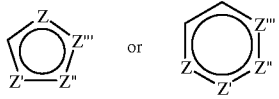

wherein Z, Z', Z" or Z'" is C, S, P, O, or N, with the proviso that one of Z, Z', Z" or Z'" is other than carbon, but is not O or S when attached to another Z atom by a double bond or when attached to another O or S atom. Furthermore, the optional substituents are understood to be attached to Z, Z', Z" or Z'" only when each is C.

The term "heteroaryl" means a fully unsaturated heterocycle.

In either "heterocycle" or "heteroaryl," the point of attachment to the molecule of interest can be at the heteroatom or elsewhere within the ring.

The term "quaternary heterocycle" means a heterocycle in which one or more of the heteroatoms, for example, O, N, S, or P, has such a number of bonds that it is positively charged. The point of attachment of the quaternary heterocycle to the molecule of interest can be at a heteroatom or elsewhere.

The term "quaternary heteroaryl" means a heteroaryl in which one or more of the heteroatoms, for example, O, N, S, or P, has such a number of bonds that it is positively charged. The point of attachment of the quaternary heteryaryl to the molecule of interest can be at a heteroatom or elsewhere.

The term "halogen" means a fluoro, chloro, bromo or iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds. Examples include radicals such as cyclopropyl, cyclobutyl, cyclopentyl, cyclohexyl, cycloalkenyl, and cycloheptyl. The term "cycloalkyl" additionally encompasses spiro systems wherein the cycloalkyl ring has a carbon ring atom in common with the seven-membered heterocyclic ring of the benzothiepine.

The term "diyl" means a diradical moiety wherein said moiety has two points of attachment to molecules of interest.

The term "oxo" means a doubly bonded oxygen.

The term "polyalkyl" means a branched or straight hydrocarbon chain having a molecular weight up to about 20,000, more preferably up to about 10,000, most preferably up to about 5,000.

The term "polyether" means a polyalkyl wherein one or more carbons are replaced by oxygen, wherein the polyether has a molecular weight up to about 20,000, more preferably up to about 10,000, most preferably up to about 5,000.

The term "polyalkoxy" means a polymer of alkylene oxides, wherein the polyalkoxy has a molecular weight up to about 20,000, more preferably up to about 10,000, most preferably up to about 5,000.

The term "cycloaklylidene" means a mono- or multi-ringed carbocycle wherein a carbon within the ring structure is doubly bonded to an atom which is not within the ring structures.

The term "carbohydrate" means a mono-, di-, tri-, or polysaccharide wherein the polysaccharide can have a molecular weight of up to about 20,000, for example, hydroxypropyl-methylcellulose or chitosan.

The term "peptide" means polyamino acid containing up to about 100 amino acid units.

The term "polypeptide" means polyamino acid containing from about 100 amino acid units to about 1000 amino acid units, more preferably from about 100 amino acid units to about 750 amino acid untis, most preferably from about 100 amino acid units to about 500 amino acid units.

The term "alkylammoniumalkyl" means a $NH_2$ group or a mono-, di- or tri-substituted amino group, any of which is bonded to an alkyl wherein said alkyl is bonded to the molecule of interest.

The term "triazolyl" includes all positional isomers. In all other heterocycles and heteroaryls which contain more than one ring heteroatom and for which isomers are possible, such isomers are included in the definition of said heterocycles and heteroaryls.

The term "sulfo" means a sulfo group, —$SO_3H$, or its salts.

The term "sulfoalkyl" means an alkyl group to which a sulfonate group is bonded, wherein said alkyl is bonded to the molecule of interest.

The term "arylalkyl" means an aryl-substituted alkyl radical such as benzyl. The term "alkylarylalkyl" means an arylalkyl radical that is substituted on the aryl group with one or more alkyl groups.

The term "heterocyclylalkyl" means an alkyl radical that is substituted with one or more heterocycle groups. Preferable heterocyclylalkyl radicals are "lower heterocyclylalkyl" radicals having one or more heterocycle groups attached to an alkyl radical having one to ten carbon atoms.

The term "heteroarylalkyl" means an alkyl radical that is substituted with one or more heteroaryl groups. Preferable heteroarylalkyl radicals are "lower heteroarylalkyl" radicals having one or more heteroaryl groups attached to an alkyl radical having one to ten carbon atoms.

The term "quaternary heterocyclylalkyl" means an alkyl radical that is substituted with one or more quaternary heterocycle groups. Preferable quaternary heterocyclylalkyl radicals are "lower quaternary heterocyclylalkyl" radicals having one or more quaternary heterocycle groups attached to an alkyl radical having one to ten carbon atoms.

The term "quaternary heteroarylalkyl" means an alkyl radical that is substituted with one or more quaternary heteroaryl groups. Preferable quaternary heteroarylalkyl radicals are "lower quaternary heteroarylalkyl" radicals having one or more quaternary heteroaryl groups attached to an alkyl radical having one to ten carbon atoms.

The term "alkylheteroarylalkyl" means a heteroarylalkyl radical that is substituted with one or more alkyl groups. Preferable alkylheteroarylalkyl radicals are "lower alkylheteroarylalkyl" radicals with alkyl portions having one to ten carbon atoms.

The term "alkoxy" an alkyl radical which is attached to the remainder of the molecule by oxygen, such as a methoxy radical. More preferred alkoxy radicals are "lower alkoxy" radicals having one to six carbon atoms. Examples of such radicals include methoxy, ethoxy, propoxy, iso-propoxy, butoxy and tert-butoxy.

The term "carboxy" means the carboxy group, —$CO_2H$, or its salts.

The term "carboxyalkyl" means an alkyl radical that is substituted with one or more carboxy groups. Preferable carboxyalkyl radicals are "lower carboxyalkyl" radicals having one or more carboxy groups attached to an alkyl radical having one to six carbon atoms.

The term "carboxyheterocycle" means a heterocycle radical that is substituted with one or more carboxy groups.

The term "carboxyheteroaryl" means a heteroaryl radical that is substituted with one or more carboxy groups.

The term "carboalkoxyalkyl" means an alkyl radical that is substituted with one or more alkoxycarbonyl groups. Preferable carboalkoxyalkyl radicals are "lower carboalkoxyalkyl" radicals having one or more alkoxycarbonyl groups attached to an alkyl radical having one to six carbon atoms.

The term "carboxyalkylamino" means an amino radical that is mono- or di-substituted with carboxyalkyl. Preferably, the carboxyalkyl substituent is a "lower carboxyalkyl" radical wherein the carboxy group is attached to an alkyl radical having one to six carbon atoms.

The term "active compound" means a compound of the present invention which inhibits transport of bile acids.

When used in combination, for example "alkylaryl" or "arylalkyl," the individual terms listed above have the meaning indicated above.

The term "a bile acid transport inhibitor" means a compound capable of inhibiting absorption of bile acids from the intestine into the circulatory system of a mammal, such as a human. This includes increasing the fecal excretion of bile acids, as well as reducing the blood plasma or serum concentrations of cholesterol and cholesterol ester, and more specifically, reducing LDL and VLDL cholesterol. Conditions or diseases which benefit from the prophylaxis or treatment by bile acid transport inhibition include, for example, a hyperlipidemic condition such as atherosclerosis.

Compounds

The compounds of the present invention can have at least two asymmetrical carbon atoms, and therefore include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis isomers or trans isomers across a double bond. All such isomers are contemplated among the compounds of the present invention.

The compounds of the present invention also include tautomers.

The compounds of the present invention as discussed below include their salts, solvates and prodrugs.

Compound Syntheses

The starting materials for use in the preparation of the compounds of the invention are known or can be prepared by conventional methods known to a skilled person or in an analogous manner to processes described in the art.

Generally, the compounds of the present invention can be prepared by the procedures described below.

For example, as shown in Scheme I, reaction of aldehyde II with formaldehyde and sodium hydroxide yields the hydroxyaldehyde III which is converted to mesylate IV with methansulfonyl chloride and triethylamine similar to the procedure described in Chem. Ber. 98, 728–734 (1965). Reaction of mesylate IV with thiophenol V, prepared by the procedure described in WO 93/16055, in the presence of triethylamine yields keto-aldehyde VI which can be cyclized with the reagent, prepared from zinc and titanium trichloride in refluxing ethylene glycol dimethyl ether (DME), to give a mixture of 2,3-dihydrobenzothiepine VII and two racemic steroisomers of benzothiepin-(5H)-4-one VIII when $R^1$ and $R^2$ are nonequivalent. Oxidation of VII with 3 equivalents of m-chloro-perbenzoic acid (MCPBA) gives isomeric sulfone-epoxides IX which upon hydrogenation with palladium on carbon as the catalyst yield a mixture of four racemic stereoisomers of 4-hydroxy-2,3,4,5-tetrahydrobenzothiepine-1,1-dioxides X and two racemic stereoisomers of 2,3,4,5-tetrahydro-benzothiepine-1,1-dioxides XI when $R^1$ and $R^2$ are nonequivalent.

Optically active compounds of the present invention can be prepared by using optically active starting material III or by resolution of compounds X with optical resolution agents well known in the art as described in *J. Org. Chem.*, 39, 3904 (1974), ibid., 42, 2781 (1977), and ibid., 44, 4891 (1979).

Scheme 1

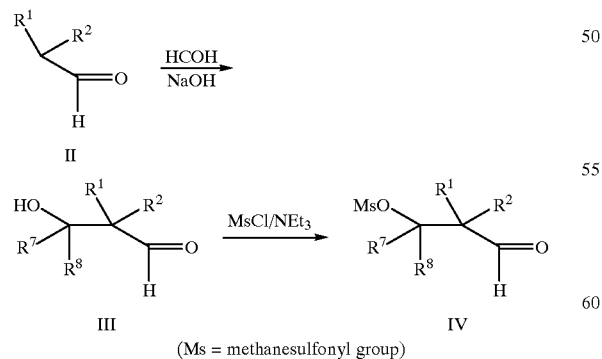

(Ms = methanesulfonyl group)

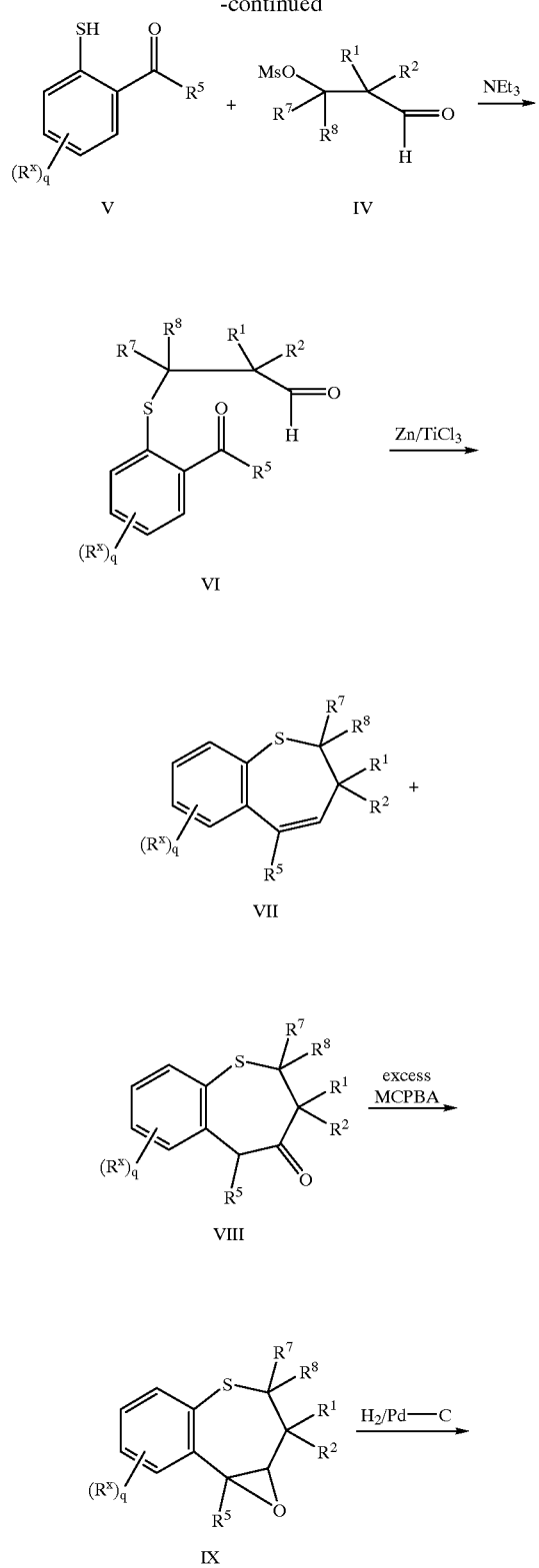

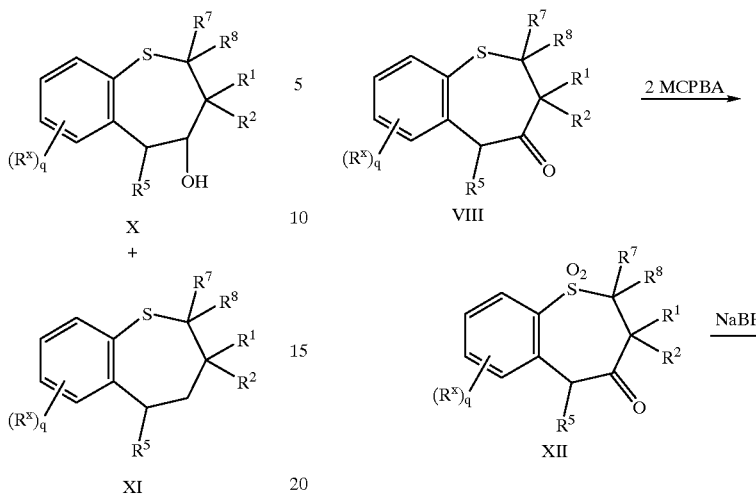

Alternatively, keto-aldehyde VI where R² is H can be prepared by reaction of thiophenol V with a 2-substituted acrolein.

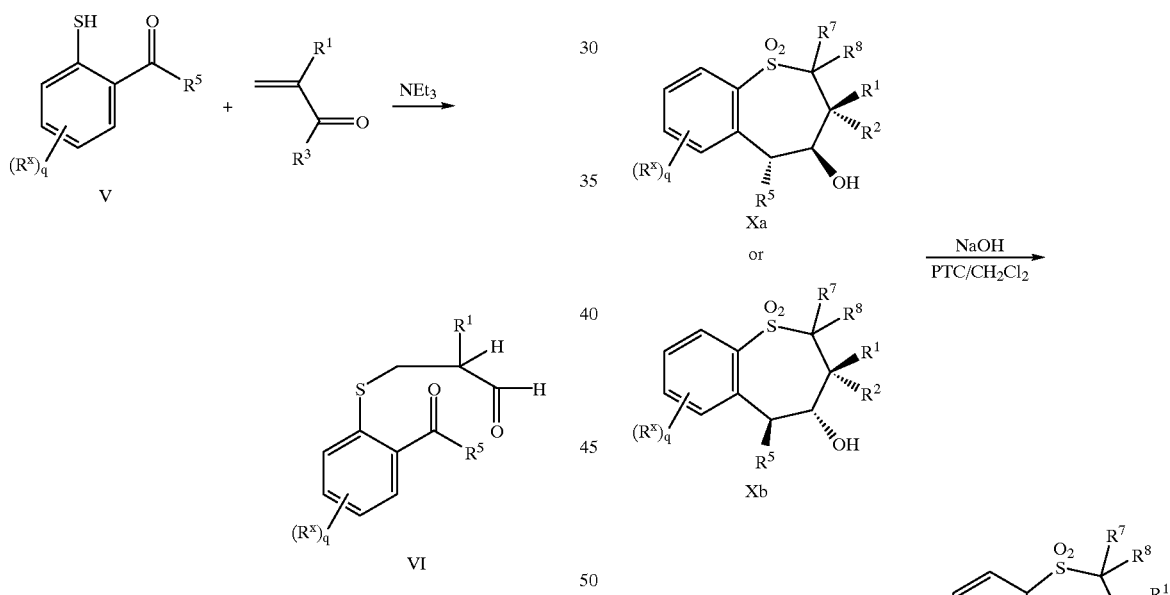

Benzothiepin-(5H)-4-one VIII can be oxidized with MCPBA to give the benzothiepin-(5H)-4-one-1,1-dioxide XII which can be reduced with sodium borohydride to give four racemic stereoisomers of X. The two stereoisomers of X, Xa and Xb, having the OH group and R⁵ on the opposite sides of the benzothiepine ring can be converted to the other two isomers of X, Xc and Xd, having the OH group and R⁵ on the same side of the benzothiepine ring by reaction in methylene chloride with 40–50% sodium hydroxide in the presence of a phase transfer catalyst (PTC). The transformation can also be carried out with potassium t-butoxide in THF.

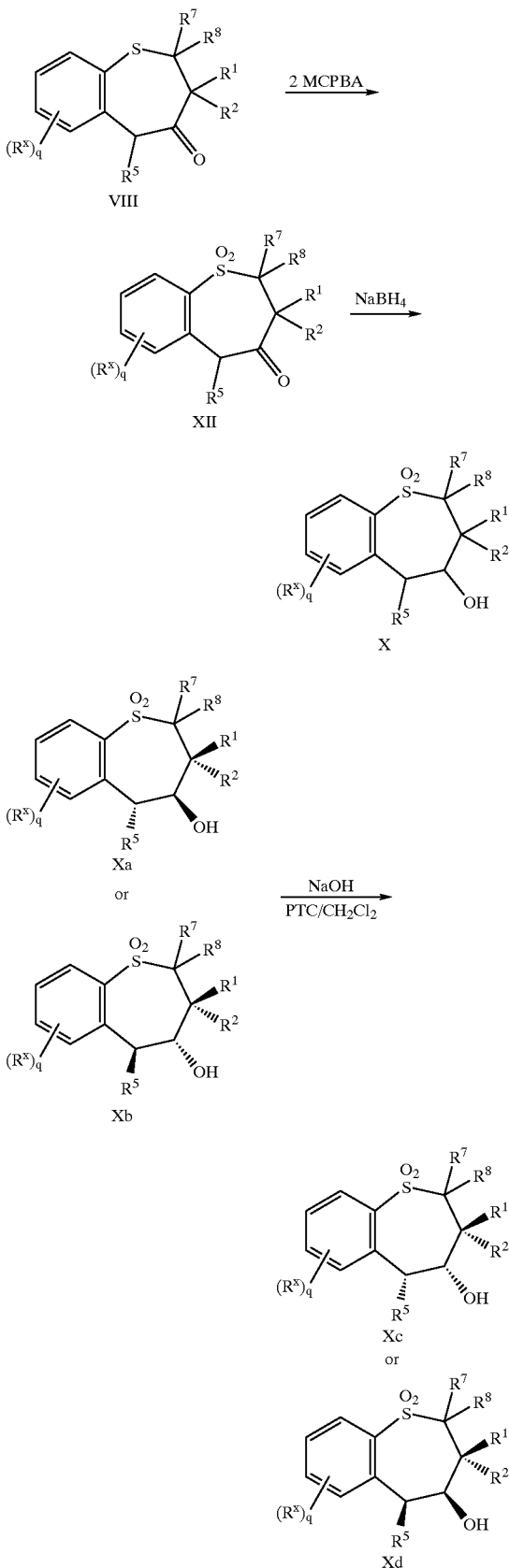

-continued

MCPBA = m-chloroperbenzoic acid
PTC = phase transfer catalyst
when $R^1$ = butyl, $R^2$ = ethyl, $R^5$ =phenyl, X = H, q = 4
6a = Xa
6b = Xb
6c = Xc
6d = Xd The compounds of the present invention where $R^5$ is OR, NRR' and $S(O)_nR$ and $R^4$ is hydroxy can be prepared by reaction of epoxide IX where $R^5$ is H with thiol, alcohol, and amine in the presence of a base.

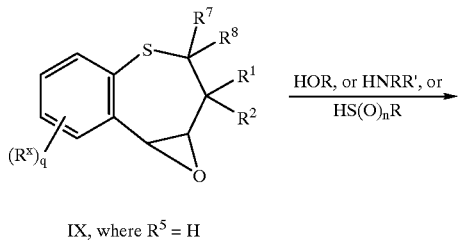

IX, where $R^5$ = H

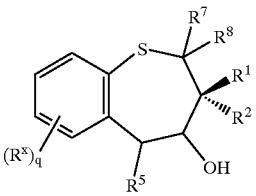

$R^5$ = OR, NRR', $S(O)_nR$

Another route to Xc and Xd of the present invention is shown in Scheme 2. Compound VI is oxidized to compound XIII with two equivalent of m-chloroperbenzoic acid. Hydrogenolysis of compound XIII with palladium on carbon yields compound XIV which can be cyclized with either potassium t-butoxide or sodium hydroxide under phase transfer conditions to a mixture of Xc and Xd. Separation of Xc and Xd can be accomplished by either HPLC or fractional crystallization.

The thiophenols XVIII and V used in the present invention can also be prepared according to the Scheme 3. Alkylation of phenol XV with an arylmethyl chloride in a nonpolar solvent according to the procedure in *J. Chem. Soc.*, 2431–2432 (1958) gives the ortho substituted phenol XVI. The phenol XVI can be converted to the thiophenol XVIII via the thiocarbamate XVII by the procedure described in *J. Org. Chem.*, 31, 3980 (1966). The phenol XVI is first reacted with dimethyl thiocarbamoyl chloride and triethylamine to give thiocarbamate XVII which is thermally rearranged at 200–300° C., and the rearranged product is hydrolyzed with sodium hydroxide to yield the thiophenol XVIII. Similarly, Thiophenol V can also be prepared from 2-acylphenol XIX via the intermediate thiocarbamate XX.

Scheme 2

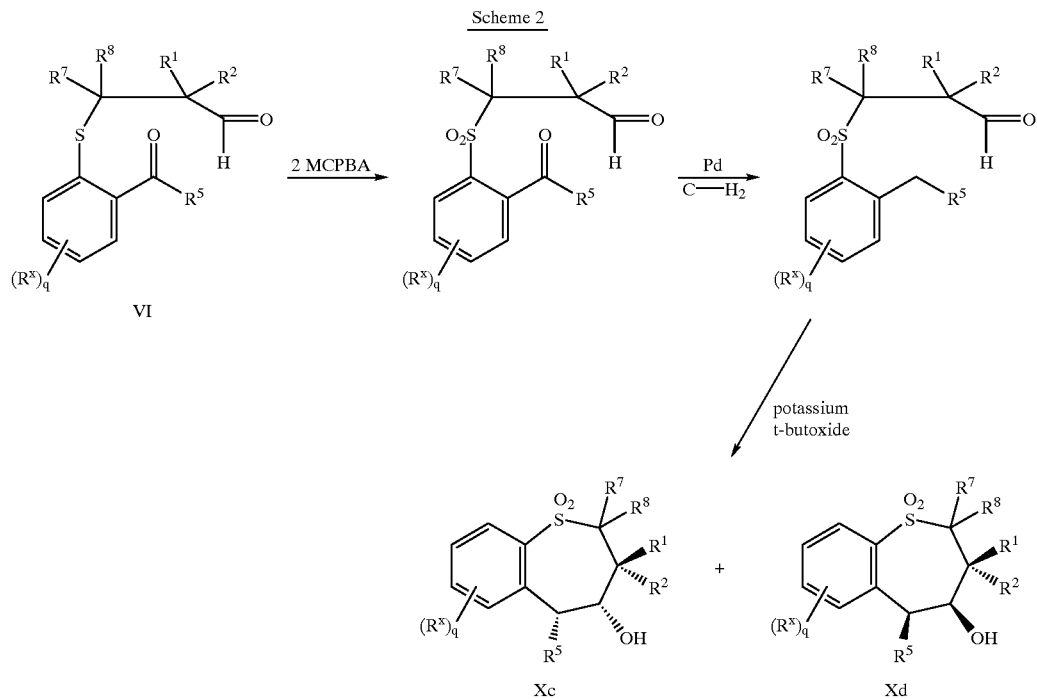

Scheme 3

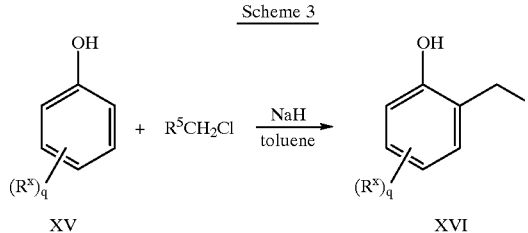

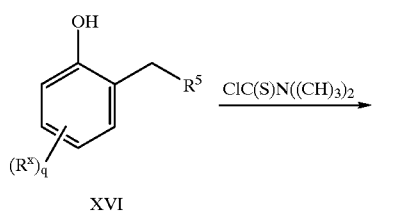

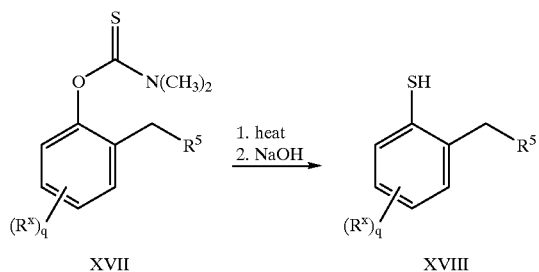

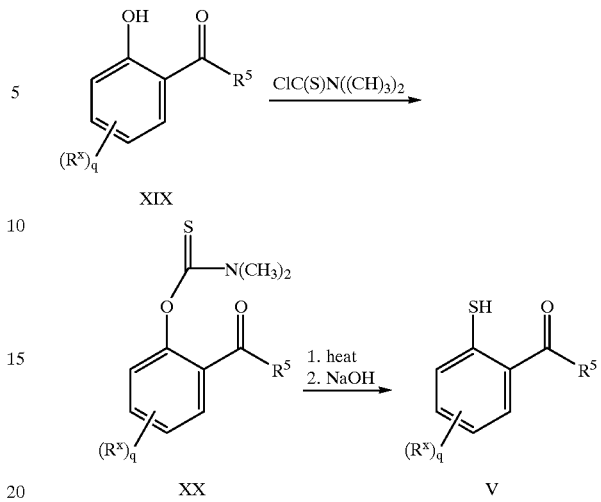

Scheme 4 shows another route to benzothiepine-1,1-dioxides Xc and Xd starting from the thiophenol XVIII. Compound XVIII can be reacted with mesylate IV to give the sulfide-aldehyde XXI. Oxidation of XXI with two equivalents of MCPBA yields the sulfone-aldehyde XIV which can be cyclized with potassium t-butoxide to a mixture of Xc and Xd. Cyclyzation of sulfide-aldehyde with potassium t-butoxide also gives a mixture of benzothiepine XXIIc and XXIId.

Scheme 4

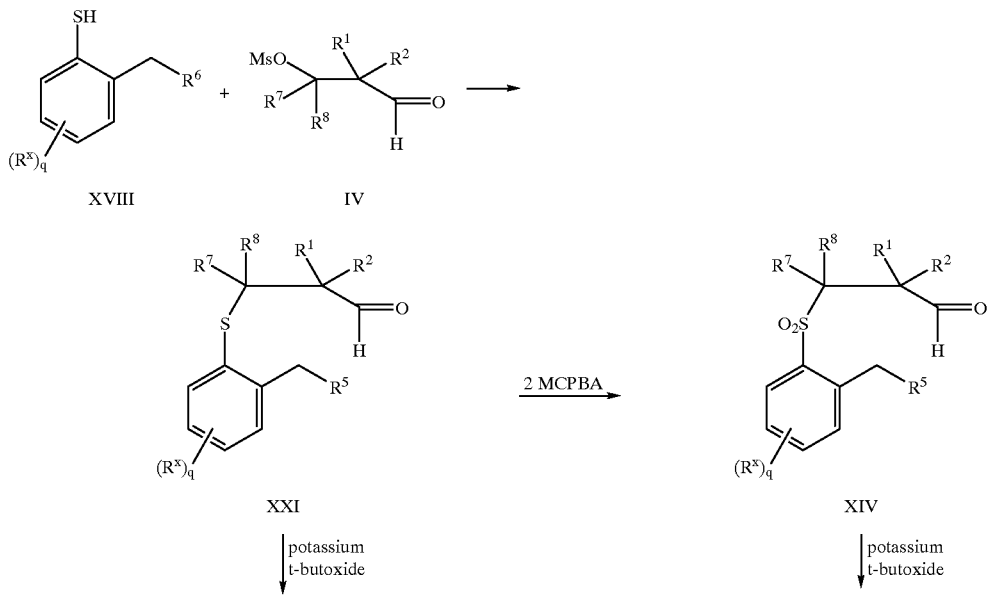

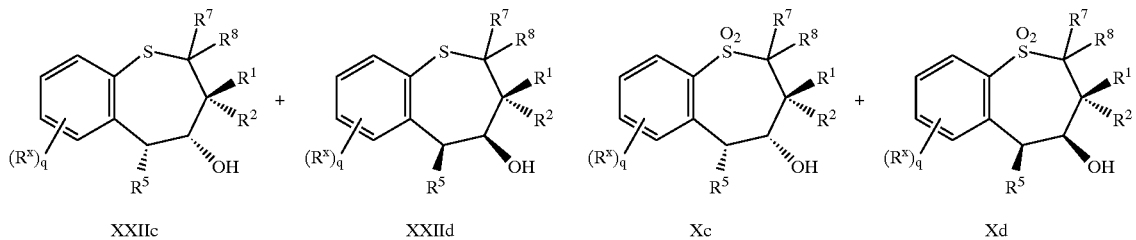

Examples of amine- and hydroxylamine-containing compounds of the present invention can be prepared as shown in Scheme 5 and Scheme 6. 2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIV which can be reduced by hydrogenation to the hydroxylamine XXV. Protecting the hydroxylamine XXV with di-t-butyldicarbonate gives the N,O-di-(t-butoxycarbonyl)hydroxylamino derivative XXVI. Cyclization of XXVI with potassium t-butoxide and removal of the t-butoxycarbonyl protecting group gives a mixture of hydroxylamino derivatives XXVIIc and XXVIId. The primary amine XXXIIIC and XXXIIId derivatives can also be prepared by further hydrogenation of XXIV or XXVIIc and XXVIId.

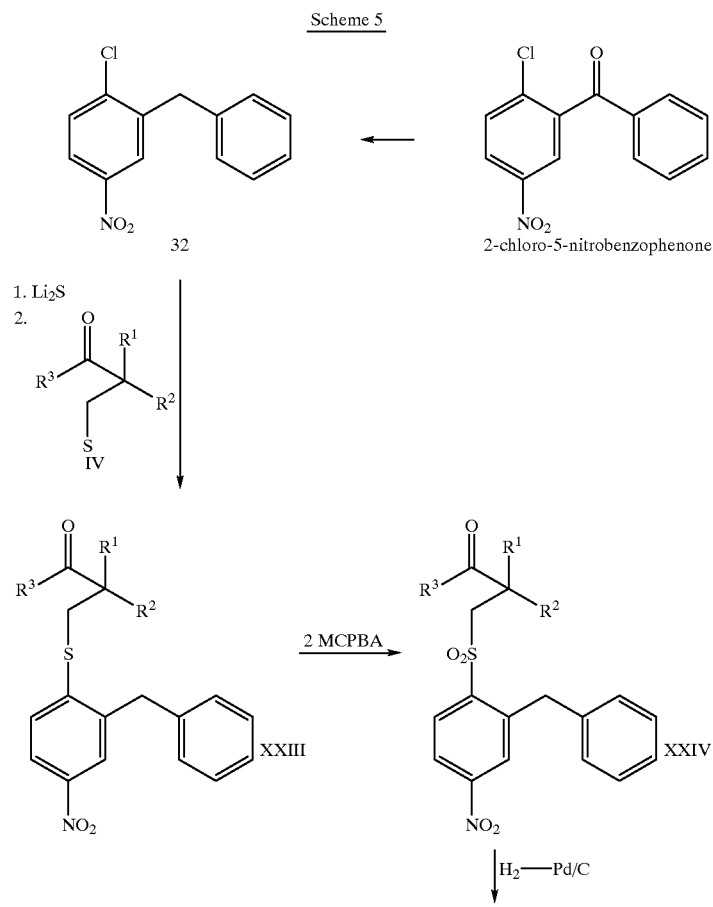

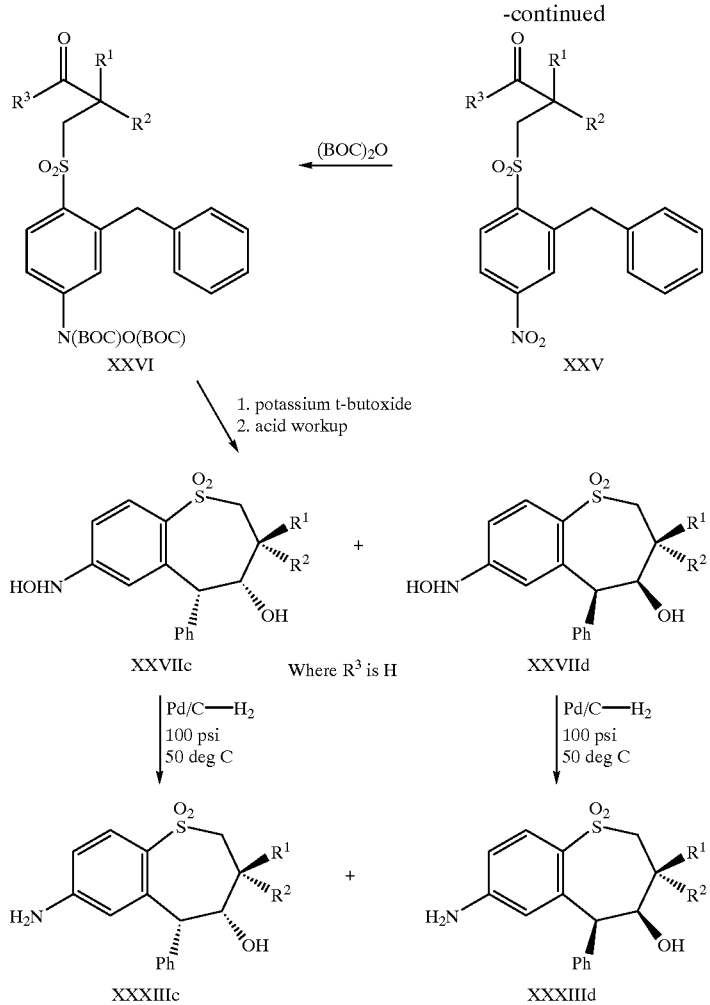

In Scheme 6, reduction of the sulfone-aldehyde XXV with hydrogen followed by reductive alkylation of the resulting amino derivative with hydrogen and an aldehyde catalyzed by palladium on carbon in the same reaction vessel yields the substituted amine derivative XXVIII. Cyclization of XXVIII with potassium t-butoxide yields a mixture of substituted amino derivatives of this invention XXIXc and XXIXd.

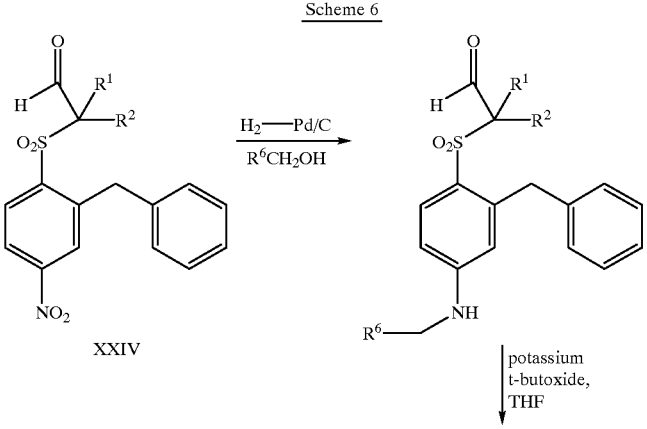

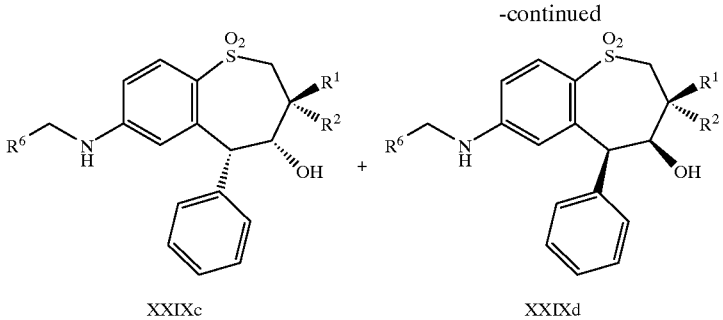

XXIXc    XXIXd

Scheme 7 describes one of the methods of introducing a substituent to the aryl ring at the 5-position of benzothiepine. Iodination of 5-phenyl derivative XXX with iodine catalyzed by mercuric triflate gives the iodo derivative XXXI, which upon palladium-catalyzed carbonylation in an alcohol yields the carboxylate XXXII. Hydrolysis of the carboxylate and derivatization of the resulting acid to acid derivatives are well known in the art.

DME—ethylene glycol dimethyl ether
BOC—t-butoxycarbonyl group
Me—methyl
Et—ethyl
Bu—butyl
EtOAc—ethyl acetate
$Et_2O$—diethyl ether
$CH_2Cl_2$—methylene chloride

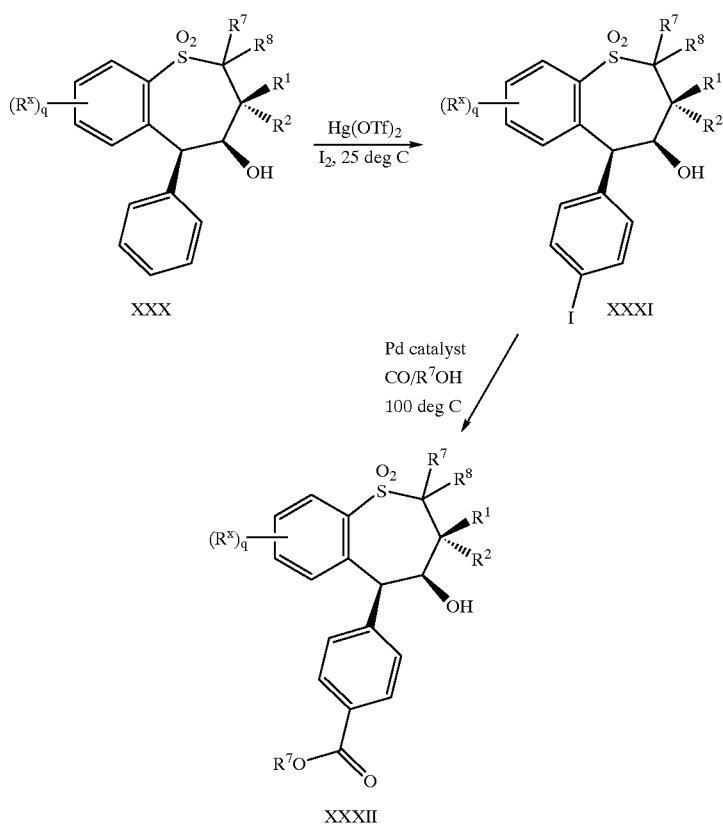

Abbreviations used in the foregoing description have the following meanings:
THF—tetrahydrofuran
PTC—phase transfer catalyst
Aliquart 336—methyltricaprylylammonium chloride
MCPBA—m-chloroperbenzoic acid
Celite—a brand of diatomaceous earth filtering aid
DMF—dimethylformamide
$MgSO_4$—magnesium sulfate
NaOH—sodium hydroxide
$CH_3OH$—methanol
HCl—hydrochloric acid
NaCl—sodium chloride
NaH—sodium hydride
LAH—lithium aluminum hydride
LiOH—lithium hydroxide Na₂SO₃—sodium sulfite
NaHCO₃—sodium bicarbonate
DMSO—dimethylsulfoxide
KOSiMe₃—potassium trimethylsilanolate
PEG—polyethylene glycol
MS—mass spectrometry
HRMS—high resolution mass spectrometry
ES—electrospray
NMR—nuclear magnetic resonance spectroscopy
GC—gas chromatography
MPLC—medium pressure liquid chromatography
HPLC—high pressure liquid chromatography
RPHPLC—reverse phase high pressure liquid chromatography
RT—room temperature
h or hr—hour(s)
min—minute(s)

"Enantiomerically-enriched" (e.e.) means that one enantiomer or set of diastereomers preponderates over the complementary enantiomer or set of diastereomers. Enantiomeric enrichment of a mixture of enantiomers is calculated by dividing the concentration of the preponderating enantiomer by the concentration of the other enantiomer, multiplying the dividend by 100, and expressing the result as a percent. Enantiomeric enrichment can be from about 1% to about 100%, preferably from about 10% to about 100%, and more preferably from about 20% to 100%.

$R^1$ and $R^2$ can be selected from among substituted and unsubstituted $C_1$ to $C_{10}$ alkyl wherein the substituent(s) can be selected from among alkylcarbonyl, alkoxy, hydroxy, and nitrogen-containing heterocycles joined to the $C_1$ to $C_{10}$ alkyl through an ether linkage. Substituents at the 3-carbon can include ethyl, n-propyl, n-butyl, n-pentyl, isobutyl, isopropyl, —CH₂C(=O)C₂H₅, —CH₂OC₂H₅, and —CH₂O—(4-picoline). Ethyl, n-propyl, n-butyl, and isobutyl are preferred. In certain particularly preferred compounds of the present invention, substituents $R^1$ and $R^2$ are identical, for example n-butyl/n-butyl, so that the compound is achiral at the 3-carbon. Eliminating optical isomerism at the 3-carbon simplifies the selection, synthesis, separation, and quality control of the compound used as an ileal bile acid transport inhibitor. In both compounds having a chiral 3-carbon and those having an achiral 3-carbon, substituents ($R^x$) on the benzo- ring can include hydrogen, aryl, alkyl, hydroxy, halo, alkoxy, alkylthio, alkylsulfinyl, alkylsulfonyl, haloalkyl, haloalkoxy, (N)-hydroxy-carbonylalkyl amine, haloalkylthio, haloalkylsulfinyl, haloalkylsufonyl, amino, N-alkylamino, N,N-dialkylamino, (N)-alkoxycarbamoyl, (N)-aryloxycarbamoyl, (N)-aralkyloxycarbamoyl, trialkylammonium (especially with a halide counterion), (N)-amido, (N)-alkylamido, —N-alkylamido, —N,N-dialkylamido, (N)-haloalkylamido, (N)-sulfonamido, (N)-alkylsulfonamido, (N)-haloalkylsulfonamido, carboxyalkylamino, trialkylammonium salt, (N)-carbamic acid, alkyl or benzyl ester, N-acylamine, hydroxylamine, haloacylamine, carbohydrate, thiophene a trialkyl ammonium salt having a carboxylic acid or hydroxy substituent on one or more of the alkyl substituents, an alkylene bridge having a quaternary ammonium salt substituted thereon, —[O(CH₂)$_w$]$_x$—X where x is 2 to 12, w is 2 or 3 and X is a halo or a quaternary ammonium salt, and (N)-nitrogen containing heterocycle wherein the nitrogen of said heterocycle is optionally quaternized. Among the preferred species which may constitute $R^x$ are methyl, ethyl, isopropyl, t-butyl, hydroxy, methoxy, ethoxy, isopropoxy, methylthio, iodo, bromo, fluoro, methylsulfinyl, methylsulfonyl, ethylthio, amino, hydroxylamine, N-methylamino, N,N-dimethylamino, N,N-diethylamino, (N)-benzyloxycarbamoyl, trimethylammonium, A⁻, —NHC(=O)CH₃, —NHC(=O)C₅H₁₁, —NHC(=O)C₆H₁₃, carboxyethylamino, (N)-morpholinyl, (N)-azetidinyl, (N)-N-methylazetidinium A⁻, (N)-pyrrolidinyl, pyrrolyl, (N)-N-methylpyridinium A⁻, (N)-N-methylmorpholinium A⁻, and N-N'-methylpiperazinyl, (N)-bromomethylamido, (N)-N-hexylamino, thiophene, —N⁺(CH₃)₂CO₂H I⁻, —NCH₃CH₂CO₂H, —(N)-N'-dimethylpiperazinium I⁻, (N)-t-butyloxycarbamoyl, (N)-methylsulfonamido, (N)N'-methylpyrrolidinium, and —(OCH₂CH₂)₃I, where A⁻ is a pharmaceutically acceptable anion. The benzo ring is can be mono-substituted at the 6, 7 or 8 position, or disubstituted at the 7- and -8 positions. Also included are the 6,7,8-trialkoxy compounds, for example the 6,7,8-trimethoxy compounds. A variety of other substituents can be advantageously present on the 6, 7, 8, and/or 9- positions of the benzo ring, including, for example, guanidinyl, cycloalkyl, carbohydrate (e.g., a 5 or 6 carbon monosaccharide), peptide, and quaternary ammonium salts linked to the ring via poly (oxyalkylene) linkages, e.g., —(OCH₂CH₂)$_x$—N⁺R¹³R¹⁴R¹⁵A⁻, where x is 2 to 10. Exemplary compounds are those set forth below in Table 1.

TABLE 1

Alternative Compounds #3 (Family F101.xxx.yyy)

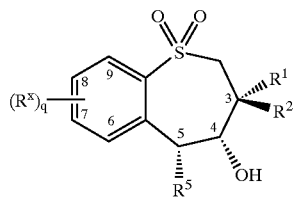

| Prefix (FFF.xxx. | Cpd# yyy) | R¹=R² | R⁵ | (Rˣ)q |
|---|---|---|---|---|
| F101.001 | 01 | ethyl | Ph- | 7-methyl |
| | 02 | ethyl | Ph- | 7-ethyl |
| | 03 | ethyl | Ph- | 7-iso-propyl |
| | 04 | ethyl | Ph- | 7-tert-butyl |
| | 05 | ethyl | Ph- | 7-OH |
| | 06 | ethyl | Ph- | 7-OCH₃ |
| | 07 | ethyl | Ph- | 7-O(iso-propyl) |

TABLE 1-continued

Alternative Compounds #3 (Family F101.xxx.yyy)

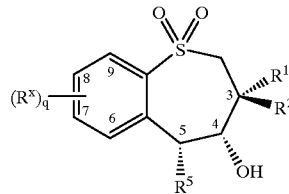

| Prefix (FFF.xxx. | Cpd# yyy) | $R^1=R^2$ | $R^5$ | $(R^x)q$ |
|---|---|---|---|---|
| | 08 | ethyl | Ph- | 7-SCH$_3$ |
| | 09 | ethyl | Ph- | 7-SOCH$_3$ |
| | 10 | ethyl | Ph- | 7-SO$_2$CH$_3$ |
| | 11 | ethyl | Ph- | 7-SCH$_2$CH$_3$ |
| | 12 | ethyl | Ph- | 7-NH$_2$ |
| | 13 | ethyl | Ph- | 7-NHOH |
| | 14 | ethyl | Ph- | 7-NHCH$_3$ |
| | 15 | ethyl | Ph- | 7-N(CH$_3$)$_2$ |
| | 16 | ethyl | Ph- | 7-N$^+$(CH$_3$)$_3$, I$^-$ |
| | 17 | ethyl | Ph- | 7-NHC(=O)CH$_3$ |
| | 18 | ethyl | Ph- | 7-N(CH$_2$CH$_3$)$_2$ |
| | 19 | ethyl | Ph- | 7-NMeCH$_2$CO$_2$H |
| | 20 | ethyl | Ph- | 7-N$^+$(Me)$_2$CH$_2$CO$_2$H, I$^-$ |
| | 21 | ethyl | Ph- | 7-(N)-morpholine |
| | 22 | ethyl | Ph- | 7-(N)-azetidine |
| | 23 | ethyl | Ph- | 7-(N)-N-methylazetidinium, I$^-$ |
| | 24 | ethyl | Ph- | 7-(N)-pyrrolidine |
| | 25 | ethyl | Ph- | 7-(N)-N-methyl-pyrrolidinium, I$^-$ |
| | 26 | ethyl | Ph- | 7-(N)-N-methyl-morpholinium, I$^-$ |
| | 27 | ethyl | Ph- | 7-(N)-N'-methylpiperazine |
| | 28 | ethyl | Ph- | 7-(N)-N'-dimethylpiperazinium, I$^-$ |
| | 29 | ethyl | Ph- | 7-NH-CBZ |
| | 30 | ethyl | Ph- | 7-NHC(O)C$_5$H$_{11}$ |
| | 31 | ethyl | Ph- | 7-NHC(O)CH$_2$Br |
| | 32 | ethyl | Ph- | 7-NH-C(NH)NH$_2$ |
| | 33 | ethyl | Ph- | 7-(2)-thiophene |
| | 34 | ethyl | Ph- | 8-methyl |
| | 35 | ethyl | Ph- | 8-ethyl |
| | 36 | ethyl | Ph- | 8-iso-propyl |
| | 37 | ethyl | Ph- | 8-tert-butyl |
| | 38 | ethyl | Ph- | 8-OH |
| | 39 | ethyl | Ph- | 8-OCH$_3$ |
| | 40 | ethyl | Ph- | 8-O(iso-propyl) |
| | 41 | ethyl | Ph- | 8-SCH$_3$ |
| | 42 | ethyl | Ph- | 8-SOCH$_3$ |
| | 43 | ethyl | Ph- | 8-SO$_2$CH$_3$ |
| | 44 | ethyl | Ph- | 8-SCH$_2$CH$_3$ |
| | 45 | ethyl | Ph- | 8-NH$_2$ |
| | 46 | ethyl | Ph- | 8-NHOH |
| | 47 | ethyl | Ph- | 8-NHCH$_3$ |
| | 48 | ethyl | Ph- | 8-N(CH$_3$)$_2$ |
| | 49 | ethyl | Ph- | 8-N$^+$(CH$_3$)$_3$, I$^-$ |
| | 50 | ethyl | Ph- | 8-NHC(=O)CH$_3$ |
| | 51 | ethyl | Ph- | 8-N(CH$_2$CH$_3$)$_2$ |
| | 52 | ethyl | Ph- | 8-NMeCH$_2$CO$_2$H |
| | 53 | ethyl | Ph- | 8-N$^+$(Me)$_2$CH$_2$CO$_2$H, I$^-$ |
| | 54 | ethyl | Ph- | 8-(N)-morpholine |
| | 55 | ethyl | Ph- | 8-(N)-azetidine |
| | 56 | ethyl | Ph- | 8-(N)-N-methylazetidinium, I$^-$ |
| | 57 | ethyl | Ph- | 8-(N)-pyrrolidine |
| | 58 | ethyl | Ph- | 8-(N)-N-methyl-pyrrolidinium, I$^-$ |
| | 59 | ethyl | Ph- | 8-(N)-N-methyl-morpholinium, I$^-$ |
| | 60 | ethyl | Ph- | 8-(N)-N'-methylpiperazine |
| | 61 | ethyl | Ph- | 8-(N)-N'-dimethylpiperazinium, I$^-$ |
| | 62 | ethyl | Ph- | 8-NH-CBZ |
| | 63 | ethyl | Ph- | 8-NHC(O)C$_5$H$_{11}$ |
| | 64 | ethyl | Ph- | 8-NHC(O)CH$_2$Br |
| | 65 | ethyl | Ph- | 8-NH-C(NH)NH$_2$ |
| | 66 | ethyl | Ph- | 8-(2)-thiophene |
| | 67 | ethyl | Ph- | 9-methyl |
| | 68 | ethyl | Ph- | 9-ethyl |
| | 69 | ethyl | Ph- | 9-iso-propyl |
| | 70 | ethyl | Ph- | 9-tert-butyl |
| | 71 | ethyl | Ph- | 9-OH |

TABLE 1-continued

Alternative Compounds #3 (Family F101.xxx.yyy)

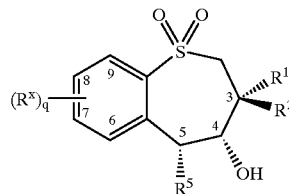

| Prefix (FFF.xxx. | Cpd# yyy) | $R^1=R^2$ | $R^5$ | $(R^x)q$ |
|---|---|---|---|---|
| | 72 | ethyl | Ph- | 9-$OCH_3$ |
| | 73 | ethyl | Ph- | 9-O(iso-propyl) |
| | 74 | ethyl | Ph- | 9-$SCH_3$ |
| | 75 | ethyl | Ph- | 9-$SOCH_3$ |
| | 76 | ethyl | Ph- | 9-$SO_2CH_3$ |
| | 77 | ethyl | Ph- | 9-$SCH_2CH_3$ |
| | 78 | ethyl | Ph- | 9-$NH_2$ |
| | 79 | ethyl | Ph- | 9-NHOH |
| | 80 | ethyl | Ph- | 9-$NHCH_3$ |
| | 81 | ethyl | Ph- | 9-$N(CH_3)_2$ |
| | 82 | ethyl | Ph- | 9-$N^+(CH_3)_3$, $I^-$ |
| | 83 | ethyl | Ph- | 9-NHC(=O)$CH_3$ |
| | 84 | ethyl | Ph- | 9-$N(CH_2CH_3)_2$ |
| | 85 | ethyl | Ph- | 9-NMe$CH_2CO_2$H |
| | 86 | ethyl | Ph- | 9-$N^+(Me)_2CH_2CO_2$H, $I^-$ |
| | 87 | ethyl | Ph- | 9-(N)-morpholine |
| | 88 | ethyl | Ph- | 9-(N)-azetidine |
| | 89 | ethyl | Ph- | 9-(N)-N-methylazetidinium, $I^-$ |
| | 90 | ethyl | Ph- | 9-(N)-pyrrolidine |
| | 91 | ethyl | Ph- | 9-(N)-N-methyl-pyrrolidinium, $I^-$ |
| | 92 | ethyl | Ph- | 9-(N)-N-methyl-morpholinum, $I^-$ |
| | 93 | ethyl | Ph- | 9-(N)-N'-methylpiperazine |
| | 93 | ethyl | Ph- | 9-(N)-N'-dimethylpiperazinium, $I^-$ |
| | 95 | ethyl | Ph- | 9-NH-CBZ |
| | 96 | ethyl | Ph- | 9-NHC(O)$C_5H_{11}$ |
| | 97 | ethyl | Ph- | 9-NHC(O)$CH_2$Br |
| | 98 | ethyl | Ph- | 9-NH-C(NH)$NH_2$ |
| | 99 | ethyl | Ph- | 9-(2)-thiophene |
| | 100 | ethyl | Ph- | 7-$OCH_3$, 8-$OCH_3$ |
| | 101 | ethyl | Ph- | 7-$SCH_3$, 8-$OCH_3$ |
| | 102 | ethyl | Ph- | 7-$SCH_3$, 8-$SCH_3$ |
| | 103 | ethyl | Ph- | 6-$OCH_3$, 7-$OCH_3$, 8-$OCH_3$ |
| F101.002 | 01 | n-propyl | Ph- | 7-methyl |
| | 02 | n-propyl | Ph- | 7-ethyl |
| | 03 | n-propyl | Ph- | 7-iso-propyl |
| | 04 | n-propyl | Ph- | 7-tert-butyl |
| | 05 | n-propyl | Ph- | 7-OH |
| | 06 | n-propyl | Ph- | 7-$OCH_3$ |
| | 07 | n-propyl | Ph- | 7-O(iso-propyl) |
| | 08 | n-propyl | Ph- | 7-$SCH_3$ |
| | 09 | n-propyl | Ph- | 7-$SOCH_3$ |
| | 10 | n-propyl | Ph- | 7-$SO_2CH_3$ |
| | 11 | n-propyl | Ph- | 7-$SCH_2CH_3$ |
| | 12 | n-propyl | Ph- | 7-$NH_2$ |
| | 13 | n-propyl | Ph- | 7-NHOH |
| | 14 | n-propyl | Ph- | 7-$NHCH_3$ |
| | 15 | n-propyl | Ph- | 7-$N(CH_3)_2$ |
| | 16 | n-propyl | Ph- | 7-$N^+(CH_3)_3$, $I^-$ |
| | 17 | n-propyl | Ph- | 7-NHC(=O)$CH_3$ |
| | 18 | n-propyl | Ph- | 7-$N(CH_2CH_3)_2$ |
| | 19 | n-propyl | Ph- | 7-NMe$CH_2CO_2$H |
| | 20 | n-propyl | Ph- | 7-$N^+(Me)_2CH_2CO_2$H, $I^-$ |
| | 21 | n-propyl | Ph- | 7-(N)-morpholine |
| | 22 | n-propyl | Ph- | 7-(N)-azetidine |
| | 23 | n-propyl | Ph- | 7-(N)-N-methylazetidinium, $I^-$ |
| | 24 | n-propyl | Ph- | 7-(N)-pyrrolidine |
| | 25 | n-propyl | Ph- | 7-(N)-N-methyl-pyrrolidinium, $I^-$ |
| | 26 | n-propyl | Ph- | 7-(N)-N-methyl-morpholinum, $I^-$ |
| | 27 | n-propyl | Ph- | 7-(N)-N'-methylpiperazine |
| | 28 | n-propyl | Ph- | 7-(N)-N'-dimethylpiperazinium, $I^-$ |
| | 29 | n-propyl | Ph- | 7-NH-CBZ |
| | 30 | n-propyl | Ph- | 7-NHC(O)$C_5H_{11}$ |
| | 31 | n-propyl | Ph- | 7-NHC(O)$CH_2$Br |
| | 32 | n-propyl | Ph- | 7-NH-C(NH)$NH_2$ |

TABLE 1-continued

Alternative Compounds #3 (Family F101.xxx.yyy)

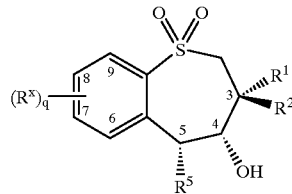

| Prefix (FFF.xxx. | Cpd# yyy) | $R^1=R^2$ | $R^5$ | $(R^x)q$ |
|---|---|---|---|---|
| | 33 | n-propyl | Ph- | 7-(2)-thiophene |
| | 34 | n-propyl | Ph- | 8-methyl |
| | 35 | n-propyl | Ph- | 8-ethyl |
| | 36 | n-propyl | Ph- | 8-iso-propyl |
| | 37 | n-propyl | Ph- | 8-tert-butyl |
| | 38 | n-propyl | Ph- | 8-OH |
| | 39 | n-propyl | Ph- | 8-OCH$_3$ |
| | 40 | n-propyl | Ph- | 8-O(iso-propyl) |
| | 41 | n-propyl | Ph- | 8-SCH$_3$ |
| | 42 | n-propyl | Ph- | 8-SOCH$_3$ |
| | 43 | n-propyl | Ph- | 8-SO$_2$CH$_3$ |
| | 44 | n-propyl | Ph- | 8-SCH$_2$CH$_3$ |
| | 45 | n-propyl | Ph- | 8-NH$_2$ |
| | 46 | n-propyl | Ph- | 8-NHOH |
| | 47 | n-propyl | Ph- | 8-NHCH$_3$ |
| | 48 | n-propyl | Ph- | 8-N(CH$_3$)$_2$ |
| | 49 | n-propyl | Ph- | 8-N$^+$(CH$_3$)$_3$, I$^-$ |
| | 50 | n-propyl | Ph- | 8-NHC(=O)CH$_3$ |
| | 51 | n-propyl | Ph- | 8-N(CH$_2$CH$_3$)$_2$ |
| | 52 | n-propyl | Ph- | 8-NMeCH$_2$CO$_2$H |
| | 53 | n-propyl | Ph- | 8-N$^+$(Me)$_2$CH$_2$CO$_2$H, I$^-$ |
| | 54 | n-propyl | Ph- | 8-(N)-morpholine |
| | 55 | n-propyl | Ph- | 8-(N)-azetidine |
| | 56 | n-propyl | Ph- | 8-(N)-N-methylazetidinium, I$^-$ |
| | 57 | n-propyl | Ph- | 8-(N)-pyrrolidine |
| | 58 | n-propyl | Ph- | 8-(N)-N-methyl-pyrrolidinium, I$^-$ |
| | 59 | n-propyl | Ph- | 8-(N)-N-methyl-morpholinium, I$^-$ |
| | 60 | n-propyl | Ph- | 8-(N)-N'-methylpiperazine |
| | 61 | n-propyl | Ph- | 8-(N)-N'-dimethylpiperazinium, I$^-$ |
| | 62 | n-propyl | Ph- | 8-NH-CBZ |
| | 63 | n-propyl | Ph- | 8-NHC(O)C$_5$H$_{11}$ |
| | 64 | n-propyl | Ph- | 8-NHC(O)CH$_2$Br |
| | 65 | n-propyl | Ph- | 8-NH-C(NH)NH$_2$ |
| | 66 | n-propyl | Ph- | 8-(2)-thiophene |
| | 67 | n-propyl | Ph- | 9-methyl |
| | 68 | n-propyl | Ph- | 9-ethyl |
| | 69 | n-propyl | Ph- | 9-iso-propyl |
| | 70 | n-propyl | Ph- | 9-tert-butyl |
| | 71 | n-propyl | Ph- | 9-OH |
| | 72 | n-propyl | Ph- | 9-OCH$_3$ |
| | 73 | n-propyl | Ph- | 9-O(iso-propyl) |
| | 74 | n-propyl | Ph- | 9-SCH$_3$ |
| | 75 | n-propyl | Ph- | 9-SOCH$_3$ |
| | 76 | n-propyl | Ph- | 9-SO$_2$CH$_3$ |
| | 77 | n-propyl | Ph- | 9-SCH$_2$CH$_3$ |
| | 78 | n-propyl | Ph- | 9-NH$_2$ |
| | 79 | n-propyl | Ph- | 9-NHOH |
| | 80 | n-propyl | Ph- | 9-NHCH$_3$ |
| | 81 | n-propyl | Ph- | 9-N(CH$_3$)$_2$ |
| | 82 | n-propyl | Ph- | 9-N$^+$(CH$_3$)$_3$, I$^-$ |
| | 83 | n-propyl | Ph- | 9-NHC(=O)CH$_3$ |
| | 84 | n-propyl | Ph- | 9-N(CH$_2$CH$_3$)$_2$ |
| | 85 | n-propyl | Ph- | 9-NMeCH$_2$CO$_2$H |
| | 86 | n-propyl | Ph- | 9-N$^+$(Me)$_2$CH$_2$CO$_2$H, I$^-$ |
| | 87 | n-propyl | Ph- | 9-(N)-morpholine |
| | 88 | n-propyl | Ph- | 9-(N)-azetidine |
| | 89 | n-propyl | Ph- | 9-(N)-N-methylazetidinium, I$^-$ |
| | 90 | n-propyl | Ph- | 9-(N)-pyrrolidine |
| | 91 | n-propyl | Ph- | 9-(N)-N-methyl-pyrrolidinium, I$^-$ |
| | 92 | n-propyl | Ph- | 9-(N)-N-methyl-morpholinium, I$^-$ |
| | 93 | n-propyl | Ph- | 9-(N)-N'-methylpiperazine |
| | 93 | n-propyl | Ph- | 9-(N)-N'-dimethylpiperazinium, I$^-$ |
| | 95 | n-propyl | Ph- | 9-NH-CBZ |
| | 96 | n-propyl | Ph- | 9-NHC(O)C$_5$H$_{11}$ |

TABLE 1-continued

Alternative Compounds #3 (Family F101.xxx.yyy)

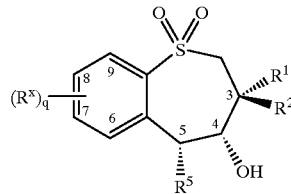

| Prefix (FFF.xxx. | Cpd# yyy) | $R^1=R^2$ | $R^5$ | $(R^x)q$ |
|---|---|---|---|---|
| | 97 | n-propyl | Ph- | 9-NHC(O)CH$_2$Br |
| | 98 | n-propyl | Ph- | 9-NH-C(NH)NH$_2$ |
| | 99 | n-propyl | Ph- | 9-(2)-thiophene |
| | 100 | n-propyl | Ph- | 7-OCH$_3$, 8-OCH$_3$ |
| | 101 | n-propyl | Ph- | 7-SCH$_3$, 8-OCH$_3$ |
| | 102 | n-propyl | Ph- | 7-SCH$_3$, 8-SCH$_3$ |
| | 103 | n-propyl | Ph- | 6-OCH$_3$, 7-OCH$_3$, 8-OCH$_3$ |
| F101.003 | 01 | n-butyl | Ph- | 7-methyl |
| | 02 | n-butyl | Ph- | 7-ethyl |
| | 03 | n-butyl | Ph- | 7-iso-propyl |
| | 04 | n-butyl | Ph- | 7-tert-butyl |
| | 05 | n-butyl | Ph- | 7-OH |
| | 06 | n-butyl | Ph- | 7-OCH$_3$ |
| | 07 | n-butyl | Ph- | 7-O(iso-propyl) |
| | 08 | n-butyl | Ph- | 7-SCH$_3$ |
| | 09 | n-butyl | Ph- | 7-SOCH$_3$ |
| | 10 | n-butyl | Ph- | 7-SO$_2$CH$_3$ |
| | 11 | n-butyl | Ph- | 7-SCH$_2$CH$_3$ |
| | 12 | n-butyl | Ph- | 7-NH$_2$ |
| | 13 | n-butyl | Ph- | 7-NHOH |
| | 14 | n-butyl | Ph- | 7-NHCH$_3$ |
| | 15 | n-butyl | Ph- | 7-N(CH$_3$)$_2$ |
| | 16 | n-butyl | Ph- | 7-N$^+$(CH$_3$)$_3$, I$^-$ |
| | 17 | n-butyl | Ph- | 7-NHC(=O)CH$_3$ |
| | 18 | n-butyl | Ph- | 7-N(CH$_2$CH$_3$)$_2$ |
| | 19 | n-butyl | Ph- | 7-NMeCH$_2$CO$_2$H |
| | 20 | n-butyl | Ph- | 7-N$^+$(Me)$_2$CH$_2$CO$_2$H, I$^-$ |
| | 21 | n-butyl | Ph- | 7-(N)-morpholine |
| | 22 | n-butyl | Ph- | 7-(N)-azetidine |
| | 23 | n-butyl | Ph- | 7-(N)-N-methylazetidinium, I$^-$ |
| | 24 | n-butyl | Ph- | 7-(N)-pyrrolidine |
| | 25 | n-butyl | Ph- | 7-(N)-N-methyl-pyrrolidinium, I$^-$ |
| | 26 | n-butyl | Ph- | 7-(N)-N-methyl-morpholinum, I$^-$ |
| | 27 | n-butyl | Ph- | 7-(N)-N'-methylpiperazine |
| | 28 | n-butyl | Ph- | 7-(N)-N'-dimethylpiperazinium, I$^-$ |
| | 29 | n-butyl | Ph- | 7-NH-CBZ |
| | 30 | n-butyl | Ph- | 7-NHC(O)C$_5$H$_{11}$ |
| | 31 | n-butyl | Ph- | 7-NHC(O)CH$_2$Br |
| | 32 | n-butyl | Ph- | 7-NH-C(NH)NH$_2$ |
| | 33 | n-butyl | Ph- | 7-(2)-thiophene |
| | 34 | n-butyl | Ph- | 8-methyl |
| | 35 | n-butyl | Ph- | 8-ethyl |
| | 36 | n-butyl | Ph- | 8-iso-propyl |
| | 37 | n-butyl | Ph- | 8-tert-butyl |
| | 38 | n-butyl | Ph- | 8-OH |
| | 39 | n-butyl | Ph- | 8-OCH$_3$ |
| | 40 | n-butyl | Ph- | 8-O(iso-propyl) |
| | 41 | n-butyl | Ph- | 8-SCH$_3$ |
| | 42 | n-butyl | Ph- | 8-SOCH$_3$ |
| | 43 | n-butyl | Ph- | 8-SO$_2$CH$_3$ |
| | 44 | n-butyl | Ph- | 8-SCH$_2$CH$_3$ |
| | 45 | n-butyl | Ph- | 8-NH$_2$ |
| | 46 | n-butyl | Ph- | 8-NHOH |
| | 47 | n-butyl | Ph- | 8-NHCH$_3$ |
| | 48 | n-butyl | Ph- | 8-N(CH$_3$)$_2$ |
| | 49 | n-butyl | Ph- | 8-N$^+$(CH$_3$)$_3$, I$^-$ |
| | 50 | n-butyl | Ph- | 8-NHC(=O)CH$_3$ |
| | 51 | n-butyl | Ph- | 8-N(CH$_2$CH$_3$)$_2$ |
| | 52 | n-butyl | Ph- | 8-NMeCH$_2$CO$_2$H |
| | 53 | n-butyl | Ph- | 8-N$^+$(Me)$_2$CH$_2$CO$_2$H, I$^-$ |
| | 54 | n-butyl | Ph- | 8-(N)-morpholine |
| | 55 | n-butyl | Ph- | 8-(N)-azetidine |
| | 56 | n-butyl | Ph- | 8-(N)-N-methylazetidinium, I$^-$ |
| | 57 | n-butyl | Ph- | 8-(N)-pyrrolidine |

TABLE 1-continued

Alternative Compounds #3 (Family F101.xxx.yyy)

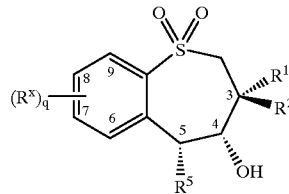

| Prefix (FFF.xxx. | Cpd# yyy) | R¹=R² | R⁵ | (Rˣ)q |
|---|---|---|---|---|
| | 58 | n-butyl | Ph- | 8-(N)-N-methyl-pyrrolidinium, I⁻ |
| | 59 | n-butyl | Ph- | 8-(N)-N-methyl-morpholinium, I⁻ |
| | 60 | n-butyl | Ph- | 8-(N)-N'-methylpiperazine |
| | 61 | n-butyl | Ph- | 8-(N)-N'-dimethylpiperazinium, I⁻ |
| | 62 | n-butyl | Ph- | 8-NH-CBZ |
| | 63 | n-butyl | Ph- | 8-NHC(O)C$_5$H$_{11}$ |
| | 64 | n-butyl | Ph- | 8-NHC(O)CH$_2$Br |
| | 65 | n-butyl | Ph- | 8-NH-C(NH)NH$_2$ |
| | 66 | n-butyl | Ph- | 8-(2)-thiophene |
| | 67 | n-butyl | Ph- | 9-methyl |
| | 68 | n-butyl | Ph- | 9-ethyl |
| | 69 | n-butyl | Ph- | 9-iso-propyl |
| | 70 | n-butyl | Ph- | 9-tert-butyl |
| | 71 | n-butyl | Ph- | 9-OH |
| | 72 | n-butyl | Ph- | 9-OCH$_3$ |
| | 73 | n-butyl | Ph- | 9-O(iso-propyl) |
| | 74 | n-butyl | Ph- | 9-SCH$_3$ |
| | 75 | n-butyl | Ph- | 9-SOCH$_3$ |
| | 76 | n-butyl | Ph- | 9-SO$_2$CH$_3$ |
| | 77 | n-butyl | Ph- | 9-SCH$_2$CH$_3$ |
| | 78 | n-butyl | Ph- | 9-NH$_2$ |
| | 79 | n-butyl | Ph- | 9-NHOH |
| | 80 | n-butyl | Ph- | 9-NHCH$_3$ |
| | 81 | n-butyl | Ph- | 9-N(CH$_3$)$_2$ |
| | 82 | n-butyl | Ph- | 9-N⁺(CH$_3$)$_3$, I⁻ |
| | 83 | n-butyl | Ph- | 9-NHC(=O)CH$_3$ |
| | 84 | n-butyl | Ph- | 9-N(CH$_2$CH$_3$)$_2$ |
| | 85 | n-butyl | Ph- | 9-NMeCH$_2$CO$_2$H |
| | 86 | n-butyl | Ph- | 9-N⁺(Me)$_2$CH$_2$CO$_2$H, I⁻ |
| | 87 | n-butyl | Ph- | 9-(N)-morpholine |
| | 88 | n-butyl | Ph- | 9-(N)-azetidine |
| | 89 | n-butyl | Ph- | 9-(N)-N-methylazetidinium, I⁻ |
| | 90 | n-butyl | Ph- | 9-(N)-pyrrolidine |
| | 91 | n-butyl | Ph- | 9-(N)-N-methyl-pyrrolidinium, I⁻ |
| | 92 | n-butyl | Ph- | 9-(N)-N-methyl-morpholinium, I⁻ |
| | 93 | n-butyl | Ph- | 9-(N)-N'-methylpiperazine |
| | 93 | n-butyl | Ph- | 9-(N)-N'-dimethylpiperazinium, I⁻ |
| | 95 | n-butyl | Ph- | 9-NH-CBZ |
| | 96 | n-butyl | Ph- | 9-NHC(O)C$_5$H$_{11}$ |
| | 97 | n-butyl | Ph- | 9-NHC(O)CH$_2$Br |
| | 98 | n-butyl | Ph- | 9-NH-C(NH)NH$_2$ |
| | 99 | n-butyl | Ph- | 9-(2)-thiophene |
| | 100 | n-butyl | Ph- | 7-OCH$_3$, 8-OCH$_3$ |
| | 101 | n-butyl | Ph- | 7-SCH$_3$, 8-OCH$_3$ |
| | 102 | n-butyl | Ph- | 7-SCH$_3$, 8-SCH$_3$ |
| | 103 | n-butyl | Ph- | 6-OCH$_3$, 7-OCH$_3$, 8-OCH$_3$ |
| F101.004 | 01 | n-pentyl | Ph- | 7-methyl |
| | 02 | n-pentyl | Ph- | 7-ethyl |
| | 03 | n-pentyl | Ph- | 7-iso-propyl |
| | 04 | n-pentyl | Ph- | 7-tert-butyl |
| | 05 | n-pentyl | Ph- | 7-OH |
| | 06 | n-pentyl | Ph- | 7-OCH$_3$ |
| | 07 | n-pentyl | Ph- | 7-O(iso-propyl) |
| | 08 | n-pentyl | Ph- | 7-SCH$_3$ |
| | 09 | n-pentyl | Ph- | 7-SOCH$_3$ |
| | 10 | n-pentyl | Ph- | 7-SO$_2$CH$_3$ |
| | 11 | n-pentyl | Ph- | 7-SCH$_2$CH$_3$ |
| | 12 | n-pentyl | Ph- | 7-NH$_2$ |
| | 13 | n-pentyl | Ph- | 7-NHOH |
| | 14 | n-pentyl | Ph- | 7-NHCH$_3$ |
| | 15 | n-pentyl | Ph- | 7-N(CH$_3$)$_2$ |
| | 16 | n-pentyl | Ph- | 7-N⁺(CH$_3$)$_3$, I⁻ |
| | 17 | n-pentyl | Ph- | 7-NHC(=O)CH$_3$ |
| | 18 | n-pentyl | Ph- | 7-N(CH$_2$CH$_3$)$_2$ |

TABLE 1-continued

Alternative Compounds #3 (Family F101.xxx.yyy)

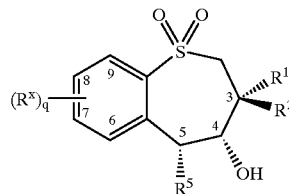

| Prefix (FFF.xxx. | Cpd# yyy) | $R^1=R^2$ | $R^5$ | $(R^x)q$ |
|---|---|---|---|---|
| | 19 | n-pentyl | Ph- | 7-NMeCH$_2$CO$_2$H |
| | 20 | n-pentyl | Ph- | 7-N$^+$(Me)$_2$CH$_2$CO$_2$H, I$^-$ |
| | 21 | n-pentyl | Ph- | 7-(N)-morpholine |
| | 22 | n-pentyl | Ph- | 7-(N)-azetidine |
| | 23 | n-pentyl | Ph- | 7-(N)-N-methylazetidinium, I$^-$ |
| | 24 | n-pentyl | Ph- | 7-(N)-pyrrolidine |
| | 25 | n-pentyl | Ph- | 7-(N)-N-methyl-pyrrolidinium, I$^-$ |
| | 26 | n-pentyl | Ph- | 7-(N)-N-methyl-morpholinium, I$^-$ |
| | 27 | n-pentyl | Ph- | 7-(N)-N'-methylpiperazine |
| | 28 | n-pentyl | Ph- | 7-(N)-N'-dimethylpiperazinium, I$^-$ |
| | 29 | n-pentyl | Ph- | 7-NH-CBZ |
| | 30 | n-pentyl | Ph- | 7-NHC(O)C$_5$H$_{11}$ |
| | 31 | n-pentyl | Ph- | 7-NHC(O)CH$_2$Br |
| | 32 | n-pentyl | Ph- | 7-NH-C(NH)NH$_2$ |
| | 33 | n-pentyl | Ph- | 7-(2)-thiophene |
| | 34 | n-pentyl | Ph- | 8-methyl |
| | 35 | n-pentyl | Ph- | 8-ethyl |
| | 36 | n-pentyl | Ph- | 8-iso-propyl |
| | 37 | n-pentyl | Ph- | 8-tert-butyl |
| | 38 | n-pentyl | Ph- | 8-OH |
| | 39 | n-pentyl | Ph- | 8-OCH$_3$ |
| | 40 | n-pentyl | Ph- | 8-O(iso-propyl) |
| | 41 | n-pentyl | Ph- | 8-SCH$_3$ |
| | 42 | n-pentyl | Ph- | 8-SOCH$_3$ |
| | 43 | n-pentyl | Ph- | 8-SO$_2$CH$_3$ |
| | 44 | n-pentyl | Ph- | 8-SCH$_2$CH$_3$ |
| | 45 | n-pentyl | Ph- | 8-NH$_2$ |
| | 46 | n-pentyl | Ph- | 8-NHOH |
| | 47 | n-pentyl | Ph- | 8-NHCH$_3$ |
| | 48 | n-pentyl | Ph- | 8-N(CH$_3$)$_2$ |
| | 49 | n-pentyl | Ph- | 8-N$^+$(CH$_3$)$_3$, I$^-$ |
| | 50 | n-pentyl | Ph- | 8-NHC(=O)CH$_3$ |
| | 51 | n-pentyl | Ph- | 8-N(CH$_2$CH$_3$)$_2$ |
| | 52 | n-pentyl | Ph- | 8-NMeCH$_2$CO$_2$H |
| | 53 | n-pentyl | Ph- | 8-N$^+$(Me)$_2$CH$_2$CO$_2$H, I$^-$ |
| | 54 | n-pentyl | Ph- | 8-(N)-morpholine |
| | 55 | n-pentyl | Ph- | 8-(N)-azetidine |
| | 56 | n-pentyl | Ph- | 8-(N)-N-methylazetidinium, I$^-$ |
| | 57 | n-pentyl | Ph- | 8-(N)-pyrrolidine |
| | 58 | n-pentyl | Ph- | 8-(N)-N-methyl-pyrrolidinium, I$^-$ |
| | 59 | n-pentyl | Ph- | 8-(N)-N-methyl-morpholinium, I$^-$ |
| | 60 | n-pentyl | Ph- | 8-(N)-N'-methylpiperazine |
| | 61 | n-pentyl | Ph- | 8-(N)-N'-dimethylpiperazinium, I$^-$ |
| | 62 | n-pentyl | Ph- | 8-NH-CBZ |
| | 63 | n-pentyl | Ph- | 8-NHC(O)C$_5$H$_{11}$ |
| | 64 | n-pentyl | Ph- | 8-NHC(O)CH$_2$Br |
| | 65 | n-pentyl | Ph- | 8-NH-C(NH)NH$_2$ |
| | 66 | n-pentyl | Ph- | 8-(2)-thiophene |
| | 67 | n-pentyl | Ph- | 9-methyl |
| | 68 | n-pentyl | Ph- | 9-ethyl |
| | 69 | n-pentyl | Ph- | 9-iso-propyl |
| | 70 | n-pentyl | Ph- | 9-tert-butyl |
| | 71 | n-pentyl | Ph- | 9-OH |
| | 72 | n-pentyl | Ph- | 9-OCH$_3$ |
| | 73 | n-pentyl | Ph- | 9-O(iso-propyl) |
| | 74 | n-pentyl | Ph- | 9-SCH$_3$ |
| | 75 | n-pentyl | Ph- | 9-SOCH$_3$ |
| | 76 | n-pentyl | Ph- | 9-SO$_2$CH$_3$ |
| | 77 | n-pentyl | Ph- | 9-SCH$_2$CH$_3$ |
| | 78 | n-pentyl | Ph- | 9-NH$_2$ |
| | 79 | n-pentyl | Ph- | 9-NHOH |
| | 80 | n-pentyl | Ph- | 9-NHCH$_3$ |
| | 81 | n-pentyl | Ph- | 9-N(CH$_3$)$_2$ |
| | 82 | n-pentyl | Ph- | 9-N$^+$(CH$_3$)$_3$, I$^-$ |

TABLE 1-continued

Alternative Compounds #3 (Family F101.xxx.yyy)

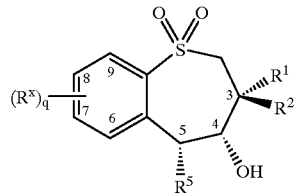

| Prefix (FFF.xxx. | Cpd# yyy) | $R^1=R^2$ | $R^5$ | $(R^x)q$ |
|---|---|---|---|---|
| | 83 | n-pentyl | Ph- | 9-NHC(=O)CH$_3$ |
| | 84 | n-pentyl | Ph- | 9-N(CH$_2$CH$_3$)$_2$ |
| | 85 | n-pentyl | Ph- | 9-NMeCH$_2$CO$_2$H |
| | 86 | n-pentyl | Ph- | 9-N$^+$(Me)$_2$CH$_2$CO$_2$H, I$^-$ |
| | 87 | n-pentyl | Ph- | 9-(N)-morpholine |
| | 88 | n-pentyl | Ph- | 9-(N)-azetidine |
| | 89 | n-pentyl | Ph- | 9-(N)-N-methylazetidinium, I$^-$ |
| | 90 | n-pentyl | Ph- | 9-(N)-pyrrolidine |
| | 91 | n-pentyl | Ph- | 9-(N)-N-methyl-pyrrolidinium, I$^-$ |
| | 92 | n-pentyl | Ph- | 9-(N)-N-methyl-morpholinum, I$^-$ |
| | 93 | n-pentyl | Ph- | 9-(N)-N'-methylpiperazine |
| | 93 | n-pentyl | Ph- | 9-(N)-N'-dimethylpiperazinium, I$^-$ |
| | 95 | n-pentyl | Ph- | 9-NH-CBZ |
| | 96 | n-pentyl | Ph- | 9-NHC(O)C$_5$H$_{11}$ |
| | 97 | n-pentyl | Ph- | 9-NHC(O)CH$_2$Br |
| | 98 | n-pentyl | Ph- | 9-NH-C(NH)NH$_2$ |
| | 99 | n-pentyl | Ph- | 9-(2)-thiophene |
| | 100 | n-pentyl | Ph- | 7-OCH$_3$, 8-OCH$_3$ |
| | 101 | n-pentyl | Ph- | 7-SCH$_3$, 8-OCH$_3$ |
| | 102 | n-pentyl | Ph- | 7-SCH$_3$, 8-SCH$_3$ |
| | 103 | n-pentyl | Ph- | 6-OCH$_3$, 7-OCH$_3$, 8-OCH$_3$ |
| F101.005 | 01 | n-hexyl | Ph- | 7-methyl |
| | 02 | n-hexyl | Ph- | 7-ethyl |
| | 03 | n-hexyl | Ph- | 7-iso-propyl |
| | 04 | n-hexyl | Ph- | 7-tert-butyl |
| | 05 | n-hexyl | Ph- | 7-OH |
| | 06 | n-hexyl | Ph- | 7-OCH$_3$ |
| | 07 | n-hexyl | Ph- | 7-O(iso-propyl) |
| | 08 | n-hexyl | Ph- | 7-SCH$_3$ |
| | 09 | n-hexyl | Ph- | 7-SOCH$_3$ |
| | 10 | n-hexyl | Ph- | 7-SO$_2$CH$_3$ |
| | 11 | n-hexyl | Ph- | 7-SCH$_2$CH$_3$ |
| | 12 | n-hexyl | Ph- | 7-NH$_2$ |
| | 13 | n-hexyl | Ph- | 7-NHOH |
| | 14 | n-hexyl | Ph- | 7-NHCH$_3$ |
| | 15 | n-hexyl | Ph- | 7-N(CH$_3$)$_2$ |
| | 16 | n-hexyl | Ph- | 7-N$^+$(CH$_3$)$_3$, I$^-$ |
| | 17 | n-hexyl | Ph- | 7-NHC(=O)CH$_3$ |
| | 18 | n-hexyl | Ph- | 7-N(CH$_2$CH$_3$)$_2$ |
| | 19 | n-hexyl | Ph- | 7-NMeCH$_2$CO$_2$H |
| | 20 | n-hexyl | Ph- | 7-N$^+$(Me)$_2$CH$_2$CO$_2$H, I$^-$ |
| | 21 | n-hexyl | Ph- | 7-(N)-morpholine |
| | 22 | n-hexyl | Ph- | 7-(N)-azetidine |
| | 23 | n-hexyl | Ph- | 7-(N)-N-methylazetidinium, I$^-$ |
| | 24 | n-hexyl | Ph- | 7-(N)-pyrrolidine |
| | 25 | n-hexyl | Ph- | 7-(N)-N-methyl-pyrrolidinium, I$^-$ |
| | 26 | n-hexyl | Ph- | 7-(N)-N-methyl-morpholinum, I$^-$ |
| | 27 | n-hexyl | Ph- | 7-(N)-N'-methylpiperazine |
| | 28 | n-hexyl | Ph- | 7-(N)-N'-dimethylpiperazinium, I$^-$ |
| | 29 | n-hexyl | Ph- | 7-NH-CBZ |
| | 30 | n-hexyl | Ph- | 7-NHC(O)C$_5$H$_{11}$ |
| | 31 | n-hexyl | Ph- | 7-NHC(O)CH$_2$Br |
| | 32 | n-hexyl | Ph- | 7-NH-C(NH)NH$_2$ |
| | 33 | n-hexyl | Ph- | 7-(2)-thiophene |
| | 34 | n-hexyl | Ph- | 8-methyl |
| | 35 | n-hexyl | Ph- | 8-ethyl |
| | 36 | n-hexyl | Ph- | 8-iso-propyl |
| | 37 | n-hexyl | Ph- | 8-tert-butyl |
| | 38 | n-hexyl | Ph- | 8-OH |
| | 39 | n-hexyl | Ph- | 8-OCH$_3$ |
| | 40 | n-hexyl | Ph- | 8-O(iso-propyl) |
| | 41 | n-hexyl | Ph- | 8-SCH$_3$ |
| | 42 | n-hexyl | Ph- | 8-SOCH$_3$ |
| | 43 | n-hexyl | Ph- | 8-SO$_2$CH$_3$ |
| | 44 | n-hexyl | Ph- | 8-SCH$_2$CH$_3$ |
| | 45 | n-hexyl | Ph- | 8-NH$_2$ |
| | 46 | n-hexyl | Ph- | 8-NHOH |
| | 47 | n-hexyl | Ph- | 8-NHCH$_3$ |
| | 48 | n-hexyl | Ph- | 8-N(CH$_3$)$_2$ |
| | 49 | n-hexyl | Ph- | 8-N$^+$(CH$_3$)$_3$, I$^-$ |
| | 50 | n-hexyl | Ph- | 8-NHC(=O)CH$_3$ |

TABLE 1-continued

Alternative Compounds #3 (Family F101.xxx.yyy)

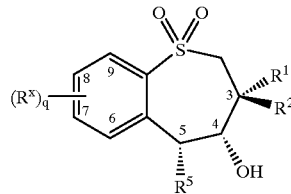

| Prefix (FFF.xxx. | Cpd# yyy) | R¹=R² | R⁵ | (Rˣ)q |
|---|---|---|---|---|
| | 68 | n-hexyl | Ph- | 9-ethyl |
| | 69 | n-hexyl | Ph- | 9-iso-propyl |
| | 70 | n-hexyl | Ph- | 9-tert-butyl |
| | 71 | n-hexyl | Ph- | 9-OH |
| | 72 | n-hexyl | Ph- | 9-OCH$_3$ |
| | 73 | n-hexyl | Ph- | 9-O(iso-propyl) |
| | 74 | n-hexyl | Ph- | 9-SCH$_3$ |
| | 75 | n-hexyl | Ph- | 9-SOCH$_3$ |
| | 76 | n-hexyl | Ph- | 9-SO$_2$CH$_3$ |
| | 77 | n-hexyl | Ph- | 9-SCH$_2$CH$_3$ |
| | 78 | n-hexyl | Ph- | 9-NH$_2$ |
| | 79 | n-hexyl | Ph- | 9-NHOH |
| | 80 | n-hexyl | Ph- | 9-NHCH$_3$ |
| | 81 | n-hexyl | Ph- | 9-N(CH$_3$)$_2$ |
| | 82 | n-hexyl | Ph- | 9-N$^+$(CH$_3$)$_3$, I$^-$ |
| | 83 | n-hexyl | Ph- | 9-NHC(=O)CH$_3$ |
| | 84 | n-hexyl | Ph- | 9-N(CH$_2$CH$_3$)$_2$ |
| | 85 | n-hexyl | Ph- | 9-NMeCH$_2$CO$_2$H |
| | 86 | n-hexyl | Ph- | 9-N$^+$(Me)$_2$CH$_2$CO$_2$H, I$^-$ |
| | 87 | n-hexyl | Ph- | 9-(N)-morpholine |
| | 88 | n-hexyl | Ph- | 9-(N)-azetidine |
| | 89 | n-hexyl | Ph- | 9-(N)-N-methylazetidinium, I$^-$ |
| | 90 | n-hexyl | Ph- | 9-(N)-pyrrolidine |
| | 91 | n-hexyl | Ph- | 9-(N)-N-methyl-pyrrolidinium, I$^-$ |
| | 92 | n-hexyl | Ph- | 9-(N)-N-methyl-morpholinum, I$^-$ |
| | 93 | n-hexyl | Ph- | 9-(N)-N'-methylpiperazine |
| | 93 | n-hexyl | Ph- | 9-(N)-N'-dimethylpiperazinium, I$^-$ |
| | 95 | n-hexyl | Ph- | 9-NH-CBZ |
| | 96 | n-hexyl | Ph- | 9-NHC(O)C$_5$H$_{11}$ |
| | 97 | n-hexyl | Ph- | 9-NHC(O)CH$_2$Br |
| | 98 | n-hexyl | Ph- | 9-NH-C(NH)NH$_2$ |
| | 99 | n-hexyl | Ph- | 9-(2)-thiophene |
| | 100 | n-hexyl | Ph- | 7-OCH$_3$, 8-OCH$_3$ |
| | 101 | n-hexyl | Ph- | 7-SCH$_3$, 8-OCH$_3$ |
| | 102 | n-hexyl | Ph- | 7-SCH$_3$, 8-SCH$_3$ |
| | 103 | n-hexyl | Ph- | 6-OCH$_3$, 7-OCH$_3$, 8-OCH$_3$ |
| F101.006 | 01 | iso-propyl | Ph- | 7-methyl |
| | 02 | iso-propyl | Ph- | 7-ethyl |
| | 03 | iso-propyl | Ph- | 7-iso-propyl |
| | 04 | iso-propyl | Ph- | 7-tert-butyl |
| | 05 | iso-propyl | Ph- | 7-OH |
| | 06 | iso-propyl | Ph- | 7-OCH$_3$ |
| | 07 | iso-propyl | Ph- | 7-O(iso-propyl) |
| | 08 | iso-propyl | Ph- | 7-SCH$_3$ |
| | 09 | iso-propyl | Ph- | 7-SOCH$_3$ |
| | 10 | iso-propyl | Ph- | 7-SO$_2$CH$_3$ |
| | 11 | iso-propyl | Ph- | 7-SCH$_2$CH$_3$ |
| | 12 | iso-propyl | Ph- | 7-NH$_2$ |
| | 13 | iso-propyl | Ph- | 7-NHOH |
| | 14 | iso-propyl | Ph- | 7-NHCH$_3$ |
| | 15 | iso-propyl | Ph- | 7-N(CH$_3$)$_2$ |
| | 16 | iso-propyl | Ph- | 7-N$^+$(CH$_3$)$_3$, I$^-$ |
| | 17 | iso-propyl | Ph- | 7-NHC(=O)CH$_3$ |
| | 18 | iso-propyl | Ph- | 7-N(CH$_2$CH$_3$)$_2$ |
| | 19 | iso-propyl | Ph- | 7-NMeCH$_2$CO$_2$H |
| | 20 | iso-propyl | Ph- | 7-N$^+$(Me)$_2$CH$_2$CO$_2$H, I$^-$ |
| | 21 | iso-propyl | Ph- | 7-(N)-morpholine |
| | 22 | iso-propyl | Ph- | 7-(N)-azetidine |
| | 23 | iso-propyl | Ph- | 7-(N)-N-methylazetidinium, I$^-$ |
| | 24 | iso-propyl | Ph- | 7-(N)-pyrrolidine |
| | 25 | iso-propyl | Ph- | 7-(N)-N-methyl-pyrrolidinium, I$^-$ |
| | 26 | iso-propyl | Ph- | 7-(N)-N-methyl-morpholinum, I$^-$ |
| | 27 | iso-propyl | Ph- | 7-(N)-N'-methylpiperazine |
| | 28 | iso-propyl | Ph- | 7-(N)-N'-dimethylpiperazinium, I$^-$ |

TABLE 1-continued

Alternative Compounds #3 (Family F101.xxx.yyy)

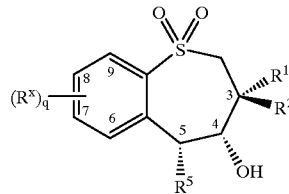

| Prefix (FFF.xxx. | Cpd# yyy) | $R^1=R^2$ | $R^5$ | $(R^x)_q$ |
|---|---|---|---|---|
| | 29 | iso-propyl | Ph- | 7-NH-CBZ |
| | 30 | iso-propyl | Ph- | 7-NHC(O)$C_5H_{11}$ |
| | 31 | iso-propyl | Ph- | 7-NHC(O)$CH_2$Br |
| | 32 | iso-propyl | Ph- | 7-NH-C(NH)$NH_2$ |
| | 33 | iso-propyl | Ph- | 7-(2)-thiophene |
| | 34 | iso-propyl | Ph- | 8-methyl |
| | 35 | iso-propyl | Ph- | 8-ethyl |
| | 36 | iso-propyl | Ph- | 8-iso-propyl |
| | 37 | iso-propyl | Ph- | 8-tert-butyl |
| | 38 | iso-propyl | Ph- | 8-OH |
| | 39 | iso-propyl | Ph- | 8-$OCH_3$ |
| | 40 | iso-propyl | Ph- | 8-O(iso-propyl) |
| | 41 | iso-propyl | Ph- | 8-$SCH_3$ |
| | 42 | iso-propyl | Ph- | 8-$SOCH_3$ |
| | 43 | iso-propyl | Ph- | 8-$SO_2CH_3$ |
| | 44 | iso-propyl | Ph- | 8-$SCH_2CH_3$ |
| | 45 | iso-propyl | Ph- | 8-$NH_2$ |
| | 46 | iso-propyl | Ph- | 8-NHOH |
| | 47 | iso-propyl | Ph- | 8-$NHCH_3$ |
| | 48 | iso-propyl | Ph- | 8-$N(CH_3)_2$ |
| | 49 | iso-propyl | Ph- | 8-$N^+(CH_3)_3$, $I^-$ |
| | 50 | iso-propyl | Ph- | 8-NHC(=O)$CH_3$ |
| | 51 | iso-propyl | Ph- | 8-$N(CH_2CH_3)_2$ |
| | 52 | iso-propyl | Ph- | 8-NMe$CH_2CO_2H$ |
| | 53 | iso-propyl | Ph- | 8-$N^+(Me)_2CH_2CO_2H$, $I^-$ |
| | 54 | iso-propyl | Ph- | 8-(N)-morpholine |
| | 55 | iso-propyl | Ph- | 8-(N)-azetidine |
| | 56 | iso-propyl | Ph- | 8-(N)-N-methylazetidinium, $I^-$ |
| | 57 | iso-propyl | Ph- | 8-(N)-pyrrolidine |
| | 58 | iso-propyl | Ph- | 8-(N)-N-methyl-pyrrolidinium, $I^-$ |
| | 59 | iso-propyl | Ph- | 8-(N)-N-methyl-morpholinium, $I^-$ |
| | 60 | iso-propyl | Ph- | 8-(N)-N'-methylpiperazine |
| | 61 | iso-propyl | Ph- | 8-(N)-N'-dimethylpiperazinium, $I^-$ |
| | 62 | iso-propyl | Ph- | 8-NH-CBZ |
| | 63 | iso-propyl | Ph- | 8-NHC(O)$C_5H_{11}$ |
| | 64 | iso-propyl | Ph- | 8-NHC(O)$CH_2$Br |
| | 65 | iso-propyl | Ph- | 8-NH-C(NH)$NH_2$ |
| | 66 | iso-propyl | Ph- | 8-(2)-thiophene |
| | 67 | iso-propyl | Ph- | 9-methyl |
| | 68 | iso-propyl | Ph- | 9-ethyl |
| | 69 | iso-propyl | Ph- | 9-iso-propyl |
| | 70 | iso-propyl | Ph- | 9-tert-butyl |
| | 71 | iso-propyl | Ph- | 9-OH |
| | 72 | iso-propyl | Ph- | 9-$OCH_3$ |
| | 73 | iso-propyl | Ph- | 9-O(iso-propyl) |
| | 74 | iso-propyl | Ph- | 9-$SCH_3$ |
| | 75 | iso-propyl | Ph- | 9-$SOCH_3$ |
| | 76 | iso-propyl | Ph- | 9-$SO_2CH_3$ |
| | 77 | iso-propyl | Ph- | 9-$SCH_2CH_3$ |
| | 78 | iso-propyl | Ph- | 9-$NH_2$ |
| | 79 | iso-propyl | Ph- | 9-NHOH |
| | 80 | iso-propyl | Ph- | 9-$NHCH_3$ |
| | 81 | iso-propyl | Ph- | 9-$N(CH_3)_2$ |
| | 82 | iso-propyl | Ph- | 9-$N^+(CH_3)_3$, $I^-$ |
| | 83 | iso-propyl | Ph- | 9-NHC(=O)$CH_3$ |
| | 84 | iso-propyl | Ph- | 9-$N(CH_2CH_3)_2$ |
| | 85 | iso-propyl | Ph- | 9-NMe$CH_2CO_2H$ |
| | 86 | iso-propyl | Ph- | 9-$N^+(Me)_2CH_2CO_2H$, $I^-$ |
| | 87 | iso-propyl | Ph- | 9-(N)-morpholine |
| | 88 | iso-propyl | Ph- | 9-(N)-azetidine |
| | 89 | iso-propyl | Ph- | 9-(N)-N-methylazetidinium, $I^-$ |
| | 90 | iso-propyl | Ph- | 9-(N)-pyrrolidine |
| | 91 | iso-propyl | Ph- | 9-(N)-N-methyl-pyrrolidinium, $I^-$ |
| | 92 | iso-propyl | Ph- | 9-(N)-N-methyl-morpholinum, $I^-$ |

TABLE 1-continued

Alternative Compounds #3 (Family F101.xxx.yyy)

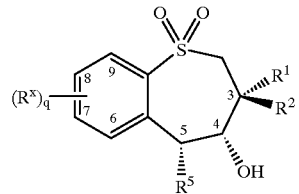

| Prefix (FFF.xxx. | Cpd# yyy) | $R^1=R^2$ | $R^5$ | $(R^x)q$ |
|---|---|---|---|---|
| | 93 | iso-propyl | Ph- | 9-(N)-N'-methylpiperazine |
| | 93 | iso-propyl | Ph- | 9-(N)-N'-dimethylpiperazinium, I$^-$ |
| | 95 | iso-propyl | Ph- | 9-NH-CBZ |
| | 96 | iso-propyl | Ph- | 9-NHC(O)C$_5$H$_{11}$ |
| | 97 | iso-propyl | Ph- | 9-NHC(O)CH$_2$Br |
| | 98 | iso-propyl | Ph- | 9-NH-C(NH)NH$_2$ |
| | 99 | iso-propyl | Ph- | 9-(2)-thiophene |
| | 100 | iso-propyl | Ph- | 7-OCH$_3$, 8-OCH$_3$ |
| | 101 | iso-propyl | Ph- | 7-SCH$_3$, 8-OCH$_3$ |
| | 102 | iso-propyl | Ph- | 7-SCH$_3$, 8-SCH$_3$ |
| | 103 | iso-propyl | Ph- | 6-OCH$_3$, 7-OCH$_3$, 8-OCH$_3$ |
| F101.007 | 01 | iso-butyl | Ph- | 7-methyl |
| | 02 | iso-butyl | Ph- | 7-ethyl |
| | 03 | iso-butyl | Ph- | 7-iso-propyl |
| | 04 | iso-butyl | Ph- | 7-tert-butyl |
| | 05 | iso-butyl | Ph- | 7-OH |
| | 06 | iso-butyl | Ph- | 7-OCH$_3$ |
| | 07 | iso-butyl | Ph- | 7-O(iso-propyl) |
| | 08 | iso-butyl | Ph- | 7-SCH$_3$ |
| | 09 | iso-butyl | Ph- | 7-SOCH$_3$ |
| | 10 | iso-butyl | Ph- | 7-SO$_2$CH$_3$ |
| | 11 | iso-butyl | Ph- | 7-SCH$_2$CH$_3$ |
| | 12 | iso-butyl | Ph- | 7-NH$_2$ |
| | 13 | iso-butyl | Ph- | 7-NHOH |
| | 14 | iso-butyl | Ph- | 7-NHCH$_3$ |
| | 15 | iso-butyl | Ph- | 7-N(CH$_3$)$_2$ |
| | 16 | iso-butyl | Ph- | 7-N$^+$(CH$_3$)$_3$, I$^-$ |
| | 17 | iso-butyl | Ph- | 7-NHC(=O)CH$_3$ |
| | 18 | iso-butyl | Ph- | 7-N(CH$_2$CH$_3$)$_2$ |
| | 19 | iso-butyl | Ph- | 7-NMeCH$_2$CO$_2$H |
| | 20 | iso-butyl | Ph- | 7-N$^+$(Me)$_2$CH$_2$CO$_2$H, I$^-$ |
| | 21 | iso-butyl | Ph- | 7-(N)-morpholine |
| | 22 | iso-butyl | Ph- | 7-(N)-azetidine |
| | 23 | iso-butyl | Ph- | 7-(N)-N-methylazetidinium, I$^-$ |
| | 24 | iso-butyl | Ph- | 7-(N)-pyrrolidine |
| | 25 | iso-butyl | Ph- | 7-(N)-N-methyl-pyrrolidinium, I$^-$ |
| | 26 | iso-butyl | Ph- | 7-(N)-N-methyl-morpholinum, I$^-$ |
| | 27 | iso-butyl | Ph- | 7-(N)-N'-methylpiperazine |
| | 28 | iso-butyl | Ph- | 7-(N)-N'-dimethylpiperazinium, I$^-$ |
| | 29 | iso-butyl | Ph- | 7-NH-CBZ |
| | 30 | iso-butyl | Ph- | 7-NHC(O)C$_5$H$_{11}$ |
| | 31 | iso-butyl | Ph- | 7-NHC(O)CH$_2$Br |
| | 32 | iso-butyl | Ph- | 7-NH-C(NH)NH$_2$ |
| | 33 | iso-butyl | Ph- | 7-(2)-thiophene |
| | 34 | iso-butyl | Ph- | 8-methyl |
| | 35 | iso-butyl | Ph- | 8-ethyl |
| | 36 | iso-butyl | Ph- | 8-iso-propyl |
| | 37 | iso-butyl | Ph- | 8-tert-butyl |
| | 38 | iso-butyl | Ph- | 8-OH |
| | 39 | iso-butyl | Ph- | 8-OCH$_3$ |
| | 40 | iso-butyl | Ph- | 8-O(iso-propyl) |
| | 41 | iso-butyl | Ph- | 8-SCH$_3$ |
| | 42 | iso-butyl | Ph- | 8-SOCH$_3$ |
| | 43 | iso-butyl | Ph- | 8-SO$_2$CH$_3$ |
| | 44 | iso-butyl | Ph- | 8-SCH$_2$CH$_3$ |
| | 45 | iso-butyl | Ph- | 8-NH$_2$ |
| | 46 | iso-butyl | Ph- | 8-NHOH |
| | 47 | iso-butyl | Ph- | 8-NHCH$_3$ |
| | 48 | iso-butyl | Ph- | 8-N(CH$_3$)$_2$ |
| | 49 | iso-butyl | Ph- | 8-N$^+$(CH$_3$)$_3$, I$^-$ |
| | 50 | iso-butyl | Ph- | 8-NHC(=O)CH$_3$ |
| | 51 | iso-butyl | Ph- | 8-N(CH$_2$CH$_3$)$_2$ |
| | 52 | iso-butyl | Ph- | 8-NMeCH$_2$CO$_2$H |
| | 53 | iso-butyl | Ph- | 8-N$^+$(Me)$_2$CH$_2$CO$_2$H, I$^-$ |

TABLE 1-continued

Alternative Compounds #3 (Family F101.xxx.yyy)

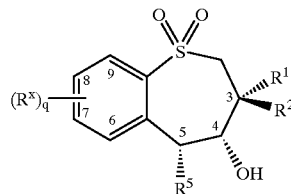

| Prefix (FFF.xxx. | Cpd# yyy) | $R^1=R^2$ | $R^5$ | $(R^x)q$ |
|---|---|---|---|---|
| | 54 | iso-butyl | Ph- | 8-(N)-morpholine |
| | 55 | iso-butyl | Ph- | 8-(N)-azetidine |
| | 56 | iso-butyl | Ph- | 8-(N)-N-methylazetidinium, I$^-$ |
| | 57 | iso-butyl | Ph- | 8-(N)-pyrrolidine |
| | 58 | iso-butyl | Ph- | 8-(N)-N-methyl-pyrrolidinium, I$^-$ |
| | 59 | iso-butyl | Ph- | 8-(N)-N-methyl-morpholinium, I$^-$ |
| | 60 | iso-butyl | Ph- | 8-(N)-N'-methylpiperazine |
| | 61 | iso-butyl | Ph- | 8-(N)-N'-dimethylpiperazinium, I$^-$ |
| | 62 | iso-butyl | Ph- | 8-NH-CBZ |
| | 63 | iso-butyl | Ph- | 8-NHC(O)C$_5$H$_{11}$ |
| | 64 | iso-butyl | Ph- | 8-NHC(O)CH$_2$Br |
| | 65 | iso-butyl | Ph- | 8-NH-C(NH)NH$_2$ |
| | 66 | iso-butyl | Ph- | 8-(2)-thiophene |
| | 67 | iso-butyl | Ph- | 9-methyl |
| | 68 | iso-butyl | Ph- | 9-ethyl |
| | 69 | iso-butyl | Ph- | 9-iso-propyl |
| | 70 | iso-butyl | Ph- | 9-tert-butyl |
| | 71 | iso-butyl | Ph- | 9-OH |
| | 72 | iso-butyl | Ph- | 9-OCH$_3$ |
| | 73 | iso-butyl | Ph- | 9-O(iso-propyl) |
| | 74 | iso-butyl | Ph- | 9-SCH$_3$ |
| | 75 | iso-butyl | Ph- | 9-SOCH$_3$ |
| | 76 | iso-butyl | Ph- | 9-SO$_2$CH$_3$ |
| | 77 | iso-butyl | Ph- | 9-SCH$_2$CH$_3$ |
| | 78 | iso-butyl | Ph- | 9-NH$_2$ |
| | 79 | iso-butyl | Ph- | 9-NHOH |
| | 80 | iso-butyl | Ph- | 9-NHCH$_3$ |
| | 81 | iso-butyl | Ph- | 9-N(CH$_3$)$_2$ |
| | 82 | iso-butyl | Ph- | 9-N$^+$(CH$_3$)$_3$, I$^-$ |
| | 83 | iso-butyl | Ph- | 9-NHC(=O)CH$_3$ |
| | 84 | iso-butyl | Ph- | 9-N(CH$_2$CH$_3$)$_2$ |
| | 85 | iso-butyl | Ph- | 9-NMeCH$_2$CO$_2$H |
| | 86 | iso-butyl | Ph- | 9-N$^+$(Me)$_2$CH$_2$CO$_2$H, I$^-$ |
| | 87 | iso-butyl | Ph- | 9-(N)-morpholine |
| | 88 | iso-butyl | Ph- | 9-(N)-azetidine |
| | 89 | iso-butyl | Ph- | 9-(N)-N-methylazetidinium, I$^-$ |
| | 90 | iso-butyl | Ph- | 9-(N)-pyrrolidine |
| | 91 | iso-butyl | Ph- | 9-(N)-N-methyl-pyrrolidinium, I$^-$ |
| | 92 | iso-butyl | Ph- | 9-(N)-N-methyl-morpholinum, I$^-$ |
| | 93 | iso-butyl | Ph- | 9-(N)-N'-methylpiperazine |
| | 93 | iso-butyl | Ph- | 9-(N)-N'-dimethylpiperazinium, I$^-$ |
| | 95 | iso-butyl | Ph- | 9-NH-CBZ |
| | 96 | iso-butyl | Ph- | 9-NHC(O)C$_5$H$_{11}$ |
| | 97 | iso-butyl | Ph- | 9-NHC(O)CH$_2$Br |
| | 98 | iso-butyl | Ph- | 9-NH-C(NH)NH$_2$ |
| | 99 | iso-butyl | Ph- | 9-(2)-thiophene |
| | 100 | iso-butyl | Ph- | 7-OCH$_3$, 8-OCH$_3$ |
| | 101 | iso-butyl | Ph- | 7-SCH$_3$, 8-OCH$_3$ |
| | 102 | iso-butyl | Ph- | 7-SCH$_3$, 8-SCH$_3$ |
| | 103 | iso-butyl | Ph- | 6-OCH$_3$, 7-OCH$_3$, 8-OCH$_3$ |
| F101.008 | 01 | iso-pentyl | Ph- | 7-methyl |
| | 02 | iso-pentyl | Ph- | 7-ethyl |
| | 03 | iso-pentyl | Ph- | 7-iso-propyl |
| | 04 | iso-pentyl | Ph- | 7-tert-butyl |
| | 05 | iso-pentyl | Ph- | 7-OH |
| | 06 | iso-pentyl | Ph- | 7-OCH$_3$ |
| | 07 | iso-pentyl | Ph- | 7-O(iso-propyl) |
| | 08 | iso-pentyl | Ph- | 7-SCH$_3$ |
| | 09 | iso-pentyl | Ph- | 7-SOCH$_3$ |
| | 10 | iso-pentyl | Ph- | 7-SO$_2$CH$_3$ |
| | 11 | iso-pentyl | Ph- | 7-SCH$_2$CH$_3$ |
| | 12 | iso-pentyl | Ph- | 7-NH$_2$ |
| | 13 | iso-pentyl | Ph- | 7-NHOH |
| | 14 | iso-pentyl | Ph- | 7-NHCH$_3$ |

TABLE 1-continued

Alternative Compounds #3 (Family F101.xxx.yyy)

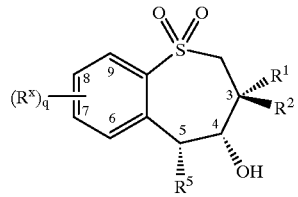

| Prefix (FFF.xxx. | Cpd# yyy) | R¹=R² | R⁵ | (Rˣ)q |
|---|---|---|---|---|
| | 15 | iso-pentyl | Ph- | 7-N(CH₃)₂ |
| | 16 | iso-pentyl | Ph- | 7-N⁺(CH₃)₃, I⁻ |
| | 17 | iso-pentyl | Ph- | 7-NHC(=O)CH₃ |
| | 18 | iso-pentyl | Ph- | 7-N(CH₂CH₃)₂ |
| | 19 | iso-pentyl | Ph- | 7-NMeCH₂CO₂H |
| | 20 | iso-pentyl | Ph- | 7-N⁺(Me)₂CH₂CO₂H, I⁻ |
| | 21 | iso-pentyl | Ph- | 7-(N)-morpholine |
| | 22 | iso-pentyl | Ph- | 7-(N)-azetidine |
| | 23 | iso-pentyl | Ph- | 7-(N)-N-methylazetidinium, I⁻ |
| | 24 | iso-pentyl | Ph- | 7-(N)-pyrrolidine |
| | 25 | iso-pentyl | Ph- | 7-(N)-N-methyl-pyrrolidinium, I⁻ |
| | 26 | iso-pentyl | Ph- | 7-(N)-N-methyl-morpholinium, I⁻ |
| | 27 | iso-pentyl | Ph- | 7-(N)-N'-methylpiperazine |
| | 28 | iso-pentyl | Ph- | 7-(N)-N'-dimethylpiperazinium, I⁻ |
| | 29 | iso-pentyl | Ph- | 7-NH-CBZ |
| | 30 | iso-pentyl | Ph- | 7-NHC(O)C₅H₁₁ |
| | 31 | iso-pentyl | Ph- | 7-NHC(O)CH₂Br |
| | 32 | iso-pentyl | Ph- | 7-NH-C(NH)NH₂ |
| | 33 | iso-pentyl | Ph- | 7-(2)-thiophene |
| | 34 | iso-pentyl | Ph- | 8-methyl |
| | 35 | iso-pentyl | Ph- | 8-ethyl |
| | 36 | iso-pentyl | Ph- | 8-iso-propyl |
| | 37 | iso-pentyl | Ph- | 8-tert-butyl |
| | 38 | iso-pentyl | Ph- | 8-OH |
| | 39 | iso-pentyl | Ph- | 8-OCH₃ |
| | 40 | iso-pentyl | Ph- | 8-O(iso-propyl) |
| | 41 | iso-pentyl | Ph- | 8-SCH₃ |
| | 42 | iso-pentyl | Ph- | 8-SOCH₃ |
| | 43 | iso-pentyl | Ph- | 8-SO₂CH₃ |
| | 44 | iso-pentyl | Ph- | 8-SCH₂CH₃ |
| | 45 | iso-pentyl | Ph- | 8-NH₂ |
| | 46 | iso-pentyl | Ph- | 8-NHOH |
| | 47 | iso-pentyl | Ph- | 8-NHCH₃ |
| | 48 | iso-pentyl | Ph- | 8-N(CH₃)₂ |
| | 49 | iso-pentyl | Ph- | 8-N⁺(CH₃)₃, I⁻ |
| | 50 | iso-pentyl | Ph- | 8-NHC(=O)CH₃ |
| | 51 | iso-pentyl | Ph- | 8-N(CH₂CH₃)₂ |
| | 52 | iso-pentyl | Ph- | 8-NMeCH₂CO₂H |
| | 53 | iso-pentyl | Ph- | 8-N⁺(Me)₂CH₂CO₂H, I⁻ |
| | 54 | iso-pentyl | Ph- | 8-(N)-morpholine |
| | 55 | iso-pentyl | Ph- | 8-(N)-azetidine |
| | 56 | iso-pentyl | Ph- | 8-(N)-N-methylazetidinium, I⁻ |
| | 57 | iso-pentyl | Ph- | 8-(N)-pyrrolidine |
| | 58 | iso-pentyl | Ph- | 8-(N)-N-methyl-pyrrolidinium, I⁻ |
| | 59 | iso-pentyl | Ph- | 8-(N)-N-methyl-morpholinium, I⁻ |
| | 60 | iso-pentyl | Ph- | 8-(N)-N'-methylpiperazine |
| | 61 | iso-pentyl | Ph- | 8-(N)-N'-dimethylpiperazinium, I⁻ |
| | 62 | iso-pentyl | Ph- | 8-NH-CBZ |
| | 63 | iso-pentyl | Ph- | 8-NHC(O)C₅H₁₁ |
| | 64 | iso-pentyl | Ph- | 8-NHC(O)CH₂Br |
| | 65 | iso-pentyl | Ph- | 8-NH-C(NH)NH₂ |
| | 66 | iso-pentyl | Ph- | 8-(2)-thiophene |
| | 67 | iso-pentyl | Ph- | 9-methyl |
| | 68 | iso-pentyl | Ph- | 9-ethyl |
| | 69 | iso-pentyl | Ph- | 9-iso-propyl |
| | 70 | iso-pentyl | Ph- | 9-tert-butyl |
| | 71 | iso-pentyl | Ph- | 9-OH |
| | 72 | iso-pentyl | Ph- | 9-OCH₃ |
| | 73 | iso-pentyl | Ph- | 9-O(iso-propyl) |
| | 74 | iso-pentyl | Ph- | 9-SCH₃ |
| | 75 | iso-pentyl | Ph- | 9-SOCH₃ |
| | 76 | iso-pentyl | Ph- | 9-SO₂CH₃ |
| | 77 | iso-pentyl | Ph- | 9-SCH₂CH₃ |
| | 78 | iso-pentyl | Ph- | 9-NH₂ |

TABLE 1-continued

Alternative Compounds #3 (Family F101.xxx.yyy)

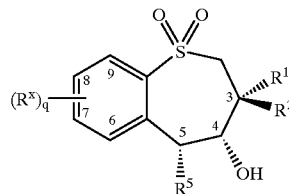

| Prefix (FFF.xxx. | Cpd# yyy) | $R^1=R^2$ | $R^5$ | $(R^x)q$ |
|---|---|---|---|---|
| | 79 | iso-pentyl | Ph- | 9-NHOH |
| | 80 | iso-pentyl | Ph- | 9-NHCH$_3$ |
| | 81 | iso-pentyl | Ph- | 9-N(CH$_3$)$_2$ |
| | 82 | iso-pentyl | Ph- | 9-N$^+$(CH$_3$)$_3$, I$^-$ |
| | 83 | iso-pentyl | Ph- | 9-NHC(=O)CH$_3$ |
| | 84 | iso-pentyl | Ph- | 9-N(CH$_2$CH$_3$)$_2$ |
| | 85 | iso-pentyl | Ph- | 9-NMeCH$_2$CO$_2$H |
| | 86 | iso-pentyl | Ph- | 9-N$^+$(Me)$_2$CH$_2$CO$_2$H, I$^-$ |
| | 87 | iso-pentyl | Ph- | 9-(N)-morpholine |
| | 88 | iso-pentyl | Ph- | 9-(N)-azetidine |
| | 89 | iso-pentyl | Ph- | 9-(N)-N-methylazetidinium, I$^-$ |
| | 90 | iso-pentyl | Ph- | 9-(N)-pyrrolidine |
| | 91 | iso-pentyl | Ph- | 9-(N)-N-methyl-pyrrolidinium, I$^-$ |
| | 92 | iso-pentyl | Ph- | 9-(N)-N-methyl-morpholinum, I$^-$ |
| | 93 | iso-pentyl | Ph- | 9-(N)-N'-methylpiperazine |
| | 93 | iso-pentyl | Ph- | 9-(N)-N'-dimethylpiperazinium, I$^-$ |
| | 95 | iso-pentyl | Ph- | 9-NH-CBZ |
| | 96 | iso-pentyl | Ph- | 9-NHC(O)C$_5$H$_{11}$ |
| | 97 | iso-pentyl | Ph- | 9-NHC(O)CH$_2$Br |
| | 98 | iso-pentyl | Ph- | 9-NH-C(NH)NH$_2$ |
| | 99 | iso-pentyl | Ph- | 9-(2)-thiophene |
| | 100 | iso-pentyl | Ph- | 7-OCH$_3$, 8-OCH$_3$ |
| | 101 | iso-pentyl | Ph- | 7-SCH$_3$, 8-OCH$_3$ |
| | 102 | iso-pentyl | Ph- | 7-SCH$_3$, 8-SCH$_3$ |
| | 103 | iso-pentyl | Ph- | 6-OCH$_3$, 7-OCH$_3$, 8-OCH$_3$ |
| F101.009 | 01 | CH$_2$C(=O)C$_2$H$_5$ | Ph- | 7-methyl |
| | 02 | CH$_2$C(=O)C$_2$H$_5$ | Ph- | 7-ethyl |
| | 03 | CH$_2$C(=O)C$_2$H$_5$ | Ph- | 7-iso-propyl |
| | 04 | CH$_2$C(=O)C$_2$H$_5$ | Ph- | 7-tert-butyl |
| | 05 | CH$_2$C(=O)C$_2$H$_5$ | Ph- | 7-OH |
| | 06 | CH$_2$C(=O)C$_2$H$_5$ | Ph- | 7-OCH$_3$ |
| | 07 | CH$_2$C(=O)C$_2$H$_5$ | Ph- | 7-O(iso-propyl) |
| | 08 | CH$_2$C(=O)C$_2$H$_5$ | Ph- | 7-SCH$_3$ |
| | 09 | CH$_2$C(=O)C$_2$H$_5$ | Ph- | 7-SOCH$_3$ |
| | 10 | CH$_2$C(=O)C$_2$H$_5$ | Ph- | 7-SO$_2$CH$_3$ |
| | 11 | CH$_2$C(=O)C$_2$H$_5$ | Ph- | 7-SCH$_2$CH$_3$ |
| | 12 | CH$_2$C(=O)C$_2$H$_5$ | Ph- | 7-NH$_2$ |
| | 13 | CH$_2$C(=O)C$_2$H$_5$ | Ph- | 7-NHOH |
| | 14 | CH$_2$C(=O)C$_2$H$_5$ | Ph- | 7-NHCH$_3$ |
| | 15 | CH$_2$C(=O)C$_2$H$_5$ | Ph- | 7-N(CH$_3$)$_2$ |
| | 16 | CH$_2$C(=O)C$_2$H$_5$ | Ph- | 7-N$^+$(CH$_3$)$_3$, I$^-$ |
| | 17 | CH$_2$C(=O)C$_2$H$_5$ | Ph- | 7-NHC(=O)CH$_3$ |
| | 18 | CH$_2$C(=O)C$_2$H$_5$ | Ph- | 7-N(CH$_2$CH$_3$)$_2$ |
| | 19 | CH$_2$C(=O)C$_2$H$_5$ | Ph- | 7-NMeCH$_2$CO$_2$H |
| | 20 | CH$_2$C(=O)C$_2$H$_5$ | Ph- | 7-N$^+$(Me)$_2$CH$_2$CO$_2$H, I$^-$ |
| | 21 | CH$_2$C(=O)C$_2$H$_5$ | Ph- | 7-(N)-morpholine |
| | 22 | CH$_2$C(=O)C$_2$H$_5$ | Ph- | 7-(N)-azetidine |
| | 23 | CH$_2$C(=O)C$_2$H$_5$ | Ph- | 7-(N)-N-methylazetidinium, I$^-$ |
| | 24 | CH$_2$C(=O)C$_2$H$_5$ | Ph- | 7-(N)-pyrrolidine |
| | 25 | CH$_2$C(=O)C$_2$H$_5$ | Ph- | 7-(N)-N-methyl-pyrrolidinium, I$^-$ |
| | 26 | CH$_2$C(=O)C$_2$H$_5$ | Ph- | 7-(N)-N-methyl-morpholinum, I$^-$ |
| | 27 | CH$_2$C(=O)C$_2$H$_5$ | Ph- | 7-(N)-N'-methylpiperazine |
| | 28 | CH$_2$C(=O)C$_2$H$_5$ | Ph- | 7-(N)-N'-dimethylpiperazinium, I$^-$ |
| | 29 | CH$_2$C(=O)C$_2$H$_5$ | Ph- | 7-NH-CBZ |
| | 30 | CH$_2$C(=O)C$_2$H$_5$ | Ph- | 7-NHC(O)C$_5$H$_{11}$ |
| | 31 | CH$_2$C(=O)C$_2$H$_5$ | Ph- | 7-NHC(O)CH$_2$Br |
| | 32 | CH$_2$C(=O)C$_2$H$_5$ | Ph- | 7-NH-C(NH)NH$_2$ |
| | 33 | CH$_2$C(=O)C$_2$H$_5$ | Ph- | 7-(2)-thiophene |
| | 34 | CH$_2$C(=O)C$_2$H$_5$ | Ph- | 8-methyl |
| | 35 | CH$_2$C(=O)C$_2$H$_5$ | Ph- | 8-ethyl |
| | 36 | CH$_2$C(=O)C$_2$H$_5$ | Ph- | 8-iso-propyl |
| | 37 | CH$_2$C(=O)C$_2$H$_5$ | Ph- | 8-tert-butyl |
| | 38 | CH$_2$C(=O)C$_2$H$_5$ | Ph- | 8-OH |
| | 39 | CH$_2$C(=O)C$_2$H$_5$ | Ph- | 8-OCH$_3$ |

TABLE 1-continued

Alternative Compounds #3 (Family F101.xxx.yyy)

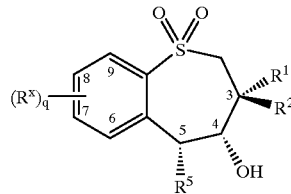

| Prefix (FFF.xxx. | Cpd# yyy) | $R^1=R^2$ | $R^5$ | $(R^x)q$ |
|---|---|---|---|---|
| | 40 | $CH_2C(=O)C_2H_5$ | Ph- | 8-O(iso-propyl) |
| | 41 | $CH_2C(=O)C_2H_5$ | Ph- | 8-$SCH_3$ |
| | 42 | $CH_2C(=O)C_2H_5$ | Ph- | 8-$SOCH_3$ |
| | 43 | $CH_2C(=O)C_2H_5$ | Ph- | 8-$SO_2CH_3$ |
| | 44 | $CH_2C(=O)C_2H_5$ | Ph- | 8-$SCH_2CH_3$ |
| | 45 | $CH_2C(=O)C_2H_5$ | Ph- | 8-$NH_2$ |
| | 46 | $CH_2C(=O)C_2H_5$ | Ph- | 8-NHOH |
| | 47 | $CH_2C(=O)C_2H_5$ | Ph- | 8-$NHCH_3$ |
| | 48 | $CH_2C(=O)C_2H_5$ | Ph- | 8-$N(CH_3)_2$ |
| | 49 | $CH_2C(=O)C_2H_5$ | Ph- | 8-$N^+(CH_3)_3$, $I^-$ |
| | 50 | $CH_2C(=O)C_2H_5$ | Ph- | 8-NHC(=O)$CH_3$ |
| | 51 | $CH_2C(=O)C_2H_5$ | Ph- | 8-$N(CH_2CH_3)_2$ |
| | 52 | $CH_2C(=O)C_2H_5$ | Ph- | 8-$NMeCH_2CO_2H$ |
| | 53 | $CH_2C(=O)C_2H_5$ | Ph- | 8-$N^+(Me)_2CH_2CO_2H$, $I^-$ |
| | 54 | $CH_2C(=O)C_2H_5$ | Ph- | 8-(N)-morpholine |
| | 55 | $CH_2C(=O)C_2H_5$ | Ph- | 8-(N)-azetidine |
| | 56 | $CH_2C(=O)C_2H_5$ | Ph- | 8-(N)-N-methylazetidinium, $I^-$ |
| | 57 | $CH_2C(=O)C_2H_5$ | Ph- | 8-(N)-pyrrolidine |
| | 58 | $CH_2C(=O)C_2H_5$ | Ph- | 8-(N)-N-methyl-pyrrolidinium, $I^-$ |
| | 59 | $CH_2C(=O)C_2H_5$ | Ph- | 8-(N)-N-methyl-morpholinum, $I^-$ |
| | 60 | $CH_2C(=O)C_2H_5$ | Ph- | 8-(N)-N'-methylpiperazine |
| | 61 | $CH_2C(=O)C_2H_5$ | Ph- | 8-(N)-N'-dimethylpiperazinium, $I^-$ |
| | 62 | $CH_2C(=O)C_2H_5$ | Ph- | 8-NH-CBZ |
| | 63 | $CH_2C(=O)C_2H_5$ | Ph- | 8-NHC(O)$C_5H_{11}$ |
| | 64 | $CH_2C(=O)C_2H_5$ | Ph- | 8-NHC(O)$CH_2Br$ |
| | 65 | $CH_2C(=O)C_2H_5$ | Ph- | 8-NH-C(NH)$NH_2$ |
| | 66 | $CH_2C(=O)C_2H_5$ | Ph- | 8-(2)-thiophene |
| | 67 | $CH_2C(=O)C_2H_5$ | Ph- | 9-methyl |
| | 68 | $CH_2C(=O)C_2H_5$ | Ph- | 9-ethyl |
| | 69 | $CH_2C(=O)C_2H_5$ | Ph- | 9-iso-propyl |
| | 70 | $CH_2C(=O)C_2H_5$ | Ph- | 9-tert-butyl |
| | 71 | $CH_2C(=O)C_2H_5$ | Ph- | 9-OH |
| | 72 | $CH_2C(=O)C_2H_5$ | Ph- | 9-$OCH_3$ |
| | 73 | $CH_2C(=O)C_2H_5$ | Ph- | 9-O(iso-propyl) |
| | 74 | $CH_2C(=O)C_2H_5$ | Ph- | 9-$SCH_3$ |
| | 75 | $CH_2C(=O)C_2H_5$ | Ph- | 9-$SOCH_3$ |
| | 76 | $CH_2C(=O)C_2H_5$ | Ph- | 9-$SO_2CH_3$ |
| | 77 | $CH_2C(=O)C_2H_5$ | Ph- | 9-$SCH_2CH_3$ |
| | 78 | $CH_2C(=O)C_2H_5$ | Ph- | 9-$NH_2$ |
| | 79 | $CH_2C(=O)C_2H_5$ | Ph- | 9-NHOH |
| | 80 | $CH_2C(=O)C_2H_5$ | Ph- | 9-$NHCH_3$ |
| | 81 | $CH_2C(=O)C_2H_5$ | Ph- | 9-$N(CH_3)_2$ |
| | 82 | $CH_2C(=O)C_2H_5$ | Ph- | 9-$N^+(CH_3)_3$, $I^-$ |
| | 83 | $CH_2C(=O)C_2H_5$ | Ph- | 9-NHC(=O)$CH_3$ |
| | 84 | $CH_2C(=O)C_2H_5$ | Ph- | 9-$N(CH_2CH_3)_2$ |
| | 85 | $CH_2C(=O)C_2H_5$ | Ph- | 9-$NMeCH_2CO_2H$ |
| | 86 | $CH_2C(=O)C_2H_5$ | Ph- | 9-$N^+(Me)_2CH_2CO_2H$, $I^-$ |
| | 87 | $CH_2C(=O)C_2H_5$ | Ph- | 9-(N)-morpholine |
| | 88 | $CH_2C(=O)C_2H_5$ | Ph- | 9-(N)-azetidine |
| | 89 | $CH_2C(=O)C_2H_5$ | Ph- | 9-(N)-N-methylazetidinium, $I^-$ |
| | 90 | $CH_2C(=O)C_2H_5$ | Ph- | 9-(N)-pyrrolidine |
| | 91 | $CH_2C(=O)C_2H_5$ | Ph- | 9-(N)-N-methyl-pyrrolidinium, $I^-$ |
| | 92 | $CH_2C(=O)C_2H_5$ | Ph- | 9-(N)-N-methyl-morpholinum, $I^-$ |
| | 93 | $CH_2C(=O)C_2H_5$ | Ph- | 9-(N)-N'-methylpiperazine |
| | 93 | $CH_2C(=O)C_2H_5$ | Ph- | 9-(N)-N'-dimethylpiperazinium, $I^-$ |
| | 95 | $CH_2C(=O)C_2H_5$ | Ph- | 9-NH-CBZ |
| | 96 | $CH_2C(=O)C_2H_5$ | Ph- | 9-NHC(O)$C_5H_{11}$ |
| | 97 | $CH_2C(=O)C_2H_5$ | Ph- | 9-NHC(O)$CH_2Br$ |
| | 98 | $CH_2C(=O)C_2H_5$ | Ph- | 9-NH-C(NH)$NH_2$ |
| | 99 | $CH_2C(=O)C_2H_5$ | Ph- | 9-(2)-thiophene |
| | 100 | $CH_2C(=O)C_2H_5$ | Ph- | 7-$OCH_3$, 8-$OCH_3$ |
| | 101 | $CH_2C(=O)C_2H_5$ | Ph- | 7-$SCH_3$, 8-$OCH_3$ |
| | 102 | $CH_2C(=O)C_2H_5$ | Ph- | 7-$SCH_3$, 8-$SCH_3$ |
| | 103 | $CH_2C(=O)C_2H_5$ | Ph- | 6-$OCH_3$, 7-$OCH_3$, 8-$OCH_3$ |

TABLE 1-continued

Alternative Compounds #3 (Family F101.xxx.yyy)

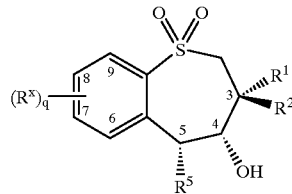

| Prefix (FFF.xxx. | Cpd# yyy) | $R^1=R^2$ | $R^5$ | $(R^x)q$ |
|---|---|---|---|---|
| F101.010 | 01 | $CH_2OC_2H_5$ | Ph- | 7-methyl |
| | 02 | $CH_2OC_2H_5$ | Ph- | 7-ethyl |
| | 03 | $CH_2OC_2H_5$ | Ph- | 7-iso-propyl |
| | 04 | $CH_2OC_2H_5$ | Ph- | 7-tert-butyl |
| | 05 | $CH_2OC_2H_5$ | Ph- | 7-OH |
| | 06 | $CH_2OC_2H_5$ | Ph- | 7-$OCH_3$ |
| | 07 | $CH_2OC_2H_5$ | Ph- | 7-O(iso-propyl) |
| | 08 | $CH_2OC_2H_5$ | Ph- | 7-$SCH_3$ |
| | 09 | $CH_2OC_2H_5$ | Ph- | 7-$SOCH_3$ |
| | 10 | $CH_2OC_2H_5$ | Ph- | 7-$SO_2CH_3$ |
| | 11 | $CH_2OC_2H_5$ | Ph- | 7-$SCH_2CH_3$ |
| | 12 | $CH_2OC_2H_5$ | Ph- | 7-$NH_2$ |
| | 13 | $CH_2OC_2H_5$ | Ph- | 7-NHOH |
| | 14 | $CH_2OC_2H_5$ | Ph- | 7-$NHCH_3$ |
| | 15 | $CH_2OC_2H_5$ | Ph- | 7-$N(CH_3)_2$ |
| | 16 | $CH_2OC_2H_5$ | Ph- | 7-$N^+(CH_3)_3$, $I^-$ |
| | 17 | $CH_2OC_2H_5$ | Ph- | 7-NHC(=O)$CH_3$ |
| | 18 | $CH_2OC_2H_5$ | Ph- | 7-$N(CH_2CH_3)_2$ |
| | 19 | $CH_2OC_2H_5$ | Ph- | 7-NMe$CH_2CO_2H$ |
| | 20 | $CH_2OC_2H_5$ | Ph- | 7-$N^+(Me)_2CH_2CO_2H$, $I^-$ |
| | 21 | $CH_2OC_2H_5$ | Ph- | 7-(N)-morpholine |
| | 22 | $CH_2OC_2H_5$ | Ph- | 7-(N)-azetidine |
| | 23 | $CH_2OC_2H_5$ | Ph- | 7-(N)-N-methylazetidinium, $I^-$ |
| | 24 | $CH_2OC_2H_5$ | Ph- | 7-(N)-pyrrolidine |
| | 25 | $CH_2OC_2H_5$ | Ph- | 7-(N)-N-methyl-pyrrolidinium, $I^-$ |
| | 26 | $CH_2OC_2H_5$ | Ph- | 7-(N)-N-methyl-morpholinum, $I^-$ |
| | 27 | $CH_2OC_2H_5$ | Ph- | 7-(N)-N'-methylpiperazine |
| | 28 | $CH_2OC_2H_5$ | Ph- | 7-(N)-N'-dimethylpiperazinium, $I^-$ |
| | 29 | $CH_2OC_2H_5$ | Ph- | 7-NH-CBZ |
| | 30 | $CH_2OC_2H_5$ | Ph- | 7-NHC(O)$C_5H_{11}$ |
| | 31 | $CH_2OC_2H_5$ | Ph- | 7-NHC(O)$CH_2Br$ |
| | 32 | $CH_2OC_2H_5$ | Ph- | 7-NH-C(NH)$NH_2$ |
| | 33 | $CH_2OC_2H_5$ | Ph- | 7-(2)-thiophene |
| | 34 | $CH_2OC_2H_5$ | Ph- | 8-methyl |
| | 35 | $CH_2OC_2H_5$ | Ph- | 8-ethyl |
| | 36 | $CH_2OC_2H_5$ | Ph- | 8-iso-propyl |
| | 37 | $CH_2OC_2H_5$ | Ph- | 8-tert-butyl |
| | 38 | $CH_2OC_2H_5$ | Ph- | 8-OH |
| | 39 | $CH_2OC_2H_5$ | Ph- | 8-$OCH_3$ |
| | 40 | $CH_2OC_2H_5$ | Ph- | 8-O(iso-propyl) |
| | 41 | $CH_2OC_2H_5$ | Ph- | 8-$SCH_3$ |
| | 42 | $CH_2OC_2H_5$ | Ph- | 8-$SOCH_3$ |
| | 43 | $CH_2OC_2H_5$ | Ph- | 8-$SO_2CH_3$ |
| | 44 | $CH_2OC_2H_5$ | Ph- | 8-$SCH_2CH_3$ |
| | 45 | $CH_2OC_2H_5$ | Ph- | 8-$NH_2$ |
| | 46 | $CH_2OC_2H_5$ | Ph- | 8-NHOH |
| | 47 | $CH_2OC_2H_5$ | Ph- | 8-$NHCH_3$ |
| | 48 | $CH_2OC_2H_5$ | Ph- | 8-$N(CH_3)_2$ |
| | 49 | $CH_2OC_2H_5$ | Ph- | 8-$N^+(CH_3)_3$, $I^-$ |
| | 50 | $CH_2OC_2H_5$ | Ph- | 8-NHC(=O)$CH_3$ |
| | 51 | $CH_2OC_2H_5$ | Ph- | 8-$N(CH_2CH_3)_2$ |
| | 52 | $CH_2OC_2H_5$ | Ph- | 8-NMe$CH_2CO_2H$ |
| | 53 | $CH_2OC_2H_5$ | Ph- | 8-$N^+(Me)_2CH_2CO_2H$, $I^-$ |
| | 54 | $CH_2OC_2H_5$ | Ph- | 8-(N)-morpholine |
| | 55 | $CH_2OC_2H_5$ | Ph- | 8-(N)-azetidine |
| | 56 | $CH_2OC_2H_5$ | Ph- | 8-(N)-N-methylazetidinium, $I^-$ |
| | 57 | $CH_2OC_2H_5$ | Ph- | 8-(N)-pyrrolidine |
| | 58 | $CH_2OC_2H_5$ | Ph- | 8-(N)-N-methyl-pyrrolidinium, $I^-$ |
| | 59 | $CH_2OC_2H_5$ | Ph- | 8-(N)-N-methyl-morpholinium, $I^-$ |
| | 60 | $CH_2OC_2H_5$ | Ph- | 8-(N)-N'-methylpiperazine |
| | 61 | $CH_2OC_2H_5$ | Ph- | 8-(N)-N'-dimethylpiperazinium, $I^-$ |
| | 62 | $CH_2OC_2H_5$ | Ph- | 8-NH-CBZ |
| | 63 | $CH_2OC_2H_5$ | Ph- | 8-NHC(O)$C_5H_{11}$ |
| | 64 | $CH_2OC_2H_5$ | Ph- | 8-NHC(O)$CH_2Br$ |

TABLE 1-continued

Alternative Compounds #3 (Family F101.xxx.yyy)

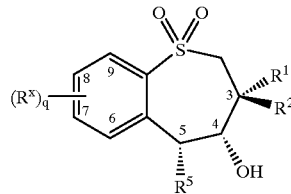

| Prefix (FFF.xxx. | Cpd# yyy) | R¹=R² | R⁵ | (Rˣ)q |
|---|---|---|---|---|
| | 65 | $CH_2OC_2H_5$ | Ph- | 8-NH-C(NH)$NH_2$ |
| | 66 | $CH_2OC_2H_5$ | Ph- | 8-(2)-thiophene |
| | 67 | $CH_2OC_2H_5$ | Ph- | 9-methyl |
| | 68 | $CH_2OC_2H_5$ | Ph- | 9-ethyl |
| | 69 | $CH_2OC_2H_5$ | Ph- | 9-iso-propyl |
| | 70 | $CH_2OC_2H_5$ | Ph- | 9-tert-butyl |
| | 71 | $CH_2OC_2H_5$ | Ph- | 9-OH |
| | 72 | $CH_2OC_2H_5$ | Ph- | 9-$OCH_3$ |
| | 73 | $CH_2OC_2H_5$ | Ph- | 9-O(iso-propyl) |
| | 74 | $CH_2OC_2H_5$ | Ph- | 9-$SCH_3$ |
| | 75 | $CH_2OC_2H_5$ | Ph- | 9-$SOCH_3$ |
| | 76 | $CH_2OC_2H_5$ | Ph- | 9-$SO_2CH_3$ |
| | 77 | $CH_2OC_2H_5$ | Ph- | 9-$SCH_2CH_3$ |
| | 78 | $CH_2OC_2H_5$ | Ph- | 9-$NH_2$ |
| | 79 | $CH_2OC_2H_5$ | Ph- | 9-NHOH |
| | 80 | $CH_2OC_2H_5$ | Ph- | 9-$NHCH_3$ |
| | 81 | $CH_2OC_2H_5$ | Ph- | 9-$N(CH_3)_2$ |
| | 82 | $CH_2OC_2H_5$ | Ph- | 9-$N^+(CH_3)_3$, $I^-$ |
| | 83 | $CH_2OC_2H_5$ | Ph- | 9-NHC(=O)$CH_3$ |
| | 84 | $CH_2OC_2H_5$ | Ph- | 9-$N(CH_2CH_3)_2$ |
| | 85 | $CH_2OC_2H_5$ | Ph- | 9-NMe$CH_2CO_2$H |
| | 86 | $CH_2OC_2H_5$ | Ph- | 9-$N^+(Me)_2CH_2CO_2$H, $I^-$ |
| | 87 | $CH_2OC_2H_5$ | Ph- | 9-(N)-morpholine |
| | 88 | $CH_2OC_2H_5$ | Ph- | 9-(N)-azetidine |
| | 89 | $CH_2OC_2H_5$ | Ph- | 9-(N)-N-methylazetidinium, $I^-$ |
| | 90 | $CH_2OC_2H_5$ | Ph- | 9-(N)-pyrrolidine |
| | 91 | $CH_2OC_2H_5$ | Ph- | 9-(N)-N-methyl-pyrrolidinium, $I^-$ |
| | 92 | $CH_2OC_2H_5$ | Ph- | 9-(N)-N-methyl-morpholinum, $I^-$ |
| | 93 | $CH_2OC_2H_5$ | Ph- | 9-(N)-N'-methylpiperazine |
| | 93 | $CH_2OC_2H_5$ | Ph- | 9-(N)-N'-dimethylpiperazinium, $I^-$ |
| | 95 | $CH_2OC_2H_5$ | Ph- | 9-NH-CBZ |
| | 96 | $CH_2OC_2H_5$ | Ph- | 9-NHC(O)$C_5H_{11}$ |
| | 97 | $CH_2OC_2H_5$ | Ph- | 9-NHC(O)$CH_2$Br |
| | 98 | $CH_2OC_2H_5$ | Ph- | 9-NH-C(NH)$NH_2$ |
| | 99 | $CH_2OC_2H_5$ | Ph- | 9-(2)-thiophene |
| | 100 | $CH_2OC_2H_5$ | Ph- | 7-$OCH_3$, 8-$OCH_3$ |
| | 101 | $CH_2OC_2H_5$ | Ph- | 7-$SCH_3$, 8-$OCH_3$ |
| | 102 | $CH_2OC_2H_5$ | Ph- | 7-$SCH_3$, 8-$SCH_3$ |
| | 103 | $CH_2OC_2H_5$ | Ph- | 6-$OCH_3$, 7-$OCH_3$, 8-$OCH_3$ |
| F101.011 | 01 | $CH_2CH(OH)C_2H_5$ | Ph- | 7-methyl |
| | 02 | $CH_2CH(OH)C_2H_5$ | Ph- | 7-ethyl |
| | 03 | $CH_2CH(OH)C_2H_5$ | Ph- | 7-iso-propyl |
| | 04 | $CH_2CH(OH)C_2H_5$ | Ph- | 7-tert-butyl |
| | 05 | $CH_2CH(OH)C_2H_5$ | Ph- | 7-OH |
| | 06 | $CH_2CH(OH)C_2H_5$ | Ph- | 7-$OCH_3$ |
| | 07 | $CH_2CH(OH)C_2H_5$ | Ph- | 7-O(iso-propyl) |
| | 08 | $CH_2CH(OH)C_2H_5$ | Ph- | 7-$SCH_3$ |
| | 09 | $CH_2CH(OH)C_2H_5$ | Ph- | 7-$SOCH_3$ |
| | 10 | $CH_2CH(OH)C_2H_5$ | Ph- | 7-$SO_2CH_3$ |
| | 11 | $CH_2CH(OH)C_2H_5$ | Ph- | 7-$SCH_2CH_3$ |
| | 12 | $CH_2CH(OH)C_2H_5$ | Ph- | 7-$NH_2$ |
| | 13 | $CH_2CH(OH)C_2H_5$ | Ph- | 7-NHOH |
| | 14 | $CH_2CH(OH)C_2H_5$ | Ph- | 7-$NHCH_3$ |
| | 15 | $CH_2CH(OH)C_2H_5$ | Ph- | 7-$N(CH_3)_2$ |
| | 16 | $CH_2CH(OH)C_2H_5$ | Ph- | 7-$N^+(CH_3)_3$, $I^-$ |
| | 17 | $CH_2CH(OH)C_2H_5$ | Ph- | 7-NHC(=O)$CH_3$ |
| | 18 | $CH_2CH(OH)C_2H_5$ | Ph- | 7-$N(CH_2CH_3)_2$ |
| | 19 | $CH_2CH(OH)C_2H_5$ | Ph- | 7-NMe$CH_2CO_2$H |
| | 20 | $CH_2CH(OH)C_2H_5$ | Ph- | 7-$N^+(Me)_2CH_2CO_2$H, $I^-$ |
| | 21 | $CH_2CH(OH)C_2H_5$ | Ph- | 7-(N)-morpholine |
| | 22 | $CH_2CH(OH)C_2H_5$ | Ph- | 7-(N)-azetidine |
| | 23 | $CH_2CH(OH)C_2H_5$ | Ph- | 7-(N)-N-methylazetidinium, $I^-$ |
| | 24 | $CH_2CH(OH)C_2H_5$ | Ph- | 7-(N)-pyrrolidine |
| | 25 | $CH_2CH(OH)C_2H_5$ | Ph- | 7-(N)-N-methyl-pyrrolidinium, $I^-$ |

TABLE 1-continued

Alternative Compounds #3 (Family F101.xxx.yyy)

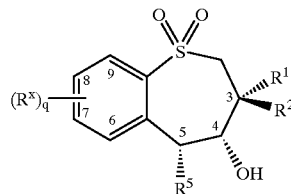

| Prefix (FFF.xxx. | Cpd# yyy) | $R^1=R^2$ | $R^5$ | $(R^x)q$ |
|---|---|---|---|---|
| | 26 | $CH_2CH(OH)C_2H_5$ | Ph- | 7-(N)-N-methyl-morpholinum, $I^-$ |
| | 27 | $CH_2CH(OH)C_2H_5$ | Ph- | 7-(N)-N'-methylpiperazine |
| | 28 | $CH_2CH(OH)C_2H_5$ | Ph- | 7-(N)-N'-dimethylpiperazinium, $I^-$ |
| | 29 | $CH_2CH(OH)C_2H_5$ | Ph- | 7-NH-CBZ |
| | 30 | $CH_2CH(OH)C_2H_5$ | Ph- | 7-NHC(O)$C_5H_{11}$ |
| | 31 | $CH_2CH(OH)C_2H_5$ | Ph- | 7-NHC(O)$CH_2Br$ |
| | 32 | $CH_2CH(OH)C_2H_5$ | Ph- | 7-NH-C(NH)$NH_2$ |
| | 33 | $CH_2CH(OH)C_2H_5$ | Ph- | 7-(2)-thiophene |
| | 34 | $CH_2CH(OH)C_2H_5$ | Ph- | 8-methyl |
| | 35 | $CH_2CH(OH)C_2H_5$ | Ph- | 8-ethyl |
| | 36 | $CH_2CH(OH)C_2H_5$ | Ph- | 8-iso-propyl |
| | 37 | $CH_2CH(OH)C_2H_5$ | Ph- | 8-tert-butyl |
| | 38 | $CH_2CH(OH)C_2H_5$ | Ph- | 8-OH |
| | 39 | $CH_2CH(OH)C_2H_5$ | Ph- | 8-$OCH_3$ |
| | 40 | $CH_2CH(OH)C_2H_5$ | Ph- | 8-O(iso-propyl) |
| | 41 | $CH_2CH(OH)C_2H_5$ | Ph- | 8-$SCH_3$ |
| | 42 | $CH_2CH(OH)C_2H_5$ | Ph- | 8-$SOCH_3$ |
| | 43 | $CH_2CH(OH)C_2H_5$ | Ph- | 8-$SO_2CH_3$ |
| | 44 | $CH_2CH(OH)C_2H_5$ | Ph- | 8-$SCH_2CH_3$ |
| | 45 | $CH_2CH(OH)C_2H_5$ | Ph- | 8-$NH_2$ |
| | 46 | $CH_2CH(OH)C_2H_5$ | Ph- | 8-NHOH |
| | 47 | $CH_2CH(OH)C_2H_5$ | Ph- | 8-$NHCH_3$ |
| | 48 | $CH_2CH(OH)C_2H_5$ | Ph- | 8-$N(CH_3)_2$ |
| | 49 | $CH_2CH(OH)C_2H_5$ | Ph- | 8-$N^+(CH_3)_3$, $I^-$ |
| | 50 | $CH_2CH(OH)C_2H_5$ | Ph- | 8-NHC(=O)$CH_3$ |
| | 51 | $CH_2CH(OH)C_2H_5$ | Ph- | 8-$N(CH_2CH_3)_2$ |
| | 52 | $CH_2CH(OH)C_2H_5$ | Ph- | 8-NMe$CH_2CO_2H$ |
| | 53 | $CH_2CH(OH)C_2H_5$ | Ph- | 8-$N^+(Me)_2CH_2CO_2H$, $I^-$ |
| | 54 | $CH_2CH(OH)C_2H_5$ | Ph- | 8-(N)-morpholine |
| | 55 | $CH_2CH(OH)C_2H_5$ | Ph- | 8-(N)-azetidine |
| | 56 | $CH_2CH(OH)C_2H_5$ | Ph- | 8-(N)-N-methylazetidinium, $I^-$ |
| | 57 | $CH_2CH(OH)C_2H_5$ | Ph- | 8-(N)-pyrrolidine |
| | 58 | $CH_2CH(OH)C_2H_5$ | Ph- | 8-(N)-N-methyl-pyrrolidinium, $I^-$ |
| | 59 | $CH_2CH(OH)C_2H_5$ | Ph- | 8-(N)-N-methyl-morpholinium, $I^-$ |
| | 60 | $CH_2CH(OH)C_2H_5$ | Ph- | 8-(N)-N'-methylpiperazine |
| | 61 | $CH_2CH(OH)C_2H_5$ | Ph- | 8-(N)-N'-dimethylpiperazinium, $I^-$ |
| | 62 | $CH_2CH(OH)C_2H_5$ | Ph- | 8-NH-CBZ |
| | 63 | $CH_2CH(OH)C_2H_5$ | Ph- | 8-NHC(O)$C_5H_{11}$ |
| | 64 | $CH_2CH(OH)C_2H_5$ | Ph- | 8-NHC(O)$CH_2Br$ |
| | 65 | $CH_2CH(OH)C_2H_5$ | Ph- | 8-NH-C(NH)$NH_2$ |
| | 66 | $CH_2CH(OH)C_2H_5$ | Ph- | 8-(2)-thiophene |
| | 67 | $CH_2CH(OH)C_2H_5$ | Ph- | 9-methyl |
| | 68 | $CH_2CH(OH)C_2H_5$ | Ph- | 9-ethyl |
| | 69 | $CH_2CH(OH)C_2H_5$ | Ph- | 9-iso-propyl |
| | 70 | $CH_2CH(OH)C_2H_5$ | Ph- | 9-tert-butyl |
| | 71 | $CH_2CH(OH)C_2H_5$ | Ph- | 9-OH |
| | 72 | $CH_2CH(OH)C_2H_5$ | Ph- | 9-$OCH_3$ |
| | 73 | $CH_2CH(OH)C_2H_5$ | Ph- | 9-O(iso-propyl) |
| | 74 | $CH_2CH(OH)C_2H_5$ | Ph- | 9-$SCH_3$ |
| | 75 | $CH_2CH(OH)C_2H_5$ | Ph- | 9-$SOCH_3$ |
| | 76 | $CH_2CH(OH)C_2H_5$ | Ph- | 9-$SO_2CH_3$ |
| | 77 | $CH_2CH(OH)C_2H_5$ | Ph- | 9-$SCH_2CH_3$ |
| | 78 | $CH_2CH(OH)C_2H_5$ | Ph- | 9-$NH_2$ |
| | 79 | $CH_2CH(OH)C_2H_5$ | Ph- | 9-NHOH |
| | 80 | $CH_2CH(OH)C_2H_5$ | Ph- | 9-$NHCH_3$ |
| | 81 | $CH_2CH(OH)C_2H_5$ | Ph- | 9-$N(CH_3)_2$ |
| | 82 | $CH_2CH(OH)C_2H_5$ | Ph- | 9-$N^+(CH_3)_3$, $I^-$ |
| | 83 | $CH_2CH(OH)C_2H_5$ | Ph- | 9-NHC(=O)$CH_3$ |
| | 84 | $CH_2CH(OH)C_2H_5$ | Ph- | 9-$N(CH_2CH_3)_2$ |
| | 85 | $CH_2CH(OH)C_2H_5$ | Ph- | 9-NMe$CH_2CO_2H$ |
| | 86 | $CH_2CH(OH)C_2H_5$ | Ph- | 9-$N^+(Me)_2CH_2CO_2H$, $I^-$ |
| | 87 | $CH_2CH(OH)C_2H_5$ | Ph- | 9-(N)-morpholine |
| | 88 | $CH_2CH(OH)C_2H_5$ | Ph- | 9-(N)-azetidine |
| | 89 | $CH_2CH(OH)C_2H_5$ | Ph- | 9-(N)-N-methylazetidinium, $I^-$ |

TABLE 1-continued

Alternative Compounds #3 (Family F101.xxx.yyy)

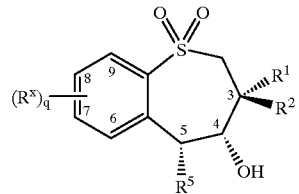

| Prefix (FFF.xxx. | Cpd# yyy) | $R^1=R^2$ | $R^5$ | $(R^x)q$ |
|---|---|---|---|---|
| | 90 | $CH_2CH(OH)C_2H_5$ | Ph- | 9-(N)-pyrrolidine |
| | 91 | $CH_2CH(OH)C_2H_5$ | Ph- | 9-(N)-N-methyl-pyrrolidinium, I$^-$ |
| | 92 | $CH_2CH(OH)C_2H_5$ | Ph- | 9-(N)-N-methyl-morpholinum, I$^-$ |
| | 93 | $CH_2CH(OH)C_2H_5$ | Ph- | 9-(N)-N'-methylpiperazine |
| | 93 | $CH_2CH(OH)C_2H_5$ | Ph- | 9-(N)-N'-dimethylpiperazinium, I$^-$ |
| | 95 | $CH_2CH(OH)C_2H_5$ | Ph- | 9-NH-CBZ |
| | 96 | $CH_2CH(OH)C_2H_5$ | Ph- | 9-NHC(O)C$_5$H$_{11}$ |
| | 97 | $CH_2CH(OH)C_2H_5$ | Ph- | 9-NHC(O)CH$_2$Br |
| | 98 | $CH_2CH(OH)C_2H_5$ | Ph- | 9-NH-C(NH)NH$_2$ |
| | 99 | $CH_2CH(OH)C_2H_5$ | Ph- | 9-(2)-thiophene |
| | 100 | $CH_2CH(OH)C_2H_5$ | Ph- | 7-OCH$_3$, 8-OCH$_3$ |
| | 101 | $CH_2CH(OH)C_2H_5$ | Ph- | 7-SCH$_3$, 8-OCH$_3$ |
| | 102 | $CH_2CH(OH)C_2H_5$ | Ph- | 7-SCH$_3$, 8-SCH$_3$ |
| | 103 | $CH_2CH(OH)C_2H_5$ | Ph- | 6-OCH$_3$, 7-OCH$_3$, 8-OCH$_3$ |
| F101.012 | 01 | $CH_2O$-(4-picoline) | Ph- | 7-methyl |
| | 02 | $CH_2O$-(4-picoline) | Ph- | 7-ethyl |
| | 03 | $CH_2O$-(4-picoline) | Ph- | 7-iso-propyl |
| | 04 | $CH_2O$-(4-picoline) | Ph- | 7-tert-butyl |
| | 05 | $CH_2O$-(4-picoline) | Ph- | 7-OH |
| | 06 | $CH_2O$-(4-picoline) | Ph- | 7-OCH$_3$ |
| | 07 | $CH_2O$-(4-picoline) | Ph- | 7-O(iso-propyl) |
| | 08 | $CH_2O$-(4-picoline) | Ph- | 7-SCH$_3$ |
| | 09 | $CH_2O$-(4-picoline) | Ph- | 7-SOCH$_3$ |
| | 10 | $CH_2O$-(4-picoline) | Ph- | 7-SO$_2$CH$_3$ |
| | 11 | $CH_2O$-(4-picoline) | Ph- | 7-SCH$_2$CH$_3$ |
| | 12 | $CH_2O$-(4-picoline) | Ph- | 7-NH$_2$ |
| | 13 | $CH_2O$-(4-picoline) | Ph- | 7-NHOH |
| | 14 | $CH_2O$-(4-picoline) | Ph- | 7-NHCH$_3$ |
| | 15 | $CH_2O$-(4-picoline) | Ph- | 7-N(CH$_3$)$_2$ |
| | 16 | $CH_2O$-(4-picoline) | Ph- | 7-N$^+$(CH$_3$)$_3$, I$^-$ |
| | 17 | $CH_2O$-(4-picoline) | Ph- | 7-NHC(=O)CH$_3$ |
| | 18 | $CH_2O$-(4-picoline) | Ph- | 7-N(CH$_2$CH$_3$)$_2$ |
| | 19 | $CH_2O$-(4-picoline) | Ph- | 7-NMeCH$_2$CO$_2$H |
| | 20 | $CH_2O$-(4-picoline) | Ph- | 7-N$^+$(Me)$_2$CH$_2$CO$_2$H, I$^-$ |
| | 21 | $CH_2O$-(4-picoline) | Ph- | 7-(N)-morpholine |
| | 22 | $CH_2O$-(4-picoline) | Ph- | 7-(N)-azetidine |
| | 23 | $CH_2O$-(4-picoline) | Ph- | 7-(N)-N-methylazetidinium, I$^-$ |
| | 24 | $CH_2O$-(4-picoline) | Ph- | 7-(N)-pyrrolidine |
| | 25 | $CH_2O$-(4-picoline) | Ph- | 7-(N)-N-methyl-pyrrolidinium, I$^-$ |
| | 26 | $CH_2O$-(4-picoline) | Ph- | 7-(N)-N-methyl-morpholinum, I$^-$ |
| | 27 | $CH_2O$-(4-picoline) | Ph- | 7-(N)-N'-methylpiperazine |
| | 28 | $CH_2O$-(4-picoline) | Ph- | 7-(N)-N'-dimethylpiperazinium, I$^-$ |
| | 29 | $CH_2O$-(4-picoline) | Ph- | 7-NH-CBZ |
| | 30 | $CH_2O$-(4-picoline) | Ph- | 7-NHC(O)C$_5$H$_{11}$ |
| | 31 | $CH_2O$-(4-picoline) | Ph- | 7-NHC(O)CH$_2$Br |
| | 32 | $CH_2O$-(4-picoline) | Ph- | 7-NH-C(NH)NH$_2$ |
| | 33 | $CH_2O$-(4-picoline) | Ph- | 7-(2)-thiophene |
| | 34 | $CH_2O$-(4-picoline) | Ph- | 8-methyl |
| | 35 | $CH_2O$-(4-picoline) | Ph- | 8-ethyl |
| | 36 | $CH_2O$-(4-picoline) | Ph- | 8-iso-propyl |
| | 37 | $CH_2O$-(4-picoline) | Ph- | 8-tert-butyl |
| | 38 | $CH_2O$-(4-picoline) | Ph- | 8-OH |
| | 39 | $CH_2O$-(4-picoline) | Ph- | 8-OCH$_3$ |
| | 40 | $CH_2O$-(4-picoline) | Ph- | 8-O(iso-propyl) |
| | 41 | $CH_2O$-(4-picoline) | Ph- | 8-SCH$_3$ |
| | 42 | $CH_2O$-(4-picoline) | Ph- | 8-SOCH$_3$ |
| | 43 | $CH_2O$-(4-picoline) | Ph- | 8-SO$_2$CH$_3$ |
| | 44 | $CH_2O$-(4-picoline) | Ph- | 8-SCH$_2$CH$_3$ |
| | 45 | $CH_2O$-(4-picoline) | Ph- | 8-NH$_2$ |
| | 46 | $CH_2O$-(4-picoline) | Ph- | 8-NHOH |
| | 47 | $CH_2O$-(4-picoline) | Ph- | 8-NHCH$_3$ |
| | 48 | $CH_2O$-(4-picoline) | Ph- | 8-N(CH$_3$)$_2$ |
| | 49 | $CH_2O$-(4-picoline) | Ph- | 8-N$^+$(CH$_3$)$_3$, I$^-$ |
| | 50 | $CH_2O$-(4-picoline) | Ph- | 8-NHC(=O)CH$_3$ |

TABLE 1-continued

Alternative Compounds #3 (Family F101.xxx.yyy)

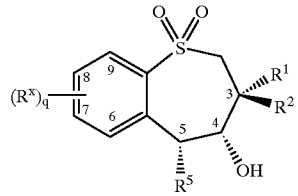

| Prefix (FFF.xxx. | Cpd# yyy) | R¹=R² | R⁵ | (Rˣ)q |
|---|---|---|---|---|
| | 51 | CH₂O-(4-picoline) | Ph- | 8-N(CH₂CH₃)₂ |
| | 52 | CH₂O-(4-picoline) | Ph- | 8-NMeCH₂CO₂H |
| | 53 | CH₂O-(4-picoline) | Ph- | 8-N⁺(Me)₂CH₂CO₂H, I⁻ |
| | 54 | CH₂O-(4-picoline) | Ph- | 8-(N)-morpholine |
| | 55 | CH₂O-(4-picoline) | Ph- | 8-(N)-azetidine |
| | 56 | CH₂O-(4-picoline) | Ph- | 8-(N)-N-methylazetidinium, I⁻ |
| | 57 | CH₂O-(4-picoline) | Ph- | 8-(N)-pyrrolidine |
| | 58 | CH₂O-(4-picoline) | Ph- | 8-(N)-N-methyl-pyrrolidinium, I⁻ |
| | 59 | CH₂O-(4-picoline) | Ph- | 8-(N)-N-methyl-morpholinium, I⁻ |
| | 60 | CH₂O-(4-picoline) | Ph- | 8-(N)-N'-methylpiperazine |
| | 61 | CH₂O-(4-picoline) | Ph- | 8-(N)-N'-dimethylpiperazinium, I⁻ |
| | 62 | CH₂O-(4-picoline) | Ph- | 8-NH-CBZ |
| | 63 | CH₂O-(4-picoline) | Ph- | 8-NHC(O)C₅H₁₁ |
| | 64 | CH₂O-(4-picoline) | Ph- | 8-NHC(O)CH₂Br |
| | 65 | CH₂O-(4-picoline) | Ph- | 8-NH-C(NH)NH₂ |
| | 66 | CH₂O-(4-picoline) | Ph- | 8-(2)-thiophene |
| | 67 | CH₂O-(4-picoline) | Ph- | 9-methyl |
| | 68 | CH₂O-(4-picoline) | Ph- | 9-ethyl |
| | 69 | CH₂O-(4-picoline) | Ph- | 9-iso-propyl |
| | 70 | CH₂O-(4-picoline) | Ph- | 9-tert-butyl |
| | 71 | CH₂O-(4-picoline) | Ph- | 9-OH |
| | 72 | CH₂O-(4-picoline) | Ph- | 9-OCH₃ |
| | 73 | CH₂O-(4-picoline) | Ph- | 9-O(iso-propyl) |
| | 74 | CH₂O-(4-picoline) | Ph- | 9-SCH₃ |
| | 75 | CH₂O-(4-picoline) | Ph- | 9-SOCH₃ |
| | 76 | CH₂O-(4-picoline) | Ph- | 9-SO₂CH₃ |
| | 77 | CH₂O-(4-picoline) | Ph- | 9-SCH₂CH₃ |
| | 78 | CH₂O-(4-picoline) | Ph- | 9-NH₂ |
| | 79 | CH₂O-(4-picoline) | Ph- | 9-NHOH |
| | 80 | CH₂O-(4-picoline) | Ph- | 9-NHCH₃ |
| | 81 | CH₂O-(4-picoline) | Ph- | 9-N(CH₃)₂ |
| | 82 | CH₂O-(4-picoline) | Ph- | 9-N⁺(CH₃)₃, I⁻ |
| | 83 | CH₂O-(4-picoline) | Ph- | 9-NHC(=O)CH₃ |
| | 84 | CH₂O-(4-picoline) | Ph- | 9-N(CH₂CH₃)₂ |
| | 85 | CH₂O-(4-picoline) | Ph- | 9-NMeCH₂CO₂H |
| | 86 | CH₂O-(4-picoline) | Ph- | 9-N⁺(Me)₂CH₂CO₂H, I⁻ |
| | 87 | CH₂O-(4-picoline) | Ph- | 9-(N)-morpholine |
| | 88 | CH₂O-(4-picoline) | Ph- | 9-(N)-azetidine |
| | 89 | CH₂O-(4-picoline) | Ph- | 9-(N)-N-methylazetidinium, I⁻ |
| | 90 | CH₂O-(4-picoline) | Ph- | 9-(N)-pyrrolidine |
| | 91 | CH₂O-(4-picoline) | Ph- | 9-(N)-N-methyl-pyrrolidinium, I⁻ |
| | 92 | CH₂O-(4-picoline) | Ph- | 9-(N)-N-methyl-morpholinum, I⁻ |
| | 93 | CH₂O-(4-picoline) | Ph- | 9-(N)-N'-methylpiperazine |
| | 93 | CH₂O-(4-picoline) | Ph- | 9-(N)-N'-dimethylpiperazinium, I⁻ |
| | 95 | CH₂O-(4-picoline) | Ph- | 9-NH-CBZ |
| | 96 | CH₂O-(4-picoline) | Ph- | 9-NHC(O)C₅H₁₁ |
| | 97 | CH₂O-(4-picoline) | Ph- | 9-NHC(O)CH₂Br |
| | 98 | CH₂O-(4-picoline) | Ph- | 9-NH-C(NH)NH₂ |
| | 99 | CH₂O-(4-picoline) | Ph- | 9-(2)-thiophene |
| | 100 | CH₂O-(4-picoline) | Ph- | 7-OCH₃, 8-OCH₃ |
| | 101 | CH₂O-(4-picoline) | Ph- | 7-SCH₃, 8-OCH₃ |
| | 102 | CH₂O-(4-picoline) | Ph- | 7-SCH₃, 8-SCH₃ |
| | 103 | CH₂O-(4-picoline) | Ph- | 6-OCH₃, 7-OCH₃, 8-OCH₃ |

Additional Structures of the Present Invention

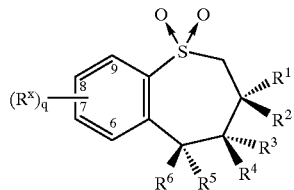

| Compound Number | R¹ | R² | R³ | R⁴ | R⁵ |
|---|---|---|---|---|---|
| 101 | ethyl | n-butyl | OH | H | phenyl |
| 102 | ethyl | n-butyl | OH | H | phenyl |
| 103 | n-butyl | ethyl | OH | H | phenyl |
| 104 | ethyl | n-butyl | OH | H | phenyl |
| 105 | ethyl | n-butyl | OH | H | phenyl |
| 106 | ethyl | n-butyl | OH | H | phenyl |
| 107 | n-butyl | ethyl | OH | H | 4-(decyloxy)phenyl |
| 108 | ethyl | n-butyl | OH | H | phenyl |
| 109 | ethyl | n-butyl | OH | H | 4-(decyloxy)phenyl |
| 110 | ethyl | n-butyl | OH | H | phenyl |
| 111 | n-butyl | ethyl | OH | H | 4-hydroxyphenyl |
| 112 | ethyl | n-butyl | OH | H | (structure shown) |
| 113 | ethyl | n-butyl | OH | H | 4-hydroxyphenyl |
| 114 | ethyl | n-butyl | OH | H | 4-methoxyphenyl |
| 115 | n-butyl | ethyl | OH | H | 4-methoxyphenyl |
| 116 | ethyl | n-butyl | OH | H | 4-methoxyphenyl |
| 117 | n-butyl | ethyl | OH | H | phenyl |
| 118 | ethyl | n-butyl | OH | H | phenyl |
| 119 | ethyl | n-butyl | OH | H | phenyl |
| 120 | n-butyl | ethyl | OH | H | phenyl |
| 121 | ethyl | n-butyl | OH | H | phenyl |
| 122 | n-butyl | ethyl | OH | H | phenyl |
| 123 | ethyl | n-butyl | OH | H | phenyl |
| 124 | n-butyl | ethyl | OH | H | phenyl |
| 125 | ethyl | n-butyl | OH | H | phenyl |
| 126 | n-butyl | ethyl | OH | H | 4-fluorophenyl |
| 127 | n-butyl | ethyl | OH | H | 4-fluorophenyl |
| 128 | ethyl | n-butyl | OH | H | 4-fluorophenyl |
| 129 | ethyl | n-butyl | OH | H | 4-fluorophenyl |
| 131 | ethyl | n-butyl | OH | H | 4-fluorophenyl |
| 132 | ethyl | n-butyl | OH | H | phenyl |
| 133 | ethyl | n-butyl | OH | H | phenyl |
| 134 | ethyl | n-butyl | OH | H | phenyl |
| 135 | ethyl | n-butyl | OH | H | phenyl |
| 136 | ethyl | n-butyl | OH | H | phenyl |
| 137 | n-butyl | ethyl | OH | H | phenyl |
| 138 | n-butyl | ethyl | OH | H | phenyl |
| 139 | n-butyl | ethyl | OH | H | phenyl |
| 140 | | | | | |
| 141 | | | | | |
| 142 | ethyl | n-butyl | H | OH | H |
| 143 | ethyl | n-butyl | OH | H | 3-methoxyphenyl |
| 144 | ethyl | n-butyl | OH | H | 4-fluorophenyl |
| 262 | ethyl | n-butyl | OH | H | 3-methoxyphenyl |
| 263 | ethyl | n-butyl | H | OH | H |
| 264 | ethyl | n-butyl | OH | H | 3-trifluoromethylphenyl |
| 265 | ethyl | n-butyl | H | OH | H |
| 266 | ethyl | n-butyl | OH | H | 3-hydroxyphenyl |
| 267 | ethyl | n-butyl | OH | H | 3-hydroxyphenyl |
| 268 | ethyl | n-butyl | OH | H | 4-fluorophenyl |

-continued

Additional Structures of the Present Invention

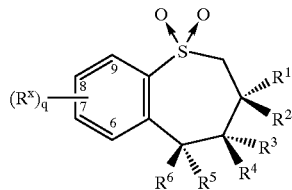

| Compound Number | $R^1$ | $R^2$ | $R^3$ | $R^4$ | $R^5$ |
|---|---|---|---|---|---|
| 269 | ethyl | n-butyl | H | OH | H |
| 270 | ethyl | n-butyl | OH | H | 4-fluorophenyl |
| 271 | ethyl | n-butyl | OH | H | 3-methoxyphenyl |
| 272 | ethyl | n-butyl | H | OH | H |
| 273 | ethyl | n-butyl | H | OH | H |
| 274 | ethyl | n-butyl | OH | H | 4-fluorophenyl |
| 275 | ethyl | n-butyl | H | OH | H |
| 276 | ethyl | n-butyl | OH | H | 3-methoxyphenyl |
| 277 | ethyl | n-butyl | OH | H | 3-fluorophenyl |
| 278 | ethyl | n-butyl | H | OH | 2-fluorophenyl |
| 279 | ethyl | n-butyl | H | OH | 3-fluorophenyl |
| 280 | ethyl | n-butyl | OH | H | 2-fluorophenyl |
| 281 | ethyl | n-butyl | OH | H | 4-fluorophenyl |
| 282 | ethyl | n-butyl | OH | H | 4-fluorophenyl |
| 283 | ethyl | n-butyl | H | OH | H |
| 284 | ethyl | n-butyl | OH | H | 4-fluorophenyl |
| 286 | ethyl | ethyl | OH | H | phenyl |
| 287 | ethyl | ethyl | OH | H | phenyl |
| 288 | methyl | methyl | OH | H | phenyl |
| 289 | n-butyl | n-butyl | OH | H | phenyl |
| 290 | n-butyl | n-butyl | OH | H | phenyl |
| 291 | n-butyl | n-butyl | OH | H | phenyl |
| 292 | n-butyl | n-butyl | OH | H | 4-fluorophenyl |
| 293 | n-butyl | n-butyl | OH | H | phenyl |
| 294 | n-butyl | n-butyl | OH | H | phenyl |
| 295 | ethyl | n-butyl | OH | H | 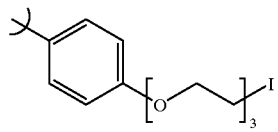 |
| 296 | ethyl | n-butyl | OH | H | 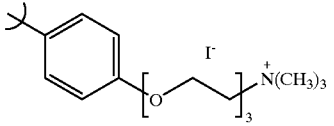 |
| 1000 | ethyl | n-butyl | OH | H | 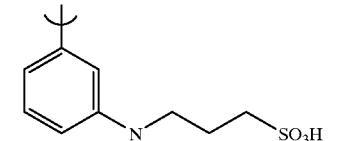 |
| 1001 | ethyl | n-butyl | OH | H | 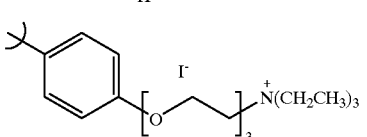 |
| 1002 | ethyl | n-butyl | OH | H | 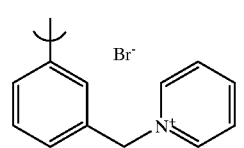 |

-continued

Additional Structures of the Present Invention

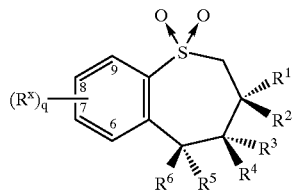

| Compound Number | R¹ | R² | R³ | R⁴ | R⁵ |
|---|---|---|---|---|---|
| 1003 | ethyl | n-butyl | OH | H | 3-(2-triethylammoniumethoxy)phenyl, iodide |
| 1004 | ethyl | n-butyl | OH | H | 3-(5-triethylammoniumpentanamido)phenyl, trifluoroacetate salt |
| 1005 | n-butyl | n-butyl | OH | H | 3-(5-triethylammoniumpentanamido)phenyl, trifluoroacetate salt |
| 1006 | n-butyl | n-butyl | OH | H | 3-fluoro-4-[2-(2-(1,4-dimethylpiperazinium)ethoxy)ethoxy]phenyl, bromide |
| 1007 | n-butyl | n-butyl | OH | H | 3-[(triethylammonium)-(OCH₂CH₂)₃-O]phenyl, iodide |
| 1008 | n-butyl | n-butyl | OH | H | 3-[(pyridazinium)-(OCH₂CH₂)₃-O]phenyl, iodide |
| 1009 | n-butyl | n-butyl | OH | H | 3-[(4-dimethylaminopyridinium)-(OCH₂CH₂)₃-O]phenyl, iodide |
| 1010 | n-butyl | n-butyl | OH | H | 3-fluoro-4-methoxyphenyl |
| 1011 | n-butyl | n-butyl | OH | H | 3-fluoro-4-(5-triethylammoniumpentyloxy)phenyl, trifluoroacetate salt |
| 1012 | n-butyl | n-butyl | OH | H | 4-hydroxyphenyl |

-continued

Additional Structures of the Present Invention

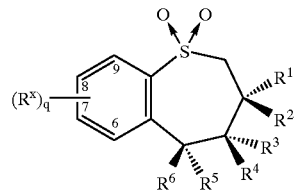

| Compound Number | $R^1$ | $R^2$ | $R^3$ | $R^4$ | $R^5$ |
|---|---|---|---|---|---|
| 1013 | n-butyl | n-butyl | OH | H | 4-[O(CH$_2$)$_2$]$_3$N$^+$(CH$_3$)$_3$ I$^-$, 2-F phenyl |
| 1014 | n-butyl | n-butyl | OH | H | 4-methoxyphenyl |
| 1015 | n-butyl | n-butyl | OH | H | 4-[O(CH$_2$)$_2$]$_2$-(N-methylpyrrolidinium) Br$^-$, 2-F phenyl |
| 1016 | n-butyl | n-butyl | OH | H | 3-[O(CH$_2$)$_2$]$_3$N$^+$(CH$_3$)$_2$CH$_2$CO$_2$H I$^-$ phenyl |
| 1017 | n-butyl | n-butyl | OH | H | 3-[O(CH$_2$)$_2$]$_3$-(4-methylquinolinium) I$^-$ phenyl |
| 1018 | n-butyl | n-butyl | OH | H | 3-[O(CH$_2$)$_2$]$_3$N$^+$(CH$_3$)$_2$CH$_2$CH$_2$N(CH$_3$)C(O)Ph I$^-$ phenyl |
| 1019 | n-butyl | n-butyl | OH | H | 4-[O(CH$_2$)$_4$O(CH$_2$)$_4$-pyridinium] CF$_3$CO$_2^-$, 2-F phenyl |
| 1020 | n-butyl | n-butyl | OH | H | 4-[OCH$_2$-(pyridine-2,6-diyl)-CH$_2$N$^+$(CH$_2$CH$_3$)$_3$] Cl$^-$, 2-F phenyl |

-continued
Additional Structures of the Present Invention
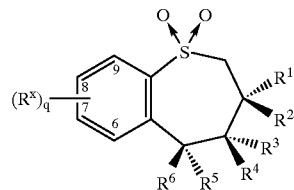
| Compound Number | R¹ | R² | R³ | R⁴ | R⁵ |
|---|---|---|---|---|---|
| 1021 | n-butyl | n-butyl | OH | H | |
| 1022 | n-butyl | n-butyl | OH | H | |
| 1023 | n-butyl | n-butyl | OH | H | |
| 1024 | n-butyl | n-butyl | OH | H | |
| 1025 | n-butyl | n-butyl | OH | H | |
| 1026 | n-butyl | n-butyl | OH | H | |

Additional Structures of the Present Invention
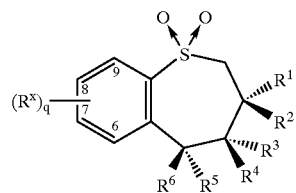
| Compound Number | R¹ | R² | R³ | R⁴ | R⁵ |
|---|---|---|---|---|---|
| 1027 | n-butyl | n-butyl | OH | H | |
| 1028 | n-butyl | n-butyl | OH | H | |
| 1029 | n-butyl | n-butyl | OH | H | |
| 1030 | n-butyl | n-butyl | OH | H | |
| 1031 | n-butyl | n-butyl | OH | H | |
| 1032 | n-butyl | n-butyl | OH | H | |
| 1033 | n-butyl | n-butyl | OH | H | |

Additional Structures of the Present Invention
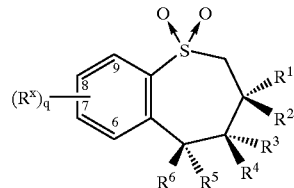
| Compound Number | R¹ | R² | R³ | R⁴ | R⁵ |
|---|---|---|---|---|---|
| 1034 | n-butyl | n-butyl | OH | H | 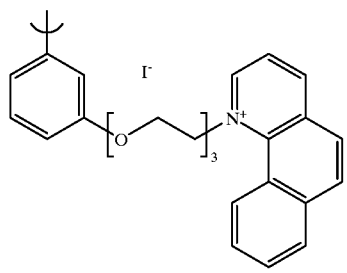 |
| 1035 | n-butyl | n-butyl | OH | H | 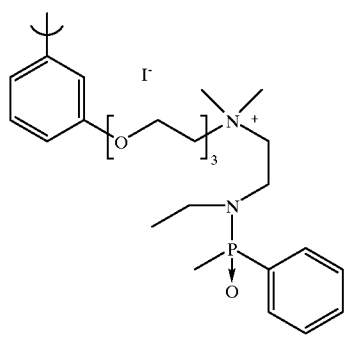 |
| 1036 | n-butyl | n-butyl | OH | H | 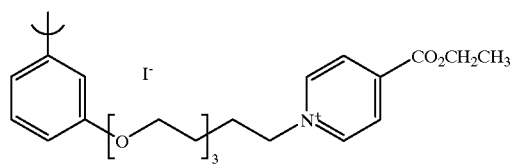 |
| 1037 | n-butyl | n-butyl | OH | H | 4-hydroxyphenyl |
| 1038 | n-butyl | n-butyl | OH | H | 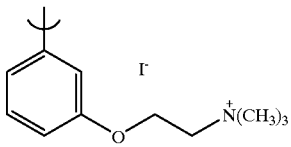 |
| 1039 | n-butyl | n-butyl | OH | H | phenyl |
| 1040 | n-butyl | n-butyl | OH | H | 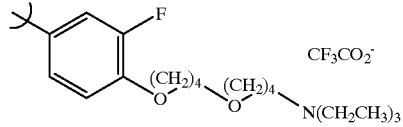 |
| 1041 | n-butyl | n-butyl | OH | H | 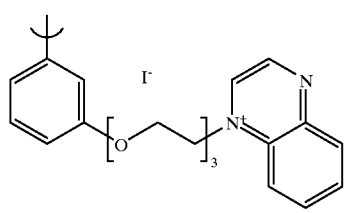 |

-continued

Additional Structures of the Present Invention

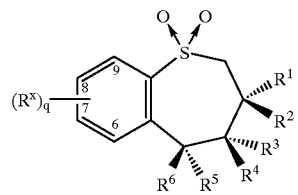

| Compound Number | $R^1$ | $R^2$ | $R^3$ | $R^4$ | $R^5$ |
|---|---|---|---|---|---|
| 1042 | n-butyl | n-butyl | OH | H | 4-[O(CH$_2$CH$_2$)$_3$N$^+$(C$_6$H$_5$)$_3$] I$^-$ phenyl |
| 1043 | n-butyl | n-butyl | OH | H | 3-(NHC(O)CH=CH$_2$)phenyl |
| 1044 | n-butyl | n-butyl | OH | H | 3-fluoro-4-[O(CH$_2$CH$_2$)$_2$N$^+$(CH$_2$CH$_3$)$_3$] CF$_3$CO$_2^-$ phenyl |
| 1045 | n-butyl | n-butyl | OH | H | 3-fluoro-4-[O(CH$_2$)$_8$N(CH$_2$CH$_3$)$_3$] CF$_3$CO$_2^-$ phenyl |
| 1046 | n-butyl | n-butyl | OH | H | 3-aminophenyl |
| 1047 | n-butyl | n-butyl | OH | H | 3-[O(CH$_2$CH$_2$)$_3$N$^+$(Et)$_2$CH$_2$CH$_2$N(CH$_2$CH$_3$)$_2$] I$^-$ phenyl |
| 1048 | n-butyl | n-butyl | OH | H | 4-[O(CH$_2$CH$_2$)$_3$N$^+$(CH$_2$CH$_3$)$_3$] I$^-$ phenyl |
| 1049 | n-butyl | n-butyl | OH | H | 3-fluoro-4-[O(CH$_2$CH$_2$)$_2$-pyridinium] Br$^-$ phenyl |
| 1050 | n-butyl | n-butyl | OH | H | 3-[O(CH$_2$CH$_2$)$_3$-N-methylpiperazinium-N'-P(O)(CH$_3$)(C$_6$H$_5$)] I$^-$ phenyl |
| 1051 | n-butyl | n-butyl | OH | H | 3-fluoro-4-[OCH$_2$-(1-methylpyridinium-4-yl)] CF$_3$CO$_2^-$ phenyl |

-continued
Additional Structures of the Present Invention
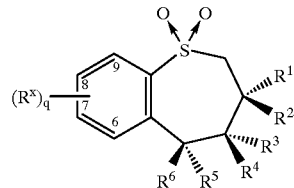
| Compound Number | R¹ | R² | R³ | R⁴ | R⁵ |
|---|---|---|---|---|---|
| 1052 | n-butyl | n-butyl | OH | H | |
| 1053 | n-butyl | n-butyl | OH | H | |
| 1054 | n-butyl | n-butyl | OH | H | |
| 1055 | n-butyl | n-butyl | OH | H | |
| 1056 | n-butyl | n-butyl | OH | H | |
| 1057 | n-butyl | n-butyl | OH | H | |
| 1058 | n-butyl | n-butyl | OH | H | |

-continued
Additional Structures of the Present Invention
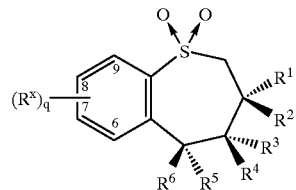
| Compound Number | R¹ | R² | R³ | R⁴ | R⁵ |
|---|---|---|---|---|---|
| 1059 | n-butyl | n-butyl | OH | H | |
| 1060 | ethyl | n-butyl | OH | H | 3-fluoro-4-methoxyphenyl |
| 1061 | n-butyl | n-butyl | OH | H | |
| 1062 | n-butyl | n-butyl | OH | H | |
| 1063 | n-butyl | n-butyl | OH | H | |
| 1064 | n-butyl | n-butyl | OH | H | |
| 1065 | n-butyl | n-butyl | OH | H | |
| 1066 | n-butyl | n-butyl | OH | H | |

Additional Structures of the Present Invention

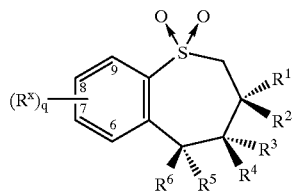

| Compound Number | R¹ | R² | R³ | R⁴ | R⁵ |
|---|---|---|---|---|---|
| 1067 | n-butyl | n-butyl | OH | H | thiophen-3-yl |
| 1068 | n-butyl | n-butyl | OH | H | |
| 1069 | n-butyl | n-butyl | OH | H | phenyl |
| 1070 | n-butyl | n-butyl | OH | H | |
| 1071 | n-butyl | n-butyl | OH | H | |
| 1072 | n-butyl | n-butyl | OH | H | |
| 1073 | n-butyl | n-butyl | OH | H | |
| 1074 | ethyl | n-butyl | OH | H | 3-fluoro-4-methoxyphenyl |
| 1075 | n-butyl | n-butyl | OH | H | 4-fluorophenyl |
| 1076 | n-butyl | n-butyl | OH | H | |
| 1077 | n-butyl | n-butyl | OH | H | 3-hydroxymethylphenyl |
| 1078 | ethyl | n-butyl | OH | H | 4-hydroxyphenyl |

-continued
Additional Structures of the Present Invention
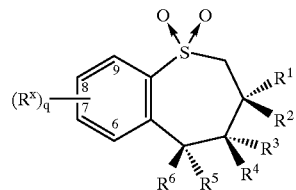
| Compound Number | R¹ | R² | R³ | R⁴ | R⁵ |
|---|---|---|---|---|---|
| 1079 | ethyl | n-butyl | OH | H | 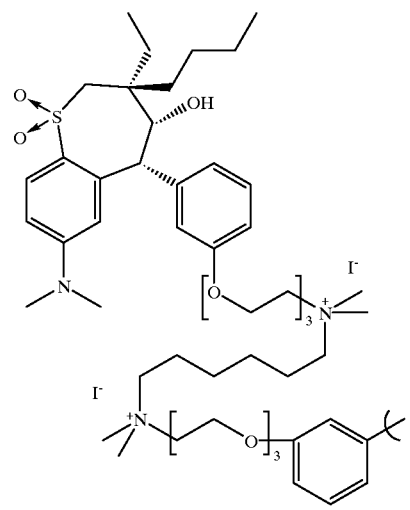 |
| 1080 | n-butyl | n-butyl | OH | H | 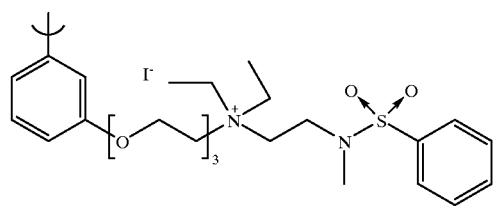 |
| 1081 | n-butyl | n-butyl | OH | H | 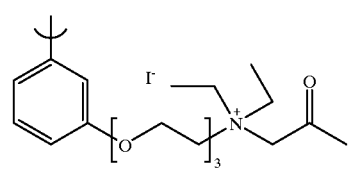 |
| 1082 | n-butyl | n-butyl | OH | H | 2-pyridyl |
| 1083 | n-butyl | n-butyl | OH | H | 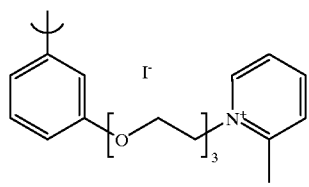 |
| 1084 | n-butyl | n-butyl | OH | H | 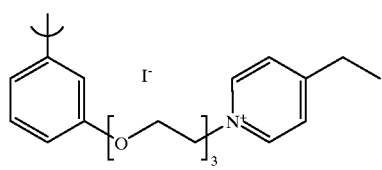 |
| 1085 | n-butyl | n-butyl | OH | H | thiophen-3-yl |

-continued
Additional Structures of the Present Invention
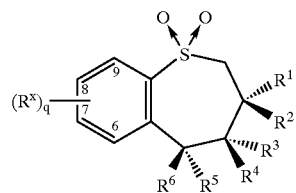
| Compound Number | R¹ | R² | R³ | R⁴ | R⁵ |
|---|---|---|---|---|---|
| 1086 | n-butyl | n-butyl | OH | H | 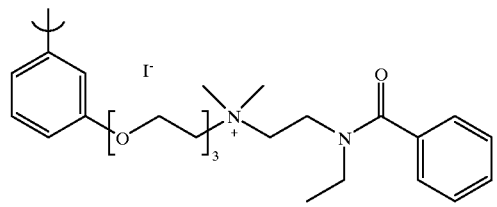 |
| 1087 | n-butyl | n-butyl | OH | H | 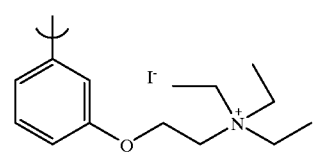 |
| 1088 | ethyl | n-butyl | OH | H | 3,4-methylenedioxyphenyl |
| 1089 | ethyl | n-butyl | OH | H | 4-methoxyphenyl |
| 1090 | n-butyl | n-butyl | OH | H | 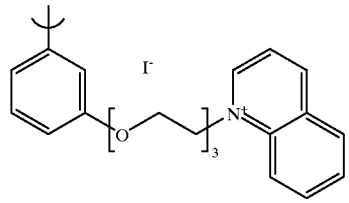 |
| 1091 | n-butyl | n-butyl | OH | H | 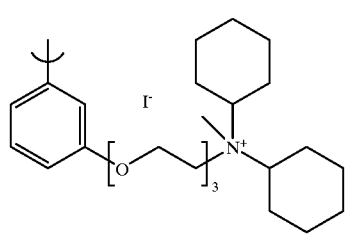 |
| 1092 | n-butyl | n-butyl | OH | H | 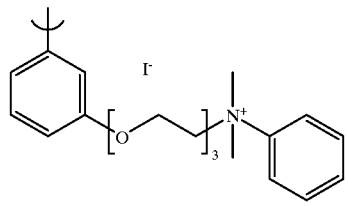 |
| 1093 | n-butyl | n-butyl | OH | H | 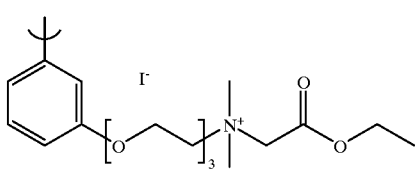 |

Additional Structures of the Present Invention
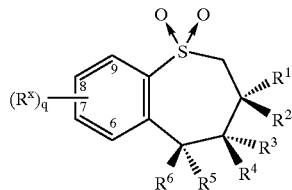
| Compound Number | R¹ | R² | R³ | R⁴ | R⁵ |
|---|---|---|---|---|---|
| 1094 | n-butyl | n-butyl | OH | H | 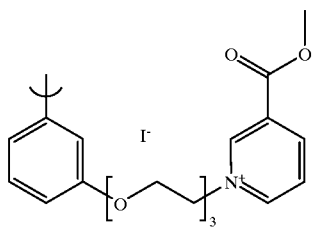 |
| 1095 | n-butyl | n-butyl | OH | H | 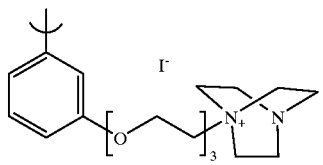 |
| 1096 | n-butyl | n-butyl | OH | H | 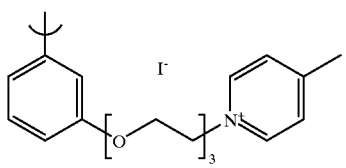 |
| 1097 | n-butyl | n-butyl | OH | H | 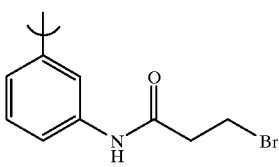 |
| 1098 | n-butyl | n-butyl | OH | H | 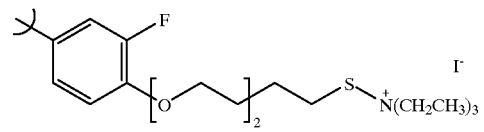 |
| 1099 | ethyl | n-butyl | OH | H | 4-methoxyphenyl |
| 1100 | n-butyl | n-butyl | OH | H | 4-methoxyphenyl |
| 1101 | n-butyl | n-butyl | OH | H | 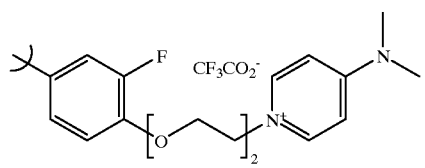 |
| 1102 | n-butyl | n-butyl | OH | H | 3-carboxymethylphenyl |
| 1103 | n-butyl | n-butyl | OH | H | 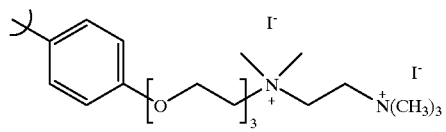 |

-continued

Additional Structures of the Present Invention

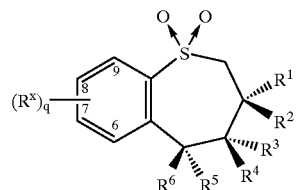

| Compound Number | R¹ | R² | R³ | R⁴ | R⁵ |
|---|---|---|---|---|---|
| 1104 | n-butyl | n-butyl | OH | H | 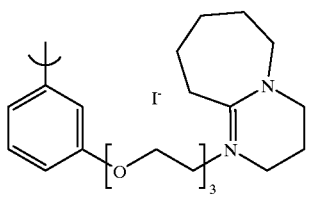 |
| 1105 | n-butyl | n-butyl | OH | H | 5-piperonyl |
| 1106 | n-butyl | n-butyl | OH | H | 3-hydroxyphenyl |
| 1107 | n-butyl | n-butyl | OH | H | 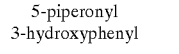 |
| 1108 | n-butyl | n-butyl | OH | H | 3-pyridyl |
| 1109 | n-butyl | n-butyl | OH | H | 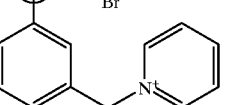 |
| 1110 | n-butyl | n-butyl | OH | H | 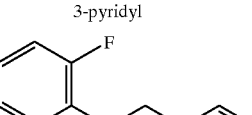 |
| 1111 | n-butyl | n-butyl | OH | H |  |
| 1112 | n-butyl | n-butyl | OH | H | 4-pyridyl |
| 1113 | n-butyl | n-butyl | OH | H | 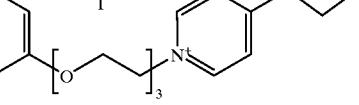 |
| 1114 | n-butyl | n-butyl | OH | H | 3-methoxyphenyl |
| 1115 | n-butyl | n-butyl | OH | H | 4-fluorophenyl |
| 1116 | ethyl | n-butyl | OH | H | 3-tolyl |
| 1117 | ethyl | n-butyl | OH | H | 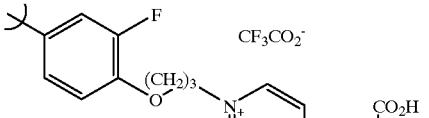 |
| 1118 | ethyl | n-butyl | OH | H | 3-fluoro-4-hydroxyphenyl |

-continued

Additional Structures of the Present Invention

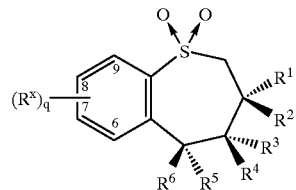

| Compound Number | R¹ | R² | R³ | R⁴ | R⁵ |
|---|---|---|---|---|---|
| 1119 | n-butyl | n-butyl | OH | H | ![structure] |
| 1120 | n-butyl | n-butyl | OH | H | ![structure] |
| 1121 | n-butyl | n-butyl | OH | H | ![structure] |
| 1122 | n-butyl | n-butyl | OH | H | ![structure] |
| 1123 | n-butyl | n-butyl | OH | H | phenyl |
| 1124 | n-butyl | n-butyl | OH | H | 3-methoxyphenyl |
| 1125 | n-butyl | n-butyl | OH | H | 3-chloro-4-methoxyphenyl |
| 1126 | ethyl | n-butyl | OH | H | ![structure] |
| 1127 | n-butyl | n-butyl | OH | H | ![structure] |
| 1128 | n-butyl | n-butyl | OH | H | 3-fluoro-4-hydroxyphenyl |
| 1129 | n-butyl | n-butyl | OH | H | 4-fluorophenyl |
| 1130 | n-butyl | n-butyl | OH | H | 3-chloro-4-fluorophenyl |
| 1131 | ethyl | n-butyl | OH | H | 4-methoxyphenyl |
| 1132 | n-butyl | n-butyl | OH | H | ![structure] |
| 1133 | n-butyl | n-butyl | OH | H | 4-cyanomethylphenyl |

-continued

Additional Structures of the Present Invention

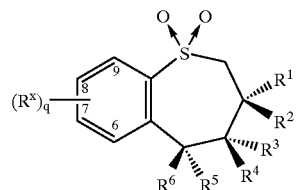

| Compound Number | $R^1$ | $R^2$ | $R^3$ | $R^4$ | $R^5$ |
|---|---|---|---|---|---|
| 1134 | ethyl | n-butyl | OH | H | ![3-(4-acetoxybutoxy)phenyl] |
| 1135 | n-butyl | n-butyl | OH | H | 3,4-dimethoxyphenyl |
| 1136 | n-butyl | n-butyl | OH | H | ![3-(triethyleneoxy iodide)phenyl] |
| 1137 | n-butyl | n-butyl | OH | H | 4-fluorophenyl |
| 1138 | n-butyl | n-butyl | OH | H | ![3-[tri(ethyleneoxy)]-N-(4-tert-butylpyridinium) iodide phenyl] |
| 1139 | n-butyl | n-butyl | OH | H | 3,4-difluorophenyl |
| 1140 | n-butyl | n-butyl | OH | H | 3-methoxyphenyl |
| 1141 | n-butyl | n-butyl | OH | H | 4-fluorophenyl |
| 1142 | n-butyl | n-butyl | OH | H | ![3-fluoro-4-[di(ethyleneoxy)-S-CH2CH2N(CH2CH3)2]phenyl] |
| 1143 | n-butyl | n-butyl | H | OH | H |
| 1144 | n-butyl | n-butyl | OH | H | 5-piperonyl |
| 1145 | n-butyl | n-butyl | OH | H | 4-methoxyphenyl |
| 1146 | n-butyl | n-butyl | OH | H | ![4-[O-(CH2)10-N+(CH3)3] iodide phenyl] |
| 1147 | n-butyl | n-butyl | OH | H | 3-methoxyphenyl |
| 1148 | n-butyl | n-butyl | OH | H | 4-fluorophenyl |
| 1149 | n-butyl | n-butyl | OH | H | 4-fluorophenyl |
| 1150 | n-butyl | n-butyl | OH | H | 3-methoxyphenyl |
| 1151 | n-butyl | ethyl | OH | H | 3-fluoro-4-methoxyphenyl |
| 1152 | n-butyl | n-butyl | OH | H | phenyl |
| 1153 | n-butyl | n-butyl | OH | H | 4-fluorophenyl |
| 1154 | n-butyl | n-butyl | OH | H | 3-methoxyphenyl |
| 1155 | n-butyl | n-butyl | OH | H | 4-fluorophenyl |
| 1156 | n-butyl | n-butyl | OH | H | 4-fluorophenyl |
| 1157 | n-butyl | n-butyl | OH | H | 4-fluorophenyl |
| 1158 | n-butyl | n-butyl | OH | H | 4-pyridinyl, hydrochloride salt |
| 1159 | n-butyl | ethyl | OH | H | phenyl |
| 1160 | n-butyl | n-butyl | OH | H | 4-fluorophenyl |
| 1161 | n-butyl | n-butyl | OH | H | 3,5-dichloro-4-methoxyphenyl |
| 1162 | n-butyl | n-butyl | OH | H | phenyl |
| 1163 | n-butyl | n-butyl | OH | H | 3-(dimethylamino)phenyl |
| 1164 | n-butyl | n-butyl | OH | H | 4-pyridinyl |
| 1165 | n-butyl | n-butyl | OH | H | 3-fluoro-4-methoxyphenyl |

-continued

Additional Structures of the Present Invention

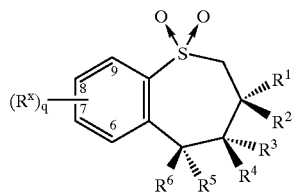

| Compound Number | R¹ | R² | R³ | R⁴ | R⁵ |
|---|---|---|---|---|---|
| 1166 | n-butyl | n-butyl | OH | H | 3-hydroxyphenyl |
| 1167 | n-butyl | n-butyl | OH | H | ![2-chloro-4-(allyloxy)phenyl] |
| 1168 | n-butyl | n-butyl | OH | H | 4-hydroxyphenyl |
| 1169 | n-butyl | n-butyl | OH | H | phenyl |
| 1170 | n-butyl | n-butyl | OH | H | 3-methoxyphenyl |
| 1171 | n-butyl | n-butyl | OH | H | 4-(trifluoromethylsulfonyloxy)phenyl |
| 1172 | n-butyl | n-butyl | OH | H | 4-pyridinyl |
| 1173 | n-butyl | n-butyl | OH | H | 4-fluorophenyl |
| 1174 | ethyl | n-butyl | OH | H | 3-methoxyphenyl |
| 1175 | ethyl | n-butyl | OH | H | 3-methoxyphenyl |
| 1176 | n-butyl | n-butyl | OH | H | 4-fluorophenyl |
| 1177 | n-butyl | n-butyl | OH | H | 3-methoxyphenyl |
| 1178 | n-butyl | n-butyl | OH | H | 3-(trifluoromethylsulfonyloxy)phenyl |
| 1179 | n-butyl | n-butyl | OH | H | phenyl |
| 1180 | n-butyl | n-butyl | OH | H | phenyl |
| 1181 | n-butyl | n-butyl | OH | H | 4-fluorophenyl |
| 1182 | n-butyl | n-butyl | OH | H | 4-(dimethylamino)phenyl |
| 1183 | n-butyl | n-butyl | OH | H | 3-methoxyphenyl |
| 1184 | n-butyl | n-butyl | OH | H | 4-fluorophenyl |
| 1185 | n-butyl | n-butyl | OH | H | 4-fluorophenyl |
| 1186 | n-butyl | n-butyl | OH | H | phenyl |
| 1187 | n-butyl | n-butyl | OH | H | 4-fluorophenyl |
| 1188 | n-butyl | n-butyl | OH | H | 4-methoxyphenyl |
| 1189 | n-butyl | n-butyl | OH | H | 3,4-difluorophenyl |
| 1190 | n-butyl | n-butyl | OH | H | 2-bromophenyl |
| 1191 | n-butyl | n-butyl | OH | H | 4-(dimethylamino)phenyl |
| 1192 | n-butyl | n-butyl | OH | H | 3-(dimethylamino)phenyl |
| 1193 | n-butyl | n-butyl | OH | H | 4-(2-(2-methylpropyl))phenyl |
| 1194 | n-butyl | n-butyl | OH | H | [complex structure shown] |
| 1195 | n-butyl | n-butyl | OH | H | 4-methoxyphenyl |
| 1196 | n-butyl | n-butyl | OH | H | [3-(trimethylammonium)phenyl iodide] |
| 1197 | n-butyl | ethyl | R3 + R4 = oxo | R3 + R4 = oxo | phenyl |
| 1198 | n-butyl | n-butyl | OH | H | 4-(pyridinyl-N-oxide) |

Additional Structures of the Present Invention

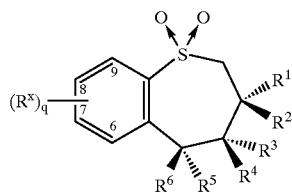

| Compound Number | R¹ | R² | R³ | R⁴ | R⁵ |
|---|---|---|---|---|---|
| 1199 | n-butyl | n-butyl | OH | H | 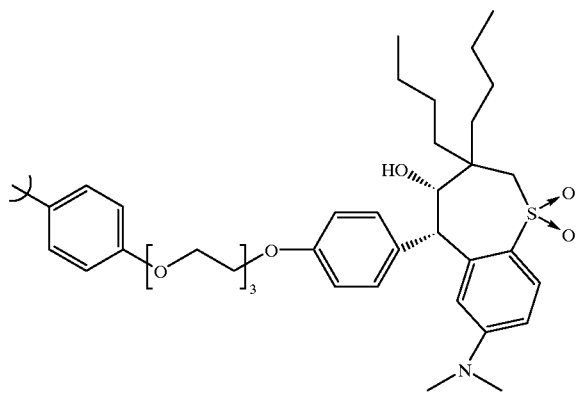 |
| 1200 | n-butyl | n-butyl | H | OH | H |
| 1201 | n-butyl | n-butyl | OH | H | H |
| 1202 | n-butyl | n-butyl | OH | H | 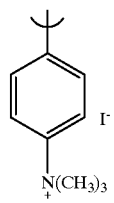 |
| 1203 | n-butyl | n-butyl | OH | H | 5-piperazinyl |
| 1204 | n-butyl | n-butyl | OH | H | 4-fluorophenyl |
| 1205 | n-butyl | n-butyl | OH | H | 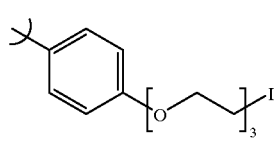 |
| 1206 | n-butyl | n-butyl | OH | H | 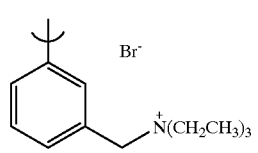 |
| 1207 | n-butyl | n-butyl | OH | H | 3,5-dichlorophenyl |
| 1208 | n-butyl | n-butyl | OH | H | 4-methoxyphenyl |
| 1209 | n-butyl | n-butyl | acetoxy | H | phenyl |
| 1210 | n-butyl | n-butyl | OH | H | 2-(dimethylamino)phenyl |

-continued

Additional Structures of the Present Invention

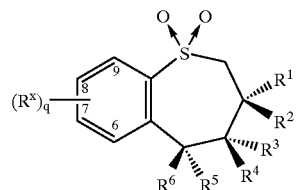

| Compound Number | R¹ | R² | R³ | R⁴ | R⁵ |
|---|---|---|---|---|---|
| 1211 | ethyl | n-butyl | OH | H | (large structure: 4-substituted phenyl linked via -O-(CH₂CH₂O)₃- to a 4-substituted phenyl attached to the benzothiepine core bearing n-butyl, ethyl, HO, and 7-N(CH₃)₂ substituents with S(=O)₂) |
| 1212 | n-butyl | n-butyl | OH | H | 4-methoxyphenyl |
| 1213 | n-butyl | ethyl | H | OH | H |
| 1214 | n-butyl | ethyl | OH | H | phenyl |
| 1215 | n-butyl | n-butyl | OH | H | 4-methoxyphenyl |
| 1216 | ethyl | n-butyl | OH | H | 5-piperonyl |
| 1217 | n-butyl | n-butyl | OH | H | 4-carboxyphenyl |
| 1218 | n-butyl | n-butyl | OH | H | 4-methoxyphenyl |
| 1219 | n-butyl | n-butyl | OH | H | 4-[O-CH₂CH₂-N(CH₃)₂]phenyl |
| 1220 | n-butyl | n-butyl | OH | H | 3-methoxyphenyl |
| 1221 | n-butyl | n-butyl | OH | H | 4-CO₂CH₃-phenyl |
| 1222 | n-butyl | n-butyl | OH | H | 3-methoxyphenyl |
| 1223 | n-butyl | n-butyl | OH | H | phenyl |
| 1224 | n-butyl | n-butyl | OH | H | 3-nitrophenyl |
| 1225 | n-butyl | ethyl | OH | H | 3-methylphenyl |
| 1226 | ethyl | n-butyl | OH | H | 5-piperonyl |
| 1227 | n-butyl | n-butyl | OH | H | 4-fluorophenyl |
| 1228 | n-butyl | n-butyl | OH | H | 2-pyrrolyl |
| 1229 | n-butyl | n-butyl | OH | H | 3-chloro-4-hydroxyphenyl |
| 1230 | n-butyl | n-butyl | OH | H | phenyl |
| 1231 | n-butyl | n-butyl | OH | H | 6-methoxy-2-naphthyl |
| 1232 | n-butyl | n-butyl | H | OH | 3-thiophenyl |
| 1233 | n-butyl | n-butyl | OH | H | 3-[CH₂-N⁺(CH₃)₂-CH₂CH₂-N(CH₃)₂]phenyl Br⁻ |

-continued

Additional Structures of the Present Invention

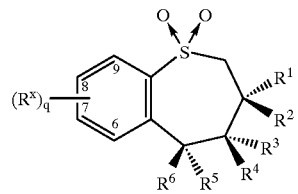

| Compound Number | R¹ | R² | R³ | R⁴ | R⁵ |
|---|---|---|---|---|---|
| 1234 | n-butyl | n-butyl | OH | H | 3-(trimethylammoniomethyl)phenyl Br⁻ |
| 1235 | n-butyl | n-butyl | OH | H | 3-(2-(diethylamino)ethoxy)phenyl |
| 1236 | n-butyl | n-butyl | OH | H | 4-(bromomethyl)phenyl |
| 1237 | n-butyl | n-butyl | OH | H | bis-quaternary ammonium PEG-phenyl, 2 I⁻ |
| 1238 | n-butyl | n-butyl | OH | H | 3-fluoro-4-(PEG-vinyl ether)phenyl |
| 1239 | n-butyl | n-butyl | OH | H | 3-fluoro-4-(PEG-Br)phenyl |
| 1240 | n-butyl | n-butyl | OH | H | 4-methoxy-3-methylphenyl |
| 1241 | n-butyl | n-butyl | OH | H | 3-(dimethylaminomethyl)phenyl |
| 1242 | n-butyl | n-butyl | OH | H | 3-fluoro-4-(PEG-Cl)phenyl |
| 1243 | n-butyl | n-butyl | OH | H | 3-(trimethylammoniomethyl)-4-hydroxyphenyl I⁻ |
| 1244 | n-butyl | n-butyl | OH | H | 3-methoxyphenyl |
| 1245 | n-butyl | n-butyl | OH | H | 3-(trimethylammonio)phenyl I⁻ |
| 1246 | n-butyl | n-butyl | OH | H | 3-(bromomethyl)phenyl |
| 1247 | n-butyl | n-butyl | OH | H | 6-hydroxy-2-naphthyl |

-continued

Additional Structures of the Present Invention

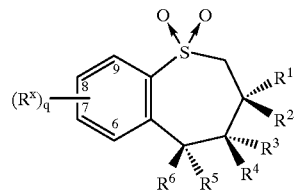

| Compound Number | R¹ | R² | R³ | R⁴ | R⁵ |
|---|---|---|---|---|---|
| 1248 | n-butyl | n-butyl | OH | H | 2-hydroxy-5-[(dimethylamino)methyl]phenyl |
| 1249 | n-butyl | n-butyl | OH | H | 4-[N-methyl-N-(2-hydroxyethyl)-N-methylammonium]methylphenyl trifluoroacetate |
| 1250 | n-butyl | n-butyl | OH | H | 3-(dimethylamino)phenyl |
| 1251 | n-butyl | n-butyl | OH | H | 1-naphthyl |
| 1252 | n-butyl | n-butyl | OH | H | 4-[3-(triethylammonium)propoxy]phenyl iodide |
| 1253 | n-butyl | n-butyl | OH | H | 2-methoxy-5-[(trimethylammonium)methyl]phenyl iodide |
| 1254 | n-butyl | n-butyl | OH | H | 4-(pyridinium-1-ylmethyl)phenyl bromide |
| 1255 | n-butyl | n-butyl | OH | H | 3-[N,N-dimethyl-N-(2-trimethylammoniumethyl)ammoniummethyl]phenyl diiodide |
| 1256 | n-butyl | n-butyl | OH | H | 3-nitrophenyl |
| 1257 | n-butyl | n-butyl | OH | H | phenyl |
| 1258 | n-butyl | n-butyl | OH | H | 4-fluorophenyl |
| 1259 | ethyl | n-butyl | H | OH | H |
| 1260 | ethyl | n-butyl | OH | H | 3-hydroxyphenyl |
| 1261 | n-butyl | n-butyl | OH | H | 4-[(triethyleneglycol)oxy]phenyl linked to dimethylamino-substituted benzothiepine dimer |
| 1262 | n-butyl | n-butyl | OH | H | 2-thiophenyl |
| 1263 | n-butyl | n-butyl | OH | H | 5-piperonyl |
| 1264 | n-butyl | n-butyl | OH | H | 4-fluorophenyl |
| 1265 | n-butyl | n-butyl | OH | H | 4-fluorophenyl |

-continued

Additional Structures of the Present Invention

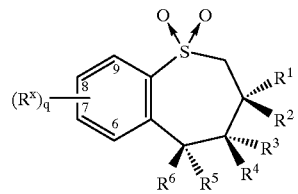

| Compound Number | R¹ | R² | R³ | R⁴ | R⁵ |
|---|---|---|---|---|---|
| 1266 | n-butyl | n-butyl | OH | H | ![2-methoxy-5-(dimethylaminomethyl)phenyl quaternary] |
| 1267 | n-butyl | ethyl | OH | H | 5-piperonyl |
| 1268 | n-butyl | n-butyl | OH | H | ![4-(O(CH2)5)-N+(CH2CH3)3 I-] |
| 1269 | n-butyl | n-butyl | OH | H | ![4-(O(CH2)5)I phenyl] |
| 1270 | n-butyl | n-butyl | OH | H | ![3-fluoro-4-(O(CH2)4Br)phenyl] |
| 1271 | n-butyl | n-butyl | OH | H | ![phenyl-O(CH2)3-N+(CH3)2-CH2CH2-N(Et)(SO2Ph) I-] |
| 1272 | n-butyl | n-butyl | OH | H | ![phenyl-O(CH2)3-(3-pyridinium-CH2CO2H) I-] |
| 1273 | n-butyl | n-butyl | OH | H | ![phenyl-O(CH2)3-N+((CH2)8CH3)3 I-] |
| 1274 | n-butyl | n-butyl | OH | H | ![3-fluoro-4-(OCH2-(6-(chloromethyl)pyridin-2-yl))phenyl] |

Additional Structures of the Present Invention

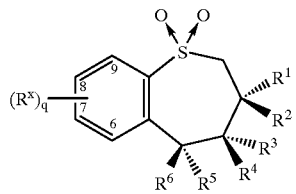

| Compound Number | R¹ | R² | R³ | R⁴ | R⁵ |
|---|---|---|---|---|---|
| 1275 | n-butyl | n-butyl | OH | H | ![structure with 2-fluorophenoxy-ethyl piperazinium diiodide] |
| 1276 | n-butyl | n-butyl | OH | H | ![phenoxy-propyl tris(isooctyl)ammonium iodide] |
| 1277 | n-butyl | n-butyl | OH | H | ![2-fluorophenoxy-ethyl N-methyl-glycine] |
| 1278 | n-butyl | n-butyl | OH | H | ![phenoxy-propyl tripentylammonium iodide] |
| 1279 | n-butyl | n-butyl | OH | H | ![phenoxy-propyl trihexylammonium iodide] |
| 1280 | n-butyl | n-butyl | OH | H | ![2-fluorophenyl acetamide with N-methyl-N-(dimethylaminomethyl)] |
| 1281 | n-butyl | n-butyl | OH | H | ![4-phenoxy-propyl iodide] |
| 1282 | ethyl | n-butyl | OH | H | 3-fluoro-4-methoxyphenyl |
| 1283 | n-butyl | n-butyl | OH | H | 4-hydroxymethylphenyl |
| 1284 | n-butyl | n-butyl | OH | H | 4-fluorophenyl |
| 1285 | n-butyl | ethyl | OH | H | phenyl |
| 1286 | n-butyl | n-butyl | OH | H | ![2-fluorophenoxy-propyl tributylammonium trifluoroacetate] |
| 1287 | n-butyl | ethyl | OH | H | 4-hydroxyphenyl |

Additional Structures of the Present Invention
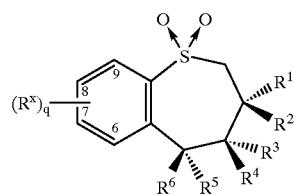
| Compound Number | R¹ | R² | R³ | R⁴ | R⁵ |
|---|---|---|---|---|---|
| 1288 | n-butyl | n-butyl | OH | H | 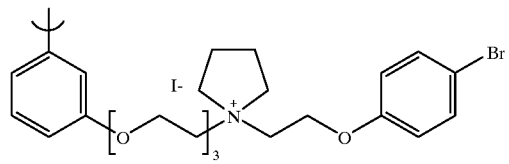 |
| 1289 | n-butyl | n-butyl | OH | H | 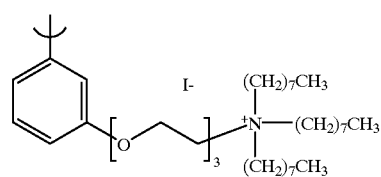 |
| 1290 | n-butyl | n-butyl | OH | H | 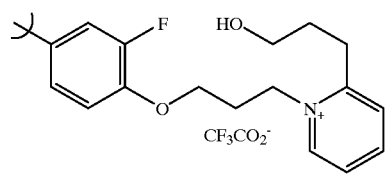 |
| 1291 | n-butyl | n-butyl | OH | H | 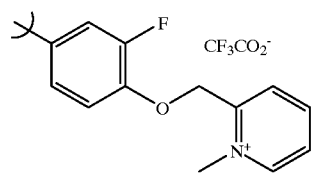 |
| 1292 | n-butyl | n-butyl | OH | H | 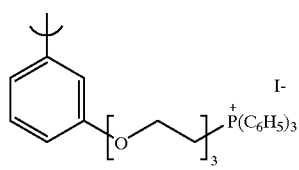 |
| 1293 | n-butyl | n-butyl | OH | H | 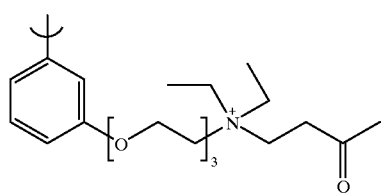 |
| 1294 | n-butyl | n-butyl | OH | H | 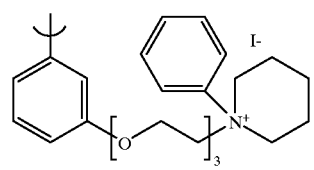 |

-continued

Additional Structures of the Present Invention

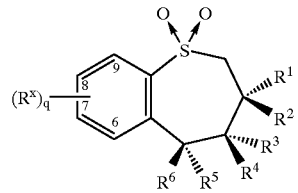

| Compound Number | R¹ | R² | R³ | R⁴ | R⁵ |
|---|---|---|---|---|---|
| 1295 | n-butyl | n-butyl | OH | H | |
| 1296 | n-butyl | n-butyl | OH | H | |
| 1297 | n-butyl | n-butyl | OH | H | |
| 1298 | n-butyl | n-butyl | OH | H | |
| 1299 | n-butyl | n-butyl | OH | H | |
| 1300 | n-butyl | ethyl | H | OH | H |
| 1301 | n-butyl | n-butyl | OH | H | 3-methoxyphenyl |
| 1302 | n-butyl | n-butyl | OH | H | 3-hydroxyphenyl |
| 1303 | n-butyl | n-butyl | OH | H | |
| 1304 | n-butyl | n-butyl | OH | H | 3-methoxyphenyl |
| 1305 | n-butyl | n-butyl | OH | H | 4-fluorophenyl |
| 1306 | n-butyl | n-butyl | OH | H | |
| 1307 | n-butyl | n-butyl | OH | H | H |

Additional Structures of the Present Invention

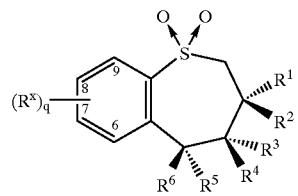

| Compound Number | R¹ | R² | R³ | R⁴ | R⁵ |
|---|---|---|---|---|---|
| 1308 | ethyl | n-butyl | OH | H | |
| 1309 | n-butyl | n-butyl | OH | H | 4-methoxyphenyl |
| 1310 | ethyl | n-butyl | OH | H | phenyl |
| 1311 | n-butyl | ethyl | OH | H | phenyl |
| 1312 | n-butyl | ethyl | OH | H | phenyl |
| 1313 | n-butyl | ethyl | OH | H | phenyl |
| 1314 | ethyl | n-butyl | OH | H | phenyl |
| 1315 | ethyl | n-butyl | OH | H | phenyl |
| 1316 | n-butyl | ethyl | OH | H | phenyl |
| 1317 | n-butyl | ethyl | OH | H | phenyl |
| 1318 | ethyl | n-butyl | OH | H | phenyl |
| 1319 | ethyl | n-butyl | OH | H | 3-methoxyphenyl |
| 1320 | ethyl | n-butyl | OH | H | phenyl |
| 1321 | n-butyl | ethyl | OH | H | phenyl |
| 1322 | n-butyl | n-butyl | OH | H | |
| 1323 | n-butyl | n-butyl | OH | H | |
| 1324 | n-butyl | n-butyl | OH | H | |
| 1325 | n-butyl | n-butyl | OH | H | 4-((diethylamino)methyl)phenyl |
| 1326 | n-butyl | n-butyl | OH | H | |
| 1327 | n-butyl | n-butyl | OH | H | 3-fluoro-4-hydroxy-5-iodophenyl |
| 1328 | n-butyl | n-butyl | OH | H | |

-continued
Additional Structures of the Present Invention
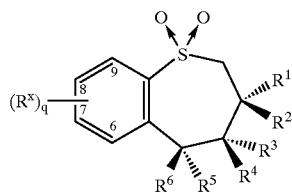
| Compound Number | R¹ | R² | R³ | R⁴ | R⁵ |
|---|---|---|---|---|---|
| 1329 | n-butyl | n-butyl | OH | H | 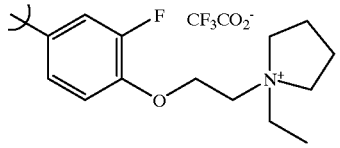 |
| 1330 | n-butyl | n-butyl | OH | H | 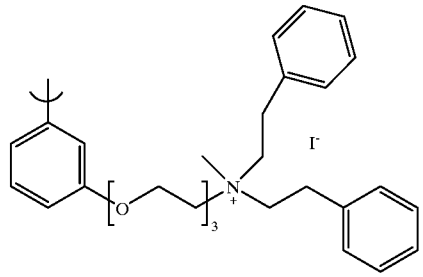 |
| 1331 | n-butyl | n-butyl | OH | H | 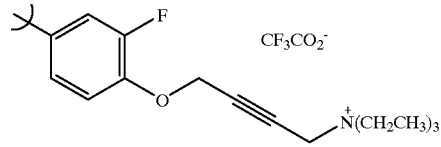 |
| 1332 | n-butyl | n-butyl | OH | H | 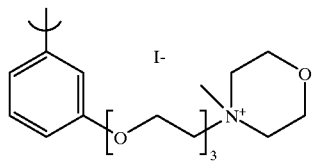 |
| 1333 | n-butyl | n-butyl | OH | H | 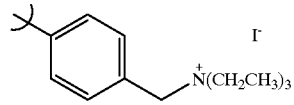 |
| 1334 | n-butyl | n-butyl | OH | H | 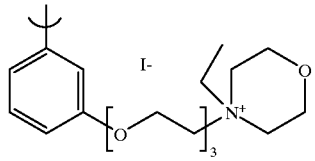 |
| 1335 | n-butyl | n-butyl | OH | H | 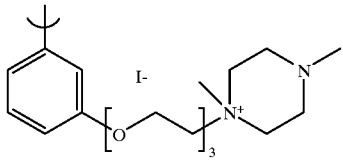 |

-continued

Additional Structures of the Present Invention

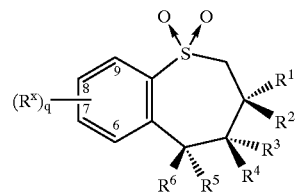

| Compound Number | R¹ | R² | R³ | R⁴ | R⁵ |
|---|---|---|---|---|---|
| 1336 | n-butyl | n-butyl | OH | H | (3-substituted phenyl)-O-(CH₂)₃-N⁺(CH₃)₂-CH₂CH₂-N(CH₃)₂, I⁻ |
| 1337 | n-butyl | n-butyl | OH | H | 4-(CH₂N⁺(CH₃)₃)phenyl, I⁻ |
| 1338 | n-butyl | n-butyl | OH | H | 4-methoxyphenyl |
| 1339 | n-butyl | n-butyl | OH | H | 2-(C(O)N(CH₃)C(CH₃)₃)-5-methylphenyl |
| 1340 | n-butyl | ethyl | OH | H | 5-piperonyl |
| 1341 | n-butyl | n-butyl | acetoxy | H | 3-methoxyphenyl |
| 1342 | n-butyl | n-butyl | OH | H | 5-piperonyl |
| 1343 | ethyl | n-butyl | OH | H | phenyl |
| 1344 | n-butyl | n-butyl | OH | H | 3-fluoro-4-methoxyphenyl |
| 1345 | ethyl | n-butyl | OH | H | phenyl |
| 1346 | ethyl | n-butyl | OH | H | phenyl |
| 1347 | n-butyl | n-butyl | OH | H | 3-fluoro-4-methoxyphenyl |
| 1348 | isobutyl | isobutyl | OH | H | phenyl |
| 1349 | ethyl | n-butyl | OH | H | phenyl |
| 1350 | n-butyl | n-butyl | OH | H | 3-fluoro-4-methoxyphenyl |
| 1351 | n-butyl | n-butyl | OH | H | 4-(O-(CH₂CH₂O)₅-(2-(N⁺(CH₂CH₃)(CH₃)₂)phenyl))phenyl, CF₃CO₂⁻ |
| 1352 | n-butyl | n-butyl | OH | H | 4-(O-(CH₂)₃-N⁺(CH₂CH₂CH₂CH₃)₃)phenyl, Br⁻ |
| 1353 | n-butyl | n-butyl | OH | H | 3-fluoro-4-(O-(CH₂)₃-N⁺(CH₂CH₃)₃)phenyl, CF₃CO₂⁻ |

Additional Structures of the Present Invention
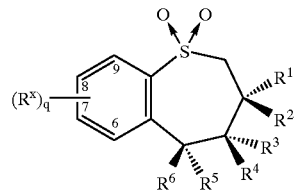
| Compound Number | R¹ | R² | R³ | R⁴ | R⁵ |
|---|---|---|---|---|---|
| 1354 | n-butyl | n-butyl | OH | H | 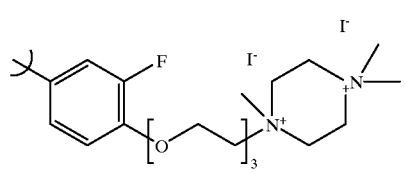 |
| 1355 | n-butyl | n-butyl | OH | H | 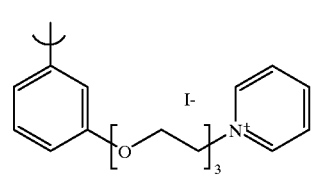 |
| 1356 | n-butyl | n-butyl | OH | H | 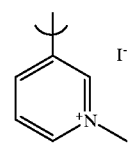 |
| 1357 | n-butyl | n-butyl | OH | H | 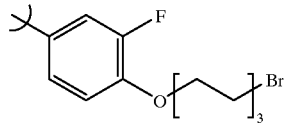 |
| 1358 | n-butyl | n-butyl | OH | H | 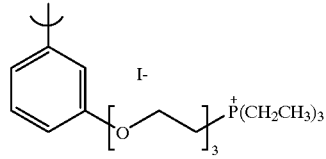 |
| 1359 | n-butyl | n-butyl | OH | H | 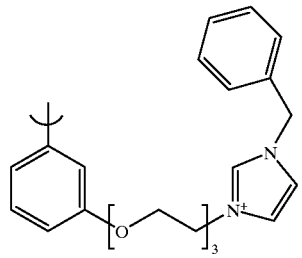 |
| 1360 | n-butyl | n-butyl | OH | H | 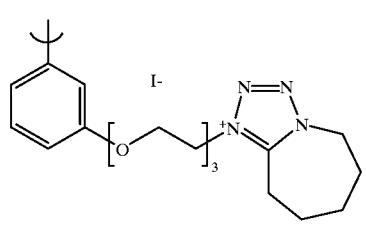 |

-continued
Additional Structures of the Present Invention
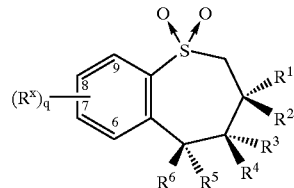
| Compound Number | R¹ | R² | R³ | R⁴ | R⁵ |
|---|---|---|---|---|---|
| 1361 | n-butyl | n-butyl | OH | H | |
| 1362 | n-butyl | n-butyl | OH | H | |
| 1363 | n-butyl | n-butyl | OH | H | |
| 1364 | n-butyl | n-butyl | OH | H | |
| 1365 | n-butyl | n-butyl | OH | H | |
| 1366 | n-butyl | n-butyl | OH | H | |
| 1367 | n-butyl | n-butyl | OH | H | |

Additional Structures of the Present Invention
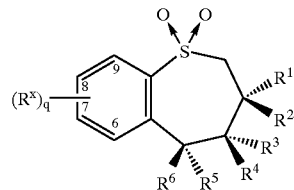
| Compound Number | R¹ | R² | R³ | R⁴ | R⁵ |
|---|---|---|---|---|---|
| 1368 | n-butyl | n-butyl | OH | H | 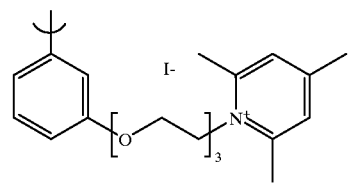 |
| 1369 | n-butyl | n-butyl | OH | H | 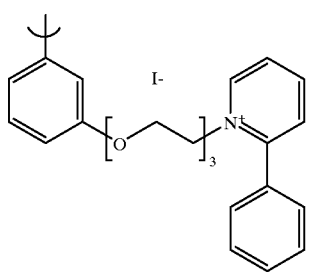 |
| 1370 | n-butyl | n-butyl | OH | H | 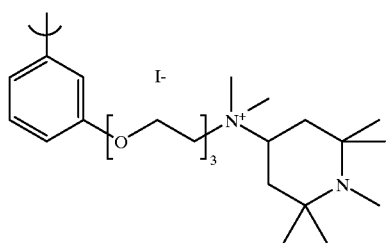 |
| 1371 | n-butyl | n-butyl | OH | H | 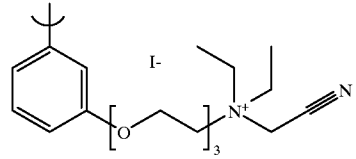 |
| 1372 | n-butyl | n-butyl | OH | H | 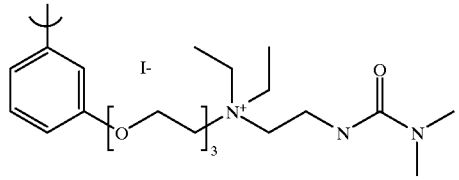 |
| 1373 | n-butyl | n-butyl | OH | H | 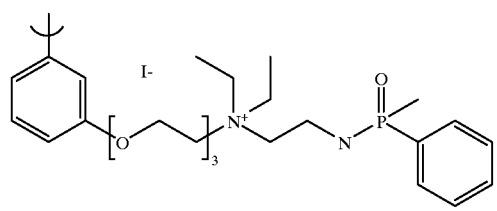 |

-continued
Additional Structures of the Present Invention
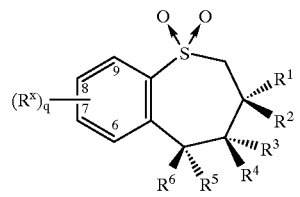
| Compound Number | $R^1$ | $R^2$ | $R^3$ | $R^4$ | $R^5$ |
|---|---|---|---|---|---|
| 1374 | n-butyl | n-butyl | OH | H | |
| 1375 | n-butyl | n-butyl | OH | H | |
| 1376 | n-butyl | n-butyl | OH | H | |
| 1377 | n-butyl | n-butyl | OH | H | |
| 1378 | n-butyl | n-butyl | OH | H | |
| 1379 | n-butyl | n-butyl | OH | H | |
| 1380 | n-butyl | n-butyl | OH | H | |
| 1381 | n-butyl | n-butyl | OH | H | |

-continued
Additional Structures of the Present Invention
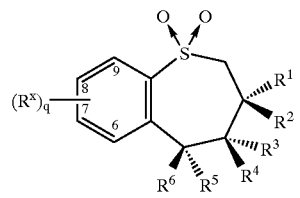
| Compound Number | R¹ | R² | R³ | R⁴ | R⁵ |
|---|---|---|---|---|---|
| 1382 | n-butyl | n-butyl | OH | H | |
| 1383 | n-butyl | n-butyl | OH | H | |
| 1384 | n-butyl | n-butyl | OH | H | |
| 1385 | n-butyl | n-butyl | OH | H | |
| 1386 | n-butyl | n-butyl | OH | H | |
| 1387 | n-butyl | n-butyl | OH | H | |
| 1388 | n-butyl | n-butyl | OH | H | |
| 1389 | n-butyl | n-butyl | OH | H | |

-continued
Additional Structures of the Present Invention
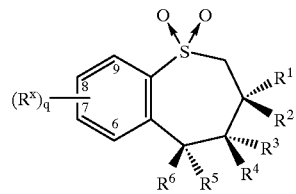
| Compound Number | $R^1$ | $R^2$ | $R^3$ | $R^4$ | $R^5$ |
|---|---|---|---|---|---|
| 1390 | n-butyl | n-butyl | OH | H | 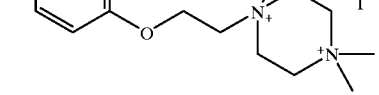 |
| 1391 | n-butyl | n-butyl | OH | H | 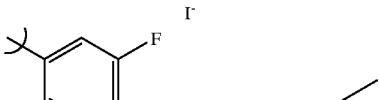 |
| 1392 | n-butyl | n-butyl | OH | H | 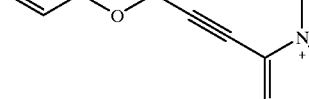 |
| 1393 | n-butyl | n-butyl | OH | H |  |
| 1394 | n-butyl | n-butyl | OH | H | 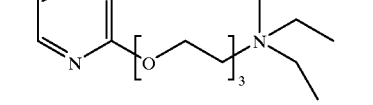 |
| 1395 | n-butyl | n-butyl | OH | H |  |
| 1396 | n-butyl | n-butyl | OH | H | 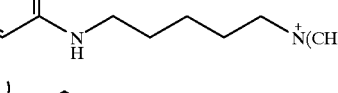 |

-continued
Additional Structures of the Present Invention
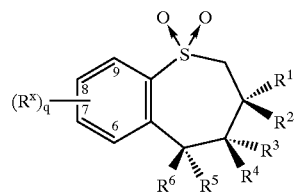
| Compound Number | R¹ | R² | R³ | R⁴ | R⁵ |
|---|---|---|---|---|---|
| 1397 | n-butyl | n-butyl | OH | H | 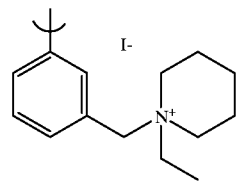 |
| 1398 | n-butyl | n-butyl | OH | H | 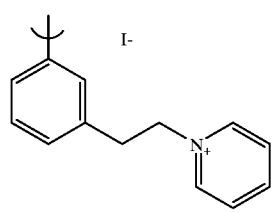 |
| 1399 | n-butyl | n-butyl | OH | H | 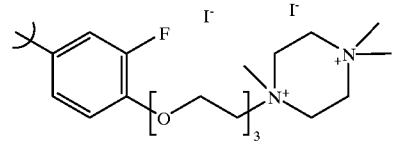 |
| 1400 | n-butyl | n-butyl | OH | H | 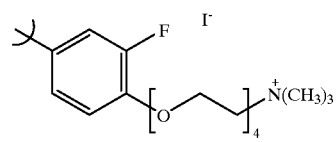 |
| 1401 | n-butyl | n-butyl | OH | H | 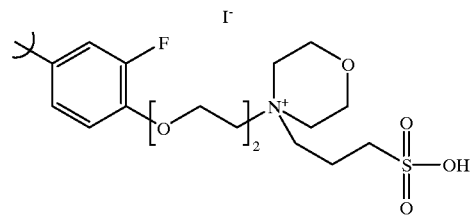 |
| 1402 | n-butyl | n-butyl | OH | H | 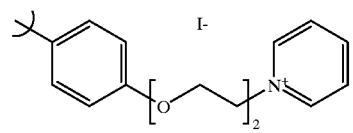 |
| 1403 | n-butyl | n-butyl | OH | H | 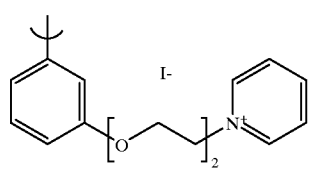 |

-continued
Additional Structures of the Present Invention
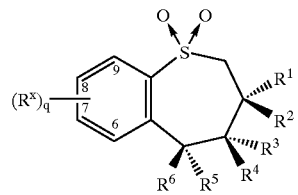
| Compound Number | R¹ | R² | R³ | R⁴ | R⁵ |
|---|---|---|---|---|---|
| 1404 | n-butyl | n-butyl | OH | H | 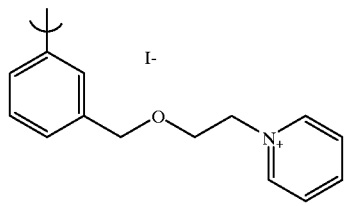 |
| 1405 | n-butyl | n-butyl | OH | H | 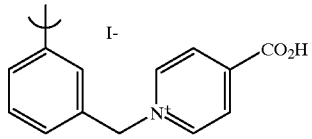 |
| 1406 | n-butyl | n-butyl | OH | H | 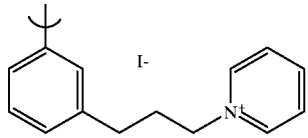 |
| 1407 | n-butyl | n-butyl | OH | H | 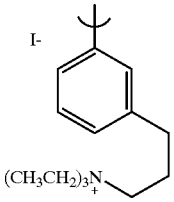 |
| 1408 | n-butyl | n-butyl | OH | H | 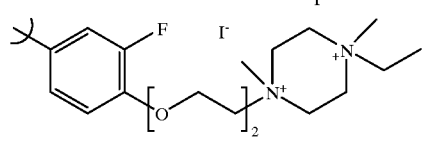 |
| 1409 | n-butyl | n-butyl | OH | H | 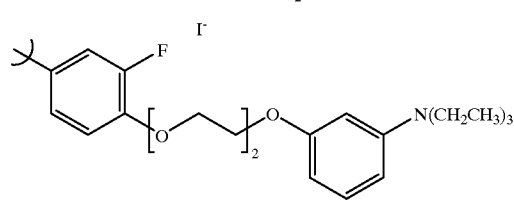 |
| 1410 | n-butyl | n-butyl | OH | H | 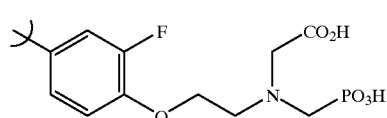 |
| 1411 | n-butyl | n-butyl | OH | H | 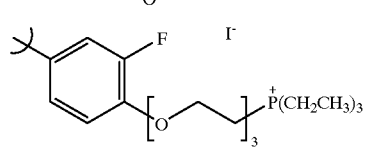 |

-continued
Additional Structures of the Present Invention
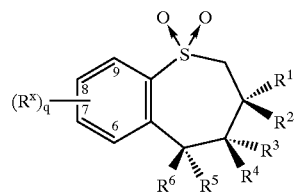
| Compound Number | R¹ | R² | R³ | R⁴ | R⁵ |
|---|---|---|---|---|---|
| 1412 | n-butyl | n-butyl | OH | H | 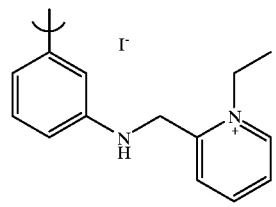 |
| 1413 | n-butyl | n-butyl | OH | H | 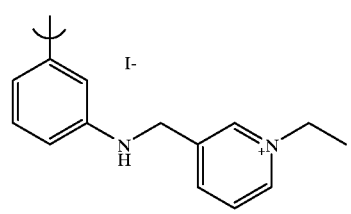 |
| 1414 | n-butyl | n-butyl | OH | H | 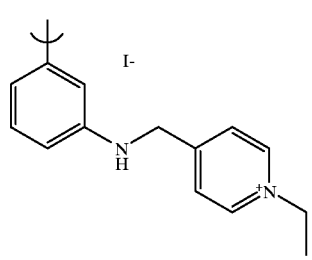 |
| 1415 | n-butyl | n-butyl | OH | H | 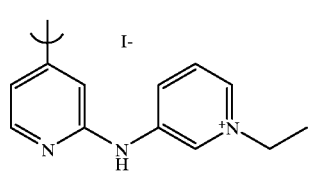 |
| 1416 | n-butyl | n-butyl | OH | H | 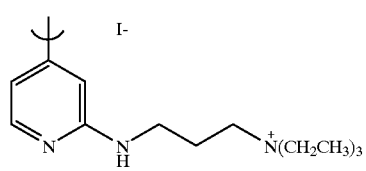 |
| 1417 | n-butyl | n-butyl | OH | H | 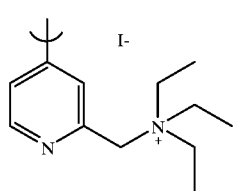 |

Additional Structures of the Present Invention
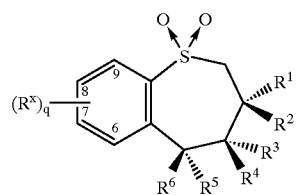
| Compound Number | R¹ | R² | R³ | R⁴ | R⁵ |
|---|---|---|---|---|---|
| 1418 | n-butyl | n-butyl | OH | H | 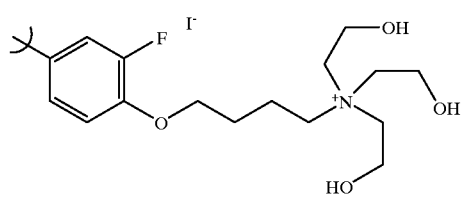 |
| 1419 | n-butyl | n-butyl | OH | H | 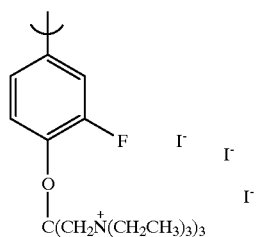 |
| 1420 | n-butyl | n-butyl | OH | H | 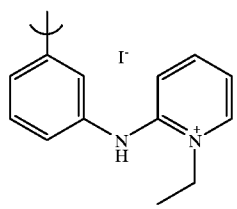 |
| 1421 | n-butyl | n-butyl | OH | H | 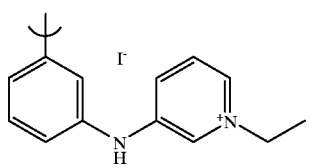 |
| 1422 | n-butyl | n-butyl | OH | H | 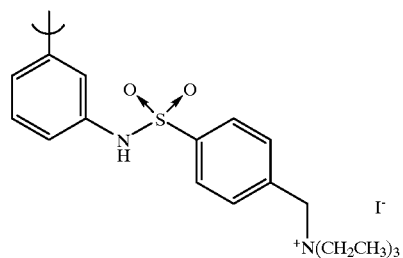 |
| 1423 | n-butyl | n-butyl | OH | H | 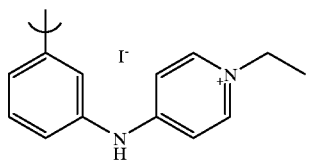 |

-continued

Additional Structures of the Present Invention

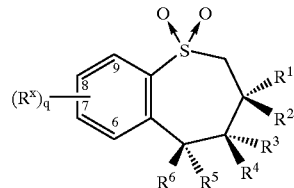

| Compound Number | R¹ | R² | R³ | R⁴ | R⁵ |
|---|---|---|---|---|---|
| 1424 | n-butyl | n-butyl | OH | H | (4-pyridyl)-NH-(1-ethyl-4-pyridinium) I⁻ |
| 1425 | n-butyl | n-butyl | OH | H | (4-pyridyl)-O-(CH₂)₅-N⁺(CH₂CH₃)₃ I⁻ |
| 1426 | n-butyl | n-butyl | OH | H | (4-pyridyl)-NH-(CH₂)₄-N⁺(CH₂CH₃)₃ I⁻ |
| 1427 | n-butyl | n-butyl | OH | H | phenyl-(OCH₂CH₂)₃-N⁺(CH₃)₂-(3-hydroxyphenyl) I⁻ |
| 1428 | n-butyl | n-butyl | OH | H | phenyl-NH-(CH₂)₃-SO₃H |
| 1429 | n-butyl | n-butyl | OH | H | phenyl-N⁺(C₆H₅)₃ Br⁻ |
| 1430 | n-butyl | n-butyl | OH | H | phenyl-CH₂-N⁺(2,6-dimethylpyridinium) Br⁻ |

US 5,994,391

-continued

Additional Structures of the Present Invention

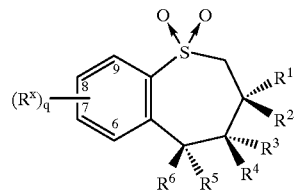

| Compound Number | R¹ | R² | R³ | R⁴ | R⁵ |
|---|---|---|---|---|---|
| 1431 | n-butyl | n-butyl | OH | H | 4-[O-(CH₂)₄-N⁺(CH₂CH₃)₃]phenyl, I⁻ (linker repeated 2×) |
| 1432 | n-butyl | n-butyl | OH | H | 4-[O-(CH₂)₂-pyridinium]phenyl, I⁻ |
| 1433 | n-butyl | n-butyl | OH | H | 2-fluoro-4-[O-(CH₂)₂-N⁺(CH₃)-piperazinium-N⁺(CH₃)-(CH₂)₃SO₃H]phenyl, 2 I⁻ |
| 1434 | n-butyl | n-butyl | OH | H | 4-[O-(CH₂)₅-N⁺(CH₂CH₃)₃]phenyl, I⁻ |
| 1435 | n-butyl | n-butyl | OH | H | 2-fluoro-4-[O-(CH₂)₂-]₃-N⁺(CH₃)₂-(3-hydroxyphenyl), I⁻ |
| 1436 | n-butyl | n-butyl | OH | H | 4-[O-(1-ethylpyridinium-4-yl)]phenyl, I⁻ |
| 1437 | n-butyl | n-butyl | OH | H | 3-[CH₂-P⁺(C₆H₅)₃]phenyl, Br⁻ |
| 1438 | n-butyl | n-butyl | OH | H | 4-[(CH₂)₅-N⁺(CH₂CH₃)₃]phenyl, I⁻ |

-continued

Additional Structures of the Present Invention

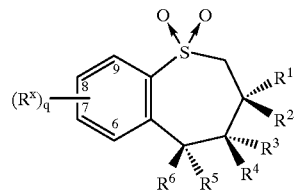

| Compound Number | R¹ | R² | R³ | R⁴ | R⁵ |
|---|---|---|---|---|---|
| 1439 | n-butyl | n-butyl | OH | H | 4-[(CH₂)₈N⁺(CH₂CH₃)₃] phenyl, I⁻ |
| 1440 | n-butyl | n-butyl | OH | H | 4-[O(CH₂)₂]₂-N⁺(pyridinium-4-yl)CH₂CH₂SO₃H, 2-F phenyl |
| 1441 | n-butyl | n-butyl | OH | H | 4-[O(CH₂)₂]₃N⁺(CH₂CH₃)₃, 2-F phenyl, I⁻ |
| 1442 | n-butyl | n-butyl | OH | H | 4-[O(CH₂)₂N⁺(Et)(CH₂PO₃H)(CH₂CO₂H)], 2-F phenyl, I⁻ |
| 1443 | n-butyl | n-butyl | OH | H | 3-(2,6-dimethylpyridinium-1-ylmethyl)phenyl, I⁻ |
| 1444 | n-butyl | n-butyl | OH | H | 4-(OCH₂-pyridin-4-yl), 2-F phenyl |
| 1445 | n-butyl | n-butyl | OH | H | 4-[(CH₂)₃SO₃Na] phenyl |
| 1446 | n-butyl | n-butyl | OH | H | 4-[O(CH₂)₂]₃N⁺(Et)₃ phenyl, Br⁻ |
| 1447 | n-butyl | n-butyl | OH | H | 3-(CH₂SO₃⁻) phenyl, Na⁺ |

-continued

Additional Structures of the Present Invention

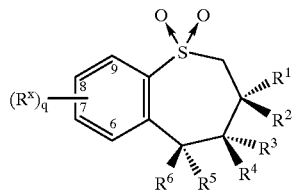

| Compound Number | R¹ | R² | R³ | R⁴ | R⁵ |
|---|---|---|---|---|---|
| 1448 | n-butyl | n-butyl | OH | H | 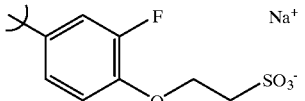 |
| 1449 | n-butyl | n-butyl | OH | H | 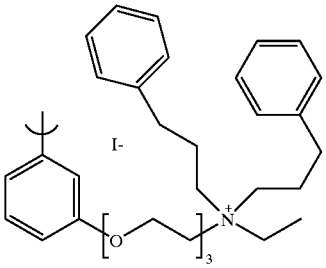 |
| 1450 | n-butyl | n-butyl | OH | H | phenyl |
| 1451 | n-butyl | n-butyl | OH | H | 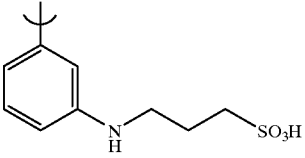 |

| Compound Number | R⁶ | (Rˣ)q |
|---|---|---|
| 101 | H | 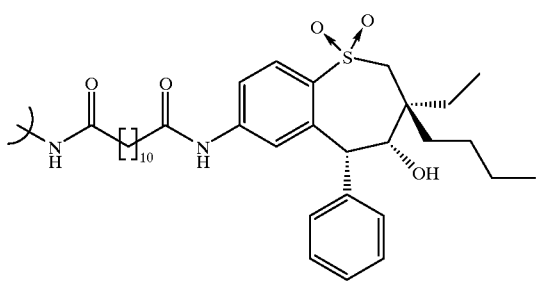<br>at the 7-position |
| 102 | H | 7-trimethylammonium iodide |
| 103 | H | 7-trimethylammonium iodide |
| 104 | H | 7-dimethylamino |
| 105 | H | 7-methanesulfonamido |
| 106 | H | 7-(2'-bromoacetamido) |
| 107 | H | 7-amino |
| 108 | H | 7-(hexylamido) |
| 109 | H | 7-amino |
| 110 | H | 7-acetamido |
| 111 | H | 7-amino |
| 112 | H | 7-amino |
| 113 | H | 7-amino |
| 114 | H | 7-amino |
| 115 | H | 7-(O-benzylcarbamato) |
| 116 | H | 7-(O-benzylcarbamato) |
| 117 | H | 7-(O-benzylcarbamato) |
| 118 | H | 7-(O-benzylcarbamato) |

-continued
| Compound Number | R⁶ | (Rˣ)q |
|---|---|---|
| 119 | H | 7-(O-tert-butylcarbamato) |
| 120 | H | 7-(O-benzylcarbamato) |
| 121 | H | 7-amino |
| 122 | H | 7-amino |
| 123 | H | 7-hexylamino |
| 124 | H | 7-(hexylamino) |
| 125 | H | I⁻ 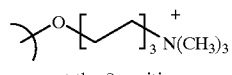 at the 8-position |
| 126 | H | 7-(O-benzylcarbamato) |
| 127 | H | 7-amino |
| 128 | H | 7-(O-benzylcarbamato) |
| 129 | H | 7-amino |
| 131 | H | 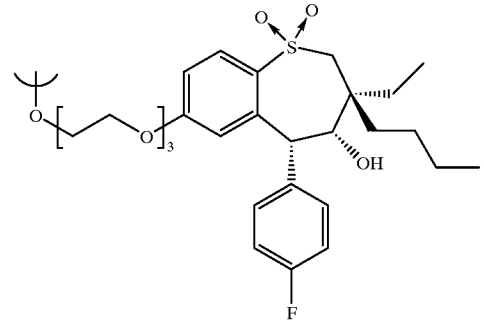 at the 7-position |
| 132 | H | 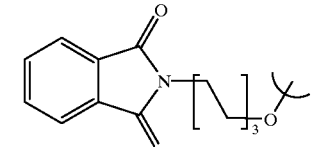 at the 8-position |
| 133 | H | 8-(hexyloxy) |
| 134 | H | 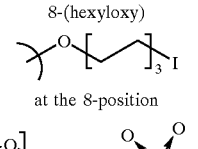 at the 8-position |
| 135 | H | 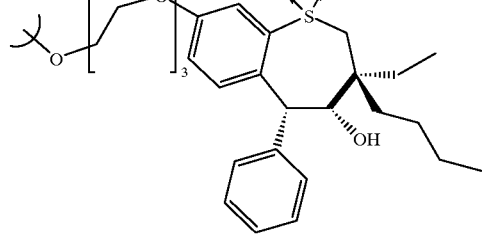 at the 8-position |
| 136 | H | 8-hydroxy |
| 137 | H | 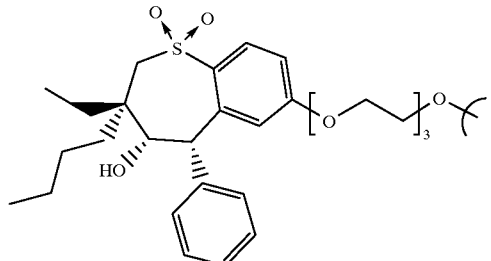 at the 7-position |
| 138 | H | 8-acetoxy |

-continued

| Compound Number | R⁶ | (Rˣ)q |
|---|---|---|
| 139 | H | [structure shown] at the 7-position |
| 140 | | |
| 141 | | |
| 142 | 3-methoxy-phenyl | 7-methylmercapto |
| 143 | H | 7-methylmercapto |
| 144 | H | 7-(N-azetidinyl) |
| 262 | H | 7-methoxy |
| 263 | 3-methoxy-phenyl | 7-methoxy |
| 264 | H | 7-methoxy |
| 265 | 3-trifluoro-methyl-phenyl | 7-methoxy |
| 266 | H | 7-hydroxy |
| 267 | H | 7-methoxy |
| 268 | H | 7-methoxy |
| 269 | 4-fluoro-phenyl | 7-methoxy |
| 270 | H | 7-hydroxy |
| 271 | H | 7-bromo |
| 272 | 3-methoxy-phenyl | 7-bromo |
| 273 | 4-fluoro-phenyl | 7-fluoro |
| 274 | H | 7-fluoro |
| 275 | 3-methoxy-phenyl | 7-fluoro |
| 276 | H | 7-fluoro |
| 277 | H | 7-methoxy |
| 278 | H | 7-methoxy |
| 279 | H | 7-methoxy |
| 280 | H | 7-methoxy |
| 281 | H | 7-methylmercapto |
| 282 | H | 7-methyl |
| 283 | 4-fluoro-phenyl | 7-methyl |
| 284 | H | 7-(4'-morpholino) |
| 286 | H | 7-(O-benzylcarbamato) |
| 287 | H | 7-amino |
| 288 | H | 7-amino |
| 289 | H | 7-amino |
| 290 | H | 7-amino |
| 291 | H | 7-(O-benzylcarbamato) |
| 292 | H | 7-amino |
| 293 | H | 7-benzylamino |
| 294 | H | 7-dimethylamino |
| 295 | H | 7-amino |
| 296 | H | 7-amino |
| 1000 | H | 7-dimethylamino |
| 1001 | H | 7-dimethylamino |
| 1002 | H | 7-dimethylamino |
| 1003 | H | 7-dimethylamino |
| 1004 | H | 7-dimethylamino |
| 1005 | H | 7-dimethylamino |
| 1006 | H | 7-dimethylamino |
| 1007 | H | 7-dimethylamino |
| 1008 | H | 7-dimethylamino |
| 1009 | H | 7-dimethylamino |
| 1010 | H | 7-dimethylamino |
| 1011 | H | 7-dimethylamino |
| 1012 | H | 7-dimethylamino; 9-methoxy |
| 1013 | H | 7-dimethylamino |
| 1014 | H | 7-dimethylamino; 9-methoxy |
| 1015 | H | 7-dimethylamino |
| 1016 | H | 7-dimethylamino |
| 1017 | H | 7-dimethylamino |
| 1018 | H | 7-dimethylamino |
| 1019 | H | 7-dimethylamino |
| 1020 | H | 7-dimethylamino |
| 1021 | H | 7-dimethylamino |
| 1022 | H | 7-dimethylamino |
| 1023 | H | 7-dimethylamino |

-continued

| Compound Number | R⁶ | (Rˣ)q |
|---|---|---|
| 1024 | H | 7-dimethylamino |
| 1025 | H | 7-dimethylamino |
| 1026 | H | 7-dimethylamino |
| 1027 | H | 7-dimethylamino |
| 1028 | H | 7-dimethylamino |
| 1029 | H | 7-dimethylamino |
| 1030 | H | 7-dimethylamino |
| 1031 | H | 7-dimethylamino |
| 1032 | H | 7-dimethylamino |
| 1033 | H | 7-dimethylamino |
| 1034 | H | 7-dimethylamino |
| 1035 | H | 7-dimethylamino |
| 1036 | H | 7-dimethylamino |
| 1037 | H | 7-dimethylamino |
| 1038 | H | 7-dimethylamino |
| 1039 | H | 7-dimethylamino |
| 1040 | H | 7-dimethylamino |
| 1041 | H | 7-dimethylamino |
| 1042 | H | 7-dimethylamino |
| 1043 | H | 7-dimethylamino |
| 1044 | H | 7-dimethylamino |
| 1045 | H | 7-dimethylamino |
| 1046 | H | 7-dimethylamino |
| 1047 | H | 7-dimethylamino |
| 1048 | H | 7-dimethylamino |
| 1049 | H | 7-dimethylamino |
| 1050 | H | 7-dimethylamino |
| 1051 | H | 7-dimethylamino |
| 1052 | H | 7-dimethylamino |
| 1053 | H | 7-dimethylamino |
| 1054 | H | 7-dimethylamino |
| 1055 | H | 7-dimethylamino |
| 1056 | H | 7-dimethylamino |
| 1057 | H | 7-dimethylamino |
| 1058 | H | 7-dimethylamino |
| 1059 | H | 7-dimethylamino |
| 1060 | H | 7-methylamino |
| 1061 | H | 7-methylamino |
| 1062 | H | 7-methylamino |
| 1063 | H | 7-methylamino |
| 1064 | H | 7-methylamino |
| 1065 | H | 7-dimethylamino |
| 1066 | H | 7-dimethylamino |
| 1067 | H | 9-dimethylamino |
| 1068 | H | 7-dimethylamino |
| 1069 | H | 7-dimethylamino; 9-dimethylamino |
| 1070 | H | 7-dimethylamino |
| 1071 | H | 7-dimethylamino |
| 1072 | H | 7-dimethylamino |
| 1073 | H | 7-dimethylamino |
| 1074 | H | 7-dimethylamino |
| 1075 | H | 7-dimethylamino; 9-dimethylamino |
| 1076 | H | 7-dimethylamino |
| 1077 | H | 7-dimethylamino |
| 1078 | H | 7-dimethylamino |
| 1079 | H | 7-dimethylamino |
| 1080 | H | 7-dimethylamino |
| 1081 | H | 7-dimethylamino |
| 1082 | H | 7-dimethylamino |
| 1083 | H | 7-dimethylamino |
| 1084 | H | 7-dimethylamino |
| 1085 | H | 7-dimethylamino |
| 1086 | H | 7-dimethylamino |
| 1087 | H | 7-dimethylamino |
| 1088 | H | 7-dimethylamino |
| 1089 | H | 7-dimethylamino |
| 1090 | H | 7-dimethylamino |
| 1091 | H | 7-dimethylamino |
| 1092 | H | 7-dimethylamino |
| 1093 | H | 7-dimethylamino |
| 1094 | H | 7-dimethylamino |
| 1095 | H | 7-dimethylamino |
| 1096 | H | 7-dimethylamino |
| 1097 | H | 7-dimethylamino |
| 1098 | H | 7-dimethylamino |
| 1099 | H | 7-dimethylamino |
| 1100 | H | 7-dimethylamino |
| 1102 | H | 7-dimethylamino |

-continued

| Compound Number | R⁶ | (Rˣ)q |
|---|---|---|
| 1103 | H | 7-dimethylamino |
| 1104 | H | 7-dimethylamino |
| 1105 | H | 7-dimethylamino |
| 1106 | H | 7-dimethylamino |
| 1107 | H | 7-dimethylamino |
| 1108 | H | 7-dimethylamino |
| 1109 | H | 7-dimethylamino |
| 1110 | H | 7-dimethylamino |
| 1111 | H | 7-dimethylamino |
| 1112 | H | 7-dimethylamino |
| 1113 | H | 7-dimethylamino |
| 1114 | H | 7-methylamino |
| 1115 | H | 7-dimethylamino |
| 1116 | H | 7-dimethylamino |
| 1117 | H | 7-dimethylamino |
| 1118 | H | 7-dimethylamino |
| 1119 | H | 7-dimethylamino |
| 1120 | H | 7-dimethylamino |
| 1121 | H | 7-dimethylamino |
| 1122 | H | 7-dimethylamino |
| 1123 | H | 7-dimethylamino |
| 1124 | H | 7-dimethylamino |
| 1125 | H | 7-dimethylamino |
| 1126 | H | 7-dimethylamino |
| 1127 | H | 7-dimethylamino |
| 1128 | H | 7-dimethylamino |
| 1129 | H | 9-dimethylamino |
| 1130 | H | 7-dimethylamino |
| 1131 | H | 7-dimethylamino |
| 1132 | H | 7-dimethylamino |
| 1133 | H | 7-dimethylamino |
| 1134 | H | 7-dimethylamino |
| 1135 | H | 7-dimethylamino |
| 1136 | H | 7-dimethylamino |
| 1137 | H | 9-(2',2'-dimethylhydrazino) |
| 1138 | H | 7-dimethylamino |
| 1139 | H | 7-dimethylamino |
| 1140 | H | 7-(2',2'-dimethylhydrazino) |
| 1141 | H | 7-ethylmethylamino |
| 1142 | H | 7-dimethylamino |
| 1143 | 3-fluoro-4-methoxy-phenyl | 7-dimethylamino |
| 1144 | H | 7-dimethylamino |
| 1145 | H | 9-dimethylamino |
| 1146 | H | 7-dimethylamino |
| 1147 | H | 7-diethylamino |
| 1148 | H | 7-dimethylsulfonium, fluoride salt |
| 1149 | H | 7-ethylamino |
| 1150 | H | 7-ethylmethylamino |
| 1151 | H | 7-dimethylamino |
| 1152 | H | 7-(ethoxymethyl) methylamino |
| 1153 | H | 7-methylamino |
| 1154 | H | 9-methoxy |
| 1155 | H | 7-methyl |
| 1156 | H | 7-methylmercapto |
| 1157 | H | 7-fluoro; 9-dimethylamino |
| 1158 | H | 7-methoxy |
| 1159 | H | 7-dimethylamino |
| 1160 | H | 7-diethylamino |
| 1161 | H | 7-dimethylamino |
| 1162 | H | 7-dimethylamino |
| 1163 | H | 7-methoxy |
| 1164 | H | 7-methoxy |
| 1165 | H | 7-trimethylammonium iodide |
| 1166 | H | 7-trimethylammonium iodide |
| 1167 | H | 7-dimethylamino |
| 1168 | H | 7-trimethylammonium iodide |
| 1169 | H | 8-dimethylamino |
| 1170 | H | 7-ethylpropylamino |
| 1171 | H | 7-dimethylamino |
| 1172 | H | 7-methoxy |
| 1173 | H | 7-ethylpropylamino |
| 1174 | H | 7-phenyl |
| 1175 | H | 7-methylsulfonyl |
| 1176 | H | 9-fluoro |
| 1177 | H | 7-butylmethylamino |
| 1178 | H | 7-dimethylamino |
| 1179 | H | 8-methoxy |
| 1180 | H | 7-trimethylammonium iodide |

-continued

| Compound Number | R⁶ | (Rˣ)q |
|---|---|---|
| 1181 | H | 7-butylmethylamino |
| 1182 | H | 7-methoxy |
| 1183 | H | 7-fluoro |
| 1184 | H | 7-fluoro; 9-fluoro |
| 1185 | H | 7-fluoro |
| 1186 | H | 7-fluoro; 9-fluoro |
| 1187 | H | 7-methyl |
| 1188 | H | 7-trimethylammonium iodide |
| 1189 | H | 7-trimethylammonium iodide |
| 1190 | H | 7-bromo |
| 1191 | H | 7-hydroxy |
| 1192 | H | 7-hydroxy |
| 1193 | H | 7-dimethylamino |
| 1194 | H | 7-dimethylamino |
| 1195 | H | 7-(4'-methylpiperazin-1-yl) |
| 1196 | H | 7-methoxy |
| 1197 | H | 7-(N-methylformamido) |
| 1198 | H | 7-methoxy |
| 1199 | H | 7-dimethylamino |
| 1200 | phenyl | 7-dimethylamino |
| 1201 | H | 7-methyl |
| 1202 | H | 7-methoxy |
| 1203 | H | 7-(4'-tert-butylphenyl) |
| 1204 | H | 7-methoxy |
| 1205 | H | 7-dimethylamino |
| 1206 | H | 7-dimethylamino |
| 1207 | H | 7-dimethylamino |
| 1208 | H | 7-dimethylamino |
| 1209 | H | 7-dimethylphenyl |
| 1210 | H | 7-dimethylamino |
| 1211 | H | 7-dimethylamino |
| 1212 | H | 9-(4'-morpholino) |
| 1213 | 3-fluoro-4-methoxy-phenyl | 7-dimethylamino |
| 1214 | H | 7-(N-methylformamido) |
| 1215 | H | 9-methylmercapto |
| 1216 | H | 7-bromo |
| 1217 | H | 7-dimethylamino |
| 1218 | H | 9-methylsulfonyl |
| 1219 | H | 7-dimethylamino |
| 1220 | H | 7-isopropylamino |
| 1221 | H | 7-dimethylamino |
| 1222 | H | 7-ethylamino |
| 1223 | H | 8-bromo; 7-methylamino |
| 1224 | H | 7-fluoro |
| 1225 | H | 7-dimethylamino |
| 1226 | H | 7-bromo |
| 1227 | H | 7-(tert-butylamino |
| 1228 | H | 8-bromo; 7-dimethylamino |
| 1229 | H | 7-dimethylamino |
| 1230 | H | 9-dimethylamino; 7-fluoro |
| 1231 | H | 7-dimethylamino |
| 1232 | H | 9-dimethylamino |
| 1233 | H | 7-dimethylamino |
| 1234 | H | 7-dimethylamino |
| 1235 | H | 7-dimethylamino |
| 1236 | H | 7-dimethylamino |
| 1237 | H | 7-dimethylamino |
| 1238 | H | 7-dimethylamino |
| 1239 | H | 7-dimethylamino |
| 1240 | H | 7-dimethylamino |
| 1241 | H | 7-dimethylamino |
| 1242 | H | 7-dimethylamino |
| 1243 | H | 7-dimethylamino |
| 1244 | H | 7-(1'-methylhydrazido) |
| 1245 | H | 7-dimethylamino |
| 1246 | H | 7-dimethylamino |
| 1247 | H | 7-dimethylamino |
| 1248 | H | 7-dimethylamino |
| 1249 | H | 7-dimethylamino |
| 1250 | H | 7-dimethylamino |
| 1251 | H | 7-dimethylamino |
| 1252 | H | 7-dimethylamino |
| 1253 | H | 7-dimethylamino |
| 1254 | H | 7-dimethylamino |
| 1255 | H | 7-dimethylamino |
| 1256 | H | 7-dimethylamino |
| 1257 | H | 8-bromo; 7-dimethylamino |
| 1258 | H | 9-(tert-butylamino) |

-continued

| Compound Number | $R^6$ | $(R^x)_q$ |
|---|---|---|
| 1259 | phenyl | 7-dimethylamino |
| 1260 | H | 7-dimethylamino |
| 1261 | H | 7-dimethylamino |
| 1262 | H | 7-dimethylamino |
| 1263 | H | 7-bromo |
| 1264 | H | 7-isopropylamino |
| 1265 | H | 9-isopropylamino |
| 1266 | H | 7-dimethylamino |
| 1267 | H | 7-carboxy, methyl ester |
| 1268 | H | 7-dimethylamino |
| 1269 | H | 7-dimethylamino |
| 1270 | H | 7-dimethylamino |
| 1271 | H | 7-dimethylamino |
| 1272 | H | 7-dimethylamino |
| 1273 | H | 7-dimethylamino |
| 1274 | H | 7-dimethylamino |
| 1275 | H | 7-dimethylamino |
| 1276 | H | 7-dimethylamino |
| 1277 | H | 7-dimethylamino |
| 1278 | H | 7-dimethylamino |
| 1279 | H | 7-dimethylamino |
| 1280 | H | 7-dimethylamino |
| 1281 | H | 7-dimethylamino |
| 1282 | H | 7-trimethylammonium iodide |
| 1283 | H | 7-dimethylamino |
| 1284 | H | 9-ethylamino |
| 1285 | H | 7-dimethylamino |
| 1286 | H | 7-dimethylamino |
| 1287 | H | 7-dimethylamino |
| 1288 | H | 7-dimethylamino |
| 1289 | H | 7-dimethylamino |
| 1290 | H | 7-dimethylamino |
| 1291 | H | 7-dimethylamino |
| 1292 | H | 7-dimethylamino |
| 1293 | H | 7-dimethylamino |
| 1294 | H | 7-dimethylamino |
| 1295 | H | 7-dimethylamino |
| 1296 | H | 7-dimethylamino |
| 1297 | H | 7-dimethylamino |
| 1298 | H | 7-dimethylamino |
| 1299 | H | 7-dimethylamino |
| 1300 | phenyl | 7-dimethylamino |
| 1301 | H | 7-trimethylammonium iodide |
| 1302 | H | 9-hydroxy |
| 1303 | H | 7-dimethylamino |
| 1304 | H | 7-tert-butylamino |
| 1305 | H | 9-methylamino |
| 1306 | H | 7-dimethylamino |
| 1307 | 4-methoxy-phenyl | 9-(4'-morpholino) |
| 1308 | H | 7-dimethylamino |
| 1309 | H | 9-fluoro |
| 1310 | H | 7-amino |
| 1311 | H | 7-(hydroxylamino) |
| 1312 | H | 8-hexyloxy |
| 1313 | H | 8-ethoxy |
| 1314 | H | 7-(hydroxylamino) |
| 1315 | H | 7-(hexyloxy) |
| 1316 | H | 8-hydroxy |
| 1317 | H | 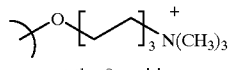 at the 8-position |
| 1318 | H | 7-dimethylamino |
| 1319 | H | 7-fluoro |
| 1320 | H | 7-amino |
| 1321 | H | 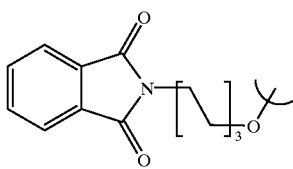 at the 8-position |
| 1322 | H | 7-dimethylamino |
| 1323 | H | 7-dimethylamino |

-continued

| Compound Number | R⁶ | (Rˣ)q |
|---|---|---|
| 1324 | H | 7-dimethylamino |
| 1325 | H | 7-dimethylamino |
| 1326 | H | 7-dimethylamino |
| 1327 | H | 7-dimethylamino |
| 1328 | H | 7-dimethylamino |
| 1329 | H | 7-dimethylamino |
| 1330 | H | 7-dimethylamino |
| 1331 | H | 7-dimethylamino |
| 1332 | H | 7-dimethylamino |
| 1333 | H | 7-dimethylamino |
| 1334 | H | 7-dimethylamino |
| 1335 | H | 7-dimethylamino |
| 1336 | H | 7-dimethylamino |
| 1337 | H | 7-dimethylamino |
| 1338 | H | 7-(4'-methylpiperazinyl) |
| 1339 | H | 7-dimethylamino |
| 1340 | H | 7-methyl |
| 1341 | H | 7-dimethylamino |
| 1342 | H | 7-(4'-fluorophenyl) |
| 1343 | H | 7-amino |
| 1344 | H | 7-dimethylamino |
| 1345 | H | 7-trimethylammonium iodide |
| 1346 | H | -O-[CH₂CH₂O]₉-CH₂-O-CH₃ at the 8-position |
| 1347 | H | 7-dimethylamino |
| 1348 | H | 7-dimethylamino |
| 1349 | H | 7-dimethylamino |
| 1350 | H | 7-trimethylammonium iodide |
| 1351 | H | 7-dimethylamino |
| 1352 | H | 7-dimethylamino |
| 1353 | H | 7-dimethylamino |
| 1354 | H | 7-dimethylamino |
| 1355 | H | 7-dimethylamino |
| 1356 | H | 7-dimethylamino |
| 1357 | H | 7-dimethylamino |
| 1358 | H | 7-dimethylamino |
| 1359 | H | 7-dimethylamino |
| 1360 | H | 7-dimethylamino |
| 1361 | H | 7-dimethylamino |
| 1362 | H | 7-dimethylamino |
| 1363 | H | 7-dimethylamino |
| 1364 | H | 7-dimethylamino |
| 1365 | H | 7-dimethylamino |
| 1366 | H | 7-dimethylamino |
| 1367 | H | 7-dimethylamino |
| 1368 | H | 7-dimethylamino |
| 1369 | H | 7-dimethylamino |
| 1370 | H | 7-dimethylamino |
| 1371 | H | 7-dimethylamino |
| 1372 | H | 7-dimethylamino |
| 1373 | H | 7-dimethylamino |
| 1374 | H | 7-dimethylamino |
| 1375 | H | 7-dimethylamino |
| 1376 | H | 7-dimethylamino |
| 1377 | H | 7-dimethylamino |
| 1378 | H | 7-dimethylamino |
| 1379 | H | 7-dimethylamino |
| 1380 | H | 7-dimethylamino |
| 1381 | H | 7-dimethylamino |
| 1382 | H | 7-dimethylamino |
| 1383 | H | 7-dimethylamino |
| 1384 | H | 7-dimethylamino |
| 1385 | H | 7-dimethylamino |
| 1386 | H | 7-dimethylamino |
| 1387 | H | 7-dimethylamino |
| 1388 | H | 7-dimethylamino |
| 1389 | H | 7-dimethylamino |
| 1390 | H | 7-dimethylamino |
| 1391 | H | 7-dimethylamino |
| 1392 | H | 7-dimethylamino |
| 1393 | H | 7-dimethylamino |
| 1394 | H | 7-dimethylamino |
| 1395 | H | 7-dimethylamino |
| 1396 | H | 7-dimethylamino |
| 1397 | H | 7-dimethylamino |

-continued

| Compound Number | R⁶ | (Rˣ)q |
|---|---|---|
| 1398 | H | 7-dimethylamino |
| 1399 | H | 7-dimethylamino |
| 1400 | H | 7-dimethylamino |
| 1401 | H | 7-dimethylamino |
| 1402 | H | 7-dimethylamino |
| 1403 | H | 7-dimethylamino |
| 1404 | H | 7-dimethylamino |
| 1405 | H | 7-dimethylamino |
| 1406 | H | 7-dimethylamino |
| 1407 | H | 7-dimethylamino |
| 1408 | H | 7-dimethylamino |
| 1409 | H | 7-dimethylamino |
| 1410 | H | 7-dimethylamino |
| 1411 | H | 7-dimethylamino |
| 1412 | H | 7-dimethylamino |
| 1413 | H | 7-dimethylamino |
| 1414 | H | 7-dimethylamino |
| 1415 | H | 7-dimethylamino |
| 1416 | H | 7-dimethylamino |
| 1417 | H | 7-dimethylamino |
| 1418 | H | 7-dimethylamino |
| 1419 | H | 7-dimethylamino |
| 1420 | H | 7-dimethylamino |
| 1421 | H | 7-dimethylamino |
| 1422 | H | 7-dimethylamino |
| 1423 | H | 7-dimethylamino |
| 1424 | H | 7-dimethylamino |
| 1425 | H | 7-dimethylamino |
| 1426 | H | 7-dimethylamino |
| 1427 | H | 7-dimethylamino |
| 1428 | H | 7-dimethylamino |
| 1429 | H | 7-dimethylamino |
| 1430 | H | 7-dimethylamino |
| 1431 | H | 7-dimethylamino |
| 1432 | H | 7-dimethylamino |
| 1433 | H | 7-dimethylamino |
| 1434 | H | 7-dimethylamino |
| 1435 | H | 7-dimethylamino |
| 1436 | H | 7-dimethylamino |
| 1437 | H | 7-dimethylamino |
| 1438 | H | 7-dimethylamino |
| 1439 | H | 7-dimethylamino |
| 1440 | H | 7-dimethylamino |
| 1441 | H | 7-dimethylamino |
| 1442 | H | 7-dimethylamino |
| 1443 | H | 7-dimethylamino |
| 1444 | H | 7-dimethylamino |
| 1445 | H | 7-dimethylamino |
| 1446 | H | 7-methoxy; 8-methoxy |
| 1447 | H | 7-dimethylamino |
| 1448 | H | 7-dimethylamino |
| 1449 | H | 7-dimethylamino |
| 1450 | H | 7-dimethylamino |
| 1451 | H | 7-dimethylamino |

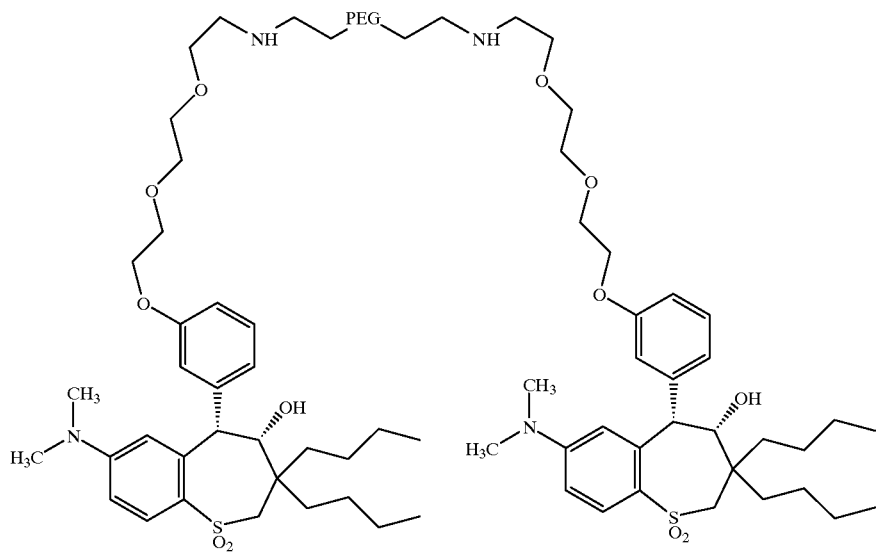
PEG = 3400 molecular weight polyethylene glycol polymer chain
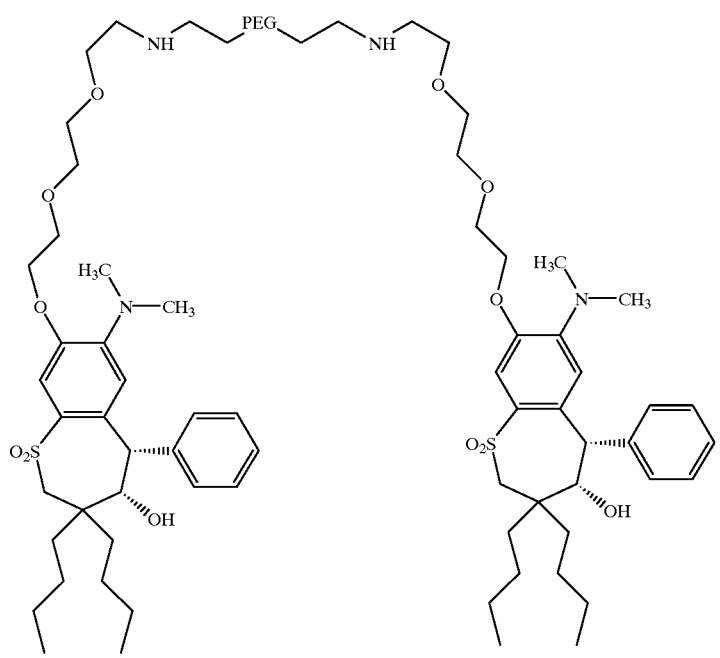
PEG = 3400 molecular weight polyethylene glycol polymer chain

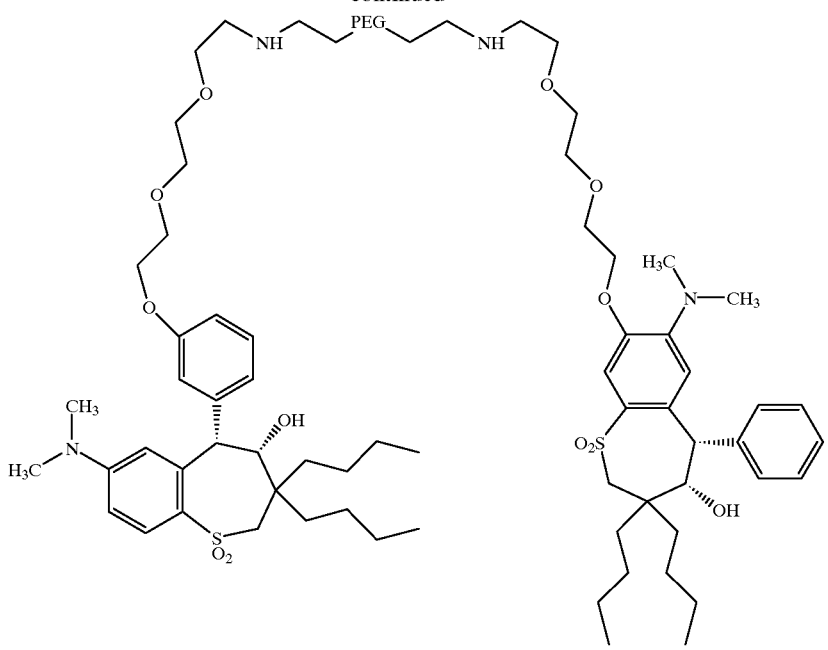
PEG = 3400 molecular weight polyethylene glycol polymer chain
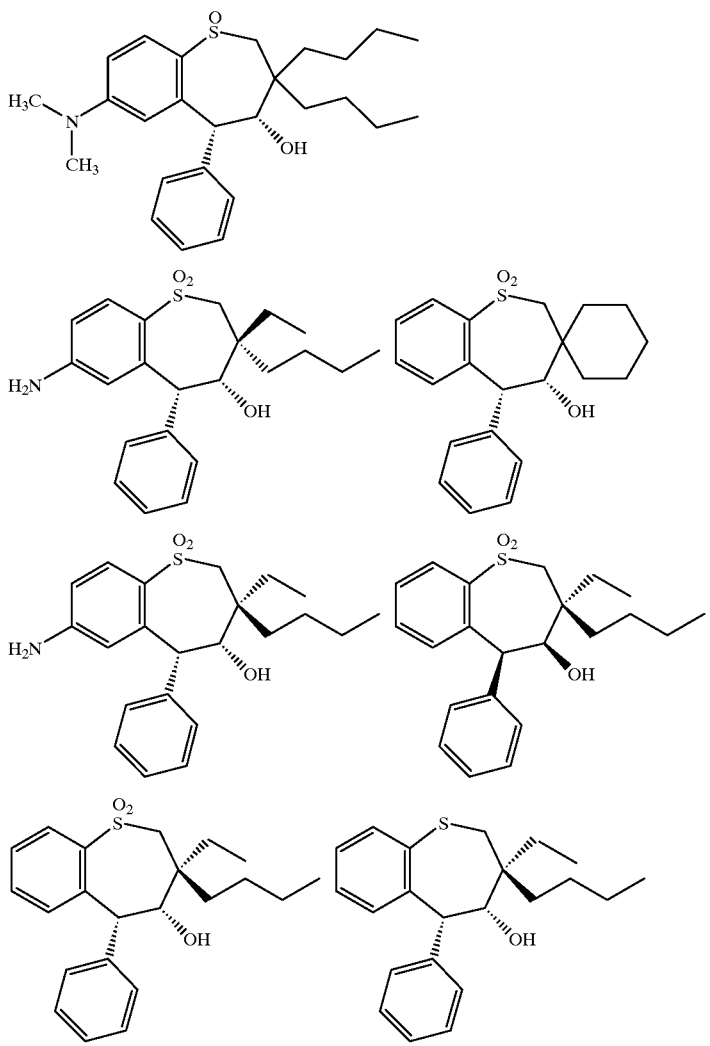

-continued
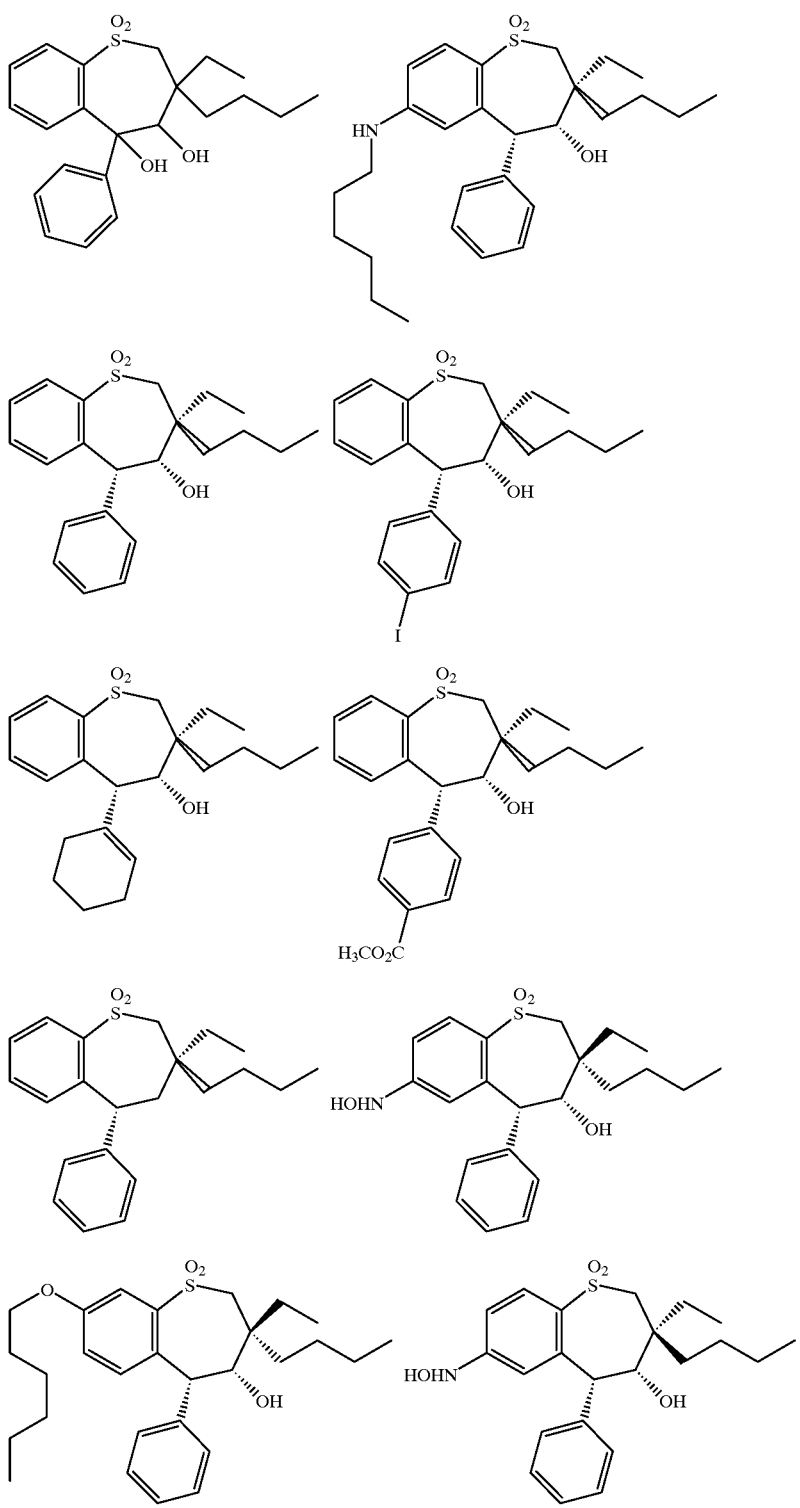

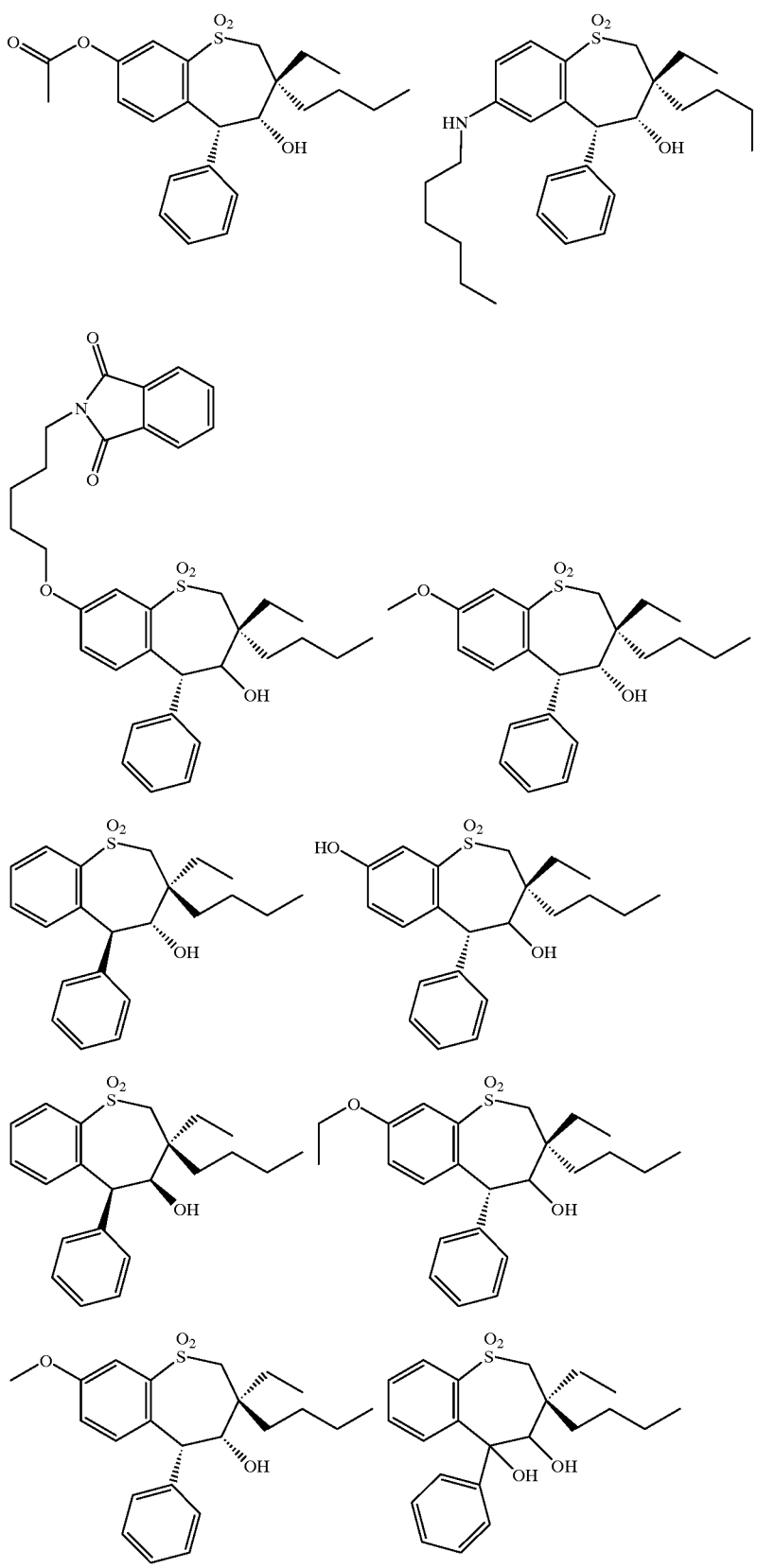

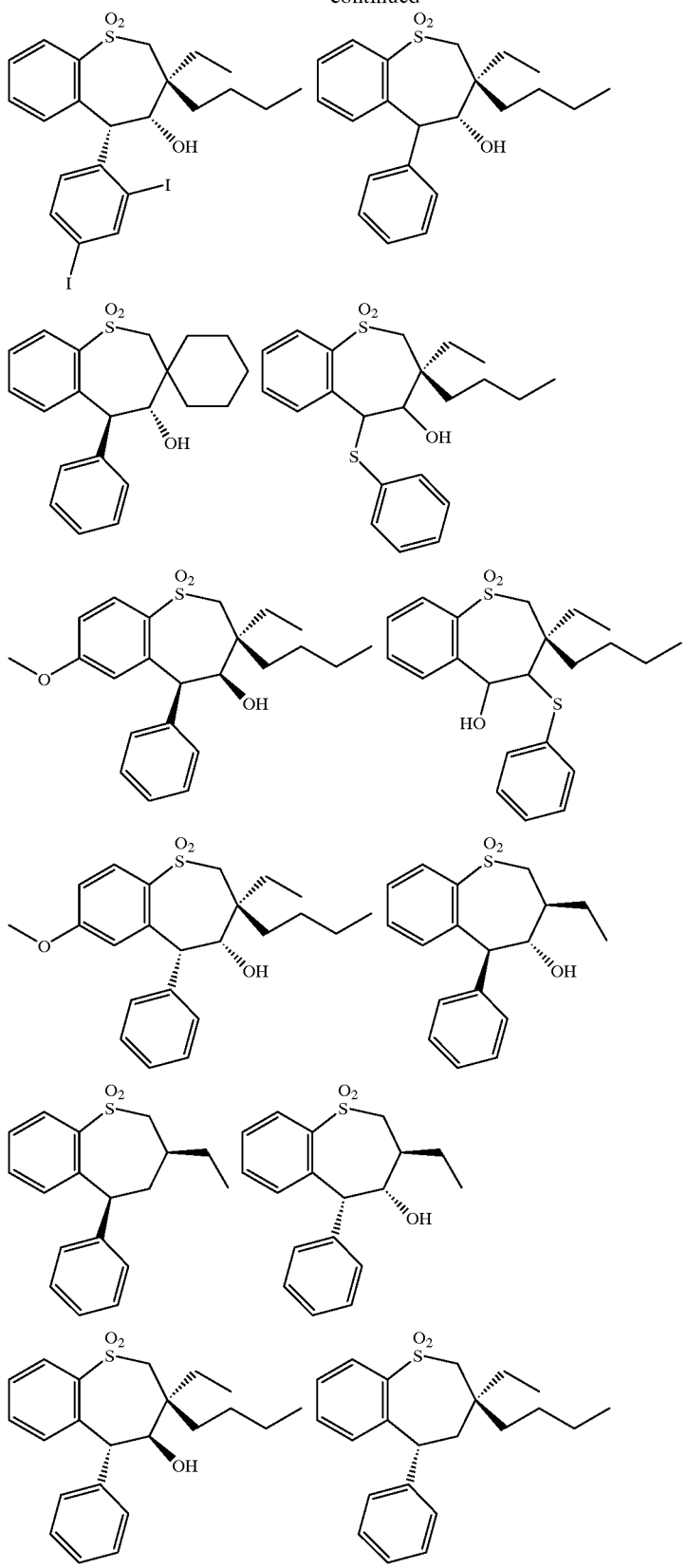

In further compounds of the present invention, $R^5$ and $R^6$ are independently selected from among hydrogen and ring-carbon substituted or unsubstituted aryl, thiophene, pyridine, pyrrole, thiazole, imidazole, pyrazole, pyrimidine, morpholine, N-alkylpyridinium, N-alkylpiperazinium, N-alkylmorpholinium, or furan in which the substituent(s) are selected from among halo, hydroxyl, trihaloalkyl, alkoxy, amino, N-alkylamino, N,N-dialkylamino, quaternary ammonium salts, a $C_1$ to $C_4$ alkylene bridge having a quaternary ammonium salt substituted thereon, alkoxycarbonyl, aryloxycarbonyl, alkylcarbonyloxy and arylcarbonyloxy, (O,O)-dioxyalkylene, —$[O(CH_2)_w]_x$ X where x is 2 to 12, w is 2 or 3 and X comprises halo or a quaternary ammonium salt, thiophene, pyridine, pyrrole, thiazole, imidazole, pyrazole, or furan. The aryl group of $R^5$ or $R^6$ is preferably phenyl, phenylene, or benzene triyl, i.e., may be unsubstituted, mono-substituted, or di-substituted. Among the species which may constitute the substituents on the aryl ring of $R^5$ or $R^6$ are fluoro, chloro, bromo, methoxy, ethoxy, isopropoxy, trimethylammonium (preferably with an iodide or chloride counterion), methoxycarbonyl, ethoxycarbonyl, formyl, acetyl, propanoyl, (N)-hexyldimethylammonium, hexylenetrimethylammonium, tri(oxyethylene)iodide, and tetra(oxyethylene)trimethyl-ammonium iodide, each substituted at the p-position, the m-position, or both of the aryl ring. Other substituents that can be present on a phenylene, benzene triyl or other aromatic ring include 3,4-dioxymethylene (5-membered ring) and 3,4-dioxyethylene (6-membered ring). Among compounds which have been or can be demonstrated to have desirable ileal bile acid transport inhibiting properties are those in which $R^5$ or $R^6$ is selected from phenyl, p-fluorophenyl, m-fluorophenyl, p-hydroxyphenyl, m-hydroxyphenyl, p-methoxyphenyl, m-methoxyphenyl, p-N,N-dimethylaminophenyl, m-N,N-dimethylaminophenyl, I⁻ p-$(CH_3)_3$-N⁺-phenyl, I⁻ m-$(CH_3)_3$-N⁺-phenyl, I⁻ m-$(CH_3)_3$-N⁺-$CH_2CH_2$-$(OCH_2CH_2)_2$-O-phenyl, I⁻ p-$(CH_3)_3$-N⁺-$CH_2CH_2$-$(OCH_2CH_2)_2$-O-phenyl, I⁻ m-(N,N-dimethylpiperazinium)-(N')-$CH_2$-$(OCH_2CH_2)_2$-O-phenyl, 3-methoxy-4-fluorophenyl, thienyl-2-yl, 5-cholorothienyl-2-yl, 3,4-difluorophenyl, I⁻ p-(N,N-dimethylpiperazinium)-(N')-$CH_2$-$(OCH_2CH_2)_2$-O-phenyl, 3-fluoro-4-methoxyphenyl, -4-pyridinyl, 2-pyridinyl, 3-pyridinyl, N-methyl-4-pyridinium, I⁻ N-methyl-3-pyridinium, 3,4-dioxymethylenephenyl, 3,4-dioxyethylenephenyl, and p-methoxycarbonylphenyl. Preferred compounds include 3-ethyl-3-butyl and 3-butyl-3-butyl compounds having each of the above preferred $R^5$ substituents in combination with the $R^x$ substituents shown in Table 1. It is particularly preferred that one but not both of $R^5$ and $R^6$ is hydrogen.

It is especially preferred that $R^4$ and $R^6$ be hydrogen, that $R^3$ and $R^5$ not be hydrogen, and that $R^3$ and $R^5$ be oriented in the same direction relative to the plane of the molecule, i.e., both in α- or both in β-configuration. It is further preferred that, where $R^2$ is butyl and $R^1$ is ethyl, then $R^1$ has the same orientation relative to the plane of the molecule as $R^3$ and $R^5$.

Set forth in Table 1A are lists of species of $R^1/R^2$, $R^5/R^6$ and $R^x$.

TABLE 1A

Alternative R Groups

| $R^1,R^2$ | $R^3,R^4$ | $R^5$ | $(R^x)q$ |
|---|---|---|---|
| ethyl | HO- | Ph- | 7-methyl |
| n-propyl | H- | p-F-Ph- | 7-ethyl |
| n-butyl | | m-F-Ph- | 7-iso-propyl |
| n-pentyl | | p-$CH_3$O-Ph- | 7-tert-butyl |
| n-hexyl | | p-$CH_3$O-Ph- | 7-OH |
| iso-propyl | | m-$CH_3$O-Ph- | 7-$OCH_3$ |
| iso-butyl | | p-$(CH_3)_2$N-Ph- | 7-O(iso-propyl) |
| iso-pentyl | | m-$(CH_3)_2$N-Ph- | 7-$SCH_3$ |
| $CH_2C(=O)C_2H_5$ | | I⁻, p-$(CH_3)_3$-N⁺-Ph- | 7-$SOCH_3$ |
| $CH_2OC_2H_5$ | | I⁻, m-$(CH_3)_3$-N⁺-Ph- | 7-$SO_2CH_3$ |
| $CH_2CH(OH)C_2H_5$ | | I⁻, p-$(CH_3)_3$-N⁺-$CH_2CH_2$-$(OCH_2CH_2)_2$-O-Ph- | 7-$SCH_2CH_3$ |
| $CH_2O$-(4-picoline) | | | 7-$NH_2$ |
| | | I⁻, m-$(CH_3)_3$-N⁺-$CH_2CH_2$-$(OCH_2CH_2)_2$-O-Ph- | 7-NHOH |
| | | | 7-$NHCH_3$ |
| | | I⁻, p-(N,N-dimethylpiperazine)-(N')-$CH_2$-$(OCH_2CH_2)_2$-O-Ph- | 7-$N(CH_3)_2$ |
| | | | 7-$N^+(CH_3)_3$, I⁻ |
| | | | 7-$NHC(=O)CH_3$ |
| | | | 7-$N(CH_2CH_3)_2$ |
| | | I⁻, m-(N,N-dimethylpiperazine)-(N')-$CH_2$-$(OCH_2CH_2)_2$-O-Ph- | 7-$NMeCH_2CO_2H$ |
| | | | 7-$N^+(Me)_2CH_2CO_2H$, I⁻ |
| | | | 7-(N)-morpholine |
| | | | 7-(N)-azetidine |
| | | m-F, p-$CH_3$O-Ph- | 7-(N)-N-methylazetidinium, I⁻ |
| | | 3,4,dioxymethylene-Ph | |
| | | m-$CH_3$O-, p-F-Ph- | 7-(N)-pyrrolidine |
| | | 4-pyridine | 7-(N)-N-methyl-pyrrolidinium, I⁻ |
| | | N-methyl-4-pyridinium, I⁻ | |

TABLE 1A-continued

Alternative R Groups

[Structure: bicyclic benzothiepine with SO₂ group, positions labeled 3, 4, 5, 6, 7, 8, 9, substituents R¹, R², R³, R⁴, R⁵, R⁶, and (Rˣ)q]

| $R^1, R^2$ | $R^3, R^4$ | $R^5$ | $(R^x)_q$ |
|---|---|---|---|
| | | 3-pyridine | 7-(N)-N-methyl-morpholinium, I⁻ |
| | | N-methyl-3-pyridinium, I⁻ | 7-(N)-N'-methylpiperazine |
| | | 2-pyridine | 7-(N)-N'-dimethylpiperazinium, I⁻ |
| | | p-CH₃O₂C-Ph- | |
| | | thienyl-2-yl | |
| | | 5-Cl-thienyl-2-yl | 7-NH-CBZ |
| | | | 7-NHC(O)C₅H₁₁ |
| | | | 7-NHC(O)CH₂Br |
| | | | 7-NH-C(NH)NH₂ |
| | | | 7-(2)-thiophene |
| | | | 8-methyl |
| | | | 8-ethyl |
| | | | 8-iso-propyl |
| | | | 8-tert-butyl |
| | | | 8-OH |
| | | | 8-OCH₃ |
| | | | 8-O(iso-propyl) |
| | | | 8-SCH₃ |
| | | | 8-SOCH₃ |
| | | | 8-SO₂CH₃ |
| | | | 8-SCH₂CH₃ |
| | | | 8-NH₂ |
| | | | 8-NHOH |
| | | | 8-NHCH₃ |
| | | | 8-N(CH₃)₂ |
| | | | 8-N⁺(CH₃)₃, I⁻ |
| | | | 8-NHC(=O)CH₃ |
| | | | 8-N(CH₂CH₃)₂ |
| | | | 8-NMeCH₂CO₂H |
| | | | 8-N⁺(Me)₂CH₂CO₂H, I⁻ |
| | | | 8-(N)-morpholine |
| | | | 8-(N)-azetidine |
| | | | 8-(N)-N-methylazetidinium, I⁻ |
| | | | 8-(N)-pyrrolidine |
| | | | 8-(N)-N-methylpyrrolidinium, I⁻ |
| | | | 8-(N)-N-methylmorpholinium, I⁻ |
| | | | 8-(N)-N'-methylpiperazine |
| | | | 8-(N)-N'-dimethylpiperazinium, I⁻ |
| | | | 8-NH-CBZ |
| | | | 8-NHC(O)C₅H₁₁ |
| | | | 8-NHC(O)CH₂Br |
| | | | 8-NH-C(NH)NH₂ |
| | | | 8-(2)-thiophene |
| | | | 9-methyl |
| | | | 9-ethyl |
| | | | 9-iso-propyl |
| | | | 9-tert-butyl |
| | | | 9-OH |
| | | | 9-OCH₃ |
| | | | 9-O(iso-propyl) |
| | | | 9-SCH₃ |
| | | | 9-SOCH₃ |
| | | | 9-SO₂CH₃ |
| | | | 9-SCH₂CH₃ |
| | | | 9-NH₂ |
| | | | 9-NHOH |
| | | | 9-NHCH₃ |
| | | | 9-N(CH₃)₂ |
| | | | 9-N⁺(CH₃)₃, I⁻ |

TABLE 1A-continued

Alternative R Groups

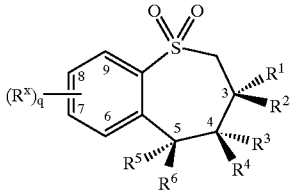

| R$^1$,R$^2$ | R$^3$,R$^4$ | R$^5$ | (R$^x$)q |
|---|---|---|---|
| | | | 9-NHC(=O)CH$_3$ |
| | | | 9-N(CH$_2$CH$_3$)$_2$ |
| | | | 9-NMeCH$_2$CO$_2$H |
| | | | 9-N$^+$(Me)$_2$CH$_2$CO$_2$H, I$^-$ |
| | | | 9-(N)-morpholine |
| | | | 9-(N)-azetidine |
| | | | 9-(N)-N-methylazetidinium, I$^-$ |
| | | | 9-(N)-pyrrolidine |
| | | | 9-(N)-N-methyl-pyrrolidinium, I$^-$ |
| | | | 9-(N)-N-methyl-morpholinium, I$^-$ |
| | | | 9-(N)-N'-methylpiperazine |
| | | | 9-(N)-N'-dimethylpiperazinium, I$^-$ |
| | | | 9-NH-CBZ |
| | | | 9-NHC(O)C$_5$H$_{11}$ |
| | | | 9-NHC(O)CH$_2$Br |
| | | | 9-NH-C(NH)NH$_2$ |
| | | | 9-(2)-thiophene |
| | | | 7-OCH$_3$, 8-OCH$_3$ |
| | | | 7-SCH$_3$, 8-OCH$_3$ |
| | | | 7-SCH$_3$, 8-SCH$_3$ |
| | | | 6-OCH$_3$, 7-OCH$_3$, 8-OCH$_3$ |

Further preferred compounds of the present invention comprise a core structure having two or more pharmaceutically active benzothiepine structures as described above, covalently bonded to the core moiety via functional linkages. Such active benzothiepine structures preferably comprise:

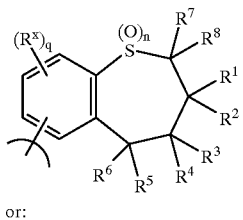

(Formula DIV)

or:

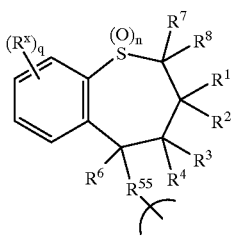

(Formula DIVA)

where R$^1$, R$^2$ R$^3$ R$^4$, R6, R$^5$, R$^6$, R$^7$, R$^8$, X, q and n are as defined above, and R$^{55}$ is either a covalent bond or arylene.

The core moiety can comprise alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, NR$^7$, N$^+$R$^7$R$^8$, S, SO, SO2, S$^+$R$^7$R$^8$, PR7, P+R7R8, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, OR$^{13}$, NR$^{13}$R$^{14}$, SR$^{13}$, S(O)R$^{13}$, SO2R$^{13}$, SO3R$^{13}$, NR$^{13}$OR$^{14}$, NR$^{13}$NR$^{14}$R$^{15}$, NO$_2$, CO$_2$R$^{13}$, CN, OM, SO$_2$OM, SO$_2$NR$^{13}$R$^{14}$, C(O)NR$^{13}$R$^{14}$, C(O)OM, COR$^{13}$, P(O)R$^{13}$R$^{14}$, P$^+$R$^{13}$R$^{14}$R15A-, P(OR$^{13}$)OR$^{14}$, S$^+$R$^{13}$R$^{14}$A-, and N$^+$R$^9$R$^{11}$R$^{12}$A-;

wherein said alkyl, alkenyl, alkynyl, polyalkyl, polyether, aryl, haloalkyl, cycloalkyl, and heterocycle can be further substituted with one or more substituent groups selected from the group consisting of OR$^7$, NR$^7$R$^8$, SR$^7$, S(O)R$^7$, SO$_2$R$^7$, SO$_3$R$^7$, CO$_2$R$^7$, CN, oxo, CONR$^7$R$^8$, N$^+$R$^7$R$^8$R$^9$A-, alkyl, alkenyl, alkynyl, aryl, cycloalkyl, heterocycle, arylalkyl, quaternary heterocycle, quaternary heteroaryl, P(O)R$^7$R$^8$, P$^+$R$^7$R$^8$A-, and P(O) (OR$^7$)OR$^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene.

Exemplary core moieties include:

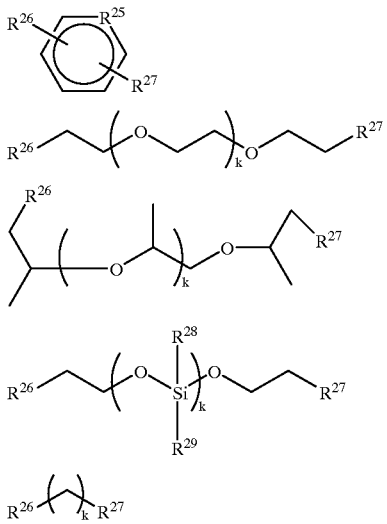

wherein:
$R^{25}$ is selected from the group consisting of C and N, and $R^{26}$ and $R^{27}$ are independently selected from the group consisting of:

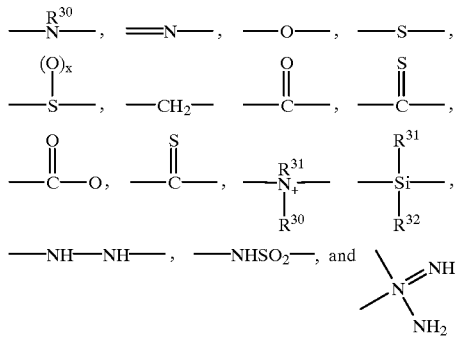

wherein $R^{26}$, $R^{29}$, $R^{30}$ and $R^{31}$ are independently selected from alkyl, alkenyl, alkylaryl, aryl, arylalkyl, cycloalkyl, heterocycle, and heterocycloalkyl, $A^-$ is a pharmaceutically acceptable anion, and k=1 to 10.

In compounds of Formula DIV, $R^{20}$, $R^{21}$, $R^{22}$ in Formulae DII and DIII, and $R^{23}$ in Formula DIII can be bonded at any of their 6-, 7-, 8-, or 9- positions to $R^{19}$. In compounds of Formula DIVA, it is preferred that $R^{55}$ comprises a phenylene moiety bonded at a m- or p-position thereof to $R^{19}$.

In another embodiment, a core moiety backbone, $R^{19}$, as discussed herein in Formulas DII and DIII can be multiply substituted with more than four pendant active benzothiepine units, i.e., $R^{20}$, $R^{21}$, $R^{22}$, and $R^{23}$ as discussed above, through multiple functional groups within the core moiety backbone. The core moiety backbone unit, $R^{19}$, can comprise a single core moiety unit, multimers thereof, and multimeric mixtures of the different core moiety units discussed herein, i.e., alone or in combination. The number of individual core moiety backbone units can range from about one to about 100, preferably about one to about 80, more preferably about one to about 50, and even more preferably about one to about 25. The number of points of attachment of similar or different pendant active benzothiepine units within a single core moiety backbone unit can be in the range from about one to about 100, preferably about one to about 80, more preferably about one to about 50, and even more preferably about one to about 25. Such points of attachment can include bonds to C, S, O, N, or P within any of the groups encompassed by the definition of $R^{19}$.

The more preferred benzothiepine moieties comprising $R^{20}$, $R^{21}$, $R^{22}$ and/or $R^{23}$ conform to the preferred structures as outlined above for Formula I. The 3-carbon on each benzothiepine moiety can be achiral, and the substituents $R^1$, $R^2$, $R^3$, $R^4$, $R^5$ and $R^x$ can be selected from the preferred groups and combinations of substituents as discussed above. The core structures can comprise, for example, poly (exyalkylene) or oligo(oxyalkylene), especially poly- or oligo(exyethylene) or poly- or oligo(oxypropylene).

Dosages, Formulations, and Routes of Administration

The ileal bile acid transport inhibitor compounds of the present invention can be administered for the prophylaxis and treatment of hyperlipidemic diseases or conditions by any means, preferably oral, that produce contact of these compounds with their site of action in the body, for example in the ileum of a mammal, e.g., a human.

For the prophylaxis or treatment of the conditions referred to above, the compounds of the present invention can be used as the compound per se.

Pharmaceutically acceptable salts are particularly suitable for medical applications because of their greater aqueous solubility relative to the parent compound. Such salts must clearly have a pharmaceutically acceptable anion or cation. Suitable pharmaceutically acceptable acid addition salts of the compounds of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions of the definition of $A^-$ in the present invention are, of course, also required to be pharmaceutically acceptable and are also selected from the above list.

The compounds of the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

In general, a daily dose can be in the range of from about 0.3 to about 100 mg/kg bodyweight/day, preferably from about 1 mg to about 50 mg/kg bodyweight/day, more preferably from about 3 to about 10 mg/kg bodyweight/day. This total daily dose can be administered to the patient in a single dose, or in proportionate multiple subdoses. Subdoses can be administered 2 to 6 times per day. Doses can be in sustained release form effective to obtain desired results.

Orally administrable unit dose formulations, such as tablets or capsules, can contain, for example, from about 0.1 to about 100 mg of benzothiepine compound, preferably about 1 to about 75 mg of compound, more preferably from about 10 to about 50 mg of compound. In the case of pharmaceutically acceptable salts, the weights indicated above refer to the weight of the benzothiepine ion derived from the salt.

Oral delivery of an ileal bile acid transport inhibitor of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

When administered intravenously, the dose can, for example, be in the range of from about 0.1 mg/kg body weight to about 1.0 mg/kg body weight, preferably from about 0.25 mg/kg body weight to about 0.75 mg/kg body weight, more preferably from about 0.4 mg/kg body weight to about 0.6 mg/kg body weight. This dose can be conveniently administered as an infusion of from about 10 ng/kg body weight to about 100 ng/kg body weight per minute. Infusion fluids suitable for this purpose can contain, for example, from about 0.1 ng to about 10 mg, preferably from about 1 ng to about 10 mg per milliliter. Unit doses can contain, for example, from about 1 mg to about 10 g of the compound of the present invention. Thus, ampoules for injection can contain, for example, from about 1 mg to about 100 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent (s). Molded tablets can be made by molding, in a suitable machine, the powdered compound moistened with an inert liquid diluent.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in *Pharmaceutical Research*, 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, and granules noted above comprise one or more compounds of the present invention admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

Treatment Regimen

The dosage regimen to prevent, give relief from, or ameliorate a disease condition having hyperlipemia as an element of the disease, e.g., atherosclerosis, or to protect against or treat further high cholesterol plasma or blood levels with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition can begin with the dosages indicated above. Treatment should generally be continued as necessary over a period of several weeks to several months or years until the hyperlipidemic disease condition has been controlled or eliminated. Patients undergoing treatment with the compounds or compositions disclosed herein can be routinely monitored by, for example, measuring serum cholesterol levels by any of the methods well known in the art, to determine the effectiveness of therapy. Continuous analysis of such data permits modification of the treatment regimen during therapy so that optimal effective amounts of compounds of the present invention are administered at any point in time, and so that the duration of treatment can be determined as well. In this way, the treatment regimen/dosing schedule can be rationally modified over the course of therapy so that the lowest amount of ileal bile acid transport inhibitor of the present invention which exhibits satisfactory effectiveness is administered, and so that administration is continued only so long as is necessary to successfully treat the hyperlipidemic condition.

The following non-limiting examples serve to illustrate various aspects of the present invention.

EXAMPLES OF SYNTHETIC PROCEDURES

Preparation 1
  2-Ethyl-2-(mesyloxymethyl)hexanal (1)

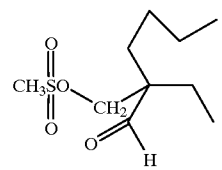

To a cold (10° C.) solution of 12.6 g (0.11 mole) of methanesulfonyl chloride and 10.3 g (0.13 mole) of triethylamine was added dropwise 15.8 g of 2-ethyl-2-(hydroxymethyl)hexanal, prepared according to the procedure described in Chem. Ber. 98, 728–734 (1965), while maintaining the reaction temperature below 30° C. The reaction mixture was stirred at room temperature for 18 h, quenched with dilute HCl and extracted with methlyene chloride. The methylene chloride extract was dried over MgSO$_4$ and concentrated in vacuo to give 24.4 g of brown oil.

Preparation 2
  2-((2-Benzoylphenylthio)methyl)-2-ethylhexanal (2)

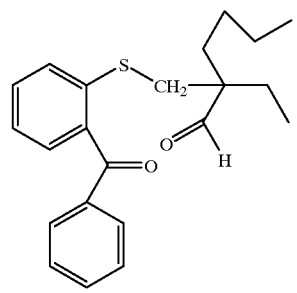

A mixture of 31 g (0.144 mol) of 2-mercaptobenzophenone, prepared according to the procedure described in WO 93/16055, 24.4 g (0.1 mole) of 2-ethyl-2-(mesyloxymethyl)-hexanal (1), 14.8 g (0.146 mole) of triethylamine, and 80 mL of 2-methoxyethyl ether was held at reflux for 24 h. The reaction mixture was poured into 3N HCl and extracted with 300 mL of methylene chloride. The methylene chloride layer was washed with 300 mL of 10% NaOH, dried over MgSO$_4$ and concentrated in vacuo to remove 2-methoxyethyl ether. The residue was purified by HPLC (10% EtOAc-hexane) to give 20.5 g (58%) of 2 as an oil.

Example 1

3-Butyl-3-ethyl-5-phenyl-2,3-dihydrobenzothiepine (3), cis-3-Butyl-3-ethyl-5-phenyl-2,3-dihydrobenzothiepin-(5H) 4-one (4a) and trans-3-Butyl-3-ethyl-5-phenyl-2,3-dihydrobenzothiepin-(5H)4-one (4b)

3

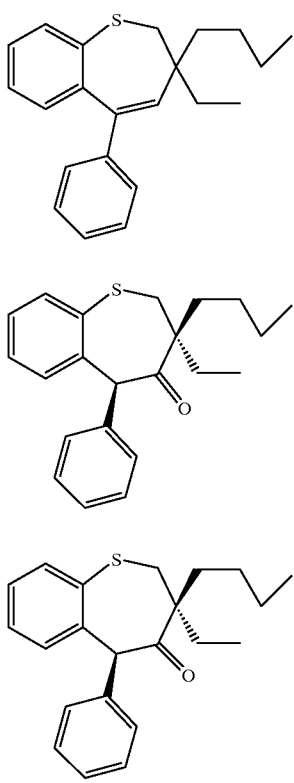

4a

4b

A mixture of 2.6 g (0.04 mole) of zinc dust, 7.2 g (0.047 mole) of TiCl$_3$ and 80 mL of anhydrous ethylene glycol dimethyl ether (DME) was held at reflux for 2 h. The reaction mixture was cooled to 5° C. To the reaction mixture was added dropwise a solution of 3.54 g (0.01 mole) of 2 in 30 mL of DME in 40 min. The reaction mixture was stirred at room temperature for 16 h and then was held at reflux for 2 h and cooled before being poured into brine. The organic was extract into methylene chloride. The methylene chloride extract was dried over MgSO$_4$ and concentrated in vacuo. The residue was purified by HPLC (hexane) to give 1.7 g (43%) of 3 as an oil in the first fraction. The second fraction was discarded and the third fraction was further purified by HPLC (hexane) to give 0.07 g (2%) of 4a in the earlier fraction and 0.1 g (3%) of 4b in the later fraction.

Example 2 cis-3-Butyl-3-ethyl-5-phenyl-2,3-dihydrobenzothiepin-(5H) 4-one-1,1-dioxide (5a) and trans-3-Butyl-3-ethyl-5-phenyl-2, 3-dihydro-benzothiepin-(5H) 4-one-1,1-dioxide (5b)

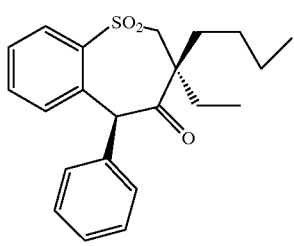

5a

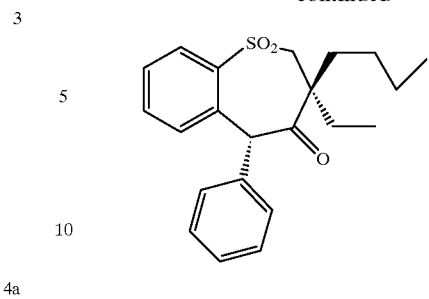

5b

To a solution of 1.2 g (3.5 mmole) of 50–60% MCPBA in 20 mL of methylene chloride was added 0.59 g (1.75 mmole) of a mixture of 4a and 4b in 10 mL of methylene chloride. The reaction mixture was stirred for 20 h. An additional 1.2 g (1.75 mmole) of 50–60% MAPBA was added and the reaction mixture was stirred for an additional 3 h then was triturated with 50 mL of 10% NaOH. The insoluble solid was filtered. The methylene chloride layer of the filtrate was washed with brine, dried over MgSO$_4$, and concentrated in vacuo. The residual syrup was purified by HPLC (5% EtOAc-hexane) to give 0.2 g (30%)of 5a as an oil in the first fraction and 0.17 g (26%) of 5b as an oil in the second fraction.

Example 3

(3α,4α,5β) 3-Butyl-3-ethyl-4-hydroxy-5-phenyl-2,3,4,5-tetrahydrobenzothiepine-1,1-dioxide (6a), (3α,4β,5α) 3-Butyl-3-ethyl-4-hydroxy-5-phenyl-2,3,4,5-tetrahydrobenzothiepine-1,1-dioxide (6b), (3α,4α,5α) 3-Butyl-3-ethyl-4-hydroxy-5-phenyl-2,3,4,5-5tetrahydrobenzothiepine-1,1-dioxide (6c), and (3α,4β,5β) 3-Butyl-3-ethyl-4-hydroxy-5-phenyl-2,3,4,5-tetrahydrobenzothiepine-1,1-dioxide (6d)

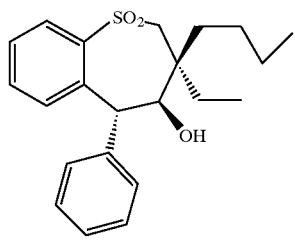

6a

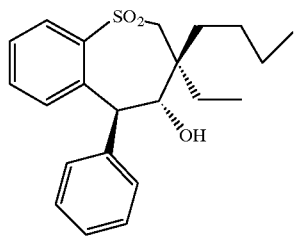

6b

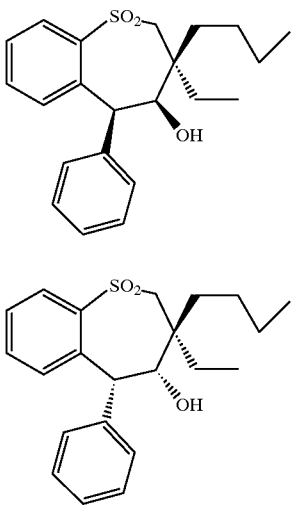

6c

6d

A. Reduction of 5a and 5b with Sodium Borohydride

To a solution of 0.22 g (0.59 mmole) of 5b in 10 mL of ethanol was added 0.24 g (6.4 mmole) of sodium borohydride. The reaction mixture was stirred at room temperature for 18 h and concentrated in vacuo to remove ethanol. The residue was triturated with water and extracted with methylene chloride. The methylene chloride extract was dried over $MgSO_4$ and concentrated in vacuo to give 0.2 g of syrup. In a separate experiment, 0.45 g of 5a was treated with 0.44 g of sodium borohydride in 10 mL of ethanol and was worked up as described above to give 0.5 g of syrup which was identical to the 0.2 g of syrup obtained above. These two materials were combined and purified by HPLC using 10% EtOAc-hexane as eluant. The first fraction was 0.18 g (27%) of 6a as a syrup. The second fraction was 0.2 g (30%) of 6b also as a syrup. The column was then eluted with 20% EtOAc-hexane to give 0.077 g (11%) of 6c in the third fraction as a solid. Recrystallization from hexane gave a solid, mp 179–181° C. Finally, the column was eluted with 30% EtOAc-hexane to give 0.08 g (12%) of 6d in the fourth fraction as a solid. Recrystallization from hexane gave a solid, mp 160–161° C.

B. Conversion of 6a to 6c and 6d with NaOH and PTC

To a solution of 0.29 g (0.78 mmole) of 6a in 10 mL $CH_2Cl_2$, was added 9 g of 40% NaOH. The reaction mixture was stirred for 0.5 h at room temperature and was added one drop of Aliquat-336 (methyltricaprylylammonium chloride) phase transfer catalyst (PTC). The mixture was stirred for 0.5 h at room temperature before being treated with 25 mL of ice-crystals then was extracted with $CH_2Cl_2$ (3×10 ml), dried over $MgSO_4$ and concentrated in vacuo to recover 0.17 g of a colorless film. The components of this mixture were separated using an HPLC and eluted with EtOAc-hexane to give 12.8 mg (4%) of 2-(2-benzylphenylsulfonylmethyl)-2-ethylhexenal in the first fraction, 30.9 mg (11%) of 6c in the second fraction and 90.0 mg (31%) of 6d in the third fraction.

Oxidation of 6a to 5b

To a solution of 0.20 g (0.52 mmole) of 6a in 5 mL of $CH_2Cl_2$ was added 0.23 g (1.0 mmole) of pyridinium chlorochromate. The reaction mixture was stirred for 2 h then was treated with additional 0.23 g of pyridinium chlorochromate and stirred overnight. The dark reaction mixture was poured into a ceramic filterfrit containing silica gel and was eluted with $CH_2Cl_2$. The filtrate was concentrated in vacuo to recover 167 mg (87%) of 5b as a colorless oil.

Example 4

3-Butyl-3-ethyl-5-phenyl-2,3-dihydrobenzothiepine-1,1-dioxide (7)

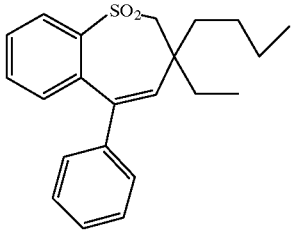

7

To a solution of 5.13 g (15.9 mmole) of 3 in 50 mL of $CH_2Cl_2$ was added 10 g (31.9 mmole) of 50–60% MCPBA (m-chloroperoxybenzoic acid) portionwise causing a mild reflux and formation of a white solid. The reaction mixture was allowed to stir overnight under $N_2$ and was triturated with 25 mL of water followed by 50 mL of 10% NaOH solution. The organic was extracted into $CH_2Cl_2$ (4×20 mL). The $CH_2Cl_2$ extract was dried over $MgSO_4$ and evaporated to dryness to recover 4.9 g (87%) of an opaque viscous oil.

Example 5

(1aα,2β,8bα) 2-Butyl-2-ethyl-8b-phenyl-1α,2,3,8b-tetrahydro-benzothiepino[4,5-b]oxirene-4,4-dioxide (8a)
(1aα,2α,8bα) 2-Butyl-2-ethyl-8b-phenyl-1a,2,3,8b-tetrahydro-benzothiepino[4,5-b]oxirene-4,4-dioxide (8b)

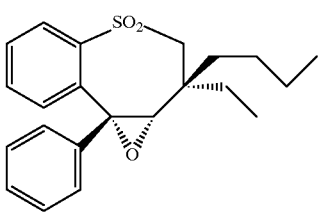

8a

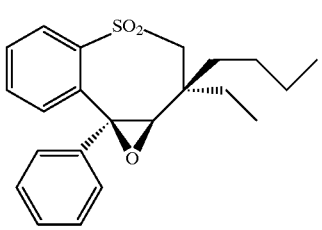

8b

To 1.3 g (4.03 mole) of 3 in 25 mL of $CHCl_3$ was added portionwise 5 g (14.1 mmole) of 50–60% MCPBA causing a mild exotherm. The reaction mixture was stirred under $N_2$ overnight and was then held at reflux for 3 h. The insoluble white slurry was filtered. The filtrate was extracted with 10% potassium carbonate (3×50 mL), once with brine, dried over $MgSO_4$, and concentrated in vacuo to give 1.37 g of a light yellow oil. Purification by HPLC gave 0.65 g of crystalline product. This product is a mixture of two isomers. Trituration of this crystalline product in hexane recovered 141.7 mg (10%) of a white crystalline product. This isomer was characterized by NMR and mass spectra to be the (1aα,2β, 8bα) isomer 8a. The hexane filtrate was concentrated in vacuo to give 206 mg of white film which is a mixture of 30% 8a and 70% 8b by $^1$H NMR.

Example 6 cis-3-Butyl-3-ethyl-5-phenyl-2,3,4,5-tetrahydro-benzothiepine-1,1-dioxide (9a), trans-3-Butyl-3-ethyl-5-phenyl-2,3,4,5-tetrahydrobenzothiepine-1,1-dioxide (9b), and 3-Butyl-3-ethyl-4-hydroxy-5-cyclohexylidine-2,3,4,5-tetrahydrobenzothiepine-1,1-dioxide (10)

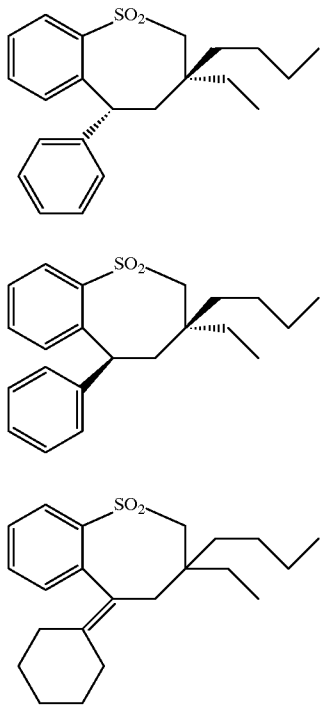

A mixture of 0.15 g (0.4 mmole) of a 3:7 mixture of 8a and 8b was dissolved in 15 ml MeOH in a 3 oz. Fisher/Porter vessel, then was added 0.1 g of 10% Pd/C catalyst. This mixture was hydrogenated at 70 psi $H_2$ for 5 h and filtered. The filtrate was evaporated to dryness in vacuo to recover 0.117 g of a colorless oil. This material was purified by HPLC eluting with EtOAc-hexane. The first fraction was 4.2 mg (3%) of 9b. The second fraction, 5.0 mg (4%), was a 50/50 mixture of 9a and 9b. The third fraction was 8.8 mg (6%) of 6a. The fourth fraction was 25.5 mg (18%) of 6b. The fifth fraction was 9.6 mg (7%) of a mixture of 6b and a product believed to be 3-butyl-3-ethyl-4,5-dihydroxy-5-phenyl-2,3,4,5-tetrahydrobenzothiepine-1,1-dioxide based on mass spectrum. The sixth fraction was 7.5 mg (5%) of a mixture of 6d and one of the isomers of 10, 10a.

Example 7

In another experiment, a product (3.7 g) from epoxidation of 3 with excess MCPBA in refluxing $CHCl_3$ under air was hydrogenated in 100 mL of methanol using 1 g of 10% Pd/C catalyst and 70 psi hydrogen. The product was purified by HPLC to give 0.9 g (25%) of 9b, 0.45 g (13%) of 9a, 0.27 g (7%) of 6a, 0.51 g (14%) of 6b, 0.02 g (1%) of 6c, 0.06 g (2%) of one isomer of 10, 10a and 0.03 g (1%) of another isomer of 10, 10b.

Example 8

2-((2-Benzoylphenylthio)methyl)butyraldehyde (11)

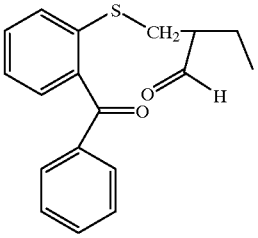

To an ice bath cooled solution of 9.76 g (0.116 mole) of 2-ethylacrolein in 40 mL of dry THF was added 24.6 g (0.116 mole) of 2-mercaptobenzophenone in 40 mL of THF followed by 13 g (0.128 mole) of triethylamine. The reaction mixture was stirred at room temperature for 3 days, diluted with ether, and was washed successively with dilute HCl, brine, and 1 M potassium carbonate. The ether layer was dried over $MgSO_4$ and concentrated in vacuo. The residue was purified by HPLC (10% EtOAc-hexane) to give 22 g (64%) of 11 in the second fraction. An attempt to further purifiy this material by kugelrohr distillation at 0.5 torr (160–190° C.) gave a fraction (12.2 g) which contained starting material indicating a reversed reaction during distillation. This material was dissolved in ether (100 mL) and was washed with 50 mL of 1 M potassium carbonate three times to give 6.0 g of a syrup which was purified by HPLC (10% EtOAc-hexane) to give 5.6 g of pure 11.

Example 9

3-Ethyl-5-phenyl-2,3-dihydrobenzothiepine (12)

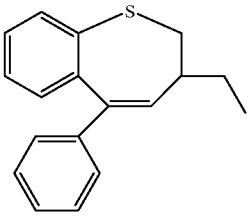

To a mixture of 2.61 g (0.04 mole) of zinc dust and 60 mL of DME was added 7.5 g (0.048 mole) of $TiCl_3$. The reaction mixture was held at reflux for 2 h. A solution of 2.98 g (0.01 mole) of 11 was added dropwise in 1 h. The reaction mixture was held at reflux for 18 h, cooled and poured into water. The organic was extracted into ether. The ether layer was washed with brine and filtered through Celite. The filtrate was dried over $MgSO_4$ and concentrated. The residual oil (2.5 g) was purified by HPLC to give 2.06 g (77%) of 12 as an oil in the second fraction.

Example 10

(1α,2α,8bα) 2-Ethyl-8b-phenyl-1a,2,3, 8b-tetrahydro-benzothiepino-[4,5-b]oxirene-4,4-dioxide (13)

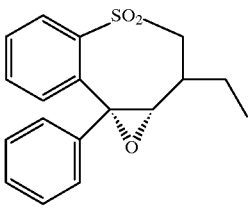

13

To a solution of 1.5 g (5.64 mmole) of 12 in 25 ml of CHCl₃ was added 6.8 g (19.4 mmole) of 50–60% MCPB portionwise causing an exothem and formation of a white solid. The mixture was stirred at room temperature overnight diluted with 100 ml methylene chloride and washed successively with 10% K₂CO₃ (4×50 ml), water (twice with 25 ml) and brine. The organic layer was then dried over MgSO₄ and evaporated to dryness to recover 1.47 g of an off white solid. ¹H NMR indicated that only one isomer is present. This solid was slurried in 200 ml of warm Et₂O and filtered to give 0.82 g (46%) of 13 as a white solid, mp 185–186.5° C.

Example 11

(3α,4β,5α)-3-Ethyl-4-hydroxy-5-phenyl-2,3,4,5-tetrahydro-benzothiepine-1,1-dioxide (14a), (3α,4β,5β) 3-Ethyl-4-hydroxy-5-phenyl-2,3,4,5-tetrahydrobenzothiepine-1,1-dioxide (14b), and cis-3-Ethyl-5-phenyl-2,3,4,5-tetrahydro-benzothiepine-1,1-dioxide (15)

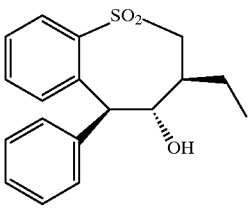

14a

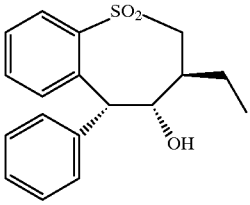

14b

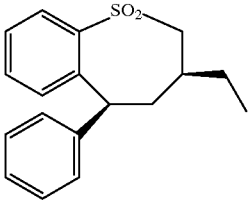

15

A mixture of 0.5 g (1.6 mole) of 13, 50 ml of acetic acid and 0.5 g of 10% Pd/C catalyst was hydrogenated with 70 psi hydrogen for 4 h. The crude reaction slurry was filtered and the filtrate was stirred with 150 ml of a saturated NaHCO₃ solution followed by 89 g of NaHCO₃ powder portionwise to neutralize the rest of acetic acid. The mixture was extracted with methylene chloride (4×25 ml), then the organic layer was dried over MgSO₄ and concentrated in vacuo to give 0.44 g (87%) of a voluminous white solid which was purified by HPLC (EtOAc-Hexane) to give 26.8 mg (6%) of 15 in the first fraction, 272 mg (54%) of 14a as a solid, mp 142–143.5° C., in the second fraction, and 35 mg (7%) of impure 14b in the third fraction.

Example 12

2-Ethyl-2-((2-Hydroxymethyphenyl)thiomethyl)hexenal (16)

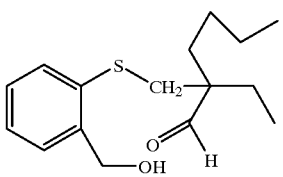

16

A mixture of 5.0 g (0.036 mole) of 2-mercaptobenzyl alcohol, 6.4 g (0.032 mole) of 1, 3.6 g (0.036 mole) of triethylamine and 25 mL of 2-methoxyethyl ether was held at reflux for 7 h. Additional 1.1 g of mercaptobenzyl alcohol and 0.72 g of triethylamine was added to the reaction mixture and the mixture was held at reflux for additional 16 h. The reaction mixture was cooled and poured into 6N HCl and extracted with methylene chloride. The methylene chloride extract was washed twice with 10% NaOH, dried over MgSO₄ and concentrated in vacuo to give 9.6 g of residue. Purification by HPLC (20% EtOAc-hexane) gave 3.7 g (41%) of 16 as an oil.

Example 13

2-Ethyl-2-((2-formylphenyl)thiomethyl)hexenal (17)

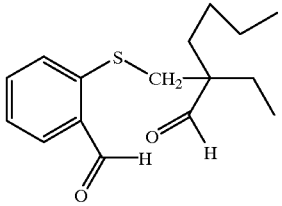

17

A mixture of 3.7 g of 16, 5.6 g (0.026 mole) of pyridinium chlorochromate, 2 g of Celite and 30 mL of methylene chloride was stirred for 18 h and filtered through a bed of silica gel. The silica gel was eluted with methylene chloride. The combined methylene chloride eluant was purified by HPLC (20% ETOAc-hexane) to give 2.4 g (66%) of an oil.

Example 14

3-Butyl-3-ethyl-2,3-dihydrobenzothiepine (18)

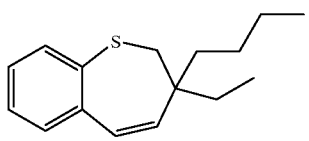

18

A mixture of 2.6 g (0.04 mole) of zinc dust, 7.2 g (0.047 mole) of TiCl$_3$, and 50 mL of DME was held at reflux for 2 h and cooled to room temperature. To this mixture was added 2.4 g (8.6 mmole) of 17 in 20 mL of DME in 10 min. The reaction mixture was stirred at room temperature for 2 h and held at reflux for 1 h then was let standing at room temperature over weekend. The reaction mixture was poured into dilute HCl and was stirred with methylene chloride. The methylene chloride-water mixture was filtered through Celite. The methylene chloride layer was washed with brine, dried over MgSO$_4$, and concentrated in vacuo to give 3.0 g of a residue. Purification by HPLC gave 0.41 g (20%) of 18 as an oil in the early fraction.

Example 15

(1aα,2α,8bα) 2-Butyl-2-ethyl-1a,2,3,8b-tetrahydro-benzothiepino[4,5-b]oxirene-4,4-dioxide (19a) and (1aα,2β,8bα) 2-Butyl-2-ethyl-8b-phenyl-1a,2,3,8b-tetrahydro-benzothiepino[4,5-b]oxirene-4,4-dioxide (19b)

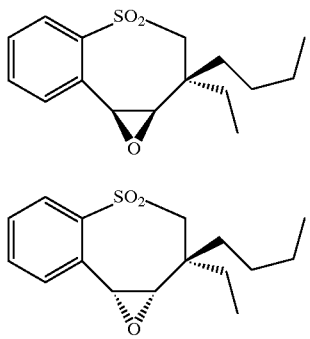

19a

19b

To a solution of 0.4 g of 0.4 g (1.6 mmole) of 18 in 30 mL of methylene chloride was added 2.2 g (3.2 mmole) of 50–60% MCPBA. The reaction mixture was stirred for 2 h and concentrated in vacuo. The residue was dissolved in 30 mL of CHCl$_3$ and was held at reflux for 18 h under N$_2$. The reaction mixture was stirred with 100 mL of 10% NaOH and 5 g of sodium sulfite. The methylene chloride layer was washed with brine, dried over MgSO$_4$ and concentrated in vacuo. The residue was purified by HPLC (20% EtOAc-hexane) to give a third fraction which was 25 further purified by HPLC (10% EtOAc-hexane) to give 0.12 g of syrup in the first fraction. Recrystallization from hexane gave 0.08 g (17%) of 19a, mp 89.5–105.5° C. The mother liquor from the first fraction was combined with the second fraction and was further purified by HPLC to give additional 19a in the first fraction and 60 mg of 19b in the second fraction. Crystallization from hexane gave 56 mg of a white solid.

Example 16

3-Butyl-3-ethyl-4,5-dihydroxy-5-phenyl-2,3,4,5-tetrahydro-benzothiepine-1,1-dioxide (20)

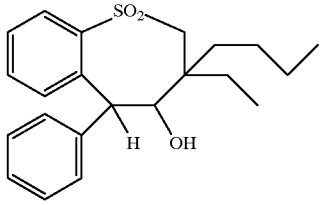

20

This product was isolated along with 6b from hydrogenation of a mixture of 8a and 8b.

Example 17

3-Butyl-3-ethyl-4-hydroxy-5-phenylthio-2,3,4,5-tetrahydro-benzothiepine-1,1-dioxide (21)

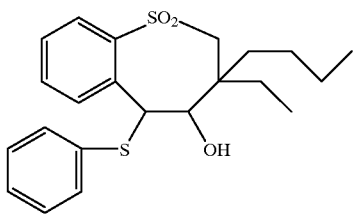

21

A mixture of 25 mg (0.085 mmole) of 19b, 0.27 g (2.7 mmole) of thiophenol, 0.37 g (2.7 mmole) of potassium carbonate, and 4 mL of DMF was stirred at room temperature under N$_2$ for 19 h. The reaction mixture was poured into water and extracted with methylene chloride. The methylene chloride layer was washed successively with 10% NaOH and brine, dried over MgSO$_4$, and concentrated in vacuo to give 0.19 g of semisolid which contain substantial amounts of diphenyl disulfide. This material was purified by HPLC (5% EtOAc-hexane) to remove diphenyl disulfide in the first fraction. The column was then eluted with 20% EtOAc-hexane to give 17 mg of a first fraction, 4 mg of a second fraction and 11 mg of a third fraction which were three different isomers of 21, i.e. 21a, 21b, and 21c, respectively, by $^1$H NMR and mass spectra.

Example 18

Alternative Synthesis of 6c and 6d

A. Preparation from 2-((2-Benzoylphenylthio)methyl)-2-ethylhexanal (2)

Step 1. 2-((2-Benzoylphenylsulfonyl)methyl)-2-ethylhexanal (44)

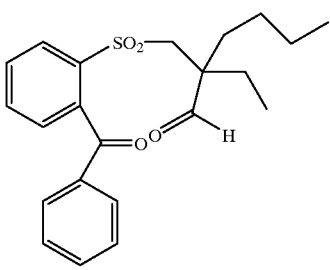

44

To a solution of 9.0 g (0.025 mole) of compound 2 in 100 ml of methylene chloride was added 14.6 g (0.025 mol) of 50–60% MCPBA portionwise. The reaction mixture was stirred at room temperature for 64 h then was stirred with 200 ml of 1 M potassium carbonate and filtered through Celite. The methylene chloride layer was washed twice with 300 ml of 1 M potassium carbonate, once with 10% sodium hydroxide and once with brine. The insoluble solid formed during washing was removed by filtration through Celite. The methylene chloride solution was dried and concentrated in vacuo to give 9.2 g (95%)of semisolid. A portion (2.6 g) of this solid was purified by HPLC(10% ethyl acetate-hexane) to give 1.9 g of crystals, mp 135–136° C.

Step 2. 2-((2-Benzylphenylsulfonyl)methyl)-2-ethylhexanal (45)

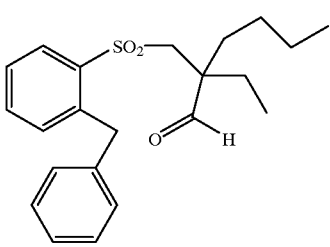

45

A solution of 50 g (0.13 mole) of crude 44 in 250 ml of methylene chloride was divided in two portions and charged to two Fisher-Porter bottles. To each bottle was charged 125 ml of methanol and 5 g of 10% Pd/C. The bottles were pressurized with 70 psi of hydrogen and the reaction mixture was stirred at room temperature for 7 h before being charged with an additional 5 g of 10% Pd/C. The reaction mixture was again hydrogenated with 70 psi of hydrogen for 7 h. This procedure was repeated one more time but only 1 g of Pd/C was charged to the reaction mixture. The combined reaction mixture was filtered and concentrated in vacuo to give 46.8 g of 45 as brown oil.

Step 3. (3α,4α,5α) 3-Butyl-3-ethyl-4-hydroxy-5-phenyl-2,3,4,5-tetrahydrobenzothiepine-1,1-dioxide (6c), and (3α, 4β,5β) 3-Butyl-3-ethyl-4-hydroxy-5-phenyl-2,3,4,5-tetrahydrobenzothiepine-1,1-dioxide (6d)

To a solution of 27.3 g (73.4 mmole) of 45 in 300 ml of anhydrous THF cooled to 2° C. with an ice bath was added 9.7 g (73.4 mmole) of 95% potassium t-butoxide. The reaction mixture was stirred for 20 min, quenched with 300 ml of 10% HCl and extracted with methylene chloride. The methylene chloride layer was dried over magnesium sulfate and concentrated in vacuo to give 24.7 g of yellow oil. Purification by HPLC (ethyl acetate-hexane) yielded 9.4 g of recovered 45 in the first fraction, 5.5 g (20%) of 6c in the second fraction and 6.5 g (24%) of 6d in the third fraction.

B. Preparation from 2-hydroxydiphenylmethane
Step 1. 2-mercaptodiphenylmethane (46)

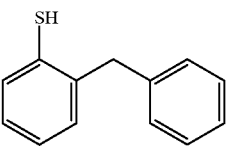

46

To a 500 ml flask was charged 16 g (0.33 mol) of 60% sodium hydride oil dispersion. The sodium hydride was washed twice with 50 ml of hexane. To the reaction flask was charged 100 ml of DMF. To this mixture was added a solution of 55.2 g (0.3 mol) of 2-hydroxydiphenylmethane in 200 ml of DMF in 1 h while temperature was maintained below 30° C. by an ice-water bath. After complete addition of the reagent, the mixture was stirred at room temperature for 30 min then cooled with an ice bath. To the reaction mixture was added 49.4 g (0.4 mole) of dimethyl thiocarbamoyl chloride at once. The ice bath was removed and the reaction mixture was stirred at room temperature for 18 h before being poured into 300 ml of water. The organic was extracted into 500 ml of toluene. The toluene layer was washed successively with 10% sodium hydroxide and brine and was concentrated in vacuo to give 78.6 g of a yellow oil which was 95% pure dimethyl O-2-benzylphenyl thiocarbamate. This oil was heated at 280–300° C. in a kugelrohhr pot under house vacuum for 30 min. The residue was kugelrohr distilled at 1 torr (180–280° C.). The distillate (56.3 g) was crystallized from methanol to give 37.3 g (46%) of the rearranged product dimethyl S-2-benzylphenyl thiocarbamate as a yellow solid. A mixture of 57 g (0.21 mole) of this yellow solid, 30 g of potassium hydroxide and 150 ml of methanol was stirred overnight then was concentrated in vacuo. The residue was diluted with 200 ml of water and extracted with ether. The aqueous layer was made acidic with concentrate HCl, The oily suspension was extracted into ether. The ether extract was dried over magnesium sulfate and concentrated in vacuo. The residue was crystallized from hexane to give 37.1 g (88%) of 2-mercaptodiphenylmethane as a yellow solid.

Step 2. 2-((2-Benzylphenylthio)methyl)-2-ethylhexanal (47)

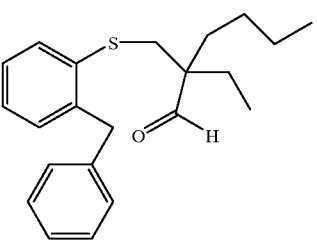

47

A mixture of 60 g (03 mole) of yellow solid from step 1, 70 g (0.3 mole) of compound 1 from preparation 1, 32.4 g (0.32 mole) of triethylamine, 120 ml of 2-methoxyethyl ether was held at reflux for 6 hr and concentrated in vacuo. The residue was triturated with 500 ml of water and 30 ml of concentrate HCl. The organic was extracted into 400 ml of ether. The ether layer was washed successively with brine, 10% sodium hydroxide and brine and was dried over magnesium sulfate and concentrated in vacuo. The residue (98.3 g) was purified by HPLC with 2–5% ethyl acetate-hexane as eluent to give 2-((2-benzylphenylthio)methyl)-2-ethylhexanal 47 as a yellow syrup.

Step 3. 2-((2-Benzylphenylsulfonyl)methyl)-2-ethylhexanal (45)

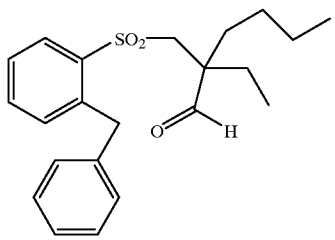

45

To a solution of 72.8 g (0.21 mole) of yellow syrup from step 2 in 1 liter of methylene chloride cooled to 10° C. was added 132 g of 50–60% MCPBA in 40 min. The reaction mixture was stirred for 2 h. An additional 13 g of 50–60% MCPBA was added to the reaction mixture. The reaction mixture was stirred for 2 h and filtered through Celite. The methylene chloride solution was washed twice with 1 liter of 1 M potassium carbonate then with 1 liter of brine. The methylene chloride layer was dried over magnesium sulfate and concentrated to 76 g of 2-((2-benzylphenylsulfonyl)methyl)-2-ethylhexanal 45 as a syrup.

Step 4. (3α,4α,5α) 3-Butyl-3-ethyl-4-hydroxy-5-phenyl-2,3,4, 5-tetrahydrobenzothiepine-l,1-dioxide (6c), and (3α,4β,5β) 3-Butyl-3-ethyl-4-hydroxy-5-phenyl-2,3,4,5-tetrahydrobenzothiepine-1,1-dioxide (6d)

Reaction of 45 with potassium t-butoxide according to the procedure in step 3 of procedure A gave pure 6c and 6d after HPLC.

Example 19

(3α,4β,5β) 3-Butyl-3-ethyl-4-hydroxy-8-methoxy-5-phenyl-2,3,4,5-tetrahydrobenzothiepine-1,1-dioxide (25) and (3α,4α,5α) 3-Butyl-3-ethyl-4-hydroxy-8-methoxy-5-phenyl-2,3,4,5-tetrahydrobenzothiepine-1,1-dioxide (26)

Step 1. Preparation of 2-((2-benzoyl-4-methoxyphenylthio)methyl)-2-ethylhexanal (22)

22

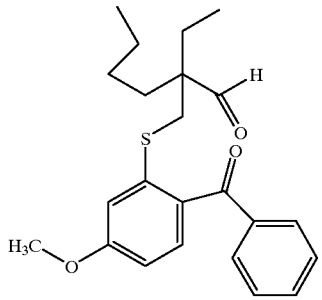

2-Hydroxy-4-methoxybenzophenone was converted to the dimethyl O-2-benzoyphenyl thiocarbamate by methods previously described in example 18. The product can be isolated by recrystallization from ethanol. Using this improved isolation procedure no chromatography was needed. The thermal rearrangement was performed by reacting the thiocarbamate (5 g) in diphenyl ether at 260° C. as previously described. The improved isolation procedure which avoided a chromatography step was described below.

The crude pyrolysis product was then heated at 65° C. in 100 ml of methanol and 100 ml of THF in the presence of 3.5 g of KOH for 4 h. After removing THF and methanol by rotary evaporation the solution was extracted with 5% NaOH and ether. The base layer was acidified and extracted with ether to obtain a 2.9 g of crude thiophenol product. The product was further purified by titrating the desired mercaptan into base with limited KOH. After acidification and extraction with ether pure 2-mercapto-4-methoxybenzophenone (2.3 g) was isolated.

2-mercapto-4-methoxybenzophenone can readily be converted to the 2-((2-benzoyl-4-methoxyphenylthio)methyl)-2-ethylhexanal (22) by reaction with 2-ethyl-2-(mesyloxymethyl)hexanal (1) as previously described.

Step 2. 2-((2-Benzoyl-5-methoxyphenylsulfonyl)methyl)-2-ethylhexanal (23)

23

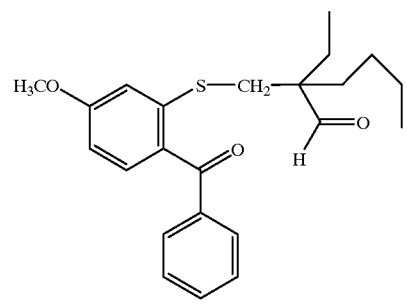

Substrate 22 was readily oxidized to 2-((2-benzoyl-5-methoxyphenyl-sulfonyl)methyl)-2-ethylhexanal (23) as described in example 18.

Step 3. 2-((2-benzyl-5-methoxyphenylsulfonyl)methyl)-2-ethylhexanal (24)

24

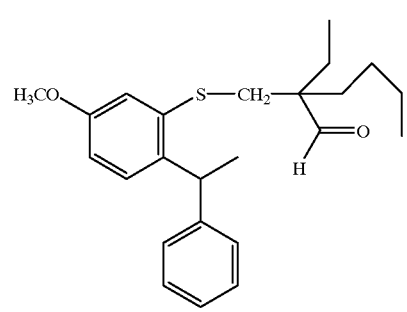

Sulfone 23 was then reduced to 2-((2-benzyl-5-methoxyphenyl-sulfonyl)methyl)-2-ethylhexanal (24) as described in example 18.

Step 4. (3α,4β,5β) 3-Butyl-3-ethyl-4-hydroxy-8-methoxy-5-phenyl-2,3,4,5-tetrahydrobenzothiepine-1,1-dioxide (25) and (3α,4α,5α) 3-Butyl-3-ethyl-4-hydroxy-8-methoxy-5-phenyl-2,3,4,5-tetrahydrobenzothiepine-1,1-dioxide (26)

25

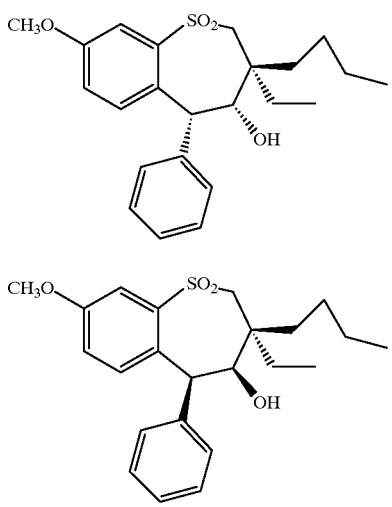

26

A 3-neck flask equipped with a powder addition funnel, thermocouple and nitrogen bubbler was charged with 19.8 g (0.05 mole) of sulfone 24 in 100 ml dry THF. The reaction was cooled to −1.6° C. internal temperature by means of ice/salt bath. Slowly add 5.61 g (0.05 mole) of potassium t-butoxide by means of the powder addition funnel. The resulting light yellow solution was maintained at −1.6° C. After 30 min reaction 400 ml of cold ether was added and this solution was extracted with cold 10% HCl. The acid layer was extracted with 300 ml of methylene chloride. The organic layers were combined and dried over magnesium sulfate and after filtration stripped to dryness to obtain 19.9 g of product. $^1$H nmr and glpc indicated a 96% conversion to a 50/50 mixture of 25 and 26. The only other observable compound was 4% starting sulfone 24.

The product was then dissolved in 250 ml of 90/10 hexane/ethyl acetate by warming to 50° C. The solution was allowed to cool to room temperature and in this way pure 26 can be isolated. The crystallization can be enhanced by addition of a seed crystal of 26. After 2 crystallizations the mother liquor which was now 85.4% 25 and has a dry weight of 8.7 g. This material was dissolved in 100 ml of 90/10 hexane/ethyl acetate and 10 ml of pure ethyl acetate at 40 C. Pure 25 can be isolated by seeding this solution with a seed crystal of 25 after storing it overnight at 0 C.

Example 20

(3α,4α,5α) 3-Butyl-3-ethyl-4,8-dihydroxy-5-phenyl-2,3,4,5-tetrahydrobenzothiepine-1,1-dioxide (27)

27

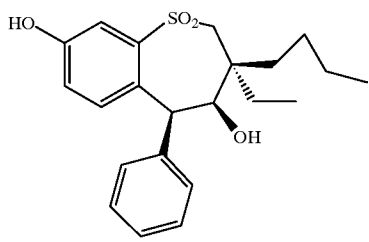

In a 25 ml round bottomed flask, 1 g of 26(2.5 mmoles) and 10 ml methylene chloride were cooled to −78° C. with stirring. Next 0.7 ml of boron tribromide(7.5 mmole) was added via syringe. The reaction was allowed to slowly warm to room temperature and stirred for 6 h. The reaction was then diluted with 50 ml methylene chloride and washed with saturated NaCl and then water.The organic layer was dried over magnesium sulfate. The product (0.88g) 27 was characterized by NMR and mass spectra.

Example 21

General Alkylation of phenol 27

A 25 ml flask was charged with 0.15 g of 27(0.38 mmole), 5 ml anhydrous DMF, 54 mg of potassium carbonate(0.38 mmole) and 140 mg ethyl iodide (0.9 mmole). The reaction was stirred at room temperature overnight. The reaction was diluted with 50 ml ethyl ether and washed with water (25 ml) then 5% NaOH (20 ml) and then sat. NaCl. After stripping off the solvent the ethoxylated product 28 was obtained in high yield. The product was characterized by NMR and mass spectra. This same procedure was used to prepare products listed in table 1 from the corresponding iodides or bromides. For higher boiling alkyl iodides and bromides only one equivalent of the alkyl halide was used.

TABLE 1

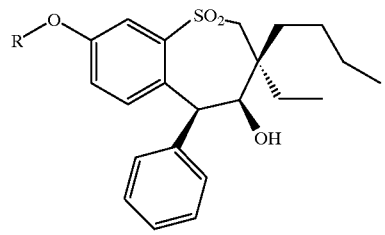

Formula for TABLE 1

| Compound No. | R |
|---|---|
| 27 | H |
| 26 | Me |
| 28 | Et |
| 29 | hexyl |
| 30 | Ac |
| 31 | (CH2)6-N-pthalimide |

Example 22

(3α,4α,5α) 3-Butyl-3-ethyl-4-hydroxy-7-hydroxyamino-5-phenyl-2,3,4,5-tetrahydrobenzothiepine-1,1-dioxide (37) and (3α,4β,5β) 3-Butyl-3-ethyl-4-hydroxy-7-hydroxyamino-5-phenyl-2,3,4,5-tetrahydrobenzothiepine-1,1-dioxide (38)

Step 1. Preparation of 2-chloro-5-nitrodiphenylmethane (32)

32

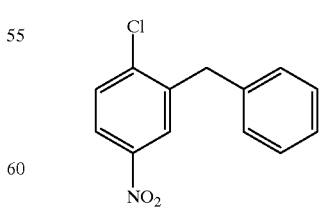

Procedure adapted from reference :Synthesis-Stuttgart 9 770–772 (1986) Olah G. Et al Under nitrogen, a 3 neck flask was charged with 45 g (0.172 mole ) of 2-chloro-5-nitrobenzophenone in 345 ml methylene chloride and the solution was cooled to ice/water temperature. By means of an additional funnel, 150 g( 0.172 mole) of trifluoromethane sulfonic acid in 345 ml methylene chloride was added slowly. Next 30 g of triethylsilane (0.172 mole) in 345 ml methylene chloride was added dropwise to the chilled solution. Both addition steps( trifluoromethane sulfonic acid and triethylsilane)were repeated. After the additions were completed the reaction was allowed to slowly warm up to room temperature and stirred for 12 h under nitrogen. The reaction mixture was then poured into a chilled stirred solution of 1600 ml of saturated sodium bicarbonate. Gas evolution occurred. Poured into a 4 liter separatory funnel and separated layers. The methylene chloride layer was isolated and combined with two 500 ml methylene chloride extractions of the aqueous layer. The methylene chloride solution was dried over magnesium sulfate and concentrated in vacuo. The residue was recrystallized from hexane to give 39 g product. Structure 32 was confirmed by mass spectra and proton and carbon NMR.

Step 2. Preparation of 2-((2-benzyl-4-nitrophenylthio)methyl)-2-ethylhexanal (33)

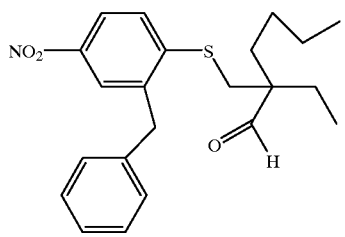

33

The 2-chloro-5-nitrodiphenylmethane product 32 (40 g, 0.156 mole) from above was placed in a 2 liter 2 neck flask with water condenser. Next 150 ml DMSO and 7.18 g (0.156 mole) of lithium sulfide was added and the solution was stirred at 75° C. for 12 h. The reaction was cooled to room temperature and then 51.7 g of mesylate IV was added in 90 ml DMSO. The reaction mixture was heated to 80° C. under nitrogen. After 12 h monitored by TLC and added more mysylate if necessary. Continued the reaction until the reaction was completed. Next the reaction mixture was slowly poured into a 1900 ml of 5% acetic aqueous solution with stirring, extracted with 4×700 ml of ether, and dried over MgSO4. After removal of ether, 82.7 g of product was isolated. The material can be further purified by silica gel chromatography using 95% hexane and 5% ethyl acetate. If pure mysylate was used in this step there was no need for further purification. The product 33 was characterized by mass spectra and NMR.

Step 3. Oxidation of the nitro product 33 to the sulfone 2-((2-benzyl-4-nitrophenylsulfonyl)methyl)-2-ethylhexanal (34)

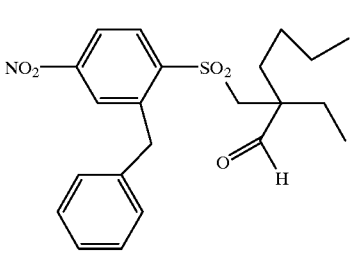

34

The procedure used to oxidize the sulfide 33 to the sulfone 34 has been previously described.

Step 4. Reduction of 34 to 2-((2-benzyl-4-hydroxyaminophenylsulfonyl)methyl)-2-ethylhexanal (35)

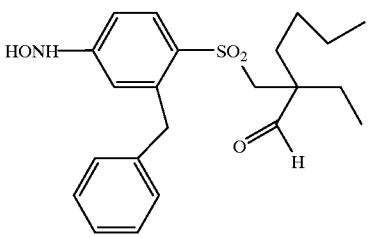

35

A 15 g sample of 34 was dissolved in 230 ml of ethanol and placed in a 500 ml rb flask under nitrogen. Next 1.5 g of 10 wt. % Pd/C was added and hydrogen gas was bubbled through the solution at room temperature until the nitro substrate 34 was consumed. The reaction could 5 be readily monitored by silica gel TLC using 80/20 hexane/EtOAc. Product 35 was isolated by filtering off the Pd/C and then stripping off the EtOH solvent. The product was characterized by NMR and mass spectra.

Step 5. Preparation of the 2-((2-benzyl-4-N,O-di-(t-butoxy-carbonyl)hydroxyaminophenylsulfonyl)methyl)-2-ethylhexanal (36).

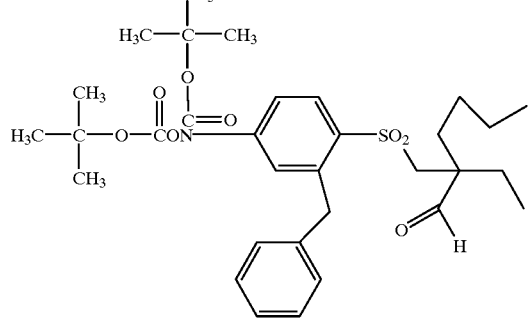

36

A 13.35 g sample of 35 (0.0344 mole) in 40 ml of dry THF was stirred in a 250 ml round bottomed flask. Next added 7.52 g (0.0344 mole) of di-t-butyl dicarbonate in 7 ml THF. Heated at 60° C. overnight. Striped off THF and redissolved in methylene chloride. Extracted with 1% HCl; and then 5% sodium bicarbonate.

The product was further purified by column chromatography using 90/10 hexane/ethyl acetate and then 70/30 hexane/ethyl acetate. The product 36 was obtained (4.12 g) which appeared to be mainly the di-(t-butoxycarbonyl) derivatives by proton NMR.

Step 6. (3α,4α,5α) 3-Butyl-3-ethyl-4-hydroxy-7-hydroxyamino-5-phenyl-2,3,4,5-tetrahydrobenzothiepine-1,1-dioxide (37) and (3α,4β,5β) 3-Butyl-3-ethyl-4-hydroxy-7-hydroxyamino-5-phenyl-2,3,4,5-tetrahydrobenzothiepine-1,1-dioxide (38)

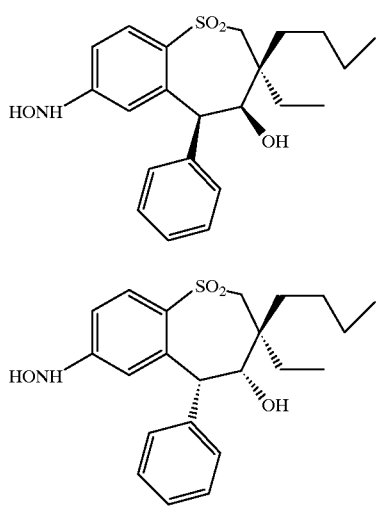

A 250ml 3-neck round bottomed flask was charged with 4 g of 36 (6.8 mmoles), and 100 ml of anhydrous THF and cooled to −78° C. under a nitrogen atmosphere. Slowly add 2.29 g potassium tert-butoxide(20.4 mmoles) with stirring and maintaining a -78° C. reaction temperature. After 1 h at −78° C. the addition of base was completed and the temperature was brought to −10° C. by means of a ice/salt bath. After 3 h at −10° C., only trace 36 remained by TLC. Next add 35 ml of deionized water to the reaction mixture at −10° C. and stirred for 5 min. Striped off most of the THF and added to separatory funnel and extracted with ether until all of the organic was removed from the water phase. The combined ether phases were washed with saturated NaCl and then dried over sodium sulfate. The only products by TLC and NMR were the two BOC protected isomers of 37 and 38. The isomers were separated by silica gel chromatography using 85% hexane and 15 % ethyl acetate; BOC-37 (0.71 g) and BOC- 38 (0.78 g).

Next the BOC protecting group was removed by reacting 0.87 g of BOC-38 (1.78 mmoles) with 8.7 ml of 4 M HCl (34.8 mmoles)in dioxane for 30 min. Next added 4.74 g of sodium acetate (34.8 mmoles) to the reaction mixture and 16.5 ml ether and stirred until clear. After transferring to a separatory funnel extracted with ether and water and then dried the ether layer with sodium sulfate. After removing the ether, 0.665 g of 38 was isolated. Isomer 37 could be obtained in a similar procedure.

Example 23

(3α,4α,5α) 3-Butyl-3-ethyl-7-(n-hexylamino)-4-hydroxy-5-phenyl-2,3,4,5-tetrahydrobenzothiepine-1,1-dioxide (40) and (3α,4β,5β) 3-Butyl-3-ethyl-7-(n-hexylamino)-4-hydroxy-5-phenyl-2,3,4,5-tetrahydrobenzothiepine-1,1-dioxide (41)

Step 1. 2-((2-Benzyl-4-(n-hexylamino)phenylsulfonyl)methyl)-2-ethylhexanal (39)

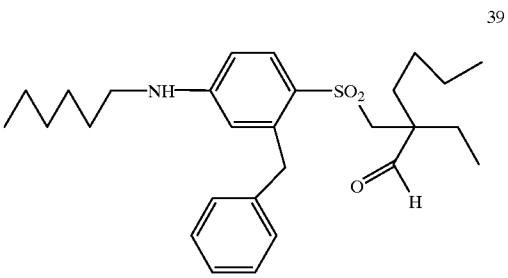

In a Fischer porter bottle weighed out 0.5 g of 34 (1.2 mmoles) and dissolved in 3.8 ml of ethanol under nitrogen. Next added 0.1 g of Pd/C and 3.8 ml of hexanal. Seal and pressure to 50 psi of hydrogen gas. Stirred for 48 h. After filtering off the catalyst and removing the solvent by rotary evaporation 39 was isolated by column chromatography (0.16 g) using 90/10 hexane ethyl acetate and gradually increasing the mobile phase to 70/30 hexane/ethyl acetate. The product was characterized by NMR and mass spectra.

Step 2. (3α,4α,5α) 3-Butyl-3-ethyl-7-(n-hexylamino)-4-hydroxy-5-phenyl-2,3,4,5-tetrahydrobenzothiepine-1,1-dioxide (40) and (3α,4β,5β) 3-Butyl-3-ethyl-7-(n-hexylamino)-4-hydroxy-5-phenyl-2,3,4,5-tetrahydrobenzothiepine-1,1-dioxide (41)

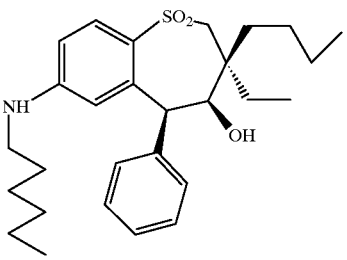

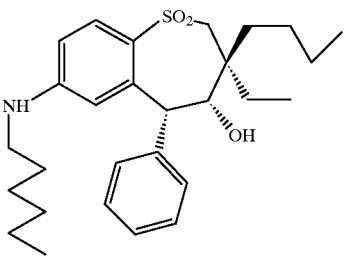

A 2-neck, 25 ml round bottomed flask with stir bar was charged with 0.158 g 39 (0.335 mmole) and 5 ml anhydrous THF under nitrogen. Cool to −10° C. by means of a salt/water bath. Slowly add 0.113 g of potassium tert butoxide (0.335 mmole). After 15 min at −10° C. all of the starting material was consumed by TLC and only the two isomers 40 and 41 were observed. Next added 5 ml of chilled 10% HCl and stirred at −10° C. for 5 min. Transferred to a separatory funnel and extract with ether. Dried over sodium sulfate. Proton NMR of the dried product (0.143 g) indicated only the presence of the two isomers 40 and 41. The two isomers were separated by silica gel chromatography using 90/10 hexane ethyl acetate and gradually increasing the mobile phase to 70/30 hexane/ethyl acetate. 40 ( 53.2 mg); 41(58.9 mg).

Example 24

Quaternization of amine substrates 40 and 41

Amine products such as 40 and 41 can be readily alkylated to quaternary salts by reaction with alkyl halides. For example 40 in DMF with 5 equivalents of methyl iodide in the presence of 2,6 dimethyl lutidine produces the dimethylhexylamino quaternary salt.

Example 25

(3α,4β,5β) 3-Butyl-3-ethyl-4-hydroxy-5-(4-iodophenyl)-2,3,4,5-tetrahydrobenzothiepine-1,1-dioxide (42)

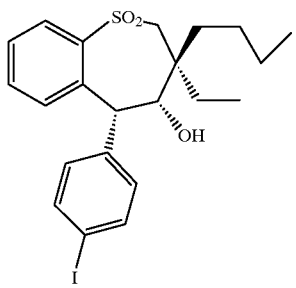

42

In a 25 ml round bottomed flask 0.5 g (1.3 mmole) of 6d, 0.67 g of mercuric triflate were dissolved in 20 ml of dry methylene chloride with stirring. Next 0.34 g of Iodine was added and the solution was stirred at room temperature for 30 h. The reaction was then diluted with 50 ml methylene chloride and washed with 10 ml of 1 M sodium thiosulfate; 10 ml of saturated KI ; and dried over sodium sulfate. See Tetrahedron, Vol.50, No. 17, pp 5139–5146 (1994) Bachki, F. Et al.Mass spectrum indicated a mixture of 6d, mono iodide 42 and a diiodide adduct. The mixture was separated by column chromatography and 42 was characterized bt NMR and mass spectra.

Example 26

(3α,4β,5β) 3-Butyl-5-(4-carbomethoxyphenyl)-3-ethyl-4-hydroxy-2, 3,4,5-tetrahydrobenzothiepine-1,1-dioxide (43)

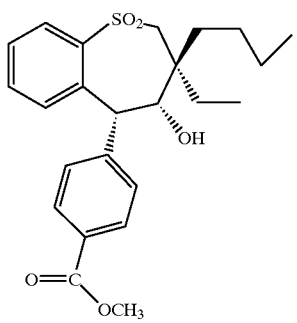

43

A 0.1 g sample of 42 ( 0.212 mmole), 2.5 ml dry methanol, 38 pl triethylamine (0.275 mmole), 0.3 ml toluene and 37 mg of palladium chloride (0.21 mmole) was charged to a glass lined mini reactor at 300 psi carbon monoxide. The reaction was heated at 100° C. overnight. The catalyst was filtered and a high yield of product was isolated.

The product was characterized by NMR and mass spectra.

Note the ester functionalized product 43 can be converted to the free acid by hydrolysis.

Example 27

(3α,4α,5α) 3-Butyl-3-ethyl-4-hydroxy-7-methoxy-5-phenyl-2,3,4,5-tetrahydrobenzothiepine-1,1-dioxide (48), and (3α,4β,5β) 3-Butyl-3-ethyl-4-hydroxy-7-methoxy-5-phenyl-2,3,4,5-tetrahydrobenzothiepine-1,1-dioxide (49)

Step 1. 2-Mercapto-5-methoxybenzophenone (50)

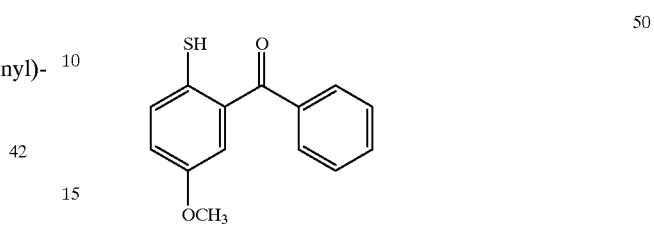

50

Reaction of 66.2 g of 4-methoxythiophenol with 360 ml of 2.5 N n-butyllithium, 105 g of tetramethylethylenediamine and 66.7 g of benzonitrile in 600 ml cyclohexane according to the procedure in WO 93/16055 gave 73.2 g of brown oil which was kugelrohr distilled to remove 4-methoxythiophenol and gave 43.86 g of crude 50 in the pot residue.

Step 2. 2-((2-Benzoyl-4-methoxyphenylthio)methyl)-2-ethylhexanal (51)

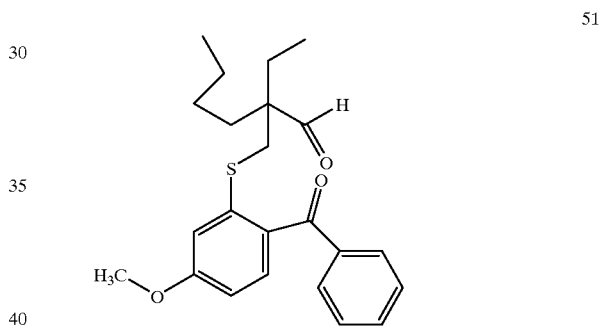

51

Reaction of 10 g (0.04 mole) of crude 50 with 4.8 g (0.02 mole) of mesylate 1 and 3.2 ml (0.23 mole) of triethylamine in 50 ml of diglyme according to the procedure for the preparation of 2 gave 10.5 g of crude product which was purified by HPLC (5% ethyl acetate-hexane) to give 1.7 g (22%) of 51.

Step 3. 2-((2-Benzoyl-4-methoxyphenylsulfonyl)methyl)-2-ethyl-hexanal (52)

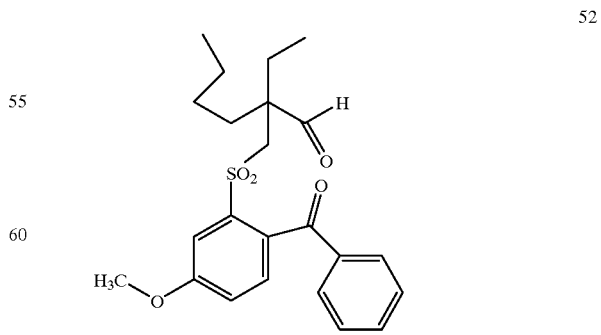

52

A solution of 1.2 g (3.1 mmoles) of 51 in 25 ml of methylene chloride was reacted with 2.0 g (6.2 mmoles) of 50–60% MCPBA according to the procedure of step 2 of procedure A in example 18 gave 1.16 g (90%) of 52 as a yellow oil.

Step 4. 2-((2-Benzyl-4-methoxyphenylsulfonyl)methyl)-2-ethylhexanal (53)

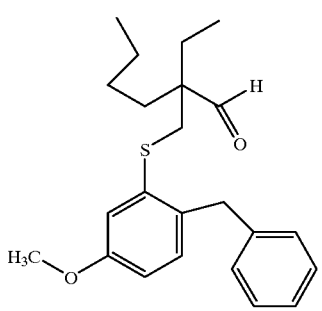

Hydrogenation of 1.1 g of 52 according to the procedure of step 3 of procedure A of example 18 gave 53 as a yellow oil (1.1 g).

Step 5. (3α,4α,5α) 3-Butyl-3-ethyl-4-hydroxy-7-methoxy-5-phenyl-2,3,4,5-tetrahydrobenzothiepine-1,1-dioxide (48), and (3α,4β,5β) 3-Butyl-3-ethyl-4-hydroxy-7-methoxy-5-phenyl-2,3,4,5-tetrahydrobenzothiepine-1,1-dioxide (49)

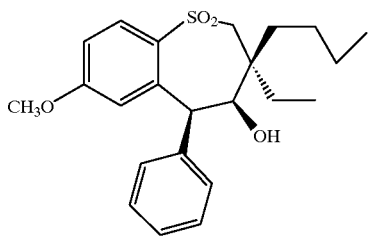

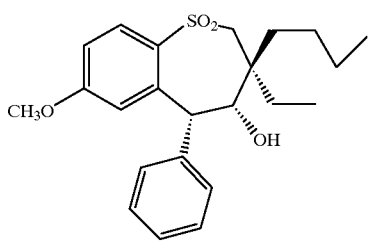

A solution of 1.1 g of 53, 0.36 g of potassium t-butoxide and 25 ml of anhydrous THF was held at reflux for 2 h and worked up as in step 4 of procedure A of example 18 to give 1.07 g of a crude product which was purified by HPLC to give 40 mg (4%) of 48 as crystals, mp 153–154° C. and 90 mg (8%) of 49 as solid, mp 136–140° C.

Example 28

5-Phenyl-2,3-dihydrospirobenzothiepine-3,1'-cyclohexane (57)

Step 1. 1-(Hydroxymethyl)-cyclohexanecarboxaldehyde (54)

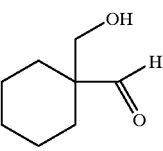

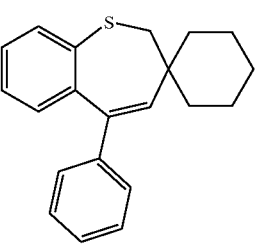

To a cold (0° C. mixture of 100 g (0.891 mole) of cyclohexanecarboxaldehyde, 76.5 g of 37% of formaldehyde in 225 ml of methanol was added dropwise 90 ml of 1 N Sodium hydroxide in 1 h. The reaction mixture was stirred at room temperature over 48 then was evaporated to remove methanol. The reaction mixture was diluted with water and extracted with methylene chloride. The organic layer was washed with water, brine, and dried over sodium sulfate and concentrated under vacuum to give 75 g (59.7%) of thick oil. Proton NMR and mass spectra were consistent with the product.

Step 2. 1-(mesyloxymethyl)cyclohexanecarboxaldehyde (55)

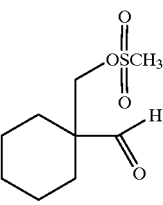

To a cold (0° C.) mixture of alcohol 54 (75 g, 0.54 mole) and 65.29 g (0.57 mole) of methanesulfonyl chloride in 80 ml of methylene chloride was added a solution of pyridine (47.96 g, 0.57 mole) in 40 ml of methylene chloride. The reaction mixture was stirred at room temperature for 18 h then quenched with water, acidified with conc. HCl and extracted with methylene chloride. The organic layer was washed with water, brine, and dried over sodium sulfate and concentrated under vacuum to give 91.63 g (77.8%) of thick oil. Proton NMR and mass spectra were consistent with the product.

Step 3. 1-((2-Benzoylphenylthio)methyl)cyclohexanecarboxaldehyde (56)

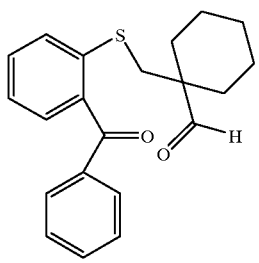

56

A mixture of 69 g (0.303 mole) of 2-mercaptobenzophenone, 82 g (0.303 mole) of mesylate 55, 32 g of triethylamine, and 150 ml of diglyme was stirred and held at reflux for 24 h. The mixture was cooled, poured into dil. HCl and extracted with methylene chloride. The organic layer was washed with 10% NaOH, water, brine, and dried over sodium sulfate and concentrated under vacuum to remove excess diglyme. This was purified by silica gel flush column (5% EtOAc: Hexane) and gave 18.6 g (75.9%) of yellow oil. Proton NMR and mass spectra were consistent with the product.

Step 4. 5-Phenyl-2,3-dihydrospirobenzothiepine-3,1'-cyclohexane (57)

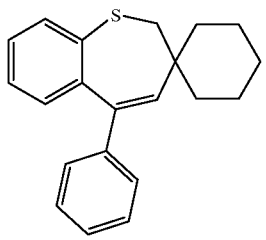

57

To a mixture of 6.19 g of zinc dust and 100 ml of dry DME was added TiCl$_3$ (16.8 g, 0.108 mole). The reaction mixture was heated to reflux for 2 h. A solution of compound 56 (8.3 g, 0.023 mole) in 50 ml of DME was added dropwise to the reaction mixture in 1 h and the mixture was held at reflux for 18 h. The mixture was cooled, poured into water and extracted with ether. The organic layer was washed with water, brine, and dried over sodium sulfate, filtered through celite and concentrated under vacuum. The residue was purified by HPLC (10% EtOAc: Hexane) to give 4.6 g (64%) of white solid, mp 90–91° C. Proton and carbon NMR and mass spectra were consistent with the product.

EXAMPLE 29

8b-Phenyl-1a,2,3,8b-tetrahydrospiro(benzothiepino[4,5-b]oxirene-2,1'-cyclohexane)-4,4-dioxide (58)

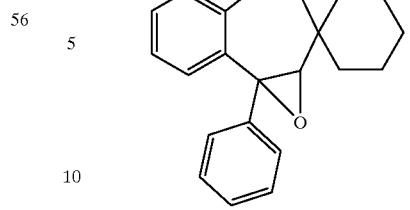

58

To a solution of 57 (4.6 g, 15 mmole) in 50 ml chloroform under nitrogen was added 55% MCPBA (16.5 g, 52.6 mmole) portionwise with spatula. The reaction was held at reflux for 18 h and washed with 10% NaOH (3×), water, brine, and dried over sodium sulfate and concentrated under vacuum to give 5 g of crude product. This was recrystallized from Hexane/EtOAc to give 4.31 g (81%) of yellow solid, mp 154–155° C. Proton and carbon NMR and mass spectra were consistent with the product.

EXAMPLE 30
trans-4-Hydroxy-5-phenyl-2,3,4,5-tetrahydro spiro (benzothiepine-3,1'-cyclohexane)-1,1-dioxide (59)

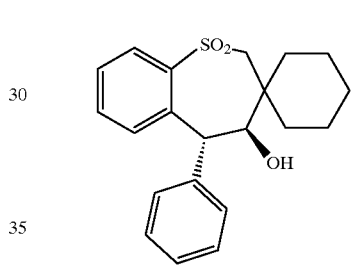

59

A mixture of 0.5 g (1.4 mmoles) of 58, 20 ml of ethanol, 10 ml of methylene chloride and 0.4 g of 10% Pd/C catalyst was hydrogenated with 70 psi hydrogen for 3 h at room temperature. The crude reaction slurry was filtered through Celite and evaporated to dryness. The residue was purified by HPLC (10% EtOAc-Hexane, 25% EtOAc-Hexane). The first fraction was 300 mg (60%) as a white solid, mp 99–100° C. Proton NMR showed this was a trans isomer. The second fraction gave 200 mg of solid which was impure cis isomer.

EXAMPLE 31
cis-4-Hydroxy-5-phenyl-2,3,4,5-tetrahydro spiro (benzothiepine-3,1'-cyclohexane)-1,1-dioxide (60)

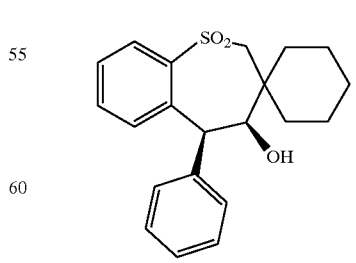

60

To a solution of 0.2 g (0.56 mmole) of 59 in 20 ml of CH$_2$Cl$_2$, was added 8 g of 50% NaOH and one drop of Aliquat-336 (methyltricaprylylammonium chloride) phase transfer catalyst. The reaction mixture was stirred for 10 h at room temperature. Twenty g of ice was added to the mixture and the mixture was extracted with CH₂Cl₂ (3×10 ml) washed with water, brine and dried over MgSO₄ and concentrated in vacuo to recover 0.15 g of crude product. This was recrystallized from Hexane/EtOAc to give 125 mg of white crystal, mp 209–210° C. Proton and carbon NMR and mass spectra were consistent with the product.

EXAMPLE 32
(3α,4α,5α) 3-Butyl-3-ethyl-4-hydroxy-5-phenyl-2,3,4,5-tetrahydrobenzothiepine (61), and (3α,4β,5β) 3-Butyl-3-ethyl-4-hydroxy-5-phenyl-2,3,4,5-tetrahydrobenzothiepine (62)

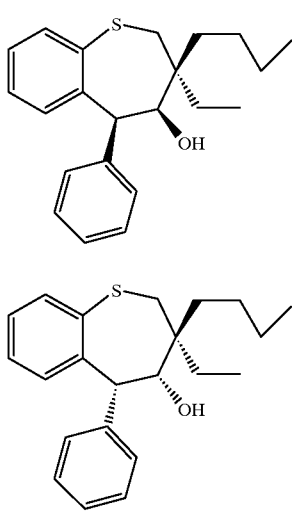

To a solution of 0.5 g (1.47 mmole) of compound 47 in 5 ml of anhydrous THF was added 0.17 g (1.47 mmole) of 95% potassium t-butoxide. The reaction mixture was stirred at room temperature for 18 h and quenched with 10 ml of 10% HCl. The organic was extracted into methylene chloride. The methylene chloride extract was dried over magnesium sulfate and concentrated in vacuo. The residue was purified by HPLC (2% EtOAc-hexane) to give 47 mg of 61 in the second fraction and 38 mg of 62 in the third fraction. Proton NMR and mass spectra were consistent with the assigned structures.

EXAMPLE 33
(3α,4α,5α) 3-Butyl-3ethyl-4-hydroxy-7-amino-5-phenyl-2,3,4,5-tetrahydrobenzothiepine-1,1-dioxide (63) and (3α,4β,5β) 3-Butyl-3-ethyl-4-hydroxy-7-amino-5-phenyl-2,3,4,5-tetrahydrobenzothiepine-1,1-dioxide (64)

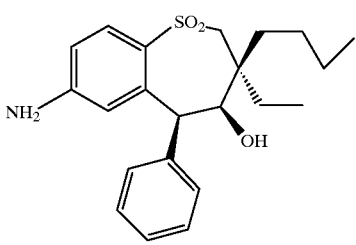

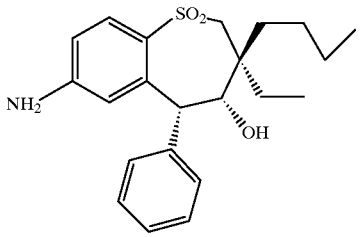

An autoclave was charged with 200 mg of 37 in 40 cc ethanol and 0.02 g 10% Pd/C. After purging with nitrogen the clave was charged with 100 psi hydrogen and heated to 55 C. The reaction was monitored by TLC and mass spec and allowed to proceed until all of 37 was consumed. After the reaction was complete the catalyst was filtered and the solvent was removed in vacuo and the only observable product was amine 63. This same procedure was used to produce 64 from 38.

EXAMPLE 34
(3α,4α,5α) 3-Butyl-3-ethyl-4-hydroxy-7-methoxy-5-(3'-methoxyphenyl)-2,3,4,5-tetrahydrobenzothiepine-1,1-dioxide (65), and (3α,4β,5β) 3-Butyl-3-ethyl-4-hydroxy-7-methoxy-5-(3'-methoxyphenyl)-2,3,4,5-tetrahydrobenzothiepine-1,1-dioxide (66).

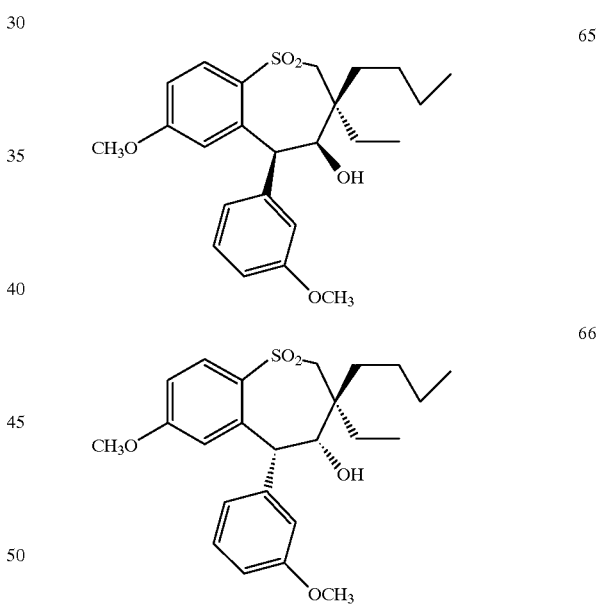

Alkylation of e-methoxyphenol with 3-methoxybenzyl chloride according to the procedure described in J. Chem. Soc, 2431 (1958) gave 4-methoxy-2-(3'-methoxybenzyl) phenol in 35% yield. This material was converted to compound 65, mp 138.5–141.5° C., and compound 66, mp 115.5–117.5° C., by the procedure similar to that in Example 18 method B.

EXAMPLE 35
(3α,4α,5α) 3-Butyl-3-ethyl-4-hydroxy-7-methoxy-5-(3'-(trifluoromethyl)phenyl)-2,3,4,5-tetrahydrobenzothiepine-1,1-dioxide (67), and (3α,4β,5β) 3-Butyl-3-ethyl-4-hydroxy-7-methoxy-5-(3'-(trifluoromethyl)phenyl)-2,3,4,5-tetrahydrobenzothiepine-1,1-dioxide (68).

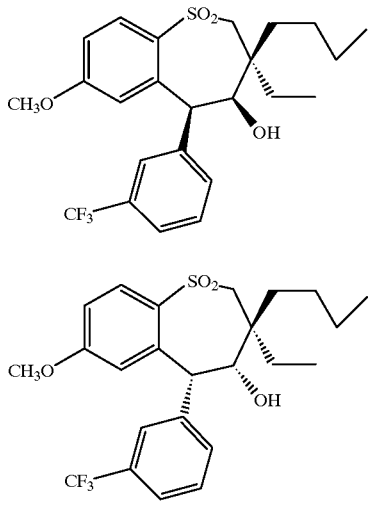

Alkylation of 4-methoxyphenol with 3-(trifluoromethyl)benzyl chloride according to the procedure described in J. Chem. Soc. 2431 (1958) gave 4-methoxy-2-(3'-(trifluoromethyl)benzyl)phenol. This material was converted to compound 67, mp 226.5–228° C., and compound 68, mp 188–190° C., byu the procedure similar to that in Example 18 method B.

EXAMPLE 36
(3α,4α,5α) 3-Butyl-3-ethyl-5-(4'-fluorophenyl)-4-hydroxy-7-methoxy-2,3,4,5-tetrahydrobenzothiepine-1,1-dioxide (69), and (3α,4β,5β) 3-Butyl-3-ethyl-5-(4'-fluorophenyl)-4-hydroxy-7-methoxy-2,3,4,5-tetrahydrobenzothiepine-1,1-dioxide (70).

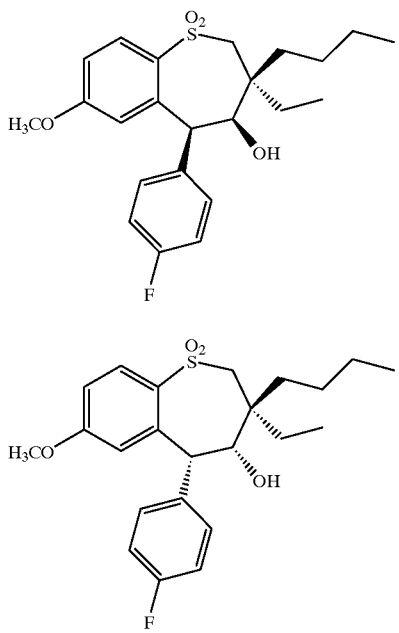

Alkylation of 4-methoxyphenol with 4-fluorobenzyl chloride according to the procedure described in J. Chem. Soc, 2431 (1958) gave 4-methoxy-2-(4'-fluorobenzyl)phenol. This material was converted to compound 69 and compound 70 by the procedure similar to that in Example 18 method B.

EXAMPLE 37
(3α,4α,5α) 3-Butyl-3-ethyl-5-(3'-fluorophenyl)-4-hydroxy-7-methoxy-2,3,4,5-tetrahydrobenzothiepine-1,1-dioxide (71), and (3α,4β,5β) 3-Butyl-3-ethyl-5-(3'-fluorophenyl)-4-hydroxy-7-methoxy-2,3,4,5-tetrahydrobenzothiepine- 1,1-dioxide (72).

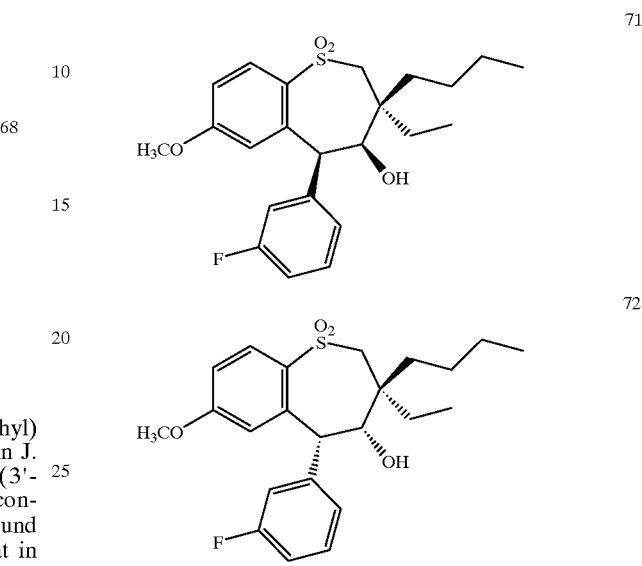

Alkylation of 4-methoxyphenol with 3-fluorobenzyl chloride according to the procedure described in J. Chem. Soc, 2431 (1958) gave 4-methoxy-2-(3'-fluorobenzyl)phenol. This material was converted to compound 71 and compound 72 by the procedure similar to that in Example 18 method B.

EXAMPLE 38
(3α,4α,5α) 3-Butyl-3-ethyl-5-(2'-fluorophenyl)-4-hydroxy-7-methoxy-2,3,4,5-tetrahydrobenzothiepine-1,1-dioxide (73), and (3α,4β,5β) 3-Butyl-3-ethyl-5-(2'-fluorophenyl)-4-hydroxy-7-methoxy-2,3,4,5-tetrahydrobenzothiepine-1,1-dioxide (74).

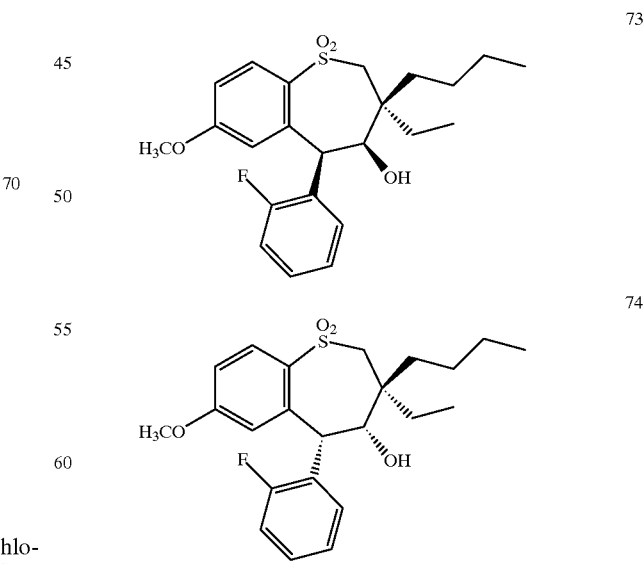

Alkylation of 4-methoxyphenol with 2-fluorobenzyl chloride according to the procedure described in J. Chem. Soc, 2431 (1958) gave 4-methoxy-2-(2'-fluorobenzyl)phenol. This material was converted to compound 73 and compound 74 by the procedure similar to that in Example 18 method B.

EXAMPLE 39

(3α,4α,5α) 3-Butyl-7-bromo-3-ethyl-4-hydroxy-5-(3'-methoxyphenyl)-2,3,4,5-tetrahydrobenzothiepine-1,1-dioxide (75), and (3α,4β,5β) 3-Butyl-7-bromo-3-ethyl-4-hydroxy-5-(3'-methoxyphenyl)-2,3,4,5-tetrahydrobenzothiepine-1,1-dioxide (76).

75

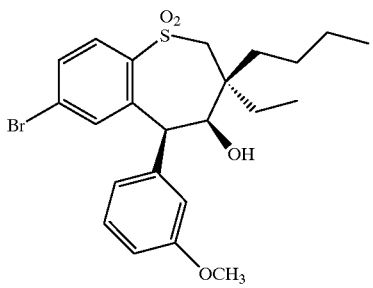

76

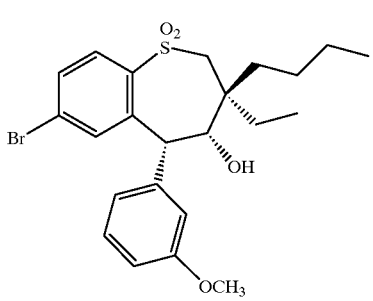

Alkylation of 4-bromophenol with 3-methoxybenzyl chloride according to the procedure described in J. Chem. Soc, 2431 (1958) gave 4-bromo-2-(3'-methoxybenzyl) phenol. This material was converted to compound 75, mp 97–101.5° C., and compound 76, mp 102–106° C., by the procedure similar to that in Example 18 method B.

EXAMPLE 40

(3α,4α,5α) 3-Butyl-3-ethyl-7-fluoro-5-(4'-fluorophenyl)-4-hydroxy-2,3,4,5-tetrahydrobenzothiepine-1,1-dioxide (77), and (3α,4β,5β) 3-Butyl-3-ethyl-7-fluoro-5-(4'-fluorophenyl)-4-hydroxy-2,3,4,5-tetrahydrobenzothiepine-1,1-dioxide (78).

77

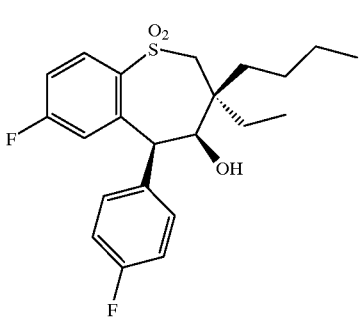

78

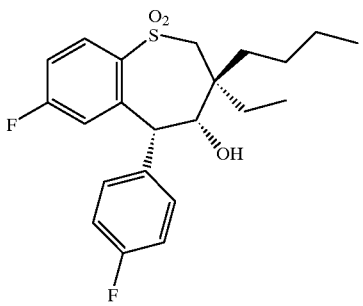

Alkylation of 4-fluorophenol with 4-fluorobenzyl chloride according to the procedure described in J. Chem. Soc, 2431 (1958) gave 4-fluoro-2-(4'-fluorobenzyl)phenol. This material was converted to compound 77, mp 228–230° C., and compound 78, mp 134.5–139° C., by the procedure similar to that in Example 18 method B.

EXAMPLE 41

(3α,4α,5α) 3-Butyl-3-ethyl-7-fluoro-4-hydroxy-5-(3'-methoxyphenyl)-2,3,4,5-tetrahydrobenzothiepine-1,1-dioxide (79), and (3α,4β,5β) 3-Butyl-3-ethyl-7-fluoro-4Ohydroxy-5-(3'-methoxyphenyl)-2,3,4,5-tetrahydrobenzothiepine-1,1-dioxide (80).

79

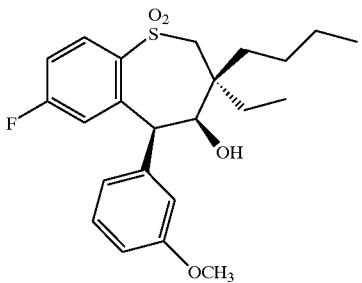

80

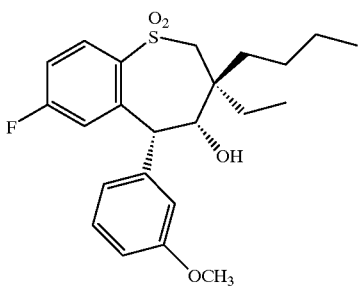

Alkylation of 4-fluorophenol with 3-methoxybenzyl chloride according to the procedure described in J. Chem. Soc, 2431 (1958) gave 4-fluoro-2-(3'-methoxybenzyl)phenol. This material was converted to compound 79, as a solid and compound 80, mp 153–155° C., by the procedure similar to that in Example 18 method B.

EXAMPLE 42

(3α,4β,5β) 3-Butyl-3-ethyl-5-(4'-fluorophenyl)-4-hydroxy-7-methylthio-2,3,4,5-tetrahydrobenzothiepine-1,1-dioxide (81).

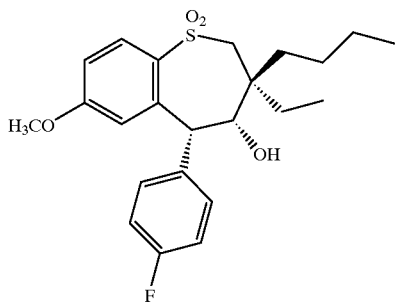

81

A mixture of 0.68 (1.66 mmol) of compound 77, 0.2 g (5 mmol) of sodium methanethiolate and 15 ml of anhydrous DMF was stirred at room temperature for 16 days. The reaction mixture was dilute with ether and washed with water and brine and dried over $M_gSO_4$. The ether solution was concentrated in vacuo. The residue was purified by HPLC (20% ethyl acetate in hexanes). The first fraction was impure (3α,4α,5α) 3-butyl-3-ethyl-4-hydroxy-7-methylthio-5-(4'-fluorophenyl)-2,3,4,5-tetrahydro-benzothiepine-1,1-dioxide. The second fraction was compound 81, mp 185–186.5° C.

EXAMPLE 43

(3α,4β,5β) 3-Butyl-3-ethyl-5-(4'-fluorophenyl)-4-hydroxy-7-(1-pyrrolidinyl)-2,3,4,5-tetrahydrobenzothiepine-1,1-dioxide (82).

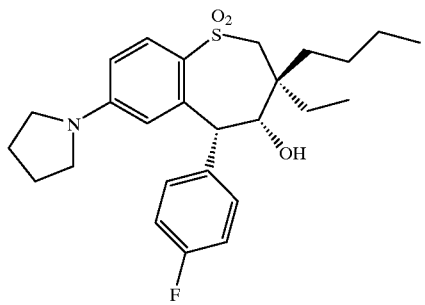

82

A mixture of 0.53 g (1.30 mmol) of compound 78 and 5 ml of pyrrolidine was held at reflux for 1 h. The reaction mixture was diluted with ether and washed with water and brine and dried over $M_gSO_4$. The ether solution was concentrated in vacuo. The residue was crystallized from ether-hexanes to give compound 82, mp 174.5–177° C.

EXAMPLE 44

(3α,4β,5β) 3-Butyl-3-ethyl-5-(4'-fluorophenyl)-4-hydroxy-7-(1-morpholinyl)-2,3,4,5-tetrahydrobenzothiepine-1,1-dioxide (83).

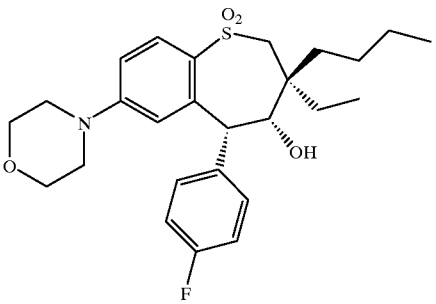

83

A mixture of 0.4 g (0.98 mmol) of compound 78 and 5.0 g (56 mmol) of morpholine was held at reflux for 2 h and concentrated in vacuo. The residue was diluted with ether (30 ml) and washed with water and brine and dried over $M_gSO_4$. The ether solution was concentrated in vacuo. The residue was recrystallized from ether-hexanes to give compound 83, mp 176.5–187.5° C.

EXAMPLE 45

(3α,4α,5α) 3-Butyl-3-ethyl-5-(4'-fluorophenyl)-4-hydroxy-7-methyl-2,3,4,5-tetrahydrobenzothiepine-1,1-dioxide (84), and (3α,4β,5β) 3-Butyl-3-ethyl-5-(4'-fluorophenyl)-4-hydroxy-7-methyl-2,3,4,5-tetrahydrobenzothiepine-1,1-dioxide (85).

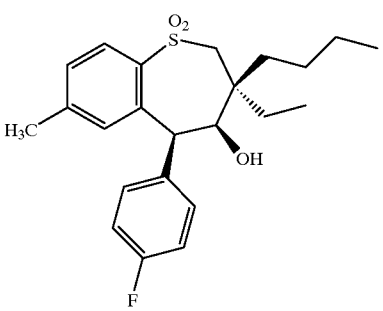

84

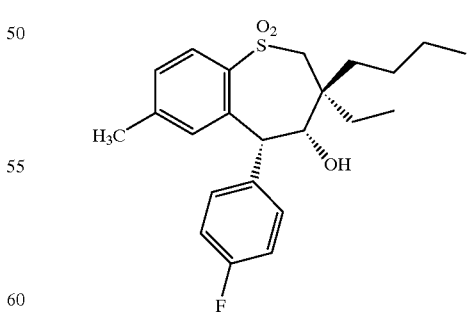

85

Alkylation of 4-methylphenol with 4-fluorobenzyl chloride according to the procedure described in J. Chem. Soc, 2431 (1958) gave 4-methyl-2-(4'-fluorobenzyl)phenyl). This material was converted to compound 84 and compound 85 by the procedure similar to that in Example 18 method B.

EXAMPLE 46

(3α,4β,5β) 3-Butyl-3-ethyl-4-hydroxy-5-(4'-hydroxyphenyl)-7-methoxy-2,3,4,5-tetrahydrobenzothiepine-1,1-dioxide (86), and (3α,4β,5β) 3-Butyl-3-ethyl-4,7-dihydroxy-5-(4'-hydroxyphenyl)-2,3,4,5-tetrahydrobenzothiepine-1,1-dioxide (87).

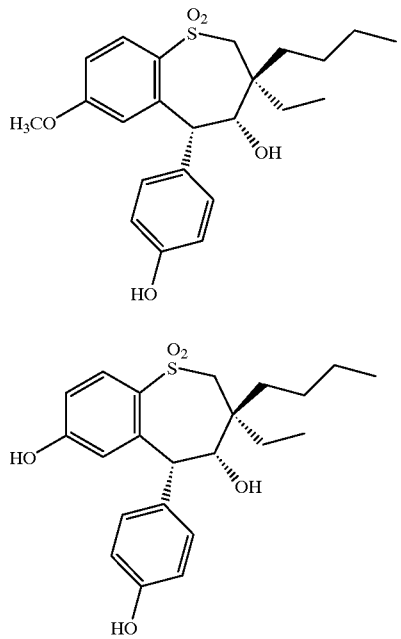

To a solution of 0.52 (1.2 mmol) of compound 66 in 20 ml of methylene chloride was added 1.7 g (6.78 mmol) of born tribromide. The reaction mixture was cooled to −78° C. and was stirred for 4 min. An additional 0.3 ml of boron tribromide was added to the reaction mixture and the reaction mixture was stirred at −78° C. for 1 h and quenced with 2 N HCl. The organic was extracted into ether. The ether layer was washed with brine, dried over $M_gSO_4$, and concentrated in vacuo. The residue (0.48 g) was purified by HPLC (30% ethyl acetate in hexanes). The first fraction was 0.11 g of compound 86 as a white solid, mp 171.5–173° C. The second fraction was crystallized from chloroform to give 0.04 g of compound 87 as a white solid, mp 264° C. (dec).

EXAMPLE 47

(3α,4β,5β) 3-Butyl-3-ethyl-4,7-dihydroxy-5-(4'-fluorophenyl)-2,3,4,5-tetrahydrobenzothiepine-1,1-dioxide (88).

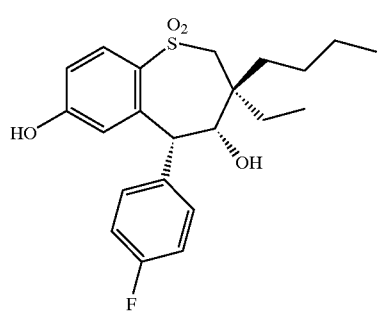

Reaction of compound 70 with excess boron tribromide at room temperature and worked up as in Example 46 gave compound 88 after an HPLC purification.

EXAMPLE 48

(3α,4β,5β) 3-Butyl-3-ethyl-5-(4'-fluorophenyl)-4-hydroxy-7-(1-azetidinyl)-2,3,4,5-tetrahydrobenzothiepine-1,1-dioxide (89).

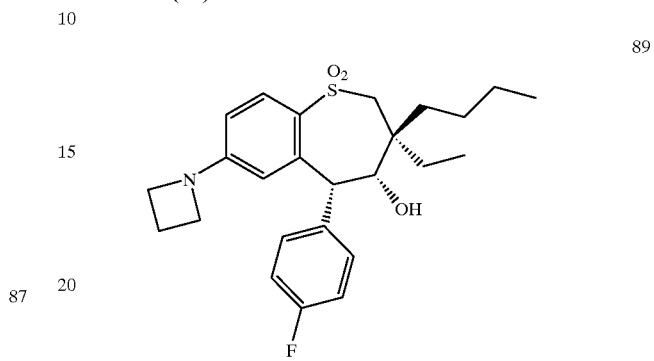

A mixture of 0.20 g (0.49 mmol) of compound 78, and 2.0 g (35 mmol) of aztidine was held at reflux for 3 h and concentrated in vacuo. The residue was diluted with ether (30 ml) and washed with water and brine and dried over MgSO4. The ether solution was concentrated on a steam bath. The separated crystals were filtered to give 0.136 g of 89 as prisms, mp 196.5–199.5° C.

EXAMPLE 49

(3α,4α,5α) 3-Butyl-3-ethyl-5-(3'-methoxyphenyl)-4-hydroxy-7-methylthio-2,3,4,5-tetrahydrobenzothiepine-1,1-dioxide (90). (3α,4β,5β) 3-Butyl-3-ethyl-5-(3'-methoxyphenyl)-4-hydroxy-7-methylthio-2,3,4,5-tetrahydrobenzothiepine-1,1-dioxide (91).

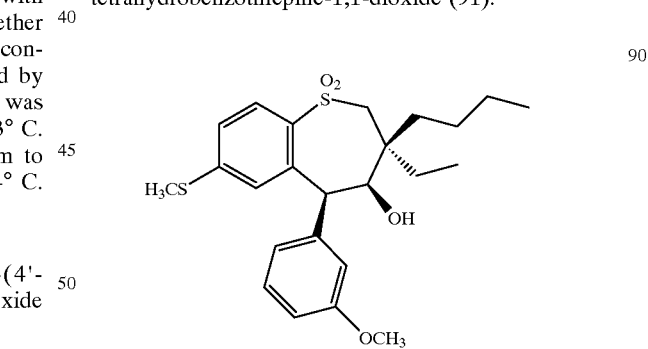

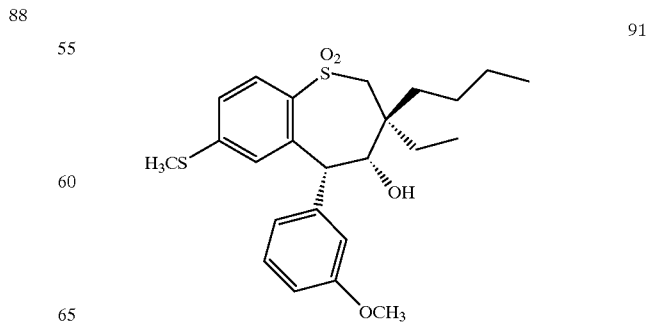

1.4 mmol of sodium methanethiolate was added to the reaction mixture and the mixture was stirred at 60° C. for an additional 2 h. The reaction mixture was triturated with 100 ml of water and extracted methylene chloride. The methylene chloride water mixture was filtered through Celite and the methylene chloride layer was dried over M$_g$SO$_4$ and concentrated in vacuo. The first fraction (0.1 g) was compound 90, mp 117–121° C. The second fraction (0.16 g) was compound 91, mp 68–76° C.

EXAMPLE 50

Preparation of polyethyleneglycol functionalized benzothiepine A

No. 141

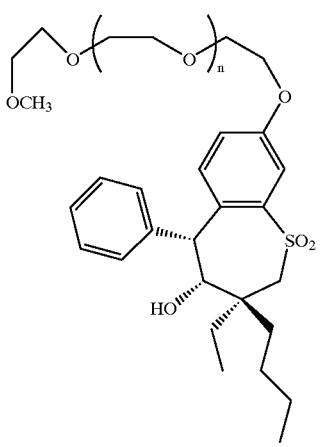

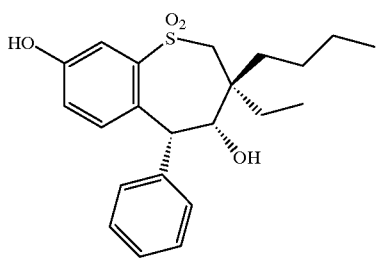

No. 136

A 50 ml rb flash under a nitrogen atmosphere was charged with 0.54 g of M-Tres-5000 (Polyethyleneglycol Tresylate [methoxy-PEG-Tres,MW 5000] purchased from Shearwater Polymers Inc., 2130 Memorial Parkway, SW, Huntsville, Ala. 35801), 0.055 g Compound No. 136, 0.326 C$_s$CO$_3$ and 2 cc anhydrous acetonitrile. The reaction was stirred at 30 C for 5 days and then the solution was filtered to remove salts. Next, the acetonitrile was removed under vacuum and the product was dissolved in THF and then precipitated by addition of hexane. The polymer precipitate was isolate by filtration from the solvent mixture (THF/hexane). This precipitation procedure was continued until no Compound No. 136 was detected in the precipitated product (by TLC SiO2). Next, the polymer precipitate was dissolved in water and filtered and the water soluble polymer was dialyzed for 48 hours through a cellulose dialysis tube (Spectrum® 7,45 mm×0.5 ft, cutoff 1,000 MW). The polymer solution was then removed from the dialysis tube and lyophilized until dried. The NMR was consistent with the desired product A and gel permeation chromatography indicated the presence of a 4500 MW polymer and also verified that no free Compound No. 136 was present. This material was active in the IBAT in vitro cell assay.

EXAMPLE 51
Preparation of Compound 140

No. 140

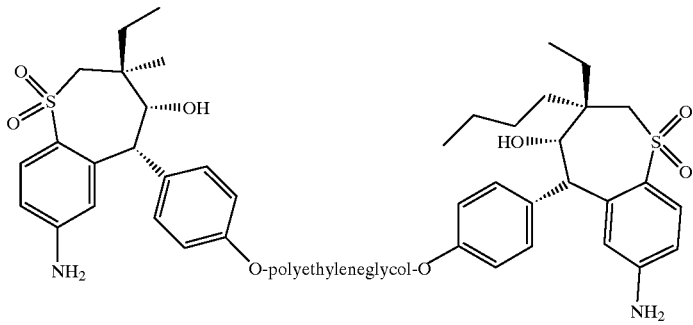

No. 111

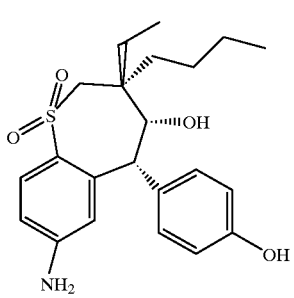

A 2-necked 50 ml round bottom Flask was charged with 0.42 g of Tres-3400 (Polyethyleneglycol Tresylate [Tres-PEG-Tres,MW 3400] purchased from Shearwater Polymers Inc., 2130 Memorial Parkway, SW, Huntsville, Ala. 35801), 0.1 potassium carbonate, 0.100 g of Compound No. 111 and 5 ml anhydrous DMF. Stir for 6 days at 27° C. TLC indicated the disappearance of the starting Compound No. 111. The solution was transferred to a separatory funnel and diluted with 50 cc methylene chloride and then extracted with water. The organic layer was evaporated to dryness by means of a rotary evaporator. Dry wgt. 0.4875 g. Next, the polymer was dissolved in water and then dialyzed for 48 hours at 40° C. through a cellulose dialysis tube (spectrum® 7,45 mm×0.5 ft, cutoff 1,000 MW). The polymer solution was then removed from the dialysis tube and lyophilized until dried 0.341 g). NMR was consistent with the desired product B.

EXAMPLE 52

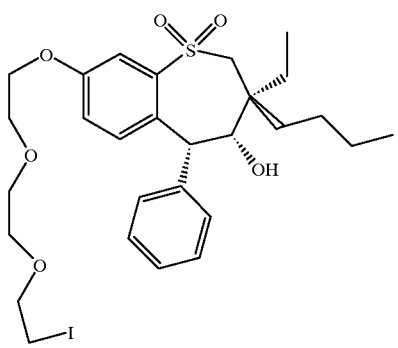

No. 134

A 10 cc vial was charged with 0.21 g of Compound No. 136 (0.5 mmoles), 0.17 g (1.3 mmoles) potassium carbonate, 0.6 g (1.5 mmoles) of 1,2-bis-(2-iodoethoxy)-ethane and 10 cc DMF. The reaction was stirred for 4 days at room temperature and then worked up by washing with ether/water. The ether layer was stripped to dryness and the desired product Compound No. 134 was isolated on a silica gel column using 80/20 hexane ethyl acetate.

EXAMPLE 53

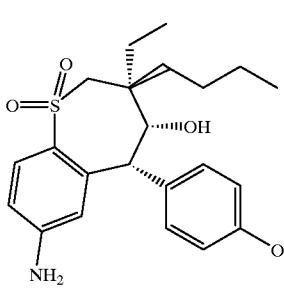

No. 112

EXAMPLE 54

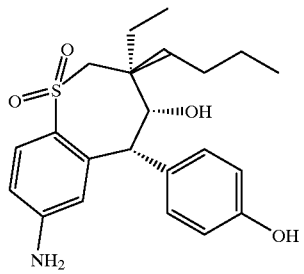

No. 113

A two necked 25 ml round bottom Flask was charged with 0.5 g (1.24 mmoles) of 69462, 13 mls of anhydrous DMF, 0.055 g of 60% NaH dispersion and 0.230 g (0.62 mmoles) of 1,2-Bis [2-iodoethoxylethane] at 10° C. under nitogen. Next, the reaction was slowly heated to 40° C. After 14 hours all of the Compound No. 113 was consumed and the reaction was cooled to room temperature and extracted with ether/water. The ether layer was evaporated to dryness and then chromatographed on Silicage (80/20 ethyl acetate/hexane). Isolated Compound No. 112 (0.28 g) was characterized by NMR and mass spec.

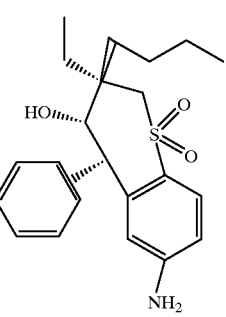

EXAMPLE 55

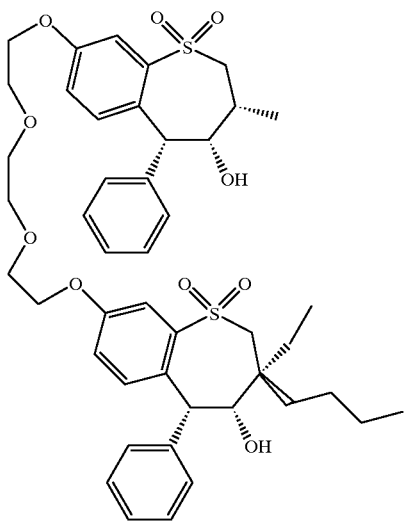

In a 50 ml round bottom Flask, add 0.7 g (1.8 mmoles) of Compound No. 136, 0.621 g of potassium carbonate, 6 ml DMF, and 0.33 g of 1,2-Bis [2-iodoethoxylethane]. Stir at 40° C. under nitrogen for 12 hours. The workup and isolation was the same procedure for Compound No. 112.

EXAMPLES 56 AND 57 (COMPOUND NOS. 131 AND 137)

The compositions of these compounds are shown in Table 3.

The same procedure as for Example 55 except appropriate benzothiepine was used.

EXAMPLE 58 (COMPOUND NO. 139)

The composition of this compound is shown in Table 3. Same procedure as for Example 55 with appropriate benzothiepine 1,6 diiodohexane was used instead of 1,2-Bis [2-iodoethoxylethane].

EXAMPLE 59 (COMPOUND NO. 101)

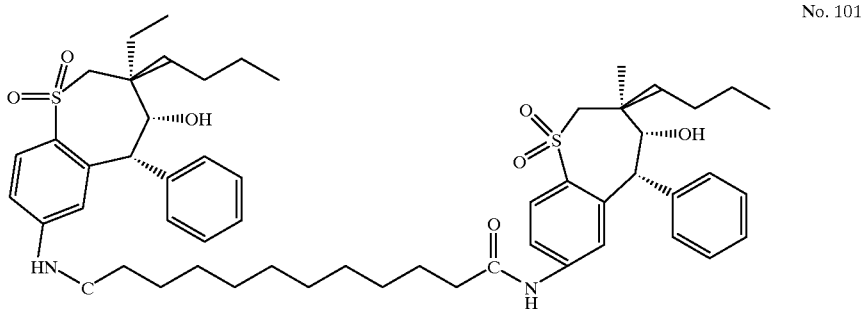

This compound is prepared by condensing the 7-NH$_2$ benzothiepine with the 1,12-dodecane dicarboxylic acid or acid halide.

EXAMPLE 60 (COMPOUND NO. 104)

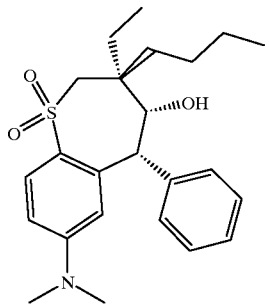

No. 104

2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIV (see Scheme 5). Reduction of the sulfone-aldehyde XXV formaldehyde and 100 psi hydrogen and 55 C for 12 hours catalyzed by palladium on carbon in the same reaction vessel yields the substituted dimethylamine derivative XXVIII. Cyclization of XXVII with potassium t-butoxide yields a mixture of substituted amino derivatives of this invention Compound No. 104.

EXAMPLE 61

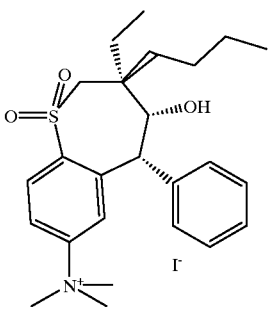

No. 102

A 1 oz. Fisher-porter bottle was charged with 0.14 g (0.34 mmoles) of 70112, 0.97 gms (6.8 mmoles) of methyl iodide, and 7 ml of anhydrous acetonitrile. Heat to 50° C. for 4 days. The quat. Salt Compound No. 192 was isolated by concentrating to 1 cc acetonitrile and then precipitating with diethyl ether.

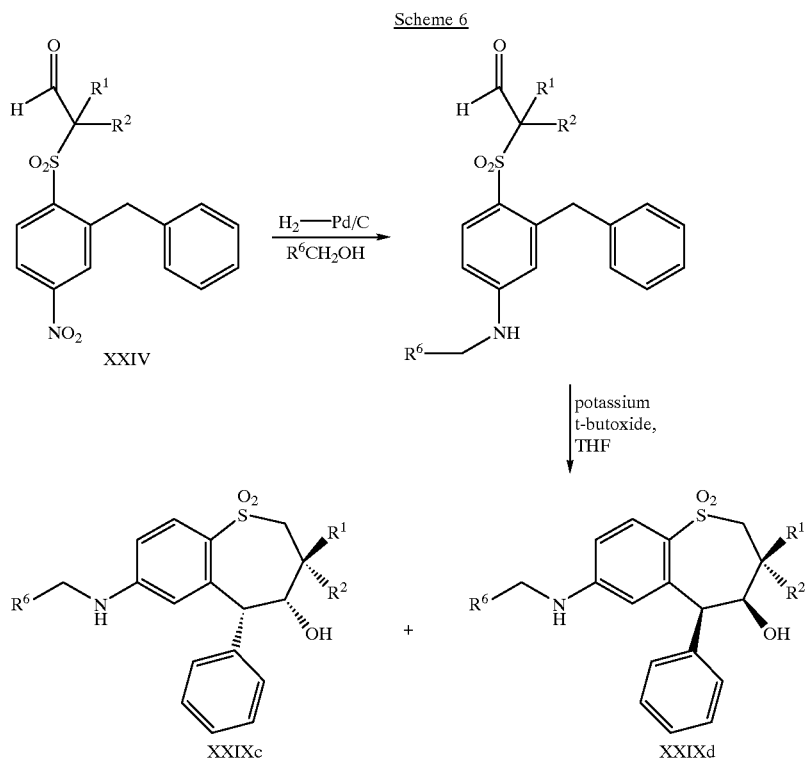

Scheme 6

EXAMPLE 62

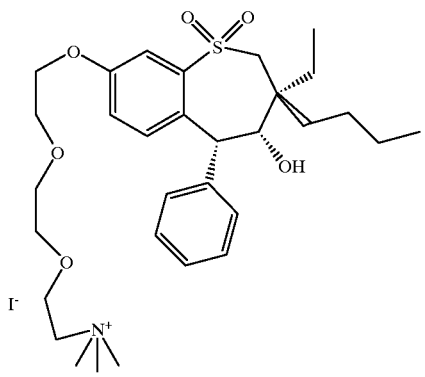

No. 125

A 0.1 g (0.159 mmoles) sample of Compound No. 134 was dissolved in 15 ml of anhydrous acetonitrile in a Fischer-porter bottle and then trimethylamine was bubbled through the solution for 5 minutes at 0° C. and then capped and warmed to room temperature. The reaction was stirred overnight and the desired product was isolated by removing solvent by rotary evaporation.

EXAMPLE 63 (COMPOUND NO. 295)

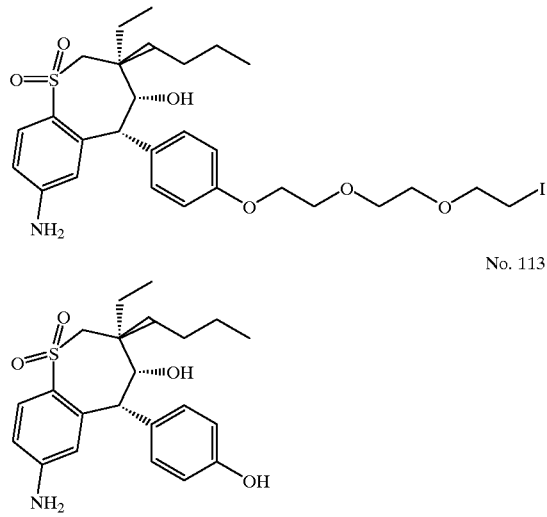

No. 295

No. 113

Sodium Hydride 60% (11 mg, 0.27 mmoles) in 1 cc of acetonitrile at 0° C. was reacted with 0.248 mmoles (0.10 g) of Compound No. 54 in 2.5 cc of acetonitrile at 0° C. Next, 0.(980 g 2.48 mmoles) of 1,2-Bis [2-iodoethoxylethane]. After warming to room temperature, stir for 14 hours. The product was isolated by column chromatography.

EXAMPLE 64 (COMPOUND NO. 286)

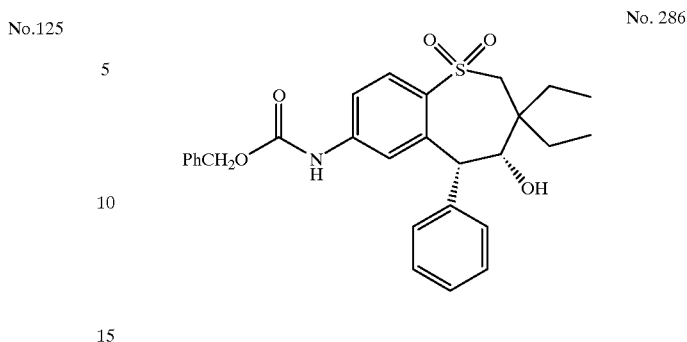

No. 286

Following a procedure similar to the one described in Example 86, infra (see Compound No. 118), the title compound was prepared and purified as a colorless solid; mp 180–181° C.; $^1$H NMR (CHCl$_3$) δ 0.85 (t, J=6 Hz, 3H__, 0.92 (t, J=6 Hz, 3H), 1.24–1.42 (m, 2H), 1.46–1.56 (m, 1H), 1.64–1.80 (m, 1H), 2.24–2.38 (m, 1H), 3.15 (AB, J$_{AB}$=15 Hz, Δv=42 Hz, 2H), 4.20 (d, J=8 Hz, 1H), 5.13 (s, 2H), 5.53 (s, 1H), 6.46 (s, 1H), 6.68 (s, 1H), 7.29–7.51 (m, 10H), 7.74 (d, J=8 Hz, 1H), 8.06 (d, J=8 Hz, 1H). FABMS m/z 494 (M+H), HRMS calcd for (M+H) 494.2001, found 494.1993.

Anal. Calcd. for C$_{28}$H$_{31}$NO$_5$S: C, 68.13; H, 6.33; N, 2.84. Found: C, 68.19; H, 6.56; N, 2.74.

EXAMPLE 65 (COMPOUND NO. 287)

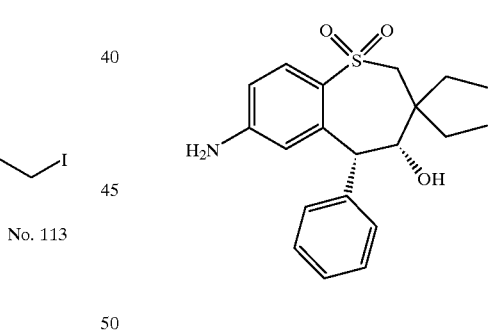

No. 287

Following a procedure similar to the one described in Example 89, infra (see Compound No. 121), the title compound was prepared and purified as a colorless solid: mp 245–246° C., $^1$H NMR (CDCl$_3$) δ 0.84 (t, J=6 Hz, 3H), 0.92 (t, J=6 Hz, 3H), 1.28, (d, J=8 Hz, 1H), 1.32–1.42 (m, 1H), 1.48–1.60 (m, 1H), 1.64–1.80 (m, 1H), 2.20–2.36 (m, 1H), 3.09 (AB, J$_{AB}$=15 Hz, Δv=42 Hz, 2H), 3.97 (bs, 2H), 4.15 (d, J=8 Hz, 1H), 5.49 (s, 1H), 5.95 (s, 1H), 6.54 (d, J=7 Hz, 1H), 7.29–7.53 (m, 5H), 7.88 (d, J=8 Hz, 1H); ESMS 366 (M+Li).

Anal. Calcd. for C$_{20}$H$_{25}$NO$_3$S: C, 66.82; H, 7.01; N, 3.90. Found: C, 66.54; H, 7.20; N, 3.69.

EXAMPLE 66 (COMPOUND NO. 288)

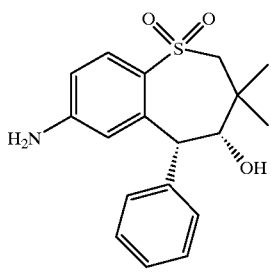

No. 288

Following a procedure similar to the one described in Example 89, infra (see Compound No. 121), the title compound was prepared and purified by silica gel chromatography to give the desired product as a colorless solid: mp 185–186° C.; $^1$H NMR (CDCl$_3$) δ 1.12 (s, 3H), 1.49 (s, 3H), 3.00 (d, J=15 Hz, 1H), 3.28 (d, J=15 Hz, 1H), 4.00 (s, 1H), 5.30 (s, 1H), 5.51 (s, 1H), 5.97 (s, 1H), 6.56 (dd, J=2.1, 8.4 Hz, 1H), 7.31–7.52 (m, 5H), 7.89 (d, J=8.4 Hz, 1H). MS (FAB+) (M+H) m/z 332.

EXAMPLE 67 (COMPOUND NO. 289)

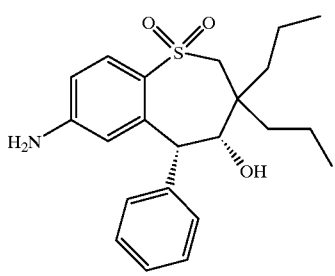

No. 289

Following a procedure similar to the one described in Example 89 (see Compound No. 121), the title compound was prepared and purified by silica gel chromatography to give the desired product as a white solid: mp 205–206° C.; $^1$H NMR (CDCl$_3$) δ 0.80–0.95 (m, 6H), 1.10–1.70 (m, 7H), 2.15 (m, 1H), 3.02 (d, J=15.3 Hz, 2H), 3.15 (d, J=15.1 Hz, 2H), 3.96 (s, br, 2H), 4.14 (d, J 7.8 Hz, 1H), 5.51 (s, 1H), 5.94 (d, J=2.2, 1H), 6.54 (dd, J=8.5, 2.2 Hz, 1H), 7.28–7.50 (m, 6H), 7.87 (d, J 8.5 Hz, 1H). MS (FAB): m/z 388 (M+H).

EXAMPLE 68 (COMPOUND NO. 290)

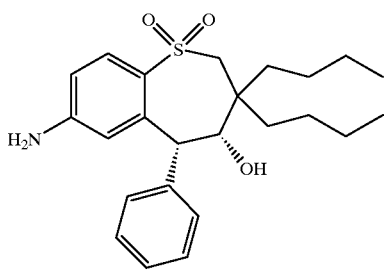

No. 290

Following a procedure similar to the one described in Example 89, infra (see Compound No. 121), the title compound was prepared and purified as a colorless solid: mp=96–98° C., $^1$H NMR (CDCl$_3$) δ 0.92 (t, J=7 Hz, 6H), 1.03–1.70 (m, 11H), 2.21 (t, J=8 Hz, 1H), 3.09 (AB, J$_{AB}$=−18 Hz, Δv=38 Hz, 2H), 3.96 (bs, 2H), 4.14 (d, J=7 Hz, 1H), 5.51 (s, 1H), 5.94 (s, 1H), 6.56 (d, J=9 Hz, 1H), 7.41–7.53 (m, 6H), 7.87 (d, J=8 Hz, 1H); FABMS m/z 416 (M+H).

EXAMPLE 69

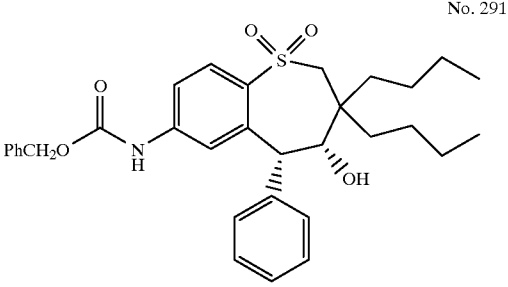

No. 291

Following a procedure similar to the one described in Example 86, infra (see Compound No. 118), the title compound was prepared and purified as a colorless solid: $^1$H NMR (CDCl$_3$) δ 0.91 (t, J=7 Hz, 6H), 1.02–1.52 (m, 11H), 1.60–1.70 (m, 1H), 2.23 (t, J=8 Hz, 1H), 3.12 (AB, J$_{AB}$=18 Hz, Δv=36 Hz, 2H), 4.18 (d, J=7 Hz, 1H), 5.13 (s, 2H), 5.53 (s, 1H), 6.43 (s, 1H), 6.65 (s, 1H), 7.29–7.52 (m, 10H), 7.74 (d, J=9 Hz, 1H), 8.03 (d, J=8 Hz, 1H); ESMS m/z 556 (M+Li).

EXAMPLE 70 (COMPOUND NO. 292)

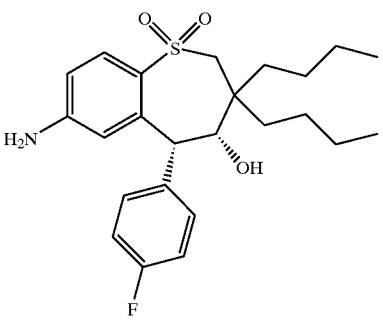

No. 292

Following a procedure similar to the one descried in Example 89, infra (see Compound No. 121), the title compound was prepared and purified as a colorless solid: mp=111–112.5° C., $^1$H NMR (CDCl$_3$) δ 0.90 (t, J=8 Hz, 6H), 1.03–1.50 (m, 10H), 1.55–1.70 (m, 2H), 2.18 (t, J=12 Hz, 2H), 3.07 (AB, J$_{AB}$=15 Hz, Δv=45 Hz, 2H), 4.09 (bs, 2H), 5.49 (s, 1H), 5.91 (s, 1H), 6.55 (d, J=9 Hz, 1H), 7.10 (t, J=7 Hz, 2H), 7.46 (t, J=6 Hz, 2H), 7.87 (d, J=9 Hz, 1H).

EXAMPLE 71 (COMPOUND NO. 293)

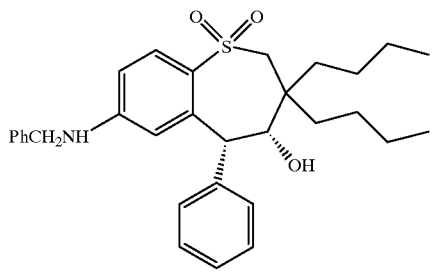

No. 293

During the preparation of Compound No. 290 from Compound No. 291 using BBr$_3$, the title compound was isolated: $^1$H NMR (CDCl$_3$) δ 0.85 (t, J=6 Hz, 6H), 0.98–1.60 (m, 10H), 1.50–1.66 (m, 2H), 2.16 (t, J=8 Hz, 1H), 3.04 (AB, J$_{AB}$=15 Hz, Δv=41 Hz, 2H), 4.08 (s, 1H), 4.12 (s, 1H), 5.44 (s, 1H), 5.84 (S, 1H), 6.42 (d, J=9 Hz, 1H), 7.12 (d, J=8 Hz, 2H), 7.16–7.26 (m, 10H), 7.83 (d, J=8 Hz, 1H); ESMS m/z 512 (M+Li).

EXAMPLE 72 (COMPOUND NO. 294)

Following a procedure similar to the one described in Example 60 (Compound No. 104), the title compound was prepared and purified as a colorless solid: $^1$H NMR (CDCl$_3$) δ 0.90 (t, J=6 Hz, 6H), 1.05–1.54 (m, 9H), 1.60–1.70 (m, 1H), 2.24 (t, J=8 Hz, 1H), 2.80 (s, 6H), 3.05 (AB, J$_{AB}$=15 Hz, Δv=42 Hz, 2H), 4.05–4.18 (m, 2H), 5.53 (s, 1H), 5.93 (s, 1H), 6.94 (d, J=9 Hz, 1H), 7.27–7.42 (m, 4H), 7.45 (d, J=8 Hz, 2H), 7.87 (d, J=9 Hz, 1H); ESMS m/z 444 (M+H).

Structures of the compounds of Examples 33 to 72 are shown in Tables 3 and 3A.

EXAMPLES 73–79, 87, 88 AND 91–102

Using in each instance a method generally described in those of Examples 1 to 72 appropriate to the substituents to be introduced, compounds were prepared having the structures set forth in Table 3. The starting materials illustrated in the reaction schemes shown above were varied in accordance with principles of organic synthesis well known to the art to introduce the indicated substituents in the 4- and 5-positions (R$^3$, R$^4$, R$^5$, R$^6$) and in the indicated position on the benzo ring (R$^x$).

Structures of the the compounds produced in Examples 73–102 are set forth in Tables 3 and 3A.

EXAMPLES 80–84

Preparation of 115, 116, 111, 113

Preparation of 4-chloro-3-[4-methoxyphenylmethyl]-nitrobenzene.

In a 500 ml 2-necked rb flask weigh out 68.3 gms phosphorus pentachloride (0.328 mole 1.1 eq). Add 50 mls chlorobenzene. Slowly add 60 gms 2-chloro-5-nitrobenzoic acid (0.298 mole). Stir at room temp overnight under N2 then heat 1 hr at 50 C.

Remove chlorobenzene by high vacuum. Wash residue with hexane. Dry wt=55.5 gms.

In the same rb flask, dissolve acid chloride (55.5 g 0.25 mole) from above with 100 mls anisole (about 3.4 eq). Chill solution with ice bath while purging with N2. Slowly add 40.3 g aluminum chloride (1.2 eq 0.3 mole). Stir under N$_2$ for 24 hrs.

After 24 hrs, the solution was poured into 300 mls 1N HCl soln. (cold). Stir this for 15 min. Extract several times with diethyl ether. Extract organic layer once with 2% aqueous NaOH then twice with water. Dry organic layer with MgSO4, dry on vac line. Solid is washed well with ether and then ethanol before drying. Wt=34.57 g (mixture of meta, ortho and para).

| Elemental | theory | found |
|---|---|---|
| C | 57.65 | 57.45 |
| H | 3.46 | 5.51 |
| N | 4.8 | 4.8 |
| Cl | 12.15 | 12.16 |

With the next step of the reduction of the ketone with trifluoromethane sulfonic aid and triethyl silane, crystallization with ethyl acetate/hexane affords pure 4-chloro-3-[4-methoxy-phenylmethyl]-nitrobenzene.

4-Chloro-3-[4-methoxy-phenylmethyl]-nitrobenzene was then reacted as specified in the synthesis of 117 and 118 from 2-chloro-4-nitrophenylmethane. From these procedures 115 and 116 can be synthesized. Compounds 111 and 113 can be synthesized from the procedure used to prepare compound 121.

Compound 114 can be prepared by reaction of 116 with ethyl mercaptan and aluminum trichloride.

EXAMPLES 85 AND 86

Preparation of 117 and 118

2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIII. Oxidation of XXIII with 2 equivalents of MCPBA yields sulfone-aldehyde XXIV (see Scheme 5).

The sulfone-aldehyde (31.8 g) was dissolved in ethanol/toluene and placed in a parr reactor with 100 ml toluene and 100 ml of ethanol and 3.2 g of 10% Pd/C and heated to 55 C and 100 psi of hydrogen gas for 14 hours. The reaction was then filtered to remove the catalyst. The amine product (0.076 moles, 29.5 g) from this reaction was then reacted with benzyl chloroformate (27.4 g) in toluene in the presence of 35 g of potassium carbonate and stirred at room temperature overnight. After work up by extraction with water, the CBZ protected amine product was further purified by precipitation from toluene/hexane.

The CBZ protected amine product was then reacted with 3 equivalents of potassium t-butoxide in THF at 0 C to yield compounds 117 and 118 which were separated by silica gel column chromatography.

EXAMPLES 89 AND 90

Preparation of 121 or 122

Compound 118 (0.013 moles, 6.79 g) is dissolved in 135 ml of dry chloroform and cooled to −78 C, next 1.85 ml of boron tribromide (4.9 g) was added and the reaction is allowed to warm to room temperature. Reaction is complete after 1.5 hours. The reaction is quenched by addition of 10% potassium carbonate at 0 C and extract with ether. Removal of ether yields compound 121. A similar procedure can be used to produce 122 from 117.

EXAMPLES 93–96

Compounds 126, 127, 128 and 129 as set forth in Table 3 were prepared substantially in the manner described above for compounds 115, 116, 111 and 113, respectively, except that fluorobenzene was used as a starting material in place of anisole.

TABLE 3

Specific Compounds (#102–111, 113–130, 132–134, 136, 138, 142–144, 262–296)

| Cp# | R¹ | R² | R³ | R⁴ | R⁵ | R⁶ | (Rˣ)q |
|---|---|---|---|---|---|---|---|
| 102 | Et- | n-Bu- | HO- | H- | Ph- | H- | I⁻, 7-(CH₃)₃N⁺- |
| 103 | n-Bu- | Et- | HO- | H- | Ph- | H- | I⁻, 7-(CH₃)₃N⁺- |
| 104 | Et- | n-Bu- | HO- | H- | Ph- | H- | 7-(CH₃)₂N- |
| 105 | Et- | n-Bu- | HO- | H- | Ph- | H- | 7-CH₃SO₂NH- |
| 106 | Et- | n-Bu- | HO- | H- | Ph- | H- | 7-Br-CH₂-CONH- |
| 107 | n-Bu- | Et- | HO- | H- | p-n-C₁₀H₂₁--O-Ph- | H- | 7-NH₂- |
| 108 | Et- | n-Bu- | HO- | H- | Ph- | H- | 7-C₅H₁₁CONH- |
| 109 | Et- | n-Bu- | HO- | H- | p-n-C₁₀H₂₁--O-Ph- | H- | 7-NH₂- |
| 110 | Et- | n-Bu- | HO- | H- | Ph- | H- | 7-CH₃CONH- |
| 111 | n-Bu- | Et- | HO- | H- | p-HO-Ph- | H- | 7-NH₂- |
| 113 | Et- | n-Bu- | HO- | H- | p-HO-Ph- | H- | 7-NH₂- |
| 114 | Et- | n-Bu- | HO- | H- | p-CH₃O-Ph- | H- | 7-NH₂- |
| 115 | n-Bu- | Et- | HO- | H- | p-CH₃O-Ph- | H- | 7-NH-CBZ |
| 116 | Et- | n-Bu- | HO- | H- | p-CH₃O-Ph- | H- | 7-NH-CBZ |
| 117 | n-Bu- | Et- | HO- | H- | Ph- | H- | 7-NH-CBZ |
| 118 | Et- | n-Bu- | HO- | H- | Ph- | H- | 7-NH-CBZ |
| 119 | Et- | n-Bu- | HO- | H- | Ph- | H- | 7-NHCO₂-t-Bu |
| 120 | n-Bu- | Et- | HO- | H- | Ph- | H- | 7-NHCO₂-t-Bu |
| 121 | Et- | n-Bu- | HO- | H- | Ph- | H- | 7-NH₂- |
| 122 | n-Bu- | Et- | HO- | H- | Ph- | H- | 7-NH₂- |
| 123 | Et- | n-Bu- | HO- | H- | Ph- | H- | 7-n-C₆H₁₃-NH- |
| 124 | n-Bu- | Et- | HO- | H- | Ph- | H- | 7-n-C₆H₁₃-NH- |
| 125 | Et- | n-Bu- | HO- | H- | Ph- | H- | I⁻, 8-(CH₃)₃N⁺(CH₂CH₂O)₃- |
| 126 | n-Bu- | Et- | HO- | H- | p-F-Ph- | H- | 7-NH-CBZ |
| 127 | n-Bu- | Et- | HO- | H- | p-F-Ph- | H- | 7-NH₂- |
| 128 | Et- | n-Bu- | HO- | H- | p-F-Ph- | H- | 7-NH-CBZ |
| 129 | Et- | n-Bu- | HO- | H- | p-F-Ph- | H- | 7-NH₂- |
| 130 | Et- | n-Bu- | HO- | H- | Ph- | H- | I⁻, 8-(CH₃)₃N⁺ C₆H₁₂O- |
| 132 | Et- | n-Bu- | HO- | H- | Ph- | H- | 8-phthalimidyl-C₆H₁₂O- |
| 133 | Et- | n-Bu- | HO- | H- | Ph- | H- | 8-n-C₁₀H₂₁- |
| 134 | Et- | n-Bu- | HO- | H- | Ph- | H- | 8- I-(C₂H₄O)₃- |
| 136 | Et- | n-Bu- | HO- | H- | Ph- | H- | 8- HO- |
| 138 | n-Bu- | Et- | HO- | H- | Ph- | H- | 8- CH₃CO₂- |
| 142 | Et- | n-Bu- | H- | HO- | H- | m-CH₃O-Ph- | 7-CH₃S- |
| 143 | Et- | n-Bu- | HO- | H- | m-CH₃O-Ph- | H- | 7-CH₃S- |
| 144 | Et- | n-Bu- | HO- | H- | p-F-Ph- | H- | 7-(N)-azetidine |
| 262 | Et- | n-Bu- | HO- | H- | m-CH₃O-Ph- | H- | 7-CH₃O- |
| 263 | Et- | n-Bu- | H- | HO- | H- | m-CH₃O-Ph- | 7-CH₃O- |
| 264 | Et- | n-Bu- | HO- | H- | m-CF₃-Ph- | H- | 7-CH₃O- |
| 265 | Et- | n-Bu- | H- | HO- | H- | m-CF₃-Ph- | 7-CH₃O- |
| 266 | Et- | n-Bu- | HO- | H- | m-HO-Ph- | H- | 7-HO- |
| 267 | Et- | n-Bu- | HO- | H- | m-HO-Ph- | H- | 7-CH₃O- |

TABLE 3-continued

Specific Compounds (#102–111, 113–130, 132–134, 136, 138, 142–144, 262–296)

| Cp# | R¹ | R² | R³ | R⁴ | R⁵ | R⁶ | (Rˣ)q |
|---|---|---|---|---|---|---|---|
| 268 | Et- | n-Bu- | HO- | H- | p-F-Ph- | H- | 7-CH₃O- |
| 269 | Et- | n-Bu- | H- | HO- | H- | p-F-Ph- | 7-CH₃O- |
| 270 | Et- | n-Bu- | HO- | H- | p-F-Ph- | H- | 7-HO- |
| 271 | Et- | n-Bu- | HO- | H- | m-CH₃O-Ph- | H- | 7-Br- |
| 272 | Et- | n-Bu- | H- | HO- | H- | m-CH₃O-Ph- | 7-Br- |
| 273 | Et- | n-Bu- | H- | HO- | H- | p-F-Ph- | 7-F- |
| 274 | Et- | n-Bu- | HO- | H- | p-F-Ph- | H- | 7-F- |
| 275 | Et- | n-Bu- | H- | HO- | H- | m-CH₃O-Ph- | 7-F- |
| 276 | Et- | n-Bu- | HO- | H- | m-CH₃O-Ph- | H- | 7-F- |
| 277 | Et- | n-Bu- | HO- | H- | m-F-Ph- | H- | 7-CH₃O- |
| 278 | Et- | n-Bu- | H- | HO- | H- | o-F-Ph- | 7-CH₃O- |
| 279 | Et- | n-Bu- | H- | HO- | H- | m-F-Ph- | 7-CH₃O- |
| 280 | Et- | n-Bu- | HO- | H- | o-F-Ph- | H- | 7-CH₃O- |
| 281 | Et- | n-Bu- | HO- | H- | p-F-Ph- | H- | 7-CH₃S- |
| 282 | Et- | n-Bu- | HO- | H- | p-F-Ph- | H- | 7-CH₃- |
| 283 | Et- | n-Bu- | H- | HO- | H- | p-F-Ph- | 7-CH₃- |
| 284 | Et- | n-Bu- | HO- | H- | p-F-Ph- | H- | 7-(N)-morpholine |
| 285 | Et- | n-Bu- | HO- | H- | p-F-Ph- | H- | 7-(N)-pyrrolidine |
| 286 | Et- | Et- | HO- | H- | Ph- | H- | 7-NH-CBZ- |
| 287 | Et- | Et- | HO- | H- | Ph- | H- | 7-NH₂- |
| 288 | CH₃- | CH₃- | HO- | H- | Ph- | H- | 7-NH₂- |
| 289 | n-C₃H₇- | n-C₃H₇- | HO- | H- | Ph- | H- | 7-NH₂- |
| 290 | n-Bu- | n-Bu- | HO- | H- | Ph- | H- | 7-NH₂- |
| 291 | n-Bu- | n-Bu- | HO- | H- | Ph- | H- | 7-NH-CBZ- |
| 292 | n-Bu- | n-Bu- | HO- | H- | p-F-Ph- | H- | 7-NH₂- |
| 293 | n-Bu- | n-Bu- | HO- | H- | Ph- | H- | 7-PhCH₂N- |
| 294 | n-Bu- | n-Bu- | HO- | H- | Ph- | H- | 7-(CH₃)₂N- |
| 295 | Et- | n-Bu- | HO- | H- | p-I-(C₂H₄O)₃-Ph- | H- | 7-NH₂- |
| 296 | Et- | n-Bu- | HO- | H- | I⁻, p-(CH₃)₃N⁺(C₂H₄O)₃-Ph- | H- | 7-NH₂- |

TABLE 3A

Bridged Benzothiepines (#101, 112, 131, 135, 137, 139–141)

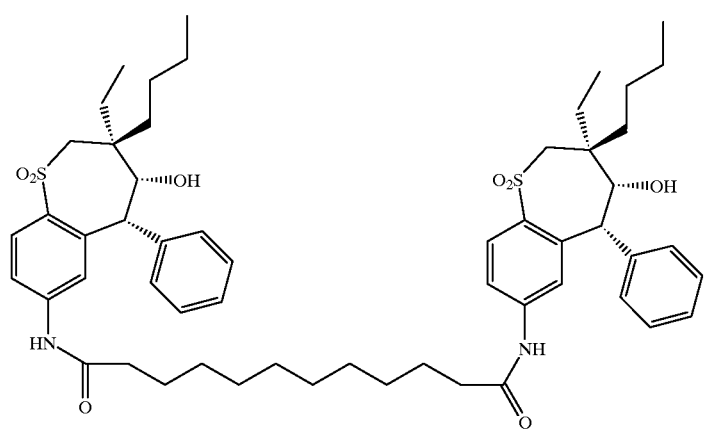

TABLE 3A-continued
Bridged Benzothiepines (#101, 112, 131, 135, 137, 139–141)
CPD # 101 (Example 59)
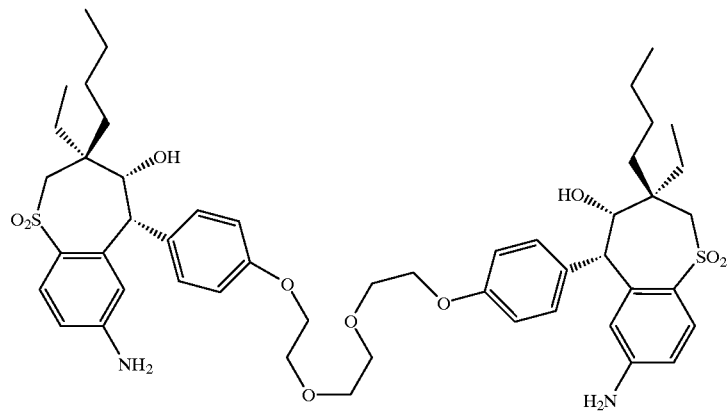
CPD #112 (Example 53)
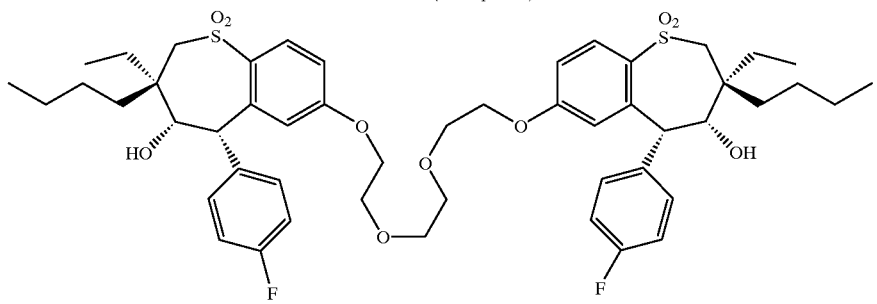
CPD #131 (Example 56)
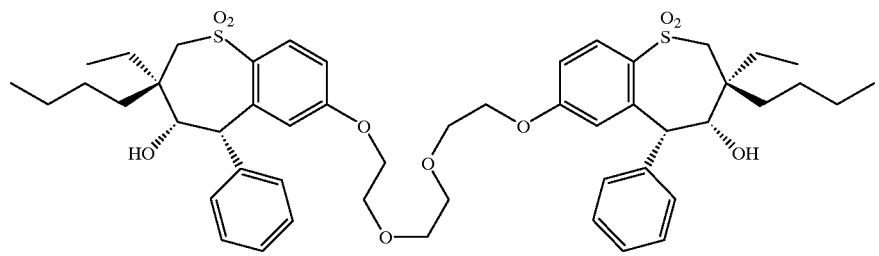
CPD #135 (Example 55)
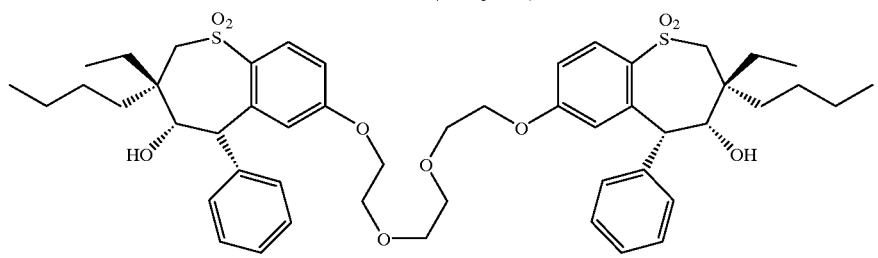
CPD #137 (Example 57)
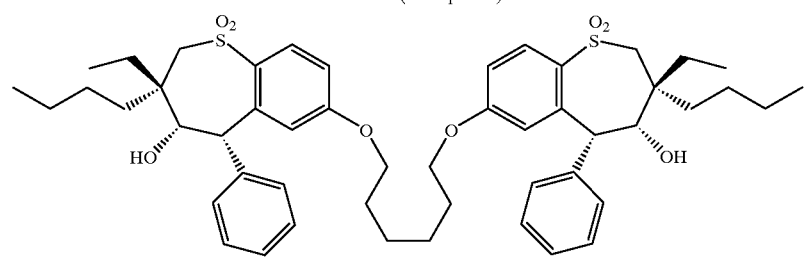
CPD #139 (Example 58)

TABLE 3A-continued

Bridged Benzothiepines (#101, 112, 131, 135, 137, 139–141)

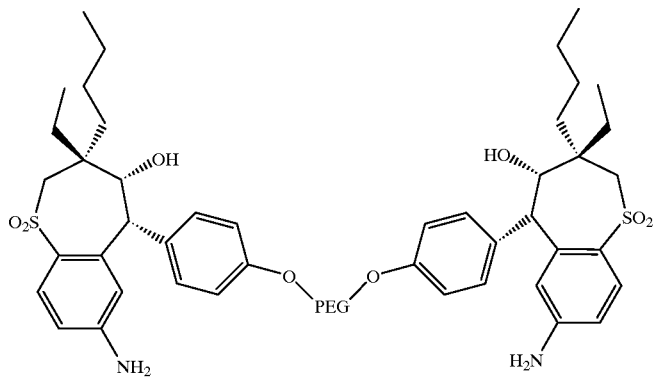

PEG = 3400 molecular weight polyethyleneglycol bridge
CPD #140 (Example 51)

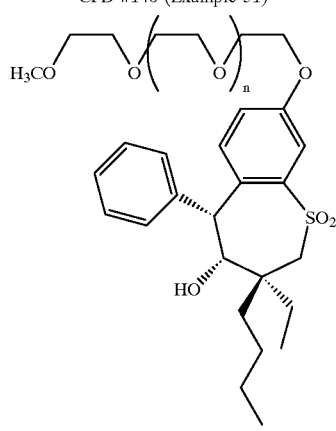

CPD #141 (Example 50)

EXAMPLES 104–231

Using in each instance a method generally described in those of Examples 1 to 72 appropriate to the substituents to be introduced, including where necessary other common synthesis expedients well known to the art, compounds are prepared having the structures set forth in Table 4. The starting materials illustrated in the reaction schemes shown above are varied in accordance with principles of organic synthesis well known to the art in order to introduce the indicated substituents in the 4- and 5-positions ($R^3$, $R^4$, $R^5$, $R^6$) and in the indicated position on the benzo ring ($R^x$).

TABLE 4

Alternative compounds #1 (#302–312, 314–430)

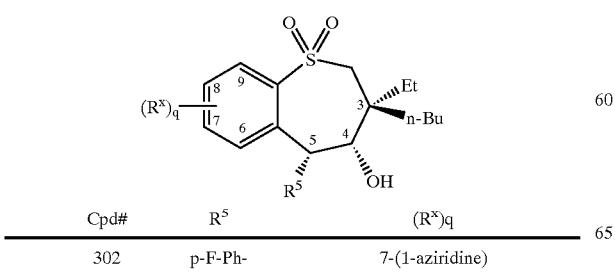

| Cpd# | $R^5$ | $(R^x)_q$ |
|---|---|---|
| 302 | p-F-Ph- | 7-(1-aziridine) |
| 303 | p-F-Ph- | 7-EtS- |
| 304 | p-F-Ph- | 7-CH$_3$S(O)- |
| 305 | p-F-Ph- | 7-CH$_3$S(O)$_2$- |
| 306 | p-F-Ph- | 7-PhS- |
| 307 | p-F-Ph- | 7-CH$_3$S- 9-CH$_3$S- |
| 308 | p-F-Ph- | 7-CH$_3$O- 9-CH$_3$O- |
| 309 | p-F-Ph- | 7-Et- |
| 310 | p-F-Ph | 7-iPr- |
| 311 | p-F-Ph- | 7-t-Bu- |
| 312 | p-F-Ph- | 7-(1-pyrazole)- |
| 314 | m-CH$_3$O-Ph | 7-(1-azetidine) |
| 315 | m-CH$_3$O-Ph- | 7-(1-aziridine) |
| 316 | m-CH$_3$O-Ph- | 7-EtS- |
| 317 | m-CH$_3$O-Ph- | 7-CH$_3$S(O)- |

TABLE 4-continued

Alternative compounds #1 (#302–312, 314–430)

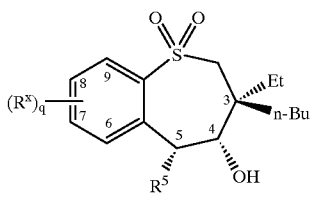 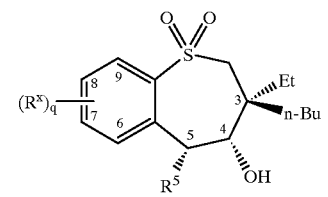

| Cpd# | R[5] | (R[x])q | | Cpd# | R[5] | (R[x])q |
|---|---|---|---|---|---|---|
| 318 | m-CH$_3$O-Ph- | 7-CH$_3$S(O)$_2$- | | 358 | m-CH$_3$O-Ph- | 7-PhS- |
| 319 | m-CH$_3$O-Ph- | 7-PhS- | | | | 9-CH$_3$- |
| 320 | m-CH$_3$O-Ph | 7-CH$_3$S- | | 359 | m-CH$_3$O-Ph- | 7-CH$_3$S- |
| | | 9-CH$_3$S- | | | | 9-CH$_3$- |
| 321 | m-CH$_3$O-Ph | 7-CH$_3$O- | | 360 | m-CH$_3$O-Ph- | 7-CH$_3$O- |
| | | 9-CH$_3$O- | | | | 9-CH$_3$- |
| 322 | m-CH$_3$O-Ph | 7-Et- | | 361 | m-CH$_3$O-Ph- | 7-CH$_3$- |
| 323 | m-CH$_3$O-Ph | 7-iPr- | | | | 9-CH$_3$- |
| 324 | m-CH$_3$O-Ph | 7-t-Bu- | | 362 | m-CH$_3$O-Ph- | 7-CH$_3$O- |
| 325 | p-F-Ph- | 6-CH$_3$O- | | | | 9-CH$_3$O- |
| | | 7-CH$_3$O- | | 363 | thien-2-yl | 7-(1-aziridine) |
| | | 8-CH$_3$O- | | 364 | thien-2-yl | 7-EtS- |
| 326 | p-F-Ph- | 7-(1-azetidine) | | 365 | thien-2-yl | 7-CH$_3$S(O)- |
| | | 9-CH$_3$- | | 366 | thien-2-yl | 7-CH$_3$S(O)$_2$- |
| 327 | p-F-Ph- | 7-EtS- | | 367 | thien-2-yl | 7-PhS- |
| | | 9-CH$_3$- | | 368 | thien-2-yl | 7-CH$_3$S- |
| 328 | p-F-Ph- | 7-CH$_3$S(O)- | | | | 9-CH$_3$S- |
| | | 9-CH$_3$- | | 369 | thien-2-yl | 7-CH$_3$O- |
| 329 | p-F-Ph- | 7-CH$_3$S(O)$_2$- | | | | 9-CH$_3$O- |
| | | 9-CH$_3$- | | 370 | thien-2-yl | 7-Et- |
| 330 | p-F-Ph- | 7-PhS- | | 371 | thien-2-yl | 7-iPr- |
| | | 9-CH$_3$- | | 372 | thien-2-yl | 7-t-Bu- |
| 331 | p-F-Ph- | 7-CH$_3$S- | | 373 | thien-2-yl | 7-(1-pyrrole)- |
| | | 9-CH$_3$- | | 374 | thien-2-yl | 7-CH$_3$O- |
| 332 | p-F-Ph- | 7-CH$_3$O- | | 375 | thien-2-yl | 7-CH$_3$S- |
| | | 9-CH$_3$- | | 376 | thien-2-yl | 7-(1-azetidine) |
| 333 | p-F-Ph- | 7-CH$_3$- | | 377 | thien-2-yl | 7-Me- |
| | | 9-CH$_3$- | | 378 | 5-Cl-thien-2-yl | 7-(1-azetidine) |
| 334 | p-F-Ph- | 7-CH$_3$O- | | 379 | 5-Cl-thien-2-yl | 7-(1-aziridine) |
| | | 9-CH$_3$O- | | 380 | 5-Cl-thien-2-yl | 7-EtS- |
| 335 | p-F-Ph- | 7-(1-pyrrole) | | 381 | 5-Cl-thien-2-yl | 7-CH$_3$S(O)- |
| 336 | p-F-Ph- | 7-(N)N'-methylpiperazine | | 382 | 5-Cl-thien-2-yl | 7-CH$_3$S(O)$_2$- |
| 337 | p-F-Ph- | Ph- | | 383 | 5-Cl-thien-2-yl | 7-PhS- |
| 338 | p-F-Ph- | 7-CH$_3$C(=CH$_2$)- | | 384 | 5-Cl-thien-2-yl | 7-CH$_3$S- |
| 339 | p-F-Ph- | 7-cyclopropyl | | | | 9-CH$_3$S- |
| 340 | p-F-Ph- | 7-(CH$_3$)$_2$NHN- | | 385 | 5-Cl-thien-2-yl | 7-CH$_3$O- |
| 341 | p-F-Ph- | 7-(N)-azetidine | | | | 9-CH$_3$O- |
| | | 9-CH$_3$S- | | 386 | 5-Cl-thien-2-yl | 7-Et- |
| 342 | p-F-Ph- | 7-(N-pyrrolidine) | | 387 | 5-Cl-thien-2-yl | 7-iPr- |
| | | 9-CH$_3$S- | | 388 | 5-Cl-thien-2-yl | 7-t-Bu- |
| 343 | p-F-Ph- | 7-(CH$_3$)$_2$N- | | 389 | 5-Cl-thien-2-yl | 7-CH$_3$O- |
| | | 9-CH$_3$S- | | 390 | 5-Cl-thien-2-yl | 7-CH$_3$S- |
| 344 | m-CH$_3$O-Ph- | 7-(1-pyrazole) | | 391 | 5-Cl-thien-2-yl | 7-Me |
| 345 | m-CH$_3$O-Ph- | 7-(N)N'-methylpiperazine | | 392 | thien-2-yl | 7-(1-azetidine) |
| 346 | m-CH$_3$O-Ph- | Ph- | | | | 9-CH$_3$- |
| 347 | m-CH$_3$O-Ph- | 7-CH$_3$C(=CH$_2$)- | | 393 | thien-2-yl | 7-EtS- |
| 348 | m-CH$_3$O-Ph- | 7-cyclopropyl | | | | 9-CH$_3$- |
| 349 | m-CH$_3$O-Ph- | 7-(CH$_3$)$_2$NHN- | | 394 | thien-2-yl | 7-CH$_3$S(O)- |
| 350 | m-CH$_3$O-Ph- | 7-(N)-azetidine | | | | 9-CH$_3$- |
| | | 9-CH$_3$S- | | 395 | thien-2-yl | 7-CH$_3$S(O)$_2$- |
| 351 | m-CH$_3$O-Ph- | 7-(N-pyrrolidine) | | | | 9-CH$_3$- |
| | | 9-CH$_3$S- | | 396 | thien-2-yl | 7-PhS- |
| 352 | m-CH$_3$O-Ph- | 7-(CH$_3$)$_2$N- | | | | 9-CH$_3$- |
| | | 9-CH$_3$S- | | 397 | thien-2-yl | 7-CH$_3$S- |
| 353 | m-CH$_3$O-Ph- | 6-CH$_3$O- | | | | 9-CH$_3$- |
| | | 7-CH$_3$O- | | 398 | thien-2-yl | 7-CH$_3$O- |
| | | 8-CH$_3$O- | | | | 9-CH$_3$- |
| 354 | m-CH$_3$O-Ph- | 7-(1-azetidine) | | 399 | thien-2-yl | 7-CH$_3$- |
| | | 9-CH$_3$- | | | | 9-CH$_3$- |
| 355 | m-CH$_3$O-Ph- | 7-EtS- | | 400 | thien-2-yl | 7-CH$_3$O- |
| | | 9-CH$_3$- | | | | 9-CH$_3$O- |
| 356 | m-CH$_3$O-Ph- | 7-CH$_3$S(O)- | | 401 | thien-2-yl | 7-(1-pyrazrole) |
| | | 9-CH$_3$- | | 402 | thien-2-yl | 7-(N)N'-methylpiperazine |
| 357 | m-CH$_3$O-Ph- | 7-CH$_3$S(O)$_2$- | | 403 | thien-2-yl | Ph- |
| | | 9-CH$_3$- | | 404 | thien-2-yl | 7-CH$_3$C(=CH$_2$)- |

TABLE 4-continued

Alternative compounds #1 (#302–312, 314–430)

| Cpd# | R⁵ | (Rˣ)q |
|---|---|---|
| 405 | thien-2-yl | 7-cyclpropyl |
| 406 | thien-2-yl | 7-(CH₃)₂NHN- |
| 407 | thien-2-yl | 7-(N)-azetidine 9-CH₃S- |
| 408 | thien-2-yl | 7-(N-pyrrolidine) 9-CH₃S- |
| 409 | thien-2-yl | 7-(CH₃)₂N- 9-CH₃S- |
| 411 | 5-Cl-thien-2-yl | 7-(1-pyrazrole) |
| 412 | 5-Cl-thien-2-yl | 7-(N)N'-methylpiperazine |
| 413 | 5-Cl-thien-2-yl | Ph- |
| 414 | 5-Cl-thien-2-yl | 7-CH₃C(=CH₂)- |
| 415 | 5-Cl-thien-2-yl | 7-cyclopropyl |
| 416 | 5-Cl-thien-2-yl | 7-(CH₃)₂NHN- |
| 417 | 5-Cl-thien-2-yl | 7-(N)-azetidine 9-CH₃S- |
| 418 | 5-Cl-thien-2-yl | 7-(N-pyrrolidine) 9-CH₃S- |
| 419 | 5-Cl-thien-2-yl | 7-(CH₃)₂N- 9-CH₃S- |
| 420 | 5-Cl-thien-2-yl | 7-(1-azetidine) 9-CH₃- |
| 421 | 5-Cl-thien-2-yl | 7-EtS- 9-CH₃- |
| 422 | 5-Cl-thien-2-yl | 7-CH₃S(O)- 9-CH₃- |
| 423 | 5-Cl-thien-2-yl | 7-CH₃S(O)₂- 9-CH₃- |
| 424 | 5-Cl-thien-2-yl | 7-PhS- 9-CH₃- |
| 425 | 5-Cl-thien-2-yl | 7-CH₃S- 9-CH₃- |
| 426 | 5-Cl-thien-2-yl | 7-CH₃O- 9-CH₃- |
| 427 | 5-Cl-thien-2-yl | 7-CH₃- 9-CH₃- |
| 428 | 5-Cl-thien-2-yl | 7-CH₃O- 9-CH₃O- |
| 429 | thien-2-yl | 6-CH₃O- 7-CH₃O- 8-CH₃O- |
| 430 | 5-Cl-thien-2-yl | 6-CH₃O- 7-CH₃O- 8-CH₃O- |

EXAMPLES 232–1394

Using in each instance a method generally described in those of Examples 1 to 72 appropriate to the substituents to be introduced, including where necessary other common synthesis expedients well known to the art, compounds are prepared having the structures set forth in Table 1. The starting materials illustrated in the reaction schemes shown above are varied in accordance with principles of organic synthesis well known to the art in order to introduce the indicated substituents in the 4- and 5-positions (R³, R⁴, R⁵, R⁶) and in the indicated position on the benzo ring (Rˣ).

EXAMPLE 1395

Dibutyl 4-fluorobenzene dialdehyde

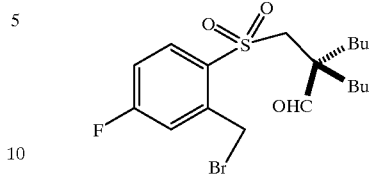

Step 1: Preparation of dibutyl 4-fluoro benzene dialdehyde

To a stirred solution of 17.5 g (123 mmol) of 2,5-difluorobenzaldehyde (Aldrich) in 615 mL of DMSO at ambient temperature was added 6.2 g (135 mmol) of lithium sulfide (Aldrich). The dark red solution was stirred at 75 C for 1.5 hours, or until the starting material was completely consumed, and then 34 g (135 mmol) of dibutyl mesylate aldehyde was added at about 50 C. The reaction mixture was stirred at 75 C for three hours or until the reaction was completed. The cooled solution was poured into water and extracted with ethyl acetate. The combined extracts were washed with water several times, dried (MgSO₄) and concentrated in vacuo. Silica gel chromatographic purification of the crude product gave 23.6 g (59%) of fluorobenzene dialdehyde as a yellow oil: ¹H NMR (CDCl₃) d 0.87 (t, J=7.05 Hz, 6H), 1.0–1.4 (m, 8H), 1.5–1.78 (m, 4H), 3.09 (s, 2H), 7.2–7.35 (m, 1H), 7.5–7.6 (m, 2H), 9.43 (s, 1H), 10.50 (d, J=2.62 Hz, 1H).

Step 2: Preparation of dibutyl 4-fluorobenzyl alcohol

To a solution of 22.6 g (69.8 mmol) of the dialdehyde obtained from Step 1 in 650 mL of THF at −60 C was added 69.8 mL (69.8 mmol) of DIBAL (1M in THF) via a syringe. The reaction mixture was stirred at −40 C for 20 hours. To the cooled solution at −40 C was added sufficient amount of ethyl acetae to quench the excess of DIBAL, followed by 3 N HCl. The mixture was extracted with ethyl acetate, washed with water, dried (MgSO₄), and concentrated in vacuo. Silica gel chromatographic purification of the crude product gave 13.5 g (58%) of recovered starting material, and 8.1 g (36%) of the desired fluorobenzyl alcohol as a colorless oil: ¹H NMR (CDCl₃) d 0.88 (t, J=7.05 Hz, 6H), 1.0–1.4 (m, 8H), 1.5–1.72 (m, 4H), 1.94 (br s, 1H), 3.03 (s, 2H), 4.79 (s, 2H), 6.96 (dt, J=8.46, 3.02 Hz, 1H), 7.20 (dd, J=9.47, 2.82 Hz, 1H), 7.42 (dd, J=8.67, 5.64, 1H), 9.40 (s, 1H).

Step 3: Preparation of dibutyl 4-fluorobenzyl bromide

To a solution of 8.1 g (25 mmol) of benzyl alcohol obtained from Step 2 in 100 mL of DMF at −40 C was added 47 g (50 mmol) of bromotriphenyphosphonium bromide (Aldrich). The resulting solution was stirred cold for 30 min, then was allowed to warm to 0 C. To the mixture was added 10% solution of sodium sulfite and ethyl acetate. The extract was washed a few times with water, dried (MgSO4), and concentrated in vacuo. The mixture was stirred in small amount of ethyl acetate/hexane mixture (1:4 ratio) and filtered through a pad of silica gel, eluting with same solvent mixture. The combined filtrate was concentrated in vacuo to give 9.5 g (98%) of the desired product as a colorless oil: ¹H NMR (CDCl₃) d 0.88 (t, J=7.05 Hz, 6H), 1.0–1.4 (m, 8H), 1.55–1.78 (m, 4H), 3.11 (s, 2H), 4.67 (s, 2H), 7.02 (dt, J=8.46, 3.02 Hz, 1H), 7.15 (dd, J=9.47, 2.82 Hz, 1H), 7.46 (dd, J=8.67, 5.64, 1H), 9.45 (s, 1H).

Step 4: Preparation of sulfonyl 4-fluorobenzyl bromide

To a solution of 8.5 g (25 mmol) of sulfide obtained from Step 3 in 200 mL of CH₂Cl₂ at 0° C. was added 15.9 g (60 mmol) of mCPBA (64% peracid). The resulting solution was stirred cold for 10 min, then was allowed to stirred ambient temperature for 5 hours. To the mixture was added 10% solution of sodium sulfite and ethyl acetate. The extract was washed several times with saturated $Na_2CO_3$, dried ($MgSO_4$), and concentrated in vacuo to give 10.2 g (98%) of the desired product as a colorless oil: $^1H$ NMR ($CDCl_3$) d 0.91 (t, J=7.05 Hz, 6H), 1.03–1.4 (m, 8H), 1.65–1.82 (m, 2H), 1.90–2.05 (m, 2H), 3.54 (s, 2H), 5.01 (s, 2H), 7.04–7.23 (m, 1H), 7.30 (dd, J=8.87, 2.42 Hz, 1H), 8.03 (dd, J 8.86, 5.64, 1H), 9.49 (s, 1H).

EXAMPLE 1396

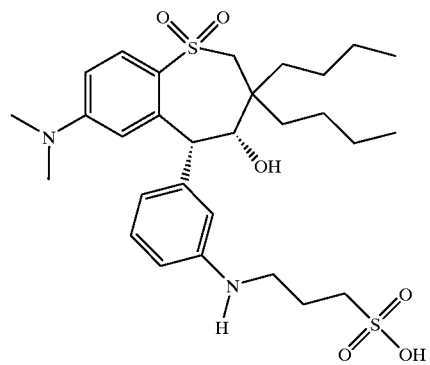

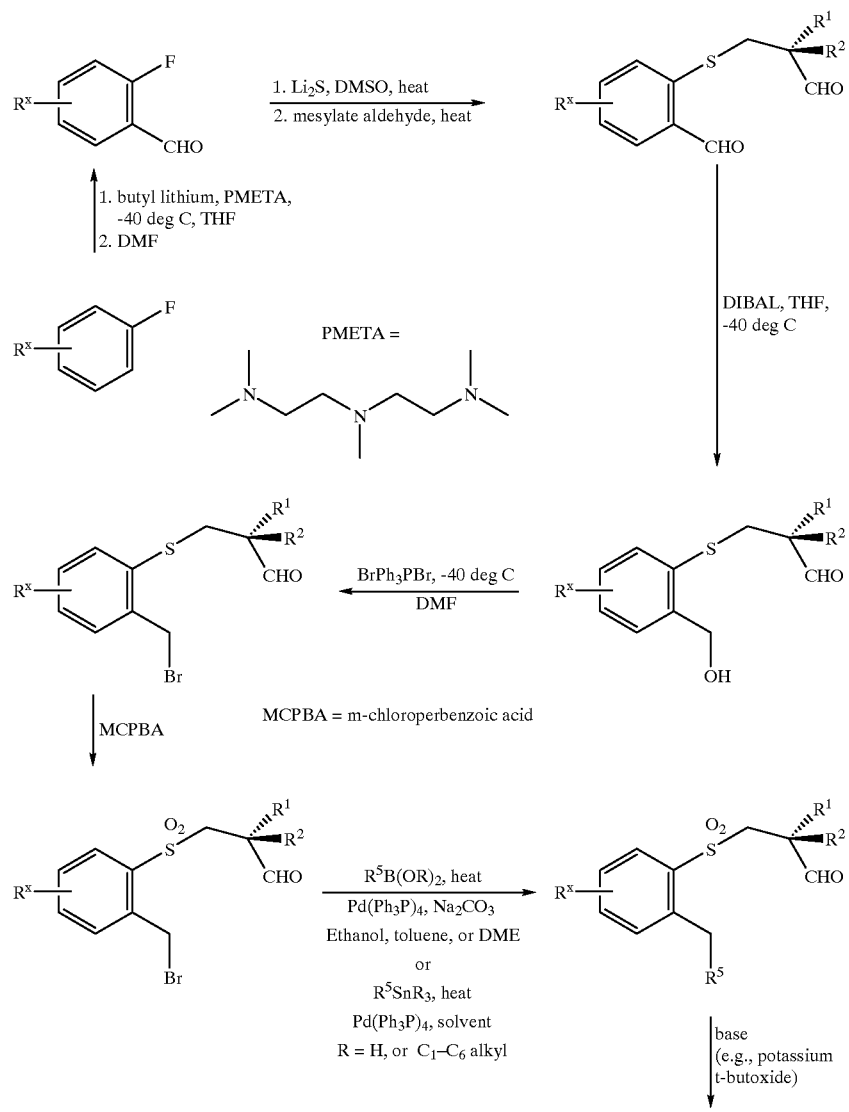

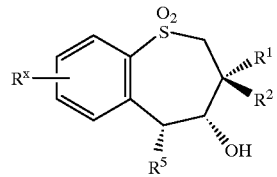

Generic Scheme X: The nucleophilic substitution of an appropriately substituted 2-fluorobenzaldehyde with lithium sulfide or other nucleophilic sulfide anion in polar solvent (such as DMF, DMA, DMSO . . . etc), followed by the addition of dialkyl mesylate aldehyde (X), provided a dialkyl benzene dialdehyde Y. DIBAL reduction of the dialdehyde at low temperature yielded benzyl alcohol monoaldehyde Z. Conversion of benzyl alcohol to benzyl bromide, followed by oxidation of sulfide to sulfone yielded the key intermediate W.

Preparation of N-propylsulfonic acid

To a solution of 51 mg (111 μm) Compound X in ethanol (400 μl) was added 1,3 propane sultone (19.5 μl, 222 μm). The reaction was stirred in a sealed vial at 55° C. for 25 hr. Sample was concentrated under a nitrogen stream and purified by reversed phase chromatography using acetonitrile/water as eluent (30–45%) and afforded the desired material as an off-white solid (28.4 mg, 44%): $^1$H NMR (CDCL$_3$) d 0.82–0.96 (m, 6H), 1.11–1.52 (m of m, 10H), 1.58–1.72 (m, 1H), 2.08–2.21 (m, 1H), 2.36–2.50 (m, 2H), 2.93 (s, 6H), 3.02–3.22 (m of m, 5H), 3.58–3.76 (m, 2H), 4.15 (s, 1H), 5.51 (s, 1H), 6.45–6.58 (m, 1H), 6.92–7.02 (m, 1H), 7.35–7.41 (m, 1H), 7.41–7.51 (m, 2H), 8.08 (d, J=8.1 Hz, 1H), 8.12–8.25 (m, 1H); MS ES- M-H m/z 579.

EXAMPLE 1397

The 7-fluoro, 9-fluoro and 7,9-difluoro analogs of benzothiepine compounds of this invention can be reacted with sulfur and nitrogen nucleophiles to give the corresponding sulfur and nitrogen substituted analogs. The following example demonstrates the synthesis of these analogs.

3,3-Dibutyl-5a-(4'-fluorophenyl)-4a-hydroxy-7-methylthio-2,3,4,5-tetrahydrobenzothiepine-1,1-dioxide.

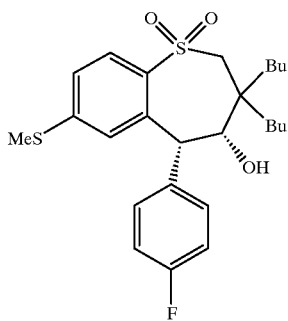

A mixture of 0.4 g of 3,3-dibutyl-7-fluoro-5a-(4'-fluorophenyl)-4a-hydroxy-2,3,4,5-tetrahydrobenzothiepine-1,1-dioxide, prepared by previously described method, 0.12 g of sodium methanethiolate and 20 ml of DMF was stirred at 50 C for 3 days. An additional 0.1 g of sodium methanethiolate was added to the reaction mixture and the mixture was stirred for additional 20 h at 50 C then was concentrated in vacuo. The residue was triturated with water and extracte wiith ether. The ether extract was dried over MgSO$_4$ and concentrated in vacuo to 0.44 g of an oil. Purification by HPLC (10% EtOAc in hexane) gave 0.26 g of needles, mp 164–165.5% C.

3,3-Dibutyl-9-dimethylamino-7-fluoro-5a-(4'-fluorophenyl)-4a-hydroxy-2,3,4,5-tetrahydrobenzothiepine-1,1-dioxide and 7,9-Bis(dimethylamino)- 3,3-dibutyl-5a-(4'-fluorophenyl)-4a-hydroxy-2,3,4,5-tetrahydrobenzothiepine-1,1-dioxide.

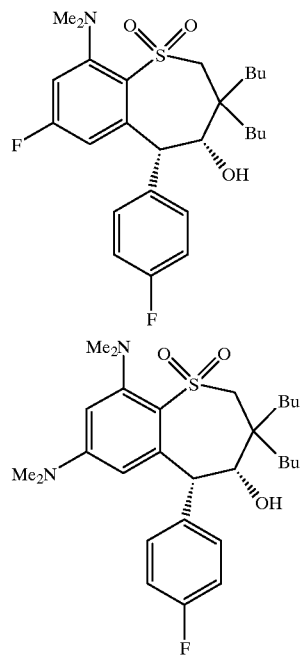

A solution of 0.105 g of 3,3-dibutyl-7,9-difluoro-5a-(4'-fluorophenyl)-4a-hydroxy-2,3,4,5-tetrahydrobenzothiepine-1,1-dioxide, prepared by the method described previously, in 20 ml of 2 N dimethylamine in THF was heated at 160 C in a sealed Parr reactor overnight. The reaction mixture was cooled and concentrated in vacuo. The residue was triturated with 25 ml of water and extracted with ether. The ether extract was dried over MgSO$_4$ and concentrated in vacuo. The resdue was purified by HPLC (10% EtOAc in hexane) to give 35 mg of an earlier fraction which was identified as 3,3-dibutyl-9-dimethylamino-7-fluoro-5a-(4'-fluorophenyl)-4a-hydroxy-2,3,4,5-tetrahydrobenzothiepine-1,1-dioxide, MS (CI) m/e 480 (M$^+$+1), and 29 mg of a later fraction which was identified as 7,9-bis(dimethylamino)-3,3-dibutyl-5a-(4'-fluorophenyl)-4a-hydroxy-2,3,4,5-tetrahydrobenzothiepine-1,1-dioxide, MS (CI) m/e 505 (M$^+$+1).

The compounds of this invention can also be synthesized using cyclic sulfate (XL, below) as the reagent as shown in the following schemes XI and XII.

The following examples describe a procedure for using the cyclic sulfate as the reagent.

SCHEME XI.

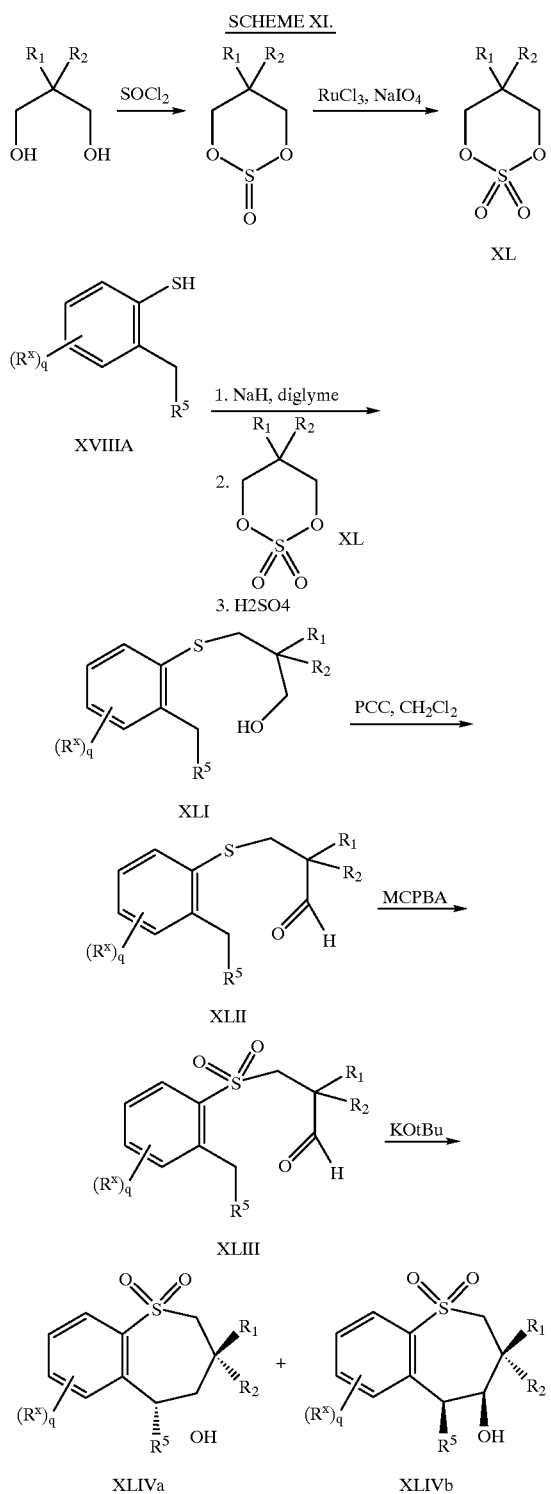

Scheme XI illustrates yet another route to benzothiepine-1,1-dioxides, particularly 3,3-dialkyl analogs, starting from the thiophenol XVIIIA. Thiophenol XVIIIA can be reacted with cyclic sulfate XL to give the alcohol XLI which can be oxidized to yield the aldehyde XLII. Aldehyde XLII itself can be further oxidized to give the sulfone XLIII which can be cyclized to give a stereoisomeric mixture of benzothiepine XLIVa and XLIVb.

Thiophenol XVIIIA can be prepared according to Scheme 3 as previously discussed and has the following formula:

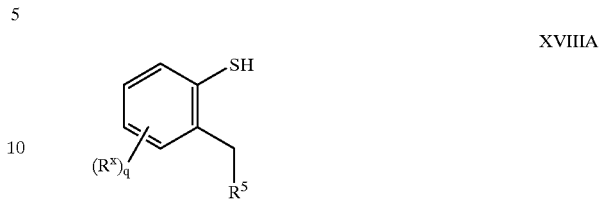

wherein $R^5$, $R^x$ and q are as previously defined for the compounds of formula I. Cyclic sulfate XL can be prepared according to synthetic procedures known in the art and has the following formula:

wherein $R^1$ and $R^2$ are as previously defined for the compounds of formula I. Preferably, $R^1$ and $R^2$ are alkyl; more preferably, they are selected from the group consisting of methyl, ethyl, propyl, isopropyl, n-butyl, iso-butyl, sec-butyl, tert-butyl, and pentyl; and still more preferably, $R^1$ and $R^2$ are n-butyl.

In the process of Scheme XI, thiophenol XVIIIA is initially reacted with cyclic sulfate XL. This reaction preferably is conducted in an aprotic solvent such as methoxy-ethyl ether. While the reaction conditions such as temperature and time are not narrowly critical, the reaction preferably is allowed to proceed at about room temperature for about two hours. The reaction preferably employs an approximately stoichiometric ratio of the starting materials, with a slight excess of cyclic sulfate XL being preferred. Reaction time and yield can be improved by using about 1.01 to 1.3 equivalents of cyclic sulfate XL for each equivalent of thiophenol XVIIIA present. More preferably, this ratio is about 1.1 equivalents of cyclic sulfate XL for each equivalent of thiophenol XVIIIA present.

In the process of the invention, thiophenol XVIIIA also is treated with an abstracting agent. The abstracting agent can be added to the solvent containing thiophenol XVIIIA prior to, concurrently with, or after the addition of cyclic sulfate XL. Without being held to a particular theory, it is believed the abstracting agent removes the hydrogen atom from the mercaptan group attached to the benzene ring of thiophenol XVIIIA. The resulting sulfur anion of the thiophenol then reacts with cyclic sulfate XL to open the sulfate ring. The sulfur anion of the thiophenol then bonds with a terminal carbon atom of the open ring sulfate. The terminal group at the unbonded end of the open ring sulfate is the sulfate group.

The abstracting agent generally is a base having a pH greater than about 10. Preferably, the base is an alkali metal hydride such as sodium hydride, lithium hydride or potassium hydride; more preferably, the base is sodium hydride. A slight excess of abstracting agent is preferred relative to thiophenol XVIIIA. Reaction time and yield is improved by using about 1.0 to about 1.1 equivalents of abstracting agent for each equivalent of thiophenol XVIIIA present. More preferably, this ratio is about 1.1 equivalents of abstracting agent for each equivalent of thiophenol XVIIIA present.

The sulfate group of the intermediate product of the reaction of thiophenol XVIIIA with cyclic sulfate XL is then removed, preferably by hydrolysis, to yield alcohol XLI. Suitable hydrolyzing agents include mineral acids, particularly hydrochloric acid and sulfuric acid.

The several reactions involving thiophenol XVIIIA, cyclic sulfate XL, the abstracting agent and the hydrolyzing agent can take place in situ without the need for isolation of any of the intermediates produced.

Alcohol XLI is then isolated by conventional methods (for example, extraction with aqueous methyl salicylate) and oxidized using standard oxidizing agents to aldehyde XLII. Preferably, the oxidizing agent is sulfur trioxide or pyridinium chlorochromate, and more preferably, it is pyridinium chlorochromate. The reaction is conducted in a suitable organic solvent such as methylene chloride or chloroform.

Aldehyde XLII is then isolated by conventional methods and further oxidized using standard oxidizing agents to sulfone-aldehyde XLIII. Preferably, the oxidizing agent is metachloroperbenzoic acid.

Sulfone-aldehyde XLIII likewise is isolated by conventional methods and then cyclized to form the stereoisomeric benzothiepines XLIVa and XLIVb. The cyclizing agent preferably is a base having a pH between about 8 and about 9. More preferably, the base is an alkoxide base, and still more preferably, the base is potassium tert-butoxide.

The two oxidation steps of Scheme XI can be reversed without adversely affecting the overall reaction. Alcohol XLI can be oxidized first to yield a sulfone-alcohol which is then oxidized to yield a sulfone-aldehyde.

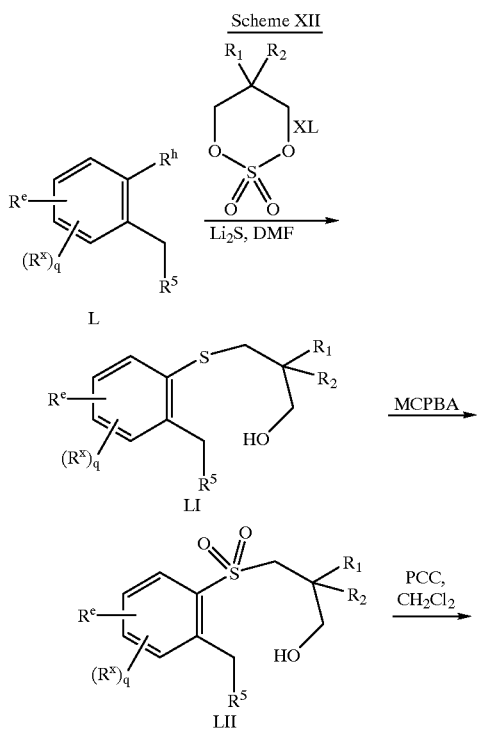

Scheme XII

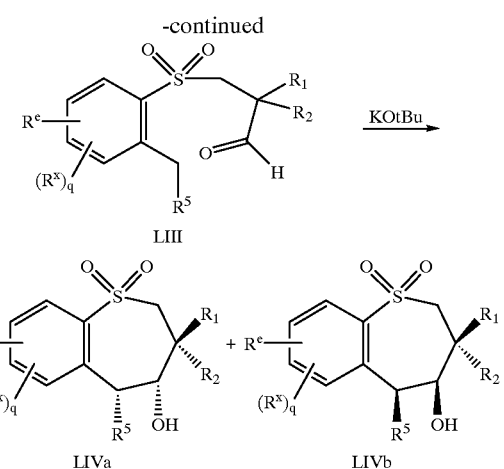

Scheme XII illustrates still another route to benzothiepine-1,1-dioxides, particularly 3,3-dialkyl analogs, starting from the halobenzene L. Halobenzene L can be reacted with cyclic sulfate XL disclosed above to give the alcohol LI which can be oxidized to yield the sulfone-alcohol LII. Sulfone-alcohol LII itself can be further oxidized to give the sulfone-aldehyde LIII which can be cyclized to give a stereoisomeric mixture of benzothiepine LIVa and LIVb.

Halobenzene L (which is commercially available or can be synthesized from commercially available halobenzenes by one skilled in the art) has the following formula:

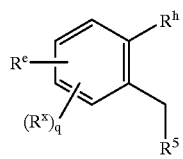

L wherein $R^5$, $R^x$, and q are as previously defined for the compounds of formula I; $R^h$ is a halogen such as chloro, bromo, fluoro or iodo; and $R^e$ is an electron withdrawing group at the ortho or para position of the halobenzene, and is preferably a p-nitro or o-nitro group. Cyclic sulfate XL can be prepared as set forth in Scheme XI and can have the following formula:

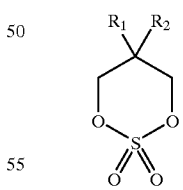

XL wherein $R^1$ and $R^2$ are as previously defined for the compounds of formula I. Preferably, $R^1$ and $R^2$ are alkyl; more preferably, they are selected from the group consisting of methyl, ethyl, propyl, isopropyl, n-butyl, iso-butyl, sec-butyl, tert-butyl, and pentyl; and still more preferably, $R^1$ and $R^2$ are n-butyl.

In the process of Scheme XII, halobenzene L is initially reacted with cyclic sulfate XL. This reaction preferably is conducted in an aprotic solvent such as dimethyl formamide or N:N-dimethylacetamide, and more preferably, in dimethyl formamide. Although the reaction conditions such as temperature and time are not narrowly critical, the reaction preferably is allowed to proceed at between about 70° C. and about 90° C. for about 8 to 12 hours. More preferably, the reaction temperature is maintained at about 80° C. The reaction preferably employs an approximately stoichiometric ratio of the starting materials, with a slight excess of cyclic sulfate XL being preferred. Reaction time and yield is improved by using about 1.1 to 1.3 equivalents of cyclic sulfate XL for each equivalent of halobenzene L present. More preferably, this ratio is about 1.1 equivalents of cyclic sulfate XL for each equivalent of halobenzene L present.

In the process of the invention, halobenzene L also is treated with an abstracting agent. The abstracting agent can be added to the solvent containing halobenzene L prior to, concurrently with, or after the addition of cyclic sulfate XL. Without being held to a particular theory, it is believed the abstracting agent removes the halogen atom attached to the benzene ring of halobenzene L and replaces that atom with a divalent sulfur atom. The resulting sulfur anion reacts with cyclic sulfate XL to open the sulfate ring. The sulfur anion of the halobenzene then bonds with a terminal carbon atom of the open ring sulfate. The terminal group at the unbonded end of the open ring sulfate is the sulfate group. The abstracting agent generally is a dialkali metal sulfide, and preferably it is dilithium sulfide. A slight excess of the abstracting agent is preferred relative to halobenzene L. Reaction time and yield is improved by using about 1.01 to 1.3 equivalents of abstracting agent for each equivalent of halobenzene L present. More preferably, this ratio is about 1.05 equivalents of abstracting agent for each equivalent of halobenzene L present.

The sulfate group of the product of the reaction of thiophenol XVIIIA with cyclic sulfate XL is then removed, preferably by hydrolysis, to yield a mixture of an ester and alcohol LI. Suitable hydrolyzing agents include mineral acids, particularly hydrochloric acid and sulfuric acid. The ester is then converted to alcohol LI by treatment with an alkali metal hydroxide, preferably sodium hydroxide.

The several reactions involving halobenzene L, cyclic sulfate XL, the abstracting agent and the hydrolyzing agent can take place in situ without the need to isolate any of the intermediates produced.

Alcohol LI is then isolated by conventional methods (for example, extraction with aqueous methyl salicylate) and oxidized using standard oxidizing agents to sulfone-alcohol LII. Preferably, the oxidizing agent is metachloroperbenzoic acid. The reaction is conducted in a suitable organic solvent such as methylene chloride or chloroform.

Sulfone-alcohol LII is then isolated by conventional methods and further oxidized using standard oxidizing agents to sulfone-aldehyde LIII. Preferably, the oxidizing agent is sulfur trioxide or pyridinium chlorochromate, and more preferably, it is pyridinium chlorochromate. The reaction is conducted in a suitable organic solvent such as methylene chloride or chloroform.

Sulfone-aldehyde XLIII is then converted to the desired benzothiepine-1,1-dioxides according to the procedure previously set forth in Scheme XI.

The two oxidation steps can be reversed without adversely affecting the overall reaction. Alcohol XLI can be oxidized first to yield an aldehyde which is then oxidized to yield a sulfone-aldehyde.

Use of the cyclic sulfate reagent instead of a mesylate reagent in Schemes XI and XII improves the overall yield and avoids many of the purification difficulties encountered relative to those reaction schemes proceeding through a mesylate intermediate. Overall yields are significantly improved when a cyclic sulfate is used instead of a mesylate reagent. In addition, chromatographic separation of the intermediate product of the cyclic sulfate coupling step of the reaction is not necessary. For example, in Schemes XI and XII the intermediate is a water soluble alkali metal salt and the impurities can be removed by extraction with ether. The intermediate is then hydrolyzed to the desired alcohol.

Example Corresponding to Scheme XI

Step 1: Preparation of 2,2-dibutyl-1,3-propanediol:

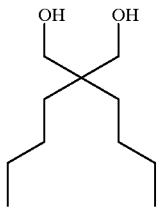

Lithium aluminum hydride (662 ml, 1.2 equivalents, 0.66 mol) in 662 mL of 1M THF was added dropwise to a stirred solution of dibutyl-diethylmalonate (150 g, 0.55 mol) (Aldrich) in dry THF (700 ml) while maintaining the temperature of the reaction mixture at between about −20° C. to about 0° C. using an acetone/dry ice bath. The reaction mixture was then stirred at room temperature overnight. The reaction was cooled to −20° C. and 40 ml of water, 80 ml of 10% NaOH and 80 ml of water were successively added dropwise. The resulting suspension was filtered. The filtrate was dried over sodium sulphate and concentrated under vacuum to give 98.4 g (yield 95%) of the diol as an oil. Proton NMR, carbon NMR and MS confirmed the product.

Step 2: Dibutyl-cyclic-sulfite:

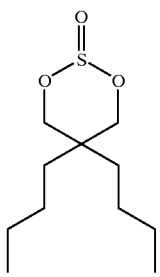

A solution of the dibutyl-diol of step 1 (103 g, 0.5478 mol) in anhydrous methylene chloride (500 ml) and triethylamine (221 g, 4 equivalents, 2.19 mol) was stirred at 0° C. under nitrogen. Thionyl chloride (97.78 g, 0.82 mol) was added dropwise to the mixture. Within 5 minutes the solution turned to yellow and then to black when the addition was completed within about half an hour. The reaction was completed within 3 hours (gas chromatography confirmed no starting material was left). The mixture was washed with ice water twice, and brine twice. The organic phase was dried over magnesium sulphate and concentrated under vacuum to give 128 g (yield 100%) of the dibutyl-cyclic-sulfite as a black oil. NMR and MS were consistent with the product.

Step 3: Dibutyl-cyclic sulfate:

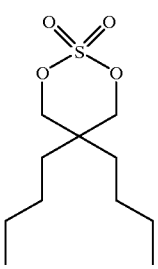

To a solution of the dibutyl-cyclic-sulfite of step 2 (127.5 g, 0.54 mol) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. Gas chromatography confirmed there was no starting material left. The mixture was extracted once with 300 ml of ether and three times with brine. The organic phase was dried over magnesium sulphate and passed through celite. The filtrate was concentrated under vacuum and gave 133 g (yield 97.8%) of the dibutyl-cyclic-sulfate as an oil. Proton NMR, carbon NMR and MS confirmed the product.

Step 4: 2-[(2-4'-fluorobenzyl-4-methylphenylthio) methyl]-2-butylhexanol:

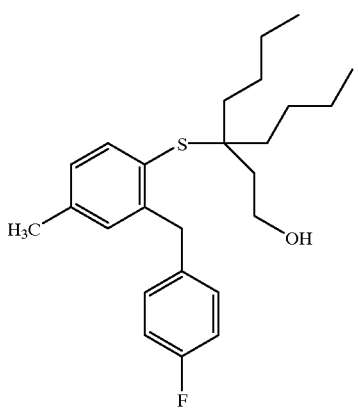

A 60% oil dispersion of sodium hydride (0.27 g, 6.68 mmole) was washed with hexane. The hexane was decanted and 20 ml of methoxyethyl ether was added to the washed sodium hydride and cooled in an ice bath. A mixture of diphenylmethane thiophenol (1.55 g, 6.68 mmole) in 10 ml of methoxyethyl ether was added dropwise over a period of 15 minutes. A mixture of the dibutyl-cyclic-sulfate of step 3 (2.17 g, 8.66 mmole) in 10 ml of methoxyethyl ether was then added. The resulting mixture was stirred for 30 minutes at 0° C. and 1 hour at room temperature under nitrogen. Gas chromatography confirmed there was no thiol left. The solvent was evaporated and washed with water and ether two times. The water layer was separated and 20 ml of 10% NaOH was added. This aqueous mixture was boiled for 30 minutes, cooled, acidified with 6N HCl, and boiled for 10 minutes. The mixture was cooled and extracted with ether. The organic layer was washed successively with water and brine, dried over magnesium sulphate, and concentrated under vacuum to give 2.47 g (yield 92.5%) of the hexanol as an oil. Proton NMR, C13-NMR and MS confirmed the product.

Step 5: 2-[(2-4'-Fluorobenzyl-4-methylphenylthio) methyl]-2-butylhexanal

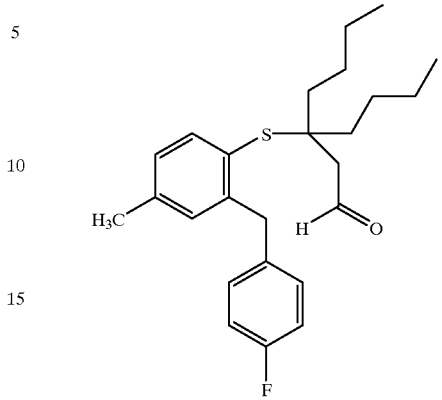

To a solution of the hexanol of step 4 (2 g, 4.9 mmole) in 40 ml of methylene chloride cooled in an ice bath under nitrogen was added pyridinium chlorochromate (2.18 g, 9.9 mmole). The reaction mixture was stirred for 3 hours and filtered through silica gel. The filtrate was concentrated under vacuum to give 1.39 g (yield 70%) of the hexanal as an oil. Proton NMR, carbon NMR and MS confirmed the product.

Step 6: 2-[(2-4'-Fluorobenzyl-4-methylphenylsulfonyl) methyl]-2-butylhexanal

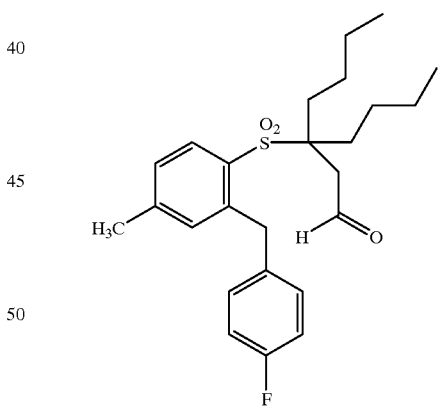

To a solution of the hexanal of step 5 (0.44 g, 1.1 mmole) in 20 ml of methylene chloride cooled by an ice bath under nitrogen was added 70% metachloroperbenzoic acid (0.54 g, 2.2 mmole). The reaction mixture was stirred for 18 hours and filtered. The filtrate was washed successively with 10% NaOH(3×), water, and brine, dried over magnesium sulphate, and concentrated under vacuum to give 0.42 g (yield 90%) of the hexanal as an oil. Proton NMR, carbon NMR and MS confirmed the product.

Step 7: Cis-3,3-dibutyl-7-methyl-5-(4'-fluorophenyl)-2,3,4,5-tetrahydrobenzothiepine-1,1-dioxide

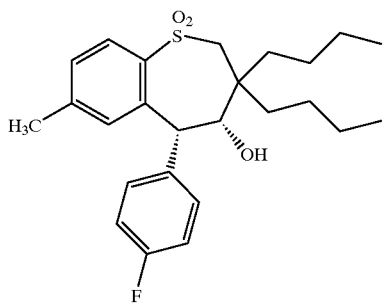

A mixture of the hexanal of step 6 (0.37 g, 0.85 mmole) in 30 ml of anhydrous THF was stirred in an ice bath at a temperature of about 0° C. Potassium-tert-butoxide (102 mg, 0.85 mmole) was then added. After 3 hours thin layer chromatography confirmed the presence of the product and a small amount of the starting material. The crude reaction mixture was acidified with 10% HCl, extracted with ether, washed successively with water and brine, dried with MgSO$_4$, and concentrated under vacuum. This concentrate was purified by HPLC (10% EtOAc-Hexane). The first fraction came as 0.1 g of the starting material in the form of an oil. The second fraction yielded 0.27 g (75% yield) of the desired benzothiepine as a white solid. Proton NMR, carbon NMR and MS confirmed the product. (M+H=433).

EXAMPLE CORRESPONDING TO SCHEME XII

Step 1: 2-[(2-4'-Methoxybenzyl-4-nitrophenylthio)-methyl]-2-butylhexanol

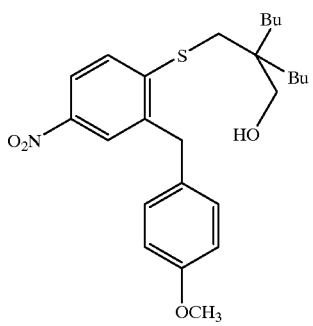

Chlorodiphenylmethane (10 g) was dissolved in 25 ml of DMF and lithium sulfide [1.75 g, 1.05 equivalents] was added. The solution color changed to red. The reaction mixture was heated at 80° C. overnight. The solution was cooled to 0° C. and dibutyl-cyclic-sulfate (9.9 g; prepared as set forth in Step 3 of the Scheme XI examples) in 10 ml of DMF was added and stirred at room temperature overnight. The solvent was evaporated and washed successively with water and ether (three times). The water layer was separated and 40 ml of concentrated sulfuric acid was added and the reaction mixture boiled overnight. The mixture was cooled and extracted with ethyl acetate. The organic layer was washed successively with water and brine, dried over magnesium sulphate, and concentrated under vacuum. The product was boiled with 3M of NaOH for 1 hour. The mixture was cooled and extracted with ethyl acetate. The organic layer was washed successively with water and brine, dried over magnesium sulphate, and concentrated under vacuum. The concentrate was dissolved in methylene chloride, filtered through silica gel, eluted with 20% ethyl acetate and hexane, and concentrated under vacuum to give 11.9 g (yield 74%) of the hexanol as an oil. Proton NMR, C13-NMR and MS confirmed the product.

Step 2: 2-[2-4'-Methoxybenzyl-4-nitrophenylthio)-methyl]-2-butylhexanal

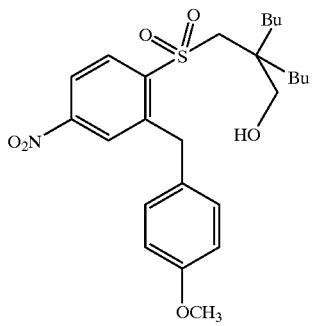

To a solution of the hexanol of step 1 (6 g, 13 mmole) in 50 ml methylene chloride cooled in ice bath under nitrogen was added 70% MCPBA (8.261 g, 33 mmole). The reaction was stirred for 18 hours at room temperature and filtered. The filtrate was washed successively with 10% NaOH (3×), water and brine, dried over magnesium sulphate, and concentrated under vacuum. The concentrate was dissolved in methylene chloride, filtered through silica gel, eluted with 20% ethyl acetate and hexane, and concentrated under vacuum to give 5 g (yield 77.7%) of the hexanal as a white solid, MP 58–60° C. Proton NMR, C13-NMR and MS confirmed the product.

EXAMPLE 1398

Step 1. Preparation of 2

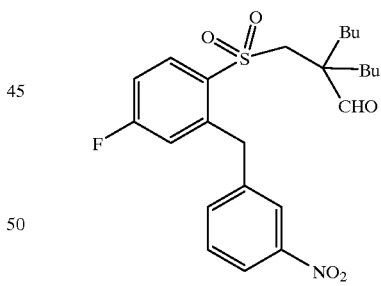

To a solution of 6.0 g of dibutyl 4-fluorobenzene dialdehyde of Example 1395 (14.3 mmol) in 72 mL of toluene and 54 mL of ethanol was added 4.7 g 3-nitrobenzeneboronic acid (28.6 mmol), 0.8 g of tetrakis (triphenylphosphine) palladium(0) (0.7 mmol) and 45 mL of a 2 M solution of sodium carbonate in water. This heterogeneous mixture was refluxed for three hours, then cooled to ambient temperature and partitioned between ethyl acetate and water. The organic layer was dried over MgSO$_4$ and concentrated in vacuo. Purification by silica gel chromatography (Waters Prep-2000) using ethyl acetate/hexanes (25/75) gave 4.8 g (73%) of the title compound as a yellow solid. $^1$H NMR (CDCl$_3$) d 0.88 (t, J=7.45 Hz, 6H), 0.99–1.38 (m, 8H), 1.62–1.75 (m, 2H), 1.85–2.00 (m, 2H), 3.20 (s, 2H), 4.59 (s, 2H), 6.93 (dd, J=10.5 and 2.4 Hz, 1H), 7.15 (dt, J=8.4 and 2.85 Hz, 1H), 7.46–7.59 (m, 2H), 8.05–8.16 (m, 3H), 9.40 (s, 1H).

Step 3. Preparation of 3

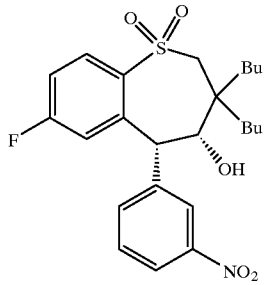

A solution of 4.8 g (10.4 mmol) of 2 in 500 mL THF was cooled to 0° C. in an ice bath. 20 mL of a 1 M solution of potassium t-butoxide was added slowly, maintaining the temperature at <5° C. Stirring was continued for 30 minutes, then the reaction was quenched with 100 mL of saturated ammonium chloride. The mixture was partitioned between ethyl acetate and water; the organic layer was washed with brine, then dried (MgSO$_4$) and concentrated in vacuo. Purification by silica gel chromatography through a 100 ml plug using CH$_2$Cl$_2$ as eluent yielded 4.3 g (90%) of 3 as a pale yellow foam. $^1$H NMR (CDCl$_3$) d 0.93 (t, J=7.25 Hz, 6H), 1.00–1.55 (m, 8H), 1.59–1.74 (m, 3H), 2.15–2.95 (m, 1H), 3.16 (q$_{AB}$, J$_{AB}$=15.0 Hz, ΔV=33.2 Hz, 2H), 4.17 (d, J=6.0 Hz, 1H), 5.67 (s, 1H), 6.34 (dd, J=9.6 and 3.0 Hz, 1H), 7.08 (dt, J=8.5 and 2.9 Hz, 1H), 7.64 (t, J=8.1 Hz, 1H), 7.81 (d, J=8.7 Hz, 1H), 8.13 (dd, J=9.9 and 3.6 Hz, 1H), 8.23–8.30 (m, 1H), 8.44 (s, 1H) MS(FABH$^+$) m/e (relative intensity) 464.5 (100), 446.6 (65). HRMS calculated for M+H 464.1907. Found 464.1905.

Step 4. Preparation of 4

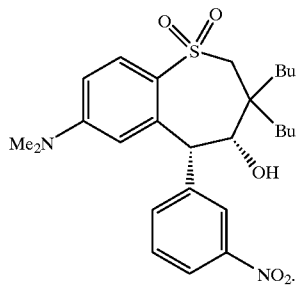

To a cooled (0° C.) solution of 4.3 g (9.3 mmol) of 3 in 30 ml THF contained in a stainless steel reaction vessel was added 8.2 g dimethyl amine (182 mmol). The vessel was sealed and heated to 110° C. for 16 hours. The reaction vessel was cooled to ambient temperature and the contents concentrated in vacuo. Purification by silica gel chromatography (Waters Prep-2000) using an ethyl acetate/hexanes gradient (10–40% ethyl acetate) gave 4.0 g (88%) of 4 as a yellow solid. $^1$H NMR (CDCl$_3$) d 0.80–0.95 (m, 6H), 0.96–1.53 (m, 8H), 1.60–1.69 (m, 3H), 2.11–2.28 (m, 1H), 2.79 (s, 6H), 3.09 (q$_{AB}$, J$_{AB}$=15.0 Hz, DV=45.6 Hz, 2H), 4.90 (d, J=9.0 Hz, 1H), 5.65 (s, 1H), 5.75 (d, J=2.1 Hz, 1H), 6.52 (dd, J=9.6 and 2.7 Hz, 1H), 7.59 (t, J=8.4 Hz, 1H), 7.85 (d, J=7.80 Hz, 1H), 7.89 (d, J=9.0 Hz, 1H), 8.20 (dd, J=8.4 and 1.2 Hz, 1H), 8.43 (s, 1H). MS(FABH$^+$) m/e (relative intensity) 489.6 (100), 471.5 (25). HRMS calculated for M+H 489.2423. Found 489.2456.

Step 5. Preparation of 5

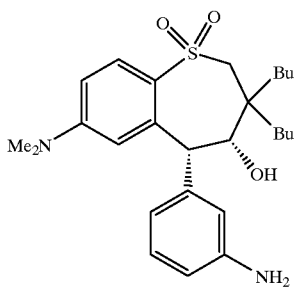

To a suspension of 1.0 g (2.1 mmol) of 4 in 100 ml ethanol in a stainless steel Parr reactor was added 1 g 10% palladium on carbon. The reaction vessel was sealed, purged twice with H$_2$, then charged with H$_2$ (100 psi) and heated to 45° C. for six hours. The reaction vessel was cooled to ambient temperature and the contents filtered to remove the catalyst. The filtrate was concentrated in vacuo to give 0.9 g (96%) of 5. $^1$H NMR (CDCl$_3$) d 0.80–0.98 (m, 6H), 1.00–1.52 (m, 1OH), 1.52–1.69 (m, 1H), 2.15–2.29 (m, 1H), 2.83 (s, 6H), 3.07 (q$_{AB}$, J$_{AB}$=15.1 Hz, DV=44.2 Hz, 2H), 3.70 (s, 2H), 4.14 (s, 1H), 5.43 (s, 1H), 6.09 (d, J=2.4 Hz, 1H), 6.52 (dd, J=12.2 and 2.6 Hz, 1H), 6.65 (dd, J=7.8 and 1.8 Hz, 1H), 6.83 (s, 1H), 6.93 (d, J=7.50 Hz, 1H), 7.19 (t, J=7.6 Hz, 1H), 7.89 (d, J=8.9 Hz, 1H). MS(FABH$^+$) m/e (relative intensity) 459.7 (100). HRMS calculated for M+H 459.2681. Found 459.2670.

Step 6. Preparation of 6

To a solution of 914 mg (2.0 mmol) of 5 in 50 ml THF was added 800 mg (4.0 mmol) 5-bromovaleroyl chloride. Next was added 4 g (39.6 mmol) TEA. The reaction was stirred 10 minutes, then partitioned between ethyl acetate and brine. The organic layer was dried (MgSO$_4$) and concentrated in vacuo. Purification by silica gel chromatography through a 70 ml MPLC column using a gradient of ethyl acetate (20–50%) in hexane as eluent yielded 0.9 g (73%) of 6 as a pale yellow oil. $^1$H NMR (CDCl$_3$) d 0.84–0.95 (m, 6H), 1.02–1.53 (m, 10H), 1.53–1.68 (m, 1H), 1.80–2.00 (m, 4H), 2.12–2.26 (m, 4H), 2.38 (t, J=6.9 Hz, 2H), 2.80 (s, 6H), 3.07 (q$_{AB}$, J$_{AB}$=15.6 Hz, DV=40.4 Hz, 2H), 3.43 (t, J=6.9 Hz, 2H), 4.10 (s, 1H), 5.51 (s, 1H), 5.95 (d, J=2.4 Hz, 1H), 6.51 (dd, J=9.3 and 2.7 Hz, 1H), 7.28 (s, 1H), 7.32–7.41 (m, 2H), 7.78 (d, J=8.1 Hz, 1H), 7.90 (d, J=9.0 Hz, 1H).

Step 7. Preparation of 7

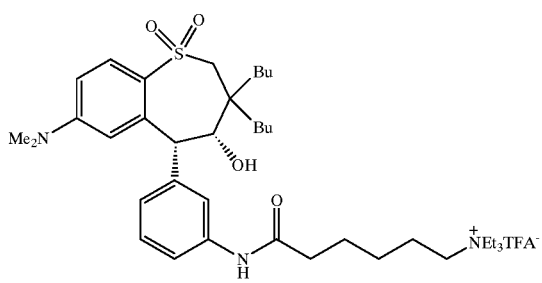

To a solution of 0.9 g (1.45 mmol) of 6 in 25 ml acetonitrile add 18 g (178 mmol) TEA. Heat at 55° C. for 16 hours. The reaction mixture was cooled to ambient temperature and concentrated in vacuo. Purification by reverse-phase silica gel chromatography (Waters Delta Prep 3000) using an acetonitrile/water gradient containing 0.05% TFA (20–65% acetonitrile) gave 0.8 g (73%) of 7 as a white foam. $^1$H NMR (CDCl$_3$) d 0.80–0.96 (m, 6H), 0.99–1.54 (m, 19H), 1.59–1.84 (m, 3H), 2.09–2.24 (m, 1H), 2.45–2.58 (m, 2H), 2.81 (s, 6H), 3.09 (q$_{AB}$, J$_{AB}$=15.6 Hz, DV=18.5 Hz, 2H), 3.13–3.31 (m, 8H), 4.16 (s, 1H), 5.44 (s, 1H), 6.08 (d, J=1.8 Hz, 1H), 6.57 (dd, J=9.3 and 2.7 Hz, 1H), 7.24 (t, J=7.5 Hz, 1H), 7.34 (t, J=8.4 Hz, 1H), 7.56 (d, J=8.4 Hz, 1H), 7.74 (s, 1H), 7.88 (d, J=9.0 Hz, 1H), 9.22 (s, 1H). HRMS calcd 642.4304; observed 642.4343.

EXAMPLE 1398a

Step 1

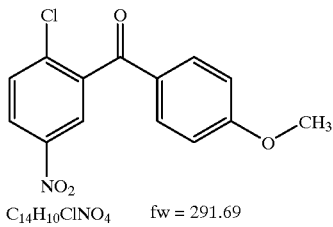

$C_{14}H_{10}ClNO_4$  fw = 291.69

In an inert atmosphere, weigh out 68.3 gms phosphorus pentachloride (0.328 mole Aldrich 15,777-5) into a 2-necked 500 ml round bottom flask. Fit flask with a N$_2$ inlet adapter and suba seal. Remove from inert atmosphere and begin N$_2$ purge. Add 50 mls anhydrous chlorobenzene (Aldrich 28,451-3) to the PCl$_5$ via syringe and begin stirring with magnetic stir bar.

Weigh out 60 gms 2-chloro-5-nitrobenzoic acid (0.298 mole Aldrich 12,511-3). Slowly add to the chlorobenzene solution while under N$_2$ purge. Stir at room temperature overnight. After stirring at room temperature for ~20hrs, place in oil bath and heat at 50 C. for 1 hr. Remove chlorobenzene by high vacuum. Wash residue with anhydrous hexane. Dry acid chloride wt=61.95 gms. Store in inert and dry atmosphere.

In inert atmosphere, dissolve acid chloride with 105 mls anhydrous anisole (0.97 mole Aldrich 29,629-5). Place solution in a 2-necked 500 ml round bottom flask.

Weigh out 45.1 gms aluminum chloride (0.34 moles Aldrich 29,471-3) and place in a solid addition funnel. Fit reaction flask with addition funnel and a N$_2$ inlet adapter. Remove from inert atmosphere. Chill reaction solution with ice bath and begin N$_2$ purge. Slowly add AlCl$_3$ to chilled solution. After addition is complete, allow to warm to room temperature. Stir overnight.

Quench reaction by pouring into a solution of 300 mls 1N HCl and ice. Stir 15 min. Extract twice with ether. Combine organic layers and extract twice with 2% NaOH, then twice with deionized H$_2$O. Dry with MgSO$_4$, filter and rotovap to dryness. Remove anisole by high vacuum. Crystalize product from 90% ethanol 10% ethyl acetate. Dry on vacuum line. Wt=35.2 gms. Yield 41%. Obtain NMR and mass spec (m/z=292).

Step 2

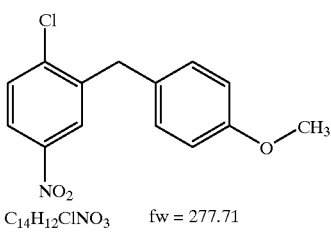

$C_{14}H_{12}ClNO_3$  fw = 277.71

Dissolve 38.10 gms (0.131 moles) of the benzophenone from step 1 in 250 mls anhydrous methylene chloride. Place in a 3 liter flask fitted with N$_2$ inlet, addition funnel and stopper. Stir with magnetic stir bar. Chill solution with ice bath.

Prepare a solution of 39.32 gms trifluoromethane sulfonic acid (0.262 mole Aldrich 15,853-4) and 170 mls anhydrous methylene chloride. Place in addition funnel and add dropwise to chilled solution under N$_2$. Stir 5 minutes after addition is complete.

Prepare a solution of 22.85 gms triethyl silane (0.197 mole Aldrich 23,019-7) and 170 mls anhydrous methylene chloride. Place in addition funnel and add dropwise to chilled solution under N$_2$. Stir 5 minutes after addition is complete.

Prepare a second solution of 39.32 gms trifluoromethane sulfonic acid and 170 mls anhydrous methylene chloride. Place in addition funnel and add dropwise to chilled solution under N$_2$. Stir 5 minutes after addition is complete.

Prepare a second solution of 22.85 gms triethyl silane and 170 mls anhydrous methylene chloride. Place in addition funnel and add dropwise to chilled solution under N$_2$. After all additions are made allow to slowly warm to room temperature overnight. Stir under N$_2$ overnight.

Prepare 1300 mls saturated NaHCO$_3$ in a 4 liter beaker. Chill with ice bath. While stirring vigorously, slowly add reaction mixture. Stir at chilled temperature for 30 min. Pour into a separatory funnel and allow separation. Remove organic layer and extract aqueous layer 2 times with methylene chloride. Dry organic layers with MgSO$_4$. Crystallize from ethanol. Dry on vacuum line. Dry wt=28.8 gms. Confirm by NMR and mass spec (m/z=278).

Step 3

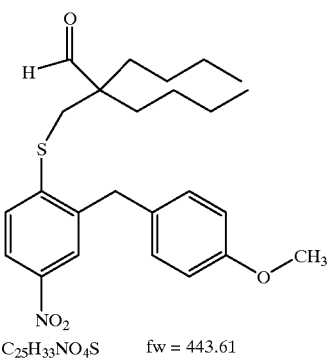

C₂₅H₃₃NO₄S    fw = 443.61

Dissolve 10.12 gms (0.036 moles) of product 2 with 200 mls anhydrous DMSO. Place in a 500 ml round bottom flask with magnetic stir bar. Fit flask with water condenser, $N_2$ inlet, and stopper. Add 1.84 gms $Li_2S$ (0.040 moles Aldrich 21,324-1). Place flask in oil bath and heat at 75° C. under $N_2$ overnight then cool to room temperature.

Weigh out 10.59 gms dibutyl mesylate (0.040 moles). Dissolve with anhydrous DMSO and add to reaction solution. Purge well with $N_2$, heat overnight at 80° C.

Cool to room temperature. Prepare 500 mls of 5% acetic acid in a 2 liter beaker. While stirring, slowly add reaction mixture. Stir 30 min. Extract with ether 3 times. Combine organic layers and extract with water and sat'd NaCl. Dry organic layer with $MgSO_4$, filter and rotovap to dryness. Dry oil on vacuum line. Obtain pure product by column chromatography using 95% hexane and 5% ethyl acetate as the mobile phase. Dry wt=7.8 gms. Obtain NMR and mass spec (m/z=444).

Step 4

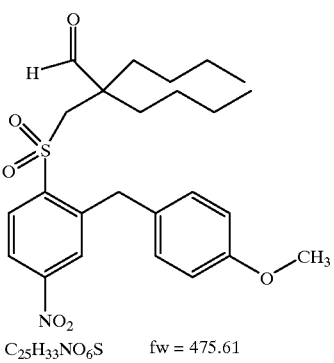

C₂₅H₃₃NO₆S    fw = 475.61

Dissolve 9.33 gms (0.021 moles) of product 3 with 120 mls anhydrous methylene chloride. Place in a 250 ml round bottom flask with magnetic stir bar. Fit flask with $N_2$ inlet and stopper. Chill solution with ice bath under $N_2$ purge. Slowly add 11.54 gms 3-chloroperbenzoic acid (0.0435 moles, Fluka 25800, ~65%). After addition is complete warm to room temperature and monitor reaction by TLC. Reaction goes quickly to the sulphoxide intermediate but takes 8 hrs to convert to the sulphone. Chill solution over night in freezer. Filter solid from reaction, extract filtrate with 10% $K_2CO_3$. Extract aqueous layer twice with methylene choride. Combine organic layers and dry with $MgSO_4$. Filter and rotovap to dryness. Obtain pure product by crystallizing from ethanol or isolating by column chromatography. Obtain NMR and mass spec (m/z=476).

Step 5

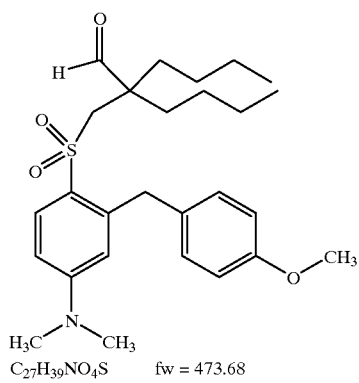

C₂₇H₃₉NO₄S    fw = 473.68

Reaction is done in a 300 ml stainless steel Parr stirred mini reactor. Place 9.68 gms (0.0204 moles) of product 4 in reactor base. Add 160 mls ethanol. For safety reasons next two compounds are added in a $N_2$ atmosphere glove bag. In glove bag, add 15.3 mls formaldehyde (0.204 moles, Aldrich 25,254-9, about 37 wt % in water) and 1.45 gms 10% Pd/Carbon (Aldrich 20,569-9). Seal reactor before removing from glove bag. Purge reactor three times with $H_2$. Heat to 55° C. under $H_2$. Run reaction at 200 psig $H_2$, 55° C., and a stir rate of 250 rpm. Run overnight under these conditions.

Cool reactor and vent $H_2$. Purge with $N_2$. Check progress of run by TLC. Reaction is a mixture of desired product and intermediate. Filter reaction mixture over a bed of celite washing well with ether. Rotovap and redissolve with ether. Extract with water. Dry organic layer with $MgSO_4$, filter and rotovap to dryness. Dry on vacuum line.

Charge reactor again with same amounts, seal reactor and run overnight under same conditions. After second run all of the material has been converted to the desired product. Cool and vent $H_2$ pressure. Purge with $N_2$. Filter over a bed of celite, washing well with ether. Rotovap to dryness. Dissolve with ether and extract with water. Dry organic layer with $MgSO_4$, filter and rotovap to dryness. Dry on vacuum line. Obtain NMR and mass spec (m/z=474).

Step 6

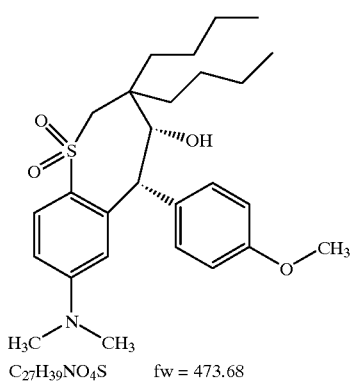

C₂₇H₃₉NO₄S    fw = 473.68

Dissolve 8.97 gms (0.0189 mole) of product 5 with 135 mls anhydrous THF. Place in a 250 ml round bottom flask with magnetic stir bar. Fit flask with $N_2$ inlet and stopper. Chill solution with ice/salt bath under $N_2$ purge. Slowly add 2.55 gms potassium t-butoxide (0.227 mole Aldrich 15,667-1). After addition is complete, continue to stir at −10° C. monitoring by TLC. Once reaction is complete, quench by adding 135 mls 10% HCl stirring 10 min. Extract three times with ether. Dry organic layer with $MgSO_4$, filter and rotovap to dryness. Crystallize from ether. Obtain NMR and mass spec (m/z=474).

Step 7

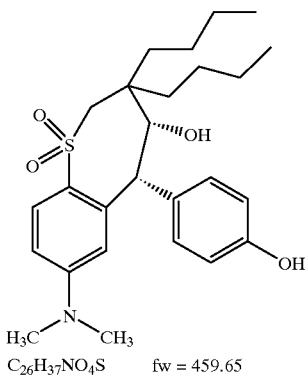

$C_{26}H_{37}NO_4S$     fw = 459.65

Dissolve 4.67 gms (0.01 moles) of product 6 with 100 mls anhydrous chloroform. Place in a 250 ml round bottom flask with magnetic stir bar. Fit flask with $N_2$ inlet adapter and suba seal. Chill solution with dry ice/acetone bath under a $N_2$ purge. Slowly add, via syringe, 2.84 mls boron tribromide (0.03 moles Aldrich 20,220-7). Stir at cold temperature for 15 min after addition then allow to warm to room temperature. Monitor reaction progress by TLC. Reaction is usually complete in 3 hrs.

Chill solution with ice bath. Quench with 100 mls 10% $K_2CO_3$ while stirring rapidly. Stir 10 min. then transfer to sep funnel and allow separation. Remove aqueous layer. Extract organic layer once with 10% HCl, once $H_2O$, and once with saturated NaCl solution. Dry organic layer with $MgSO_4$, filter and rotovap to dryness. Crystallize product from ether. Obtain NMR and mass spec (m/z=460).

Step 8

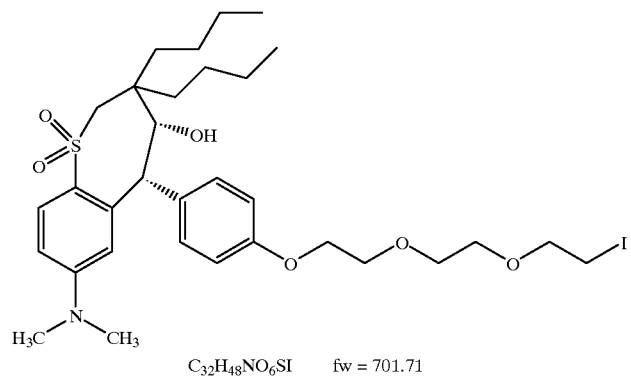

$C_{32}H_{48}NO_6SI$     fw = 701.71

Weigh 0.38 gms NaH (9.57 mmoles Aldrich 19,923-0 60% disp. in mineral oil) in a 250 ml round bottom flask with magnetic stir bar. Fit flask with $N_2$ inlet and stopper. Chill NaH with ice bath and begin $N_2$ purge.

Dissolve 4.0 gms (8.7 mmoles) of product 7 with 60 mls anhydrous DMF. Add to the cold NaH. Stir at cold temperature for 30 min. Add 1.33 gms $K_2CO_3$ (9.57 mmoles Fisher P-208).

Dissolve 16.1 gms 1,2-bis-(2-iodoethoxy)ethane (43.5 mmoles Aldrich 33,343-3) with 60 mls anhydrous DMF. Add to cold reaction mixture. Warm to room temperature then heat to 40° C. overnight under $N_2$.

Cleanup by diluting with ether and extracting sequentially with 5% NaOH, $H_2O$, and saturated NaCl. Dry organic layer with $MgSO_4$, filter and dry. Obtain pure product by column chromatography using 75% hexane 25% ethyl acetate as the mobile phase. Obtain NMR and mass spec (m/z=702).

Step 9

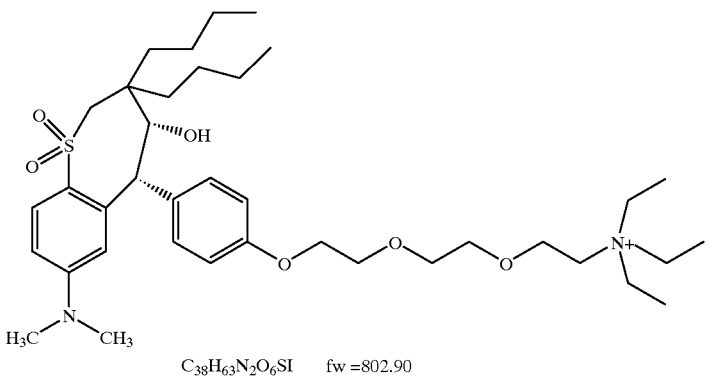

C₃₈H₆₃N₂O₆SI    fw =802.90

Dissolve 1.0 gms (1.43 mmoles) of product 8 with 10 mls anhydrous acetonitrile. Place in a 3 ounce Fischer-Porter pressure reaction vessel with magnetic stir bar. Add 2.9 gms triethyl amine (28.6 mmoles Aldrich 23,962-3) dissolved in 10 mls anhydrous acetonitrile. Purge well with $N_2$ then close system Heat at 45° C. Monitor reaction by TLC. Reaction is usually complete in 48 hrs.

Perform cleanup by removing acetonitrile under vacuum. Redissolve with anhydrous chloroform and precipitate quaternary ammonium salt with ether. Repeat several times. Dry to obtain crystalline product. Obtain NMR and mass spec (m/z=675).

EXAMPLE 1399

Step 1. Preparation of 1

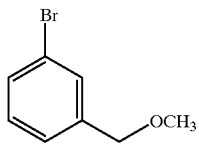

To a solution of 144 g of KOH (2560 mmol) in 1.1 L of DMSO was added 120 g of 2-bromobenzyl alcohol (641 mmol) slowly via addition funnel. Then was added 182 g of methyliodide (80 mL, 1282 mmol) via addition funnel. Stirred at ambient temperature for fifteen minutes. Poured reaction contents into 1.0 L of water and extracted three times with ethyl acetate. The organic layer was dried over $MgSO_4$ and concentrated in vacuo. Purified by silica-gel chromatography through a 200 mL plug using hexanes (100%) as elutant yielded 103.2 g (80%) of 1 as a clear colorless liquid. ¹H NMR (CDCl₃) d 3.39 (s, 3H), 4.42 (s, 2H), 7.18–7.27 (m, 2H), 7.12 (d, J=7.45, 1H), 7.50 (s, 1H).

Step 2. Preparation of 2

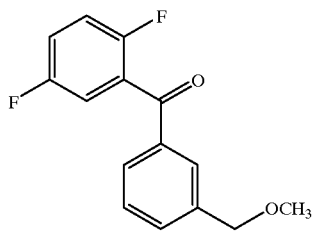

To a cooled (−78° C.) solution of 95 g (472 mmol) of 1 in 1.5 L THF was added 240 mL of 2.5 M n-butyl lithium (576 mmol). The mixture was stirred for one hour, and then to it was added 180 g of zinc iodide (566 mmol) dissolved in 500 ml THF. The mixture was stirred thirty minutes, allowed to warm to 5 C., cooled to −10° C. and to it was added 6 g of Pd(PPh₃)₄ (5.2 mmol) and 125 g 2,5-difluorobenzoyl chloride (708 mmol). The mixture was stirred at ambient temperature for 18 hoursand then cooled to 10° C., quenched with water, partitioned between ethyl acetate and water, and washed organic layer with 1N HCL and with 1N NaOH. The organic layer was dried over $MgSO_4$ and concentrated in vacuo. Purification by silica gel chromatography (Waters Prep-500) using 5% ethyl acetate/hexanes as elutant gave 53.6 g (43%) of 2 as an orange oil. ¹H NMR (CDCl₃) d 3.40 (s, 3H), 4.51 (s, 2H), 7.12–7.26 (m, 3H), 7.47 (t, J=7.50, 1H), 7.57 (d, J=7.45, 1H), 7.73 (d, J=7.45, 1H), 7.80 (s, 1H).

Step 3. Preparation of 3

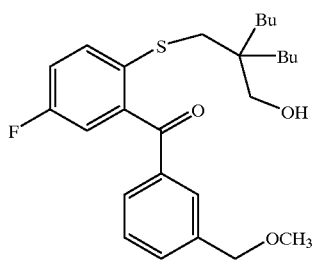

A solution of 53 g (202.3 mmol) of 2 and 11.2 g Li2S (242.8 mmol) in 250 mL DMF was heated to 100° C. for 18 hours. The reaction was cooled (0° C.) and 60.7 g of X' (the cyclic sulfate compound of example 1397) (242.8 mmol) in 50 mL DMF was added. Stirred at ambient temperature for 18 hours then condensed in vacuo. Added 1 L water to organic residue and extracted twice with diethyl ether. Aqueous layer acidified (pH 1) and refluxed 2 days. Cooled to ambient temperature and extracted with methylene chloride, dried organic layer over MgSO$_4$ and condensed in vacuo. Purification by silica gel chromatography (Waters Prep-500) using 10% ethyl acetate/hexanes as elutant gave 42.9 g (48%) of 3 as a yellow oil. $^1$H NMR (CDCl$_3$) d 0.86 (t, J=7.25 Hz, 6H), 1.10–1.26 (m, 12H), 2.83 (s, 2H), 3.32 (s, 2H), 3.40 (s, 3H), 4.48 (s, 3H), 7.02 (dd, J=8.26 Hz and 2.82 Hz, 1H), 7.16 (dt, J=8.19 Hz and 2.82 Hz, 1H), 7.45 (t, J=7.65 Hz, 1H), 7.56–7.61 (m, 2H), 7.69 (d, J=7.85 Hz, 1H), 7.74 (s, 1H).

Step 4. Preparation of 4

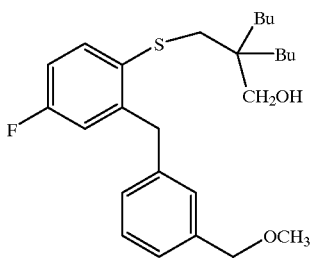

To a cooled (–40° C.) solution of 42.9 g (96.2 mmol) of 3 in 200 mL of methylene chloride was added 21.6 g trifluoromethane sulfonic acid (12.8 mL, 144 mmol) followed by the addition of 22.4 g triethyl silane (30.7 mL, 192.4 mmol). Stirred at –20° C. for two hours, quenched with water and warmed to ambient temperature. Partitioned between methylene chloride and water, dried the organic layer over MgSO$_4$ and condensed in vacuo. Purification by silica gel chromatography (Waters Prep-500) using 10% ethyl acetate/hexanes as elutant gave 24.2 g (60%) of 4 as a oil. $^1$H NMR (CDCl$_3$) d 0.89 (t, J=7.05 Hz, 6H), 1.17–1.40 (m, 12H), 1.46 (t, J=5.84 Hz, 1H), 2.81 (s, 2H), 3.38 (s, 3H), 3.43 (d, J=5.23 Hz, 2H), 4.16 (s, 2H), 4.42 (s, 2H), 6.80 (d, J=9.67 Hz, 1H), 6.90 (t, J=8.46 Hz, 1H), 7.09 (d, J=7.45 Hz, 1H), 7.15–7.21 (m, 2H), 7.25–7.32 (m, 2H), 7.42 (m, 1H).

Step 5. Preparation of 5

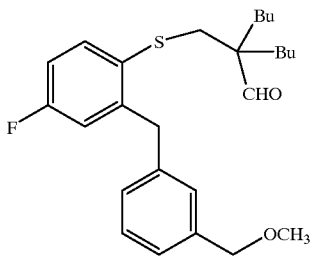

To a cooled (15–18° C.) solution of 24.2 g (55.8 mmol) of 4 in 100 mL DMSO was added 31.2 g sulfur trioxide pyridine complex (195 mmol). Stirred at ambient temperature for thirty minutes. Poured into cold water and extracted three times with ethyl acetate. Washed organics with 5% HCl (300 mL) and then with brine (300 mL), dired organics over MgSO$_4$ and condensed in vacuo to give 23.1 g (96%) of 5 as a light brown oil. $^1$H NMR (CDCl$_3$) d 0.87 (t, J=7.05 Hz, 6H), 1.01–1.32 (m, 8H), 1.53–1.65 (m, 4H), 2.98 (s, 2H), 3.38 (s, 3H), 4.15 (s, 2H), 4.43 (s, 2H), 6.81 (dd, J=9.66 Hz and 2.82 Hz, 1H), 6.91 (t, J=8.62 Hz, 1H), 7.07 (d, J=7.46 Hz, 1H), 7.14 (s, 1H), 7.19 (d, J=7.65 Hz, 1H), 7.26–7.32 (m, 1H), 7.42 (dd, J=8.66 Hz and 5.64 Hz, 1H), 9.40 (s, 1H).

Step 6. Preparation of 6

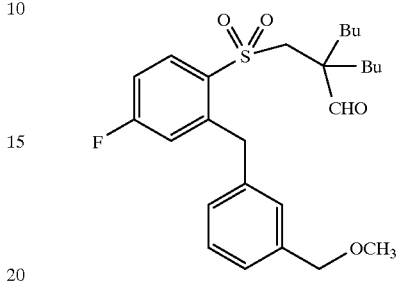

To a cooled (0° C.) solution of 23.1 g (53.6 mmol) of 5 in 200 mL methylene chloride was added 28.6 g meta cholorperoxy-benzoic acid (112.6 mmol). Stirred at ambient temperature for 24 hours. Quenched with 100 mL 10% Na$_2$SO$_3$, partitioned between water and methylene chloride. Dried organic layer over MgSO$_4$ and condensed in vacuo to give 24.5 g (98%) of 6 as a light yellow oil. $^1$H NMR (CDCl$_3$) d 0.86–1.29 (m, 14H), 1.58–1.63 (m, 2H), 1.82–1.91 (m, 2H), 3.13 (s, 2H), 3.39 (s, 3H), 4.44 (s, 2H), 4.50 (s, 2H), 6.93 (d, J=9.07 Hz, 1H), 7.10–7.33 (m, 5H), 8.05 (s, 1H), 9.38 (s, 1H).

Step 7. Prepararation of 7

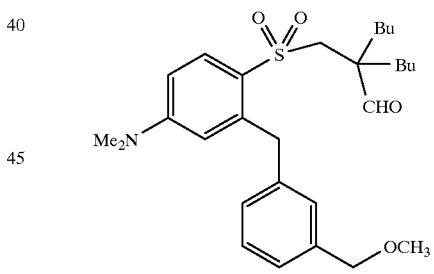

To a solution of 24.5 g (52.9 mmol) of 6 in 20 mL of THF contained in a stainless steel reaction vessel was added 100 mL of a 2.0 M solution of dimethyl amine and 20 mL of neat dimethyl amine. The vessel was sealed and heated to 110° C. for 16 hours. The reaction vessel was cooled to ambient temperature and the contents concentrated in vacuo. Purification by silica gel chromatography (Waters Prep-500) using 15% ethyl acetate/hexanes gave 21.8 g (84%) of 7 as a clear colorless oil. $^1$H NMR (CDCl$_3$) d 0.85 (t, J=7.25 Hz, 6H), 0.93–1.29 (m, 8H), 1.49–1.59 (m, 2H), 1.70–1.80 (m, 2H), 2.98 (s, 8H), 3.37 (s, 3H), 4.41 (s, 2H), 4.44 (s, 2H), 6.42 (s, 1H), 6.58 (dd, J=9.0 Hz and 2.61 Hz, 1H), 7.13 (d, J=7.45 Hz, 1H), 7.21 (s, 1H), 7.28 (t, J=7.85 Hz, 1H), 7.82 (d, J=9.06 Hz, 1H), 9.36 (s, 1H).

Step 8. Preparation of 8

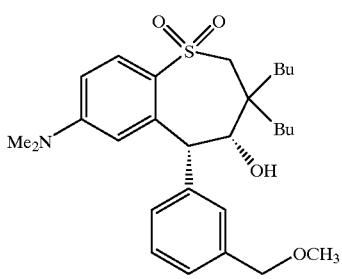

A solution of 21.8 g (44.8 mmol) of 7 in 600 mL of THF was cooled to 0° C. 58.2 mL of a 1 M solution of potassium t-butoxide was added slowly, maintaining the temperature at <5° C. Stirred for 30 minutes, then quenched with 50 mL of saturated ammonium chloride. The organic layer was partitioned between ethyl acetate and water, dried over $MgSO_4$ and concentrated in vacuo. Purification by recrystalization from ~10% ethyl acetate/hexanes gave 15.1 g of 8 as a white solid. The mother liquor was purified by silica gel chromatography (Waters Prep-500) using 30% ethyl acetate/hexanes as the elutant to give 3.0 g of 8 as a white solid. MS (FABLi$^+$) m/e 494.6. HRMS (EI$^+$) calculated for M+H 487.2756. Found 487.2746.

Step 9. Preparation of 9

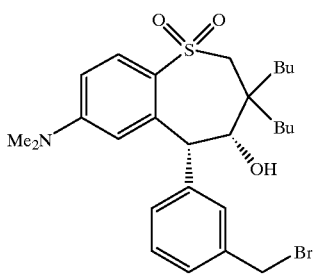

A solution of 2.0 g (4.1 mmol) of 8 in 20 mL of methylene chloride was cooled to –60° C. 4.1 mL of a 1M solution of boron tribromide was added. Stirred at ambient temperature for thirty minutes. Cooled reaction to ~10° C. and quenched with 50 mL of water. The organic layer was partitioned between methylene chloride and water, dried over $MgSO_4$ and concentrated in vacuo. Purification by recrystalization from 50% ethyl acetate/methylene chloride gave 1.95 g (89%) of 9 as a white solid. MS (FABH$^+$) m/e 537. HRMS (FAB) calculated for M 536.1834. Found 536.1822.

Step 10. Preparation of 10

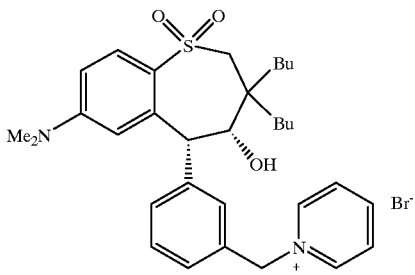

A solution of 1.09 g (2.0 mmol) of 9 and 4.9 g (62 mmol) of pyridine in 30 mL of acetonitrile was stirred at ambient temperature for 18 hours. The reaction was concentrated in vacuo. Purification by recrystallization from methanol/diethyl ether gave 1.19 g (96%) of 10 as an off white solid. MS (FAB+) m/e 535.5.

EXAMPLE 1400

Step 1

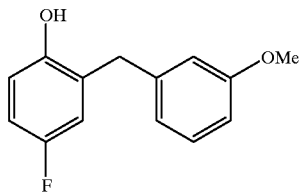

$C_{14}H_{13}O_2F$ fw = 232.25

A 12-liter, 4-neck round-bottom flask was equipped with reflux condenser, $N_2$ gas adaptor, mechanical stirrer, and an addition funnel. The system was purged with $N_2$. A slurry of sodium hydride (126.0 g/4.988 mol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into $H_2O$ (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aq. KOH solutions were combined and acidified with concentrated HCl. The acidic solution was extracted three times with ethyl ether, dried ($MgSO_4$), filtered and concentrated in vacuo. The crude product was purified by Kugelrohr distillation to give a clear, colorless oil (449.0 g/39% yield). b.p.: 120–130 C./50 mtorrHg. $^1$H NMR and MS [(M+H)$^+$=233] confirmed desired structure.

Step 2

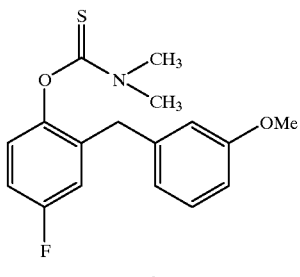

C₁₇H₁₈NO₂FS  fw = 319.39

A 12-liter, 3-neck round-bottom flask was fitted with mechanical stirrer and N₂ gas adaptor. The system was purged with N₂. 4-Fluoro-2-(3-methoxybenzyl)-phenol (455.5 g/1.961 mol) and dimethylformamide were added. The solution was cooled to 6 C., and sodium hydride (55.5 g/2.197 mol) was added slowly. After warming to room temperature, dimethylthiocarbamoyl chloride (242.4 g/1.961 mol) was added. After 15 h, the reaction mixture was poured into H₂O (4.0 L), and extracted two times with ethyl ether. The combined organic layers were washed with H₂O and saturated aqueous NaCl, dried (MgSO₄), filtered, and concentrated in vacuo to give the product (605.3 g, 97% yield). ¹H NMR and MS [(M+H)⁺=320] confirm desired structure.

Step 3

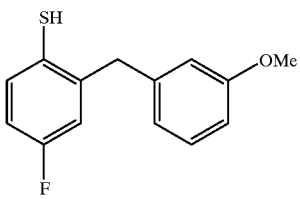

C₁₄H₁₃OFS  fw = 248.32

A 12-liter, round-bottom flask was equipped with N₂ gas adaptor, mechanical stirrer, and reflux condenser. The system was purged with N₂. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temparature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temparature, the mixture was concentrated by rotavap, dissolved in ethyl ether (1.0 L), and extracted with H₂O. The aqueous extracts were combined, acidified with concentrated HCl, and extracted with ethyl ether. The ether extracts were dried (MgSO₄), filtered, and concentrated in vacuo to give an amber oil (463.0 g, 98% yield). ¹H NMR confirmed desired structure.

Step 4

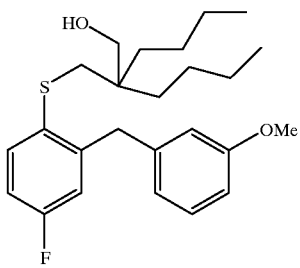

C₂₅H₃₅O₂FS  fw = 418.61

A 5-liter, 3-neck, round-bottom flask was equipped with N₂ gas adaptor and mechanical stirrer. The system was purged with N₂. 4-Fluoro-2-(3-methoxybenzyl)thiophenol (100.0 g/403.2 mmol) and 2-methoxyethyl ether (1.0 L) were added and the solution was cooled to 0 C. Sodium hydride (9.68 g/383.2 mmol) was added slowly, and the mixture was allowed to warm to room temparature, 2,2-Dibutylpropylene sulfate (110.89 g/443.6 mmol) was added, and the mixture was stirred for 64 h. The reaction mixture was concentrated by rotavap and dissolved in H₂O. The aqueous solution was washed with ethyl ether, and concentrated H₂SO₄ was added. The aqueous solution was heated to reflux for 30 min, cooled to room temperature, and extracted with ethyl ether. The ether solution was dried (MgSO₄), filtered, and conc'd in vacuo to give an amber oil (143.94 g/85% yield). ¹H NMR and MS [(M+H)⁺=419] confirm the desired structure.

Step 5

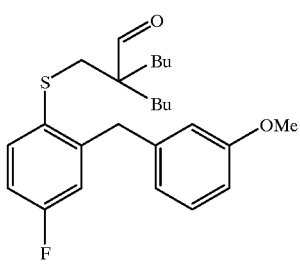

C₂₅H₃₃O₂FS  fw = 416.59

A 2-liter, 4-neck, round-bottom flask was equipped with N₂ gas adaptor, and mechanical stirrer. The system was purged with N₂. The corresponding alcohol (143.94 g/343.8 mmol) and CH₂Cl₂ (1.0 L) were added and cooled to 0 C. Pyridinium chlorochromate (140.53 g/651.6 mmol) was added. After 6 h., CH₂Cl₂ was added. After 20 min, the mixture was filtered through silica gel, washing with CH₂Cl₂. The filtrate was concentrated in vacuo to give a dark yellow-red oil (110.6 g, 77% yield). ¹H NMR and MS [(M+H)⁺=417] confirm the desired structure.

Step 6

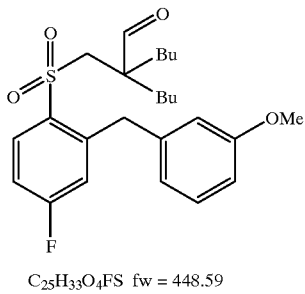

C$_{25}$H$_{33}$O$_4$FS  fw = 448.59

A 2-liter, 4-neck, round-bottom flask was equipped with N$_2$ gas adaptor and mechanical stirrer. The system was purged with N$_2$. The corresponding sulfide (110.6 g/265.5 mmol) and CH$_2$Cl$_2$ (1.0 L) were added. The solution was cooled to 0 C., and 3-chloroperbenzoic acid (158.21 g/531.7 mmol) was added portionwise. After 30 min, the reaction mixture was allowed to warm to room temperature. After 3.5 h, the reaction mixture was cooled to 0 C. and filtered through a fine fritted funnel. The filtrate was washed with 10% aqueous K$_2$CO$_3$. An emulsion formed which was extracted with ethyl ether. The organic layers were combined, dried (MgSO$_4$), filtered, and concentrated in vacuo to give the product (93.2 g, 78% yield). $^1$H NMR confirmed the desired structure.

Step 7

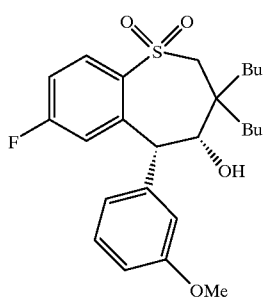

C$_{25}$H$_{33}$O$_4$FS  fw = 448.59

A 2-liter, 4-neck, round-bottom flask was equipped with N$_2$ gas adaptor, mechanical stirrer, and a powder addition funnel. The system was purged with N$_2$. The corresponding aldehyde (93.2 g/208 mmol) and THF (1.0 L) were added, and the mixture was cooled to 0 C. Potassium tert-butoxide (23.35 g/208.1 mmol) was added via addition funnel. After 1 h, 10% aq/ HCl (1.0 L) was added. After 1 h, the mixture was extracted three times with ethyl ether, dried (MgSO$_4$), filtered, and concentrated in vacuo. The crude product was purified by recryst. from 80/20 hexane/ethyl acetate to give a white solid (32.18 g). The mother liquor was concentrated in vacuo and recrystelized from 95/5 toluene/ethyl acetate to give a white solid (33.60 g/combined yield: 71%). $^1$H NMR confirmed the desired product.

Step 8

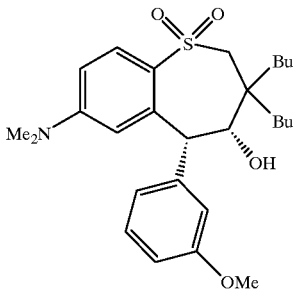

C$_{27}$H$_{39}$O$_4$NS  fw = 473.67

A Fisher porter bottle was fitted with N$_2$ line and magnetic stirrer. The system was purged with N$_2$. The corresponding fluoro-compound (28.1 g/62.6 mmol) was added, and the vessel was sealed and cooled to –78 C. Dimethylamine (17.1 g/379 mmol) was condensed via a CO$_2$/acetone bath and added to the reaction vessel. The mixture was allowed to warm to room temperature and was heated to 60 C. After 20 h, the reaction mixture was allowed to cool and was dissolved in ethyl ether. The ether solution was washed with H$_2$O, saturated aqueous NaCl, dried (MgSO$_4$), filtered, and concentrated in vacuo to give a white solid (28.5 g/96% yield). $^1$H NMR confirmed the desired structure.

Step 9

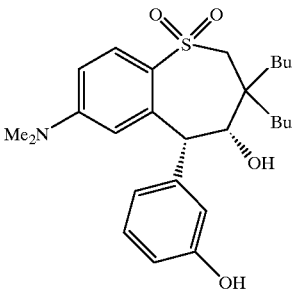

C$_{26}$H$_{37}$O$_4$NS  fw = 459.64

A 250-mL, 3-neck, round-bottom flask was equipped with N$_2$ gas adaptor and magnetic stirrer. The system was purged with N$_2$. The corresponding methoxy-compound (6.62 g/14.0 mmol) and CHCl$_3$ (150 mL) were added. The reaction mixture was cooled to –78 C., and boron tribromide (10.50 g/41.9 mmol) was added. The mixture was allowed to warm to room temperature After 4 h, the reaction mixture was cooled to 0 C. and was quenched with 10% K$_2$CO$_3$ (100 mL). After 10 min, the layers were separated, and the aqueous layer was extracted two times with ethyl ether. The CHCl$_3$ and ether extracts were combined, washed with saturated aqueous NaCl, dried (MgSO$_4$), filtered, and concentrated in vacuo to give the product (6.27 g/98% yield). $^1$H NMR confirmed the desired structure.

287

Step 10

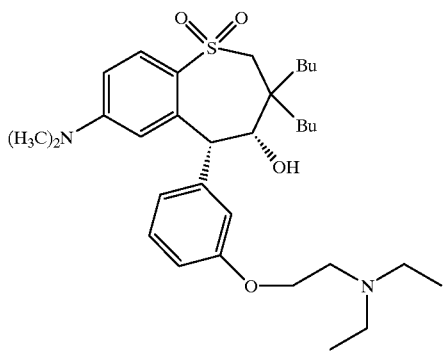

In a 250 ml single neck round bottom Flask with stir bar place 2- diethylamineoethyl chloride hydochloride (fw 172.10 g/mole) Aldrich D8, 720-1 (2.4 mmol,4.12 g), 34 ml dry ether and 34 ml of 1N KOH(aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, 2.6 mmol) and 34 ml of DMF. Cool to ice temperature. Next add phenol product(previous step) 1.1 g (2.4 mmilomoles in 5 ml DMF and the ether solution prepared above. Heat to 40 C. for 3 days. The product which contained no starting material by TLC was diluted with ether and extracted with 1 portion of 5% NaOH, followed by water and then brine. The ether layer was dried over magnesium sulfate and isolated by removing ether by rotary evaporation (1.3 gms). The product may be further purified by chromatography (SiO2 99% ethyl acetate/1% NH4OH at 5 ml/min.). Isolated yield: 0.78 g (mass spec, and H1 NMR)

Step 11

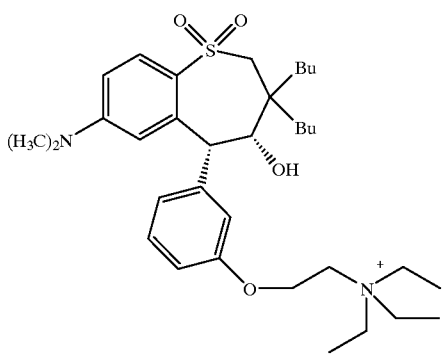

The product from step 10 ( 0.57 gms, 1.02 millimole fw 558.83 g/mole) and 1.6 gms iodoethane (10.02 mmol) was placed in 5 ml acetonitrile in a fischer-porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M-I=587.9, H NMR).

288

EXAMPLE 1401

Step 1

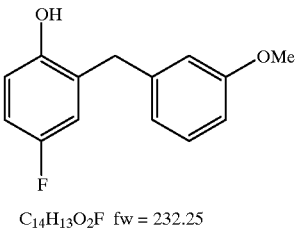

$C_{14}H_{13}O_2F$ fw = 232.25

A 12-liter, 4-neck round-bottom flask was equipped with reflux condenser, $N_2$ gas adaptor, mechanical stirrer, and an addition funnel. The system was purged with $N_2$. A slurry of sodium hydride (126.0 g/4.988 mol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into $H_2O$ (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aqueous KOH solutions were combined and acidified with concentrated HCl. The acidic solution was extracted three times with ethyl ether, dried over $MgSO_4$, filtered and concentrated in vacuo. The crude product was purified by Kugelrohr distillation to give a clear, colorless oil (449.0 g/39% yield). b.p.: 120–130 C./50 mtorrHg. $^1H$ NMR and MS $[(M+H)^+=233]$ confirmed desired structure.

Step 2

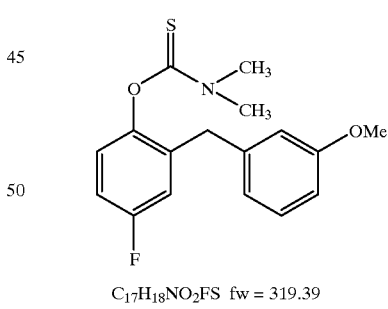

$C_{17}H_{18}NO_2FS$ fw = 319.39

A 12-liter, 3-neck round-bottom flask was fitted with mechanical stirrer and $N_2$ gas adaptor. The system was purged with $N_2$. 4-Fluoro-2-(3-methoxybenzyl)phenol (455.5 g/1.961 mol) and dimethylformamide were added. The solution was cooled to 6 C., and sodium hydride (55.5 g/2.197 mol) was added slowly. After warming to room temperature, dimethylthiocarbamoyl chloride (242.4 g/1.961 mol) was added. After 15 h, the reaction mixture was poured into $H_2O$ (4.0 L), and extracted two times with ethyl ether. The combined organic layers were washed with $H_2O$ and saturated aqueous NaCl, dried over $MgSO_4$, filtered, and concentrated in vacuo to give the product (605.3 g, 97% yield). $^1$H NMR and MS [(M+H)+=320] confirm desired structure.

Step 3

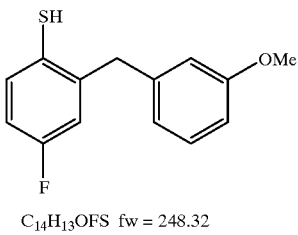

C$_{14}$H$_{13}$OFS  fw = 248.32

A 12-liter, round-bottom flask was equipped with N$_2$ gas adaptor, mechanical stirrer, and reflux condenser. The system was purged with N$_2$. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temperature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temperature, the mixture was concentrated by rotavap, dissolved in ethyl ether (1.0 L), and extracted with H$_2$0. The aqueous extracts were combined, acidified with conc. HCl, and extracted with ethyl ether. The ether extracts were dried (MgSO$_4$), filtered, and concentrated in vacuo to give an amber oil (463.0 g, 98% yield). $^1$H NMR confirmed desired structure.

Step 4

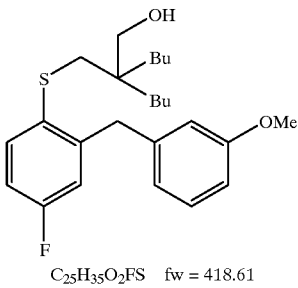

C$_{25}$H$_{35}$O$_2$FS  fw = 418.61

A 5-liter, 3-neck, round-bottom flask was equipped with N$_2$ gas adaptor and mechanical stirrer. The system was purged with N$_2$. 4-Fluoro-2-(3-methoxybenzyl)thiophenol (100.0 g/403.2 mmol) and 2-methoxyethyl ether (1.0 L) were added and the solution was cooled to 0 C. Sodium hydride (9.68 g/383.2 mmol) was added slowly, and the mixture was allowed to warm to room temperature 2,2-Dibutylpropylene sulfate (110.89 g/443.6 mmol) was added, and the mixture was stirred for 64 h. The reaction mixture was concentrated by rotavap and dissolved in H$_2$O. The aqueous solution was washed with ethyl ether, and conc. H$_2$SO$_4$ was added. The aqueous solution was heated to reflux for 30 min, cooled to room temperature, and extracted with ethyl ether. The ether solution was dried (MgSO$_4$), filtered, and concentrated in vacuo to give an amber oil (143.94 g/85% yield). $^1$H NMR and MS [(M+H)$^+$=419] confirm the desired structure.

Step 5

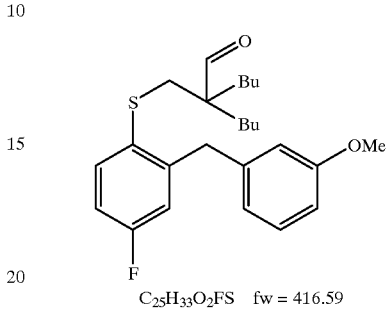

C$_{25}$H$_{33}$O$_2$FS  fw = 416.59

A 2-liter, 4-neck, round-bottom flask was equipped with N$_2$ gas adaptor, and mechanical stirrer. The system was purged with N$_2$. The corresponding alcohol (143.94 g/343.8 mmol) and CH$_2$Cl$_2$ (1.0 L) were added and cooled to 0 C. Pyridinium chlorochromate (140.53 g/651.6 mmol) was added. After 6 h., CH$_2$Cl$_2$ was added. After 20 min, the mixture was filtered through silica gel, washing with CH$_2$Cl$_2$. The filtrate was concentrated in vacuo to give a dark yellow-red oil (110.6 g, 77% yield). $^1$H NMR and MS [(M+H)$^+$=417] confirm the desired structure.

Step 6

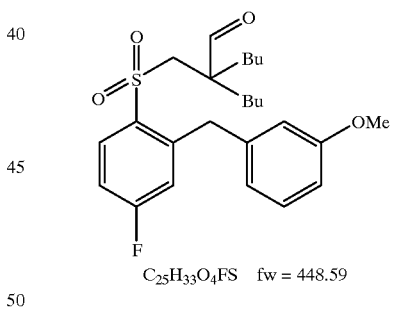

C$_{25}$H$_{33}$O$_4$FS  fw = 448.59

A 2-liter, 4-neck, round-bottom flask was equipped with N$_2$ gas adaptor and mechanical stirrer. The system was purged with N$_2$. The corresponding sulfide (110.6 g/265.5 mmol) and CH$_2$Cl$_2$ (1.0 L) were added. The solution was cooled to 0 C., and 3-chloroperbenzoic acid (158.21 g/531.7 mmol) was added portionwise. After 30 min, the reaction mixture was allowed to warm to room temperature After 3.5 h, the reaction mixture was cooled to 0 C. and filtered through a fine fritted funnel. The filtrate was washed with 10% aqueous K$_2$CO$_3$. An emulsion formed which was extracted with ethyl ether. The organic layers were combined, dried (MgSO$_4$), filtered, and concentrated in vacuo to give the product (93.2 g, 78% yield). $^1$H NMR confirmed the desired structure.

291
Step 7

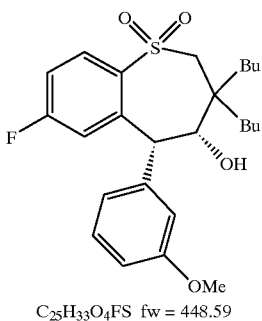

C25H33O4FS fw = 448.59

A 2-liter, 4-neck, round-bottom flask was equipped with N₂ gas adaptor, mechanical stirrer, and a powder addition funnel. The system was purged with N₂. The corresponding aldehyde (93.2 g/208 mmol) and THF (1.0 L) were added, and the mixture was cooled to 0 C. Potassium tert-butoxide (23.35 g/208.1 mmol) was added via addition funnel. After 1 h, 10% aq/ HCl (1.0 L) was added. After 1 h, the mixture was extracted three times with ethyl ether, dried (MgSO₄), filtered, and concentrated in vacuo. The crude product was purified by recrystallized from 80/20 hexane/ethyl acetate to give a white solid (32.18 g). The mother liquor was concentrated in vacuo and recrystallized from 95/5 toluene/ethyl acetate to give a white solid (33.60 g, combined yield: 71%). ¹H NMR confirmed the desired product.

Step 8

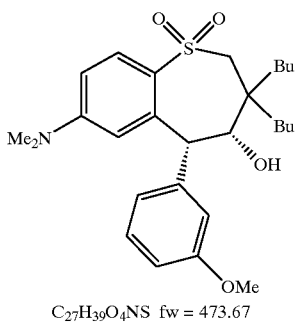

C27H39O4NS fw = 473.67

A Fisher porter bottle was fitted with N₂ line and magnetic stirrer. The system was purged with N₂. The corresponding fluoro-compound (28.1 g/62.6 mmol) was added, and the vessel was sealed and cooled to −78 C. Dimethylamine (17.1 g/379 mmol) was condensed via a CO₂/acetone bath and added to the reaction vessel. The mixture was allowed to warm to room temperature and was heated to 60 C. After 20 h, the reaction mixture was allowed to cool and was dissolved in ethyl ether. The ether solution was washed with H₂O, saturated aqueous NaCl, dried over MgSO₄, filtered, and concentrated in vacuo to give a white solid (28.5 g/96% yield). ¹H NMR confirmed the desired structure.

292
Step 9

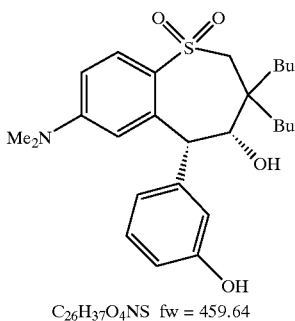

C26H37O4NS fw = 459.64

A 250-mL, 3-neck, round-bottom flask was equipped with N₂ gas adaptor and magnetic stirrer. The system was purged with N₂. The corresponding methoxy-compound (6.62 g/14.0 mmol) and CHCl₃ (150 mL) were added. The reaction mixture was cooled to −78 C., and boron tribromide (10.50 g/41.9 mmol) was added. The mixture was allowed to warm to room temperature After 4 h, the reaction mixture was cooled to 0 C. and was quenched with 10% K₂CO₃ (100 mL). After 10 min, the layers were separated, and the aqueous layer was extracted two times with ethyl ether. The CHCl₃ and ether extracts were combined, washed with saturated aqueous NaCl, dried over MgSO₄, filtered, and concentrated in vacuo to give the product (6.27 g/98% yield). ¹H NMR confirmed the desired structure.

Step 10

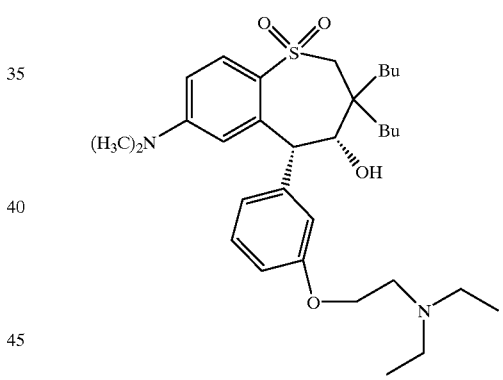

In a 250 ml single neck round bottom flask with stir bar place 2-diethylamineoethyl chloride hydochloride (fw 172.10 g/mole) Aldrich D8, 720-1 (2.4 millimoles, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, (2.6 mmol) and 34 ml of DMF. Cool to ice temperature. Next add phenol product (previous step) 1.1 g (2.4 mmol in 5 ml DMF and the ether solution prepared above. Heat to 40 C. for 3 days. The product which contained no starting material by TLC was diluted with ether and extracted with 1 portion of 5% NaOH, followed by water and then brine. The ether layer was dried over Magnesium sulfate and isolated by removing ether by rotary evaporation (1.3 gms). The product may be further purified by chromatography (silica 99% ethyl acetate/1% NH4OH at 5 ml/min.). Isolated yield: 0.78 g (mass spec, and H1 NMR)

Step 11

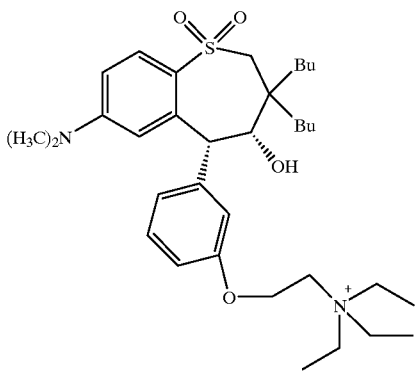

The product from step 10 (0.57 gms, 1.02 millimole fw 558.83 g/mole) and iodoethane (1.6 gms (10.02 mmilimoles)was place in 5 ml acetonitrile in a Fischer-Porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M–I=587.9, $^1$H NMR).

EXAMPLE 1402

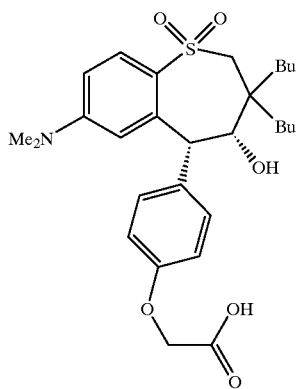

(4R-cis)-5-[[5-[4-[3,3-Dibutyl-7-(dimethylamino)-2,3,4,5-tetrahydro-4-hydroxy-1,1-dioxido-1-benzothiepin-5-yl]phenoxy]pentyl]thio]-1H-tetrazole-1-acetic Acid

Step 1. Preparation of 4-Fluoro-2-((4-methoxyphenyl)methyl)-phenol

To a stirred solution of 23.66 g of 95% sodium hydride (0.94 mol) in 600 mL of dry toluene was added 100.0 g of 4-fluorophenol (0.89 mol) at 0° C. The mixture was stirred at 90° C. for 1 hour until gas evolution stopped. The mixture was cooled down to room temperature and a solution of 139.71 g of 3-methoxybenzyl chloride (0.89 mol) in 400 mL of dry toluene was added. After refluxing for 24 hours, the mixture was cooled to room temperature and quenched with 500 mL of water. The organic layer was separated, dried over $MgSO_4$, and concentrated under high vacuum. The remaining starting materials were removed by distillation. The crude dark red oil was filtered through a layer of 1 L of silica gel with neat hexane to yield 53.00 g (25.6%) of the product as a pink solid: $^1$H NMR ($CDCl_3$) δ3.79 (s, 3H), 3.90 (s, 2H), 4.58 (s, 1H), 6.70–6.74 (m, 1H), 6.79–6.88 (m, 4H), 7.11–7.16 (m, 2H).

Step 2. Preparation of 4-Fluoro-2-((4-methoxyphenyl)methyl)-thiophenol

Step 2a. Preparation of Thiocarbamate

To a stirred solution of 50.00 g (215.30 mmol) of 4-fluoro-2-((4-methoxyphenyl)methyl)-phenol in 500 mL of dry DMF was added 11.20 g of 60% sodium hydride dispersion in mineral oil (279.90 mmol) at 2° C. The mixture was allowed to warm to room temperature and 26.61 g of dimethylthiocarbamoyl chloride (215.30 mmol) was added. The reaction mixture was stirred at room temperature overnight. The mixture was quenched with 100 mL of water in an ice bath. The solution was extracted with 500 mL of diethyl ether. The ether solution was washed with 500 mL of water and 500 mL of brine. The ether solution was dried over $MgSO_4$ and stripped to dryness. The crude product was filtered through a plug of 500 mL silica gel using 5% ethyl acetate/hexane to yield 48.00 g (69.8%) of the product as a pale white solid: $^1$H NMR ($CDCl_3$) δ3.21 (s, 3H), 3.46 (s, 3H), 3.80 (s, 3H), 3.82 (s, 2H), 6.78–6.86 (m, 3H), 6.90–7.00 (m, 2H), 7.09 (d, $J$=8.7 Hz, 2H).

Step 2b. Rearrangement and Hydrolysis of Thiocarbamate to 4-Fluoro-2-((4-methoxyphenyl)methyl)-thiophenol A stirred solution of 48.00 g (150.29 mmol) of thiocarbamate (obtained from Step 2a) in 200 mL of diphenyl ether was refluxed at 270° C. overnight. The solution was cooled down to room temperature and filtered through 1 L of silica gel with 2 L of hexane to remove phenyl ether. The rearrangement product was washed with 5% ethyl acetate/hexane to give 46.00 g (95.8%) of the product as a pale yellow solid: $^1$H NMR ($CDCl_3$) δ3.02 (s, 3H), 3.10 (s, 3H), 3.80 (s, 3H), 4.07 (s, 2H), 6.82–6.86 (m, 3H), 6.93 (dt, $J$=8.4 Hz, 2.7 Hz, 1H), 7.08 (d, $J$=8.7 Hz, 2H), 7.49 (dd, $J$=6.0 Hz, 8.7 Hz, 1H).

To a solution of 46.00 g (144.02 mmol) of the rearrangement product (above) in 200 mL of methanol and 200 mL of THF was added 17.28 g of NaOH (432.06 mmol). The mixture was refluxed under nitrogen overnight. The solvents were evaporated off and 200 mL of water was added. The aqueous solution was washed with 200 mL of diethyl ether twice and placed in an ice bath. The aqueous mixture was acidified to pH 6 with concentrated HCl solution. The solution was extracted with 300 mL of diethyl ether twice. The ether layers were combined, dried over $MgSO_4$ and stripped to dryness to afford 27.00 g (75.5%) of the product as a brown oil: $^1$H NMR ($CDCl_3$) δ3.24 (s, 1H), 3.80 (s, 3H), 3.99 (s, 2H), 6.81–6.87 (m, 4H), 7.09 (d, $J$=8.7 Hz, 2H), 7.27–7.33 (m, 1H).

Step 3. Preparation of Dibutyl Cyclic Sulfate

Step 3a. Preparation of 2,2-Dibutyl-1,3-propanediol

To a stirred solution of di-butyl-diethylmalonate (Aldrich) (150 g, 0.55 mol in dry THF (700 ml) in an acetone/dry ice bath was added LAH (1 M THF) 662 ml (1.2 eq., 0.66 mol) dropwise maintaining the temperature between –20 to 0° C. The reaction was stirred at RT overnight. The reaction was cooled to –20° C. and 40 ml of water, and 80 mL of 10% NaOH and 80 ml of water were added dropwise. The resulting suspension was filtered. The filtrate was dried over sodium sulphate and concentrated in vacuo to give diol 98.4 g (yield 95%) as an oil. MS spectra and proton and carbon NMR spectra were consistent with the product.

Step 3b. Preparation of Dibutyl Cyclic Sulfite

A solution of 2,2-dibutyl-1,3-propanediol (103 g, 0.548 mol, obtained from Step 3a) and triethylamine (221 g, 2.19 mol) in anhydrous methylene chloride (500 ml) was stirred at 0° C. under nitrogen. To the mixture, thionyl chloride (97.8 g, 0.82 mol) was added dropwise and within 5 min the solution turned yellow and then black when the addition was completed within half an hour. The reaction mixture was stirred for 3 hrs. at 0° C. GC showed that there was no starting material left. The mixture was washed with ice water twice then with brine twice. The organic phase was dried over magnesium sulfate and concentrated under vacuum to give 128 g (100%) of the dibutyl cyclic sulfite as a black oil. Mass spectrum (MS) was consistent with the product.

Step 3c. Oxidation of Dibutyl Cyclic Sulfite to Dibutyl Cyclic Sulfate

To a solution of the dibutyl cyclic sulfite (127.5 g, 0.54 mol, obtained from Step 3b) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and to give 133 g (97.8%) of the dibutyl cyclic sulfate as an oil. Proton and carbon NMR and MS were consistent with the product.

Step 4. Preparation of Aryl-3-hydroxypropylsulfide

To a stirred solution of 27.00 g (108.73 mmol) of 4-fluoro-2-((4-methoxyphenyl)methyl)thiophenol (obtained from Step 2) in 270 mL of diglyme was added 4.35 g of 60% sodium hydride dispersion in mineral oil (108.73 mmol) at 0° C. After gas evolution ceased, 29.94 g (119.60 mmol) of the dibutyl cyclic sulfate (obtained from Step 3c) was added at 0° C. and stirred for 10 minutes. The mixture was allowed to warm up to room temperature and stirred overnight. The solvent was evaporated and 200 mL of water was added. The solution was washed with 200 mL of diethyl ether and added 25 mL of concentrated sulfuric acid to make a 2.0 M solution that was refluxed overnight. The solution was extracted with ethyl acetate and the organic solution was dried over $MgSO_4$ and concentrated in vacuo. The crude aryl-3-hydroxypropylsulfide was purified by silica gel chromatography (Waters Prep 500) using 8% ethyl acetate/hexane to yield 33.00 g (72.5%) of the product as a light brown oil: $^1H$ NMR ($CDCl_3$) δ 0.90 (t, J=7.1 Hz, 6H), 1.14–1.34 (m, 12H), 2.82 (s, 2H), 3.48 (s, 2H), 3.79 (s, 3H), 4.10 (s, 2H), 6.77–6.92 (m, 4H), 7.09 (d, J=8.7 Hz, 2H), 7.41 (dd, J=8.7 Hz, 5.7 Hz, 1H).

Step 5. Preparation of Enantiomerically-enriched Aryl-3-hydroxypropylsulfoxide

To a stirred solution of 20.00 g (47.78 mmol) of aryl-3-hydroxypropylsulfide (obtained from Step 4) in 1 L of methylene chloride was added 31.50 g of 96% (1R)-(-)-(8,8-dichloro-10-camphor-sulfonyl)oxaziridine (100.34 mmol, Aldrich) at 2° C. After all the oxaziridine dissolved the mixture was placed into a −30° C. freezer for 72 hours. The solvent was evaporated and the crude solid was washed with 1 L of hexane. The white solid was filtered off and the hexane solution was concentrated in vacuo. The crude oil was purified on a silica gel column (Waters Prep 500) using 15% ethyl acetate/hexane to afford 19.00 g (95%) of the enantiomerically-enriched aryl-3-hydroxypropylsulfoxide as a colorless oil: $^1H$ NMR ($CDCl_3$) δ 0.82–0.98 (m, 6H), 1.16–1.32 (m, 12H), 2.29 (d, J=13.8 Hz, 1H), 2.77 (d, J=13.5 Hz, 1H), 3.45 (d, J=12.3 Hz, 1H), 3.69 (d, J =12.3 Hz, 1H), 3.79 (s, 3H), 4.02 (q, J=15.6 Hz, 1H), 6.83–6.93 (m, 3H), 7.00 (d, J=8.1 Hz, 2H), 7.18–7.23 (m, 1H), 7.99–8.04 (m, 1H). Enantiomeric excess was determined by chiral HPLC on a (R,R)-Whelk-O column using 5% ethanol/hexane as the eluent. It showed to be 78% e.e. with the first eluting peak as the major product.

Step 6. Preparation of enantiomerically-enriched aryl-3-propanalsulfoxide

To a stirred solution of 13.27 g of triethylamine (131.16 mmol, Aldrich) in 200 mL dimethyl sulfoxide were added 19.00 g (43.72 mmol) of enantiomerically-enriched aryl-3-hydroxypropylsulfoxide (obtained from Step 5) and 20.96 g of sulfur trioxide-pyridine (131.16 mmol, Aldrich) at room temperature. After the mixture was stirred at room temperature for 48 hours, 500 mL of water was added to the mixture and stirred vigorously. The mixture was then extracted with 500 mL of ethyl acetate twice. The ethyl acetate layer was separated, dried over $MgSO_4$, and concentrated in vacuo. The crude oil was filtered through 500 mL of silica gel using 15% ethyl acetate/hexane to give 17.30 g (91%) of the enantiomerically-enriched aryl-3-propanalsulfoxide as a light orange oil: $^1H$ NMR ($CDCl_3$) δ 0.85–0.95 (m, 6H), 1.11–1.17 (m, 4H), 1.21–1.39 (m, 4H), 1.59–1.76 (m, 4H), 1.89–1.99 (m, 1H), 2.57 (d, J=14.1 Hz, 1H), 2.91 (d, J=13.8 Hz, 1H), 3.79 (s, 3H), 3.97 (d, J=15.9 Hz, 1H), 4,12 (d, J=15.9 Hz, 1H), 6.84–6.89 (m, 3H), 7.03 (d, J=8.4 Hz, 2H), 7.19 (dt, J=8.4 Hz, 2.4 Hz, 1H), 8.02 (dd, J=8.7 Hz, 5.7 Hz, 1H), 9.49 (s, 1H).

Step 7. Preparation of the Enantiomerically-Enriched Tetrahydrobenzothiepine-1-Oxide (4R,5R)

To a stirred solution of 17.30 g (39.99 mmol) of enantiomerically-enriched aryl-3-propanalsulfoxide (obtained from Step 6) in 300 mL of dry THF at −15° C. was added 48 mL of 1.0 M potassium t-butoxide in THF (1.2 equivalents) under nitrogen. The solution was stirred at −15° C. for 4 hours. The solution was then quenched with 100 mL of water and neutralized with 4 mL of concentrated HCl solution at 0° C. The THF layer was separated, dried over $MgSO_4$, and concentrated in vacuo. The enantiomerically-enriched tetrahydrobenzothiepine-1-oxide (4R,5R) was purified by silica gel chromatography (Waters Prep 500) using 15% ethyl acetate/hexane to give 13.44 g (77.7%) of the product as a white solid: $^1H$ NMR ($CDCl_3$) δ 0.87–0.97 (m, 6H), 1.16–1.32 (m, 4H), 1.34–1.48 (m, 4H), 1.50–1.69 (m, 4H), 1.86–1.96 (m, 1H), 2.88 (d, J=13.0 Hz, 1H), 3.00 (d, J=13.0 Hz, 1H), 3.85 (s, 3H), 4.00 (s, 1H), 4.48 (s, 1H), 6.52 (dd, J=9.9 Hz, 2.4 Hz, 1H), 6.94 (d, J =9 Hz, 2H), 7.13 (dt, J=8.4 Hz, 2.4 Hz, 1H), 7.38 (d, J=8.7 Hz, 2H), 7.82 (dd, J=8.7 Hz, 5.7 Hz, 1H).

Step 8. Preparation of Enantiomerically-Enriched Tetrahydrobenzothiepine-1,1-Dioxide (4R,5R)

To a stirred solution of 13.44 g (31.07 mmol) of enantiomerically-enriched tetrahydrobenzothiepine-1-oxide (obtained from Step 7) in 150 mL of methylene chloride was added 9.46 g of 68% m-chloroperoxybenzoic acid (37.28 mmol, Sigma) at 0° C. After stirring at 0° C. for 2 hours, the mixture was allowed to warm up to room temperature and stirred for 4 hours. 50 mL of saturated $Na_2SO_3$ was added into the mixture and stirred for 30 minutes. The solution was then neutralized with 50 mL of saturated $NaHCO_3$ solution. The methylene chloride layer was separated, dried over $MgSO_4$, and concentrated in vacuo to give 13.00 g (97.5%) of the enantiomerically-enriched tetrahydrobenzothiepine-1,1-dioxide (4R,5R) as a light yellow solid: $^1H$ NMR ($CDCl_3$) δ 0.89–0.95 (m, 6H), 1.09–1.42 (m, 12H), 2.16–2.26 (m, 1H), 3.14 (q, J=15.6 Hz, 1H), 3.87 (s, 3H), 4.18 (s, 1H), 5.48 (s, 1H), 6.54 (dd, J 10.2 Hz, 2.4 Hz, 1H), 6.96–7.07 (m, 3H), 7.40 (d, J 8.1 Hz, 2H), 8.11 (dd, J=8.6 Hz, 5.9 Hz, 1H).

Step 9. Preparation of enantiomerically-enriched 7-(dimethylamino)tetrahydrobenzothiepine-1,1-dioxide (4R,5R)

To a solution of 13.00 g (28.98 mmol) of enantiomerically-enriched tetrahydrobenzothiepine-1,1-dioxide (obtained from Step 8) in 73 mL of dimethylamine (2.0 M in THF, 146 mmol) in a Parr Reactor was added about 20 mL of neat dimethylamine. The mixture was sealed and stirred at 110° C. overnight, and cooled to ambient temperature. The excess dimethylamine was evaporated. The crude oil was dissolved in 200 mL of ethyl acetate and washed with 100 mL of water, dried over $MgSO_4$ and concentrated in vacuo. Purification on a silica gel column (Waters Prep 500) using 20% ethyl acetate/hexane gave 12.43 g (90.5%) of the enantiomerically-enriched 7-(dimethylamino) tetrahydrobenzothiepine-1,1-dioxide (4R,5R) as a colorless solid: $^1H$ NMR ($CDCl_3$) δ 0.87–0.93 (m, 6H), 1.10–1.68 (m, 12H), 2.17–2.25 (m, 1H), 2.81 (s, 6H), 2.99 (d, J=15.3 Hz, 1H), 3.15 (d, J=15.3 Hz, 1H), 3.84 (s, 3H), 4.11 (d, J=7.5 Hz, 1H), 5.49 (s, 1H), 5.99 (d, J=2.4 Hz, 1H), 6.51 (dd, J=8.7 Hz, 2.4 Hz, 1H), 6.94 (d, J=8.7 Hz, 2H), 7.42 (d, J=8.4 Hz, 2H), 7.90 (d, J=8.7 Hz, 1H). The product was determined to have 78% e.e. by chiral HPLC on a Chiralpak AD column using 5% ethanol/hexane as the eluent. Recrystallization of this solid from ethyl acetate/hexane gave 1.70 g of the racemic product. The remaining solution was concentrated and recrystallized to give 9.8 g of colorless solid. Enantiomeric excess of this solid was determined by chiral HPLC on a Chiralpak AD column using 5% ethanol/hexane as the eluent. It showed to have 96% e.e with the first eluting peak as the major product.

Step 10: Demethylation of 5-(4'-methoxyphenyl)-7-(dimethylamino)tetrahydrobenzothiepine-1,1-dioxide (4R, 5R)

To a solution of 47 g (99 mmol) of enantiomeric-enriched (dimethylamino)tetrahydrobenzothiepine-1,1-dioxide (obtained from Step 9) in 500 mL of methylene chloride at −10 ° C. was added dropwise a solution of boron tribromide (297 mL, 1M in methylene chloride, 297 mmol), and the resulting solution was stirred cold (−5° C. to 0° C.) for 1 hour or until the reaction was complete. The reaction was cooled in an acetone-dry ice bath at −10° C., and slowly quenched with 300 mL of water. The mixture was warmed to 10° C., and further diluted with 300 mL of saturated sodium bicarbonate solution to neutralize the mixture. The aqueous layer was separated and extracted with 300 mL of methylene chloride, and the combined extracts were washed with 200 mL of water, brine, dried over $MgSO_4$ and concentrated in vacuo. The residue was dissolved in 500 mL of ethyl acetate and stirred with 50 mL of glacial acetic acid for 30 minutes at ambient temperature. The mixture was washed twice with 200 mL of water, 200 mL of brine, dried over $MgSO_4$ and concentrated in vacuo to give the crude 4-hydroxyphenyl intermediate. The solid residue was recrystallized from methylene chloride to give 37.5 g (82%) of the desired 5-(4'-hydroxyphenyl)-7-(dimethylamino) tetrahydrobenzothiepine-1,1-dioxide as a white solid: $^1H$ NMR ($CDCl_3$) 50.84–0.97 (m, 6H), 1.1–1.5 (m, 10H), 1.57–1.72 (m, 1H), 2.14–2.28 (m, 1H), 2.83 (s, 6H), 3.00 (d, J=15.3 Hz, 1H), 3.16 (d, J=15.3 Hz, 1H), 4.11 (s, 2H), 5.48 (s, 1H), 6.02 (d, J=2.4 Hz, 1H), 6.55 (dd, J=9, 2.4 Hz, 1H), 6.88 (d, 8,7 Hz, 2H), 7.38 (d, J=8.7 Hz, 2H), 7.91 (d, J=9 Hz, 2H).

Alternatively, enantiomeric-enriched 5-(4'-hydroxyphenyl)-7-(dimethylamino) tetrahydrobenzothiepine-1,1-dioxide, the intermediate just described, can be prepared via non-enantioselective synthesis followed by chiral chromatography separation. Oxidation of aryl-3-hydroxypropylsulfide (obtained from Step 4) with m-chloroperbenzoic acid (under the similar conditions as in Step 8, but with 2.2 equivalent of m-CPBA) gave the racemic sulfone intermediate. The sulfone was carried through the synthetic sequences (under the same conditions as in Step 7 and Step 9) to give the racemic 5-(4'-hydroxyphenyl)-7-(dimethylamino) tetrahydrobenzothiepine-1,1-dioxide. The two enantiomers were further separated into the desired enantiomeric-enriched 5-(4'-hydroxyphenyl)-7-(dimethylamino) tetrahydrobenzothiepine-1,1-dioxide by appropriate chiral chromatographic purification.

Step 11: Preparation of Ester Intermediate

To a solution of 1.0 g (2.18 mmol) of 5-(4'-hydroxyphenyl)-7-(dimethylamino)tetrahydrobenzo-thiepine-1,1-dioxide (obtained from Step 10) in 10 mL dimethylformamide was added 60 mg (2.38 mmol) of 95% sodium hydride and stirred for 15 minutes. To the reaction mixture was added 400 μL (2.52 mmol) of benzyl 2-bromoacetate and stirred for two hours. Water was added to the reaction mixture, extracted with ethyl acetate, washed with brine, dried over magnesium sulfate, filtered and the solvent evaporated to afford 1.30 g (98%) of the ester intermediate: $^1H$ NMR ($CDCl_3$) δ 0.88–0.94 (m, 6H), 1.13–1.46 (m, 10H), 1.60–1.64 (m, 1H), 2.20–2.24 (m, 1H), 2.81 (s, 6H), 3.00 (d, J=15.1 Hz, 1H), 3.16 (t, J=15.1 Hz, 1H), 4.11 (s, 1H), 5.26 (s, 2H), 5.49 (s, 1H), 6.04 (d, J=2.4 Hz, 1H), 6.63 (dd, J=8.9, 2.4 Hz, 1H), 6.95 (d, J=8.7 Hz, 2H), 7.37 (s, 5H), 7.42 (d, J=8.5 Hz, 2H), 7.93 (d, J=8.9 Hz, 1H).

Step 12: Preparation of Acid

A solution of 1.30 g (2.14 mmol) of ester intermediate (obtained from Step 1) in 40 mL ethanol with 10% palladium on carbon was placed under an atmosphere of hydrogen gas (40 psi) for three hours. The reaction mixture was filtered through celite and the solvent was evaporated to afford the desired title compound as a white solid: mp 119–123° C.; $^1H$ NMR ($CDCl_3$) δ 0.89–0.94 (m, 6H), 1.19–1.43 (m, 10H), 1.61–1.65 (m, 1H), 2.17–2.21 (m, 1H), 2.85 (s, 6H), 3.02 (d, J=15.1 Hz, 1H), 3.17 (t, J=14.9 Hz, 1H), 4.12 (s, 1H), 4.72 (s, 2H), 5.51 (s, 1H), 6.17 (s, 1H), 6.74 (d, J=9.1 Hz, lH), 6.99 (d, J=8.3 Hz, 2H), 7.46 (d, J=8.5 Hz, 2H), 7.97 (d, J=8.7 Hz, 1H). HRMS. Calc'd for $C_{28}H_{40}NO_6S$: 518.2576. Found: 518.2599.

Example 1403

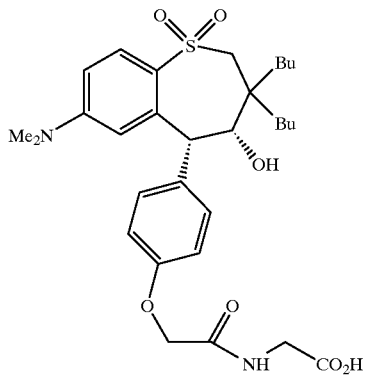

(4R-cis)-N-[[4-[3,3-Dibutyl-7-(dimethylamino)-2,3,4,5-tetrahydro-4-hydroxy-1,1-dioxido-1-benzothiepin-5-yl]phenoxyacetyl]glycine Step 1: Preparation of Glycine Ester Intermediate To a solution of 6.4 g (13.9 mmol) of 5-(4'-hydroxyphenyl)-7-(dimethylamino)tetrahydrobenzothiepine-1,1-dioxide (obtained from Example 1402, Step 10) and 2.9 g (21.0 mmol) of potassium carbonate in 100 ml of acetone was added 3.8 g (21.0 mmol) of N-(chloroacetyl)glycine ethyl ester and 50 mg (0.14 mmol) of tetrabutylammonium iodide. The reaction was heated to reflux for 2 days, cooled to ambient temperature and stirred for 20 hours, then partitioned between ethyl acetate and water. The organic layer was washed with brine, dried over $MgSO_4$, and concentrated in vacuo. Purification by silica gel chromatography (Waters Prep-500) using 50% ethyl acetate/hexanes afforded 7.5 g (90%) of glycine ester intermediate as a white foam: $^1$H NMR ($CDCl_3$) δ 0.86–0.98 (m, 6H), 1.04–1.56 (m, 13H), 1.58–1.71 (m, 1H), 2.14–2.29 (m, 1H), 2.73 (s, 6H), 3.08 ($AB_q$, $J_{AB}$=15.3 Hz, J=48.9 Hz, 2H), 4.06–4.19 (m, 6H), 4.25 (q, J=7.0 Hz, 2H), 4.57 (s, 2H), 5.50 (s, 1H), 5.98 (s, 1H), 6.56 (d, J=8.6 Hz, 1H), 6.98 (d, J=8.5 Hz, 2H), 7.17 (s, 1H), 7.47 (d, J=8.3 Hz, 2H), 7.91 (d, J=8.7 Hz, 1H).

Step 2: Preparation of Acid

A solution of 7.3 g (12.1 mmol) of glycine ester intermediate (obtained from Step 1) and 1.5 g $LiOH \cdot H_2O$ (36.3 mmol) in 60 mL of THF and 60 mL of water was heated to 45° C. for 2 hours. This was then cooled to ambient temperature, acidified with 1 N HCl and partitioned between ethyl acetate and water. The organic layer was washed with brine, dried over $MgSO_4$, and concentrated in vacuo. Purification by recrystallization from ethyl acetate gave 5.45 g (78%) of the desired title compound as a white crystalline solid: mp 149–150° C.; $^1$H NMR ($CD_3OD$) δ 0.88–0.98 (m, 6H), 1.06–1.56 (m, 10H), 1.70–1.84 (m, 1H), 2.06–2.20 (m, 1H), 2.79 (s, 6H), 3.11 ($AB_q$, $J_{AB}$=15.3 Hz, J=21.6 Hz, 2H), 4.01 (s, 2H), 4.07 (s, 1H), 4.61 (s, 2H), 5.31 (s, 1H), 6.04 (s, 1H), 6.57 (d, J=9.0 Hz, 1H), 7.08 (d, J=7.8 Hz, 2H), 7.44 (d, J=8.1 Hz, 2H), 7.76 (d, J=9.0 Hz, 1H), 8.42 (m, 1H). HRMS(ES+) Calc'd for $C_{30}H_{42}N_2O_7S$: 575.2712. Found: 575.2790. Anal. Calc'd for: $C_{30}H_{42}N_2O_7S$ C, 62.69; H, 7.37; N, 4.87. Found: C, 62.87; H, 7.56; N, 4.87.

Example 1404

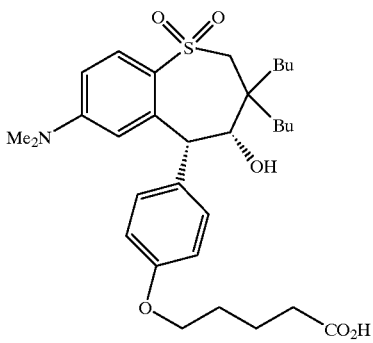

(4R-cis)-5-[4-[3,3-Dibutyl-7-(dimethylamino)-2,3,4,5-tetrahydro-4-hydroxy-1,1-dioxido-1-benzothiepin-5-yl]phenoxy]pentanoic acid Step 1: Preparation of Ester Intermediate A solution of 5-(4'-hydroxyphenyl)-7-(dimethylamino)tetrahydrobenzothiepine-1,1-dioxide (1.0 g, 2.2 mmol, obtained from Example 1402, Step 10) in acetone (10 mL) at 25° C. under $N_2$ was treated with powdered $K_2CO_3$ (0.45 g, 3.3 mmol, 1.5 eq.), benzyl 5-bromovalerate (0.88 g, 3.3 mmol, 1.5 eq.) and a catalytic amount of tetra-n-butylammonium iodide (2 mg), and the resulting solution was stirred at 65° C. for 24 hours. The pale amber slurry was cooled to 25° C. and was concentrated in vacuo to provide a yellow residue. Purification by flash chromatography (2.4×30 cm silica, 20–40% EtOAc/hexane) afforded the ester intermediate (1.2 g, 86%) as a colorless oil: $^1$H NMR (CDCl$_3$) δ 0.91 (m, 6H), 1.11–1.47 (br m, 10H), 1.64 (m, 1H), 1.86 (m, 2H), 2.21 (m, 1H), 2.47 (m, 2H), 2.81 (s, 6H), 3.05 (ABq, J=15.1 Hz, J=47.7 Hz, 2H), 4.10 (d, J=7.9 Hz, 1H), 5.13 (s, 2H), 5.47 (s, 1H), 6.00 (d, J=2.5 Hz, 1H), 6.50 (dd, J=8.9, 2.5 Hz, 1H), 6.91 (d, J=8.7 Hz, 2H), 7.36 (m, 5H), 7.40 (d, J=8.5 Hz, 2H), 7.86 (d, J=8.9 Hz, 1H); HRMS. Calc'd for $C_{38}H_{51}NO_6S$: 650.3515. Found: 650.3473.

Step 2: Preparation of Acid

A solution of the ester intermediate (0.99 g, 1.5 mmol, obtained from Step 1) in ethanol (7.5 mL) at 25° C. was treated with 5% palladium on carbon (0.15 g, 10 wt %) then stirred under an atmosphere (1 atm) of $H_2$ via hydrogen balloon. Every 10 min, hydrogen gas was bubbled through the slurry for 1 min, for a total reaction time of 4 hours. The slurry was placed under an atmosphere of $N_2$ and nitrogen was bubbled through the reaction mixture for 10 min. The mixture was filtered through a plug of Celite® (10 g) and concentrated in vacuo to give a white foam. Purification by flash chromatography (2.6×25 cm silica, 1.5% EtOH/CH$_2$Cl$_2$) afforded the desired title compound (0.54 g, 63%) as a white foam: mp: 76–79° C.; $^1$H NMR (CDCl$_3$) δ 0.90 (m, 6H), 1.10–1.46 (br m, 10H), 1.62 (m, 1H), 1.87 (m, 4H), 2.20 (m, 1H), 2.45 (m, 2H), 2.81 (s, 6H), 3.05 (ABq, J=15.1 Hz, J=49.7 Hz, 2H), 4.00 (s, 2H), 4.09 (s, 1H), 5.45 (s, 1H), 5.99 (d, J=2.4 Hz, 1H), 6.48 (dd, J=8.9, 2.4 Hz, 1H), 6.91 (d, J=8.7 Hz, 2H), 7.39 (m, 5H), 7.39 (d, J=8.3 Hz, 2H), 7.84 (d, J=8.9 Hz, 1H); HRMS. Calc'd for $C_{31}H_{45}NO_6S$: 560.3046. Found: 560.3043.

Example 1405

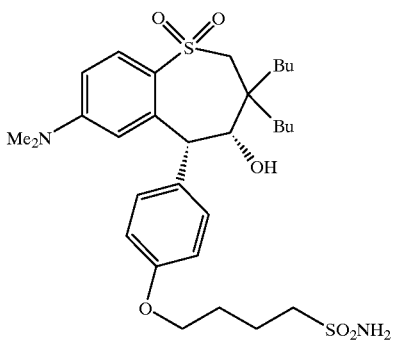

(4R-cis)-4-[4-[3,3-Dibutyl-7-(dimethylamino)-2,3,4,5-tetrahydro-4-hydroxy-1,1-dioxido-1-benzothiepin-5-yl]phenoxy-1-butanesulfonamide Step 1: Preparation of Sulfonic Acid Intermediate A solution of 7.4 g (16.1 mmol) of 5-(4'-hydroxyphenyl)-7-(dimethylamino)tetrahydrobenzothiepine-1,1-dioxide (obtained from Example 1402, Step 10) in acetone (35 mL) at 25° C. under $N_2$ was treated with powdered potassium carbonate (3.3 g, 24.1 mmol, 1.5 equiv.) and 1,4-butane sultone (2.5 mL, 24.1 mmol, 1.5 equiv.) and stirred and heated at 65° C. for 64 h. The solution was allowed to cool to 25° C. and quenched by the addition of water (50 mL), until a homogeneous mixture was obtained. The clear and colorless solution was added dropwise to a 4 N HCl solution cooled to 0° C. over a 30 min period. The mixture was vigorously stirred for 4 h then allowed to warm to ambient temperature and stirred for an additional 16 h. The resultant white precipitate was filtered and washed with water and dried in vacuo to provide 8.8 g (92%) of the desired sulfonic acid as a white solid. A portion of the white solid was recrystallized from CH$_3$CN/hexane to give the desired sulfonic acid as colorless needles: mp 229–236° C. (decomposed); $^1$H NMR (DMSO-d$_6$) δ 0.82 (m, 6H), 1.02–1.33 (br m, 10H), 1.59 (m, 1H), 1.73 (m, 4H), 2.00 (s, 1H), 2.48 (m, 2H), 2.71 (s, 6H), 2.98 (s, 1H), 3.86 (s, 1H), 3.93 (m, 2H), 5.08 (s, 1H), 5.89 (s, 1H), 6.52 (dd, J=8.9, 2.4 Hz, 1H), 6.92 (d, J=8.3 Hz, 2H), 7.29 (d, J=8.1 Hz, 2H), 7.60 (d, J=8.9 Hz, 1H); Anal. Calc'd for $C_{30}H_{45}NO_7S_2$: C, 60.48; H, 7.61; N, 2.35. Found: C, 60.53; H, 7.70; N, 2.42.

Step 2: Preparation of 7-(dimethylamino)-benzothiepin-5-yl]phenoxy-1-butanesulfonamide To a solution of 1.12 g (1.88 mmol) of the sulfonic acid (obtained from Step 1) in 10 mL CH$_2$Cl$_2$ was added 785 mg (3.77 mmol) PCl$_5$ and stirred for 1 hour. Water was added and the mixture was extracted and washed with brine. Dried with MgSO$_4$, filtered and solvent evaporated. To the residue was added 30 mL of 0.5M NH$_3$ in dioxane and stirred 16 hours. The precipitate was filtered and the solvent evaporated. The residue was purified by MPLC (33% EtOAc in hexane) to afford the desired title compound as a beige solid (125 mg, 11%): mp 108–110° C.; $^1$H NMR (CDCl$_3$) δ 0.85–0.93 (m, 6H), 1.13–1.59 (m, 10H), 1.60–1.67 (m, 1H), 1.94–2.20 (m, 5H), 2.82 (s, 6H), 2.99 (d, J=15.3 Hz, 1H), 3.15 (t, J=15.3 Hz, 1H), 3.23 (t, J=7.7 Hz, 2H), 4.03 (t, J=5.8 Hz, 2H), 4.08–4.10 (m, 1H), 4.79 (s, 2H), 5.47 (s, 1H), 6.02 (d, J=2.4 Hz, 1H), 6.52 (dd, J=8.9, 2.6 Hz, 1H), 6.91 (d, J=8.9 Hz, 2H), 7.41 (d, J=8.5 Hz, 2H), 7.89 (d, J=8.9 Hz, 1H). HRMS. Calc'd for $C_{30}H_{47}N_2O_6S_2$: 595.2876. Found: 595.2874.

Example 1406

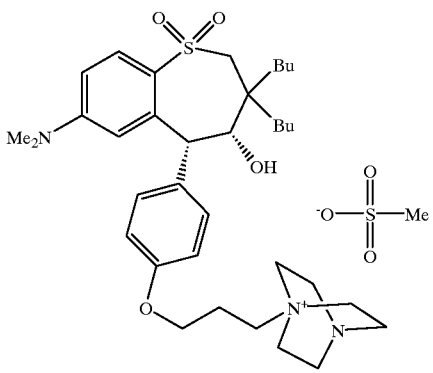

(4R-cis)-1-[3-[4-3, 3-Dibutyl-7-(dimethylamino)-2,
3,4,5-tetrahydro-4-hydroxy-1,1-dioxido-1-
benzothiepin-5-yl]phenoxy]propyl]-4-aza-1-
azoniabicyclo[2.2.2]octane, methanesulfonate (salt)

Step 1: Preparation of Dimesylate Intermediate

To a cooled (−20° C.) solution of 5.0 g (65.7 mmol) of 1,3-propanediol in 50 mL of triethylamine and 200 mL of methylene chloride was added 15.8 g (137.9 mmol) of methanesulfonyl chloride. The mixture was stirred for 30 minutes, then warmed to ambient temperature and partitioned between ethyl acetate and 1N HCl. The organic layer was washed with brine, dried over $MgSO_4$, and concentrated in vacuo to give 13.5 g (89%) of dimesylate intermediate as a clear yellowish oil: $^1H$ NMR ($CDCl_3$) δ 2.12 (quintet, J=4.5 Hz, 4H), 3.58 (s, 6H), 4.38 (t, J=5.4 Hz)

Step 2: Preparation of Propyl Mesylate Intermediate

To a solution of 2.4 g (5.2 mmol) of 5-(4'-hydroxyphenyl)-7-(dimethylamino) tetrahydrobenzothiepine-1,1-dioxide (obtained from Example 1402, Step 10) and 6.0 g (26.1 mmol) of dimesylate intermediate (obtained from Step 1) in 50 mL of acetone was added 3.6 g (26.1 mmol) of $K_2CO_3$. The reaction was heated to reflux overnight then cooled to ambient temperature and concentrated in vacuo. The residue was partitioned between ethyl acetate and water. The organic layer was washed with brine, dried over $MgSO_4$, and concentrated in vacuo. Purification by silica gel chromatography (Waters-Prep 500) using 36% ethyl acetate/hexanes afforded 2.8 g (90%) of the propyl mesylate intermediate as a white foam: $^1H$ NMR ($CDCl_3$) δ 0.86–0.95 (m, 6H), 1.06–1.52 (m, 10H), 1.57–1.70 (m, 1H), 2.14–2.32 (m, 3H), 2.84 (s, 6H), 3.02 (s, 3H), 3.08 ($AB_q$, $J_{AB}$=15.0 Hz, J=46.9 Hz, 4.09–4.18 (m, 3H), 4.48 (t, J=6.0 Hz, 2H), 5.49 (s, 1H), 6.11 (s, 1H), 6.65 (d, J=8.7 Hz, 1H), 6.94(d, J=8.6 Hz, 2H), 7.43 (d, J=8.5 Hz, 2H), 7.94 (d, J=8.9 Hz, 1H).

Step 3: Preparation of Quaternary Salt

To a solution of 1.2 g (2.0 mmol) of propyl mesylate intermediate (obtained from Step 2) in 20 ml of acetonitrile was added 0.3 g (2.9 mmol) of 1,4-diazabicyclo[2.2.2] octane (DABCO). The reaction mixture was stirred at 60° C. for three hours, then cooled to ambient temperature and concentrated in vacuo. Purification by trituration with methylene chloride/ethyl ether gave 1.3 g (91%) of the desired title compound as a white solid: mp. (dec) 230–235° C.; $^1H$ NMR ($CDCl_3$) δ 0.86–0.95 (m, 6H), 1.04–1.52 (m, 10H), 1.57–1.70 (m, 1H), 2.12–2.25 (m, 3H), 2.28–2.39 (m, 2H), 2.83 (s, 6H), 3.04 (s, 3H), 3.09 ($AB_q$, $J_{AB}$=15.6 Hz, J=42.2 Hz, 2H) 3.22–3.32 (m, 6H), 3.56–3.66 (m, 6H), 3.73–3.83 (m, 2H), 4.06–4.17 9m, 3H), 5.47 (s, 1H), 5.97 (s, 1H), 6.51 (d, J=8.6 Hz, 1H), 6.90 (d, J=8.6 Hz, 2H), 7.41 (d, J=8.7 Hz, 2H), 7.89 (d, J=8.9 Hz, 1H). MS (ES+) m/e 612.4. HRMS (ES+) Calc'd for $C_{35}H_{54}N_3O_4S^+$: 612.3835. Found: 612.3840.

Example 1407

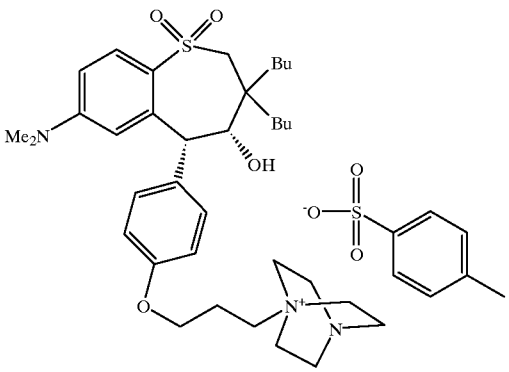

(4R-cis)-1-[3-[4-[3,3-Dibutyl-7-(dimethylamino)-2,
3,4,5-tetrahydro-4-hydroxy-1,1-dioxido-1-
benzothiepin-5-yl]phenoxy]propyl]-4-aza-1-
azoniabicyclo[2.2.2]octane,4-
methylbenzenesulfonate (salt)

Step 1: Preparation of Propyl Tosylate Intermediate

A solution of 5-(4'-hydroxyphenyl)-7-(dimethylamino) tetrahydrobenzothiepine-1,1-dioxide (5.0 g, 10.9 mmol, obtained from Example 1402, Step 10) in acetone (100 mL) at 25° C. under $N_2$ was treated with powdered $K_2CO_3$ (3.8 g, 27.2 mmol, 2.5 eq.) and 1,3-propanediol di-p-tosylate (13.0 g, 32.6 mmol, 3.0 eq.), and the resulting mixture was stirred at 65° C. for 21 hours. The cream-colored slurry was cooled to 25° C. and was filtered through a sintered glass funnel. The filtrate was concentrated and the residue was dissolved in EtOAc (150 mL). The organic layer was washed with saturated aqueous $NaHCO_3$ (2×150 mL) and saturated aqueous NaCl (2×150 mL), and was dried ($MgSO_4$) and concentrated in vacuo to provide a pale orange oil. Purification by flash chromatography (4.4×35 cm silica, 20–30% EtOAc/hexane) afforded the propyl tosylate intermediate (6.0 g, 80%) as a white foam: $^1H$ NMR ($CDCl_3$) δ 0.91 (m, 6H), 1.11–1.47 (br m, 10H), 1.63 (m, 1H), 2.14 (m, 2H), 2.21 (m, 1H), 2.41 (s, 3H), 2.81 (s, 6H), 3.06 (ABq, J=15.1 Hz, J=49.0 Hz, 2H), 4.01 (t, J=5.3 Hz, 2H), 4.10 (m, 1H), 4.26 (t, J=5.9 Hz, 2H), 5.29 (s, 1H), 5.48 (s, 1H), 5.98 (s, 1H), 6.51 (dd, J=8.9, 1.8 Hz, 1H), 6.83 (d, J=8.4 Hz, 2H), 7.30 (d, J=8.1 Hz, 2H), 7.39 (d, J=8.3 Hz, 2H), 7.78 (d, J=8.3 Hz, 2H), 7.88 (d, J=8.9 Hz, 1H)

Step 2: Preparation of Quaternary Salt

A solution of the propyl tosylate intermediate (1.05 g, 1.56 mmol, obtained from Step 1) in acetonitrile (15 mL) at 25° C. under $N_2$ was treated with diazabicyclo[2.2.2]octane (DABCO, 0.26 g, 2.34 mmol, 1.5 eq.) and stirred at 50° C. for 6 hours, then at 25° C. for 14 hours. The pale amber solution was cooled to 25° C. and concentrated in vacuo to provide an amber oil. The residue was dissolved in a minimal amount of $CH_2Cl_2$ (5 mL) and diluted with $Et_2O$ (100 mL) while vigorously stirring for 4 hours, during which time a white solid precipitated. The white solid was collected ($Et_2O$ wash) to give the desired title compound (1.11 g, 90%) as a white amorphous solid: mp 136.5–142° C. (decomposed); $^1H$ NMR ($CDCl_3$) δ 0.89 (m, 6H), 1.12–1.43 (br m, 9H), 1.61 (m, 1H), 1.65 (m, 1H), 2.18 (m, 1H), 2.22

(m, 2H), 2.27 (s, 3H), 2.78 (s, 6H), 3.07 (ABq, J=15.1 Hz, J=39.5 Hz, 2H), 3.49 (br s, 6H), 3.68 (m, 1H), 3.74 (br s, 6H), 3.96 (br s, 2H), 4.09 (d, J=7.3 Hz, 1H), 5.46 (s, 1H), 5.96 (d, J=2.4 Hz, 1H), 6.49 (dd, J=8.9, 2.4 Hz, 1H), 6.83 (d, J=8.5 Hz, 2H), 7.11 (d, J=8.1 Hz, 2H), 7.40 (d, J=8.3 Hz, 2H), 7.74 (d, J=8.1 Hz, 2H), 7.87 (d, J=8.9 Hz, 1H); HRMS. Calc'd for $C_{35}H_{54}N_3O_4S$: 612.3835. Found: 612.3832.

Example 1408

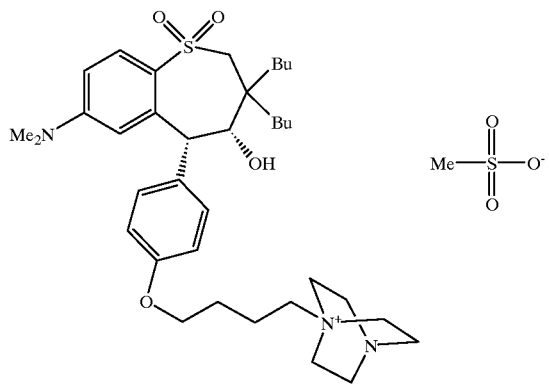

(4R-cis)-1-[4-[4-[3,3-Dibutyl-7-(dinmethylamino)-2,3,4,5-tetrahydro-4-hydroxy-1,1-dioxido-1-benzothiepin-5-yl]phenoxy]butyl]-4-aza-1-azoniabicyclo[2.2.2]octanemethanesulfonate (salt)

Step 1: Preparation of Butyl Mesylate Intermediate

A mixture of 1.00 g (2.18 mmol) of 5-(4'-hydroxyphenyl)-7-(dimethylamino)tetrahydrobenzo-thiepine-1,1-dioxide (obtained from Example 1402, Step 10), 2.68 g (10.88 mmol) of busulfan, and 1.50 g (10.88 mmol) of potassium carbonate in 20 mL of acetone was stirred at reflux overnight. The mixture was concentrated in vacuo and the crude was dissolved in 30 mL of ethyl acetate. The insoluble solid was filtered off and the filtrate was concentrated in vacuo. The resulting white foam was chromatographed through silica gel column, and eluted with 30% ethyl acetate/hexane to give 1.02 g (77%) of butyl mesylate intermediate as a white solid: $^1$H NMR (CDCl$_3$) δ 0.90 (m, 6H), 1.20–1.67 (m, 12H), 1.98 (m, 4H), 2.22 (m, 1H), 2.83 (s, 6H), 3.04 (s, 3H), 3.08 (ABq, 2H), 4.05 (t, J=5.55 Hz, 2H), 4.11 (d, J=6.90 Hz, 1H), 4.35 (t, J=6.0 Hz, 2H), 5.49 (s, 1H), 6.00 (d, J=2.4 Hz, 1H), 6.52 (dd, J=9.0 Hz, 2.7 Hz, 1H), 6.93 (d, J=9.0 Hz, 2H), 7.42 (d, J=8.4 Hz, 2H), 7.90 (d, J=9.0 Hz, 1H)

Step 2: Preparation of Ester Intermediate

A solution of 520 mg (0.85 mmol) of butyl mesylate intermediate (obtained from Step 1) and 191 mg (1.71 mmol) of DABCO in 10 mL of acetonitrile was stirred at 80° C. for 4 hours. The reaction mixture was concentrated in vacuo to yield a white foam. The foam was crushed and washed with ether. The solid was filtered off and dried in vacuo to give 540 mg (88%) of the desired title compound which was recrystallized from methylene chloride and acetone as a white solid: mp 248–251° C.; $^1$H NMR (CDCl$_3$) δ 0.91 (m, 6H), 1.14–1.47 (m, 14H), 1.63 (m, 1H), 1.96 (m, 4H), 2.21 (m, 1H), 2.77 (s, 3H), 2.82 (s, 3H), 3.07 (ABq, 2H), 3.26 (t, J=7.1 Hz, 6H), 3.60 (m, 8H), 4.08 (m, 3H), 5.47 (s, 1H), 5.99 (d, J=2.4 Hz, 1H), 6.51 (dd, J=8.9 Hz, 2.6 Hz, 1H), 6.91 (d, J=8.7 Hz, 2H), 7.41 (d, J=8.1 Hz, 2H), 7.89 (d, J=9.0 Hz, 1H).

Example 1409

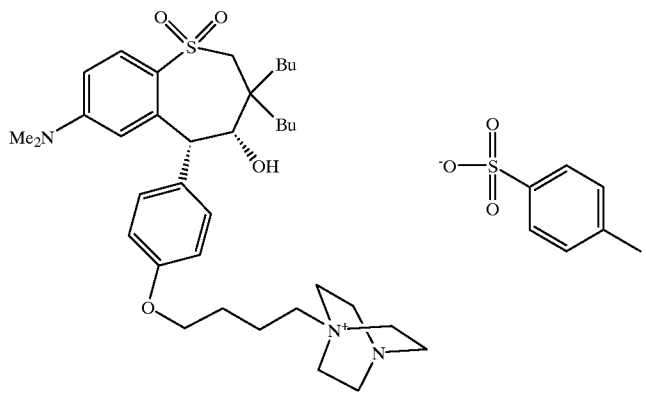

(4R-cis)-1-[4-[4-[3,3-Dibutyl-7-(dimethylamino)-2,3,4,5-tetrahydro-4-hydroxy-1,1-dioxido-1-benzothiepin-5-yl]phenoxy]butyl]-4-aza-1-azoniabicyclo[2.2.2]octane-4-methylbenzenesulfonate (salt)

Step 1: Preparation of Propyl Tosylate Intermediate

A solution of 5-(4'-hydroxyphenyl)-7-(dimethylamino) tetrahydrobenzothiepine-1,1-dioxide (5.0 g, 10.9 mmol, obtained from Example 1402, Step 10) in acetone (100 mL) at 25° C. under N$_2$ was treated with powdered K$_2$CO$_3$ (3.8 g, 27.2 mmol, 2.5 eq.) and 1,4-butanediol di-p-tosylate (13.0 g, 32.6 mmol, 3.0 eq.), and the resulting solution was stirred at 65° C. for 21 hours. The cream-colored slurry was cooled to 25° C. and filtered through a sintered glass funnel. The filtrate was concentrated and the residue was dissolved in EtOAc (150 mL). The organic layer was washed with saturated aqueous NaHCO$_3$ (2×150 mL) and saturated aqueous NaCl (2×150 mL). The extract was dried (MgSO$_4$) and concentrated in vacuo to provide a pale orange oil. Purification by flash chromatography (4.4×35 cm silica, 20–30% EtOAc/hexane) afforded the propyl tosylate intermediate (6.0 g, 80%) as a white foam: $^1$H NMR (CDCl$_3$) δ 0.89 (m, 6H), 1.10–1.44 (br m, 10H), 1.61 (m, 1H), 1.84 (m, 4H), 2.19 (m, 1H), 2.43 (s, 3H), 2.80 (s, 6H), 3.03 (ABq, J=15.1 Hz, J=46.3 Hz, 2H), 3.93 (m, 2H), 4.06–4.13 (m, 4H), 5.44 (s, 1H), 5.96 (s, 1H), 6.46 (dd, J=8.9, 1.4 Hz, 1H), 6.85 (d, J=8.1 Hz, 2H), 7.33 (d, J=8.1 Hz, 2H), 7.38 (d, J=8.1 Hz, 2H), 7.78 (d, J=8.9 Hz, 2H), 7.83 (m, 1H).

Step 2: Preparation of Quaternary Salt

A solution of propyl tosylate intermediate (5.8 g, 8.5 mmol, obtained from Step 1) in acetonitrile (100 mL) at 25° C. under $N_2$ was treated with diazabicyclo[2.2.2]octane (DABCO, 1.1 g, 10.1 mmol, 1.2 eq.) and stirred at 45° C. for 6 hours. The pale yellow solution was cooled to 25° C. and concentrated in vacuo to provide an off-white solid. The residue was dissolved in a minimal amount of $CH_2Cl_2$ (5 mL) and diluted with $Et_2O$ (100 mL) while vigorously stirring for 3 hours, during which time a white solid precipitated. The white solid was collected and recrystallized from EtOAc/hexane to give the desired title compound (5.7 g, 85%) as colorless needles: mp 223–231° C. (decomposed); $^1H$ NMR ($CDCl_3$) δ 0.86 (m, 6H), 1.09–1.43 (br m, 12H), 1.61–1.90 (br m, 5H), 2.13 (m, 1H), 2.25 (s, 3H), 2.75 (s, 6H), 3.03 (ABq, J=15.1 Hz, J=30.0 Hz, 2H), 3.05 (br s, 6H), 3.37 (br s, 6H), 3.89 (m, 2H), 4.07 (d, J=7.5 Hz, 1H), 5.39 (s, 2H), 5.97 (d, J=1.6 Hz, 1H), 6.44 (dd, J=8.9, 2.0 Hz, 1H), 6.87 (d, J=8.3 Hz, 2H), 7.08 (d, J=8.1 Hz, 2H), 7.37 (d, J=8.3 Hz, 2H), 7.71 (d, J=8.1 Hz, 2H), 7.80 (d, J=8.9 Hz, 1H); HRMS. Calc'd for $C_{36}H_{56}N_3O_4S$: 626.3992. Found: 626.3994. Anal. Calc'd for $C_{43}H_{63}N_3O_7S_2$: C, 64.71; H, 7.96; N, 5.27. Found: C, 64.36; H, 8.10; N, 5.32.

Example 1410

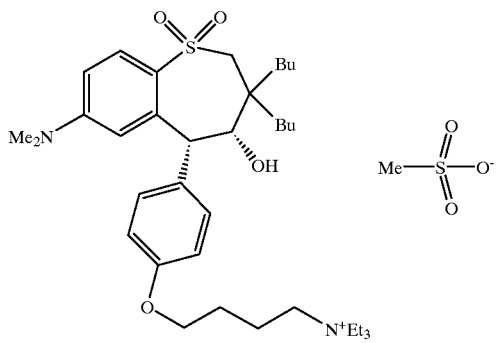

(4R-cis)-4-[4-[3,3-Dibutyl-7-(dimethylamino)-2,3,4,
5-tetrahydro-4-hydroxy-1,1-dioxido-1-benzothiepin-
5-yl]phenoxy]-N,N,N-triethyl-1-butanaminium A solution of 1 g (1.64 mmol) of the butyl mesylate intermediate (obtained from Example 1408, Step 1) and 15 mL of triethylamine in 10 mL of acetonitrile was heated at 50° C. for 2 days. The solvent was evaporated and the residue was triturated with ether and ethyl acetate to afford 500 mg (43%) of product as a semi-solid. $^1H$ NMR ($CDCl_3$) δ 0.8 (m, 6 H), 1–1.6 (m, 24 H), 2.1 (m, 1 H), 2.6 (s, 3 H), 2.7 (s, 6 H), 2.9 (d, J=15 Hz, 1 H), 3.0 (d, J=15 Hz, 1 H), 3.3 (m, 8 H), 4.0 (m, 4 H), 5.3 (s, 1 H), 5.9 (s, 1 H), 6.4 (m, 1 H), 6.8 (d, J=9 Hz, 2 H), 7.4 (d, J 9 Hz, 2 H), 7.8 (d, J 7 Hz, 1 H). MS m/e 615.

Example 1411

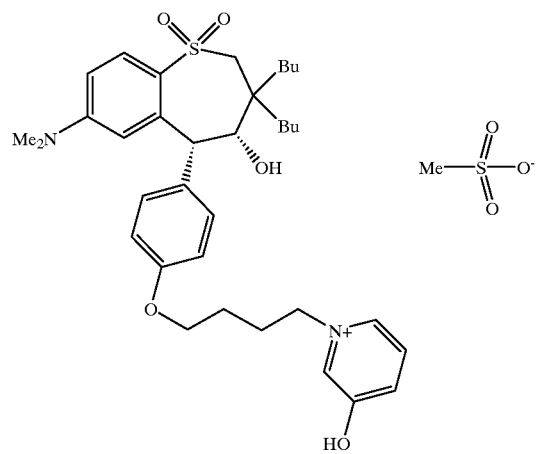

(4R-cis)-1-[4-[4-[3,3-Dibutyl-7-(dimethylamino)-2,
3,4,5-tetrahydro-4-hydroxy-1,1-dioxido-1-
benzothiepin-5-yl]phenoxy]butyl]-3-
hydroxypyridinium, methanesulfonate (salt)

A solution of 1 g (1.64 mmol) of the butyl mesylate intermediate (obtained from Example 1408, Step 1) and 234 mg (2.46 mmol) of 3-hydroxy pyridine in 1 mL of dimethylformamide was heated at 70° C. for 20 hours. The solvent was evaporated and the residue was triturated with ether and ethyl acetate to afford 990 mg (86%) of product as a semi-solid: $^1H$ NMR ($CDCl_3$) δ 0.9 (m, 6 H), 1–1.5 (m, 10 H), 1.7 (m, 1 H), 1.9 (m, 2 H), 2–2.4 (m, 3 H), 2.9 (s, 6 H), 3.1 (d, J=15 Hz, 1 H), 3.2 (d, J=15 Hz, 1 H), 4.1 (m, 3 H), 4.7 (m, 2 H), 5.5 (s, 1 H), 6.1 (s, 1 H), 6.6 (m, 1 H), 6.9 (d, J=9 Hz, 2 H), 7.4 (d, J=9 Hz, 2 H), 7.7 (m, 1 H), 8.0 (m, 2 H), 8. 2 (m, 1 H), 9.1 (s, 1 H). MS m/e 609.

Example 1412

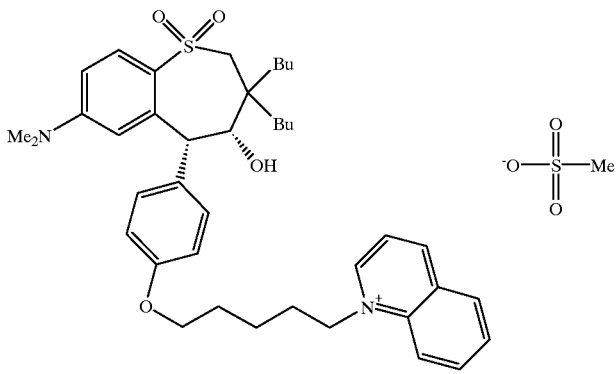

(4R-cis)-1-[5-[4-[3,3-Dibutyl-7-(dimethylamino)-2,
3,4,5-tetrahydro-4-hydroxy-1,1-dioxido-1-
benzothiepin-5-yl]phenoxy]pentyl]quinolinium,
methanesulfonate (salt)

Step 1: Preparation of Pentyl Mesylate Intermediate

To a stirred solution of 231 mg (5.79 mmol, 60% disp.) of NaH in 22 mL of DMF was added 2.05 g (4.45 mmol) of 5-(4'-hydroxyphenyl)-7-(dimethylamino) tetrahydrobenzothiepine-1,1-dioxide (obtained from Example 1402, Step 10), and the resulting solution was stirred at ambient temperature for 1 hour. To the mixture was added 18.02 g (55.63 mmol) of 1,5-diiodopentane and the solution was stirred overnight at ambient temperature. DMF was removed by high vacuum and the residue was extracted with ethyl acetate and washed with brine. The extract was dried over $MgSO_4$, and the concentrated residue was purified by column chromatography to give the pentyl mesylate intermediate: $^1$H NMR ($CDCl_3$) δ 0.90(q, 6H), 1.05–2.0 (m, 17H), 2.2 (t, 1H), 2.8 (s, 6h), 3.0 (q, 2H), 3.22 (t, 2H), 3.95 (t, 2H), 4.1 (s, 1H), 5.42 (s, 1H), 6.1 (d, 1H), 6.6 (d, 1H), 6.9 (d, 2H), 7.4 (d, 2H), 7.9 (d, 1H).

Step 2: Preparation of Quaternary Salt

To 1.0 g (1.53 mmol) of the pentyl mesylate intermediate (obtained from Step 1) was added 3.94 g (30.5 mmol) of quinoline and 30 mL of acetonitrile. The solution was heated at 45° C. under $N_2$ for 10 days. The concentrated residue was purified by reverse phase C18 column chromatography. The obtained material was exchanged to its mesylate anion by ion exchange chromatography to give the desired title compound as a solid: mp 136° C.; $^1$H NMR ($CDCl_3$) δ 0.95(q, 6H), 1.05–2.25 (m, 18H), 2.8 (s, 9H), 3.0 (q, 2H), 3.95 (t, 2H), 4.1 (s, 1H), 5.28 (t, 2H), 5.42 (s, 1H), 5.95 (s, 1H), 6.45 (d, 1H), 6.82 (d, 2H), 7.4 (d, 2H), 7.82 (d, 1H), 7.9 (t, 1H), 8.2 (t, 2H), 8.3 (q, 2H), 8.98 (d, 1H), 10.2 (d, 1H). HRMS. Calc'd for $C_{40}H_{53}N_2O_4S$: 657.3726. Found: 657.3736. Anal. Calc'd for $C_{40}H_{53}N_2O_4S \cdot CH_3O_3S$: C, 65.40; H, 7.50; N, 3.72; S, 8.52. Found: C, 62.9; H, 7.42; N, 3.56; S, 8.41.

Example 1413

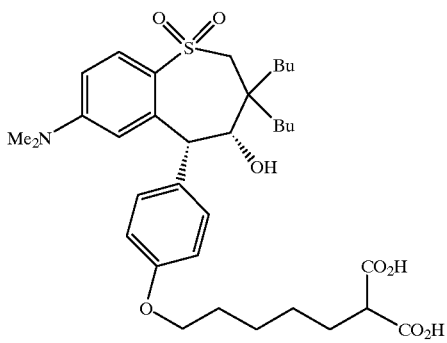

(4S-cis)-[5-[4-[3,3-Dibutyl-7-(dimethylamino)-2,3,4,
5-tetrahydro-4-hydroxy-1,1-dioxido-1-benzothiepin-
5-yl]phenoxy]pentyl]propanedioic acid Step 1: Preparation of Pentyl Bromide Intermediate To a stirred solution of 0.63 g (15.72 mmol, 60% disp) of NaH in 85 mL of DMF was added 6.0 g (13.1 mmol) of 5-(4'-hydroxyphenyl)-7-(dimethylamino) tetrahydrobenzothiepine-1,1-dioxide (obtained from Example 1402, Step 10), and the resulting solution was stirred at ambient temperature for 1 hour. To the solution was added 37.7 g (163.75 mmol) of 1,5-dibromopentane, and the mixture was stirred overnight at ambient temperature. DMF was removed in vacuo and the residue was extracted with ethyl acetate and washed with brine. The extract was dried over $MgSO_4$, and the concentrated residue was purified by column chromatography to give the pentyl bromide intermediate: $^1$H NMR ($CDCl_3$) δ 0.90 (q, 6H), 1.05–2.0 (m, 17H), 2.2 (t, 1H), 2.8 (s, 6H), 3.0 (q, 2H), 3.4 (t, 2H), 3.95 (t, 2H), 4.1 (s, 1H), 5.42 (s, 1H), 6.0 (s, 1H), 6.5 (d, 1H), 6.9 (d, 2H), 7.4 (d, 2H), 7.9 (d, 1H).

Step 2: Preparation of Dibenzyl Ester Intermediate

To the mixture of 59 mg (1.476 mmol, 60% disp) of NaH in 27 mL of THF and 9 mL of DMF at 0° C. was added 0.84 g (2.952 mmol) of dibenzyl malonate (Aldrich), and the resulting solution was stirred at ambient temperature for 15 min. To the solution was added 0.5987 g (0.984 mmol) of the pentyl bromide intermediate, and the mixture was stirred at 80 ° C. overnight. Solvent was removed in vacuo, and the residue was extracted with methylene chloride and washed with brine. The extract was dried over $MgSO_4$, and the concentrated residue was purified by column chromatography to give the dibenzyl ester intermediate: ¹H NMR (CDCl₃) δ 0.90 (q, 6H), 1.05–2.0 (m, 19H), 2.2 (t, 1H), 2.8 (s, 6H), 3.0 (q, 2H), 3.4 (t, 1H), 3.9 (t, 2H), 4.1 (d, 1H), 5.18 (s, 4H), 5.42 (s, 1H), 5.95 (s, 1H), 6.5 (d, 1H), 6.9 (d, 2H), 7.2–7.4 (m, 12H), 7.85 (d, 1H).

Step 3: Preparation of Diacid

A suspension of 0.539 g (0.664 mmol) of the dibenzyl ester intermediate (obtained from Step 2) and 25 mg of 10% Pd/C in 30 mL of ethanol was agitated at ambient temperature under 20 psi of hydrogen gas for 2 hours. The catalyst was filtered off, and the filtrate was concentrated to give the desired title compound as a solid: mp 118° C.; ¹H NMR (CDCl₃) δ 0.9 (d, 6H), 1.05–2.2 (m, 20H), 2.8 (s, 6H), 3.0 (q, 2H), 3.4 (s, 1H), 3.95 (s, 2H), 4.1 (s, 1H), 5.42 (s, 1H), 5.95 (s, 1H), 6.5 (d, 1H), 6.9 (d, 2H), 7.4 (d, 2H), 7.85 (d, 1H). HRMS. Calc'd for C₃₄H₄₉NO₈S: 632.3257. Found: 632.3264. Anal. Calc'd for C₃₄H₄₉NO₈S: C, 64.63; H, 7.82; N, 2.22; S, 5.08. Found: C, 63.82; H, 7.89; N, 2.14; S, 4.93.

Example 1414

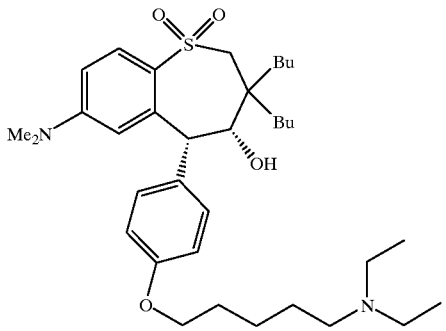

(4R-cis)-3,3-Dibutyl-5-[4-[[5-(diethylamino)pentyl]oxy]phenyl]-7-(dimethylamino)-2,3,4,5-tetrahydro-1-benzothiepin-4-ol 1,1-dioxide Step 1: Preparation of Pentyl Iodide Intermediate To a solution of 5-(4'-hydroxyphenyl)-7-(dimethylamino)tetrahydrobenzothiepine-1,1-dioxide (3 g, 6.53 mmol, obtained from Example 1402, Step 10) in 100 mL of dimethylformamide was added 198 mg (7.83 mmol) of 95% sodium hydride. The mixture was stirred 15 minutes at room temperature and diiodopentane was added. After one hour at room temperature the mixture was diluted in ethyl acetate and water. The aqueous layer was extracted with ethyl acetate and the combined organic layer was washed with brine, dried over magnesium sulfate and concentrated in vacuo. The residue was chromatographed over silica gel, eluting with hexane/ethyl acetate (1/5) to afford 2.92 g (4.46 mmol) of the pentyl iodide intermediate: ¹H NMR (CDCl₃) δ 0.9 (m, 6 H), 1–1.5 (m, 11 H), 1.6 (m, 3 H), 1.8 (m, 4 H), 2.2 (m, 1 H), 2.8 (s, 6 H), 3.0 (d, J=15 Hz, 1 H), 3.2 (d, J=15 Hz, 1 H), 3.3 (m, 2 H), 4.0 (m, 1 H), 4.1 (s, 1 H), 5.5 (s, 1 H), 6.1 (s, 1 H), 6.6 (m, 1 H), 6.9 (d, J=9 Hz, 2 H), 7.4 (d, J 9 Hz, 2 H), 7.9 (d, J=7 Hz, 1 H).

Step 2: Preparation of Amine

A solution of 550 mg (0.76 mmol) of the pentyl iodide intermediate (obtained from Step 1) and 279 mg (3.81 mmol) of diethylamine in 3 mL of acetonitrile was stirred at 100° C. overnight. The mixture was concentrated in vacuo to yield a yellowish brown foam. The foam was dissolved in 10 mL of ethyl acetate and washed with 50 mL of saturated sodium carbonate solution twice. The ethyl acetate layer was dried over magnesium sulfate and concentrated to yield 390 mg (85%) of the desired title compound as a yellow foamy solid: ¹H NMR (CDCl₃) δ 0.89 (m, 6H), 1.20–1.47 (m, 12H), 1.53–1.67 (m, 4H), 1.76–1.90 (m, 8H), 2.21 (m, 1H), 2.74–2.92 (m, 12H), 3.07 (ABq, 2H), 4.00 (t, J=6.3 Hz, 2H), 4.10 (d, J=7.8 Hz, 1H), 5.48 (s, 1H), 6.00 (d, J=2.4 Hz, 1H), 6.51 (dd, J=9.2 Hz, 2.6 Hz, 1H), 6.92 (d, J=8.7 Hz, 2H), 7.41 (d, J=8.4 Hz, 2H), 7.90 (d, J=9.0 Hz, 1H).

Example 1415

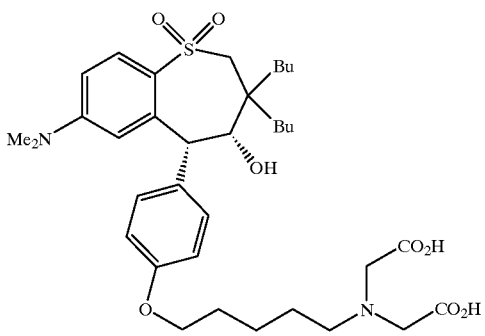

(4R-cis)-N-(Carboxymethyl)-N-[5-[4-[3,3-dibutyl-7-(dimethylanino)-2,3,4,5-tetrahydro-4-hydroxy-1,1-dioxido-1-benzothiepin-5-yl]phenoxy]pentyl]glycine Step 1: Preparation of Diester Intermediate A mixture of 8.6 g (14.1 mmol) of pentyl bromide intermediate (obtained from Example 1413, Step 1), 65 g (0.35 mol) of diethylaminodiacetate and 7.5 g (71 mmol) of anhydrous Na₂CO₃ was stirred at 160° C. for 3 hours. The reaction mixture was diluted with water and extracted with methylene chloride. The volatiles was removed in vacuo to give 9.6 g (95%) of the diester intermediate. ¹H NMR spectrum was consistent with the structure; MS (M+H) m/e 717.

Step 2: Preparation of Diacid

The mixture of the diester intermediate (obtained from Step 1) and 2.7 g (64.3 mmol) of LiOH in THF (75 mL) and water (50 mL) was stirred at 40° C. for 18 hours. The reaction mixture was acidified with 1% HCl and extracted with dichloromethane. The residue was triturated with hexane, filtered to give 8.9 g (93%) of the desired title compound as a solid: mp 148–162 0C.; ¹H NMR (CD₃OD) δ 0.92 (t, 6H), 1.1–1.9 (m, 31H), 2.15 (t, 1H),2.8(s, 6H), 3.15 (ABq, 2H), 3.75(m, 1H), 4.1 (m, 6H), 5.3(s, 1H), 6.1 (s, 1H), 6.6 (d, 1H), 7.0(d, 2H), 7.4 (d, 2H), 7.8 (d, 1H); MS (M+H) m/e 661. Anal. Calc'd for [C₃₅H₅₂N₂O₈S+1.5H₂O]: C,61.11; H,8.06; N,4.07; S,4.66. Found: C,61.00; H,7.72; N,3.89; S,4.47.

Example 1416

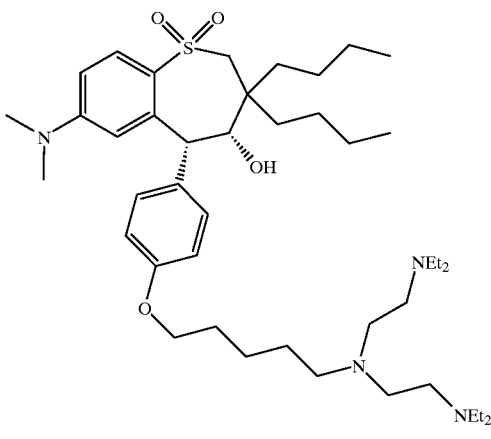

(4R-cis)-5-[4-[[5-[bis[2-(Diethylamino)ethyl] amino]pentyl]oxy]phenyl]-3,3-dibutyl-7-(dimethylamino)-2,3,4,5-tetrahydro-1-benzothiepin-4-ol 1,1-dioxide A solution of 1 g of pentyl iodide intermediate (1.53 mmol, obtained from Example 1414, Step 1) in N,N,N',N'-tetraethyl diethylenetriamine was heated to 80° C. for 4 hours. The mixture was dissolved in ethyl acetate and saturated NaHCO₃. The organic layer was washed with brine, dried over magnesium sulfate, and concentrated in vacuo. The residue was purified by reverse phase chromatography. The fractions containing the product were concentrated in vacuo, dissolved in ethyl acetate and washed with saturated NaHCO₃. The residue was dried and concentrated in vacuo to afford 840 mg (74%) of the desired title compound as a thick oil. $^1$H NMR (CDCl₃) δ 0.8 (m, 6 H), 1–1.6 (m, 28 H), 1.8 (m, 2 H), 2.1 (m, 1 H), 2.5 (m, 18 H), 2.7 (s, 6 H), 2.9 (d, J=15 Hz, 1 H), 3.1 (d, J=15 Hz, 1 H), 3.9 (m, 2 H), 4.0 (m, 1 H), 4.1 (s, 1 H), 5.4 (S, 1 H), 6.0 (s, 1 H), 6.4 (m, 1 H), 6.9 (d, J=9 Hz, 2 H), 7.4 (d, J=9 Hz, 2 H), 7.8 (d, J=7 Hz, 1 H). MS (M+H) m/e 743.

Example 1417

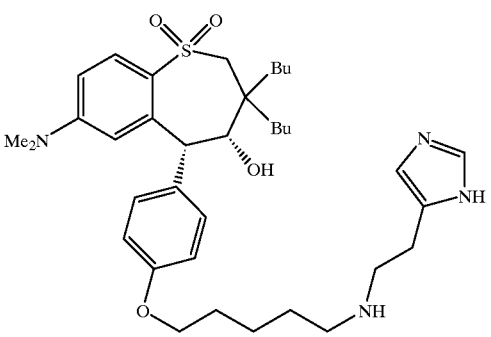

(4R-cis)-3,3-Dibutyl-7-(dimethylamino)-2,3,4,5-tetrahydro-5-[4-[[5-[[2-(1H-imidazol-4-yl) ethyl] amino]pentyl]oxy]phenyl]-1-benzothiepin-4-ol 1,1-dioxide A solution of 1 g of pentyl iodide intermediate (1.53 mmol, obtained from Example 1414, Step 1) and 3.4 g (30.6 mmol) of histamine was heated to 50° C. for 17 hours. The mixture was dissolved in ethyl acetate and saturated NaHCO₃. The organic layer was washed with brine, dried over magnesium sulfate, and concentrated in vacuo. The residue was triturated with ether to afford 588 mg (60%) of the desired title compound as a semi-solid: $^1$H NMR (CDCl₃) δ 0.9 (m, 6 H), 1–1. 7 (m, 14 H), 1.9 (m, 3 H), 2.0 (m, 2 H), 2.2 (m, 1 H), 2.8 (s, 6 H), 3.0 (m, 3 H), 3.2 (m, 2 H), 4.0 (m, 2 H), 4.1 (m, 3 H), 5.5 (s, 1 H), 6.0 (s, 1 H), 6.5 (m, 1 H), 6.8 (s, 1 H), 6.9 (d, J=9 Hz, 2 H), 7.4 (m, 3 H), 7.9 (d, J=8 Hz, 1 H). MS (M+H) m/e 639.

Example 1418

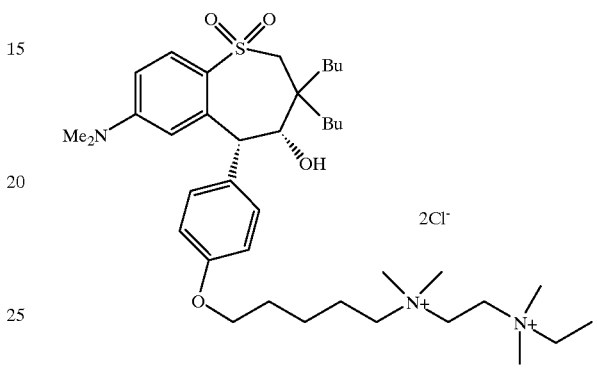

(4R-cis)-N-[5-[4-[3,3-Dibutyl-7-(dimethylamino)-2,3,4,5-tetrahydro-4-hydroxy-1,1-dioxido-1-benzothiepin-5-yl]phenoxy]pentyl]-N'-ethyl-N,N,N', N'-tetramethyl-1,2-ethanediaminium dichloride Step 1: Preparation of Pentyl Bromide Intermediate A mixture of 5-(4'-hydroxyphenyl)-7-(dimethylamino) tetrahydrobenzothiepine-1,1-dioxide (1.680 g, 3.66 mmol, obtained from Example 1402, Step 10) and sodium hydride (0.250 g, 6.25 mmol) in 30 mL of DMF was stirred in a dry 100 mL round-bottom flask under N₂. To this solution was added 1,5-dibromopentane (6.0 mL/44.0 mmol), and the resulting mixture was stirred for 18 hours. The reaction was diluted with brine (100 mL) and H₂O (20 mL), and the mixture was extracted with EtOAc (3×50 mL). Organic layers were combined, dried (MgSO₄), filtered and concentrated in vacuo. Purification by filtration through silica gel eluting with 20% EtOAc/hexane and evaporation in vacuo gave pentyl bromide intermediate as a white foamy solid (1.783 g, 80%): $^1$H NMR (CDCl₃) δ 0.84–0.95 (m, 6H), 1.02–1.56 (m, 10H), 1.58–1.70 (m, 3H), 1.78–2.03 (m, 4H), 2.15–2.24 (m, 1H), 2.77 (s, 1H), 2.80 (s, 6H), 3.05 (ABq, 2H), 3.42 (t, 2H), 3.98 (t, 2H), 4.10 (s, 1H), 5.47 (s, 1H), 5.99 (d, 1H), 6.50 (dd, 1H), 6.91 (d, 2H), 7.40 (d, 2H), 7.88 (d, 1H).

Step 2: Preparation of Mono-Quaternary Salt

The mixture of pentyl bromide intermediate (0.853 g, 1.40 mmol, obtained from Step 1), N,N,N',N'-tetramethylethylenediamine (1.0 mL/6.62 mmol) in 30 mL of acetonitrile was stirred at 40° C. for 12 hours, and the reaction mixture was concentrated in vacuo to give an off-white foamy solid (1.052 g). The crude product was dissolved in acetonitrile (1.5 mL) and triturated with ethyl ether. The solvent was decanted to yield a sticky solid. This trituration method was repeated twice, and the resulting sticky solid was concentrated in vacuo to give the mono-quaternary salt as an off-white foamy solid (0.951 g, 94%): $^1$H NMR (CDCl₃) δ 0.81 (t, 6H), 0.96–1.64 (m, 13H), 1.62–1.85 (m, 4H), 2.03–2.18 (m, 1H), 2.20 (s, 6H), 2.67 (t, 2H), 2.74 (s, 6H), 2.98 (ABq, 2H), 3.30–3.42 (m, 1H), 3.38 (s, 6H), 3.60–3.75 (m, 4H), 3.90 (t, 2H), 4.01 (s, 1H), 5.37 (s, 1H), 5.92 (s, 1H), 6.41 (dd, 1H), 6.81 (d, 2H), 7.32 (d, 2H), 7.77 (d, 1H).

Step 3: Preparation of Di-Quaternary Salt

The mono-quaternary salt (0.933 g, 1.29 mmol, obtained from Step 2), iodoethane (0.300 mL/3.75 mmol), and acetonitrile (30.0 mL) were combined in a 4 oz. Fischer Porter bottle. The reaction vessel was purged with $N_2$, sealed, equipped with magnetic stirrer, and heated to 50° C. After 24 hours, the reaction mixture was cooled to ambient temperature and concentrated in vacuo to give a yellow foamy solid (1.166 g). The solid was dissolved in methylene chloride/acetonitrile and precipitated with ethyl ether. After cooling to 0° C. overnight, the resulting solid was filtered, washed with ethyl ether and concentrated in vacuo to yield the di-quaternary salt as an off-white solid (1.046 g, 92%): $^1$H NMR (CD$_3$OD) δ 0.59 (t, 6H), 0.70–1.10 (m, 9H), 1.16 (t, 3H), 1.22–1.80 (m, 9H), 2.42 (s, 6H), 2.78 (d, 2H), 2.98 (s, 6H), 3.02 (s, 6H), 3.22–3.37 (m, 4H), 3.63–3.78 (m, 4H), 3.80 (s, 4H), 4.93 (s, 1H), 5.71 (s, 1H), 6.22 (dd, 1H), 6.61 (d, 2H), 7.02 (d, 2H), 7.40 (d, 1H).

Step 4: Preparation of Quaternary Di-Chloride Salt

The iodobromosalt (obtained from Step 3) was converted to its corresponding dichloride salt using Biorad AG 2×8 resin and eluting with 70% H$_2$O/acetonitrile to give the desired title compound as a white foamy solid (0.746 g, 84%): mp 193.0–197.0 ° C.; $^1$H NMR (CD$_3$OD) δ 0.59 (t, J=6.0 Hz, 6H), 0.70–1.12 (m, 9H), 1.16 (t, J=6.6 Hz, 3H), 1.24–1.90 (m, 9H), 2.50 (s, 6H), 2.78 (s, 2H), 3.08 (s, 6H), 3.11 (s, 6H), 3.24–3.50 (m, 4H), 3.68 (s, 2H), 3.81 (s, 2H), 4.16 (s, 4H), 5.02 (s, 1H), 5.72 (s, 1H), 6.19 (d, J=8.4 Hz, 1H), 6.61 (d, J=8.1 Hz, 2H), 7.10 (d, J=7.8 Hz, 2H), 7.46 (d, J=8.7 Hz, 1H). HRMS. Calc'd for C$_{39}$H$_{67}$N$_3$O$_4$SCl: 708.4541. Found: 708.4598.

tetramethyl-1,6-hexanediamine (0.100 g, 0.580 mmol) in 5 mL of acetonitrile were placed in a 4 oz. Fischer Porter bottle. The reaction vessel was purged with $N_2$, sealed, equipped with magnetic stirrer and heated to 50° C. After 15 hours, the reaction mixture was cooled to ambient temperature and concentrated in vacuo to give an off-white foamy solid (1.141 g). The solid was dissolved in acetonitrile and precipitated with ethyl ether. After cooling to 0° C., the solvent was decanted to yield a sticky off-white solid. This trituration method was repeated, and the resulting sticky solid was concentrated in vacuo to give the desired dibromide salt as an off-white foamy solid (0.843 g, quantitative): $^1$H NMR (CDCl$_3$) δ 0.85 (m, 12H), 1.01–1.70 (m, 30H), 1.76–2.08 (m, 12H), 2.18 (t, J=12.3 Hz, 2H), 2.79 (s, 12H), 3.03 (ABq, 4H), 3.35 (s, 12H), 3.52 (br s, 6H), 3.72 (br s, 4H), 3.97 (br s, 4H), 4.08 (br s, 2H), 5.42 (s, 2H), 6.00 (s, 2H), 6.51 (d, J=9.0 Hz, 2H), 6.86 (d, J=7.8 Hz, 4H), 7.38 (d, J=7.8 Hz, 4H), 7.83 (d, J=8.7 Hz, 2H). The dibromide salt was converted to its corresponding dichloride salt using Biorad AG 2×8 resin and eluting with 70% H$_2$O/CH$_3$CN to give the desired title compound as a white foamy solid (0.676 g, 86%): mp 178.0–182.0° C.; $^1$H NMR (CDCl$_3$) δ 0.80–0.90 (m, 12H), 1.01–1.70 (m, 30H), 1.75–2.06 (m, 12H), 2.16 (t, J=12.9 Hz, 2H), 2.79 (s, 12H), 3.03 (ABq, 4H), 3.33 (s, 12H), 3.49 (br s, 6H), 3.70 (br s, 4H), 3.96 (t, J=5.4 Hz, 4H), 4.08 (s, 2H), 5.42 (s, 2H), 5.986 (s, 1H), 5.993 (s, 1H), 6.49 (d, J=9.0 Hz, 1H), 6.50 (d, J=9.0 Hz, 1H), 6.87 (d, J=8.4 Hz, 4H), 7.38 (d, J=8.1 Hz, 4H), 7.84 (d, J=8.7 Hz, 2 H). HRMS. Calc'd for C$_{36}$H$_{58}$N$_2$O$_4$S: 614.4118. Found: 614.4148.

Example 1419

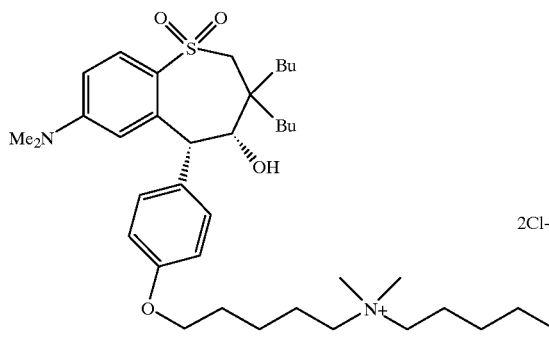

[4R-[4a,5a(4R*,5R*)]]-N,N'-bis[5-[4-[3,3-Dibutyl-7-(dimethylamino)-2,3,4,5-tetrahydro-4-hydroxy-1,1-dioxido-1-benzothiepin-5-yl]phenoxy]pentyl]-N,N,N'N'-tetramethyl-1,6-hexanediaminium dichloride The pentyl bromide intermediate (1.002 g, 1.64 mmol, obtained from Example 1418, Step 1) and N,N,N',N'-

Example 1420

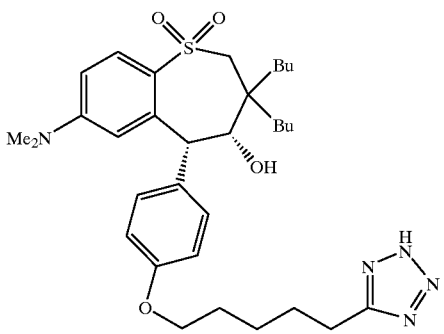

(4R-cis)-3,3-Dibutyl-7-(dimethylamino)-2,3,4,5-tetrahydro-5-[4-[[5-(1H-tetrazol-5-yl)pentyl]oxy]phenyl]-1-benzothiepin-4-ol 1,1-dioxide Step 1: Preparation of Pentyl Bromide Intermediate To a stirred suspension of 1.01 g (25.4 mmol, 60% oil dispersion) of sodium hydride in 150 mL of DMF was added 9.0 g (19.5 mmol) of 5-(4'-hydroxyphenyl)-7-(dimethylamino)tetrahydrobenzothiepine-1,1-dioxide (obtained from Example 1402, Step 10) in portions. After 30 minutes the reaction was cooled in a water bath (15° C.) and 4.48 g (195 mmol) of 1,5-dibromopropane was added. The reaction was stirred at ambient temperature for 1.5 hours and quenched with 50 mL of saturated $NH_4Cl$. The reaction was diluted with ethyl acetate, washed with water, brine, dried over $MgSO_4$, filtered and concentrated in vacuo. Purification by silica gel chromatography (Waters-Prep 500) using 25% ethyl acetate/hexanes afforded 10.17 g (85%) of the pentyl bromide intermediate as a colorless foam: mp 65–70° C.; $^1H$ NMR ($CDCl_3$) δ 0.84–0.98 (M, 6H), 1.04–1.52 (m, 10H), 1.58–1.65 (m, 3H), 1.82 (p, J=6.8 Hz, 2H), 1.94 (p, J=7.0 Hz, 2H), 2.12–2.26 (m, 1H), 2.82 (s, 6H), 3.06 ($AB_q$, $J_{AB}$=15.2, 45.3 Hz, 2H), 3.44 (t, J=6.7 Hz, 2H), 3.99 (t, J=6.3 Hz, 2H), 4.10 (s, 1H), 5.47 (s, 1H), 6.15 (d, J=2.7 Hz, 1H), 6.68 (dd, J=2.5, 8.4 Hz, 1H), 6.91 (d, J=8.4 Hz, 2H), 7.39 (d, J=8.4 Hz, 2H), 7.93 (d, J=8.7 Hz, 1H).

Step 2: Preparation of Pentyl Nitrile Intermediate

To a stirred solution of 378 mg (0.621 mmol) of the pentyl bromide intermediate (obtained from Step 1) in 1 mL of DMSO was added 37 mg (0.745 mmol) of sodium cyanide. The reaction was stirred at ambient temperature for 16 hours. The reaction was concentrated under a nitrogen stream and the residue partitioned between ethyl acetate and water. The organic layer was washed with brine, dried over $MgSO_4$, filtered, and concentrated in vacuo to afford 278 mg (93% RPHPLC purity, ca. 75%) of the pentyl nitrile intermediate as a colorless foam: $^1H$ NMR ($CDCl_3$) δ 0.86–0.96 (m, 6H), 1.02–1.21(m, 1H), 1.21–1.52 (m, 19H), 1.58–1.92 (m, 7H), 2.16–2.28 (m, 1H), 2.41 (t, J=6.9 Hz, 2H), 2.83 (s, 6H), 3.08 ($AB_q$, 15.0, 47.5 Hz, 2H), 4.01 (t, J=6.2 Hz, 2H), 4.1 (s, 1H), 5.49 (s, 1H), 6.07 (d, J=2.1 Hz, 1H), 6.59 (dd, J=2.4, 8.7 Hz, 1H), 6.92 (d, J=8.1 Hz, 2H), 7.42 (d, J=8.4 Hz, 2H), 7.92 (d, J=8.7 Hz, 1H). MS (ES, M+H) m/e 555.

Step 3: Preparation of Tetrazole

A solution of 275 mg (0.5 mmol) of the nitrile intermediate (obtained from Step 2) and 666 mg (3.23 mmol) of azidotrimethyltin in 5 mL of toluene was stirred with heating at 80° C. for 60 hours. The reaction was concentrated under a nitrogen stream. Purification by reversed phase chromatography (Waters-Delta prep) using 60% water/acetonitrile afforded 226 mg of the desired title compound (75%) as a colorless foam: mp 80–85° C.; $^1H$ NMR ($CDCl_3$) δ 0.83–0.95 (m, 6H), 1.30–1.52 (m, 10H), 1.52–1.73 (m, 3H), 1.79–1.99 (m, 4H), 2.14–2.26 (m, 1H), 2.91 (s, 6H), 3.02–3.22 (m, 4H), 3.92–4.06 (m, 2H), 4.16 (s, 1H), 5.47 (s, 1H), 6.28 (d, J=2.4 Hz, 1H), 6.74 (dd, J=2.7, 8.8 Hz, 1H), 6.89 (d, J=8.7 Hz, 2H), 7.37 (d, J=8.1 Hz, 2H), 7.98 (d, J=8.7 Hz, 1H). HRMS Calc'd for $C_{32}H_{48}N_5O_4S$: 598.3427. Found: 598.3443.

Example 1421

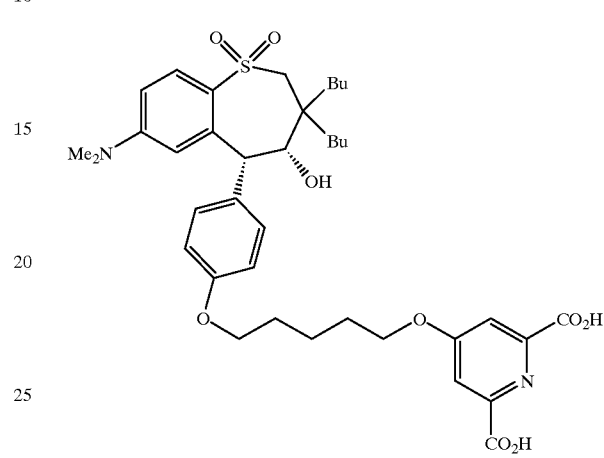

(4R-cis)-4-[[5-[4-[3,3-Dibutyl-7-(dimethylamino)-2,3,4,5-tetrahydro-4-hydroxy-1,1-dioxido-1-1benzothiepin-5-yl]phenoxy]pentyl]oxyl-2,6-pyridinecarboxylic acid Step 1: Preparation of Pentyl Bromide Intermediate To a solution of 0.63 g (15.72 mmol, 60% disp) of NaH in 85 mL of DMF was add 6.0 g (13.1 mmol) of 5-(4'-hydroxyphenyl)-7-(dimethylamino) tetrahydrobenzothiepine-1,1-dioxide (obtained from Example 1402, Step 10), and the resulting solution was stirred at ambient temperature for 1 hour. To the solution was added 37.7 g (163.75 mmol) of 1,5-dibromopentane, and stirred overnight at ambient temperature. DMF was removed in vacuo and the residue was extracted with ethyl acetate and washed with brine. The extract was dried over $MgSO_4$, and the concentrated residue was purified by column chromatography to give the pentyl bromide intermediate: $^1H$ NMR ($CDCl_3$) δ 0.90 (q, 6H), 1.05–2.0 (m, 17H), 2.2 (t, 1H), 2.8 (s, 6H), 3.0 (q, 2H), 3.4 (t, 2H), 3.95 (t, 2H), 4.1 (s, 1H), 5.42 (s, 1H), 6.0 (s, 1H), 6.5 (d, 1H), 6.9 (d, 2H), 7.4 (d, 2H), 7.9 (d, 1H).

Step 2: Esterification of Chelidamic Acid

A solution of 10 g (54.6 mmol) of chelidamic acid, 23.0 g (120.12 mmol) of 1-(3-dimethyl amino propyl)-3 ethyl carbodiimide hydrochloride, 1.33 g (10.8 mmol) of 4-dimethyl amino pyridine, and 12.4 mL (120.12 mmol) of benzyl alcohol in 100 mL of DMF was stirred at ambient temperature overnight under $N_2$. DMF was removed in vacuo and the residue was extracted with methylene chloride, washed with 5% $NaHCO_3$, 5% acetic acid, $H_2O$, and brine. The extract was dried over $MgSO_4$, and the concentrated residue was purified by column chromatography to give dibenzyl chelidamic ester: $^1H$ NMR ($CDCl_3$) δ 5.4 (s, 4H), 7.4 (m, 12H)

Step 3: Preparation of Pyridinyl Benzyl Ester Intermediate

A solution of 79 mg (1.972 mmol, 60% disp) of NaH and 0.716 g (1.972 mmol) of dibenzyl chelidamic ester (obtained from Step 2) in 17.5 mL of DMF was stirred at ambient temperature for 1 hour. To the solution was added 1.0 g (1.643 mmol) of the pentyl bromide intermediate and the mixture was stirred under $N_2$ overnight at 40° C. DMF was removed in vacuo, and the residue was extracted with ethyl acetate and washed with brine. The extract was dried over $MgSO_4$, and the concentrated residue was purified by column chromatography to give the pyridinyl dibenzyl ester intermediate: $^1$H NMR (CDCl$_3$) δ 0.90 (q, 6H), 1.05–2.0 (m, 19H), 2.2 (t, 1H), 2.8 (s, 6H), 3.0 (q, 2H), 4.0 (t, 2H), 4.1 (s, 1H), 5.4 (s, 4H), 5.42 (s, 1H), 6.0 (s, 1H), 6.5 (d, 1H), 6.9 (d, 2H), 7.3–7.5 (m, 12H), 7.78 (s, 2H), 7.9 (d, 1H).

Step 4: Preparation of Pyridinyl Diacid

A suspension of 0.8813 g (0.99 mmole) of dibenzyl ester (obtained from Step 3) and 40 mg of 10% Pd/C in 35 mL of ethanol and 5 mL of THF was agitated at ambient temperature under 20 psi of hydrogen gas for 2 hours. The catalyst was filtered off, and the filtrate was concentrated to give the desired title compound as a solid: mp 143° C.; $^1$H NMR (THF-d8) 0.95 (q, 6H), 1.05–1.65 (m, 15H), 1.9 (m, 4H), 2.22 (t, 1H), 2.8 (s, 6H), 3.0 (t, 2H), 4.1 (s, 3H), 4.3 (s, 2H), 5.4 (s, 1H), 6.05 (s, 1H), 6.5 (d, 1H), 6.9 (d, 2H), 7.4 (d, 2H), 7.78 (d, 1H), 7.82 (s, 2H). HRMS. Calc'd for $C_{38}H_{50}N_2O_9S$: 711.3315. Found: 711.3322. Anal. Calc'd for $C_{38}H_{50}N_2O_9S$: C, 64.20; H, 7.09; N, 3.94.; S, 4.51. Found: C, 62.34; H, 6.97; N, 4.01; S, 4.48.

Example 1422

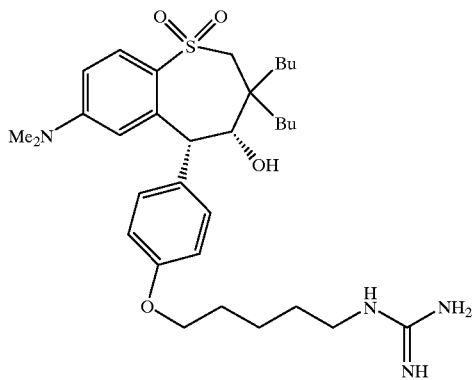

(4R-cis)-[5-[4-[3,3-Dibutyl-7-(dimethylamino)-2,3,4,5-tetrahydro-4-hydroxy-1,1-dioxido-1-benzothiepin-5-yl]phenoxy]pentyl]guanidine Step 1: Preparation of Pentyl Azide Intermediate To a stirred solution of 200 mg (0.328 mmol) of the pentyl bromide intermediate (obtained from Example 1420, Step 1) in 0.75 mL of DMSO was added 32 mg (0.493 mmol) of sodium azide and a catalytic amount of sodium iodide. The reaction was stirred at ambient temperature for 64 hours. The reaction was concentrated under a nitrogen stream and the residue partitioned between ethyl acetate and water. The organic layer was washed with brine, dried over $MgSO_4$, filtered, and concentrated in vacuo to afford 155 mg (92% RPHPLC purity, about 76% yield) of the pentyl azide intermediate as a colorless foam. Sample was used without further purification: mp 45–50 ° C.; $^1$H NMR (CDCl$_3$) δ 0.83–0 93 (m, 6H), 1.03–1.48 (m, 10H), 1.54–1.74 (m, 5H), 1.78–1.86 (m, 1H), 2.14–2.26 (m, 1H), 2.81 (s, 6H), 3.06 (AB$_q$, J$_{AB}$=15.0, 48.0 Hz, 2H), 3.31 (t, J=6.3 Hz, 2H), 3.98 (t, J=6.3 Hz, 2H), 4.09 (s, 1H), 5.47 (s, 1H), 6.10 (d, J=1.8 Hz, 1H), 6.63 (dd, J=2.7, 9.0 Hz, 1H), 6.91 (d, J=9.0 Hz, 2H), 7.39 (d, J=8.4 Hz, 2H), 7.91 (d, J=8.7 Hz, 1H). MS (FAB, M+H) m/e 571.

Step 2: Preparation of Pentyl Amine Intermediate

To a solution of 0.67 g (1.17 mmol) of the azide intermediate (obtained from Step 1) in 75 mL of ethanol was added 0.10 g of 10% palladium on carbon and the mixture shaken under 49 psi of hydrogen at ambient temperature for 3.5 hours. The reaction was filtered through celite and concentrated in vacuo to give 0.62 g (86% RPHPLC purity, ca. 84%) of pentyl amine intermediate as an off-white foam. The sample was used without further purification: mp 70–85° C.; $^1$H NMR (CDCl$_3$) δ 0.86–0.96 (m, 6H), 1.06–1.75 (m, 15H), 1.79–1.93 (m, 4H), 2.15–2.28 (m, 1H), 2.82 (s, 6H), 2.96–3.20 (m, 4H), 3.99 (t, J=6.0 Hz, 2H), 4.04–4.14 (m, 1H), 5.49 (s, 1H), 6.00 (d, J=1.5 Hz, 1H), 6.51 (d, J=9.0 Hz, 1H), 6.91 (d, J=8.4 Hz, 2H), 7.41 (d, J=8.1 Hz, 2H), 7.90 (d, J=8.7 Hz, 1H). MS (ES, M+H) m/e 545.

Step 3: Preparation of Guanidine

To a stirred solution of 258 mg (0.474 mmol) of pentyl amino intermediate (obtained from Step 2) and 81 mg (0.551 mmol) of 1H-pyrazole-1-carboxamidine hydrochloride in 1.5 mL of DMF was added 71 mg (0.551 mmol) of diisopropylethylamine. The reaction was stirred at ambient temperature for 16 hours. Purification by reversed phase chromatography (Waters-Delta prep) using 60% water/acetonitrile afforded 120 mg (43%) of the desired title compound as colorless foamy solid: mp 67.0–72.5° C.; 1H NMR (CDCl$_3$) δ 0.89–0.93 (m, 6H), 1.05–1.17 (m, 1H), 1.26–1.90 (m, 16H), 2.07–2.24 (m, 1H), 2.81 (s, 6H), 2.99–3.19 (m, 4H), 3.98 (br s, 2H), 4.12 (s, 1H), 5.46 (s, 1H), 6.01 (d, J=2.1 Hz, 1H), 6.51 (dd, J=2.1, 8.0 Hz, 1H), 6.92 (d, J=8.1 Hz, 2H), 7.41 (d, J=7.8 Hz, 2H), 7.89 (d, J=8.7 Hz, 1H). HRMS. Calc'd for $C_{32}H_{50}N_4O_4S$:586.3552. Found (M+H): 587.3620.

Example 1423

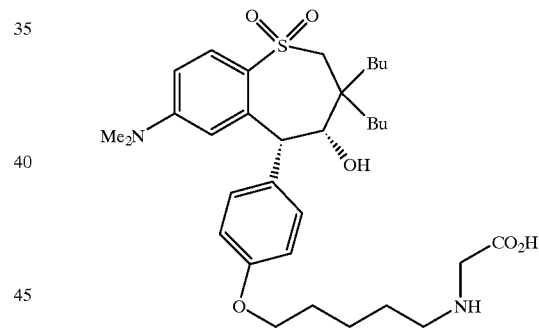

(4R-cis)-N-[5-[4-[3,3-Dibutyl-7-(dimethylamino)-2,3,4,5-tetrahydro-4-hydroxy-1,1-dioxido-1-benzothiepin- 5-yl]phenoxylpentyl]glycine Step 1: Preparation of Pentyl Azide Intermediate To a solution of pentyl bromide intermediate (400 mg, 0.657 mmol, obtained from Example 1420, Step 1) in dimethyl sulfoxide (20 mL) was added sodium azide (47 mg, 0.723 mmol, 1.1 eq), and the resulting clear solution was stirred at 23° C. for 16 h. The reaction solution was diluted with 100 mL ethyl acetate, then washed with water (2×100 mL) and brine (1×100 mL). The organic layer was dried (MgSO$_4$) and concentrated in vacuo to give 390 mg (quantitative) of pentyl azide intermediate as a yellow oil: $^1$H NMR (CDCl$_3$) δ 0.82–0.90 (m, 7H), 1.05–1.56 (m, 12H), 1.59–1.71 (m, 3H), 1.78–2.01 (m, 4H), 2.20 (t, J=8.3 Hz, 1H), 2.82 (s, 6H), 3.08 (q, 2H), 3.44 (t, J=7.7 Hz, 2H), 3.99 (t, J=7.7 Hz, 2H), 4.91 (br s, 1H), 5.47 (s, 1H), 6.13 (d, J=7.58 Hz, 1H), 6.68 (d, J=7.7 Hz, 1H), 7.14 (ABq, 4H), 7.91 (d, J=7.8 Hz, 1H).

Step 2: Preparation of Amino Ester Intermediate

A suspension of pentyl azide intermediate (390 mg, 0.684 mmol, obtained from Step 1) and 100 mg of palladium on carbon in ethanol (15 mL) was agitated under an atmosphere of hydrogen gas (48 psi) for 4.5 hours. The ethanolic suspension was filtered through celite and concentrated in vacuo to give a yellow oil. The oil was immediately diluted with acetonitrile (15 mL), followed by the addition of triethylamine (0.156 g, 1.54 mmol, 2.25 eq) and bromo acetic acid benzyl ester (0.212 g, 0.925 mmol, 1.35 eq). The reaction was stirred at 23° C. for 48 hours. The reaction was concentrated in vacuo, and the residue was dissolved in ethyl acetate (20 mL) and washed with water (2×20 mL) and brine (1×20 mL). The organic layer was dried (MgSO$_4$) and dried in vacuo to give 420 mg (89%) of the amino ester intermediate as a yellow oil: $^1$H NMR (CDCl$_3$) δ 0.82–0.90 (m, 6H), 1.05–1.56 (m, 14H), 1.58–1.71 (m, 3H), 1.78–2.01 (m, 4H), 2.20 (t, J=8.3 Hz, 1H), 2.75 (d, J=7.83 Hz, 1H), 2.795 (s, 6H), 3.08 (q, 2H), 3.68–3.85 (m, 2H), 3.87–4.04 (m, 2H), 4.09 (s, 1H), 5.147 (s, 1H), 5.46 (s, 1H), 5.98 (d, J=7.58, 1H), 6.50 (dd, 1H), 6.85–6.87 (m, 2H), 7.28–7.45 (m, 5H), 7.89 (d, J=8.0 Hz, 1H). MS (ES) m/e 693.

Step 3: Preparation of Acid

A suspension of benzyl ester intermediate (0.420 g, 0.61 mmol, obtained from Step 2) and 100 mg of palladium on carbon in ethanol (15 mL) was agitated under an atmosphere of hydrogen gas (48 psi) for 16h. The suspension was filtered through celite, and concentrated in vacuo to give 0.330 g of a yellow semi-solid. The material was triturated with diethyl ether and the remaining semi-solid was dried in vacuo to give 0.19 g (52%) of the desired title compound as a yellow semi solid: $^1$H NMR (CDCl$_3$) δ 0.86 (br s, 7H), 1.0–1.72 (m, 18H), 1.79 (br s, 2H), 1.98 (s, 2H), 2.09–2.24 (m, 2H), 2.78 (s, 6H), 2.99 (q, 2H), 3.96 (bs, 2H), 4.08 (s, 1H), 5.46 (s, 1H), 5.97 (s, 1H), 6.40–6.49 (m, 1H), 7.14 (ABq, 4H), 7.85 (t, J=7.93 Hz, 1H). MS (ES) m/e 603.

Example 1424

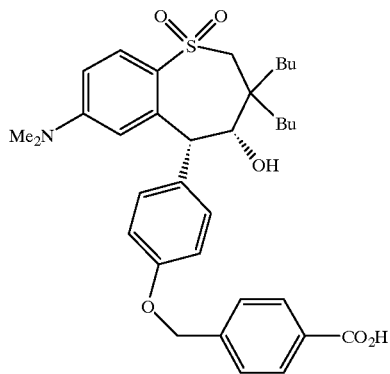

(4R-cis)-4-[[4-[3,3-Dibutyl-7-(dimethylamino)-2,3,4,5-tetrahydro-4-hydroxy-1,1-dioxido-1-benzothiepin-5-yl]phenoxy]methyl]benzoic acid Step 1: Preparation of Benzoate Intermediate To a solution of 0.53 g (1.15 mmol) of 5-(4'-hydroxyphenyl)-7-(dimethylamino) tetrahydrobenzothiepine-1,1-dioxide (obtained from Example 1402, Step 10) in 10 mL dimethylformamide was added 35 mg (1.39 mmol) of 95% sodium hydride and stirred for 10 minutes. To the reaction mixture was added 525 mg (2.29 mmol) methyl 4-(bromomethyl)benzoate and stirred for 16 hours. Water was added to the reaction mixture, extracted with ethyl acetate, washed with brine, dried over magnesium sulfate, filtered and the solvent evaporated to afford 0.51 g (73%) of the benzoate intermediate: $^1$H NMR (CDCl$_3$) δ 0.86–0.96 (m, 6H), 1.14–1.47 (m, 1OH), 1.60–1.64 (m, 1H), 2.20–2.23 (m, 1H), 2.80 (s, 6H), 2.99 (d, J=15.1 Hz, 1H), 3.15 (t, J=15.1 Hz, 1H), 3.92 (s, 3H), 4.09–4.15 (m, 1H), 5.17 (s, 2H), 5.49 (s, 1H), 5.94 (d, J=2.2 Hz, 1H), 6.50 (dd, J=8.9, 2.6 Hz, 1H), 7.00 (d, J=8.7 Hz, 2H), 7.43 (d, J=8.5 Hz, 2H), 7.53 (d, J=8.5 Hz, 2H), 7.93 (d, J=8.9 Hz, 1H), 8.06 (d, J=8.5 Hz, 2H).

Step 2: Preparation of Acid

A solution of 0.51 g (0.84 mmol) of the benzoate intermediate (obtained from Step 1) and 325 mg (2.53 mmol) of KOSi(CH$_3$)$_3$ (Aldrich) in 16 mL THF was stirred for 3.5 hours. The THF was evaporated, water added, extracted with ethyl acetate, dried over magnesium sulfate, filtered and the solvent evaporated to afford 0.30 g (60%) of the desired title compound as a white solid: mp 156–159° C.; $^1$H NMR (CDCl$_3$) δ 0.89–0.94 (m, 6H), 1.24–1.43 (m, 1OH), 1.62–1.66 (m, 1H), 2.20–2.24 (m, 1H), 2.84 (s, 6H), 3.02 (d, J=15.1 Hz, 1H), 3.17 (d, J=15.1 Hz, 1H), 4.14 (s, 1H), 5.20 (s, 2H), 5.50 (s, 1H), 6.16 (s, 1H), 6.71 (d, J=9.1 Hz, 2H), 7.03 (d, J=8.3 Hz, 2H), 7.44 (d, J=8.1 Hz, 2H), 7.57 (d, J=8.3 Hz, 2H), 7.95 (d, J=8.9 Hz, 1H), 8.13 (d, J=8.1 Hz, 2H). HRMS. Calc'd for C$_{34}$H$_{44}$NO$_6$S: 594.2889.

Found: 594.2913.

Example 1425

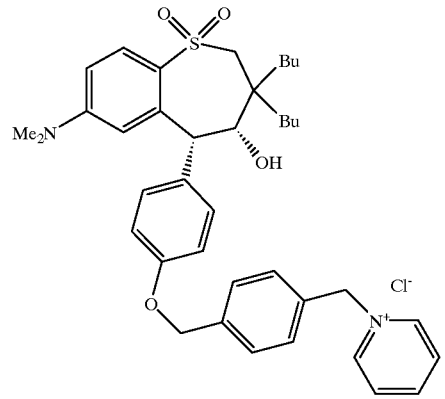

(4R-cis)-1-[[4-[[4-[3,3-Dibutyl-7-(dimethylanmino)-2,3,4,5-tetrahydro-4-hydroxy-1,1-dioxido-1-benzothiepin-5-yl]phenoxy]methyl]phenyl]methyl]-pyridinium chloride Step 1: Preparation of Chlorobenzyl Intermediate A solution of 5-(4'-hydroxyphenyl)-7-(dimethylamino) tetrahydrobenzothiepine-1,1-dioxide (5.0 g, 10.9 mmol, obtained from Example 1402, Step 10) in acetone (100 mL) at 25° C. under N$_2$ was treated with powdered K$_2$CO$_3$ (2.3 g, 16.3 mmol, 1.5 eq.) and α, α'-dichloro-p-xylene (6.7 g, 38.1 mmol, 3.5 eq.) and the resulting solution was stirred at 65° C. for 48 hours. The reaction mixture was cooled to 25° C. and concentrated to ⅕ of original volume. The residue was dissolved in EtOAc (150 mL) and washed with water (2×150 mL). The aqueous layer was extracted with EtOAc (2×150 mL) and the combined organic extracts were washed with saturated aqueous NaCl (2×150 mL. The combined extracts were dried (MgSO$_4$) and concentrated in vacuo to provide a yellow oil. Purification by flash chromatography (5.4×45 cm silica, 25–40% EtOAc/hexane) afforded the chlorobenzyl intermediate (4.7 g, 72%) as a white foam: $^1$H NMR (CDCl$_3$) δ 0.89–0.94 (m, 6H), 1.12–1.48 (br m, 10H), 1.63 (m, 1H), 2.22 (m, 1H), 2.81 (s, 6H), 3.05 (ABq, J=15.1 Hz, J=50.0 Hz, 2H), 4.11 (d, J=8.1 Hz, 1H), 4.60 (s, 2H), 5.11 (s, 2H), 5.48 (s, 1H), 5.96 (d, J=2.4 Hz, 1H), 6.48 (dd, J=8.9, 2.6 Hz, 1H), 7.00 (d, J=8.9 Hz, 2H), 7.36–7.47 (m, 5H), 7.85 (d, J=8.9 Hz, 1H).

Step 2: Preparation of Quaternary Salt

A solution of the chlorobenzyl intermediate (1.0 g, 1.7 mmol, obtained from Step 1) in acetonitrile (5 mL) at 25° C. under N$_2$ was treated with pyridine (5 mL) and stirred at 35° C. for 36 hours. The pale amber solution was cooled to 25° C. and concentrated in vacuo to give the desired title compound (1.08 g, 96%) as a yellow solid: mp 154–156° C.; $^1$H NMR (CDCl$_3$) δ 0.83 (m, 6H), 1.06–1.44 (br m, 10H), 1.60 (m, 1H), 2.13 (m, 1H), 2.71 (s, 6H), 3.02 (ABq, J=15.1 Hz, J=28.4 Hz, 2H), 4.09 (s, 1H), 5.00 (s, 2H), 5.38 (s, 1H), 5.91 (d, J=2.4 Hz, 1H), 6.26 (s, 2H), 6.41 (dd, J=8.9, 2.4 Hz, 1H), 6.91 (d, J=8.7 Hz, 2H), 7.26 (m, 1H), 7.40 (d, J=7.7 Hz, 4H), 7.73 (d, J=7.9 Hz, 2H), 7.78 (d, J=8.9 Hz, 2H), 7.93 (t, J=6.8 Hz, 1H), 8.34 (t, J=7.7 Hz, 1H), 8.58 (br s, 1H), 9.69 (d, J=5.8 Hz, 2H); HRMS. Calc'd for C$_{39}$H$_{49}$N$_2$O$_4$S: 641.3413. Found: 641.3425.

Example 1426

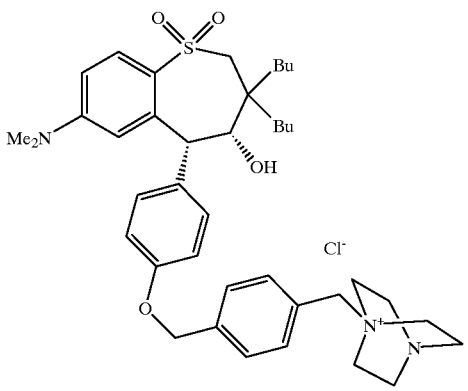

(4R-cis)-1-[4-[[4-[3,3-Dibutyl-7-(dimethylamino)-2,3,4,5-tetrahydro-4-hydroxy-1,1-dioxido-1-benzothiepin-5-yl]phenoxylmethyl]phenyl]methyl]-4-aza-1-azoniabicyclo[2.2.2]octane chloride Under N$_2$, a solution of 8.7 g (14.5 mmol) of the chlorobenzyl intermediate (obtained from a procedure similar to the one outlined in Example 1425, Step 1) in 60 mL of acetonitrile was added dropwise over a 30 min period to a solution of 2.9 g (26.2 mmol) of diazabicyclo[2.2.2]octane (DABCO) in 40 mL of acetonitrile at 35° C.; during the addition, a colorless precipitate was formed. The slurry was stirred at 35° C. for an additional 2 h. The product was collected and washed with 1 L of acetonitrile to give 9.6 g (93%) the title compound as a colorless crystalline solid: mp 223–230° C. (decomposed); $^1$H NMR (CDCl$_3$) δ 0.89 (m, 6H), 1.27–1.52 (br m, 10H), 1.63 (m, 1H), 2.20 (m, 1H), 2.81 (s, 6H), 3.06 (ABq, J=15.1 Hz, J=43.3 Hz, 2H), 3.16 (s, 6H), 3.76 (s, 6H), 4.11 (d, J=7.7 Hz, 1H), 5.09 (s, 2H), 5.14 (s, 2H), 5.48 (s, 1H), 5.96 (s, 1H), 6.49 (d, J=8.9 Hz, 1H), 6.99 (d, J=8.0 Hz, 2H), 7.26 (m, 1H), 7.44 (d, J=8.0 Hz, 2H), 7.52 (d, J=7.4 Hz, 2H), 7.68 (d, J=7.4 Hz, 2H), 7.87 (d, J=8.9 Hz, 1H); HRMS. Calc'd for C$_{40}$H$_{56}$N$_3$O$_4$S: 674.3992. Found: 674.4005.

Example 1426a

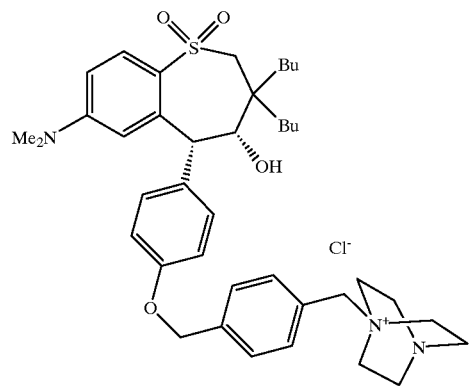

(4R-cis)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride A solution of the chlorobenzyl intermediate (4.6 g, 7.7 mmol, obtained from Example 1425, Step 1) in acetonitrile (100 mL) at 25° C. under N$_2$ was treated with diazabicyclo[2.2.2]-octane (DABCO, 0.95 g, 8.5 mmol, 1.1 eq.) and stirred at 35° C. for 2 hours, during which time a white solid precipitated out. The white solid was collected, washed with CH$_3$CN and recrystallized from CH$_3$OH/Et$_2$O to give the title compound (4.95 g, 91%) as a white solid: mp 223–230° C. (decomposed); $^1$H NMR (CDCl$_3$) δ 0.89 (m, 6H), 1.27–1.52 (br m, 10H), 1.63 (m, 1H), 2.20 (m, 1H), 2.81 (s, 6H), 3.06 (ABq, J=15.1 Hz, J=43.3 Hz, 2H), 3.16 (s, 6H), 3.76 (s, 6H), 4.11 (d, J=7.7 Hz, 1H), 5.09 (s, 2H), 5.14 (s, 2H), 5.48 (s, 1H), 5.96 (s, 1H), 6.49 (d, J=8.9 Hz, 1H), 6.99 (d, J=8.0 Hz, 2H), 7.26 (m, 1H), 7.44 (d, J=8.0 Hz, 2H), 7.52 (d, J=7.4 Hz, 2H), 7.68 (d, J=7.4 Hz, 2H), 7.87 (d, J=8.9 Hz, 1H); HRMS. Calc'd for C$_{40}$H$_{56}$N$_3$O$_4$S: 674. 3992. Found: 674.4005.

Example 1427

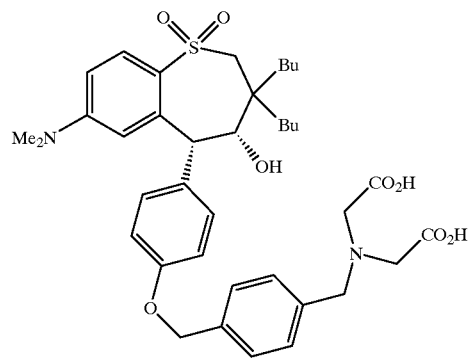

4R-cis)-N-(Carboxymethyl)-N-[[4-[[4-[3,3-dibutyl-7-(dimethylamino)-2,3,4,5-tetrahydro-4-hydroxy-1,1-dioxido-1-benzothiepin-5-yl]phenoxylmethyl]phenyl3methyl]glycine Step 1: Preparation of Chlorobenzyl Intermediate To a stirred solution of 144 mg (3.59 mmol, 60% disp) of NaH in 29 mL of DMF was added 1.5 g (3.26 mmol) of 5-(4'-hydroxyphenyl)-7-(dimethylamino)

tetrahydrobenzothiepine-1,1-dioxide (obtained from Example 1402, Step 10), and the resulting solution was stirred at ambient temperature for 45 min. To the solution was added 7.13 g (40.75 mmol) of dichloro p-xylene, and the mixture was stirred overnight. DMF was removed in vacuo, and the residue was extracted with ethyl acetate and washed with brine. The extract was dried over MgSO$_4$, and the concentrated residue was purified by column chromatography to give the chlorobenzyl intermediate: $^1$H NMR (CDCl$_3$) δ 0.90 (q, 6H), 1.05–1.65 (m, 11H), 2.2 (t, 1H), 2.8 (s, 6H), 3.0 (q, 2H), 4.1 (d, 1H), 4.6 (s, 2H), 5.1 (s,2H), 5.5 (s, 1H), 6.0 (s, 1H), 6.6 (d,1H), 7.0 (d, 2H), 7.4 (m, 6H), 7.8 (d,1H).

Step 2: Preparation of Amino Diester

A mixture of 1.03 g (1.72 mmol) of chlorobenzyl intermediate (obtained from Step 1), 1.63 g (8.6 mmol) of diethyl amino diacetate, and 0.72 g (8.6 mmol) of NaHCO$_3$ in 30 mL of DMF was stirred at 100° C. for 6 hours. DMF was removed in vacuo and the residue was extracted with ether and washed with brine. The extract was dried over MgSO$_4$, and the concentrated residue was purified by column chromatography to give amino diester intermediate: $^1$H NMR (CDCl$_3$) δ 0.90 (q, 6H), 1.05–1.65 (m, 17H), 2.2 (t, 1H), 2.8 (s, 6H), 3.0 (q, 2H), 3.55 (s, 4H), 3.95 (s, 2H), 4.1–4.2 (m, 5H), 5.05 (s, 2H), 5.42 (s, 1H), 5.95 (s, 1H), 6.5 (d, 1H), 7.0 (d, 2H), 7.4 (s, 6H), 7.8 (d, 1H).

Step 3: Preparation of Amino Diacid

A solution of 0.863 g (1.15 mmol) of dibenzyl ester (obtained from Step 2) and 0.232 g (5.52 mmol) of LiOH in 30 mL of THF and 30 mL of water was stirred at 40° C. under N$_2$ for 4 hours. The reaction mixture was diluted with ether and washed with 1% HCl. The aqueous layer was extracted twice with ether, and the combined extracts were washed with brine, dried over MgSO$_4$, and concentrated in vacuo to give the desired title compound as a solid: mp 175° C.; $^1$H NMR (THF-d8) 0.95 (q, 6H), 1.05–1.65 (m, 11H), 2.22 (t, 1H), 2.8 (s, 6H), 3.0 (t, 2H), 3.5 (s, 4H), 3.9 (s, 2H), 4.1 (d, 1H), 5.1 (s, 2H), 5.4 (s, 1H), 6.05 (s, 1H), 6.5 (d, 1H), 7.0 (d, 2H), 7.4 (m, 6H), 7.78 (d, 1H). HRMS. Calc'd for C$_{38}$H$_{50}$N$_2$O$_8$S: 695.3366. Found: 695.3359. Anal. Calc'd for C$_{38}$H$_{50}$N$_2$O$_8$S: C, 65.68; H, 7.25; N, 4.03; S, 4.61. Found: C, 64.95; H, 7.32; N, 3.94; S, 4.62.

Example 1428

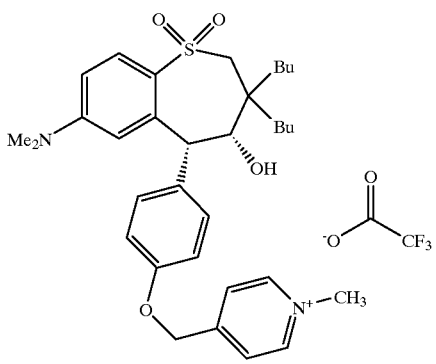

(4R-cis)-4-[[4-[3,3-Dibutyl-7-(dimethylamino)-2,3,4,5-tetrahydro-4-hydroxy-1,1-dioxido-1,1-dioxido-1-benzothiepin-5-yl]phenoxy]methyl]-1-methylpyridinium salt with trifluoroacetic acid (1:1)

Step 1: Preparation of Picolyl Intermediate

To a stirred solution of 12.0 g (26.1 mmol) of 5-(4'-hydroxyphenyl)-7-(dimethylamino) tetrahydrobenzothiepine-1,1-dioxide (obtained from Example 1402, Step 10) in 200 mL of DMF was added 1.4 g (60% oil dispersion, 35 mmol) of sodium hydride and the reaction stirred at ambient temperature for one hour. 5.99 g (36.5 mmol) of 4-picolyl chloride hydrochloride was treated with cold saturated NaHCO$_3$ solution and extracted with diethyl ether. The ethereal extracts were washed with brine, dried over MgSO$_4$, and filtered. The reaction was cooled in an ice bath and the solution of 4-picolyl chloride in diethyl ether was added. The reaction was stirred at ambient temperature for 17 hours. The reaction was quenched with 25 mL of saturated NH$_4$Cl, diluted with 600 mL ethyl acetate washed with 4×250 mL water, brine, dried over MgSO$_4$, filtered and concentrated in vacuo. Purification by silica gel chromatography (Waters-prep 500) using 60% ethyl acetate/hexanes afforded 11.05 g (77%) of the picolinyl intermediate as a colorless solid: mp 95–98° C.; $^1$H NMR (CDCl$_3$) δ 0.86–0.96 (m, 6H), 1.02–1.52 (m, 10H), 1.58–1.70 (m, 1H), 2.16–2.29 (m, 1H), 2.81 (s, 6H), 3.07 (AB$_q$, J$_{AB}$=15.3, 49.6 Hz, 2H), 4.10 (d, J=7.5 Hz, 1H), 5.15 (s, 2H), 5.50 (s, 1H), 5.94 (d, J=2.7 Hz, 1H), 6.51 (dd, J=2.4, 8.7 Hz, 1H), 7.00 (d, J=9.0 Hz, 2H), 7.39 (d, 6.0 Hz, 2H), 7.44 (s, J=8.7 Hz, 2H), 7.89 (d, J=9.0 Hz, 2H), 8.63 (dd, J=1.6, 4.8 Hz, 2H).

Step 2: Preparation of Quaternary Salt

To a stirred solution of 0.41 g (0.74 mmol) of picolinyl intermediate (obtained from Step 1) in 10 mL of acetonitrile and 3 mL of dichloromethane was added 137 mg (0.97 mmol) of iodomethane. The reaction was stirred at ambient temperature for 16 hours, then concentrated under a nitrogen stream. Purification by reversed phase chromatography (Waters-Delta prep) using 60–55% water/acetonitrile afforded 0.304 g (60%) of the desired title compound as a colorless solid: mp 96–99° C.; $^1$H NMR (CDCl$_3$) δ 0.85–0.95 (m, 6H), 1.03–1.52 (m, 10H), 1.57–1.70 (m, 1H), 2.12–2.27 (m, 1H), 2.84 (s, 6H), 3.09 (AB$_q$, J$_{AB}$=15.0, 27.9 Hz, 2H), 4.11 (s, 1H), 4.46 (s, 3H), 5.37 (s, 2H), 5.50 (s, 1H), 6.07 (d, J=2.4 Hz, 1H), 6. 61 (dd, J=2.5, 8.7 Hz, 1H), 7.02 (d, J=8.7 Hz, 2H), 7.48 (d, J=7.2 Hz, 2H), 7.90 (d, J=8.7 Hz, 1H), 8.14 (d, J=6.3 Hz, 2H), 8.80 (d, J=6.6 Hz, 2H). HRMS Calc'd for C$_{33}$H$_{45}$N$_2$O$_4$S: 565.3100. Found: 565.3125.

Example 1429

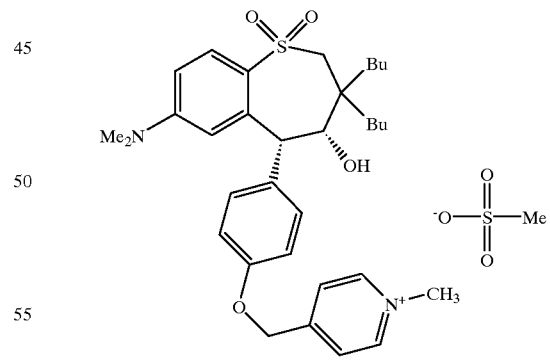

(4R-cis)-4-[[4-[3,3-Dibutyl-7-(dimethylamino)-2,3,4,5-tetrahydro-4-hydroxy-1,1-dioxido-1,1-dioxido-1-benzothiepin-5-yl]phenoxy]methyl]-1-methylpyridinium, methanesulfonate (salt)

To a stirred solution of 6.5 g (11.8 mmol) of picolyl intermediate (obtained from Example 1428, Step 1) in 140 mL of acetonitrile heated at 70° C. was added 1.56 g (14.6 mmol) methanesulfonic acid methyl ester. Heating was continued at 70° C. for 15 hours. The reaction was cooled and diluted with 50 mL of ethyl acetate. The solid was collected by vacuum filtration to give 6.14 g (79%). The filtrate was concentrated in vacuo and the residue crystallized from hot acetonitrile to give 1.09 g (14%). A total of 7.23 g (93%) of the desired title compound was obtained as an off-white solid: mp 232–233.5° C.; $^1$H NMR (CDCl$_3$) δ 0.66–0.76 (m, 6H), 0.85–0.95 (m, 1H), 0.95–1.35 (m, 9H), 1.42–1.54 (m, 1H), 1.95–2.22 (m, 1H), 2.50 (s, 1H), 2.56 (s, 3H), 2.63 (s, 6H), 2.91 (AB$_q$, J=16.5, 24.0 Hz, 2H), 3.88 (s, 1H), 4.40 (s, 3H), 5.21 (s, 3H), 5.78 (d, J=2.4 Hz, 1H), 6.31 (dd, J=2.5, 8.7 Hz, 1H), 6.84 (d, J=8.7 Hz, 2H), 7.31 (d, J=8.4 Hz, 2H), 7.64 (d, J=8.7 Hz, 1H), 8.0 (d, J=6.6 Hz, 2H), 9.02 (d, J=6.6 Hz, 2H). HRMS Calc'd for $C_{33}H_{45}N_2O_4S$: 565.3100. Found: 656.3087. Anal. Calc'd for $C_{34}H_{48}N_2O_7S_2$: C, 61.79; H, 7.32; N, 4.24; S, 9.70. Found: C, 61.38, H, 7.47; N, 4.22; S, 9.95.

Example 1430

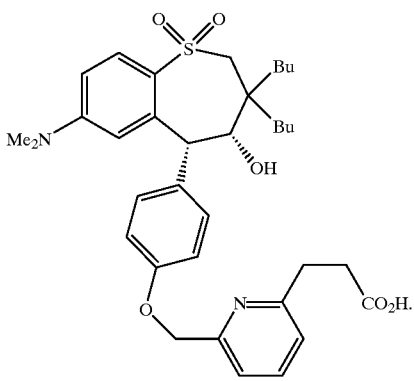

(4R-cis)-6-[[4-[3,3-Dibutyl-7-(dimethylamino)-2,3,4,5-tetrahydro-4-hydroxy-1,1-dioxido-1-benzothiepin-5-yl]phenoxylmethyl]-2-pyridinepropanoic acid Step 1: Preparation of Picolinyl Chloride Intermediate To a solution of 5-(4'-hydroxyphenyl)-7-(dimethylamino) tetrahydrobenzothiepine-1,1-dioxide (1 g, 2.1 mmol, obtained from Example 1402, Step 10) in acetone (50 mL) was added anhydrous K$_2$CO$_3$ (0.45 g, 3.2 mmol), tetrabutylammonium iodide (0.1 g, 0.2 mmol) and 2,6-bischloromethylpyridine (1.2 g, 10.8 mmol). The flask was equipped with nitrogen gas adapter and magnetic stirrer. The reaction was heated to reflux for overnight. After 18 hours, the reaction was diluted with ether and washed with water and brine (30 mL). The organic layers were dried over MgSO$_4$, filtered and concentrated in vacuo. Chromatographic purification through silica gel, eluting with 25% EtOAc/Hexane gave 0.75 g (55%) of the picolyl chloride intermediate as an oil (0.70 g, 55%): $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H) 3.05 (ABq, 2H), 4.10 (d, 2H), 4.65 (s, 2H), 5.20 (s, 2H), 5.45 (s, 1H), 5.95 (s, 1H), 6.50 (d, 1H), 7.0 (d, 2H),7.35–7.50 (m, 4H), 7.70–7.85 (m, 2H).

Step 2: Preparation of Pyridinyl Malonate Intermediate

Dibenzyl malonate (1.42 g, 5.01 mmol) in DMF (20.0 mL) and sodium hydride (0.13 g, 3.3 mmol) were placed in a dry three-neck flask. The flask was equipped with nitrogen gas adapter and magnetic stirrer. The picolyl chloride intermediate (1 g, 1.67 mmol) was added and heated at 90° C. for overnight. The reaction was cooled and extracted with 5% HCl with methylene chloride and washed with water (25 mL), and brine (50 mL). The organic layers were dried over MgSO$_4$, filtered and concentrated. The residue was purified by C-18 reversed phase column eluting with 50% acetonitrile/water and gave pyridinyl malonate intermediate as a white foamy solid (1 g, 71%): $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H) 3.05 (ABq, 2H), 3.22 (d, 2H), 4.05 (d, 1H), 4.16 (t, 1H), 5.02 (s, 2H), 5.08 (s, 4H), 5.44 (s, 1H), 5.97 (s, 1H), 6.96–7.10 (m, 3H), 7.20–7.32 (m, 12H), 7.5 (t, 1H), 7.9 (d, 1H).

Step 3: Preparation of Pyridinyl Acid

The pyridinyl malonate intermediate (0.6 g, 0.7 mmol, obtained from Step 2), THF/water (25.0 mL, 1:1) and lithium hydroxide monohydrate (0.14 g, 3.4 mmol) were placed in a 100 mL round-bottom flask. The reaction was stirred at ambient temperature overnight. After 18 hours, the reaction was extracted with 1% HCl and ether and then washed with water (20 mL) and brine (30 mL). The organic layers were dried over MgSO$_4$, filtered and concentrated in vacuo gave the desired title compound as a white solid (0.44 g, 90%): mp 105–107° C.; $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H),3.05 (m, 2H), 3.10 (ABq, 2H), 3.22 (m, 2H), 4.05 (s, 1H), 5.30 (s, 2H), 5.50 (s, 1H), 5.97 (s, 1H), 6.50 (d, 1H), 7.02 (d, 2H), 7.3 (d, 1H), 7.42 (d, 2H), 7.58 (d, 1H), 7.8–7.9 (m, 2H). HRMS. Calc'd for $C_{35}H_{46}N_2O_6S$: 623.3155. Found: 623.3188.

Example 1431

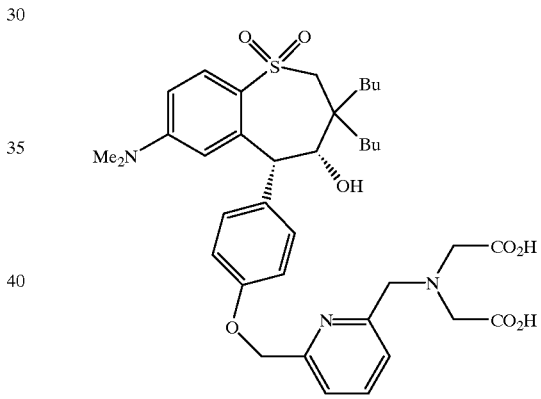

(4R-cis)-N-(Carboxymethyl)-N-[[6-[[4-[3,3-dibutyl-7-(dimethylamino)-2,3,4,5-tetrahydro-4-hydroxy-1,1-dioxido-1-benzothiepin-5-yl]phenoxy]methyl]-2-pyridinyl]methyl]glycine Step 1: Preparation of Pyridinyl Diester Intermediate A mixture of diethyl aminodiacetate (8 g, 68 mmol) and sodium carbonate (0.63 g, 5.9 mmol) was treated with picolyl chloride intermediate (0.72 g, 1.2 mmol, obtained from Example 1430, Step 1), and stirred at 160° C. for three hours. The reaction was cooled and diluted with ether and washed with 1% HCl, water (25 mL), and brine (50 mL). The combined extracts were dried over MgSO$_4$, filtered and concentrated in vacuo. The residue was purified by distillation in the Kugelrohr to give pyridinyl diester intermediate as a yellowish foamy solid (0.72 g, 80%): $^1$H NMR (CDCl$_3$) δ 0.84–0.95 (m, 6H), 1.02–1.5 (m, 16H), 1.56–1.66 (m, 1H), 2.14–2.24 (m, 1H), 2.80 (s, 6H) 3.05 (ABq, 2H), 3.70 (s, 4H), 4.2–4.4 (m, 6H), 5.30 (s, 2H), 5.56 (s, 1H),6.02 (s, 1H), 6.60 (d, 1H), 7.10 (d, 2H),7.50 (m, 3H), 7.61 (d, 1H), 7.80 (t, 1H), 7.95 (d, 1H). HRMS. Calc'd for $C_{41}H_{57}N_3O_8S$: 752.3945. Found: 752.3948.

Step 2: Preparation of Pyridinyl Diacid

A mixture of pyridine-aminodiacetate intermediate (0.7 g, 0.93 mmol, obtained from Step 1), and lithium hydroxide monohydrate (0.18 g, 4.5 mmol) in THF/water (25.0 mL, 1:1) was stirred at 40° C. overnight (18 hours). The reaction mixture was diluted with ether and washed with 1% HCl, water (20 mL), and brine (30 mL). The organic layers were dried over $MgSO_4$, filtered and concentrated in vacuo to give the desired title compound as a white solid (0.44 g, 90%): mp 153–155° C.; $^1$H NMR ($CDCl_3$) δ 0.84–0.95 (m, 6H), 1.02–1.5 (m, 10H), 1.56–1.66 (m, 1H), 2.14–2.24 (m, 1H), 2.80 (s, 6H), 3.10 (ABq, 2H), 3.90 (m, 3H), 4.05 (s, 1H), 4.40 (s, 2H), 5.20 (s, 2H), 5.50 (s, 1H), 5.97 (s, 1H), 6.50 (d, 1H), 7.02 (d, 2H), 7.3 (d, 1H), 7.42 (d, 2H), 7.58 (d, 1H), 7.8–7.9 (m, 2H). HRMS. Calc'd for $C_{37}H_{49}N3O_8S$: 696.3319. Found: 696.3331.

EXAMPLE 1432

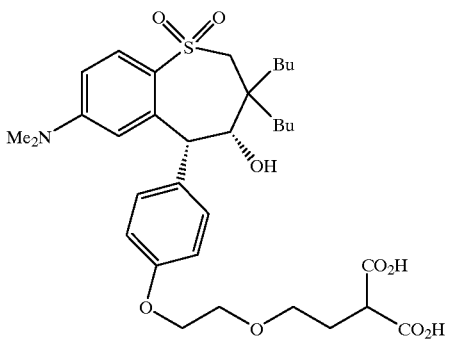

(4S-cis)-[2-[2-[4-[3,3-Dibutyl-7-(dimethylamino)-2,3,4,5-tetrahydro-4-hydroxy-1,1-dioxido-1-benzothiepin-5-yl]phenoxy]ethoxy]ethyl] propanedioic Acid Step 1: Preparation of bromoethyl ether intermediate To a stirred solution of 0.192 g (4.785 mmol, 60% disp) of NaH in 28 mL of DMF was added 2.0 g (4.35 mmol) of 5-(4'-hydroxyphenyl)-7-(dimethylamino) tetrahydrobenzothiepine-1,1-dioxide (obtained from Example 1402, Step 10), and the resulting solution was stirred at ambient temperature for 30 min. To the solution was added 13.2 g (54.38 mmol) of bis(2-bromoethyl)ether, and stirring was continued at ambient temperature under $N_2$ overnight. DMF was removed in vacuo and the residue was extracted with ethyl acetate and washed with brine. The extract was dried over $MgSO_4$, and the concentrated residue was purified by column chromatography to give bromoethyl ether intermediate: $^1$H NMR ($CDCl_3$) δ 0.90 (q, 6h), 1.05–1.65 (m, 11H), 2.2 (t, 1H), 2.8 (s, 6H), 3.0 (q, 2H), 3.5 (t, 2H), 3.9 (m, 4H), 4.1 (d, 1H), 4.2 (d, 2H), 5.42 (s, 1H), 5.95 (s, 1H), 6.5 (d, 1H), 6.95 (d, 2H), 7.4 (d, 2H), 7.9 (d, 1H).

Step 2: Preparation of diester intermediate

To a mixture of 94 mg (2.34 mmol, 60% disp) of NaH in 45 mL of THF and 15 mL of DMF at 0° C. was added 1.33 g (4.68 mmol) of dibenzyl malonate (Aldrich), and the resulting solution was stirred at ambient temperature for 15 min, followed by the addition of 0.95 g (1.56 mmol) of bromoethyl ether intermediate (obtained from Step 1). The mixture was stirred under $N_2$ at 80° C. overnight. Solvent was removed in vacuo and the residue was extracted with methylene chloride and washed with brine. The extract was dried over $MgSO_4$, and the concentrated residue was puri-fied by column chromatography to give the diester intermediate: $^1$H NMR ($CDCl_3$) δ 0.90 (q, 6H), 1.05–1.65 (m, 11H), 2.2–2.3 (m, 3H), 2.8 (s, 6H), 3.0 (q, 2H), 3.6 (t, 2H), 3.7 (m, 3H), 4.1 (m, 3H), 5.1 (s, 4H), 5.42 (s, 1H), 5.9 (s, 1H), 6.5 (d, 1H), 6.9 (d, 2H), 7.3 (m, 10H), 7.4 (d, 2H), 7.9 (d, 1H).

Step 3: Preparation of diacid

A suspension of 0.761 g (0.935 mmol) of the diester intermediate (obtained from Step 2) and 35 mg of 10% Pd/C in 25 mL of ethanol and 5 mL of THF was agitated at ambient temperature under 20 psi of hydrogen gas for 2 hours. The catalyst was filtered off, and the filtrate was concentrated to give the desired title compound as a solid: mp 119.5° C.; $^1$H NMR (THF-d8) 0.95 (q, 6H), 1.05–1.65 (m, 11H), 2.1 (q, 2H), 2.25 (t, 1H), 2.8 (s, 6H), 3.0 (t, 2H), 3.47 (q, 2H), 3.58 (s, 1H), 3.78 (t, 2H), 4.08 (d, 1H), 4.15 (t, 2H.), 5.4 (s, 1H), 6.05 (s, 1H), 6.55 (d, 1H), 6.98 (d, 2H), 7.42 (d, 2H), 7.8 (d, 1H). HRMS. Calc'd for $C_{33}H_{47}NO_9S$: 632.2893. Found: 632.2882. Anal. Calc'd for $C_{33}H_{47}NO_9S$: C, 62.54; H, 7.47; N, 2.21; S, 5.06. Found: C, 61.75; H, 7.56; N, 2.13; S, 4.92.

EXAMPLE 1433

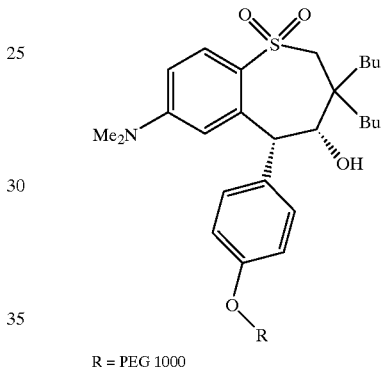

R = PEG 1000

(4R-cis)-a-[[4-[3,3-Dibutyl-7-(dimethylamino)-2,3,4,5-tetrahydro-4-hydroxy-1,1-dioxido-1-benzothiepin-5-yl]phenoxy]methyl]-w-methoxypoly(oxy-1,2-ethanediyl)

Step 1: Preparation of monomethyl PEG mesylate intermediate

To a solution of 20 g of monomethyl ether PEG in 100 mL of methylene chloride was added 2.2 g (22 mmol) of triethyl amine, and to the resulting solution at 0° C. was added dropwise 2.5 g (22 mmol) of methanesulfonyl chloride. The resulting solution was stirred overnight at ambient temperature, and the triethyl amine hydrochloride was filtered off to give the monomethyl PEG mesylate intermediate which was used in the next Step without further purification and characterization.

Step 2: Preparation of polyethylene-linked benzothiepene

A mixture of 38 mg (1.52 mmol 95%) of NaH and 0.7 g (1.52 mmol) of 5-(4'-hydroxyphenyl)-7-(dimethylamino) tetrahydrobenzothiepine-1,1-dioxide (obtained from Example 1402, Step 10) in 5.5 mL of DMF was stirred at ambient temperature under $N_2$ for 30 min. To the solution was added 0.55 g (0.51 mmol) of the mesylate PEG intermediate (obtained from Step 1) in 5.5 mL of DMF, and the resulting solution was stirred overnight under $N_2$ at 50° C. DMF was removed in vacuo and the residue was extracted with methylene chloride and washed with brine. The extract was dried over $MgSO_4$, and the concentrated residue was purified by column chromatography to give the desired title compound as an oil: $^1$H NMR (CDCl$_3$) δ 0.9 (q, 6H), 1.05–1.65 (m, 11H), 2.2 (t, 1H), 2.8 (s, 6H), 3.0 (q, 2H), 3.4 (s, 4H), 3.5–3.85 (m, 95H), 4.1 (s, 1H), 4.15 (t, 2H), 5.5 (s, 1H), 6.05 (s, 1H), 6.6 (d, 1H), 6.9 (d, 2H), 7.4 (d, 2H), 7.9 (d, 1H).

EXAMPLE 1434

Preparation of:

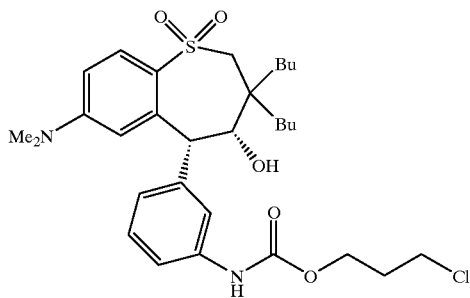

The 3-aminobenzothiepene prepared in Step 5 of Example 1398 (0.380 g, 0.828 mmol), sodium hydroxide (0.35 mL, 0.875 mmol, 10% in H$_2$O) and toluene (0.50 mL) were combined in a 10 mL round-bottom flask. The reaction flask was purged with N$_2$, equipped with magnetic stirrer, and cooled to 0° C. A solution of 3-chloropropyl chloroformate (1.440 g, 1.10 mmol, 12% in CH$_2$Cl$_2$/THF) was added. After 3.5 hrs, toluene (3.0 mL) was added, and the mixture was washed with H$_2$O (2×4 mL), dried (MgSO$_4$), filtered and concentrated in vacuo. Purification by flash chromatography on silica gel eluting with 20% EtOAc/hexane and concentrated in vacuo gave a white solid (0.269 g, 56%). $^1$H NMR (CDCl$_3$) δ 0.87–0.93 (m, 6H), 1.05–1.70 (m, 11H), 2.14 (t, J=6.3 Hz, 2H), 2.15–2.25 (m, 1H), 2.81 (s, 6H), 3.07 (ABq, 2H), 3.64 (t, J=6.3 Hz, 2H), 4.11 (d, J=7.5 Hz, 1H), 4.33 (t, J=6.0 Hz, 2H), 5.50 (s, 1H), 5.99 (d, J=2.4 Hz, 1H), 6.51 (dd, J=9.0, 2.7 Hz, 1H), 6.65 (s, 1H), 7.23 (d, J=7.8 Hz, 1H), 7.34–7.39 (m, 2H), 7.54 (d, J=7.2 Hz, 1H), 7.89 (d, 8.7 Hz, 1H). HRMS (M+H). Calc'd for C$_{30}$H$_{44}$N$_2$O$_5$SCl: 579.2659. Found: 579.2691.

EXAMPLE 1435

Preparation of:

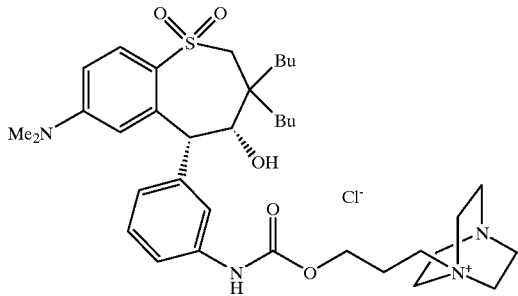

1,4-Diazabicyclo(2.2.2)octane (0.0785 g, 0.700 mmol) and acetonitrile (1.0 mL) were combined in a 10 mL round-bottom flask. The reaction flask was purged with N$_2$, equipped with magnetic stirrer, and heated to 37° C. A solution of the product of Example 1434 (0.250 g, 0.432 mmol) in acetonitrile (2.50 mL) was added. After 2.5 hrs, 1,4-diazabicyclo(2.2.2)octane (0.0200 g, 0.178 mmol) was added. After 64 hrs, 1,4-diazabicyclo(2.2.2)octane (0.0490 g, 0.437 mmol) was added. After 24 hrs, the reaction mixture was cooled to R.T. and concentrated in vacuo. The crude product was dissolved in acetonitrile (2.0 mL) and precipitated with ethyl ether (10.0 mL). The precipitate was filtered to yield a white solid. This trituration method was repeated, followed by concentrated in vacuo to give a white solid (0.185 g, 62%). mp 218.0–225.0° C.; $^1$H NMR (CD$_3$OD) δ 0.90 (m, 6H), 1.05–1.55 (m, 10H), 1.16 (t, J=6.6 Hz, 2H), 1.78 (m, 1H), 2.12 (m, 3H), 2.76 (s, 6H), 3.10 (m, 2H), 3.17 (t, J=7.2 Hz, 6H), 3.30–3.50 (m, 8H), 4.10 (s, 1H), 4.21 (t, J=5.4 Hz, 2H), 5.31 (s, 1H), 6.10 (s, 1H), 6.55 (d, J=7.2 Hz, 1H), 7.25 (d, J=6.9 Hz, 1H), 7.33–7.42 (m, 2H), 7.56 (s, 1H), 7.76 (d, J=9.0 Hz, 1H). HRMS. Calc'd for C$_{36}$H$_{55}$N$_4$O$_5$SCl: 655.3893. Found: 655.3880.

EXAMPLE 1436

Preparation of:

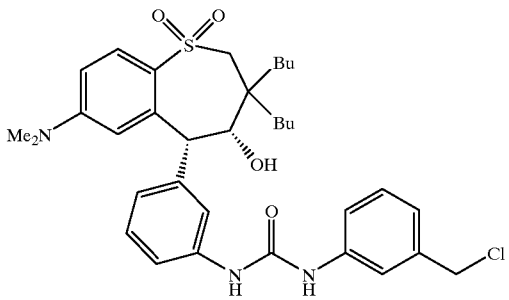

Step 1. Preparation of:

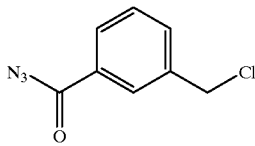

3-Chloromethylbenzoyl chloride (2.25 mL/15.8 mmol) and acetone (8.0 mL) were combined in a 25 mL round-bottom flask. The reaction flask was cooled to 0° C., and an aqueous solution of sodium azide (1.56 g in 5.50 mL/24.0 mmol) was added. After 1.5 hrs, the reaction mixture was poured into ice water (80.0 mL), extracted with ethyl ether (2×25 mL), dried (MgSO$_4$), and concentrated in vacuo to give a colorless oil (2.660 g, 86%). $^1$H NMR (CDCl$_3$) δ 4.62 (s, 2H), 7.47 (t, J=7.8 Hz, 1H), 7.66 (d, J=7.8 Hz, 1H), 7.99 (d, J=7.8 Hz, 1H), 8.05 (s, 1H).

Step 2.

3-Chloromethylbenzoyl azide (0.142 g, 0.726 mmol) and toluene (2.0 mL) were combined in a 10 mL round-bottom flask. The reaction flask was purged with N$_2$, equipped with magnetic stirrer, and heated to 110° C. After 2 hrs, the reaction mixture was cooled to R.T, and the 3-aminobenzothiepene prepared in Step 5 of Example 1398 (0.365 g, 0.796 mmol) was added. After 2.25 hrs, the mixture was heated to 50° C. After 0.75 hrs, 3-chloromethylbenzoyl azide (0.025 g, 0.128 mmol) was added, and the reaction mixture was heated to reflux. After 0.5 hrs, the reaction mixture was cooled to R.T. and concentrated in vacuo. Purification by flash chromatography on silica gel eluting with 20–30% EtOAc/hexane and concentrated in vacuo gave a white foamy solid (0.309 g, 62%). $^1$H NMR (CDCl$_3$) δ 0.71 (t, J=5.4 Hz, 3H), 0.88 (t, J=6.3 Hz, 3H), 1.03–1.60 (m, 11H), 1.85 (d, 6.3 Hz, 1H), 2.27 (m, 1H), 2.76 (s, 6H), 3.15 (t, 2H), 4.17 (d, J=6.6 Hz, 1H), 4.48 (s, 2H), 5.42 (s, 1H), 6.07 (s, 1H), 6.99 (d, J=7.5 Hz), 7.18–7.26 (m, 2H), 7.30–7.41 (m, 3H), 7.63 (s, 1H), 7.86 (d, J=9.0 Hz, 2H), 7.96 (s, 1H), 8.17 (s, 1H). HRMS (M+Li). Calculated for $C_{34}H_{44}N_3O_4SClLi$: 632.2901. Found: 632.2889.

EXAMPLE 1437

Preparation of:

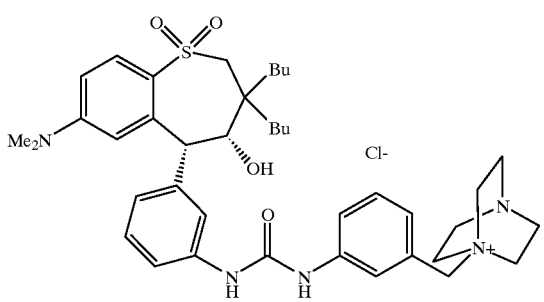

1,4-Diazabicyclo(2.2.2)octane (0.157 g, 1.40 mmol) and acetonitrile (1.00 mL) were combined in a 10 mL round-bottom flask. The reaction flask was purged with $N_2$ and equipped with magnetic stirrer. A solution of the product of Example 1436 (0.262 g, 0.418 mmol) in acetonitrile (2.70 mL) was added. After 2.5 hrs, a white precipitate had had formed. Ethyl ether (6.0 mL) was added, and the precipitate was filtered, washed with ethyl ether, and dried in vacuo to yield a white solid (0.250 g, 80%). mp 246.0–248.0° C.; $^1$H NMR (CD$_3$OD) δ 0.88 (m, 6H), 1.03–1.55 (m, 10H), 1.76 (m, 1H), 2.11 (m, 1H), 2.74 (s, 6H), 3.11 (m, 8H), 3.37 (m, 6H), 4.12 (s, 1H), 4.39 (s, 2H), 5.31 (s, 1H), 6.11 (s, 1H), 6.52 (dd, J=8.7, 1.8 Hz, 1H), 7.09 (d, J=7.2 Hz, 1H), 7.23 (d, J=6.9 Hz, 1H), 7.32–7.38 (m, 2H), 7.47 (m, 2H), 7.58 (s, 1H), 7.73 (d, J=8.7 Hz, 2H). HRMS. Calculated for $C_{40}H_{56}N_5O_4SCl$: 702.4053. Found: 702.4064. Anal. Calculated for $C_{40}H_{56}N_5O_4SCl$: C, 65.06; H, 7.64; N, 9.48; S, 4.34; Cl, 4.80. Found: C, 64.90; H, 7.77; N, 9.42; S, 4.16; Cl, 4.89.

EXAMPLES 1438–1454

The compounds of Examples 1438 through 1454 can be prepared in accordance with one or more of the synthetic schemes previously disclosed in this application or using methods known to those skilled in the art.

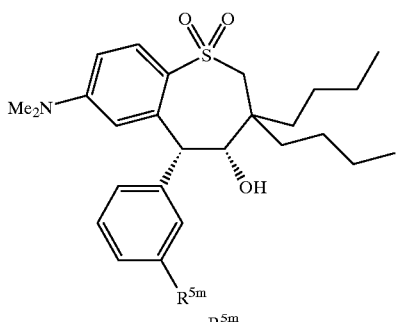

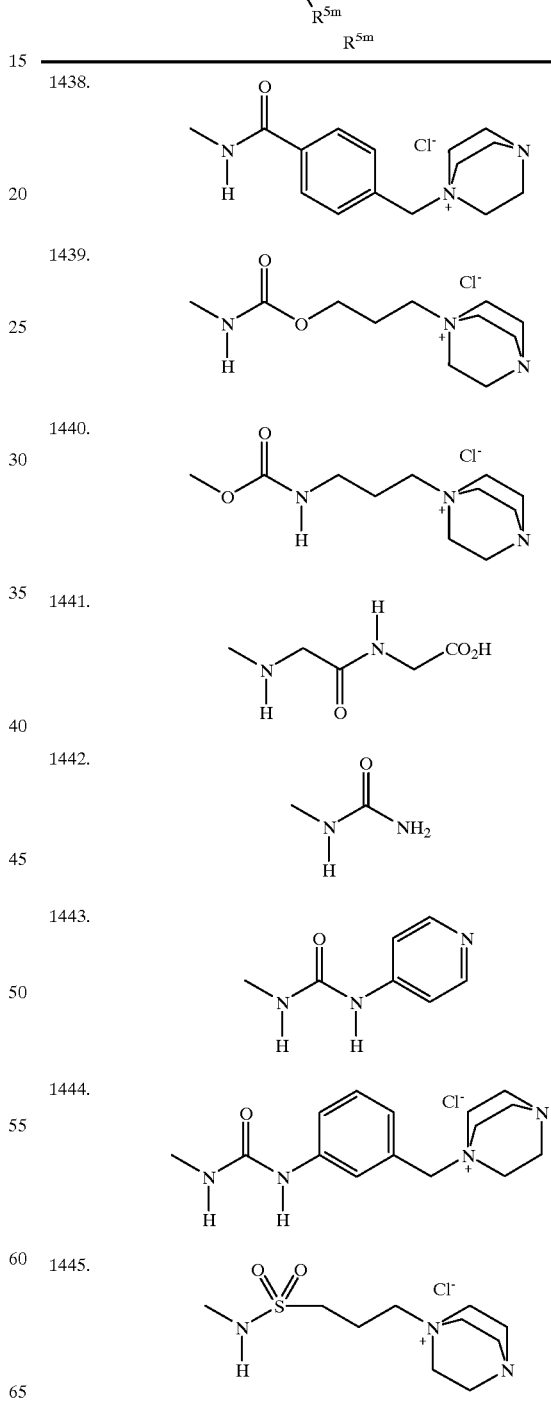

| 335 -continued | 336 -continued |
|---|---|
| 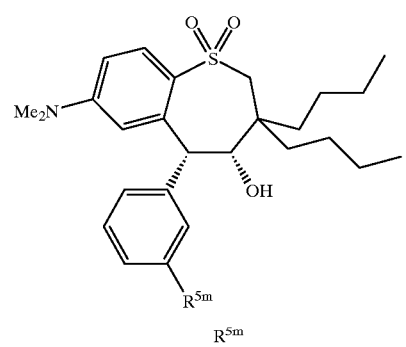 | 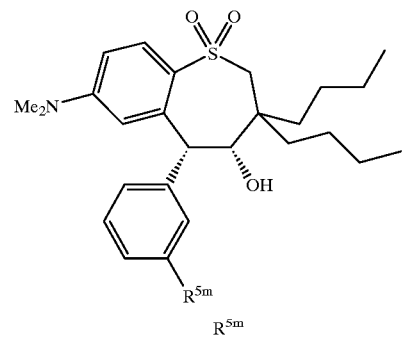 |
| 1446. 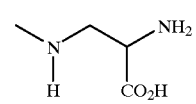 | 1450. 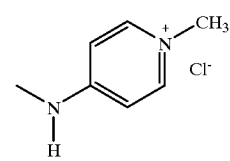 |
| 1446. 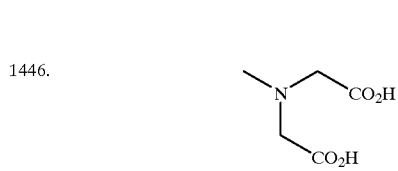 | 1451. 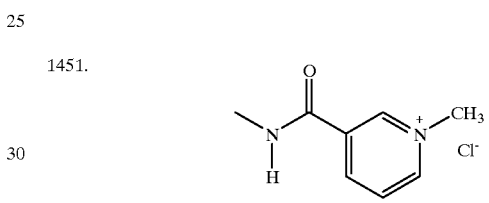 |
| 1447. 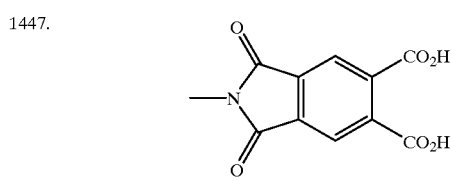 | 1452. 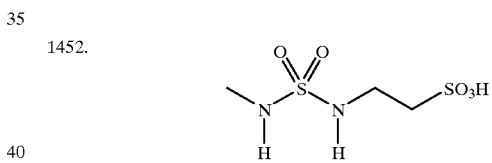 |
| 1448. 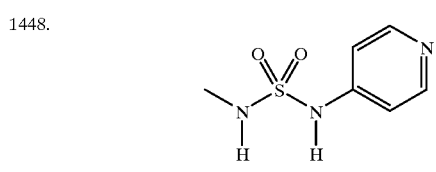 | 1453. 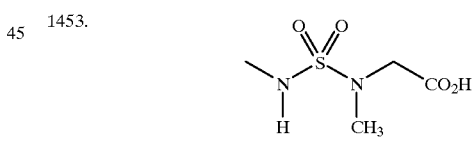 |
| 1449. 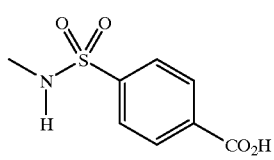 | 1454. 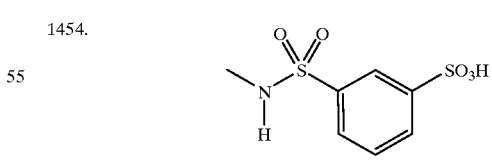 |

EXAMPLE 1455

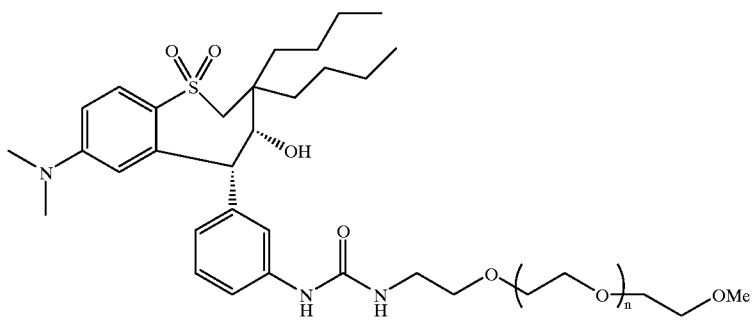

The 3-aminobenzothiepine of step 5 of Example 1398 (0.0165 g/0.0360 mmol), M-NCO-5000 (0.150 g/0.30 mmol) (Methoxy-PEG-NCO, MW 5000, purchased from Shearwater Polymers Inc., 2130 Memorial Parkway, SW, Huntsville, Ala. 35801), and $CDCl_3$ (0.7 mL) were combined in an 8 mm NMR tube. The tube was purged with $N_2$. After 72 hrs, the reaction mixture was heated to 50° C. After 24 hrs, an additional aliquot of the 3-aminobenzothiepine of step 5 of Example 1398 (0.0077 g/0.017 mmol) was added. After 24 hrs, the reaction mixture was transferred to a 2 mL vial and evaporated to dryness with a $N_2$ purge. The resulting white solid was dissolved in hot ethyl ether (2.0 mL) and ethyl acetate (0.057 mL/4 drops), cooled to precipitate and filtered. This precipitation procedure was repeated until no starting material was detected in the precipitate (TLC: $SiO_2$/80% EtOAc/hexanes). Concentrated in vacuo to give a white solid (0.0838 g/51%). $^1$H NMR ($CDCl_3$) d 0.82–0.90 (m, 6H), 1.05–1.49 (m, 14H), 1.18 (t, J=6.8 Hz, 2H), 1.59 (bt, 1H), 2.18 (bt, 1H), 2.34 (s, 2H), 2.78 (s, 6H), 3.04 (ABq, 2H), 3.35–3.80 (m, 625H), 4.09 (d, J=7.2 Hz, 2H), 5.42 (s, 1H), 5.78 (s, 1H), 6.04 (d, J=1.6 Hz, 1H), 6.47 (dd, J=6.4, 3.2 Hz, 1H), 7.07 (d, J=7.6 Hz, 1H), 7.31 (bs, 1H), 7.60 (d, J=7.6 Hz, 1H), 7.66 (s, 1H), 7.85 (d, J=8.8 Hz, 1H). Mass spectroscopy data also verified desired product.

BIOLOGICAL ASSAYS

The utility of the compounds of the present invention is shown by the following assays. These assays are performed in vitro and in animal models essentially using a procedure recognized to show the utility of the present invention.

In Vitro Assay of Compounds that Inhibit IBAT-Mediated Uptake of [$^{14}$C]-Taurocholate (TC) in H14 Cells Baby hamster kidney cells (BHK) transfected with the cDNA of human IBAT (H14 cells) are seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 μl assay buffer (Dulbecco'Modified Eagle's medium with 4.5 g/L glucose +0.2% (w/v) fatty acid free bovine serum albumin-(FAF)BSA). To each well 50 μl of a two-fold concentrate of test compound in assay buffer is added along with 50 μl of 6 μM [$^{14}$C]-taurocholate in assay buffer (final concentration of 3 μM [$^{14}$C]-taurocholate). The cell culture plates are incubated 2 hours at 37° C. prior to gently washing each well twice with 100 μl 4° C Dulbecco's phosphate-buffered saline (PBS) containing 0.2% (w/v) (FAF)BSA. The wells are then gently washed once with 100 μl 40° C. PBS without (FAF)BSA. To each 200 μl of liquid scintillaltic counting fluid is added, the plates are heat sealed and shaken for 30 minutes at room temperature prior to measuring the amount of radioactivity in each well on a Packard Top-Count instrument.

In Vitro Assay of Compounds that Inhibit Uptake of [$^{14}$C]-Alanine

The alanine uptake assay is performed in an identical fashion to the taurocholate assay, with the exception that labeled alanine is substituted for the labeled taurocholate.

In Vivo Assay of Compounds that Inhibit Rat Ileal Uptake of [$^{14}$C]-Taurocholate Into Bile (See "Metabolism of 3α,7β-dihydroxy-7α-methyl-5β-cholanoic acid and 3α,7β-dihydroxy-7α-methyl-5β--cholanoic acid in hamsters" in Biochimica et Biophysica Acta 833 (1985) 196–202 by Une et al.)

Male wistar rats (200–300 g) are anesthetized with inactin @100 mg/kg. Bile ducts are cannulated with a 10" length of PE10 tubing. The small intestine is exposed and laid out on a gauze pad. A canulae (⅛" luer lock, tapered female adapter) is inserted at 12 cm from the junction of the small intestine and the cecum. A slit is cut at 4 cm from this same junction (utilizing a 8 cm length of ileum). 20 ml of warm Dulbecco's phosphate buffered saline, pH 6.5 (PBS) is used to flush out the intestine segment. The distal opening is cannulated with a 20 cm length of silicone tubing (0.02" I.D.×0.037" O.D.). The proximal cannulae is hooked up to a peristaltic pump and the intestine is washed for 20 min with warm PBS at 0.25 ml/min. Temperature of the gut segment is monitored continuously. At the start of the experiment, 2.0 ml of control sample ([$^{14}$C]-taurocholate @0.05 mi/ml with 5 mM cold taurocholate) is loaded into the gut segment with a 3 ml syringe and bile sample collection is begun. Control sample is infused at a rate of 0.25 ml/min for 21 min. Bile samples fractions are collected every 3 minute for the first 27 minutes of the procedure. After the 21 min of sample infusion, the ileal loop is washed out with 20 ml of warm PBS (using a 30 ml syringe), and then the loop is washed out for 21 min with warm PBS at 0.25 ml/min. A second perfusion is initiated as described above but this with test compound being administered as well (21 min administration followed by 21 min of wash out) and bile sampled every 3 min for the first 27 min. If necessary, a third perfusion is performed as above that typically contains the control sample.

Measurement of Hepatic Cholesterol Concentration (HEPATIC CHOL)

Liver tissue was weighed and homogenized in chloroform:methanol (2:1). After homogenization and centrifugation the supernatant was separated and dried under nitrogen. The residue was dissolved in isopropanol and the cholesterol content was measured enzymatically, using a combination of cholesterol oxidase and peroxidase, as described by Allain, C. A., et al. (1974) Clin. Chem. 20, 470.

Measurement of Hepatic HMG CoA-Reductase Activity (HMG COA)

Hepatic microsomes were prepared by homogenizing liver samples in a phosphate/sucrose buffer, followed by centrifugal separation. The final pelleted material was resuspended in buffer and an aliquot was assayed for HMG CoA reductase activity by incubating for 60 minutes at 37° C. in the presence of $^{14}$C-HMG-CoA (Dupont-NEN). The reaction was stopped by adding 6N HCl followed by centrifugation. An aliquot of the supernatant was separated, by thin-layer chromatography, and the spot corresponding to the enzyme product was scraped off the plate, extracted and radioactivity was determined by scintillation counting. (Reference: Akerlund, J. and Bjorkhem, I. (1990) J. Lipid Res. 31, 2159).

Determination of Serum Cholesterol (SER.CHOL, RDL-CHOL, TGI and VLDL+LDL)

Total serum cholesterol (SER.CHOL) was measured enzymatically using a commercial kit from Wako Fine Chemicals (Richmond, Va.); Cholesterol C11, Catalog No. 276-64909. HDL cholesterol (HDL-CHOL) was assayed using this same kit after precipitation of VLDL and LDL with Sigma Chemical Co. HDL Cholesterol reagent, Catalog No. 352-3 (dextran sulfate method). Total serum triglycerides (blanked) (TGI) were assayed enzymatically with Sigma Chemical Co. GPO-Trinder, Catalog No. 337-B. VLDL and LDL (VLDL+LDL) cholesterol concentrations were calculated as the difference between total and HDL cholesterol.

Measurement of Hepatic Cholesterol 7-α-Hydroxylase Activity (7a-OHase)

Hepatic microsomes were prepared by homogenizing liver samples in a phosphate/sucrose buffer, followed by centrifugal separation. The final pelleted material was resuspended in buffer and an aliquot was assayed for cholesterol 7-α-hydroxylase activity by incubating for 5 minutes at 37° C. in the presence of NADPH. Following extraction into petroleum ether, the organic solvent was evaporated and the residue was dissolved in acetonitrile/methanol. The enzymatic product was separated by injecting an aliquot of the extract onto a $C_{18}$ reversed phase HPLC column and quantitating the eluted material using UV detection at 240 nm. (Reference: Horton, J. D., et al. (1994) J. Clin. Invest. 93, 2084).

Rat Gavage Assay

Male Wister rats (275–300 g) are administered IBAT inhibitors using an oral gavage procedure. Drug or vehicle (0.2% Tween 80 in water) is administered once a day (9:00–10:00 a.m.) for 4 days at varying dosages in a final volume of 2 mL per kilogram of body weight. Total fecal samples are collected during the final 48 hours of the treatment period and analyzed for bile acid content using an enzymatic assay as described below. Compound efficacy is determined by comparison of the increase in fecal bile acid (FBA) concentration in treated rats to the mean FBA concentration of rats in the vehicle group.

Measurement of Fecal Bile Acid Concentration (FBA)

Total fecal output from individually housed hamsters was collected for 24 or 48 hours, dried under a stream of nitrogen, pulverized and weighed. Approximately 0.1 gram was weighed out and extracted into an organic solvent (butanol/water). Following separation and drying, the residue was dissolved in methanol and the amount of bile acid present was measured enzymatically using the 3α-hydroxysteroid steroid dehydrogenase reaction with bile acids to reduce NAD. (Reference: Mashige, F., et al. (1981) Clin. Chem. 27, 1352).

[$^3$H]taurocholate Uptake In Rabbit Brush Border Membrane Vesicles (BBMV)

Rabbit Ileal brush border membranes were prepared from frozen ileal mucosa by the calcium precipitation method describe by Malathi et al. (Reference: (1979) Biochimica Biophysica Acta, 554, 259). The method for measuring taurocholate was essentially as described by Kramer et al. (Reference: (1992) Biochimica Biophysica Acta, 1111, 93) except the assay volume was 200 µl instead of 100 µl. Briefly, at room temperature a 190 µl solution containing 2 µM [$^3$H]-taurocholate(0.75 µCi), 20 mM tris, 100 mM NaCl, 100 mM mannitol pH 7.4 was incubated for 5 sec with 10 µl of brush border membrane vesicles (60–120 µg protein). The incubation was initiated by the addition of the BBMV while vortexing and the reaction was stopped by the addition of 5 ml of ice cold buffer (20 mM Hepes-tris, 150 mM KCl) followed immediately by filtration through a nylon filter (0.2 µm pore) and an additional 5 ml wash with stop buffer.

Acyl-CoA; cholesterol Acyl Transferase (ACAT)

Hamster liver and rat intestinal microsomes were prepared from tissue as described previously (Reference: (1980) J. Biol. Chem. 255, 9098) and used as a source of ACAT enzyme. The assay consisted of a 2.0 ml incubation containing 24 µM Oleoyl-CoA (0.05 µCi) in a 50 mM sodium phosphate, 2 mM DTT ph 7.4 buffer containing 0.25 % BSA and 200 µg of microsomal protein. The assay was initiated by the addition of oleoyl-CoA. The reaction went for 5 min at 37° C. and was terminated by the addition of 8.0 ml of chloroform/methanol (2:1). To the extraction was added 125 µg of cholesterol oleate in chloroform methanol to act as a carrier and the organic and aqueous phases of the extraction were separated by centrifugation after thorough vortexing. The chloroform phase was taken to dryness and then spotted on a silica gel 60 TLC plate and developed in hexane/ethyl ether (9:1). The amount of cholesterol ester formed was determined by measuring the amount of radioactivity incorporated into the cholesterol oleate spot on the TLC plate with a Packard instaimager.

Data from each of the noted compounds in the assays described above is as set forth in TABLES 5, 6, 7, and 8 as follows:

TABLE 5

| COMPOUND | IC50 µM* | In vitro % Inhibition of TC Uptake @ 100 µM # | % Inhibition of Alanine Uptake @ 100 µM # | % of Control Transport of TC in Rat Ileum @ 0.1 mM # |
|---|---|---|---|---|
| Benzothiazepine= | 2 | | 0 | 45.4 +/- 0.7 |

TABLE 5-continued

| COMPOUND | IC50 μM* | In vitro % Inhibition of TC Uptake @ 100 μM # | % Inhibition of Alanine Uptake @ 100 μM # | % of Control Transport of TC in Rat Ileum @ 0.1 mM # |
|---|---|---|---|---|
| 12 | | 25 | | |
| 3 | | 0 | | |
| 4a | | 3 | | |
| 5a | | 34 | | |
| 5b | 40 | | 0 | 72.9 ± 5.4 @ 0.5 mM |
| 4b | | 9 | | |
| 18 | | 6 | | |
| 14b | | 18 | | |
| 14a | | 13 | | |
| 13 | | 23 | | |
| 15 | 60 | | | |
| 19a | | 0 | | |
| 19b | | 15 | | |
| 8a | | 41 | | |
| Mixture of 8a and 8b | | 69 | | |
| Mixture of 9a and 9b | 6 | | | |
| 6a | 5 | | | |
| 6b | | 85 | | |
| 9a | 5 | | 0% @ 25 μM | 53.7 +/- 3.9 |
| Mixture of 6a and 20 | 13 | | | |
| Mixture of 6d and 10a | 0.8 | | 14% @ 25 μM | |
| 21a | | 37 | | |
| 21c | | 52 | | |
| 21b | | 45 | | |
| 6c | 2 | | 58.5 | 68.8 +/- 5.7 at 0.4 mM |
| 6d | 0.6 | | 77.7 | 16.1 +/- 1.1 @ 0.5 mM 30.2 +/- 0.9 @ 0.15 mM |
| 17 | | 10 | | |
| 7 | 50 | | 49.3 | |
| 10a | 7 | | 77.6 | 62.4 =/- 2.5 @ 0.2 mM |
| 10b | 15 | | 68.6 | |
| 25 | 0.1 | | 4% @ 10 μM | 26.0 +/- 3.3 |
| 26 | 2 | | 31% @ 25 μM | 87.9 +/- 1.5 |
| 27 | 5 | | 7% @ 20 μM | |
| 28 | 8 | | 31% @ 20 μM | |
| 29 | | | 88 @ 50μM | |
| 30 | | | 96 @ 50μM | |
| 31 | | | 41 @ 50μM | |
| 37 | 3 | | 0% @ 5 μM | |
| 38 | 0.3 | | 11% @ 5 μM | 20.6 +/- 5.7 |
| 40 | | | 49 @ 50μM | |
| 41 | 2 | | 0% @ 20 μM | |
| 42 | 1.5 | | | |
| 43 | 1.5 | | 16% @ 25 μM | |
| 48 | 2 | | 22% @ 20 μM | |
| 49 | 0.15 | | 21% @ 200 μM | 21.2 +/- 2.7 |
| 57 | | | 51 @ 50μM | |
| 58 | | | 20 @ 50μM | |
| 59 | 70 | | | |
| 60 | 9 | | 59 | |
| 61 | 30 | | 175 | |
| 62 | 10 | | | |
| 63 | | 90 @ 6μM | | |
| 64 | | 100 @ 6μM | | |

*In vitro Taurocholate Cell Uptake
Unless otherwise noted
=Comparative Example is Example No.1 in WO 93/16055

TABLE 6

| Compound | TC-uptake (H14 cells) IC(50) | TC-uptake Ileal Loop EC(50) | TC-uptake (BBMV) IC(50) | ACAT (liver) IC(50) | ACAT intestine IC(50) |
|---|---|---|---|---|---|
| COMP. EXAMPLE* | 1 μM | 74 μM | 3 μM | 20 μM | 20 μM |
| 6d | 0.6 μM | 31 μM | 1.5 μM | 25 μM | 20 μM |
| * 38 | 0.3 μM | 12 μM | 2 μM | 15 μM | N.D. |
| 49 | 0.1 μM | 12 μM | N.D. | 6 μM | N.D. |
| 25 | 0.1 μM | 20 μM | 0.8 μM | 8 μM | 8 μM |

Comparative Example is Example No. 1 in WO 93/16055

TABLE 7

EFFICACY OF COMPOUND NO. 25 IN CHOLESTEROL-FED HAMSTERS (mean ± SEM, *p < 0.05, A-Student's t, B-Dunnett's)

| PARAMETER WEIGHT (G) | CONTROL | 4% CHOLES-TYRAMINE | 0.2% CPD. NO. 25 |
|---|---|---|---|
| day 1 | 117(2) | 114(6) | 117(5) |
| day 14 | 127(3) | 127(3) | 132(4) |
| LIVER WEIGHT (G) | 5.4(0.3) | 4.9(0.4) | 5.8(0.2) |
| SER.CHOL(mg%) | 143(7) | 119(4)*A,B | 126(2)*A,B |
| HDL-CHOL(mg%) | 89(4) | 76(3)*A,B | 76(1)*A,B |
| VLDL + LDL | 54(7) | 42(3)*A | 50(3) |
| TGI(mg%) | 203(32) | 190(15) | 175(11) |
| HEPATIC CHOL(mg/g) | 2.5(0.3) | 1.9(0.1)*A,B | 1.9(0.1)*A,B |
| HMG COA (pm/mg/min.) | 15.8(7.6) | 448.8(21.6)*A,B | 312.9(37.5)*A,B |
| 7a-OHase (pm/mg/min.) | 235.3(25.1) | 357.2(28.3)*A,B | 291.0(6.0)*A |
| 24 HR. FECAL Wt (G) | 2.3(0.1) | 2.7(0.1)*A,B | 2.4(0.04) |
| FBA (mM/24 H/100 g) | 6.2(0.8) | 12.3(1.5)*A,B | 11.9(0.5)*A,B |

TABLE 8

EFFICACY OF COMPOUND NO. 25 IN RAT ALZET MINIPUMP MODEL (mean ± SEM, *p < 0.05, A-Student's t, B-Dunnett's)

| PARAMETER WEIGHT (G) | CONTROL | 20 MPL/DAY CPD. NO. 25 |
|---|---|---|
| day 1 | 307 (4) | 307 (3) |
| day 8 | 330 (4) | 310 (4)*A,B |

TABLE 8-continued

EFFICACY OF COMPOUND NO. 25 IN RAT ALZET MINIPUMP MODEL (mean ± SEM, *p < 0.05, A-Student's t, B-Dunnett's)

| PARAMETER WEIGHT (G) | CONTROL | 20 MPL/DAY CPD. NO. 25 |
|---|---|---|
| LIVER WEIGHT (G) | 15.5 (0.6) | 14.6 (0.4) |
| SER.CHOL(mg%) | 85 (3) | 84 (3) |
| HEPATIC CHOL(mg/g) | 21 (0.03) | 2.0 (0.03) |
| HMG COA pm/mg/min | 75.1 (6.4) | 318.0 (40.7)*A,B |
| 7a-OHase (pm/mg/min) | 281.9 (13.9) | 535.2 (35.7)*A,B |
| 24 HR. FECAL WT (G) | 5.8 (0.1) | 5.7 (0.4) |
| FBA (mM/24 H/100 g) | 17.9 (0.9) | 39.1 (4.5)*A,B |

Additional in vitro taurocholate uptake tests were conducted in the following compounds listed in Table 9.

TABLE 9

Biological Data for Some Compounds of the Present Invention

| Compound Number | Human TC $IC_{50}$ ($\mu M$) | Alanine Uptake Percent Inhibition @ $\mu M$ |
|---|---|---|
| 101 | | 0 @ 1.0 |
| 102 | 0.083 | |
| 103 | | 13 @ 0.25 |
| 104 | 0.0056 | |
| 105 | 0.6 | |
| 106 | 0.8 | |
| 107 | | 14.0 @ 0.063 |
| 108 | 0.3 | |
| 109 | | 2.0 @ 0.063 |
| 110 | 0.09 | |
| 111 | 2.5 | |
| 112 | 3.0 | |
| 113 | 0.1 | |
| 114 | 0.19 | |
| 115 | 8.0 | |
| 116 | 0.3 | |
| 117 | | 12.0 @ 0.625 |
| 118 | 0.4 | |
| 119 | 1.3 | |
| 120 | | 34.0 @ 5.0 |
| 121 | 0.068 | |
| 122 | 1.07 | |
| 123 | 1.67 | |
| 124 | | 14.0 @ 6.25 |
| 125 | 18.0 | |
| 126 | | 18 @ 1.25 |
| 127 | 0.55 | |
| 128 | 0.7 | |
| 129 | 0.035 | |
| 131 | 1.28 | |
| 132 | | 5.4 @ 0.063 |
| 133 | 16.0 | |
| 134 | 0.3 | |
| 135 | 22.0 | |
| 136 | 0.09 | |
| 137 | 2.4 | |
| 138 | 3.0 | |
| 139 | >25.0 | |
| 140 | | |
| 141 | | |
| 142 | 0.5 | |
| 143 | 0.03 | |
| 144 | 0.053 | |
| 262 | 0.07 | |
| 263 | 0.7 | |
| 264 | 0.2 | |
| 265 | 2.0 | |
| 266 | 0.5 | |
| 267 | 0.073 | |
| 268 | 0.029 | |
| 269 | 0.08 | |
| 270 | 0.12 | |
| 271 | 0.07 | |
| 272 | 0.7 | |
| 273 | 1.9 | |
| 274 | 0.18 | |
| 275 | | 5.0 @ 0.25 |
| 276 | 0.23 | |
| 277 | 0.04 | |
| 278 | 3.0 | |
| 279 | 0.4 | |
| 280 | 0.18 | |
| 281 | 0.019 | |
| 282 | 0.021 | |
| 283 | 0.35 | |
| 284 | 0.08 | |
| 285 | | |
| 286 | 19.0 | |
| 287 | 4.0 | |
| 288 | | 10.0 @ 6.25 |
| 289 | 0.23 | |
| 290 | 0.054 | |
| 291 | 0.6 | |
| 292 | 0.046 | |
| 293 | 1.9 | |
| 294 | 0.013 | |
| 295 | 1.3 | |
| 296 | 1.6 | |
| 1000 | | |
| 1001 | | |
| 1002 | | |
| 1003 | | |
| 1004 | | |
| 1005 | 0.0004 | |
| 1006 | 0.001 | |
| 1007 | 0.001 | |
| 1008 | 0.001 | |
| 1009 | 0.001 | |
| 1010 | 0.001 | |
| 1011 | 0.001 | |
| 1012 | 0.0015 | |
| 1013 | 0.002 | |
| 1014 | 0.002 | |
| 1015 | 0.002 | |
| 1016 | 0.002 | |
| 1017 | 0.002 | |
| 1018 | 0.002 | |
| 1019 | 0.002 | |
| 1020 | 0.002 | |
| 1021 | 0.002 | |
| 1022 | 0.002 | |
| 1023 | 0.002 | |
| 1024 | 0.002 | |
| 1025 | 0.002 | |
| 1026 | 0.002 | |
| 1027 | 0.002 | |
| 1028 | 0.002 | |
| 1029 | 0.002 | |
| 1030 | 0.002 | |
| 1031 | 0.002 | |
| 1032 | 0.002 | |
| 1033 | 0.002 | |
| 1034 | 0.002 | |
| 1035 | 0.002 | |
| 1036 | 0.002 | |
| 1037 | 0.0022 | |
| 1038 | 0.0025 | |
| 1039 | 0.0026 | |

TABLE 9-continued

Biological Data for Some Compounds of the Present Invention

| Compound Number | Human TC IC$_{50}$ ($\mu$M) | Alanine Uptake Percent Inhibition @ $\mu$M |
|---|---|---|
| 1040 | 0.003 | |
| 1041 | 0.003 | |
| 1042 | 0.003 | |
| 1043 | 0.003 | |
| 1044 | 0.003 | |
| 1045 | 0.003 | |
| 1046 | 0.003 | |
| 1047 | 0.003 | |
| 1048 | 0.003 | |
| 1049 | 0.003 | |
| 1050 | 0.003 | |
| 1051 | 0.003 | |
| 1052 | 0.003 | |
| 1053 | 0.003 | |
| 1054 | 0.003 | |
| 1055 | 0.003 | |
| 1056 | 0.003 | |
| 1057 | 0.003 | |
| 1058 | 0.003 | |
| 1059 | 0.003 | |
| 1060 | 0.0036 | |
| 1061 | 0.004 | |
| 1062 | 0.004 | |
| 1063 | 0.004 | |
| 1064 | 0.004 | |
| 1065 | 0.004 | |
| 1066 | 0.004 | |
| 1067 | 0.004 | |
| 1068 | 0.004 | |
| 1069 | 0.004 | |
| 1070 | 0.004 | |
| 1071 | 0.004 | |
| 1072 | 0.004 | |
| 1073 | 0.004 | |
| 1074 | 0.004 | |
| 1075 | 0.0043 | |
| 1076 | 0.0045 | |
| 1077 | 0.0045 | |
| 1078 | 0.0045 | |
| 1079 | 0.005 | |
| 1080 | 0.005 | |
| 1081 | 0.005 | |
| 1082 | 0.005 | |
| 1083 | 0.005 | |
| 1084 | 0.005 | |
| 1085 | 0.005 | |
| 1086 | 0.005 | |
| 1087 | 0.005 | |
| 1088 | 0.0055 | |
| 1089 | 0.0057 | |
| 1090 | 0.006 | |
| 1091 | 0.006 | |
| 1092 | 0.006 | |
| 1093 | 0.006 | |
| 1094 | 0.006 | |
| 1095 | 0.006 | |
| 1096 | 0.006 | |
| 1097 | 0.006 | |
| 1098 | 0.006 | |
| 1099 | 0.0063 | |
| 1100 | 0.0068 | |
| 1101 | 0.007 | |
| 1102 | 0.007 | |
| 1103 | 0.007 | |
| 1104 | 0.007 | |
| 1105 | 0.007 | |
| 1106 | 0.0073 | |
| 1107 | 0.0075 | |
| 1108 | 0.0075 | |
| 1109 | 0.008 | |
| 1110 | 0.008 | |
| 1111 | 0.008 | |
| 1112 | 0.008 | |
| 1113 | 0.009 | |
| 1114 | 0.009 | |
| 1115 | 0.0098 | |
| 1116 | 0.0093 | |
| 1117 | 0.01 | |
| 1118 | 0.01 | |
| 1119 | 0.01 | |
| 1120 | 0.01 | |
| 1121 | 0.01 | |
| 1122 | 0.011 | |
| 1123 | 0.011 | |
| 1124 | 0.011 | |
| 1125 | 0.012 | |
| 1126 | 0.013 | |
| 1127 | 0.013 | |
| 1128 | 0.017 | |
| 1129 | 0.018 | |
| 1130 | 0.018 | |
| 1131 | 0.02 | |
| 1132 | 0.02 | |
| 1133 | 0.02 | |
| 1134 | 0.02 | |
| 1135 | 0.021 | |
| 1136 | 0.021 | |
| 1137 | 0.021 | |
| 1138 | 0.022 | |
| 1139 | 0.022 | |
| 1140 | 0.023 | |
| 1141 | 0.023 | |
| 1142 | 0.024 | |
| 1143 | 0.027 | |
| 1144 | 0.028 | |
| 1145 | 0.029 | |
| 1146 | 0.029 | |
| 1147 | 0.029 | |
| 1148 | 0.03 | |
| 1149 | 0.03 | |
| 1150 | 0.03 | |
| 1151 | 0.031 | |
| 1152 | 0.036 | |
| 1153 | 0.037 | |
| 1154 | 0.037 | |
| 1155 | 0.039 | |
| 1156 | 0.039 | |
| 1157 | 0.04 | |
| 1158 | 0.06 | |
| 1159 | 0.06 | |
| 1160 | 0.062 | |
| 1161 | 0.063 | |
| 1162 | 0.063 | |
| 1163 | 0.09 | |
| 1164 | 0.093 | |
| 1165 | 0.11 | |
| 1166 | 0.11 | |
| 1167 | 0.12 | |
| 1168 | 0.12 | |
| 1169 | 0.12 | |
| 1170 | 0.13 | |
| 1171 | 0.14 | |
| 1172 | 0.14 | |
| 1173 | 0.15 | |
| 1174 | 0.15 | |
| 1175 | 0.17 | |
| 1176 | 0.18 | |
| 1177 | 0.18 | |
| 1178 | 0.19 | |
| 1179 | 0.19 | |
| 1180 | 0.2 | |
| 1181 | 0.22 | |

TABLE 9-continued

Biological Data for Some Compounds of the Present Invention

| Compound Number | Human TC IC$_{50}$ ($\mu$M) | Alanine Uptake Percent Inhibition @ $\mu$M |
|---|---|---|
| 1182 | 0.25 | |
| 1183 | 0.28 | |
| 1184 | 0.28 | |
| 1185 | 0.28 | |
| 1186 | 0.3 | |
| 1187 | 0.32 | |
| 1188 | 0.35 | |
| 1189 | 0.35 | |
| 1190 | 0.55 | |
| 1191 | 0.65 | |
| 1192 | 1.0 | |
| 1193 | 1.0 | |
| 1194 | 1.6 | |
| 1195 | 1.7 | |
| 1196 | 2.0 | |
| 1197 | 2.2 | |
| 1198 | 2.5 | |
| 1199 | 4.0 | |
| 1200 | 6.1 | |
| 1201 | 8.3 | |
| 1202 | 40.0 | |
| 1203 | | 0 @ 0.063 |
| 1204 | 0.05 | |
| 1205 | 0.034 | |
| 1206 | 0.035 | |
| 1207 | 0.068 | |
| 1208 | 0.042 | |
| 1209 | | 0 @ 0.063 |
| 1210 | 0.14 | |
| 1211 | 0.28 | |
| 1212 | 0.39 | |
| 1213 | 1.7 | |
| 1214 | 0.75 | |
| 1215 | 0.19 | |
| 1216 | 0.39 | |
| 1217 | 0.32 | |
| 1218 | 0.19 | |
| 1219 | 0.34 | |
| 1220 | 0.2 | |
| 1221 | 0.041 | |
| 1222 | 0.065 | |
| 1223 | 0.28 | |
| 1224 | 0.33 | |
| 1225 | 0.12 | |
| 1226 | 0.046 | |
| 1227 | 0.25 | |
| 1228 | 0.083 | |
| 1229 | 0.049 | |
| 1230 | 0.062 | |
| 1231 | 0.075 | |
| 1232 | 1.2 | |
| 1233 | 0.15 | |
| 1234 | 0.067 | |
| 1235 | 0.045 | |
| 1236 | 0.05 | |
| 1237 | 0.07 | |
| 1238 | 0.8 | |
| 1239 | 0.035 | |
| 1240 | 0.016 | |
| 1241 | 0.047 | |
| 1242 | 0.029 | |
| 1243 | 0.63 | |
| 1244 | 0.062 | |
| 1245 | 0.32 | |
| 1246 | 0.018 | |
| 1247 | 0.017 | |
| 1248 | 0.33 | |
| 1249 | 10.2 | |
| 1250 | 0.013 | |
| 1251 | 0.62 | |
| 1252 | 29. | |
| 1253 | 0.3 | |
| 1254 | 0.85 | |
| 1255 | 0.69 | |
| 1256 | 0.011 | |
| 1257 | 0.1 | |
| 1258 | 0.12 | |
| 1259 | 16.5 | |
| 1260 | 0.012 | |
| 1261 | 0.019 | |
| 1262 | 0.03 | |
| 1263 | 0.079 | |
| 1264 | 0.21 | |
| 1265 | 0.24 | |
| 1266 | 0.2 | |
| 1267 | 0.29 | |
| 1268 | 0.035 | |
| 1269 | 0.026 | |
| 1270 | 0.026 | |
| 1271 | 0.011 | |
| 1272 | 0.047 | |
| 1273 | 0.029 | |
| 1274 | 0.028 | |
| 1275 | 0.024 | |
| 1276 | 0.029 | |
| 1277 | 0.018 | |
| 1278 | 0.017 | |
| 1279 | 0.028 | |
| 1280 | 0.76 | |
| 1281 | 0.055 | |
| 1282 | 0.17 | |
| 1283 | 0.17 | |
| 1284 | 0.011 | |
| 1285 | 0.027 | |
| 1286 | 0.068 | |
| 1287 | 0.071 | |
| 1288 | 0.013 | |
| 1289 | 0.026 | |
| 1290 | 0.017 | |
| 1291 | 0.013 | |
| 1292 | 0.025 | |
| 1293 | 0.019 | |
| 1294 | 0.011 | |
| 1295 | 0.014 | |
| 1296 | 0.063 | |
| 1297 | 0.029 | |
| 1298 | 0.018 | |
| 1299 | 0.012 | |
| 1300 | 1.0 | |
| 1301 | 0.15 | |
| 1302 | 1.4 | |
| 1303 | 0.26 | |
| 1304 | 0.25 | |
| 1305 | 0.25 | |
| 1306 | 1.2 | |
| 1307 | 3.1 | |
| 1308 | 0.04 | |
| 1309 | 0.24 | |
| 1310 | 1.16 | |
| 1311 | 3.27 | |
| 1312 | 5.0 | |
| 1313 | 6.1 | |
| 1314 | 0.26 | |
| 1315 | 1.67 | |
| 1316 | 3.9 | |
| 1317 | 21.0 | |
| 1318 | | |
| 1319 | | 11.0 @ 0.25 |
| 1320 | | |
| 1321 | | 11.1 @ 5.0 |
| 1322 | | 3.0 @ 0.0063 |
| 1323 | | 4.0 @ 0.0063 |

TABLE 9-continued

Biological Data for Some Compounds of the Present Invention

| Compound Number | Human TC IC$_{50}$ ($\mu$M) | Alanine Uptake Percent Inhibition @ $\mu$M |
|---|---|---|
| 1324 | | 43.0 @ 0.0008 |
| 1325 | | 1.0 @ 0.0063 |
| 1326 | | 3.60 @ 0.0008 |
| 1327 | | 3.0 @ 0.0063 |
| 1328 | | 68.0 @ 0.0063 |
| 1329 | | 2.0 @ 0.0063 |
| 1330 | | 9.0 @ 0.0063 |
| 1331 | | 57.0 @ 0.0008 |
| 1332 | | 43.0 @ 0.0008 |
| 1333 | | 0 @ 0.0063 |
| 1334 | | 50.0 @ 0.0008 |
| 1335 | | 38.0 @ 0.0008 |
| 1336 | | 45.0 @ 0.0008 |
| 1337 | | 0 @ 0.0063 |
| 1338 | | 1.0 @ 0.25 |
| 1339 | | 0 @ 0.063 |
| 1340 | | 9.0 @ 0.063 |
| 1341 | | 1.0 @ 0.063 |
| 1342 | | 1.0 @ 0.063 |
| 1343 | | |
| 1344 | | |
| 1345 | | 13.0 @ 0.25 |
| 1346 | | |
| 1347 | 0.0036 | |
| 1348 | | |
| 1349 | | |
| 1350 | | |
| 1351 | 0.44 | |
| 1352 | 0.10 | |
| 1353 | 0.0015 | |
| 1354 | 0.006 | |
| 1355 | 0.0015 | |
| 1356 | 0.22 | |
| 1357 | 0.023 | |
| 1358 | 0.008 | |
| 1359 | 0.014 | |
| 1360 | 0.003 | |
| 1361 | 0.004 | |
| 1362 | 0.019 | |
| 1363 | 0.008 | |
| 1364 | 0.006 | |
| 1365 | 0.008 | |
| 1366 | 0.015 | |
| 1367 | 0.002 | |
| 1368 | 0.005 | |
| 1369 | 0.005 | |
| 1370 | 0.002 | |
| 1371 | 0.004 | |
| 1372 | 0.004 | |
| 1373 | 0.008 | |
| 1374 | 0.007 | |
| 1375 | 0.002 | |
| 1449 | 0.052 | |
| 1450 | 0.039 | |
| 1451 | 0.014 | |

Additional in vitro taurocholate uptake tests and in vivo rat gavage tests were conducted on the following compounds listed in Tables 10 and 11.

TABLE 10

In Vitro Taurocholate Uptake Assay Data for Some Additional Compounds of the Present Invention

| Compound of Example Number | Human TC IC50 (nM) |
|---|---|
| 1402 | 25 |
| 1403 | 23 |
| 1404 | 10 |
| 1405 | 21 |
| 1406 | 4 |
| 1407 | 3 |
| 1408 | 1 |
| 1409 | 0.9 |
| 1410 | 2 |
| 1411 | 2 |
| 1412 | 3 |
| 1413 | 3 |
| 1414 | 15 |
| 1415 | 2 |
| 1416 | 14 |
| 1417 | 2 |
| 1418 | <1 |
| 1419 | 3 |
| 1420 | 11 |
| 1421 | 4 |
| 1422 | 3 |
| 1423 | 3 |
| 1424 | 14 |
| 1425 | 2 |
| 1426 | 0.3 |
| 1427 | 2 |
| 1428 | 0.7 |
| 1429 | |
| 1430 | 3 |
| 1431 | 5 |
| 1432 | 26 |
| 1433 | 67 |

TABLE 11

Rat Gavage Assay Data for Some Additional Compounds of the Present Invention

| Compound of Example No. | Study No. | Dose (mg/kg/day) | Delta (micromoles fecal bile acid per day) |
|---|---|---|---|
| 1402 | 28 | 5 | 58.2 |
| | | .2 | 1.3 |
| | | .04 | 0.3 |
| 1402 | 30 | 2 | 50.3 |
| | | .4 | 40.9 |
| | | .08 | 48.5 |
| | | .016 | 22.9 |
| 1403 | 30 | 2 | 41.6 |
| | | .4 | 35.2 |
| | | .08 | 11.9 |
| | | .016 | 3 |
| 1404 | 28 | 5 | 93.7 |
| | | .2 | 59.1 |
| | | .04 | 33.5 |
| 1406 | 32 | 2 | 47.8 |
| | | .4 | 31.6 |
| | | .08 | 12.8 |
| | | .016 | -8.5 |
| 1407 | 32 | 2 | 51.9 |
| | | .4 | 30.1 |
| | | .08 | 27.5 |
| | | .016 | 6.4 |
| 1407 | 33 | 2 | 35 |
| | | .4 | 12.7 |
| | | .08 | -.04 |
| | | .016 | -4.5 |
| 1408 | 37 | 2 | 41.2 |

TABLE 11-continued

Rat Gavage Assay Data for Some Additional Compounds of the Present Invention

| Compound of Example No. | Study No. | Dose (mg/kg/day) | Delta (micromoles fecal bile acid per day) |
|---|---|---|---|
| | | .4 | 36.8 |
| | | .08 | 16.8 |
| | | .016 | −3.3 |
| 1408 | 29 | 2 | 26.2 |
| | | .4 | 45.2 |
| | | .08 | 26.3 |
| | | .016 | 6.6 |
| 1409 | 33 | 2 | 19.2 |
| | | .4 | 28.7 |
| | | .08 | 14.1 |
| | | .016 | −1.7 |
| 1409 | 41 | 2 | 44.2 |
| | | .4 | 35.9 |
| | | .08 | 14.5 |
| | | .016 | 11 |
| 1410 | 33 | 32.4 | |
| | | 34.3 | |
| | | 27.9 | |
| | | 9.3 | |
| 1410 | 35 | 2 | 26.2 |
| | | .4 | 36.5 |
| | | .08 | 18.5 |
| | | .016 | 20.4 |
| 1411 | 34 | 2 | 63.4 |
| | | .4 | 54.1 |
| | | .08 | 33 |
| | | 0.16 | 22.3 |
| 1413 | 26 | 5 | 52.3 |
| | | .2 | 42.4 |
| | | .04 | 19 |
| 1414 | 27 | 5 | 45.2 |
| | | .2 | 39.5 |
| | | .04 | 14.3 |
| 1414 | 31 | 2 | 41.5 |
| | | .4 | 33.7 |
| | | .08 | 29 |
| | | .016 | 3.8 |
| 1415 | 28 | 5 | 59.9 |
| | | .2 | 48.1 |
| | | .04 | 23.9 |
| 1415 | 37 | 2 | 48.9 |
| | | .4 | 25.7 |
| | | .08 | 27.1 |
| | | .016 | 12.7 |
| 1416 | 29 | 2 | 46.1 |
| | | .4 | 21.9 |
| | | .08 | 25 |
| | | .016 | −7.8 |
| 1417 | 31 | 2 | 51.4 |
| | | .4 | 42 |
| | | .08 | 39.6 |
| | | .016 | 29.3 |
| 1418 | 29 | 2 | 20.3 |
| | | .4 | 29.5 |
| | | .08 | −4.6 |
| | | .016 | −10 |
| 1419 | 31 | 2 | 28.5 |
| | | .4 | 13.9 |
| | | .08 | 10.3 |
| | | .016 | 5.8 |
| 1420 | 31 | 2 | 53.1 |
| | | .4 | 45 |
| | | .08 | 38.1 |
| | | .016 | 29.6 |
| 1421 | 32 | 2 | 57.8 |
| | | .4 | 27.7 |
| | | .08 | 25.3 |
| | | .016 | 4.7 |
| 1423 | 34 | 2 | 56.5 |
| | | .4 | 69.3 |
| | | .08 | 35.3 |
| | | .016 | 14.4 |
| 1425 | 21 | 5 | 91.8 |
| | | .2 | 100. |
| | | .04 | 66.4 |
| 1425 | 30 | 2 | 44.6 |
| | | .4 | 62 |
| | | .08 | 69.5 |
| | | .016 | 31.6 |
| 1425 | 40 | 2 | 48.3 |
| | | .4 | 45 |
| | | .08 | 31.2 |
| | | .016 | 30 |
| 1426 | 33 | 2 | 52.4 |
| | | .4 | 19.5 |
| | | .08 | 23.1 |
| | | .016 | 24.6 |
| 1426 | 35 | 2 | 37.7 |
| | | .4 | 41.7 |
| | | .08 | 40.5 |
| | | .016 | 24.6 |
| 1426 | 39 | 2 | 54.3 |
| | | .4 | 48.7 |
| | | .08 | 51.8 |
| | | .016 | 26.8 |
| 1426 | 43 | 2 | 40.8 |
| | | .4 | 21.7 |
| | | .08 | 5.9 |
| | | .016 | 4.1 |
| 1427 | 40 | 2 | 36.7 |
| | | .4 | 35.8 |
| | | .08 | 27.3 |
| | | .016 | 13.8 |
| 1428 | 34 | 2 | 40.4 |
| | | .4 | 64.9 |
| | | .08 | 24.4 |
| | | .016 | 12.2 |
| 1428 | 42 | 2 | 46 |
| | | .4 | 40.7 |
| | | .08 | 26 |
| | | .016 | 1.1 |
| 1429 | 41 | 2 | 34.5 |
| | | .4 | 24.9 |
| | | .08 | 18.7 |
| | | .016 | 9.2 |
| 1429 | 42 | 2 | 47.1 |
| | | .4 | 31.1 |
| | | .08 | 35.5 |
| | | .016 | 4.8 |
| 1430 | 30 | 2 | 51.2 |
| | | .4 | 50.4 |
| | | .08 | 20.7 |
| | | .016 | −5.6 |
| 1431 | 32 | 28.3 | |
| | | 45.8 | |
| | | 21.9 | |
| | | 1.1 | |
| 1432 | 28 | 5 | 36.2 |
| | | .2 | 9.7 |
| | | .04 | 2.4 |
| 1433 | 24 | 20 | 66.5 |
| | | 2 | 47.4 |
| | | .2 | 26.5 |

The examples herein can be repeated with similar success by substituting the generically or specifically described reactants and/or operating conditions of this invention for those used in the preceding examples.

Novel compositions of the invention are further illustrated in attached Exhibits A and B.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

Exhibit A
Table C2: Alternative Compounds #2 (Families F101–F123)

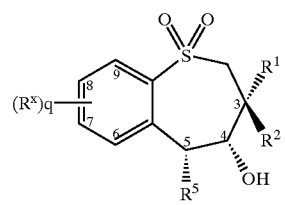

| Family | Cpd # | $R^1=R^2$ | $R^5$ | $(R^x)q$ |
|---|---|---|---|---|
| F101 | | CHOSEN FROM TABLE 1 | Ph— | CHOSEN FROM TABLE 1 |
| F102 | | CHOSEN FROM TABLE 1 | p-F—Ph— | CHOSEN FROM TABLE 1 |
| F103 | | CHOSEN FROM TABLE 1 | m-F—Ph— | CHOSEN FROM TABLE 1 |
| F104 | | CHOSEN FROM TABLE 1 | p-CH$_3$O—Ph— | CHOSEN FROM TABLE 1 |
| F105 | | CHOSEN FROM TABLE 1 | m-CH$_3$O—Ph— | CHOSEN FROM TABLE 1 |
| F106 | | CHOSEN FROM TABLE 1 | p-(CH$_3$)$_2$N—Ph— | CHOSEN FROM TABLE 1 |
| F107 | | CHOSEN FROM TABLE 1 | m-(CH$_3$)$_2$N—Ph | CHOSEN FROM TABLE 1 |
| F108 | | CHOSEN FROM TABLE 1 | I$^-$, p-(CH$_3$)$_3$—N$^+$—Ph— | CHOSEN FROM TABLE 1 |
| F109 | | CHOSEN FROM TABLE 1 | I$^-$, m-(CH$_3$)$_3$—N$^+$—Ph— | CHOSEN FROM TABLE 1 |
| F110 | | CHOSEN FROM TABLE 1 | I$^-$, p-(CH$_3$)$_3$—N$^+$—CH$_2$CH$_2$—(OCH$_2$CH$_2$)$_2$—O—Ph— | CHOSEN FROM TABLE 1 |
| F111 | | CHOSEN FROM TABLE 1 | I$^-$, m-(CH$_3$)$_3$—N$^+$—CH$_2$CH$_2$—(OCH$_2$CH$_2$)$_2$—O—Ph— | CHOSEN FROM TABLE 1 |
| F112 | | CHOSEN FROM TABLE 1 | I$^-$, p-(N,N-dimethylpiperazine)-(N')-CH$_2$—(OCH$_2$CH$_2$)$_2$—O—Ph— | CHOSEN FROM TABLE 1 |
| F113 | | CHOSEN FROM TABLE 1 | I$^-$, m-(N,N-dimethylpiperazine)-(N')-CH$_2$—(OCH$_2$CH$_2$)$_2$—O—Ph— | CHOSEN FROM TABLE 1 |
| F114 | | CHOSEN FROM TABLE 1 | m-F—Ph— p-CH$_3$O— | CHOSEN FROM TABLE 1 |
| F115 | | CHOSEN FROM TABLE 1 | 3,4-dioxy-methylene-Ph— | CHOSEN FROM TABLE 1 |
| F116 | | CHOSEN FROM TABLE 1 | m-F—Ph— p-F—Ph— | CHOSEN FROM TABLE 1 |
| F117 | | CHOSEN FROM TABLE 1 | m-CH$_3$O— p-F—Ph— | CHOSEN FROM TABLE 1 |

Exhibit A
Table C2: Alternative Compounds #2 (Families F101–F123)

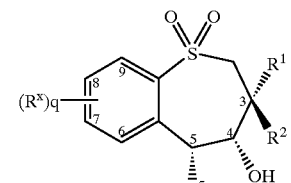

| Family | Cpd # | $R^1=R^2$ | $R^5$ | $(R^x)q$ |
|---|---|---|---|---|
| F118 | | CHOSEN FROM TABLE 1 | 4-pyridine | CHOSEN FROM TABLE 1 |
| F119 | | CHOSEN FROM TABLE 1 | N-methyl-4-pyridinium | CHOSEN FROM TABLE 1 |
| F120 | | CHOSEN FROM TABLE 1 | 3-pyridine | CHOSEN FROM TABLE 1 |
| F121 | | CHOSEN FROM TABLE 1 | N-methyl-3-pyridinium | CHOSEN FROM TABLE 1 |
| F122 | | CHOSEN FROM TABLE 1 | 2-pyridine | CHOSEN FROM TABLE 1 |
| F123 | | CHOSEN FROM TABLE 1 | p-CH$_3$O$_2$C—Ph— | CHOSEN FROM TABLE 1 |

Similar families can be generated where $R^1$ is not equal to $R^2$, such as $R^1$ = Et and $R^2$ = n-Bu, but $(R^x)q$ is chosen from table C1.

Exhibit B

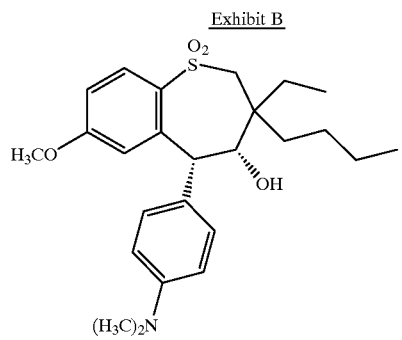

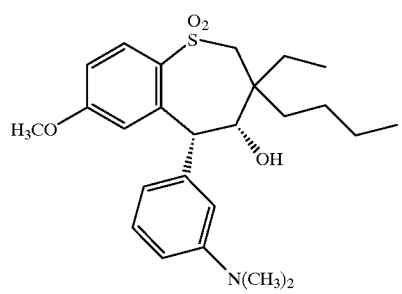

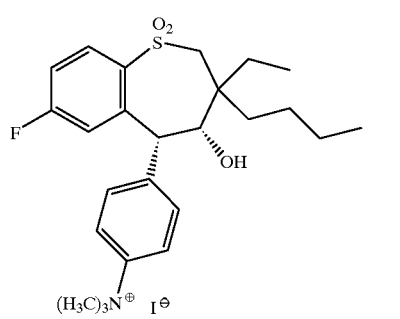
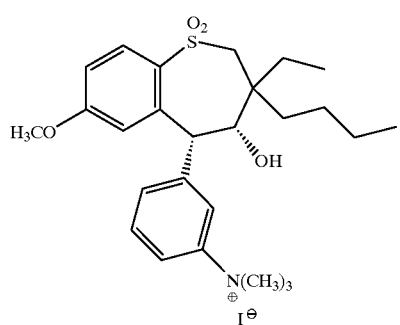
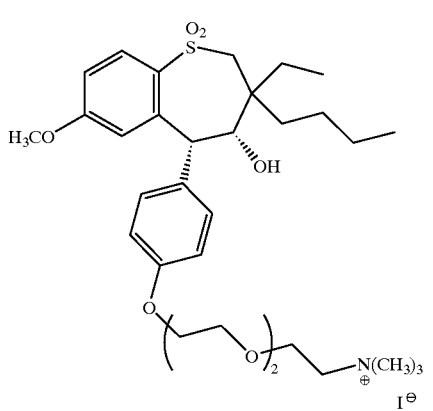
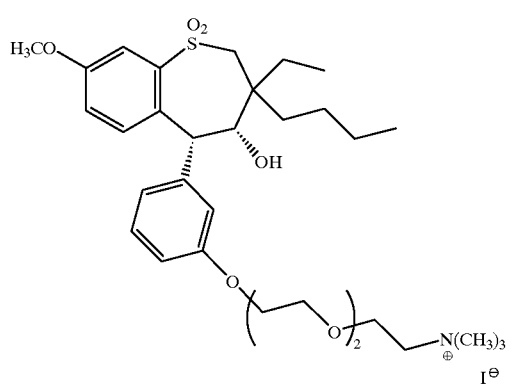
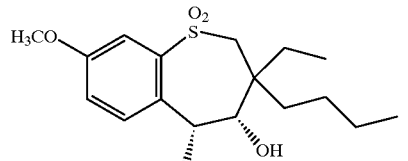
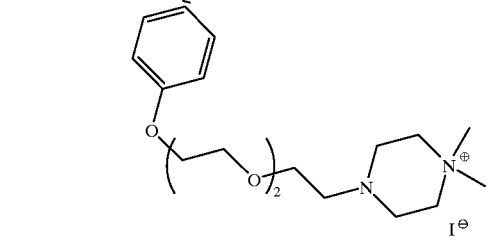
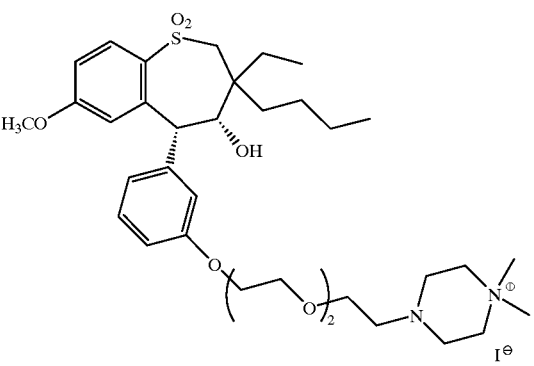
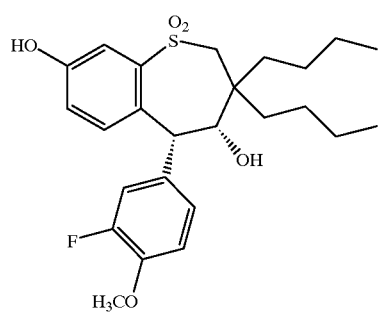
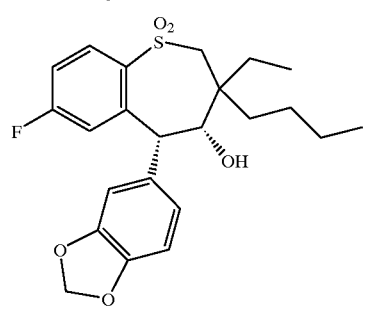
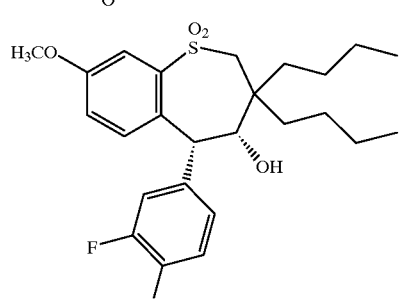

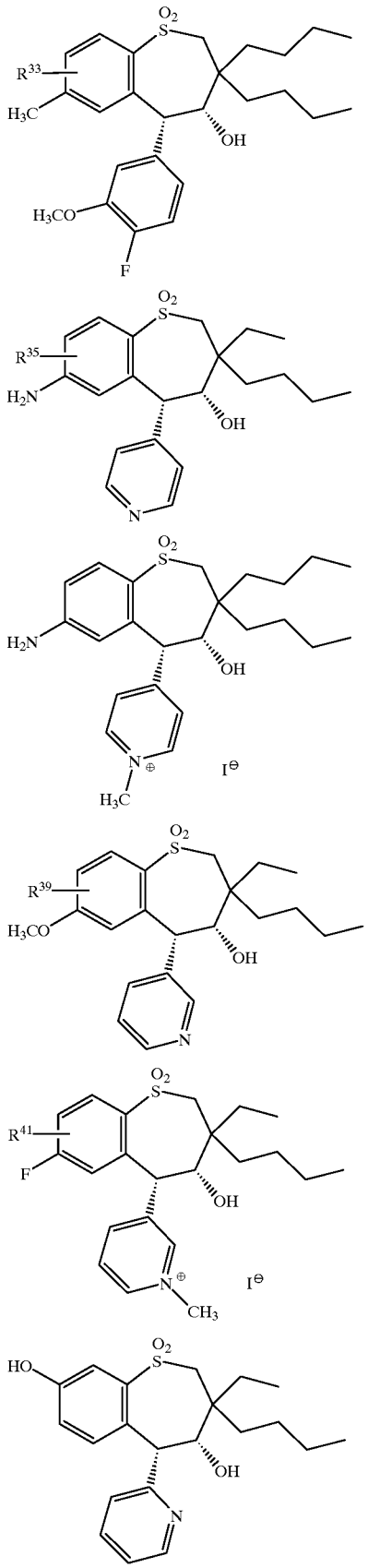

What is claimed is:
1. A compound of formula (I):

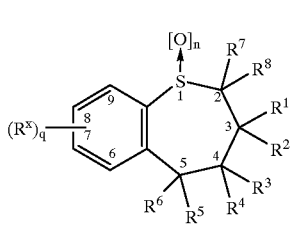

(I)

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}\ A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$–$C_{10}$ cycloalkyl;
$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or
$R^3$ and $R^4$ together =O, =$NOR^{11}$, =S, =$NNR^{11}R^{12}$, =$NR^9$, or =$CR^{11}R^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ and $R^6$ are independently selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$,
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, amino acid, peptide, or polypeptide, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and $C(O)OM$, wherein $R^{16}$ and $R^{17}$ are independently selected from the substituents constituting $R^9$ and M; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, $C(O)OM$, $COR^{13}$, $OR^{18}$, $S(O)_nNR^{18}$, $NR^{13}R^{18}$, $NR^{18}R^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or $C(O)M$, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and $C(O)OM$, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

2. A compound of claim 1, wherein $R^5$ and $R^6$ are independently selected from the group consisting of H, aryl, heterocycle, quaternary heterocycle, and quaternary heteroaryl, wherein said aryl, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+P^7R^8A^-$, or phenylene, wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, SR, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$.

3. A compound of claim 2, wherein $R^5$ or $R^6$ has the formula

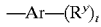

wherein:
t is an integer from 0 to 5;
Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and
one or more $R^y$ are independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,
wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene.

4. A compound of claim 3, wherein $R^5$ or $R^6$ has the formula (II)

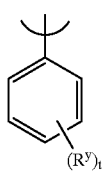

(II)

5. A compound of claim 4, wherein n is 1 or 2.
6. A compound of claim 5, wherein one of $R^7$ or $R^8$ is H and the other of $R^7$ or $R^8$ is alkyl.
7. A compound of claim 5, wherein both $R^7$ and $R^8$ are H.
8. A compound of claim 7, wherein $R^1$ and $R^2$ are independently selected from the group consisting of H and alkyl.
9. A compound of claim 8, wherein said alkyl is a $C_1$–$C_{10}$ alkyl.
10. A compound of claim 8, wherein $R^1$ and $R^2$ are both alkyl.
11. A compound of claim 10, wherein said alkyl is a $C_1$–$C_{10}$ alkyl.
12. A compound of claim 11, wherein said alkyl is a $C_2$–$C_7$ alkyl.
13. A compound of claim 12, wherein said alkyl is a $C_2$–$C_4$ alkyl.
14. A compound of claim 13, wherein said alkyl is independently selected from the group consisting of ethyl, n-propyl, n-butyl, and isobutyl.
15. A compound of claim 8, wherein $R^1$ and $R^2$ are each n-butyl.
16. A compound of claim 8, wherein one of $R^1$ and $R^2$ is ethyl and the other of $R^1$ and $R^2$ is n-butyl.
17. A compound of claim 15, wherein q is 1, 2, or 3.
18. A compound of claim 16, wherein q is 1, 2, or 3.
19. A compound of claim 17, wherein q is 1 or 2.
20. A compound of claim 19, wherein q is 1.
21. A compound of claim 18, wherein q is 1 or 2.
22. A compound of claim 21, wherein q is 1.
23. A compound of claim 19, wherein $R^3$ and $R^4$ are independently selected from the group consisting of H and $OR^9$.
24. A compound of claim 21, wherein $R^3$ and $R^4$ are independently selected from the group consisting of H and $OR^9$.
25. A compound of claim 23, wherein $R^9$ is H.
26. A compound of claim 24, wherein $R^9$ is H.
27. A compound of claim 25, wherein one or more $R^x$ are in the 7-, 8-, or 9-position of the benzo ring of formula (I).
28. A compound of claim 26, wherein said $R^x$ is in the 7-, 8-, or 9-position of the benzo ring of formula (I).
29. A compound of claim 27, wherein said $R^x$ are in the 7- and 9-positions of the benzo ring of formula (I).
30. A compound of claim 28, wherein said $R^x$ is in the 7-position of the benzo ring of formula (I).
31. A compound of claim 29, wherein said one or more $R^x$ are independently selected from the group consisting of alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$,
wherein alkyl, aryl, cycloalkyl, heterocycle, polyalkyl, acyloxy, and polyether, can be further substituted with $OR^9$, $NR^9R^{10}$, $N^+R^9R^{10}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and
wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, and
wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$.

32. A compound of claim 30, wherein said $R^x$ is selected from the group consisting of alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$,
wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and
wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$.

33. A compound of claim 31, wherein said one or more $R^x$ are independently selected from the group consisting of polyether, $OR^{13}$, $NR^{13}R^{14}$, and $N^+R^9R^{11}R^{12}A^-$.

34. A compound of the claim 32, wherein said $R^x$ is selected from the group consisting of polyether, $OR^{13}$, $NR^{13}R^{14}$, and $N^+R^9R^{11}R^{12}A^-$.

35. A compound of claim 33, wherein said one or more $R^x$ are independently selected from the group consisting of $OR^{13}$ and $NR^{13}R^{14}$.

36. A compound of claim 34, wherein said $R^x$ is independently selected from the group consisting of $OR^{13}$ and $NR^{13}R^{14}$.

37. A compound of claim 35, wherein $R^{13}$ and $R^{14}$ each methyl.

38. A compound of the claim 36, wherein $R^{13}$ and $R^{14}$ each methyl.

39. A compound of claim 31, wherein one or more $R^y$ are independently in the 3- or the 4-position of the phenyl ring of formula (II).

40. A compound of claim 32, wherein one or more $R^y$ are independently in the 3- or the 4-position of the phenyl ring of formula (II).

41. A compound of claim 39, wherein t is 1 or 2.

42. A compound of claim 40, wherein t is 1 or 2.

43. A compound of claim 41, wherein said one or more $R^y$ are independently selected from the group consisting of alkyl, polyether, fluoride, chloride, bromide, iodide, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

44. A compound of claim 42, wherein said $R^y$ is independently selected from the group consisting of alkyl, polyether, fluoride, chloride, bromide, iodide, $NR^{13}R^{14}$, $NR^{14}C(O)R^3$, and $OR^{13}$, wherein alkyl and polyether can be further substituted with $SO_3R^9$, $N^+R^9R^{11}R^{12}A^-$, and quaternary heteroaryl.

45. A compound of claim 43, wherein said one or more $R^y$ are independently selected from the group consisting of alkyl, polyether, fluoride, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

46. A compound of claim 44 wherein said $R^y$ is independently selected from the group consisting of alkyl, polyether, fluoride, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

47. A compound of claim 45, wherein said $R^{13}$ and $R^{14}$ are alkyl, wherein alkyl can be further substituted with $SO^3R^9$, $N^+R^9R^{11}R^{12}A^-$, and quaternary heteroaryl.

48. A compound of claim 46, wherein said $R^9$ and $R^{10}$ are alkyl, wherein alkyl can be further substituted with $SO^3R^9$, $N^+R^9R^{11}R^{12}A^-$, and quaternary heteroaryl.

49. A compound of claim 47, wherein n is 2.

50. A compound of claim 48, wherein n is 2.

51. A compound of claim 49, wherein said OH group is in a syn relationship to said structure of formula (II).

52. A compound of claim 50, wherein said OH group is in a syn relationship to said structure of formula (II).

53. A compound of claim 51, having the formula:

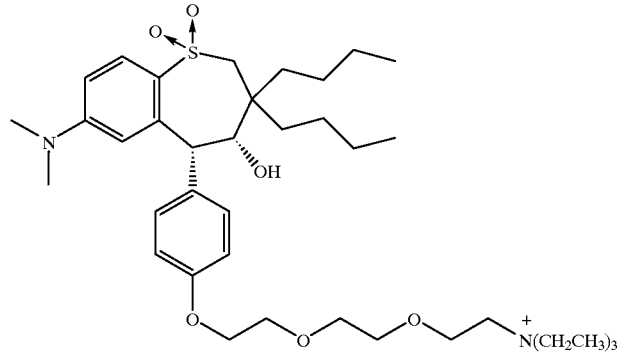

[A⁻]

54. A compound of claim 51, having the formula:
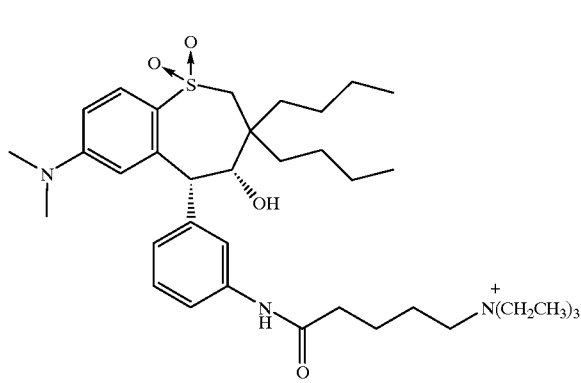
55. A compound of claim 51, having the formula:
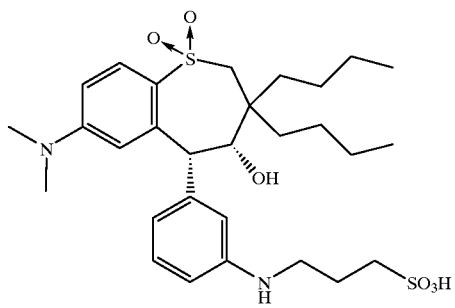
56. A compound of claim 51, having the formula:
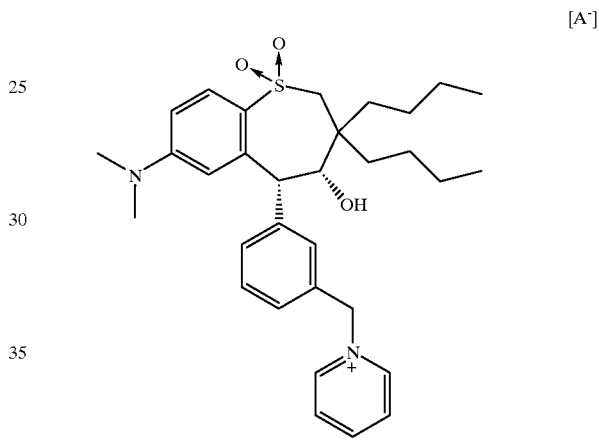
57. A compound of claim 51, having the formula:
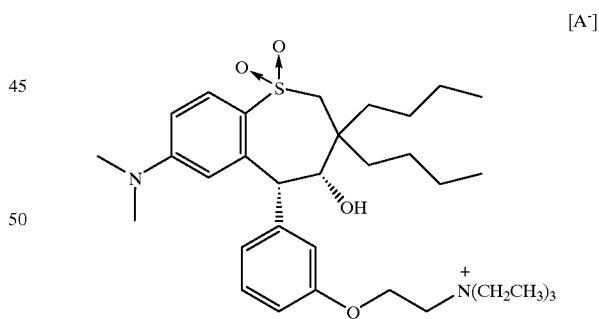

58. A compound of claim 52, having the formula:
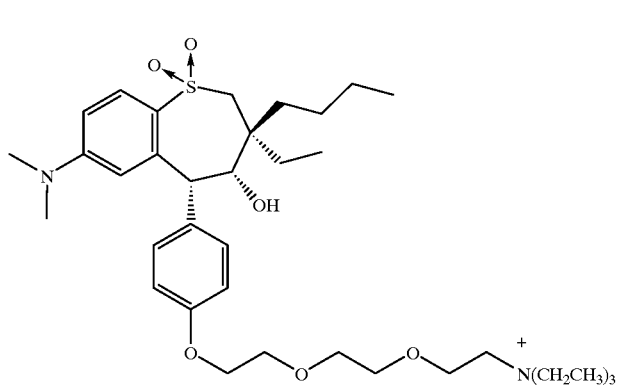
59. A compound of claim 52, having the formula:
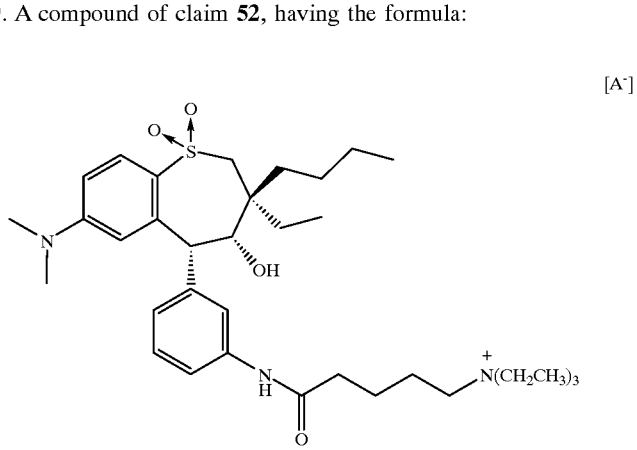
60. A compound of claim 52, having the formula:
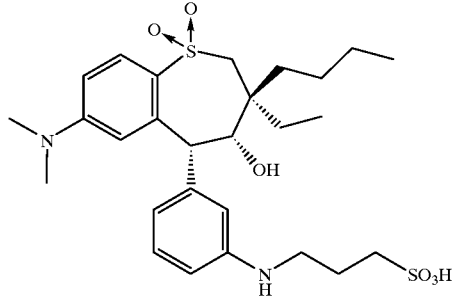
61. A compound of claim 52, having the formula:
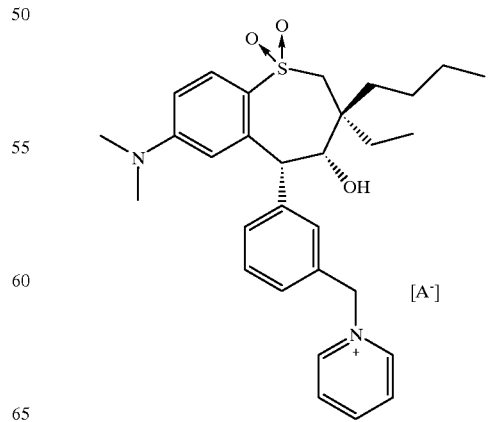

62. A compound of claim 52, having the formula:

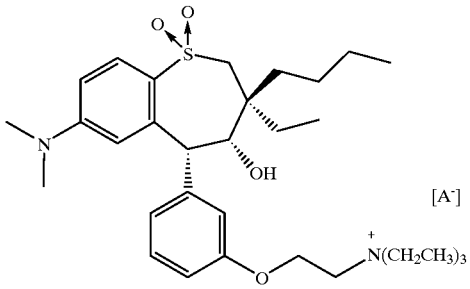

[A⁻]

63. A compound of claim 31, wherein n is 1.
64. A compound of claim 63, wherein $R^y$ is H.
65. A compound of claim 64, having the formula

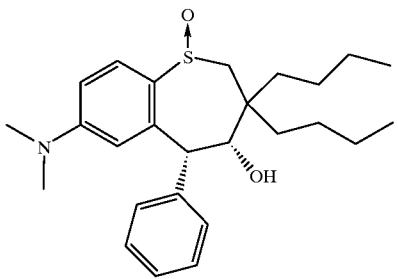

66. A compound of claim 4, wherein $R^1$ and $R^2$ are independently selected from the group consisting of H and alkyl.
67. A compound of claim 66, wherein said alkyl is $C_1$–$C_{10}$ alkyl.
68. A compound of claim 67, wherein said alkyl is $C_2$–$C_7$ alkyl.
69. A compound of claim 68, wherein said alkyl is $C_2$–$C_4$ alkyl.
70. A compound of claim 69, wherein $R^1$ and $R^2$ are independently selected from the group consisting of ethyl, n-propyl, n-butyl, and isobutyl.
71. A compound of claim 4, wherein $R^3$ and $R^4$ are independently selected from the group consisting of H and $OR^9$.
72. A compound of claim 71, wherein $R^9$ is H.
73. A compound of claim 4, wherein n is 2.
74. A compound of claim 3, wherein $R^3$ and $R^4$ are independently selected from the group consisting of H and $OR^9$.
75. A compound of claim 74, wherein R is H.
76. A compound of claim 3, wherein one of R or R is H.
77. A compound of claim 76, wherein both $R^7$ and $R^8$ are H.
78. A compound of claim 3, wherein said one or more $R^x$ are independently selected from the group consisting of alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein in $R^x$, one or more carbons are optionally replaced by O, $NR^{13}$, $N^+R^{13}R^{14}A-$, S, SO, $SO_2$, $S^+R^{13}A-$, $PR^{13}$, $P(O)R^{13}$, $P^+R^{13}R^{14}A^{31}$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$.

79. A compound of claim 78, wherein said one or more $R^x$ are independently selected from the group consisting of polyether, $OR^{13}$, $NR^{13}R^{14}$, and $N^+R^9R^{11}R^{12}A^-$.
80. A compound of claim 79, wherein said one or more $R^x$ are independently selected from the group consisting of $OR^{13}$ and $NR^{13}R^{14}$.
81. A compound of claim 80, wherein $R^{13}$ and $R^{14}$ are each methyl.
82. A compound of claim 3, wherein one or more $R^y$ are independently in the 3- or the 4-position of the phenyl ring of formula (II).
83. A compound of claim 82, wherein one or more $R^y$ is selected from the group consisting of alkyl, polyether, fluoride, chloride, bromide, iodide, $NR^9R^{10}$, and $NC(O)R^9$, wherein alkyl and polyether can be substituted with $SO_3R^9$, $N^+R^9R^{11}R^{12}A^-$, and quaternary heteroaryl.

84. A compound of claim 83, wherein $R^9$ and $R^{10}$ are alkyl.
85. A compound of claim 84, wherein one or more $R^y$ is selected from the group consisting of alkyl, polyether, fluoride, chloride, bromide, iodide, $NR^9R^{10}$, and $NC(O)R^9$.
86. A compound of claim 1, wherein said one or more $R^x$ are independently selected from the group consisting of alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein in $R^x$, one or more carbons are optionally replaced by O, $NR^{13}$, $N^+R^{13}R^{14}A^-$, S, SO, $SO_2$, $S^+R^{13}A-$, $PR^{13}$, $P(O)R^{13}$, $P^+R^{13}R^{14}A-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A-$, S, SO, $SO_2$, $S^+R^9A-$, $PR^9$, $P^+R^9R^{10}A-$, or $P(O)R^9$.

87. A compound of claim 1, wherein n is 1 or 2.
88. A compound of claim 87, wherein n is 2.
89. A compound of claim 1, wherein $R^1$ and $R^2$ are independently selected from the group consisting of H and alkyl.
90. A compound of claim 89, wherein said alkyl is $C_1$–$C_{10}$ alkyl.
91. A compound of claim 90, wherein said alkyl is $C_2$–$C_7$ alkyl.
92. A compound of claim 91, wherein said alkyl is $C_2$–$C_4$ alkyl.
93. A compound of claim 92, wherein $R^1$ and $R^2$ are independently selected from the group consisting of ethyl, n-propyl, n-butyl, and isobutyl.
94. A compound of claim 1, wherein $R^3$ and $R^4$ are independently selected from the group consisting of H and $OR^9$.

95. A compound of claim 94, wherein $R^9$ is H.
96. A compound of claim 1, wherein one of $R^7$ or $R^8$ is H.
97. A compound of claim 96, wherein both $R^7$ and $R^8$ are H.
98. A compound of the formula (III)

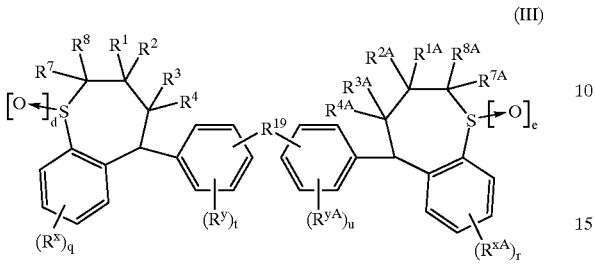

(III)

wherein
q and r are independently integers from 0 to 4;
d and e are independently integers from 0 to 2;
t and u are independently integers from 0 to 4;
$R^1$, $R^{1A}$, $R^2$, and $R^{2A}$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituent selected from the group consisting of $OR^9$, $NR^9R^{10}$, $N^+R^9R^{10}R^wA^-$, $SR^9$, $SR^9A-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, polyalkyl, aryl, and cycloalkyl optionally have one or more carbons replaced by O, $NR^9$, $N^+R^9R^{10}A-$, S, SO, $SO_2$, $S^+R^9A-$, $P^+R^9R^{10}A-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, alkylammoniumalkyl, and arylalkyl; or
$R^1$ and $R^2$ taken together with the carbon to which they are attached form $C_3$–$C_{10}$ cycloalkylidene, or $R^{1A}$ and $R^{2A}$ taken together with the carbon to which they are attached form $C_3$–$C_{10}$ cycloalkylidene;
$R^3$, $R^3A$, $R^4$, and $R^{4A}$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or
$R^3$ and $R^4$ together form =O, =$NOR^{11}$, =S, =$NNR^{11}R^{12}$, =$NR^9$, or =$CR^{11}R^{12}$, or
$R^{3A}$ and $R^{4A}$ together form =O, =$NOR^{11}$, =S, =$NNR^{11}R^{12}$, =$NR^9$, or =$CR^{11}R^{12}$,
wherein R and R are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$ CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;

wherein $A^-$ is a pharmaceutically acceptable anion and M is a pharmaceutically acceptable cation;
$R^7$, $R^{7A}$, $R^8$, and $R^{8A}$ are independently selected from the group consisting of hydrogen and alkyl; and
one or more $R^x$ and $R^{xA}$ are independently selected from the group consisting of H, alkyl, alkenyl, alkynyl, polyalkyl, acyloxy, aryl, arylalkyl, halogen, haloalkyl, cycloalkyl, heterocycle, polyether, quaternary heterocycle, quaternary heteroaryl, $OR^{13}$, $NR^{13}R^{14}$ $SR^{13}$ $S(O)^{13}$, $(O)2^{13}$ $SO_3R$, $S^+R^{13}R^{14}A—$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A—$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R_9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and
wherein $R^{18}$ is selected from the group consisting of acyl, arylalkoxycarbonyl, arylalkyl, heterocycle, heterocycle, alkyl, wherein acyl, arylalkoxycarbonyl, arylalkyl, heterocycle, heterocycle, alkyl quaternary heterocycle, and quaternary heteroaryl optionally are substituted with one or more substituent selected from the group consisting of $OR^9$, $NR^9R^{10}$, $N^+R^9R^{11}R^{12}A^-$, $SR^9$, $S(O)R^9$, $SO_2R$, $SO_3R$, oxo, $CO_2R^9$, CN, halogen, $CONR^9R^{10}$, $SO_3R^9$, $SO_2OM$, $SO_2NR^9R^{10}$, $PO(OR^{16})$ $OR^{17}$, and C(O)OM,
wherein in $R^x$ and $R^{xA}$, one or more carbons are optionally replaced by O, $NR^{13}$, $N^+R^{13}R^{14}A—$, S, SO, $SO_2$, $S^+R^{13}$ $A—$, $PR^{13}$, P(O)R13, $P^{+R13}R^{14}A—$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A—$, S, SO, $SO_2$, $S^+R^9A—$, $PR^9$, $P^+R^9R^{10}A—$, or $P(O)R^9$;
wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A—$, $P(OR^{13})OR^{14}$, $SR^{13}R^{14}A^-$, and $N^+R^9R^{11}R^{12}A^-$,
$R^{19}$ is selected from the group consisting of alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, $NR^7$, $N^+R^7R^8$, S, SO, $SO^2$, $S^+R^7R^8$, $PR^7$, $P^+R^7R^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$ CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A-$, $P(OR^{13})OR^{14}$, $S^+R^{13}R^{14}A^-$, and $N^+R^9R^{11}R^{12}A^-$;

wherein one or more $R^y$ and $R^{yA}$ are independently selected from from the group consisting of H, alkyl, alkenyl, alkynyl, aryl, cycloalkyl, heterocycle, quaternary heterocycle, $OR^9$, $SR^9$, $S(O)R^9$, $SO_2R^9$, and $SO_3R^9$, wherein alkyl, alkenyl, alkynyl, aryl, cycloalkyl, and heterocycle can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$ $NO_2$, $CO_2R^{13}$, CN, OM, $SO_2OM$, $SO_2NR^{13}R^{14}$, $C(O)NR^{13}R^{14}$, $C(O)OM^{13}$, $P(O)R^{13}R^{14}$, $P^+R^{13}R^{14}R15A-$, $P(OR^{13})OR^{14}$, $S^{+R13}R^{14}A^-$, and $N^+R^9R^{11}R^{12}A^-$, wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene.

99. A compound of claim 98, wherein $R^1$, $R^{1A}$, $R^2$, and $R^{2A}$ are independently selected from the group consisting of H and alkyl.

100. A compound of claim 99, wherein $R^1$, $R^{1A}$, $R^2$, and $R^{2A}$ are independently selected from the group consisting of H and $C_1$–$C_{10}$ alkyl.

101. A compound of claim 100, wherein said alkyl is a $C_2$–$C_7$ alkyl.

102. A compound of claim 101, wherein $R^1$, $R^{1A}$, $R^2$, and $R^{2A}$ are independently $C_2$–$C_4$ alkyl.

103. A compound of claim 102, wherein $R^1$, $R^{1A}$, $R^2$, and $R^{2A}$ are independently selected from the group consisting of ethyl, n-propyl, n-butyl, and isobutyl.

104. A compound of claim 98, wherein $R^3$, $R^{3A}$, $R^4$, and $R^{4A}$ are independently selected from the group consisting of H and $OR^9$.

105. A compound of claim 104, wherein $R^9$ is H.

106. A compound of claim 98, wherein $R^7$, $R^{7A}$, $R^8$, and $R^{8A}$ are H.

107. A compound of claim 98, wherein d and e are independently 1 or 2.

108. A compound of claim 107, wherein d and e are both 2.

109. A compound of claim 98, wherein one or more $R^x$ and one or more $R^{xA}$ are independently selected from the group consisting of alkyl, aryl, cycloalkyl, heterocycle, polyalkyl, acyloxy, polyether, halogen, $OR^{13}$, $NR^{13}R^{14}$, $NR^3NR^{14}R^{15}N^+R^9R^{11}R^{12}A-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R^{10}$, $PO(OR^{16})OR^{17}$, $P^+R^9R^{11}R^{12}A-$, $S^+R^9R^{10}A-$, or C(O)OM, and wherein in $R^x$, one or more carbons are optionally replaced by O, $NR^{13}$, $N^+R^{13}R^{14}A-$, S, SO, $SO_2$, $S^+R^{13}A-$, $PR^{13}$, $P(O)R^{13}$, $P^+R^{13}R^{14}A-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A-$, S, SO, $SO_2$, $S^+R^9A-$, $PR^9$, $P^+R^9R^{10}A-$, or $P(O)R^9$.

110. A compound of claim 98, wherein one or more $R^y$ and one or more $R^{yA}$ are independently selected from the group consisting of alkyl, polyether, fluoride, chloride, bromide, iodide, $NR^{13}R^{14}$, $NR^{14}C(O)R^{13}$, and $OR^{13}$, wherein alkyl and polyether can be further substituted with $SO_3R^9$, $N^+R^9R^{11}R^{12}A-$, and quaternary heteroaryl.

111. A compound of claim 98, wherein $R^{19}$ is selected from the group consisting of alkane diyl, polyalkane diyl, alkoxy diyl, and polyalkoxy diyl, wherein alkane diyl and polyalkane diyl can optionally have one or more carbon replaced by O, NR7, N+R7R8, S, SO, $SO_2$, S+R7R8, PR7, P+R7R8, or phenylene.

112. A compound of claim 111, wherein $R^{19}$ is selected from the group consisting of alkoxy diyl and polyalkoxydiyl wherein one or more carbons are optionally replaced by O, $NR^9$, $N^+R^9R^{10}$, S, SO, $SO_2$, $S^+R^9R^{10}$, $PR^9$, $P^+R^9R^{10}$, phenylene, amino acid, peptide, polypeptide, carbohydrate, or polyalkyl.

113. A compound of claim 112, wherein $R^1$, $R^{1A}$, $R^2$, and $R^{2A}$ are independently selected from the group consisting of H and alkyl.

114. A compound of claim 113, wherein $R^3$, $R^{3A}$, $R^4$, and $R^{4A}$ are independently selected from the group consisting of H and $OR^9$.

115. A compound of claim 114, wherein $R^9$ is H.

116. A compound of claim 115, wherein $R^7$, $R^{7A}$, $R^8$, and $R^{8A}$ are each H.

117. A compound of claim 116, wherein d and e are independently 1 or 2.

118. A compound of claim 117, wherein one or more $R^x$ and one or more $R^{xA}$ are independently selected from the group consisting of alkyl, aryl, cycloalkyl, heterocycle, polyalkyl, acyloxy, polyether, halogen, $R^{13}$, $NR^{13}R$, $NR^{13}NR^{14}R^{15}$, $N^+R^9R^{11}R^{12}A-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R^{10}$, $PO(OR^{16})OR^{17}$, $P^+R^9R^1R^2A-$, $S^+R^9R^{10}A-$, or C(O)OM, and wherein in $R^x$, one or more carbons are optionally replaced by O, $NR^{13}$, $N^+R^{13}R^{14}A-$, S, SO, $SO_2$, $S^+R^{13}A-$, $PR^{13}$, $P(O)R^{13}$, $P^+R^{13}R^{14}A-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A-$, S, SO, $SO_2$, $S^+R^9A-$, $PR^9$, $P^+R^9R^{10}A-$, or $P(O)R^9$.

119. A compound of claim 118, wherein one or more $R^y$ and one or more $R^{yA}$ are independently selected from the group consisting of alkyl, polyether, fluoride, chloride, bromide, iodide, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

120. A compound of claim 119, having the formula:

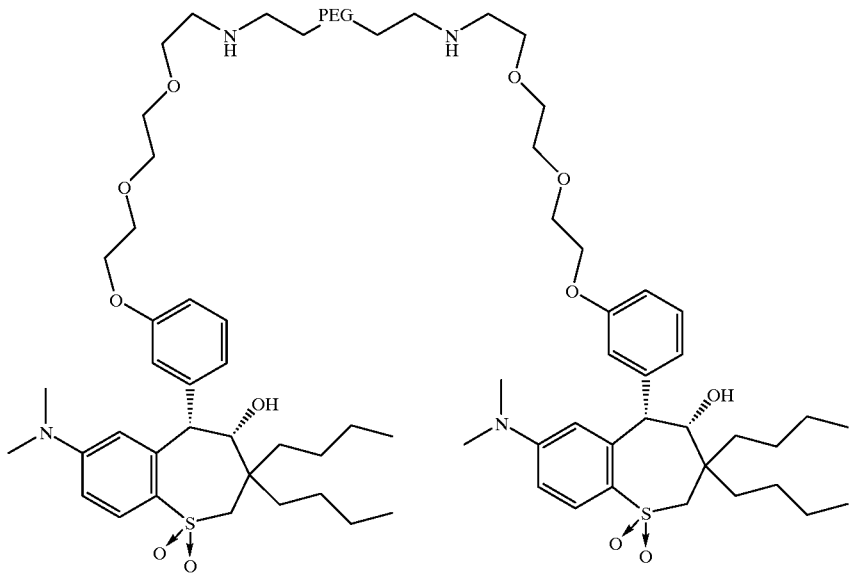

121. A compound of the formula (IV)

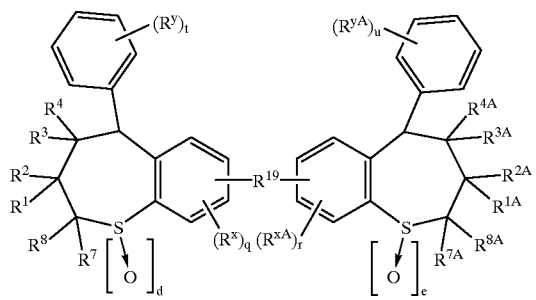

wherein q and r are independently integers from 0 to 3;
d and e are independently integers from 0 to 2;
t and u are independently integers from 0 to 5;
$R^1$, $R^{1A}$, $R^2$, and $R^{2A}$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituent selected from the group consisting of $OR^9$, $NR^9R^{10}$, $N^{+R9}R^{10}R^wA^-$, $SR^9$, $S^+R^9A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, polyalkyl, aryl, and cycloalkyl optionally have one or more carbons replaced by O, $NR^9$, $N^{+R9}R^{10}A-$, S, SO, $SO_2$, $S^+R^9A-$, $P^+R^9R^{10}A-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, alkylammoniumalkyl, and arylalkyl; or $R^1$ and $R^2$ taken together with the carbon to which they are attached form $C_3$–$C_{10}$ cycloalkylidene, or $R^{1A}$ and $R^{2A}$ taken together with the carbon to which they are attached form $C_3$–$C_{10}$ cycloalkylidene;

$R^3$, $R^{3A}$, $R^4$, and $R^{4A}$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^1$, =S, =$NNR^{11}R^{12}$, =$NR^9$, or =$C^{11}R^{12}$, or $R^{3A}$ and $R^{4A}$ together form =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and R4 cannot be OH, NH2, and SH, or $R^{11}$ and $R^{12}$ together with the nitrogen or carbon atom to which they are attached form a cyclic ring;

wherein $A^-$ is a pharmaceutically acceptable anion and M is a pharmaceutically acceptable cation;

$R^7$, $R^{7A}$, $R^8$, and $R^{8A}$ are independently selected from the group consisting of hydrogen and alkyl; and one or more $R^x$ and $R^{xA}$ are independently selected from the group consisting of H, alkyl, alkenyl, alkynyl, polyalkyl, acyloxy, aryl, arylalkyl, halogen, haloalkyl, cycloalkyl, heterocycle, heterocycle, polyether, quaternary heterocycle, quaternary heteroaryl, $OR^{13}$, $NR^{13}R^{14}$, $SR^{13}$, $S(O)R^{13}$, $SO_2R^{13}$, $SO_3R^{13}$, $S^+R^{13}R^{14}A-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, $C(O)OM$, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O) OM, and wherein $R^{18}$ is selected from the group consisting of acyl, arylalkoxycarbonyl, arylalkyl, heterocycle, heterocycle, alkyl, wherein acyl, arylalkoxycarbonyl, arylalkyl, heterocycle, heterocycle, alkyl quaternary heterocycle, and quaternary heteroaryl optionally are substituted with one or more substituent selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$ and $R^{xA}$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^4$, $P^+R^{13}R^{14}R^{15}A^-$, $P(OR^{13})OR^{14}$, $S^+R^{13}R^{14}A^-$, and $N^+R^9R^{11}R^{12}A^-$, $R^{19}$ is selected from the group consisting of alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, $NR^7$, $N^+R^7R^8$, S, SO, $SO^2$, $S^+R^7R^8$, $PR^7$, $P^+R^7R^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, OR, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R15A$—, $P(OR^{13})OR^{14}$, $SO^+R^{13}R^{14}A^-$, and $N^+R^9R^{11}R^{12}A^-$;

wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A$—, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A$—, S, SO, $SO_2$, $S^+R^7A$—, $PR^7$, $P(O)R^7$, $P^+R^7R^8A$—, or phenylene.

122. A compound of claim 121, wherein $R^1$, $R^{1A}$, $R^2$, and $R^{2A}$ are independently selected from the group consisting of H and alkyl.

123. A compound of claim 122, wherein $R^1$, $R^{1A}$, $R^2$, and $R^{2A}$ are independently selected from the group consisting of H and $C_1$–$C_{10}$ alkyl.

124. A compound of claim 123, wherein said alkyl is a $C_2$–$C_7$ alkyl.

125. A compound of claim 124, wherein $R^1$, $R^{1A}$, $R^2$, and $R^{2A}$ are independently $C_2$–$C_7$ alkyl.

126. A compound of claim 125, wherein $R^1$, $R^{1A}$, $R^2$, and $R^{2A}$ are independently selected from the group consisting of ethyl, n-propyl, n-butyl, and isobutyl.

127. A compound of claim 125, wherein $R^3$, $R^{3A}$, $R^4$, and $R^{4A}$ are independently selected from the group consisting of H and $OR^9$.

128. A compound of claim 127, wherein $R^9$ is H.

129. A compound of claim 121, wherein $R^7$, $R^{7A}$, $R^8$, and $R^{8A}$ are H.

130. A compound of claim 121, wherein d and e are independently 1 or 2.

131. A compound of claim 130, wherein d and e are both 2.

132. A compound of claim 121, wherein one or more $R^x$ and one or more $R^{xA}$ are independently selected from the group consisting of alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein in $R^x$, one or more carbons are optionally replaced by O, $NR^{13}$, $N^+R^{13}R^{14}A$—, S, SO, $SO_2$, $S^+R^{13}A$—, $PR^{13}$, $P(O)R^{13}$, $P^+R^{13}R^{14}A$—, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A$—, S, SO, $SO_2$, $S^+R^9A$—, $PR^9$, $P^+R^9R^{10}A$—, or $P(O)R^9$.

133. A compound of claim 121, wherein one or more $R^y$ and one or more $R^{yA}$ are independently selected from the group consisting of alkyl, polyether, fluoride, chloride, bromide, iodide, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

134. A compound of claim 121, wherein $R^{19}$ is selected from the group consisting of alkane diyl, polyalkane diyl, alkoxy diyl, and polyalkoxy diyl, wherein alkane diyl and polyalkane diyl can optionally have one or more carbon replaced by O, $NR^7$, $N^+R^7R^{8,}$ S, SO, $SO_2$, $S^+R^7R^8$, $PR^7$, $P^+R^7R^8$, or phenylene.

135. A compound of claim 134, wherein $R^{19}$ is selected from the group consisting of alkoxy diyl and polyalkoxydiyl wherein one or more carbons are optionally replaced by O, $NR^9$, $N^+R^9R^{19}$, S, SO, $SO_2$, $S^+R^9R^{10}$, $PR^9$, $P^+R^9R^{10}$, phenylene, amino acid, peptide, polypeptide, carbohydrate, or polyalkyl.

136. A compound of claim 135, wherein $R^1$, $R^{1A}$, $R^2$, and $R^{2A}$ are independently selected from the group consisting of H and alkyl.

137. A compound of claim 136, wherein $R^3$, $R^{3A}$, $R^4$, and $R^{4A}$ are independently selected from the group consisting of H and $OR^9$.

138. A compound of claim 137, wherein $R^9$ is H.

139. A compound of claim 138, wherein $R^7$, $R^{7A}$, $R^8$, and $R^{7A}$ are each H.

140. A compound of claim 139, wherein d and e are independently 1 or 2.

141. A compound of claim 140, having the formula:

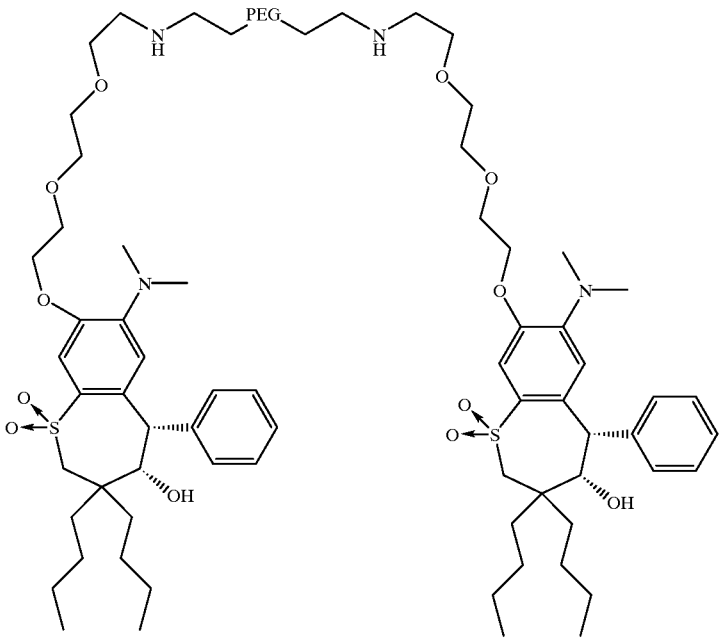

142. A compound of formula (V)

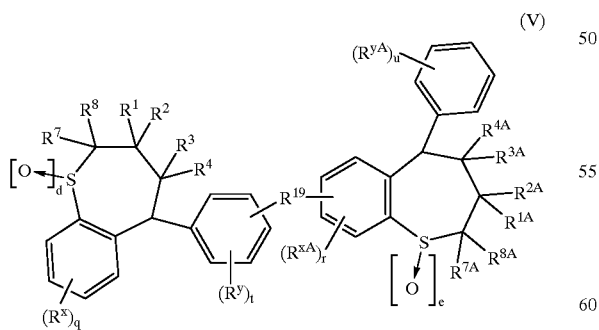

wherein q is an integer from 0 to 4;

r is an integer from 0 to 3;

d and e are independently integers from 0 to 2;

t is an integer from 0 to 4;

u is an integer from 0 to 5;

$R^1$, $R^{1A}$, $R^2$, and $R^{2A}$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituent selected from the group consisting of $OR^9$, $NR^9R^{10}$, $N^+R^9R^{10}R^wA^-$, $SR^9$, $S^+R^9A-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, polyalkyl, aryl, and cycloalkyl optionally have one or more carbons replaced by O, $NR^9$, $N^+R^9R^{10}A-$, S, SO, $SO_2$, $S^+R^9A-$, $P^+R^9R^{10}A-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, alkylammoniumalkyl, and arylalkyl; or $R^1$ and $R^2$ taken together with the carbon to which they are attached form $C_3$–$C_{10}$ cycloalkylidene, or $R^{1A}$ and $R^{2A}$ taken together with the carbon to which they are attached form $C_3$–$C_{10}$ cycloalkylidene;

$R^3$, $R^{3A}$, $R^4$, and $R^{4A}$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^{11}$, =S, =$NNR^{11}R^{12}$, =$NR^9$, or =$CR^{11}R^{12}$, or $R^{3A}$ and $R^{4A}$ together form =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, NH2, and SH, or $R^{11}$ and $R^{12}$ together with the nitrogen or carbon atom to which they are attached form a cyclic ring;

wherein $A^-$ is a pharmaceutically acceptable anion and M is a pharmaceutically acceptable cation;

$R^7$, $R^{7A}$, $R^8$, and $R^8$ are independently selected from the group consisting of hydrogen and alkyl; and one or more $R^x$ and $R^{xA}$ are independently selected from the group consisting of H, alkyl, alkenyl, alkynyl, polyalkyl, acyloxy, aryl, arylalkyl, halogen, haloalkyl, cycloalkyl, heterocycle, heterocycle, polyether, quaternary heterocycle, quaternary heteroaryl, $OR^{13}$, $NR^{13}R^{14}$, SR $S(O)R^{13}$, $SO_2R^{13}$, $SO_3R^{13}$, $S^+R^{13}R^{14}A^-$, $NR^{13}OR^{14}$, $NR^{13}NR^{14}R^{15}NO_2$, $CO_2R^{13}$, CN, OM, $SO_2OM$, $SO_2NR^{13}R^{14}$, $NR^{14}C(O)R^3$, $C(O)NR^{13}R^{14}$, $NR^{14}C(O)R^{13}$, C(O)OM, $COR^{13}$, $OR^{18}$, $S(O)_nNR^{18}NR^{13}R^{18}$, $NR^{18}R^{14}$, $N^+R^9R^{11}R^{12}A^-$, $P^+R^9R^1A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R$ CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heterocycle, alkyl, wherein acyl, arylalkoxycarbonyl, arylalkyl, heterocycle, heterocycle, alkyl quaternary heterocycle, and quaternary heteroaryl optionally are substituted with one or more substituent selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR$ $R^{10}$, $PO(OR^{16})OR^{17}$, and C(O)OM, wherein in $R^{x\ and\ RxA}$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}$ $A^-$, $R^{19}$ is selected from the group consisting of alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, $NR^7$, $N^+R^7R^8$, S, SO, $SO^2$, $S^+R^7R^8$, $PR^7$, $P^+R^7R^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}NO_2$, $CO_2R^{13}$ CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R15A—$, $P(OR^{13})OR^{14}$, $S^+R^{13}R^{14}A^-$, and $N^+R^9R^{11}R^{12}A^-$;

wherein one or more $R^y$ and $R^{yA}$ are independently selected from from the group consisting of H, alkyl, alkenyl, alkynyl, aryl, cycloalkyl, heterocycle, quaternary heterocycle, $OR^9$, $SR^9$, $S(O)R^9$, $SO_2R^9$, and $SO_3R^9$, wherein alkyl, alkenyl, alkynyl, aryl, cycloalkyl, and heterocycle can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$ $NO_2$, $CO_2R^{13}$ CN, OM, $SO_2OM$, $SO_2NR^{13}R^{14}$, $C(O)NR^{13}R^{14}C(O)OM$, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R$, $SO_3R^7$, $CO_2R^7$, CN, oxo, $CONR^7R^8$, $N^+R^7R^8R^9A—$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O) (OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A—$, S, SO, $SO_2$, $S^+R^7A—$, $PR^7$, $P(O)R^7$, $P^+R^7R^8A—$, or phenylene.

143. A compound of claim 142, wherein $R^1$, $R^{1A}$, $R^2$, and $R^{2A}$ are independently selected from the group consisting of H and alkyl.

144. A compound of claim 143, wherein $R^1$, $R^{1A}$, $R^2$, and $R^{2A}$ are independently selected from the group consisting of H and $C_1–C_{10}$ alkyl.

145. A compound of claim 144, wherein said alkyl is a $C_2–C_7$ alkyl.

146. A compound of claim 145, wherein $R^1$, $R^{1A}$, $R^2$, and $R^{2A}$ are independently $C_2–C_4$ alkyl.

147. A compound of claim 146, wherein $R^1$, $R^{1A}$, $R^2$, and $R^{2A}$ are independently selected from the group consisting of ethyl, n-propyl, n-butyl, and isobutyl.

148. A compound of claim 142, wherein $R^3$, $R^{3A}$, $R^4$, and $R^{4A}$ are independently selected from the group consisting of H and $OR^9$.

149. A compound of claim 148, wherein $R^9$ is H.

150. A compound of claim 142, wherein $R^7$, $R^{7A}$, $R^8$, and $R^8A$ are H.

151. A compound of claim 142, wherein d and e are independently 1 or 2.

152. A compound of claim 151, wherein d and e are both 2.

153. A compound of claim 142, wherein one or more $R^x$ and one or more $R^{xA}$ are independently selected from the group consisting of alkyl, aryl, cycloalkyl, heterocycle, polyalkyl, acyloxy, polyether, halogen, $R^{13}$, $NR^{13}R$, $NR^{13}NR^{14}R^{15}N^+R^9R^{11}$ $R^{12}A^-$, $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$ $SO_2OM$, $SO_2NR^9R$, $PO(OR^{16})OR^{17}$, $P^+R^9R^{11}R^{12}A^-$, $S^+R^9R^{10}A^-$, or C(O)OM, and wherein in $R^x$, one or more carbons are optionally replaced by O, $NR^{13}$, $N^+R^{13}R^{14}A-$, S, SO, $SO_2$, $S^+R^{13}A-$, $PR^{13}$, $P(O)R^{13}$, $P^+R^{13}R^{14}A-$, phenylene, amino acid, peptide, polypeptide, carbohydrate, polyether, or polyalkyl, and wherein in said polyalkyl, phenylene, amino acid, peptide, polypeptide, and carbohydrate, one or more carbons are optionally replaced by O, $NR^9$, $N^+R^9R^{10}A-$, S, SO, $SO_2$, $S^+R^9A-$, $PR^9$, $P^+R^9R^{10}A-$, or $P(O)R^9$.

154. A compound of claim 142, wherein one or more $R^y$ and one or more $R^{yA}$ are independently selected from the group consisting of alkyl, polyether, fluoride, chloride, bromide, iodide, $NR^{13}R^{14}$, $NR^{14}C(O)R^{13}$, and $OR^{13}$, wherein alkyl and polyether can be further substituted with $SO_3R^9$, $N^+R^9R^{11}R^{12}A^-$, and quaternary heteroaryl.

155. A compound of claim 142, wherein $R^{19}$ is selected from the group consisting of alkane diyl, polyalkane diyl, alkoxy diyl, and polyalkoxy diyl, wherein alkane diyl and polyalkane diyl can optionally have one or more carbon replaced by O, NR7, N+R7R8, S, SO, SO2, S+R7R8, PR7, P+R7R8, or phenylene.

156. A compound of claim 155, wherein $R^{19}$ is selected from the group consisting of alkoxy diyl and polyalkoxydiyl wherein one or more carbons are optionally replaced by O, $NR^9$, $N^+R^9R^{10}$, S, SO, $SO_2$, $S^+R^9R^{10}$, $PR^9$, $P^+R^9R^{10}$, phenylene, amino acid, peptide, polypeptide, carbohydrate, or polyalkyl.

157. A compound of claim 156, wherein $R^1$, $R^{1A}$, $R^2$, and $R^{2A}$ are independently selected from the group consisting of H and alkyl.

158. A compound of claim 157, wherein $R^3$, $R^{3A}$, $R^4$, and $R^{4A}$ are independently selected from the group consisting of H and $OR^9$.

159. A compound of claim 158, wherein $R^9$ is H.

160. A compound of claim 159, wherein $R^7$, $R^{7A}$, $R^8$, and $R^{8A}$ are each H.

161. A compound of claim 160, wherein d and e are independently 1 or 2.

162. A compound of claim 161, having the formula:

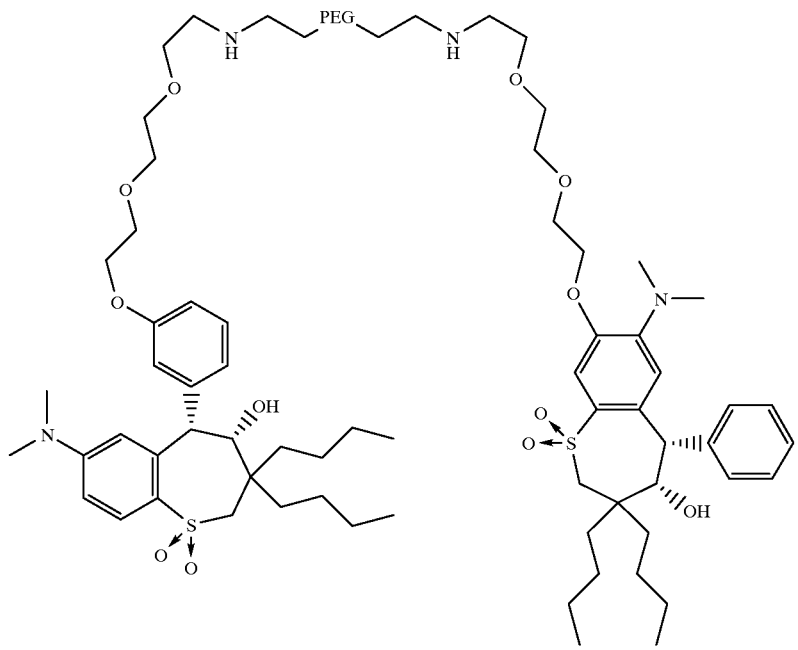

163. A pharmaceutical composition comprising an antihyperlipidemic condition effective amount of a compound of formula (I) of claim 1, and a pharmaceutically acceptable carrier.

164. A pharmaceutical composition comprising an antiatherosclerotic effective amount of a compound of formula (I) of claim 1, and a pharmaceutically acceptable carrier.

165. A pharmaceutical composition comprising an antihypercholesterolemia effective amount of a compound of formula (I) of claim 1, and a pharmaceutically acceptable carrier.

166. A method for the prophylaxis or treatment of a hyperlipidemic condition comprising administering to a patient in need thereof a composition of claim 164 in unit dosage form.

167. A method for the prophylaxis or treatment of an atherosclerotic condition comprising administering to a patient in need thereof a composition of claim 165 in unit dosage form.

168. A method for the prophylaxis or treatment of hypercholesterolemia comprising administering to a patient in need thereof a composition of claim 166 in unit dosage form.

169. A compound of formula 1:

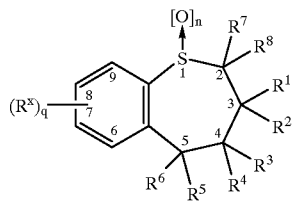

(I)

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A—$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$–$C_{10}$ cycloalkyl;
$R^3$ and $R^4$ are independently selected from the group consisting of H, alkyl, alkenyl, alkynyl, acyloxy, aryl, heterocycle, $OR^9$, $SR^9$, $S(O)R^9$, $SO_2R^9$, and $SO_3R^9$, wherein $R^9$ and $R^{10}$ are as defined above; or
$R^3$ and $R^4$ together form =O, =$NOR^{11}$, S, =$NNR^{11}R^{12}$, =$NR^9$, or =$CR^{11}R^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ is selected from the group consisting of H, alkyl, alkenyl, alkynyl, aryl, cycloalkyl, heterocycle, quaternary heterocycle, $OR^9$, $SR^9$, $S(O)R^9$, $SO_2R^9$, and $SO_3R^9$,
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}R^{14}$, $NR^{13}NR^{14}R^{15}$, $NO_2$, $CO_2R^{13}$, CN, OM, $SO_2OM$, $SO_2NR^{13}R^{14}$, C(O) $NR^{13}R^{14}$, C(O)OM, $CR^{13}$, $P(O)R^{13}R^{14}$, $P^+R^{13}R^{14}R^{15}A^-$, $P(OR^{13})OR^4$, $S^+R^{13}R^{14}A^-$, and $N^+R^9R^{11}R^{12}A^-$;

wherein:
$A^-$ is a pharmaceutically acceptable anion and M is a pharmaceutically acceptable cation,
said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A—$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A—$, S, SO, $SO_2$, $S^+R^7A—$, $PR^7$, $P(O)R^7$, $P^+R^7R^8A—$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl,
wherein alkyl, alkenyl, alkynyl, arylalkyl, heterocycle, and polyalkyl optionally have one or more carbons replaced by O, $NR^9$, $N^+R^9R^{10}A—$, S, SO, $SO_2$, $S^+R^9A^-$, $PR^9$, $^+P^9R^{10}A—$, $P(O)R^9$, phenylene, carbohydrate, amino acid, peptide, or polypeptide, and
$R^{13}$, $R^{14}$, and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A—$, $S^+R^9R^{10}A—$, and C(O)OM,
wherein $R^{16}$ and $R^{17}$ are independently selected from the substituents constituting $R^9$ and M; or
$R^{14}$ and $R^{15}$, together with the nitrogen atom to which they are attached, form a cyclic ring; and
$R^6$ is hydroxy; and
$R^7$ and $R^8$ are independently selected from the group consisting of hydrogen and alkyl; and
one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, NR $^3R^{14}$, $SR^{13}$, $S(O)R^{13}$, $SO_2R^{13}$, $SO_3R^{13}$, $S^+R^{13}R^{14}A—$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}R^{14}$, $N^+R^9R^{11}R^{12}A^-$, $P^+R^9R^{11}R^{12}A^-$, amino acid, peptide, polypeptide, and carbohydrate,
wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A—$, S, SO, $SO_2$, $S^+R^{13}A^-$, $PR^{13}$, $P(O)R^{13}$, $P^+R^{13}R^{14}A—$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A—$, $PR^9$, $P^+R^9R^{10}A—$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $N^+R^9R^{11}R^{12}A^-$, provided that both $R^5$ and $R^6$ cannot be hydrogen, OH, or SH;

provided that when $R^5$ is phenyl, only one of $R^1$ or $R^2$ is H; or a pharmaceutically acceptable salt, solvate, or prodrug thereof.

170. A compound of formula I:

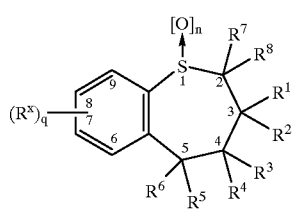

(I)

wherein:

q is 1 or 2;

n is 2;

$R^1$ and $R^2$ are each alkyl;

$R^3$ is hydroxy;

$R^4$ and $R^6$ are hydrogen;

$R^5$ has the formula (II)

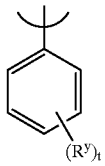

(II)

wherein t is an integer from 0 to 5;

one or more $R^y$ are $OR^{13}$;

$R^{13}$ is selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl;

said $R^{13}$ alkyl, alkenyl, alkynyl, arylalkyl, heterocycle, and polyalkyl groups optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide;

$R^{13}$ is optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein A is a pharmaceutically acceptable anion, and M is a pharmaceutically acceptable cation, $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH; or $R^{11}$ and $R^{12}$ together with the nitrogen or carbon atom to which they are attached form a cyclic ring; and $R^{16}$ and $R^{17}$ are independently selected from the substituents constituting $R^9$ and M;

$R^7$ and $R^8$ are hydrogen; and one or more $R^x$ are independently selected from the group consisting of alkoxy, alkylamino and dialkylamino; or a pharmaceutically acceptable salt, solvate, or prodrug thereof.

171. A compound of claim 170 wherein $R^1$ and $R^2$ are each n-butyl.

172. A compound of claim 171 wherein t is 1, $R^y$ is $OR^3$, and $R^{13}$ is as defined in claim 170.

173. A compound of claim 172 wherein one or more $R^x$ are independently selected from methoxy and dimethylamino.

174. A compound of claim 172 wherein $R^x$ is dimethylamino.

175. A compound of claim 172 wherein:

t is 1;

$R^y$ is para-$OR^3$; and $R^3$ is as defined in claim 170.

176. A compound of claim 172 wherein:

t is 1;

$R^{13}$ is meta-$OR^{13}$; and $R^{13}$ is as defined in claim 170.

177. A compound of claim 172 having the 4R,5R configuration.

178. A compound of claim 170 having the structural formula:

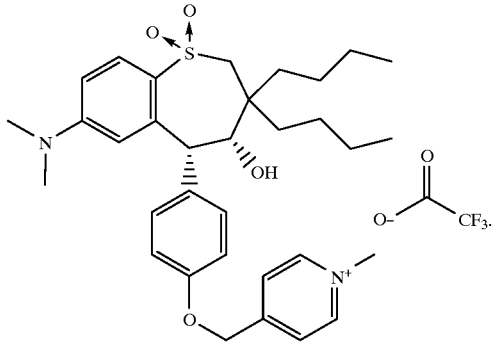

179. A compound of claim 170 having the structural formula:

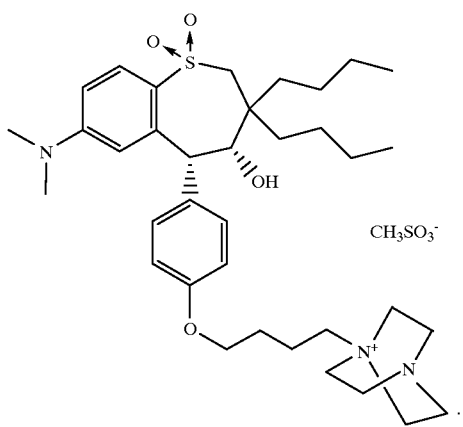

180. A compound of formula (I):

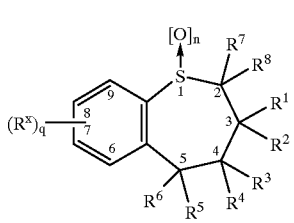

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^{11}$, =S, =$NNR^{11}R^{12}$, =$N^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

R is aryl substituted with one or more $OR^{13a}$, wherein $R^{13a}$ is selected from the group consisting of polyether, aryl, alkylarylalkyl, alkylheteroarylalkyl, alkylheterocyclylalkyl, heterocyclylalkyl, heteroarylalkyl, quaternary heterocyclylalkyl, alkylammoniumalkyl, and carboxyalkylaminocarbonylalkyl, $R^{13a}$ is optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $A^-$ is an pharmaceutically acceptable anion and M is a pharmaceutically acceptable cation, wherein $R^{16}$ and $R^{17}$ are independently selected from the substituents constituting $R^9$ and M; and $R^6$ is selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}C(O)OM$, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, arylalkyl, quaternary heterocycle, quaternary heteroaryl, $P(O)R^7R^8$, wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A-$, S, SO, $SO_2$, $S^+R^9A^-$, $PR^9$, $P^+R^9R^{10}A-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(R^{16})R^{17}$, $P^+R^9R^{10}R^{11}A-$, $S^+R^{9\ R10}A-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, NR14C(O)R13, C(O)OM, $COR^{13}$, $OR^{18}$, $S(O)_nNR^{18}$, $NR^{13}R^{18}$, $NR^{18}OR^{14}$, $N^+R^9R^{11}R^{12}A-$, $R^+R^9R^{11}R^{12}A-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A-$, $S^+R^9R^{10}A-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^7$, and C)O)OM, wherein in $R^x$, one or more carbons are optionally replaced by O, $NR^{13}$, $NR^{13}$, $N^+R^{13}R^{14}A-$, S, SO, $SO_2$, $S^+R^{13}A^-$, $PR^{13}$, $P(O)R^{13}$, $P^+R^{13}R^{14}A-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A-$, $PR^9$, $P^+R^9R^{10}A-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}$, $P(OR^{13})OR^{14}$, $S^+R^{13}R^{14}A-$, and $N^+R^9R^{11}R^{12}A-$, or a pharmaceutically acceptable salt, solvate, or prodrug thereof.

181. A compound of claim 180 wherein:

$R^5$ is phenyl substituted with $OR^{13a}$;

$R^{13a}$ is independently selected from the group consisting of polyether, alkylarylalkyl, alkylheteroarylalkyl, alkylheterocyclylalkyl, and carboxyalkylaminocarbonylalkyl; and $R^{13a}$ is optionally substituted with one or more groups selected from the group consisting of carboxy, quaternary heterocycle, quaternary heteroaryl, and $NR^9R^{10}$.

182. A compound of claim 180 wherein n is 1 or 2.

183. A compound of claim 180 wherein $R^7$ and $R^8$ are independently selected from the group consisting of hydrogen and alkyl.

184. A compound of claim 180 wherein $R^7$ and $R^8$ are hydrogen.

185. A compound of claim 180 wherein $R^3$ and $R^4$ are independently selected from the group consisting of hydrogen and $OR^9$.

186. A compound of claim 180 wherein $R^3$ is hydrogen and $R^4$ is hydroxy.

187. A compound of claim 180 wherein one or more $R^x$ are independently selected from the group consisting of $OR^{13}$ and $NR^{13}R^{14}$.

188. A compound of claim 180 wherein one or more $R^x$ are independently selected from methoxy and dimethylamino.

189. A compound of claim 180 wherein $R^1$ and $R^2$ are independently selected from the group consisting of hydrogen and alkyl.

190. A compound of claim 180 wherein $R^1$ and $R^2$ are independently selected from the group consisting alkyl.

191. A compound of claim 180 wherein $R^1$ and $R^2$ are the same alkyl.

192. A compound of claim 180 wherein $R^1$ and $R^2$ are each n-butyl.

193. A compound of claim 180 wherein n is 1 or 2;

$R^1$ and $R^2$ are n-butyl;

$R^3$ and $R^6$ are hydrogen;

$R^4$ is hydroxy;

$R^7$ and $R^8$ are hydrogen; and one or more $R^x$ are independently selected from methoxy and dimethylamino.

194. A compound of claim 180 having the structural formula:

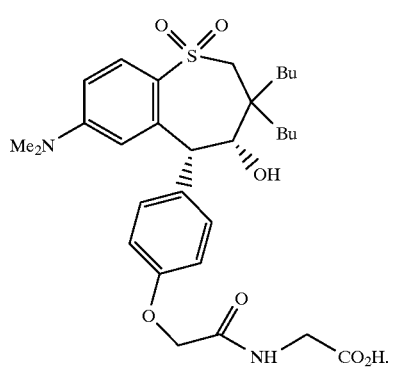

195. A compound of claim 180 having the structural formula:

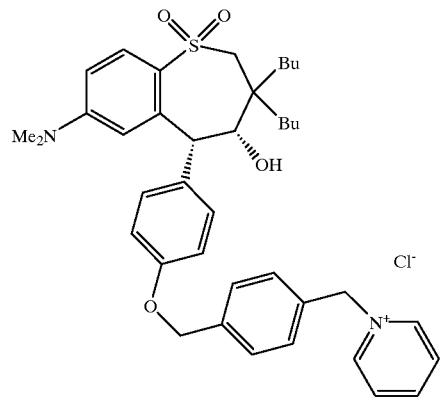

196. A compound of claim 180 having the structural formula:

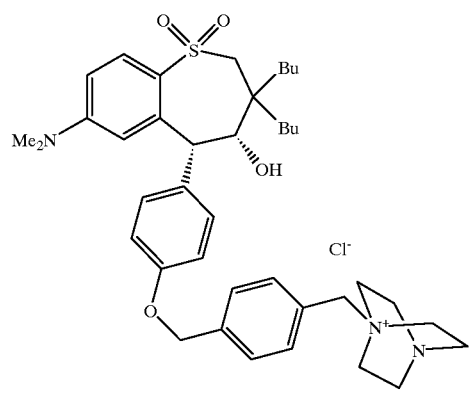

197. A compound of claim 180 having the structural formula:

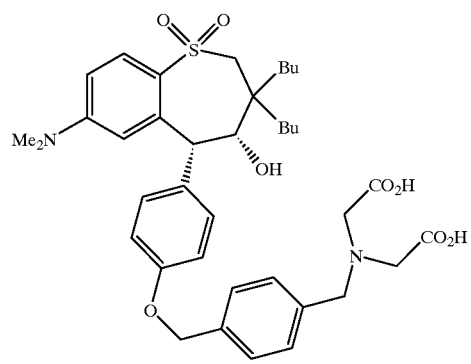

198. A compound of claim 180 having the structural formula:

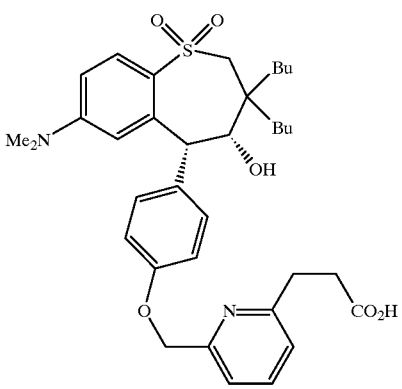

199. A compound of claim 180 having the structural formula:

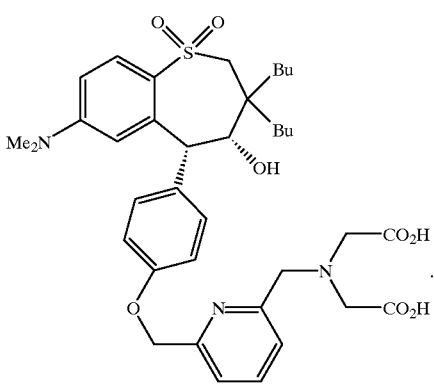

200. A compound of claim 180 having the structural formula:

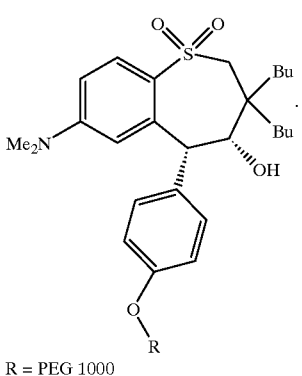

R = PEG 1000

201. A compound of formula (I):

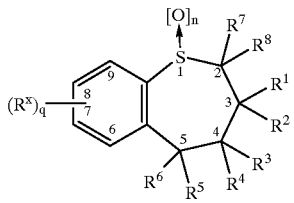

(I)

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ is aryl substituted with one or more $OR^{13b}$, wherein $R^{13b}$ is selected from the group consisting of alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, $R^{13b}$ is substituted with one or more groups selected from the group consisting of hydroxy, amino, sulfo, carboxy, carboxyalkyl, heterocycle, heteroaryl, sulfoalkyl, quaternary heterocyclylalkyl, quaternary heteroarylalkyl, or guanidinyl, and $R^6$ is selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, NR14C(O)R13, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, or a pharmaceutically acceptable salt, solvate, or prodrug thereof.

202. A compound of claim 201 wherein:

$R^5$ is phenyl substituted with $OR^{13b}$;

$R^{13b}$ is independently selected from the group consisting of alkyl, quaternary heteroarylalkyl, and quaternary heterocyclylalkyl; and $R^{13b}$ is substituted with one or more groups selected from the group consisting of hydroxy, heterocycle, heteroaryl, and guanidinyl.

203. A compound of claim 201 wherein n is 1 or 2.

204. A compound of claim 201 wherein $R^7$ and $R^8$ are independently selected from the group consisting of hydrogen and alkyl.

205. A compound of claim 201 wherein $R^7$ and $R^8$ are hydrogen.

206. A compound of claim 201 wherein $R^3$ and $R^4$ are independently selected from the group consisting of hydrogen and $OR^9$.

207. A compound of claim 201 wherein $R^3$ is hydrogen and $R^4$ is hydroxy.

208. A compound of claim 201 wherein one or more $R^x$ are independently selected from the group consisting of $OR^{13}$ and $NR^{13}R^{14}$.

209. A compound of claim 201 wherein one or more $R^x$ are independently selected from methoxy and dimethylamino.

210. A compound of claim 201 wherein $R^1$ and $R^2$ are independently selected from the group consisting of hydrogen and alkyl.

211. A compound of claim 201 wherein $R^1$ and $R^2$ are independently selected from the group consisting alkyl.

212. A compound of claim 201 wherein $R^1$ and $R^2$ are the same alkyl.

213. A compound of claim 201 wherein $R^1$ and $R^2$ are each n-butyl.

214. A compound of claim 201 wherein n is 1 or 2;

$R^1$ and $R^2$ are n-butyl;

$R^3$ and $R^6$ are hydrogen;

$R^4$ is hydroxy;

$R^7$ and $R^8$ are hydrogen; and one or more $R^x$ are independently selected from methoxy and dimethylamino.

215. A compound of claim 201 having the structural formula:

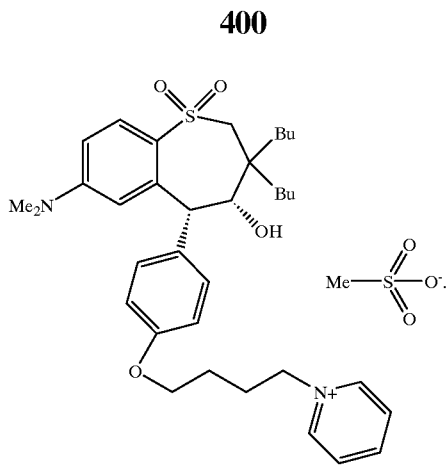

216. A compound of claim 201 having the structural formula:

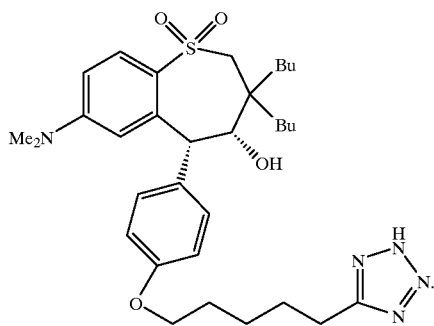

217. A compound of claim 201 having the structural formula:

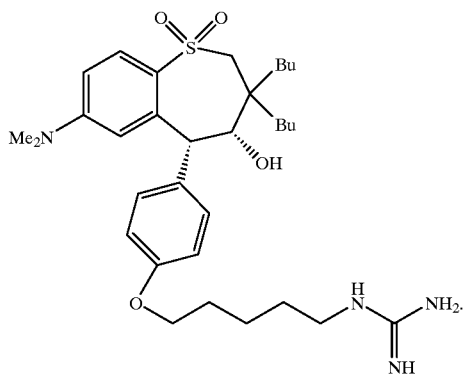

218. A compound of formula (I):

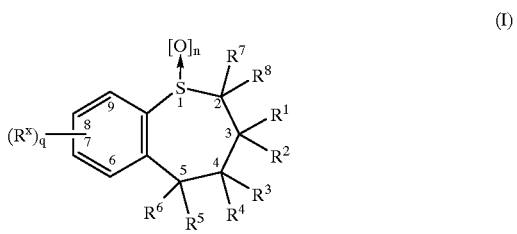

(I)

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$-$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form $=O$, $=NOR^{11}$, $=S$, $=NNR^{11}R^{12}$, $=NR^9$, or $=CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ is aryl substituted with one or more $OR^{13b}$, wherein $R^{13b}$ is selected from the group consisting of alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, $R^{13b}$ is substituted with one or more groups selected from the group consisting of $OR^{9a}$, $NR^{9a}R^{10}$, $N^+R^{9a}R^{11}R^{12}A^-$, $SR^{9a}$, $S(O)R^{9a}$, $SO_2R^{9a}$, $SO_3R^{9a}$, $CO_2R^{9a}$, $CONR^{9a}R^{10}$, $SO_2NR^{9a}R^{10}$, $P^+R^{9a}R^{10}R^{11}A^-$, and $S^+R^{9a}R^{10}A^-$, wherein $A^-$ is an pharmaceutically acceptable anion and M is a pharmaceutically acceptable cation, and wherein $R^{9a}$ is selected from the group consisting of carboxyalkyl, carboxyheteroaryl, carboxyheterocycle, carboalkoxyalkyl, and carboxyalkylamino;

$R^6$ is selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A-$, S, SO, $SO_2$, $S^+R^7A-$, $PR^7$, $P(O)R^7$, $P^+R^7R^8A-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A-$, S, SO, $SO_2$, $S^+R^9A^-$, $PR^9$, $P^+R^9R^{10}A-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A-$, $S^+R^9R^{10}A-$, and $C(O)OM$, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}R^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR14C(O)R13$, $C(O)OM$, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or $C(O)OM$, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and $C(O)OM$, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, or a pharmaceutically acceptable salt, solvate, or prodrug thereof.

219. A compound of claim 218 wherein:

$R^5$ is phenyl substituted with $OR^{13b}$;

$R^{13b}$ is alkyl; and $R^{13b}$ is substituted with one or more groups selected from the group consisting of $OR^{9a}$ and $NR^{9a}R^{10}$; and $R^{9a}$ is selected from the group consisting of carboxyalkyl, carboxyheteroaryl, and carboxyheterocycle; and $R^{10}$ is carboxyalkyl.

220. A compound of claim 218 wherein n is 1 or 2.

221. A compound of claim 218 wherein $R^7$ and $R^8$ are independently selected from the group consisting of hydrogen and alkyl.

222. A compound of claim 218 wherein $R^7$ and $R^8$ are hydrogen.

223. A compound of claim 218 wherein $R^3$ and $R^4$ are independently selected from the group consisting of hydrogen and $OR^9$.

224. A compound of claim 218 wherein $R^3$ is hydrogen and $R^4$ is hydroxy.

225. A compound of claim 218 wherein one or more $R^x$ are independently selected from the group consisting of $OR^{13}$ and $NR^{13}R^{14}$.

226. A compound of claim 218 wherein one or more $R^x$ are independently selected from methoxy and dimethylamino.

227. A compound of claim 218 wherein $R^1$ and $R^2$ are independently selected from the group consisting of hydrogen and alkyl.

228. A compound of claim 218 wherein $R^1$ and $R^2$ are independently selected from the group consisting alkyl.

229. A compound of claim 218 wherein $R^1$ and $R^2$ are the same alkyl.

230. A compound of claim 218 wherein $R^1$ and $R^2$ are each n-butyl.

231. A compound of claim 218 wherein n is 1 or 2;

$R^1$ and $R^2$ are n-butyl;

$R^3$ and $R^6$ are hydrogen;

$R^4$ is hydroxy;

$R^7$ and $R^8$ are hydrogen; and one or more $R^x$ are independently selected from methoxy and dimethylamino.

232. A compound of claim 218 having the structural formula:

233. A compound of claim 218 having the structural formula:

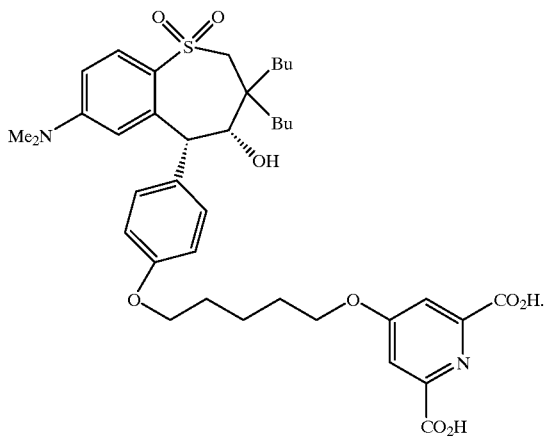

234. A compound of formula (I):

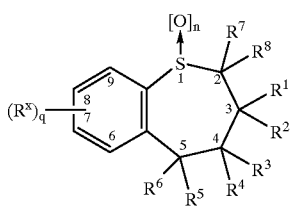

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^{w}A^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together form =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ is aryl substituted with one or more $OR^{13b}$, wherein $R^{13b}$ is selected from the group consisting of alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, $R^{13b}$ is substituted with one or more groups selected from the group consisting of $NR^9R^{10a}$, $CONR^9R^{10a}$, $SO_2NR^9R^{10a}$, $P^+R^9R^{10a}R^{11}A^-$, and $S^+R^9R^{10a}A^-$, wherein $A^-$ is an pharmaceutically acceptable anion and M is a pharmaceutically acceptable cation, wherein $R^{10a}$ is selected from the group consisting of carboxyalkyl, carboalkoxyalkyl, carboxyalkylamino, heteroarylalkyl, and heterocyclylalkyl; or $R^6$ is selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, C(O)$NR^{13}R^{14}$, C(O)OM, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:
$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR14C(O)R13$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, or a pharmaceutically acceptable salt, solvate, or prodrug thereof.

235. A compound of claim 234 wherein:
$R^5$ is phenyl substituted with $OR^{13b}$;
$R^{13b}$ is alkyl; and
$R^{13b}$ is substituted with $NR^9R^{10a}$; and
$R^9$ is hydrogen; and
$R^{10}$ is heteroarylalkyl.

236. A compound of claim 234 wherein n is 1 or 2.

237. A compound of claim 234 wherein $R^7$ and $R^8$ are independently selected from the group consisting of hydrogen and alkyl.

238. A compound of claim 234 wherein $R^7$ and $R^8$ are hydrogen.

239. A compound of claim 234 wherein $R^3$ and $R^4$ are independently selected from the group consisting of hydrogen and $OR^9$.

240. A compound of claim 234 wherein $R^3$ is hydrogen and $R^4$ is hydroxy.

241. A compound of claim 234 wherein one or more $R^x$ are independently selected from the group consisting of $OR^{13}$ and $NR^{13}R^{14}$.

242. A compound of claim 234 wherein one or more $R^x$ are independently selected from methoxy and dimethylamino.

243. A compound of claim 234 wherein $R^1$ and $R^2$ are independently selected from the group consisting of hydrogen and alkyl.

244. A compound of claim 234 wherein $R^1$ and $R^2$ are independently selected from the group consisting alkyl.

245. A compound of claim 234 wherein $R^1$ and $R^2$ are the same alkyl.

246. A compound of claim 234 wherein $R^1$ and $R^2$ are each n-butyl.

247. A compound of claim 234 wherein
n is 1 or 2;
$R^1$ and $R^2$ are n-butyl;
$R^3$ and $R^6$ are hydrogen;
$R^4$ is hydroxy;
$R^7$ and $R^8$ are hydrogen; and
one or more $R^x$ are independently selected from methoxy and dimethylamino.

248. A compound of claim 234 having the structural formula:

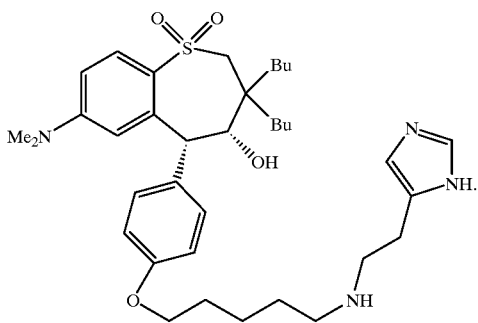

249. A compound of formula (I):

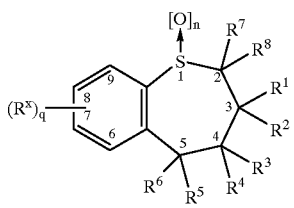

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or
$R^1$ and $R^2$ taken together with the carbon to which they are attached form $C_3$–$C_{10}$ cycloalkyl;
$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or
$R^3$ and $R^4$ together form =O, =$NOR^{11}$, =S, =$NNR^{11}R^{12}$, =$NR^9$, or =$CR^{11}R^{12}$,
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$,
wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ is aryl substituted with one or more substituent groups independently selected from the group consisting of $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, and $NR^{13}SO_2NR^{14}R^{15}$,
wherein:
$R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl,
$R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM,
wherein $A^-$ is an pharmaceutically acceptable anion and M is a pharmaceutically acceptable cation,
wherein $R^{16}$ and $R^{17}$ are independently selected from the substituents constituting $R^9$ and M; or
$R^{13}$ and $R^{14}$, together with the nitrogen atom to which they are attached form a mono- or polycyclic heterocycle that is optionally substituted with one or more radicals selected from the group consisting of oxo, carboxy and quaternary salts; or
$R^{14}$ and $R^{15}$, together with the nitrogen atom to which they are attached, form a cyclic ring; and
$R^6$ is selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$,
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,
wherein:

A⁻ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR14C(O)R13$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, or a pharmaceutically acceptable salt, solvate, or prodrug thereof.

250. A compound of claim 249 wherein $R^5$ is aryl substituted with a radical selected from the group consisting of $NR^{13}C(O)NR^{14}R^{15}$ and $NR^{13}CO_2R^{14}$.

251. A compound of claim 249 wherein $R^5$ is phenyl substituted with a radical selected from the group consisting of $NR^{13}C(O)NR^{14}R^{15}$ and $NR^{13}CO_2R^{14}$.

252. A compound of claim 249 wherein n is 1 or 2.

253. A compound of claim 249 wherein $R^7$ and $R^8$ are independently selected from the group consisting of hydrogen and alkyl.

254. A compound of claim 249 wherein $R^7$ and $R^8$ are hydrogen.

255. A compound of claim 249 wherein $R^3$ and $R^4$ are independently selected from the group consisting of hydrogen and $OR^9$.

256. A compound of claim 249 wherein $R^3$ is hydrogen and $R^4$ is hydroxy.

257. A compound of claim 249 wherein one or more $R^x$ are independently selected from the group consisting of $OR^{13}$ and $NR^3R^{14}$.

258. A compound of claim 249 wherein one or more $R^x$ are independently selected from methoxy and dimethylamino.

259. A compound of claim 249 wherein $R^1$ and $R^2$ are independently selected from the group consisting of hydrogen and alkyl.

260. A compound of claim 249 wherein $R^1$ and $R^2$ are independently selected from the group consisting alkyl.

261. A compound of claim 249 wherein $R^1$ and $R^2$ are the same alkyl.

262. A compound of claim 249 wherein $R^1$ and $R^2$ are each n-butyl.

263. A compound of claim 249 wherein n is 1 or 2;

$R^1$ and $R^2$ are n-butyl;

$R^3$ and $R^6$ are hydrogen;

$R^4$ is hydroxy;

$R^7$ and $R^8$ are hydrogen; and one or more $R^x$ are independently selected from methoxy and dimethylamino.

264. A compound of claim 98 having the structural formula:

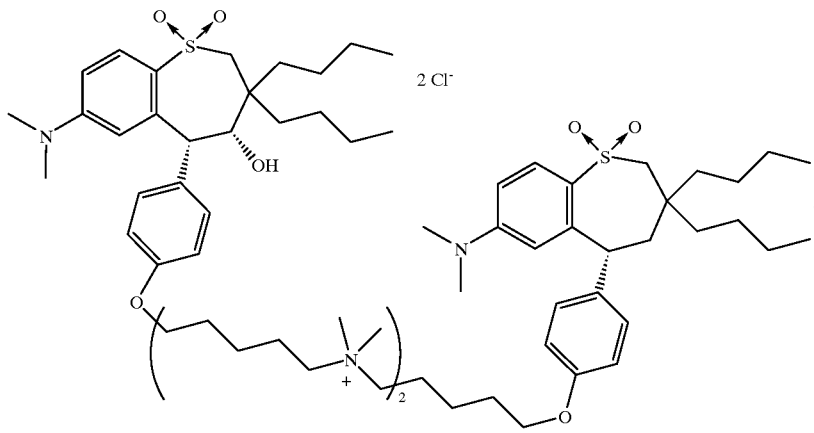

265. A pharmaceutical composition comprising an anti-hyperlipidemic condition effective amount of a compound of formula (I) of claim 170, and a pharmaceutically acceptable carrier.

266. A pharmaceutical composition comprising an anti-atherosclerotic effective amount of a compound of formula (I) of claim 170, and a pharmaceutically acceptable carrier.

267. A pharmaceutical composition comprising an anti-hypercholesterolemia effective amount of a compound of formula (I) of claim 170, and a pharmaceutically acceptable carrier.

268. A method for the prophylaxis or treatment of a hyperlipidemic condition comprising administering to a patient in need thereof a composition of claim 265 in unit dosage form.

269. A method for the prophylaxis or treatment of an atherosclerotic condition comprising administering to a patient in need thereof a composition of claim 266 in unit dosage form.

270. A method for the prophylaxis or treatment of hypercholesterolemia comprising administering to a patient in need thereof a composition of claim 267 in unit dosage form.

271. A pharmaceutical composition comprising an anti-hyperlipidemic condition effective amount of a compound of formula (I) of claim 180, and a pharmaceutically acceptable carrier.

272. A pharmaceutical composition comprising an anti-atherosclerotic effective amount of a compound of formula (I) of claim 180, and a pharmaceutically acceptable carrier.

273. A pharmaceutical composition comprising an anti-hypercholesterolemia effective amount of a compound of formula (I) of claim 180, and a pharmaceutically acceptable carrier.

274. A method for the prophylaxis or treatment of a hyperlipidemic condition comprising administering to a patient in need thereof a composition of claim 271 in unit dosage form.

275. A method for the prophylaxis or treatment of an atherosclerotic condition comprising administering to a patient in need thereof a composition of claim 272 in unit dosage form.

276. A method for the prophylaxis or treatment of hypercholesterolemia comprising administering to a patient in need thereof a composition of claim 273 in unit dosage form.

277. A pharmaceutical composition comprising an anti-hyperlipidemic condition effective amount of a compound of formula (I) of claim 201, and a pharmaceutically acceptable carrier.

278. A pharmaceutical composition comprising an anti-atherosclerotic effective amount of a compound of formula (I) of claim 201, and a pharmaceutically acceptable carrier.

279. A pharmaceutical composition comprising an anti-hypercholesterolemia effective amount of a compound of formula (I) of claim 201, and a pharmaceutically acceptable carrier.

280. A method for the prophylaxis or treatment of a hyperlipidemic condition comprising administering to a patient in need thereof a composition of claim 277 in unit dosage form.

281. A method for the prophylaxis or treatment of an atherosclerotic condition comprising administering to a patient in need thereof a composition of claim 278 in unit dosage form.

282. A method for the prophylaxis or treatment of hypercholesterolemia comprising administering to a patient in need thereof a composition of claim 279 in unit dosage form.

283. A pharmaceutical composition comprising an anti-hyperlipidemic condition effective amount of a compound of formula (I) of claim 218, and a pharmaceutically acceptable carrier.

284. A pharmaceutical composition comprising an anti-atherosclerotic effective amount of a compound of formula (I) of claim 218, and a pharmaceutically acceptable carrier.

285. A pharmaceutical composition comprising an antihypercholesterolemia effective amount of a compound of formula (I) of claim 218, and a pharmaceutically acceptable carrier.

286. A method for the prophylaxis or treatment of a hyperlipidemic condition comprising administering to a patient in need thereof a composition of claim 283 in unit dosage form.

287. A method for the prophylaxis or treatment of an atherosclerotic condition comprising administering to a patient in need thereof a composition of claim 284 in unit dosage form.

288. A method for the prophylaxis or treatment of hypercholesterolemia comprising administering to a patient in need thereof a composition of claim 285 in unit dosage form.

289. A pharmaceutical composition comprising an antihyperlipidemic condition effective amount of a compound of formula (I) of claim 234, and a pharmaceutically acceptable carrier.

290. A pharmaceutical composition comprising an antiatherosclerotic effective amount of a compound of formula (I) of claim 234, and a pharmaceutically acceptable carrier.

291. A pharmaceutical composition comprising an antihypercholesterolemia effective amount of a compound of formula (I) of claim 234, and a pharmaceutically acceptable carrier.

292. A method for the prophylaxis or treatment of a hyperlipidemic condition comprising administering to a patient in need thereof a composition of claim 289 in unit dosage form.

293. A method for the prophylaxis or treatment of an atherosclerotic condition comprising administering to a patient in need thereof a composition of claim 290 in unit dosage form.

294. A method for the prophylaxis or treatment of hypercholesterolemia comprising administering to a patient in need thereof a composition of claim 291 in unit dosage form.

295. A pharmaceutical composition comprising an antihyperlipidemic condition effective amount of a compound of formula (I) of claim 249, and a pharmaceutically acceptable carrier.

296. A pharmaceutical composition comprising an antiatherosclerotic effective amount of a compound of formula (I) of claim 249, and a pharmaceutically acceptable carrier.

297. A pharmaceutical composition comprising an antihypercholesterolemia effective amount of a compound of formula (I) of claim 249, and a pharmaceutically acceptable carrier.

298. A method for the prophylaxis or treatment of a hyperlipidemic condition comprising administering to a patient in need thereof a composition of claim 295 in unit dosage form.

299. A method for the prophylaxis or treatment of an atherosclerotic condition comprising administering to a patient in need thereof a composition of claim 296 in unit dosage form.

300. A method for the prophylaxis or treatment of hypercholesterolemia comprising administering to a patient in need thereof a composition of claim 297 in unit dosage form.

301. A process for the preparation of a compound having the formula:

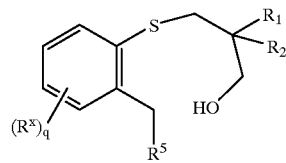

XLI comprising:

treating a thiophenol with an abstracting agent;

coupling the thiophenyl and a cyclic sulfate to form an intermediate comprising a sulfate group; and removing the sulfate group of the intermediate to form the compound of formula XLI;

wherein q is an integer from 1 to 4;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^-R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^-R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ is hydroxy;

$R^4$ is hydrogen;

$R^5$ and $R^6$ are independently selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $COR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

A⁻ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are hydrogen; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, and alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$.

302. The process of claim 301 wherein the cyclic sulfate has the formula:

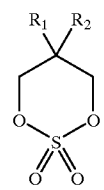

XL and the thiophenol has the formula:

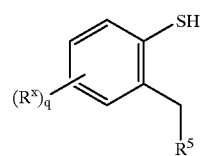

XVIIIA wherein $R^1$, $R^2$, $R^5$, $R^x$ and q are as defined in claim 301.

303. The process of claim 301 wherein the sulfate group is removed by treating the intermediate with a hydrolyzing agent.

304. The process of claim 303 wherein the hydrolyzing agent is a mineral acid.

305. The process of claim 303 wherein the hydrolyzing agent is selected from the group consisting of hydrochloric acid and sulfuric acid.

306. The process of claim 302 wherein the abstracting agent is a base having a pH of at least about 10.

307. The process of claim 302 wherein the abstracting agent is an alkali metal hydride.

308. The process of claim 302 wherein the abstracting agent is sodium hydride.

309. The process of claim 302 wherein the $R^1$ and $R^2$ are alkyl.

310. The process of claim 302 wherein the $R^1$ and $R^2$ are selected from the group consisting of ethyl, n-butyl, iso-butyl and pentyl.

311. The process of claim 302 wherein the $R^1$ and $R^2$ are n-butyl.

312. A process for the preparation of a compound having the formula I:

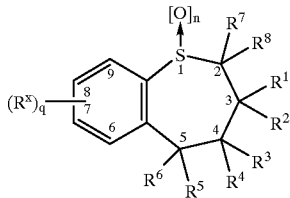

(I)

comprising:
  reacting a cyclic sulfate with a thiophenol to form an alcohol;
  oxidizing said alcohol to form a sulfone-aldehyde; and
  cyclizing said sulfone-aldehyde to form the compound of formula I;
wherein:
  q is an integer from 1 to 4;
  n is 2;
  $R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
  wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^w A^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
  wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
  wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or
  $R^1$ and $R^2$ taken together with the carbon to which they are attached form $C_3$–$C_{10}$ cycloalkyl;
  $R^3$ is hydroxy;
  $R^4$ is hydrogen;

$R^5$ and $R^6$ are independently selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:
  $A^-$ is a pharmaceutically acceptable anion and M is a pharmaceutically acceptable cation,
  said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and
  wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl,
  wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and
  $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM,
  wherein $R^{16}$ and $R^{17}$ are independently selected from the substituents constituting $R^9$ and M; or
  $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are hydrogen; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, and alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$.

313. The process of claim 312 wherein the cyclic sulfate has the formula:

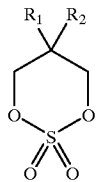

XL and the thiophenol has the formula:

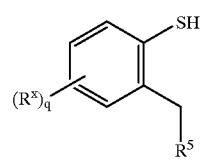

XVIIIA wherein $R^1$, $R^2$, $R^5$, $R^x$ and q are as defined in claim 312.

314. The process of claim 313 wherein the $R^1$ and $R^2$ are alkyl.

315. The process of claim 313 wherein the $R^1$ and $R^2$ are selected from the group consisting of ethyl, n-butyl, iso-butyl and pentyl.

316. The process of claim 313 wherein the $R^1$ and $R^2$ are n-butyl.

317. The process of claim 313 wherein the alcohol is oxidized with an oxidizing agent to form an aldehyde.

318. The process of claim 317 wherein the aldehyde is oxidized with an oxidizing agent to form a sulfone-aldehyde.

319. The process of claim 313 wherein the sulfone-aldehyde is cyclized with a cyclizing agent that is a base having a pH between about 8 to about 9.

320. The process of claim 313 wherein the sulfone-aldehyde is cyclized with a cyclizing agent that is an alkali alkoxide base.

321. The process of claim 313 wherein the sulfone-aldehyde is cyclized with potassium tert-butoxide.

322. The process of claim 313 wherein the alcohol is oxidized with pyridinium chlorochromate to form an aldehyde; the aldehyde is oxidized with metachloroperbenzoic acid to form a sulfone-aldehyde; and the sulfone-aldehyde is cyclized with potassium tert-butoxide.

323. A process for the preparation of a compound having the formula LI:

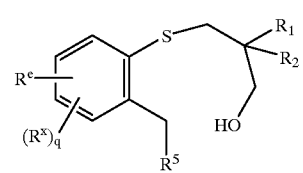

LI comprising:
treating a halobenzene with an abstracting agent;
coupling the halobenzene and a cyclic sulfate to form an intermediate comprising a sulfate group; and
removing the sulfate group of the intermediate to form the compound of formula LI; wherein
q is an integer from 1 to 4;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or $R^1$ and $R^2$ taken together with the carbon to which they are attached form $C_3$–$C_{10}$ cycloalkyl;

$R^3$ is hydroxy;

$R^4$ is hydrogen;

$R^5$ and $R^6$ are independently selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $CR^{13}$, $NR^{13}C(O)R^{14}$, $NR^{13}C(O)NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and $C(O)OM$, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are hydrogen; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, $C(O)OM$, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or $C(O)OM$, and wherein $R^{18}$ is selected from the group consisting of acyl, arylalkoxycarbonyl, arylalkyl, heterocycle, heteroaryl, and alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and $C(O)OM$, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$; and $R^e$ is an electron-withdrawing group located at the para or ortho position.

324. The process of claim 323 wherein the cyclic sulfate has the formula:

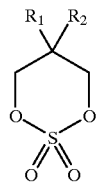

XL and the halobenzene has the formula:

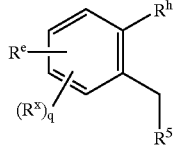

L wherein $R^h$ is halogen, and $R^1$, $R^2$, $R^5$, $R^x$, $R^e$ and q are as defined in claim 323.

325. The process of claim 324 wherein the sulfate group is removed by treating the intermediate with a hydrolyzing agent.

326. The process of claim 325 wherein the hydrolyzing agent is a mineral acid.

327. The process of claim 325 wherein the hydrolyzing agent is selected from the group consisting of hydrochloric acid and sulfuric acid.

328. The process of claim 324 wherein the abstracting agent is a dialkali metal sulfide.

329. The process of claim 324 wherein the abstracting agent is dilithium sulfide.

330. The process of claim 324 wherein $R^1$ and $R^2$ are alkyl.

331. The process of claim 324 wherein $R^1$ and $R^2$ selected from the group consisting of ethyl, n-butyl, iso-butyl and pentyl.

332. The process of claim 324 wherein $R^1$ and $R^2$ are n-butyl.

333. The process of claim 324 wherein $R^h$ is chloro.

334. The process of claim 324 wherein $R^e$ is p-nitro.

335. A process for the preparation of a compound having the formula I:

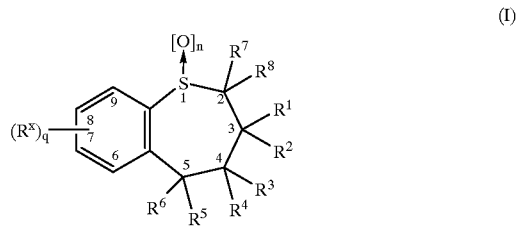

(I)

comprising:
  reacting a cyclic sulfate with a halobenzene to form an alcohol;
  oxidizing said alcohol to form a sulfone-aldehyde; and
  cyclizing said sulfone-aldehyde to form the compound of formula I;
wherein
  q is an integer from 1 to 4;
  n is 2;
  $R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
  wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$,
  wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
  wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; or
  $R^1$ and $R^2$ taken together with the carbon to which they are attached form $C_3$–$C_{10}$ cycloalkyl;
  $R^3$ is hydroxy;
  $R^4$ is hydrogen;
  $R^5$ and $R^6$ are independently selected from the group consisting of H, alkyl, alkenyl, alkynyl, aryl, cycloalkyl, heterocycle, quaternary heterocycle, $OR^{30}$, $SR^9$, $S(O)R^9$, $SO_2R^9$, and $SO_3R^9$,
  wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $NR^{13}C(O)R^{14}$, $NR^{13}C(O)$ $NR^{14}R^{15}$, $NR^{13}CO_2R^{14}$, $OC(O)R^{13}$, $OC(O)NR^{13}R^{14}$, $NR^{13}SOR^{14}$, $NR^{13}SO_2R^{14}$, $NR^{13}SONR^{14}R^{15}$, $NR^{13}SO_2NR^{14}R^{15}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$, and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, polyether, aryl, arylalkyl, alkylarylalkyl, alkylheteroarylalkyl, alkylheterocyclylalkyl, cycloalkyl, heterocycle, heteroaryl, quaternary heterocycle, quaternary heteroaryl, heterocyclylalkyl, heteroarylalkyl, quaternary heterocyclylalkyl, quaternary heteroarylalkyl, alkylammoniumalkyl, and carboxyalkylaminocarbonylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide, and $R^{13}$, $R^{14}$, and $R^{15}$ are optionally substituted with one or more groups selected from the group consisting of hydroxy, amino, sulfo, carboxy, alkyl, carboxyalkyl, heterocycle, heteroaryl, sulfoalkyl, quaternary heterocycle, quaternary heteroaryl, quaternary heterocyclylalkyl, quaternary heteroarylalkyl, guanidinyl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{13}$ and $R^{14}$, together with the nitrogen atom to which they are attached form a mono- or polycyclic heterocycle that is optionally substituted with one or more radicals selected from the group consisting of oxo, carboxy and quaternary salts; or $R^{14}$ and $R^{15}$, together with the nitrogen atom to which they are attached, form a cyclic ring; and $R^{30}$ is selected from the group consisting of alkyl, alkenyl, alkynyl, cycloalkyl, aryl, acyl, heterocycle, ammoniumalkyl, alkylammoniumalkyl, arylalkyl, carboxyalkyl, carboxyheteroaryl, carboxyheterocycle, carboalkoxyalkyl, carboxyalkylamino, heteroarylalkyl, heterocyclylalkyl, and alkylammoniumalkyl; and $R^7$ and $R^8$ are hydrogen; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)OM, and wherein $R^{18}$ is selected from the group consisting of acyl, arylalkoxycarbonyl, arylalkyl, heterocycle, heteroaryl, and alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$; and $R^e$ is an electron-withdrawing group located at the para or ortho position.

336. The process of claim 335 wherein the cyclic sulfate has the formula:

XL and the halobenzene has the formula:

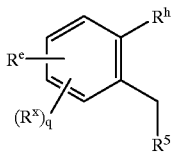

L wherein $R^1$, $R^2$, $R^5$, $R^x$ and $R^e$ are as defined in claim 335, and $R^h$ is halogen.

337. The process of claim 336 wherein the sulfate group is removed by treating the intermediate with a hydrolyzing agent.

338. The process of claim 337 wherein the hydrolyzing agent is a mineral acid.

339. The process of claim 336 wherein the hydrolyzing agent is selected from the group consisting of hydrochloric acid and sulfuric acid.

340. The process of claim 336 wherein the abstracting agent is a dialkali metal sulfide.

341. The process of claim 336 wherein the abstracting agent is dilithium sulfide.

342. The process of claim 336 wherein $R^1$ and $R^2$ are alkyl.

343. The process of claim 336 wherein $R^1$ and $R^2$ are selected from the group consisting of ethyl, n-butyl, isobutyl and pentyl.

344. The process of claim 336 wherein $R^1$ and $R^2$ are n-butyl.

345. The process of claim 336 wherein $R^h$ is chloro.

346. The process of claim 336 wherein $R^e$ is p-nitro.

347. The process of claim 336 wherein the alcohol is oxidized with an oxidizing agent to form a sulfone.

348. The process of claim 336 wherein the sulfone is oxidized with an oxidizing agent to form a sulfone-aldehyde.

349. The process of claim 336 wherein the sulfone-aldehyde is cyclized with a cyclizing agent that is a base having a pH between about 8 to about 9.

350. The process of claim 336 wherein the sulfone-aldehyde is cyclized with a cyclizing agent that is an alkali alkoxide base.

351. The process of claim 336 wherein the sulfone-aldehyde is cyclized with potassium tert-butoxide.

352. The process of claim 336 wherein the alcohol is oxidized with metachloroperbenzoic acid to form a sulfone; the aldehyde is oxidized with pyridinium chlorochromate to form a sulfone-aldehyde; and the sulfone-aldehyde is cyclized with potassium tert-butoxide.

353. A pharmaceutical composition comprising an anti-hyperlipidemic condition effective amount of a compound of claim 196, and
a pharmaceutically acceptable carrier.

354. A pharmaceutical composition comprising an anti-atherosclerotic effective amount of a compound of claim 196, and
a pharmaceutically acceptable carrier.

355. A pharmaceutical composition comprising an anti-hypercholesterolemia effective amount of a compound of claim 196, and
a pharmaceutically acceptable carrier.

356. A method for the prophylaxis or treatment of a hyperlipidemic condition comprising administering to a patient in need thereof a composition of claim 353 in unit dosage form.

357. A method for the prophylaxis or treatment of an atherosclerotic condition comprising administering to a patient in need thereof a composition of claim 354 in unit dosage form.

358. A method for the prophylaxis or treatment of hypercholesterolemia comprising administering to a patient in need thereof a composition of claim 355 in unit dosage form.

* * * * *